(12) United States Patent
Shoshi et al.

(10) Patent No.: US 6,849,367 B2
(45) Date of Patent: Feb. 1, 2005

(54) ELECTROPHOTOGRAPHIC PHOTOCONDUCTOR, PROCESS FOR FORMING AN IMAGE, IMAGE FORMING APPARATUS AND A PROCESS CARTRIDGE FOR THE SAME

(75) Inventors: Masayuki Shoshi, Shizuoka (JP); Yuuko Komai, Shizuoka (JP); Hongguo Li, Shizuoka (JP); Masaomi Sasaki, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 15 days.

(21) Appl. No.: 10/242,485

(22) Filed: Sep. 13, 2002

(65) Prior Publication Data

US 2003/0190540 A1 Oct. 9, 2003

(30) Foreign Application Priority Data

| Sep. 14, 2001 | (JP) | ......................................... | 2001-279714 |
| Sep. 14, 2001 | (JP) | ......................................... | 2001-280158 |
| Sep. 18, 2001 | (JP) | ......................................... | 2001-283210 |
| Sep. 25, 2001 | (JP) | ......................................... | 2001-290435 |
| Oct. 31, 2001 | (JP) | ......................................... | 2001-334190 |
| Nov. 6, 2001 | (JP) | ......................................... | 2001-341226 |
| Nov. 9, 2001 | (JP) | ......................................... | 2001-344986 |
| Jan. 10, 2002 | (JP) | ......................................... | 2002-003693 |
| Jan. 11, 2002 | (JP) | ......................................... | 2002-004521 |
| Mar. 1, 2002 | (JP) | ......................................... | 2002-056659 |

(51) Int. Cl.$^7$ .......................... G03G 5/06; C09B 56/00
(52) U.S. Cl. ........................ 430/79; 430/78; 534/790; 534/755; 534/757; 534/761; 534/653
(58) Field of Search ................. 534/653, 790, 534/755, 757, 761; 430/78, 79, 58.7

(56) References Cited

U.S. PATENT DOCUMENTS

| 3,526,618 | A | * | 9/1970 | Siegel et al. ................. 534/740 |
| 3,634,388 | A | * | 1/1972 | Hartsmann et al. ......... 534/745 |
| 5,569,749 | A | * | 10/1996 | Kouno et al. ............... 534/653 |
| 5,578,405 | A | * | 11/1996 | Ikegami et al. .......... 430/58.15 |
| 5,910,561 | A | | 6/1999 | Adachi et al. |
| 5,942,362 | A | | 8/1999 | Tadokoro et al. |
| 5,976,746 | A | | 11/1999 | Tanaka et al. |

(List continued on next page.)

FOREIGN PATENT DOCUMENTS

JP 06118674 A * 4/1994

OTHER PUBLICATIONS

U.S. Appl. No. 10/804,030, filed Mar. 19, 2004, Suzuki, et al.
U.S. Appl. No. 10/804,043, filed Mar. 19, 2004, Suzuki, et al.
U.S. Appl. No. 10/000,082, filed Dec. 4, 2001, pending.
U.S. Appl. No. 09/635,127, filed Aug. 9, 2000, pending.
U.S. Appl. No. 10/051,230, filed Jan. 22, 2002, pending.
U.S. Appl. No. 09/904,896, filed Jul. 16, 2001, allowed.
U.S. Appl. No. 09/691,265, filed Oct. 19, 2000, allowed.
U.S. Appl. No. 10/458,626, filed Jun. 11, 2003, Nagai, et al.
U.S. Appl. No. 10/405,843, filed Apr. 3, 2003, Tamoto, et al.

*Primary Examiner*—Christopher RoDee
(74) *Attorney, Agent, or Firm*—Oblon, Spivak, McClelland, Maier & Neustadt, P.C.

(57) ABSTRACT

Providing an electrophotographic photoconductor comprising a conductive support and a photoconductive layer disposed on the photoconductive support; wherein the photoconductive layer contains an azo compound expressed by a general formula <<1>>.

$$Ar(\!\!-\!\!N\!\!=\!\!N\!\!-\!\!Cp)_n \qquad \text{general formula <<1>>}$$

(in the general formula <<1>>, Ar expresses one of a substituted or non-substituted aromatic carbon hydride group and heterocyclic ring aromatic series group which can be combined by way of a bond group; Cp expresses a coupler residual group; n expresses an integer of one of 1, 2, 3, and 4; at least one of the Cp is a coupler residual group selected from one of the following general formulae <<2>>, <<3>>, and <<4>>.)

general formula <<2>>

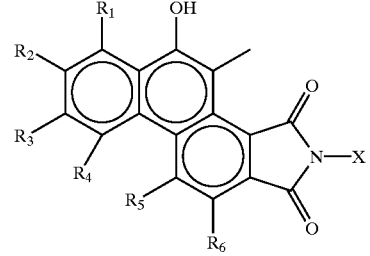

general formula <<3>>

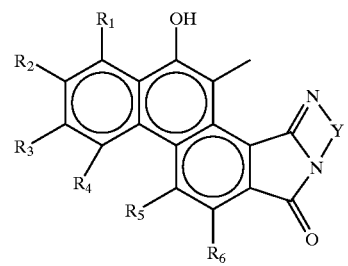

general formula <<4>>

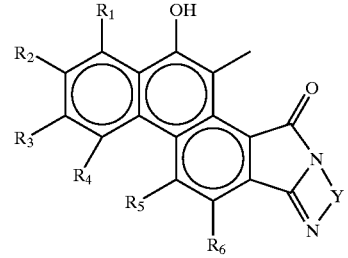

38 Claims, 80 Drawing Sheets

U.S. PATENT DOCUMENTS

| | | |
|---|---|---|
| 6,045,959 A | 4/2000 | Katayama et al. |
| 6,066,428 A | 5/2000 | Katayama et al. |
| 6,068,956 A | 5/2000 | Namba et al. |
| 6,074,792 A | 6/2000 | Ri et al. |
| 6,130,310 A | 10/2000 | Katayama et al. |
| 6,172,176 B1 | 1/2001 | Tanaka et al. |
| 6,187,492 B1 | 2/2001 | Ri et al. |
| 6,187,494 B1 | 2/2001 | Kawamura et al. |
| 6,194,535 B1 | 2/2001 | Katayama et al. |
| 6,210,848 B1 | 4/2001 | Nagai et al. |
| 6,303,736 B1 | 10/2001 | Kawamura et al. |
| 6,313,288 B1 | 11/2001 | Shimada et al. |
| 6,444,387 B2 | 9/2002 | Ri et al. |

\* cited by examiner

ELECTROPHOTOGRAPHIC PHOTOCONDUCTOR, PROCESS FOR FORMING AN IMAGE, IMAGE FORMING APPARATUS AND A PROCESS CARTRIDGE FOR THE SAME

BACKGROUND OF THE INVENTION

1. Field of the Invention

The present invention relates to an electrophotographic photoconductor containing a novel azo compound, a process for forming an image, an apparatus for forming an image and a process cartridge for the apparatus.

Specifically, the present invention relates to novel azo compounds and materials for producing the azo compounds, and the method for producing them, in particular, the azo compounds useful as an organic optical conductor, coupler compounds, which are the material for producing the azo compounds, and the method for producing them.

2. Description of the Related Art

Conventionally, there have been known optical conductive photoconductors used for electrophotography, which are largely divided into various kinds of inorganic optical conductors and organic optical conductors. "System for electrophotography" referred to herein is an image forming process, so-called Carlson Process. In the Carlson Process, generally, first, the optical conductive photoconductor is charged in the dark, by, for example, corona discharge treatment. Thereafter, an image is exposed to light to selectively scatter charges from exposed portions only in order to obtain a latent electrostatic image, and finally the electrostatic image is developed with toner made of a mixture of coloring agents such as pigment, dye, and the like, and a polymeric material to visualize images for formation. Since the photoconductor using the organic optical conductor has an advantage over those using the inorganic optical conductor within freedom, a photosensitive wavelength band, film forming ability, flexibility, transparency of a film, mass-productivity, toxicity, cost, and the like, at present, the organic optical conductor is used for most of the photoconductors. The photoconductors repeatedly used in the electrophotographic system and the similar processes are required to have electrostatic properties as typified by sensitivity, acceptable potential, potential retainability, potential stability, residual potential, spectral sensitivity characteristic, and the like.

From the above-mentioned viewpoint, there are known organic optical conductors, which have been proposed and practically used, such as azo compounds (disclosed in Japanese Patent Application Laid-Open (JP-A) No. 54-22834 and JP-A No. 61-151659), phthalocyanine compounds (disclosed in JP-A No. 48-34189 and JP-A No. 57-14874), perylene compounds (disclosed in JP-A No. 53-98825 and JP-A No. 63-266457), a polycyclic quinone compound (disclosed in JP-A No. 61-48861), squaleririum compounds (disclosed in JP-A No. 49-105536 and JP-A No. 58-21416), and the like.

The azo compounds, in particular, are easy to synthesize, have considerably free molecular design, and they widely vary in electrophotographic properties and spectral sensitive regions according to their differences in molecular structures of azo components, coupler components, and binding modes, and the like.

Therefore, a great deal of study on the azo compounds has been done not only on analog recording photoconductors but also on digital recording photoconductors.

This means that the azo compounds are synthesized generally by inducing a coupling reaction of a "diazonium compound" and a "coupler compound." For the diazonium compound and the coupler, a various kind of compounds with difference structures are used depending on the intended application for azo dye or azo pigment. The types of the compounds selected for the diazonium compound and the coupler compound determine such properties of the obtained azo dye or azo pigment as an absorption wavelength and its intensity, water-solubility, light fastness, and resin dispersion.

Conventionally, there have been known the azo compounds used for these types of photoconductors, for example, benzidine bis-azo compounds disclosed in the JP-A No. 47-37543 and No. 52-55643, a stilbenzene bis-azo compound disclosed in the JP-A No. 52-8832, a diphenyl-hexatriene bis-azo compound disclosed in the JP-A No. 58-222152, diphenylbutadiene bis-azo compounds disclosed in the JP-A No. 58-222153. Further, the compounds, which have been known for the better properties, include the azo compound having a carbazole skeleton (disclosed in the JP-A No. 53-95033), the azo compound having a distilyl-benzene skeleton (disclosed in the JP-A No. 53-133445), the azo compound having a triphenylamine skeleton (disclosed in the JP-A No. 53-132347), the azo compound having a dibenzothiophene skeleton (disclosed in the JP-A No. 54-21728), the azo compound having an oxadiazole skeleton (disclosed in the JP-A No. 54-12742), the azo compound having a fluorenone skeleton (disclosed in the JP-A No. 54-22834), the azo compound having a bis-stilbene skeleton (disclosed in the JP-A No. 54-17733), the azo compound having a distilyloxadiazole skeleton (disclosed in the JP-A No. 54-2129), the azo compound having a distilylcarbazole skeleton (disclosed in the JP-A No. 54-14967), and the like.

Further, there have been known the coupler compounds used for the above-mentioned compounds including a naphthol coupler (disclosed in the JP-A No. 47-37543), a benzocarbazole coupler (disclosed in the JP-A No. 58-122967), a naphthalimide coupler (disclosed in the JP-A No. 54-79632), a perinon coupler (disclosed in the JP-A No. 57-176055), an azulene coupler (disclosed in the JP-A No. 60-10256), an anthracene coupler (disclosed in the JP-A No. 61-257953), and the like.

Nevertheless, when used for a laminated photoconductor, the conventionally used azo compound, which is one form of photoconductors for electrophotography, generally do not have always sufficient sensitivity and durability to put into practical use. Hence, further improvement in their sensitivity and durability is desired to meet a various types of requirements essential for the electrophotographic process.

The inventors of the present invention have done a great deal of research to solve the above-mentioned subject and succeeded in obtaining such a finding that the Electrophotographic photoconductor containing a novel azo compound using a specific coupler mentioned later has sufficient sensitivity and durability for practical use.

On the other hand, from the viewpoints of the structure of and charging process of a photoconductive layer, most of practically applied photoconductors have laminated compositions, which are composed of a layer (CGL) having a charge generating function and a layer (CTL) having a charge transporting function, and are particularly used in the negatively-charging process. That is because: ① the laminated composition achieves mechanical strength and enables the photoconductors to retain sufficient mechanical strength during undergoing the process by disposing the CTL, for which film thickness can be designed, on its surface top layer, and ② The organic materials having enough charge mobility to use even in the high-speed copying process with no difficulty are, at present, almost limited to donor compounds exhibiting hole mobility. Therefore, the photoconductor has such a composition that the CTL formed by the donor compound is disposed on its surface side, which achieves negative electrostatic polarity. This type of function-separated composition, however, has given new problems.

The first one of these problems is derived from negatively charged photoconductors. A reliable charging method in the electrophotographic process is corona charging or contact charging, either of which is used for most copiers and printers. Nevertheless, as known well, negative charging is less stable than positive charging. Furthermore, negative corona charging involves generation of larger amounts of ozone and NOx, both of which are substances causing chemical damages, leading to problems such as environmental pollution and damages to photoconductors. In addition, in the contact charging method, which involves generation of far less amounts of ozone and NOx, a close approach to the photoconductors is needed, leading to considerable damages to photoconductors themselves.

The second one of the problems is derived from the laminated structures of the photoconductors. In manufacturing the photoconductors using organic materials, the solution coating method, which is more economical than the vacuum evaporation method, can be used. Although two coating operations are required to manufacture this laminated type of photoconductors, in general, three coating operations are required to dispose an interlayer on a photoconductive support (between the photoconductive support and the photoconductor) to ensure the electrostatic property of the photoconductor and this requirement for several times of coating operations increases the manufacturing cost of photoconductors. Moreover, the requirement for ensuring a better balance between sensitivity and durability, as well as another requirement for controlling the thickness of the GCL within the order of sub-microns to achieve better images are factors for further increasing the manufacturing cost.

Considering these problems, it can be understood that the photoconductors using organic materials have preferably a single-layer composition, which can be used in the positive charging process. Further, it can be understood that if the photoconductor can be used with no or a slight modification in the negative charging process, it is possible that the inexpensive photoconductors having an advantage of being considerably free to use in any environment will be newly manufactured.

Conventionally, there have been known the single-type of photoconductors including ① a charge mobile complex photoconductor made of polyvinylcarbazole and trinitrofluorenone (disclosed in the specification of U.S. Pat. No. 3,489,237), ② an eutectic complex made of thiapyrylium dye and polycarbonate (described in j. Appl. Phys. 49 5555 (1978)) and ③ a photoconductor having perilene pigment and a hydrazole compound dispersed in a resin (disclosed in the JP-A No. 2-37354).

Among them, the photoconductors described in ① and ② have low sensitivity, as well as low electrostatic and mechanical durability, which gives a problem when it is repeatedly used. The photoconductor described in ③ has a disadvantage of being unsuitable for the high-speed copying process because of its low sensitivity. Moreover, the system, in which components of the practically-used laminated photoconductor are simply dispersed, has a disadvantage of large variation in electrostatic properties when it is repeatedly used because of its low electrostatic potential and sensitivity, in particular, low light fastness and electrostatic and mechanical durability.

Thus, there is a subject that high sensitive and durability of organic materials for the single-layer photoconductors should be developed and in particular, for charge generating substances, higher light-fastness and durability are required than those used for the laminated photoconductors because of their charge generating point being on the surface top sides of the photoconductive layers unlike the laminated photoconductors.

SUMMARY OF THE INVENTION

The present invention provides a photoconductor for electrophotography, a process for forming an image, an apparatus for forming an image, and a process cartridge for the apparatus for forming an image, all of which are practical to a laser printer as well as a high speed copier. Further, the present invention provides a single layer type Electrophotographic photoconductor, the process for forming an image using this photoconductor, the Electrophotographic photoconductor apparatus, and the process cartridge for the electrophotographic apparatus which have excellent charge properties, sensitivity, light resistance, durability, and stable electrostatic properties even if a copying process is operated repeatedly.

Further, the present invention provides a novel azo compound which is of use as an organic optical conductor used in a high sensitive Electrophotographic photoconductor which is of practical use as a laser printer as well as a high speed copying machine, a novel coupler compound which is capable of manufacturing the azo compound, and a method for manufacturing the same.

The present invention includes various aspects and modes which will be described hereinafter in detail.

In first aspect of the present invention, there is provided an electrophotographic photoconductor comprising: a conductive support; and a photoconductive layer disposed on the photoconductive support; wherein the photoconductive layer contains an azo compound expressed by a general formula <<1>>.

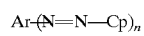            General formula <<1>>

(In the general formula <<1>>, Ar expresses one of a substituted or non-substituted aromatic carbon hydride group and heterocyclic ring aromatic group which can be combined by way of a bond group; Cp expresses a coupler residual group; n expresses an integer of one of 1, 2, 3, and 4; at least one of the Cp is a coupler residual group selected from one of the following general formulae <<2>>, <<3>>, and <<4>>.)

General formula <<2>>

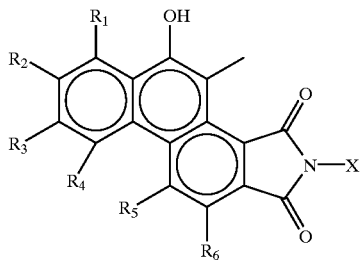

General formula <<3>>

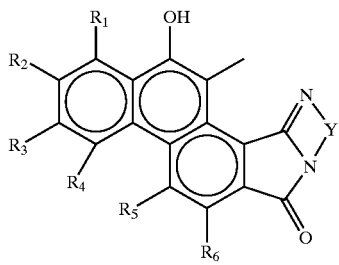

General formula <<4>>

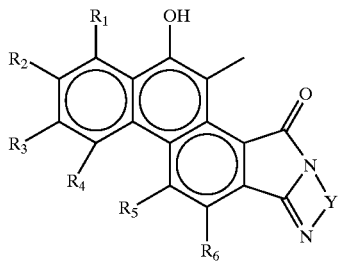

(In the general formulae <<2>>, <<3>>, and <<4>>, $R_1$, $R_2$, $R_3$, $R_4$, $R_5$ and $R_6$ each expresses one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; and Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group (here, Z represents one of a substituted or non-substituted alkylene group, a substituted or non-substituted aromatic series divalent organic residual group, and a substituted or non-substituted heterocyclic ring aromatic series divalent organic residual group).)

The present invention also provides a mode in which the coupler residual group in the electrophotographic photoconductor aforementioned expressed by the general formula <<2>> is a coupler residual group expressed by a general formula <<5>>.

General formula <<5>>

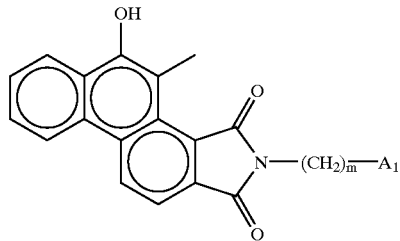

(In the general formula <<5>>, $A_1$ expresses one of a substituted or non-substituted aromatic series hydrocarbon group, and a substituted or non-substituted heterocyclic ring group; and m is an integer of 1 to 6.)

The present invention also provides a mode in which in the aforementioned azo compound, at least one of the Cp is a coupler residual group expressed by the general formula <<6>>, when n is one of 2, 3, and 4.

General formula <<6>>

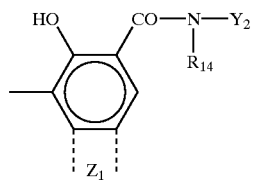

(In the general formula <<6>>, $Z_1$ represents one of a hydrocarbon ring or its substituent, and a heterocyclic ring group or its substituent; $R_{14}$ is one of hydrogen, an alkyl group or its substituent, and a phenyl group or its substituent; $Y_2$ represents one of a hydrocarbon ring group or its substituent, and a heterocyclic ring group or its substituent.)

The present invention also provides a mode in which in the aforementioned azo compound, at least one of the Cp is a coupler residual group selected from one of a general formula <<7>> and a general formula <<8>>, when n is one of 2,3, and 4.

General formula <<7>>

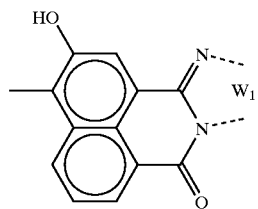

General formula <<8>>

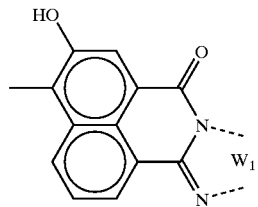

(In the general formulae <<7>> and <<8>>, $W_1$ represents an aromatic series hydrogen divalent group or a heterocyclic ring divalent group having a nitrogen atom in a ring. These rings may be substituted or non-substituted.)

The present invention also provides a mode in which the aforementioned azo compound is a disazo compound expressed by a general formula <<9>>.

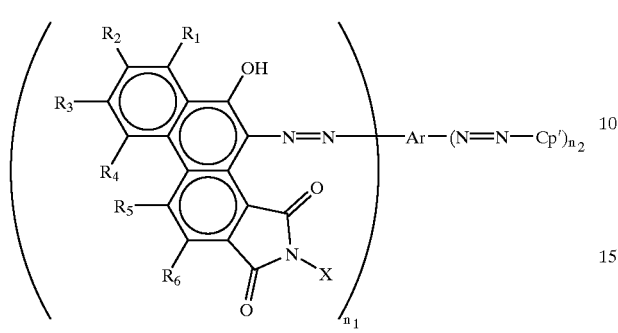

General formula <<9>>

(In the general formula <<9>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2 and $n_2$ expresses an integer of 0 or 1.)

The present invention also provides a mode in which the aforementioned disazo compound is a disazo compound expressed by a general formula <<10>>.

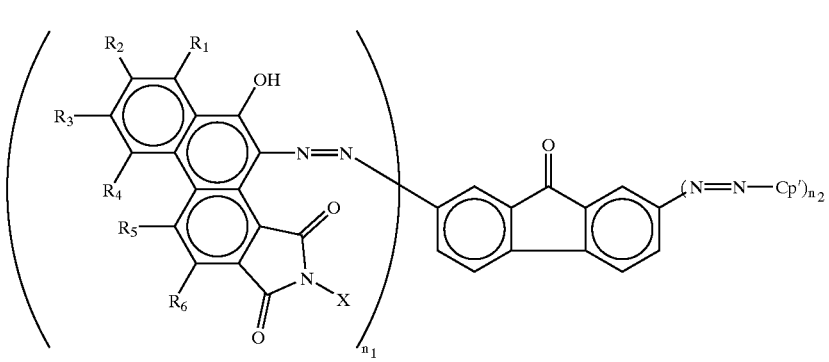

General formula <<10>>

(In the general formula <<10>>, Cp' represents a coupler residual group; $R_1$, $R_2$, $R_3$, $R_4$, $R_5$ and $R_6$ each represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2; $n_2$ expresses an integer of 0 or 1.)

The present invention also provides a mode in which the aforementioned azo compound is a disazo compound expressed by one of general formulae <<11>> and <<12>>.

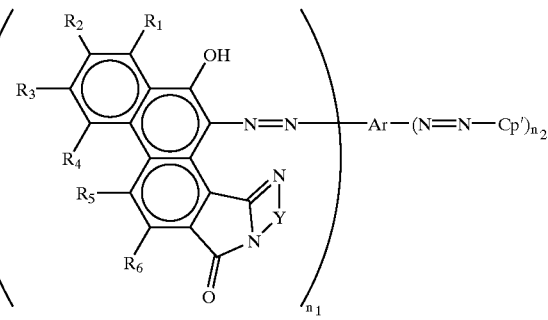

General formula <<11>>

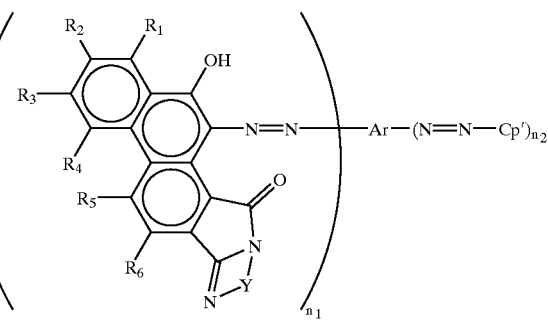

General formula <<12>>

(In the general formulae <<11>> and <<12>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and carbonyl group containing divalent organic residual group expressed by —CO—Z—, (here, Z represents one of a substituted or non-substituted alkylene group, a substituted or non-substituted aromatic series divalent organic residual group, and a substituted or non-substituted heterocyclic ring aromatic series divalent organic residual group); $n_1$ expresses an integer of 1 or 2; and $n_2$ expresses an integer of 0 or 1.)

The present invention also provides a mode in which the aforementioned disazo compound is a disazo compound expressed by one of a general formulae <<13>> and <<14>>.

General formula <<13>>

General formula <<14>>

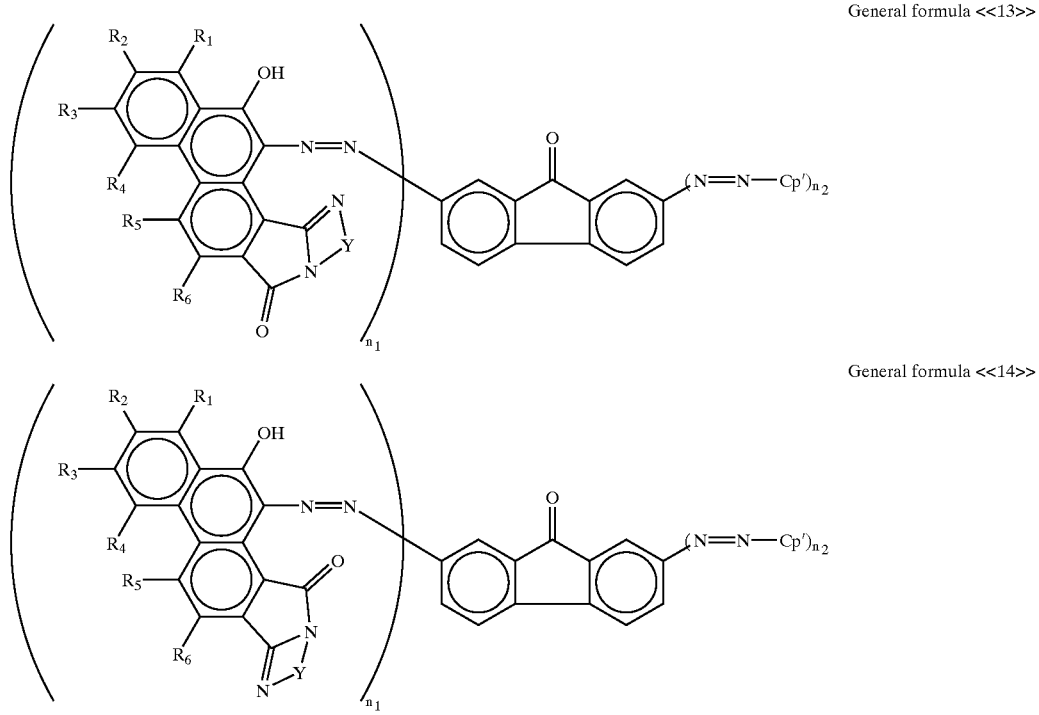

(In the general formulae <<13>> and <<14>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, (here, Z represents one of a substituted or non-substituted alkylene group, a substituted or non-substituted aromatic series divalent organic residual group, and a substituted or non-substituted heterocyclic ring aromatic series divalent organic residual group); $n_1$ expresses an integer of 1 or 2; and $n_2$ expresses an integer of 0 or 1.)

The present invention also provides a mode in which the aforementioned azo compound of the general formula <<1>> is an azo compound which is obtained by reacting a diazonium salts compound expressed by a general formula <<15>> to a coupler compound expressed by a general formula <<16>>.

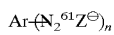          General formula <<15>>

          general formula <<16>>

(In the general formulae <<15>> and <<16>>, Ar represents one of a substituted or non-substituted aromatic series hydrocarbon group, and an aromatic series heterocyclic ring group which may be combined by way of a bonding group; Cp represents a coupler residual group; Z— represents an anion function; and n expresses an integer of 1, 2, 3 and 4.)

The present invention also provides a mode in which the aforementioned photoconductive layer is a single layer formed on a conductive support by one of directly and intervening an intermediate layer.

The present invention also provides a mode in which the aforementioned photoconductive layer further contains a charge transporting substance.

The present invention also provides a mode in which the aforementioned charge transporting substance is a stilbene compound expressed by a general formula <<17>>.

General formula <<17>>

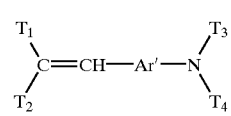

(In the general formula <<17>>, $T_1$ and $T_2$ may each independently represents one of a substituted or non-substituted alkyl group, and a substituted or non-substituted aryl group; $T_3$ and $T_4$ may each independently represents one of a hydrogen atom, a substituted or non-substituted alkyl group, a substituted or non-substituted aryl group, and a heterocyclic ring group; $T_1$ and $T_2$ may form a ring with each other; Ar' expresses one of a substituted or non-substituted aryl group, and a heterocyclic ring group.)

The present invention also provides a mode in which the aforementioned charge transporting substance is a high polymer charge transporting substance.

The present invention also provides a mode in which the aforementioned high polymer charge transporting substance is a polymer of at least one of polycarbonate, polyurethane, polyester, and polyether.

The present invention also provides a mode in which the aforementioned high polymer charge transporting substance is a high polymer compound having a structure of triaryl amine.

The present invention also provides a mode in which the aforementioned high polymer charge transporting substance is a polycarbonate having a triaryl amine structure.

The present invention also provides a mode in which the aforementioned polycarbonate having the triaryl amine structure is a high polymer charge transporting substance expressed by a general formula (1D).

General formula (1D)

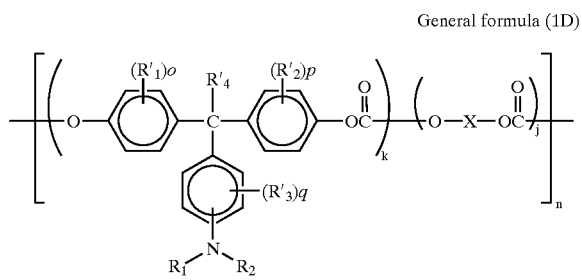

(in the formula, $R'_1$, $R'_2$, and $R'_3$ may each independently expresses a substituted or non-substituted alkyl group or a halogen atom; $R'_4$ represents a hydrogen atom or a substituted or non-substituted alkyl group; $R_1$ and $R_2$ may each represents a substituted or non-substituted aryl group; o, p, and q may each independently represents an integer of 0 to 4; k and j each represents a composition, and satisfies $0.1 \leq k \leq 1$ and $0 \leq j \leq 0.9$; and n represents a repeating unit of 5 to 5000; X is one of an aliphatic divalent group, a ring type aliphatic divalent group, and a general formula (A):

general formula (A)

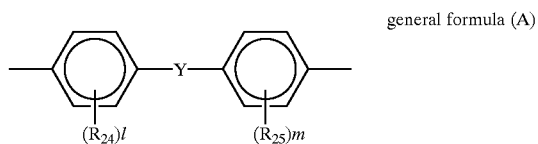

(in the formula, $R_{24}$ and $R_{25}$ may each independently represents one of a substituted or non-substituted alkyl group, an aryl group, and a halogen atom; l and m each represents an integer of 0 to 4. Y represents one of a single bond, a linear chain having a carbon atom number of 1 to 12, a branched or a ring type alkylene group, —O—, —S—, —SO—, —SO$_2$—, —CO—, —CO—O—Z—O—CO— (in the formula, Z represents an aliphatic divalent group), and a group expressed by a general formula (B):

general formula (B)

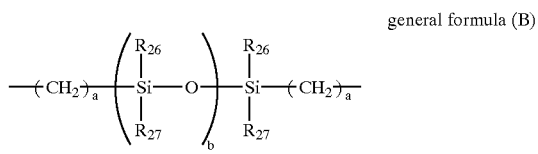

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.])

The present invention also provides a mode in which the aforementioned polycarbonate having the triaryl amine structure is a high polymer charge transporting substance expressed by a general formula (2D).

general formula (2D)

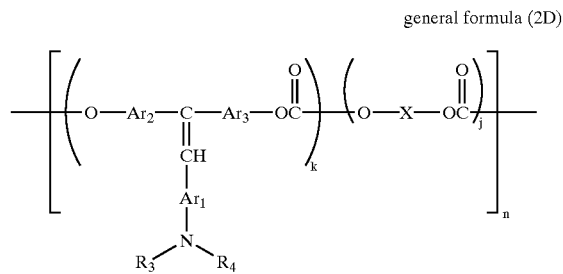

{in the formula, $R_3$ and $R_4$ may represent a substituted or non-substituted aryl group; $Ar_1$, $Ar_2$ and $Ar_3$ may each represents the same or different arylene group. Each of k and j represents a composition, and satisfies $0.1 \leq k \leq 1$ and $0 \leq j \leq 0.9$; n represents a repeating unit of 5 to 5000; X is one of an aliphatic divalent group, a ring type aliphatic divalent group, and a general formula (A):

general formula (A)

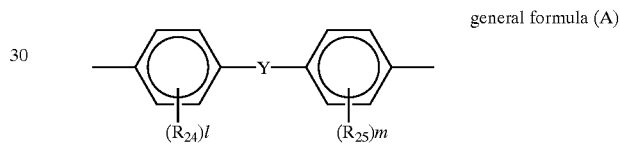

{(in the formula, $R_{24}$ and $R_{25}$ may each independently represents a substituted or non-substituted alkyl group, an aryl group or a halogen atom; each of l and m represents an integer of 0 to 4. Y represents one of a single bond, a linear chain having a carbon atom number 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

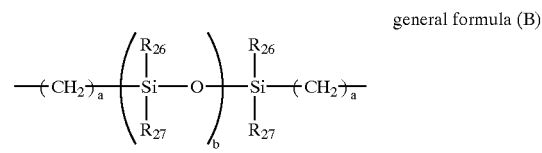

(in the formula, a represents an integer of 1 to 20; b represents an integer of 1 to 2000; $R_{26}$ and $R_{27}$ may each represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (3D).

general formula (3D)

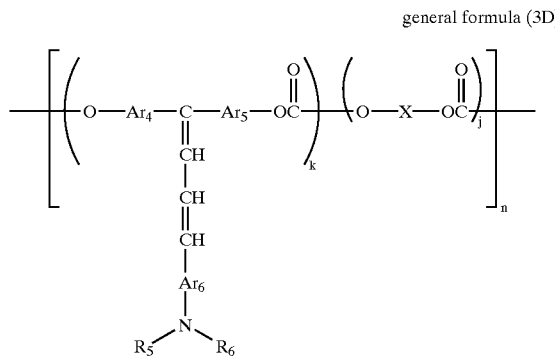

{in the formula, $R_5$ and $R_6$ may each represents a substituted or non-substituted aryl group; $Ar_4$, $Ar_5$, and $Ar_6$ may each represents a same or different arylene group; k and j each represents a composition and satisfies $0.1 \leq k \leq 1$ and $0 \leq j \leq 0.9$; n represents a repeating unit of 5 to 5000; X is one of an aliphatic divalent group, a ring type aliphatic divalent group, and a general formula (A):

general formula (A)

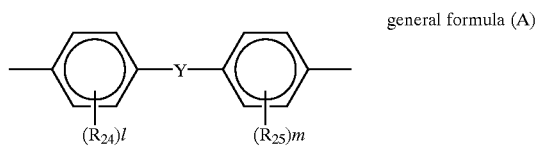

[in the formula, $R_{24}$ and $R_{25}$ may each independently represents a substituted or non-substituted alkyl group, an aryl group or a halogen atom; each of l and m represents an integer of 0 to 4. Y represents one of a single bond, a linear chain having a carbon atom number 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

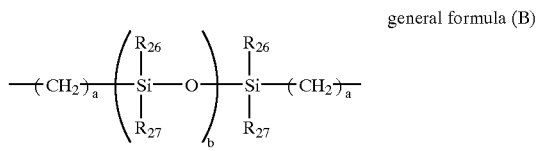

(in the formula, a represents an integer of 1 to 20; b represents an integer of 1 to 2000. $R_{26}$ and $R_{27}$ may each represents a substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (4D).

general formula (4D)

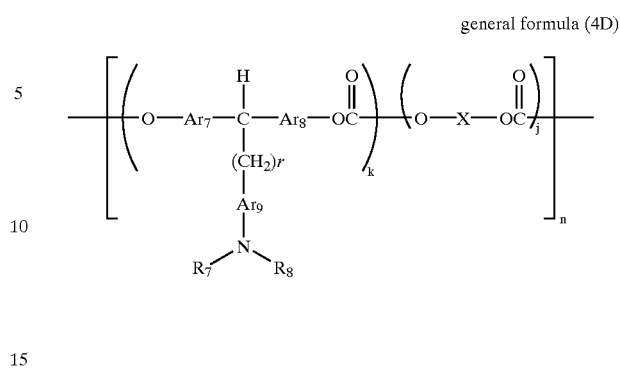

{in the formula, each of $R_7$ and $R_8$ represents a substituted or non-substituted aryl group; each of $Ar_7$, $Ar_8$, and $Ar_9$ represents the same or a different arylene group; each of k and j represents a composition and satisfies $0.1 \leq k \leq 1$ and $0 \leq j \leq 0.9$; n represents a repeating unit of 5 to 5000; r represents an integer of 1 to 5; X is one of an aliphatic divalent group, a ring type aliphatic divalent group, and a substance expressed by the general formula (A):

general formula (A)

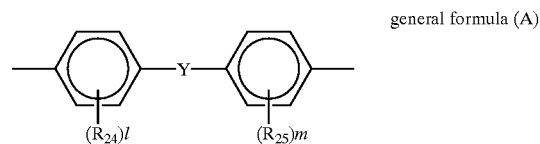

[in the formula, $R_{24}$ and $R_{25}$ may each independently represents a substituted or non-substituted alkyl group, an aryl group or a halogen atom; each of l and m represents an integer of 0 to 4; Y represents one of a single bond, a linear chain having a carbon atom number of 1 to 12, a branched or a ring type alkylene group, —O—, —S—, —SO—, —SO$_2$—, —CO—, —CO—O—Z—O—CO— (here, Z represents an aliphatic divalent group), and a divalent group expressed by a general formula (B):

general formula (B)

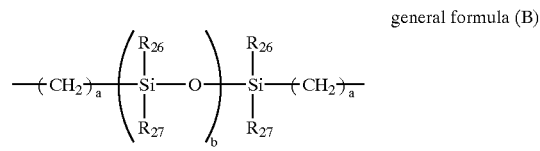

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (5D).

general formula (5D)

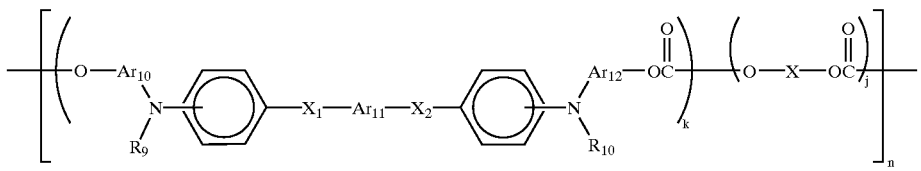

{in the formula, each of $R_9$ and $R_{10}$ represents one of a substituted and non-substituted aryl group; each of $Ar_{10}$, $Ar_{11}$, and $Ar_{12}$ represents the same or a different arylene group; each of $X_1$ and $X_2$ represents one of a substituted or non-substituted ethylene group, and a substituted or non-substituted vinylene group; each of k and j represents a composition which satisfies $0.1 \leq k \leq 1$ and $0 \leq j \leq 0.9$; n represents a repeating unit numbers of 5 to 5000. X is one of an aliphatic divalent group, a ring type aliphatic divalent group, and a general formula (A):

general formula (A)

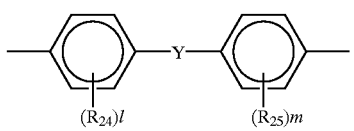

[in the formula, $R_{24}$ and $R_{25}$ may each independently represents one of a substituted or non-substituted alkyl group, an aryl group and a halogen atom; each of l and m represents an integer of 0 to 4; Y represents one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

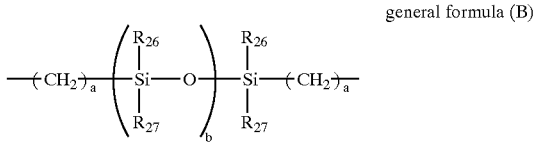

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (6D).

general formula (6D)

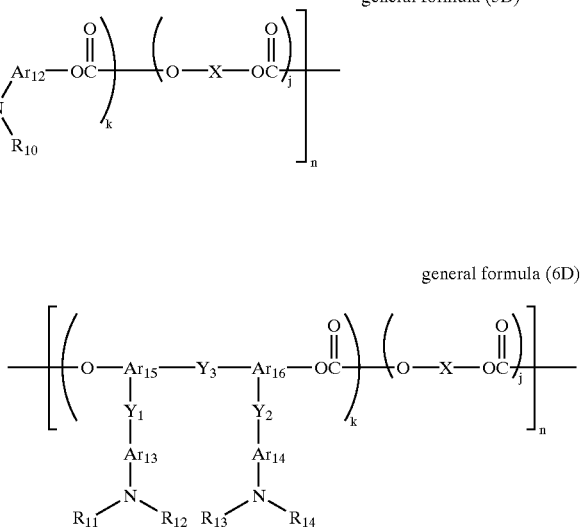

{in the formula, each of $R_{11}$, $R_{12}$, $R_{13}$ and $R_{14}$ represents one of a substituted and a non-substituted aryl group; each of $Ar_{13}$, $Ar_{14}$, $Ar_{15}$ and $Ar_{16}$ represents the same or a different arylene group; each of $Y_1$, $Y_2$, and $Y_3$ represents one of a single bond, a substituted or non-substituted alkylene group, a substituted or non-substituted cyclo alkylene group, a substituted or non-substituted alkyl ether group, oxygen atom, sulfur atom, and a vinylene group, which may be the same or maybe different. Each of k and j represents a composition which satisfies $0.1 \leq k \leq 1$ and $0 \leq j \leq 0.9$; n represents a repeating unit number of 5 to 5000; X is one of an aliphatic divalent group, a ring type aliphatic divalent group, and a general formula (A):

general formula (A)

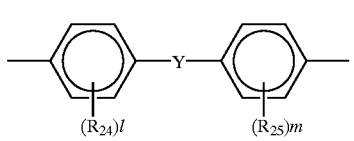

[in the formula, $R_{24}$ and $R_{25}$ may independently represents a substituted or non-substituted alkyl group, an aryl group or a halogen atom; each of l and m represents an integer of 0 to 4; Y represents a one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

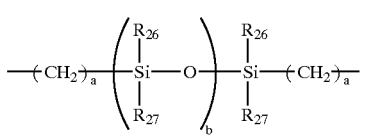

(in the formula, a represents an integer of 1 to 20, and b represents an integer of 1 to 2000. Each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (7D).

general formula (7D)

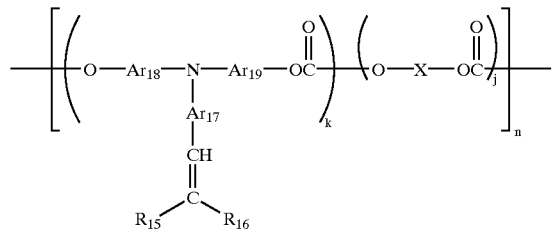

{in the formula, each of $R_{15}$ and $R_{16}$ represents a hydrogen atom, a substituted or non-substituted aryl group, and each of $R_{15}$ and $R_{16}$ may form a ring. $Ar_{17}$, $Ar_{18}$ and $Ar_{19}$ may each represents the same or a different arylene group. Each of k and j represents a composition which satisfies $0.1 \leq k \leq 1$ and $0 \leq j \leq 0.9$; n represents a repeating uint of 5 to 5000. X is one of an aliphatic divalent group, a ring type aliphatic divalent group, and a general formula (A):

general formula (A)

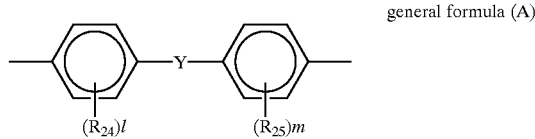

[in the formula, each of $R_{24}$ and $R_{25}$ may independently represents a substituted or non-substituted alkyl group, an aryl group, or a halogen atom; each of l and m represents an integer of 0 to 4; Y represents a one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

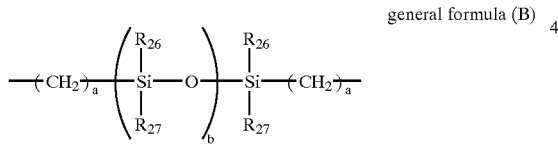

(in the formula, a represents an integer of 1 to 20, and b represents an integer of 1 to 2000. Each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (8D).

general formula (8D)

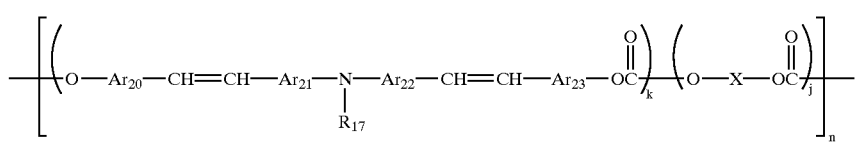

{in the formula, $R_{17}$ represents a substituted or non-substituted aryl group; each of $Ar_{20}$, $Ar_{21}$, $Ar_{22}$ and $Ar_{23}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

general formula (A)

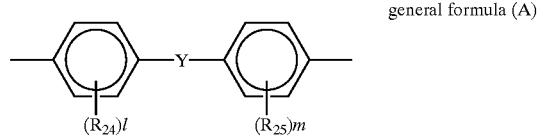

[in the formula, each of $R_{24}$ and $R_{25}$ may independently represents one of a substituted or non-substituted alkyl group, and an aryl group or a halogen atom; each of l and m represents an integer of 0 to 4; Y represents one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

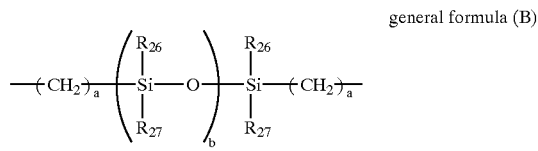

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (9D).

general formula (9D)

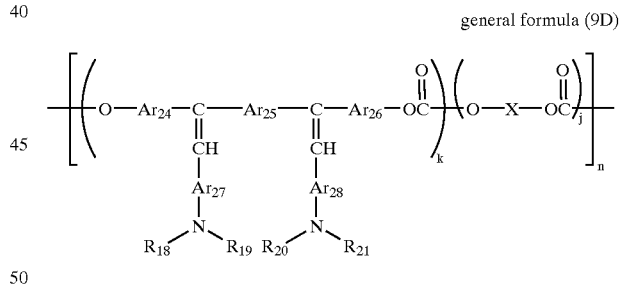

{in the formula, each of $R_{18}$, $R_{19}$, $R_{20}$ and $R_{21}$ represents a substituted or non-substituted aryl group; each of $Ar_{24}$, $Ar_{25}$, $Ar_{26}$, $Ar_{27}$, and $Ar_{28}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

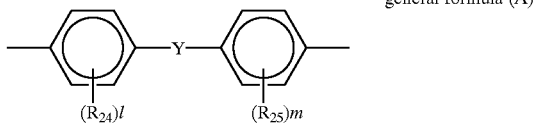

general formula (A)

[in the formula, each of $R_{24}$ and $R_{25}$ may independently represents one of a substituted or non-substituted alkyl group, and an aryl group or a halogen atom; each of l and m represents an integer of 0 to 4; Y represents a one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

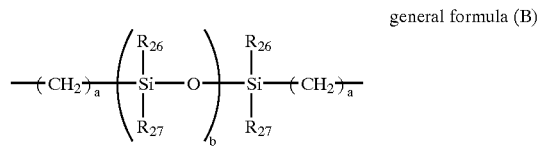

general formula (B)

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having the triaryl amine structure is a high polymer charge transporting substance expressed by a general formula (10D).

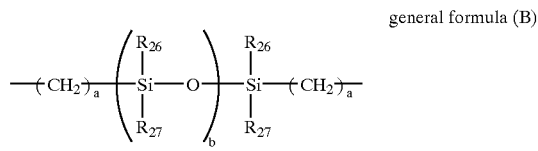

general formula (10D)

{in the formula, each of $R_{22}$, and $R_{23}$ represents a substituted or non-substituted aryl group; each of $Ar_{29}$, $Ar_{30}$, and $Ar_{31}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

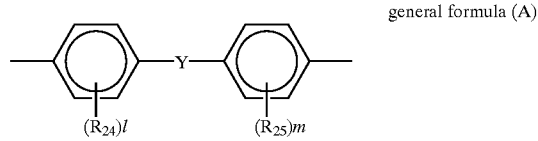

general formula (A)

[in the formula, each of $R_{24}$ and $R_{25}$ may independently represents a substituted or non-substituted alkyl group, an aryl group or a halogen atom; each of l and m represents an integer of 0 to 4; Y represents a one of a single bond, a linear chain having carbon atom numbers of 1 to 12, a branched or a ring type alkylene group, —O—, —S—, —SO—, —SO$_2$—, —CO—, —CO—O—Z—O—CO—(in the formula, Z represents an aliphatic divalent group), and a divalent group expressed by a general formula (B):

general formula (B)

$$-\text{(CH}_2\text{)}_a-\left(\begin{array}{c}R_{26}\\|\\\text{Si}\\|\\R_{27}\end{array}-O\right)_b\begin{array}{c}R_{26}\\|\\\text{Si}\\|\\R_{27}\end{array}-\text{(CH}_2\text{)}_a-$$

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which the aforementioned polycarbonate having a triaryl amine is a high polymer charge transporting substance expressed by a general formula (11D).

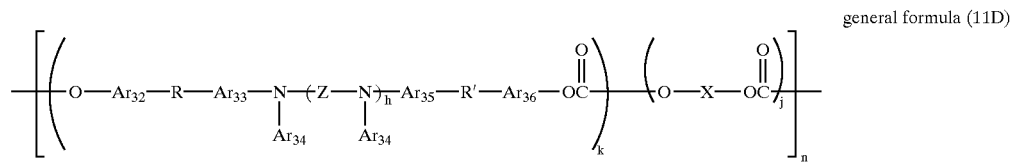

general formula (11D)

(in the formula (11D), each of $Ar_{32}$, $Ar_{33}$, $Ar_{35}$ and $Ar_{36}$ represents substituted or non-substituted arylene group; $Ar_{34}$ represents a substituted or non-substituted aryl group; Z represents arylene group or —$Ar_{37}$—Za—$Ar_{37}$—, $Ar_{37}$ represents substituted or non-substituted arylene group; Za represents O, S, or an alkylene group; each of R and R' represents a linear chain or branched alkylene group or —O—; h represents 0 or 1; each of k and j represents a composition which satisfies $0.1 \leq k \leq 1$ and $0 \leq j \leq 0.9$; n represents a repeating uint of 5 to 5000; X is one of a substituted or non-substituted aliphatic divalent group, a substituted or non-substituted ring aliphatic divalent group, a substituted or non-substituted aromatic series divalent group, a divalent group formed by bonding them, and a divalent group expressed by one of general formulae (A'), (F), and (G):

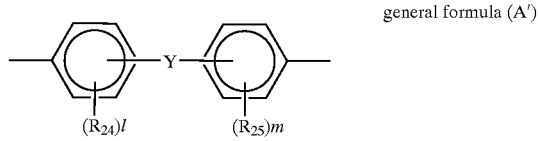

general formula (A')

-continued general formula (F)

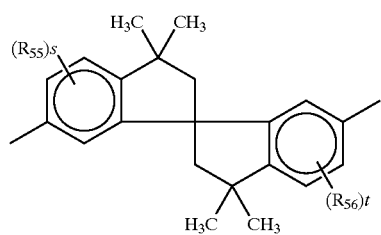

general formula (G)

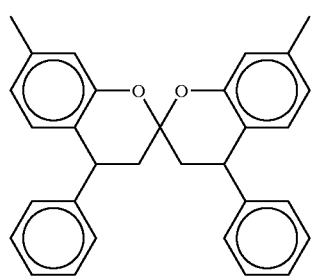

-continued general formul (K)

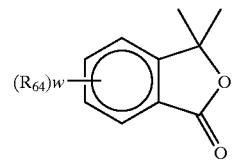

general formula (L)

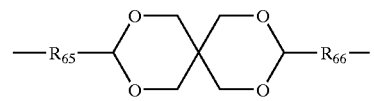

general formula (M)

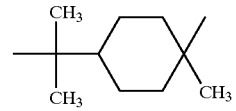

General formula (N)

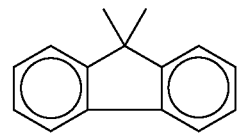

(in the formulae (A'), (F) and (G), each of $R_{24}$, $R_{25}$, $R_{55}$ and $R_{56}$ may each independently represents a substituted or non-substituted alkyl group, a substituted or non-substituted aryl group or a halogen atom; 1 and m may each independently represents an integer of 0 to 4; each of s and t independently represents an integer of 0 to 3; when $R_{24}$, $R_{25}$, $R_{55}$ and $R_{56}$ respectively has a plurality of elements, they may be the same or may be different.), Y represents one of a single bond, a linear chain having a carbon atom number of 1 to 12, a branched or a ring type alkylene group, a divalent group formed of at least one alkylene group having a carbon atom number of 1 to 10 and at least one oxygen atom and sulfur atom, —O—, —S—, —SO—, $SO_2$—, —CO—, —COO—, —CO—O—$Z_1$—O—CO—, —CO—$Z_2$—CO—(in the formula, each of $Z_1$ and $Z_2$ is a substituted or non-substituted aliphatic divalent group, or substituted or non-substituted arylene group), and one of general formulae (B), and general formulae (H) to (N).

general formula (B)

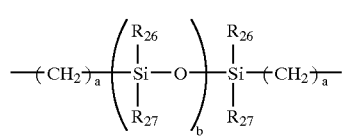

general formula (H)

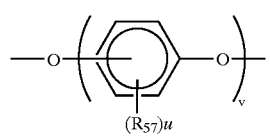

general formula (I)

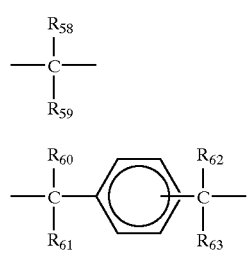

general formula (J)

[in the formulae (B), (H) to (N), each of $R_{26}$ and $R_{27}$ independently represents one of a substituted or non-substituted alkyl group, and a substituted or non-substituted aryl group; each of $R_{57}$, $R_{58}$ and $R_{64}$ represents a halogen atom, a substituted or non-substituted alkyl group, a substituted or non-substituted alkoxy group, a substituted or non-substituted aryl group; each of $R_{59}$, $R_{60}$, $R_{61}$, $R_{62}$ and $R_{63}$ independently represents one of a hydrogen atom or halogen atom, a substituted or non-substituted alkyl group, a substituted or non-substituted alkoxy group, and a substituted or non-substituted aryl group; $R_{58}$ and $R_{59}$ may be combined and form a carbon ring having a carbon numbers of 5 to 12; each of $R_{65}$ and $R_{66}$ represents an edge bond or an alkylene group having a carbon number of 1 to 4; a represents an integer of 1 to 20; b represents an integer of 1 to 2000; each of u and w is an integer of 0 to 4; and v represents 1 or 2; When each of the $R_{26}$, $R_{27}$, $R_{57}$ and $R_{64}$ has a plurality of elements, they may be the same or may be different.]]

The present invention also provides a mode in which the aforementioned photoconductive layer further contains an acceptor compound.

The present invention also provides a mode in which the aforementioned acceptor compound is a 2,3-diphenyl indene compound expressed by a general formula <<18>>.

general formula <<18>>

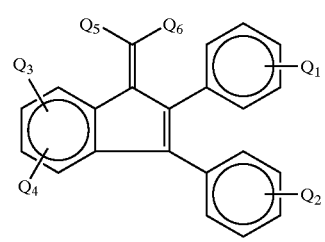

(in the formula <<18>>, each of $Q_1$, $Q_2$, $Q_3$ and $Q_4$ is a one of a hydrogen atom, a halogen atom, a substituted or non-substituted alkyl group, a cyano group, and a nitro group; each of $Q_5$ and $Q_6$ is one of a hydrogen atom, substituted or non-substituted aryl group, a cyano group, an alkoxy carbonyl group, and an aryl oxy carbonyl group.)

The present invention also provides a mode in which the aforementioned photoconductive layer further contains a phenol compound.

The present invention also provides a mode in which the aforementioned phenol compound is a phenol compound expressed by a general formula <<19>>.

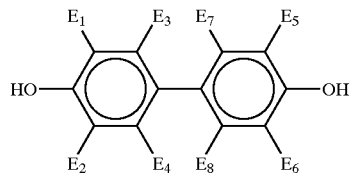

general formula <<19>>

(in general formula <<19>>, each of $E_1$ to $E_4$ is one of a hydrogen atom, a substituted or non-substituted alkyl group, a substituted or non-substituted alkoxy carbonyl group, substituted or non-substituted aryl group, and a substituted or non-substituted alkoxy group.)

Further, in the second aspect of the present invention, there is provided an electrophotographic photoconductor comprising: a conductive support; and a photoconductive layer disposed on the photoconductive support; wherein the photoconductive layer contains an azo compound expressed by a general formula <<101>>.

$$Ar(N=N-Cp)_n$$ general formula <<101>>

(in the general formula <<101>>, Ar is a substituted or non-substituted aromatic series hydrocarbon group or an aromatic series heterocyclic ring group which can be bonded by way of a bonding group. Cp is a coupler residual group, n represents an integer of 1, 2, 3, or 4. At least one of the Cp is a coupler residual group selected from one of general formulae <<102>>, <<103>>, and <<104>>.)

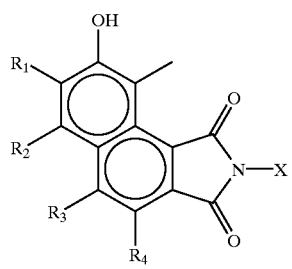

General formula <<102>>

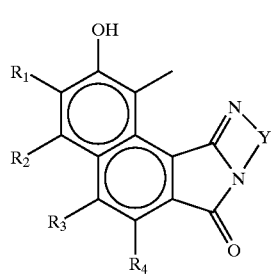

General formula <<103>>

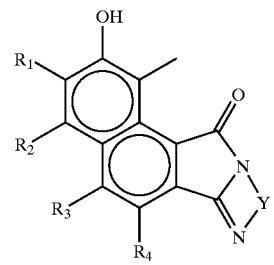

General formula <<104>>

(in the general formula <<102>>, <<103>>, and <<104>>, each of $R_1$, $R_2$, $R_3$ and $R_4$ expresses one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and carbonyl group containing a divalent organic residual group expressed by —CO—Z— (Here, Z represents a substituted or non-substituted alkylene group, a substituted or non-substituted aromatic series divalent organic residual group, a substituted or non-substituted heterocyclic ring aromatic series divalent organic residual group). Here, each of the alkyl groups $R_1$ and $R_2$ may form a ring with each other.)

The present invention also provides a mode in which the aforementioned electrophotographic photoconductor in the second aspect has the coupler residual group expressed by the general formula <<102>> of an azo compound is a coupler residual group expressed by a general formula <<105>>.

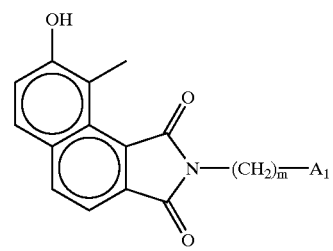

general formula <<105>>

(in general formula <<105>>, $A_1$ is a substituted or non-substituted aromatic series hydrocarbon group, or a substituted or non-substituted heterocyclic ring group, and m expresses an integer of 1 to 6.)

The present invention also provides a mode in which the aforementioned coupler residual group expressed by one of the general formulae <<103>> and <<104>> of an azo compound in the second aspect is a coupler residual group expressed by one of a general formula <<131>> and a general formula <<132>>.

general formula <<131>>

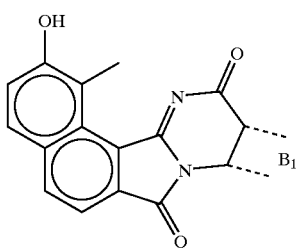

general formula <<132>>

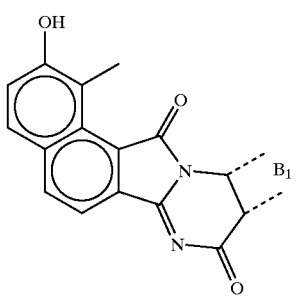

(in the general formulae <<131>> and <<132>>, B₁ represents one of a substituted or non-substituted aromatic series hydrocarbon ring divalent group, and a substituted or non-substituted aromatic series heterocyclic ring divalent group.)

The present invention also provides a mode in which the aforementioned coupler residual group expressed by one of the general formulae <<103>> and <<104>> of an azo compound in the second aspect is a coupler residual group expressed by one of general formulae <<133>> and <<134>>.

general formula <<133>>

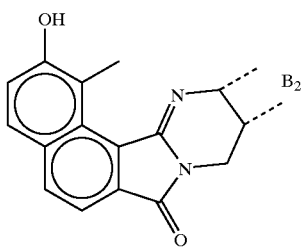

general formula <<134>>

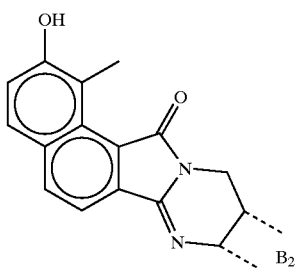

(in the general formulae <<133>> and <<134>>, B₂ represents one of a substituted or non-substituted aromatic series hydrocarbon ring divalent group, and a substituted or non-substituted aromatic series heterocyclic ring divalent group.)

The present invention also provides a mode in which in the aforementioned electrophotographic photoconductor of the second aspect, at least one of the Cp is a coupler residual group expressed by the general formula <<6>> when n of the azo compound expressed by the general formula <<101>> is 2, 3, and 4.

general formula <<6>>

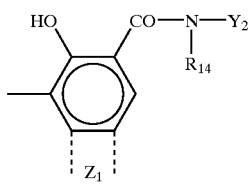

(in general formula <<6>>, $Z_1$ represents a hydrocarbon ring or substituent thereof, or a heterocyclic ring group or substituent thereof; $R_{14}$ represents one of hydrogen, an alkyl group or substituent thereof, and a phenyl group or substituent thereof; $Y_2$ represents a hydrocarbon ring group or substituent thereof, or a heterocyclic ring group or substituent thereof.

The present invention also provides a mode in which in the aforementioned electrophotographic photoconductor of the second aspect, at least one of the Cp is a coupler residual group selected from one of general formulae <<7>> and <<8>>, when n of the azo compound expressed by the general formula <<101>> is 2, 3, and 4.

general formula <<7>>

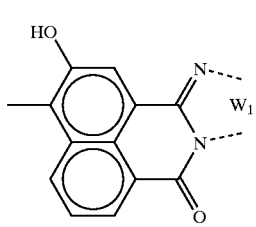

general formula <<8>>

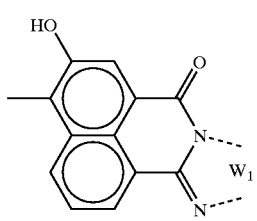

(in the general formulae <<7>> and <<8>>, $W_1$ represents an aromatic series hydrogen divalent group or a heterocyclic ring divalent group including a nitrogen atom in a ring. These rings may be substituted of non-substituted.)

The present invention also provides a mode in which in the aforementioned electrophotographic photoconductor of the second aspect, the azo compound is a disazo compound expressed by a general formula <<109>>.

general formula <<109>>

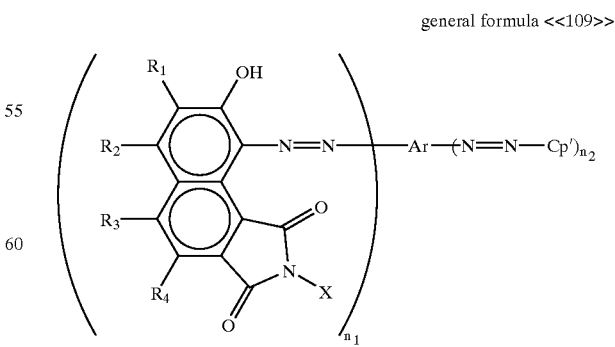

(in the general formula <<109>>, Ar represents a substituted or non-substituted aromatic series hydrocarbon group, or an aromatic series heterocyclic ring group which may be combined by way of a bonding group; Cp' represents a coupler residual group; each of $R_1$, $R_2$, $R_3$, and $R_4$ represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2; and $n_2$ expresses an integer of 0 or 1. Here, each of the alkyl groups $R_1$ and $R_2$ may form a ring.)

The present invention also provides a mode in which in the aforementioned electrophotographic photoconductor of the second aspect, the disazo compound is a disazo compound expressed by a general formula <<110>>.

general formula <<110>>

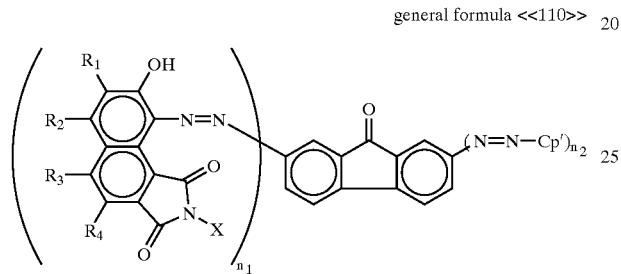

(in the general formula <<110>>, Cp' represents a coupler residual group; each of $R_1$, $R_2$, $R_3$, and $R_4$ represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2; $n_2$ expresses an integer of 0 or 1. Here, each of the alkyl groups $R_1$ and $R_2$ may form a ring.)

The present invention also provides a mode in which in the aforementioned electrophotographic photoconductor of the second aspect, the disazo compound is a disazo compound expressed by a general formula <<135>>.

general formula <<135>>

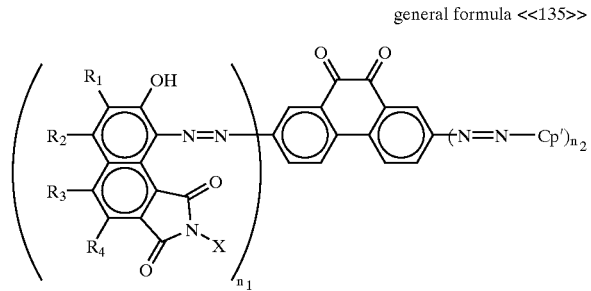

(in the general formula <<135>>, Cp' represents a coupler residual group; each of $R_1$, $R_2$, $R_3$, and $R_4$ represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2; $n_2$ expresses an integer of 0 or 1. Here, each of the alkyl groups $R_1$ and $R_2$ may form a ring.)

The present invention also provides a mode in which in the aforementioned electrophotographic photoconductor of the second aspect, the azo compound is a disazo compound expressed by one of general formulae <<111>> and <<112>>.

general formula <<111>>

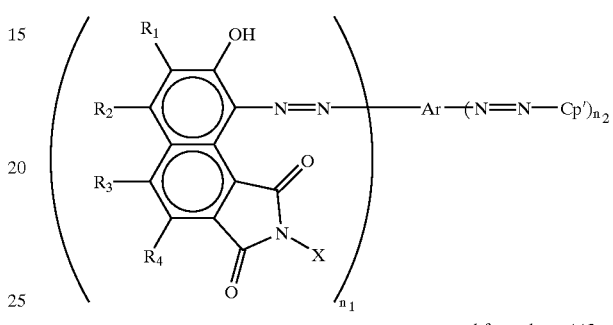

general formula <<112>>

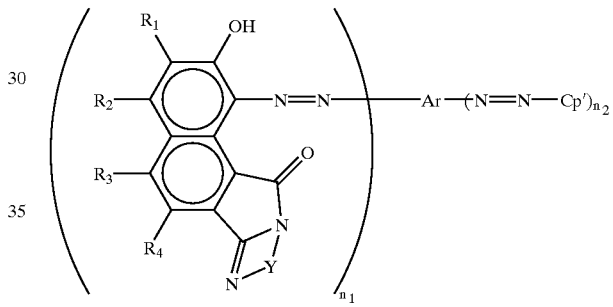

(in the general formulae <<111>> and <<112>>, Ar represents a substituted or non-substituted aromatic series hydrocarbon group or an aromatic series heterocyclic ring group which may be combined by way of a bonding group; Cp' represents a coupler residual group; each of $R_1$, $R_2$, $R_3$, and $R_4$ represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, (here, Z represents one of a substituted or non-substituted alkylene group, a substituted or non-substituted aromatic series divalent organic residual group, and substituted or non-substituted heterocyclic ring aromatic series divalent organic residual group) when $n_1$ expresses an integer of 1 or 2; and $n_2$ expresses an integer of 0 or 1. Here, each of the alkyl groups $R_1$ and $R_2$ may form a ring.) The present invention also provides a mode in which in the aforementioned electrophotographic photoconductor of the second aspect, the disazo compound is a disazo compound expressed by one of general formulae <<113>> and <<134>>.

general formula <<113>>

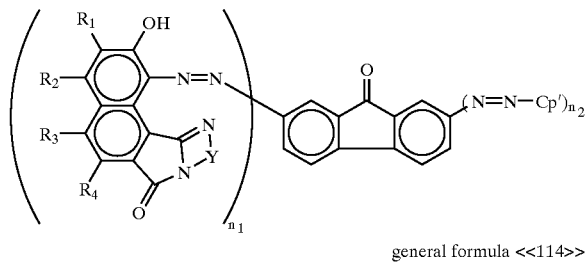

general formula <<114>>

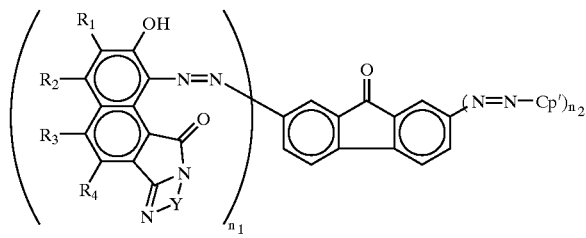

(in the general formulae <<113>> and <<114>>, Ar represents a substituted or non-substituted aromatic series hydrocarbon group or an aromatic series heterocyclic ring group which may be combined by way of a bonding group; Cp' represents a coupler residual group; each of $R_1$, $R_2$, $R_3$, and $R_4$ represents one of a hydrogen atom, an alkyl group, an alkoxy group, a halogen atom, an amino group, a hydroxy group, a nitro group, and a cyano group; Y represents a one of substituted or non-substituted alkylene group, a substituted or non-substituted aromatic series divalent organic residual group, a substituted or non-substituted heterocyclic ring aromatic series divalent organic residual group, and carbonyl group containing divalent organic residual group expressed by —CO—Z—, (here, Z represents one of a substituted or non-substituted alkylene group, a substituted or non-substituted aromatic series divalent organic residual group, and a substituted or non-substituted heterocyclic ring aromatic series divalent organic residual group); $n_1$ expresses an integer of 1 or 2; $n_2$ expresses an integer of 0 or 1. Here, each of the alkyl groups $R_1$ and $R_2$ may form a ring.)

The present invention also provides a mode in which in the aforementioned electrophotographic photoconductor of the second aspect, the disazo compound is a disazo compound expressed by one of a general formula <<136>> and a general formula <<137>>.

general formula <<136>>

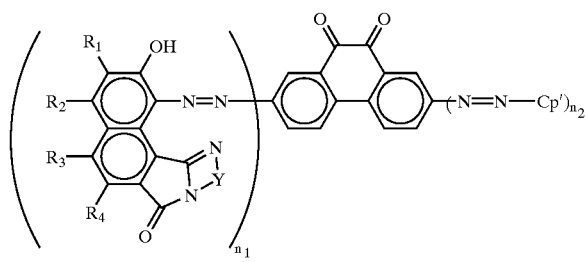

general formula <<137>>

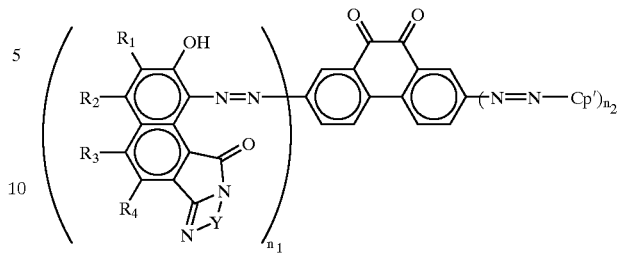

(in the general formula <<136>> and general formula <<137>>, Ar represents a substituted or non-substituted aromatic series hydrocarbon group or an aromatic series heterocyclic ring group which may be combined by way of a bonding group; Cp' represents a coupler residual group; each of $R_1$, $R_2$, $R_3$, and $R_4$ represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and carbonyl group containing divalent organic residual group expresses by —CO—Z— (here, Z represents a substituted or non-substituted alkylene group, a substituted or non-substituted aromatic series divalent organic residual group, or substituted or non-substituted heterocyclic ring aromatic series divalent organic residual group); where $n_1$ expresses an integer of 1 or 2; and $n_2$ expresses an integer of 0 or 1. Here, each of the alkyl groups $R_1$ and $R_2$ may form a ring.)

The present invention also provides a mode in which in the aforementioned electrophotographic photoconductor of the second aspect, the azo compound of the general formula <<101>> is an azo compound which is obtained by reacting a diazonium salts compound expressed by a general formula <<15>> and a coupler compound expressed by a general formula <<16>>.

$Ar\text{-}(N_2^{\oplus}Z^{\ominus})_n$         general formula <<15>>

$H\text{—}Cp$         general formula <<16>>

(In the general formula <<15>> and general formula <<16>>, Ar represents a substituted or non-substituted aromatic series hydrocarbon group or an aromatic series heterocyclic ring group which may be combined by way of a bonding group; Cp represents a coupler residual group; Z— represents an anion function; and n expresses an integer of any one of 1, 2, 3 or 4.)

The present invention also provides a mode in which in the aforementioned electrophotographic photoconductor of the second aspect, the photoconductive layer is a single layer formed on a conductive support by one of directly and intervening an intermediate layer.

The present invention also provides a mode in which in the aforementioned electrophotographic photoconductor of the second aspect, the photoconductive layer further contains a charge transporting substance.

The present invention also provides a mode in which in the aforementioned electrophotographic photoconductor of the second aspect, the charge transporting substance is a stilbene compound expressed by a general formula <<17>>.

general formula <<17>>

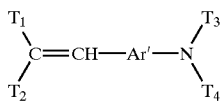

(in the general formula <<17>>, $T_1$ and $T_2$ may each independently represents a substituted or non-substituted alkyl group or a substituted or non-substituted aryl group; $T_3$ and $T_4$ may each independently represents one of a hydrogen atom, a substituted or non-substituted alkyl group, a substituted or non-substituted aryl group, and a heterocyclic ring group. $T_1$ and $T_2$ may form a ring with each other. Ar' expresses a substituted or non-substituted aryl group or a heterocyclic ring group.)

The present invention also provides a mode in which in the aforementioned electrophotographic photoconductor of the second aspect, the charge transporting substance is a high polymer charge transporting substance.

The present invention also provides a mode in which in the aforementioned electrophotographic photoconductor of the second aspect, the high polymer charge transporting substance is a polymer of at least one of polycarbonate, polyurethane, polyester, and polyether.

The present invention also provides a mode in which in the aforementioned electrophotographic photoconductor of the second aspect, the high polymer charge transporting substance is a high polymer compound having a structure of triaryl amine.

The present invention also provides a mode in which in the aforementioned electrophotographic photoconductor of the second aspect, the high polymer charge transporting substance is a polycarbonate having a triaryl amine structure.

The present invention also provides a mode in which in the aforementioned electrophotographic photoconductor of the second aspect, the polycarbonate having the triaryl amine structure is a high polymer charge transporting substance expressed by a general formula (1D).

general formula (1D)

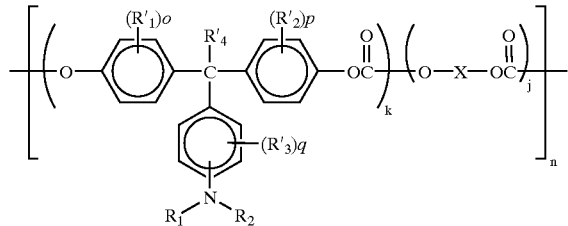

(in the formula, $R'_1$, $R'_2$, and $R'_3$ may each independently expresses a substituted or non-substituted alkyl group or a halogen atom; $R'_4$ represents a hydrogen atom or a substituted or non-substituted alkyl group. $R_1$ and $R_2$ may each represents a substituted or non-substituted aryl group. The o, p, and q may each independently represents an integer of 0 to 4. k and j each represents a composition, and satisfies $1 \leq k \leq 1$ and $0 \leq j \leq 0.9$; and n represents a repeating unit of 5 to 5000; X is one of an aliphatic divalent group, a ring type aliphatic divalent group, and a general formula (A):

general formula (A)

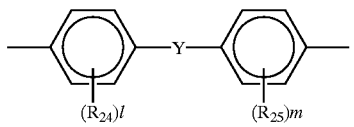

(in the formula, $R_{24}$ and $R_{25}$ may each independently represents a substituted or non-substituted alkyl group, an aryl group or a halogen atom, and 1 and m each represents an integer of 0 to 4. Y represents one of a single bond, a linear chain having a carbon atom number of 1 to 12, a branched or a ring type alkylene group, —O—, —S—, —SO—, —SO$_2$—, —CO—, —CO—O—Z—O—CO— (in the formula, Z represents an aliphatic divalent group), and a group expressed by a general formula (B):

general formula (B)

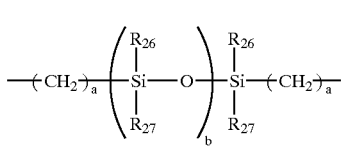

(in the formula, a represents an integer of 1 to 20, and b represents an integer of 1 to 2000. Each of $R_{26}$ and $R_{27}$ represents substituted or non-substituted alkyl group or aryl group.) $R_{24}$, $R_{25}$, $R_{26}$, and $R_{27}$ may be the same or may be different.])

The present invention also provides a mode in which in the aforementioned electrophotographic photoconductor of the second aspect, the polycarbonate having the triaryl amine structure is a high polymer charge transporting substance expressed by a general formula (2D).

general formula (2D)

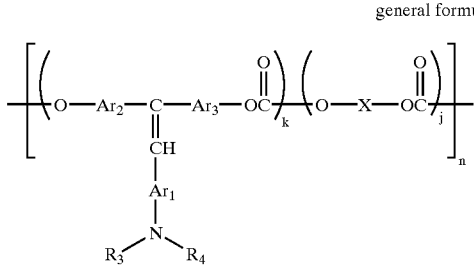

{in the formula, $R_3$ and $R_4$ may represents a substituted or non-substituted aryl group, $Ar_1$, $Ar_2$, and $Ar_3$ may each represents the same or different arylene group. Each of k and j represents a composition, and satisfies $0.1 \leq k \leq 1$ and $0 \leq j \leq 0.9$; n represents a repeating unit of 5 to 5000: X is one of an aliphatic divalent group, a ring type aliphatic divalent group, and a general formula (A):

general formula (A)

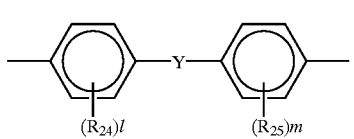

(in the formula, $R_{24}$ and $R_{25}$ may each independently represents one of a substituted or non-substituted alkyl group, an aryl group, and a halogen atom; each of l and m represents an integer of 0 to 4; Y represents one of a single bond, a linear chain having a carbon atom number 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

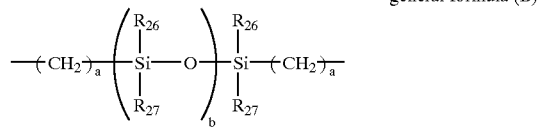

(in the formula, a represents an integer of 1 to 20; and b represents an integer of 1 to 2000. $R_{26}$ and $R_{27}$ may each represents substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (3D).

general formula (3D)

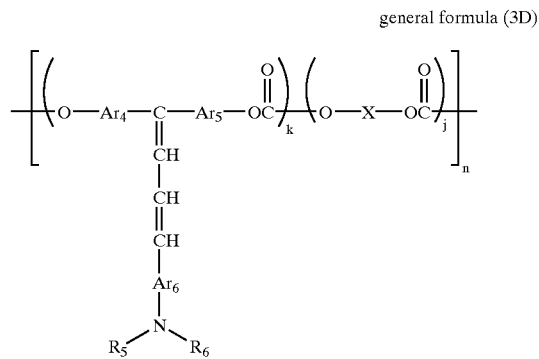

{in the formula, $R_5$ and $R_6$ may each represents a substituted or non-substituted aryl group; $Ar_4$, $Ar_5$, and $Ar_6$ may each represents a same or different arylene group; k and j each represents a composition and satisfies $0.1 \leq k \leq 1$ and $0 \leq j \leq 0.9$; n represents a repeating unit of 5 to 5000; X is one of an aliphatic divalent group, a ring type aliphatic divalent group, and a general formula (A):

general formula (A)

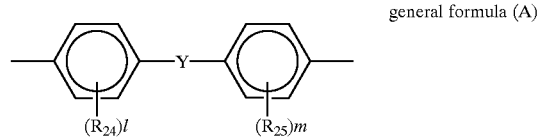

[in the formula, $R_{24}$ and $R_{25}$ may each independently represents a substituted or non-substituted alkyl group, an aryl group or a halogen atom; each of l and m represents an integer of 0 to 4; Y represents one of a single bond, a linear chain having a carbon atom number 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

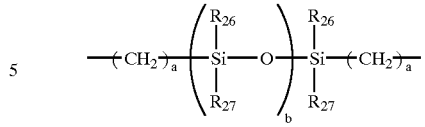

(in the formula, a represents an integer of 1 to 20; and b represents an integer of 1 to 2000. $R_{26}$ and $R_{27}$ may each represents a substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, polycarbonate having the triaryl amine structure is a high polymer charge transporting substance expressed by a general formula (4D).

General formula (4D)

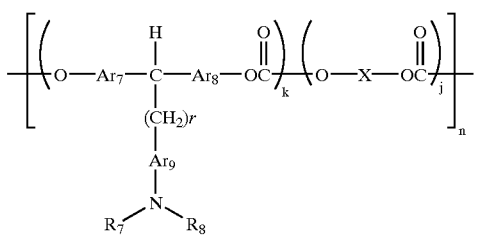

{in the formula, each of $R_7$ and $R_8$ represents a substituted or non-substituted aryl group; each of $Ar_7$, $Ar_8$, and $Ar_9$ represents the same or a different arylene group; each of k and j represents a, composition and satisfies $0.1 \leq k \leq 1$ and $0 \leq j \leq 0.9$; n represents a repeating unit of 5 to 5000; r represents an integer of 1 to 5; X is one of an aliphatic divalent group, a ring type aliphatic divalent group, and a substance expressed by the general formula (A):

general formula (A)

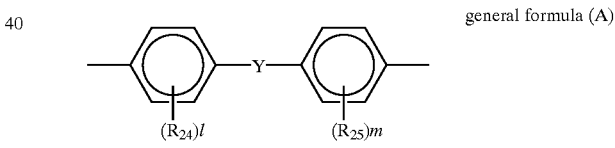

[in the formula, $R_{24}$ and $R_{25}$ may each independently represents a substituted or non-substituted alkyl group, an aryl group or a halogen atom; each of l and m represents an integer of 0 to 4; Y represents one of a single bond, a linear chain having a carbon atom number of 1 to 12, a branched or a ring type alkylene group, —O—, —S—, —SO—, —SO$_2$—, —CO—, —CO—O—Z—O—CO—(here, Z represents an aliphatic divalent group), and a divalent group expressed by a general formula (B):

general formula (B)

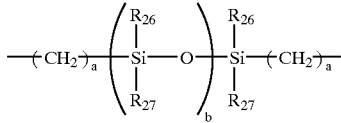

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (5D).

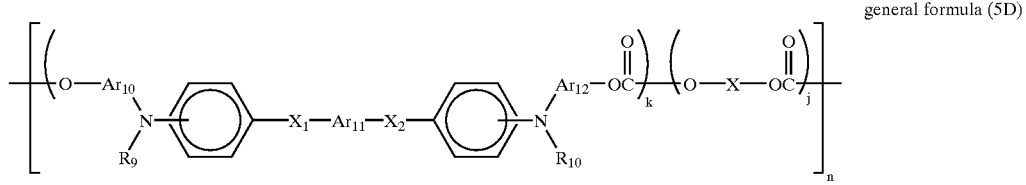

general formula (5D)

{in the formula, each of $R_9$ and $R_{10}$ represents a substituted or non-substituted aryl group; each of $Ar_{10}$, $Ar_{11}$, and $Ar_{12}$ represents the same or a different arylene group; each of $X_1$ and $X_2$ represents a substituted or non-substituted ethylene group or substituted or non-substituted vinylene group; each of k and j represents a composition which satisfies $0.1 \leq k \leq 1$ and $0 \leq j \leq 0.9$; n represents a repeating unit numbers of 5 to 5000; X is one of an aliphatic divalent group, a ring type aliphatic divalent group, and a general formula (A):

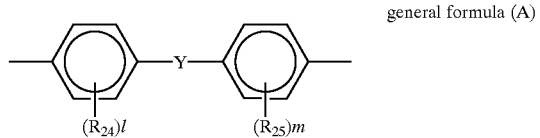

general formula (A)

[in the formula, each of $R_{24}$ and $R_{25}$ may independently represents one of a substituted or non-substituted alkyl group, and an aryl group or a halogen atom; each of l and m represents an integer of 0 to 4; Y represents one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

$$-(-CH_2-)_a \left( \begin{array}{c} R_{26} \\ | \\ Si-O \\ | \\ R_{27} \end{array} \right) \left[ \begin{array}{c} R_{26} \\ | \\ Si-(-CH_2-)_a \\ | \\ R_{27} \end{array} \right]_b$$

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (6D).

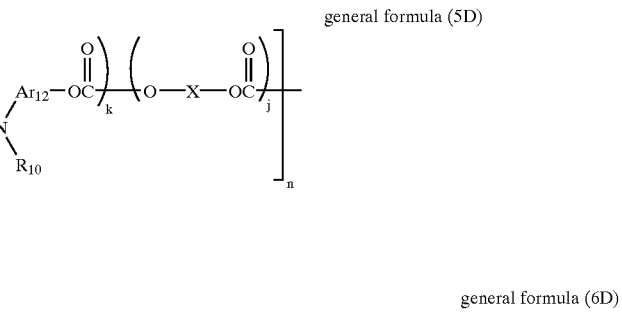

general formula (6D)

{in the formula, each of $R_{11}$, $R_{12}$, $R_{13}$ and $R_{14}$ represents a substituted or non-substituted aryl group; each of $Ar_{13}$, $Ar_{14}$, $Ar_{15}$ and $Ar_{16}$ represents the same or a different arylene group; each of $Y_1$, $Y_2$, and $Y_3$ represents one of a single bond, a substituted or non-substituted alkylene group, a substituted or non-substituted cyclo alkylene group, a substituted or non-substituted alkyl ether group, oxygen atom, sulfur atom, and a vinylene group, which may be the same or maybe different; each of k and j represents a composition which satisfies $0.1 \leq k \leq 1$ and $0 \leq j \leq 0.9$; n represents a repeating unit number of 5 to 5000; X is one of an aliphatic divalent group, a ring type aliphatic divalent group, and a general formula (A):

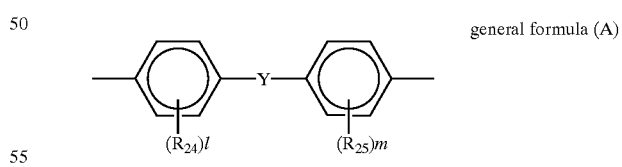

general formula (A)

[in the formula, $R_{24}$ and $R_{25}$ may independently represents a substituted or non-substituted alkyl group, an aryl group or a halogen atom; each of l and m represents an integer of 0 to 4; Y represents one of a single bond, a linear chain having carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

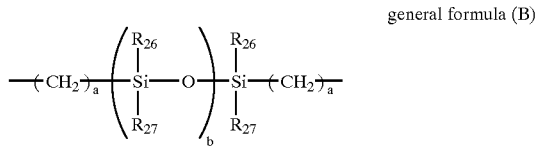

general formula (B)

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (7D).

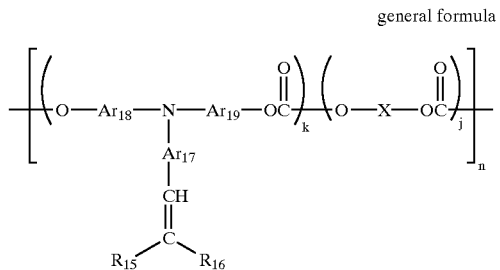

general formula (7D)

{in the formula, each of $R_{15}$ and $R_{16}$ represents one of a hydrogen atom, and a substituted or non-substituted aryl group; each of $R_{15}$ and $R_{16}$ may form a ring; $Ar_7$, $Ar_{18}$ and $Ar_{19}$ may each represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

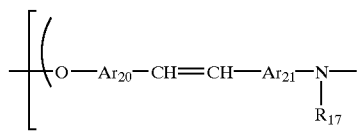

general formula (A)

[in the formula, each of $R_{24}$ and $R_{25}$ may independently represents a substituted or non-substituted alkyl group, an aryl group or a halogen atom; each of l and m represents an integer of 0 to 4; Y represents one of a single bond, a linear chain having a carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

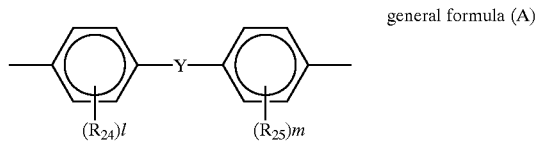

general formula (B)

(in the formula, a represents an integer of 1 to 20; b represents an integer of 1 to 2000; each of $R_{26}$ and $R_{27}$ represents substituted or non-substituted alkyl group or aryl group.) $R_{24}$, $R_{25}$, $R_{26}$, and $R_{27}$ may be the same or may be different.]}

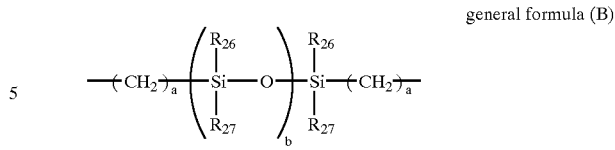

general formula (B)

(in the formula, a represents an integer of 1 to 20; b represents an integer of 1 to 2000: each of $R_{26}$ and $R_{27}$ represents substituted or non-substituted alkyl group or aryl group.) $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (8D).

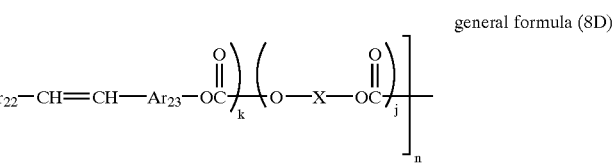

general formula (8D)

{in the formula, $R_{17}$ represents a substituted or non-substituted aryl group; each of $Ar_{20}$, $Ar_{21}$, $Ar_{22}$ and $Ar_{23}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

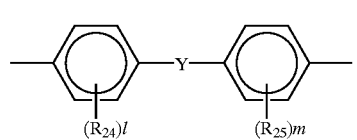

general formula (A)

[in the formula, each of $R_{24}$ and $R_{25}$ may independently represents a substituted or non-substituted alkyl group, an aryl group or a halogen atom; each of l and m represents an integer of 0 to 4; Y represents one of a single bond, a linear chain having a carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

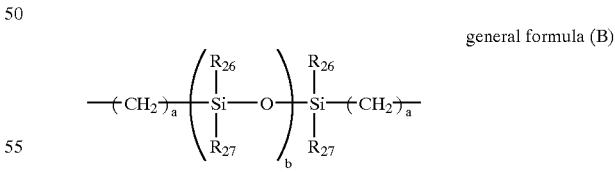

general formula (B)

(in the formula, a represents an integer of 1 to 20; b represents an integer of 1 to 2000; each of $R_{26}$ and $R_{27}$ represents substituted or non-substituted alkyl group or aryl group); $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (9D).

general formula (9D)

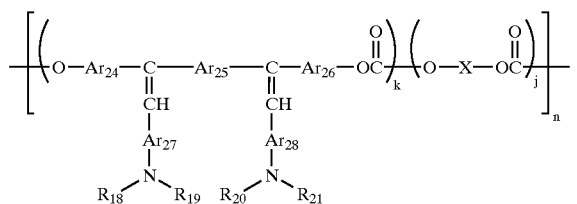

{in the formula, each of $R_{18}$, $R_{19}$, $R_{20}$ and $R_{21}$ represents a substituted or non-substituted aryl group; each of $Ar_{24}$, $Ar_{25}$, $Ar_{26}$, $Ar_{27}$, and $Ar_{28}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

general formula (A)

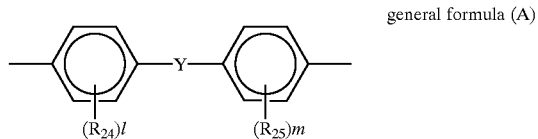

[in the formula, each of $R_{24}$ and $R_{25}$ may independently represents a substituted or non-substituted alkyl group, an aryl group or a halogen atom; each of l and m represents an integer of 0 to 4; Y represents one of a single bond, a linear chain having a carbon atom numbers of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

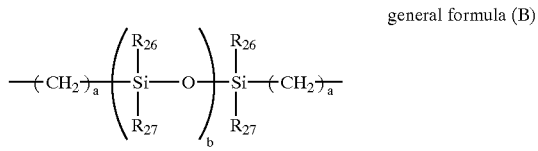

(in the formula, a represents an integer of 1 to 20; b represents an integer of 1 to 2000; each of $R_{26}$ and $R_{27}$ represents substituted or non-substituted alkyl group or aryl group); $R_{24}$, $R_{25}$, $R_{26}$, and $R_{27}$ may be the same or may be different.]}

The present invention also provides a mode in which in the aforementioned electrophotographic photoconductor of the second aspect, the polycarbonate having the triaryl amine structure is a high polymer charge transporting substance expressed by a general formula (10D).

general formula (10D)

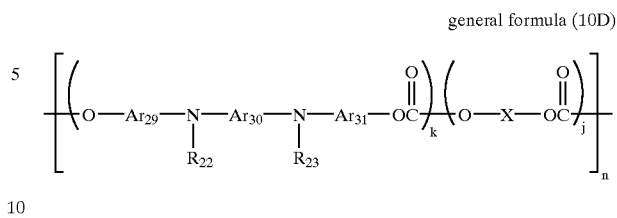

{in the formula, each of $R_{22}$, and $R_{23}$ represents a substituted or non-substituted aryl group, each of $Ar_{29}$, $Ar_{30}$, and $Ar_{31}$ represents the same or a different arylene group; each of k and j represents a composition which satisfies $0.1 \leq k \leq 1$ and $0 \leq j \leq 0.9$; n represents a repeating uint of 5 to 5000; X is one of an aliphatic divalent group, a ring type aliphatic divalent group, and a general formula (A):

general formula (A)

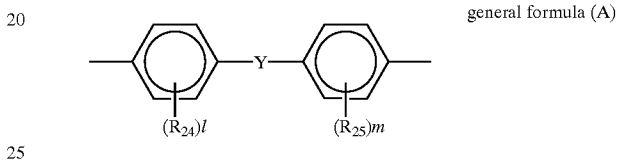

[in the formula, each of $R_{24}$ and $R_{25}$ may independently represents a substituted or non-substituted alkyl group, an aryl group or a halogen atom; each of l and m represents an integer of 0 to 4; Y represents one of a single bond, a linear chain having a carbon atom number of 1 to 12, a branched or a ring type alkylene group, —O—, —S—, —SO—, —SO$_2$—, —CO—, —CO—O—Z—O—CO— (in the formula, Z represents an aliphatic divalent group), and a divalent group expressed by a general formula (B):

general formula (B)

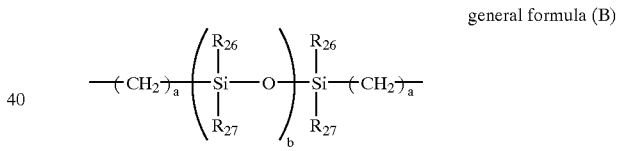

(in the formula, a represents an integer of 1 to 20; b represents an integer of 1 to 2000. Each of $R_{26}$ and $R_{27}$ represents substituted or non-substituted alkyl group or aryl group); $R_{24}$, $R_{25}$, $R_{26}$, and $R_{27}$ may be the same or may be different.]}

The present invention also provides a mode in which in the aforementioned electrophotographic photoconductor of the second aspect, a polycarbonate having a triaryl amine is a high polymer charge transporting substance expressed by a general formula (11D).

general formula (11D)

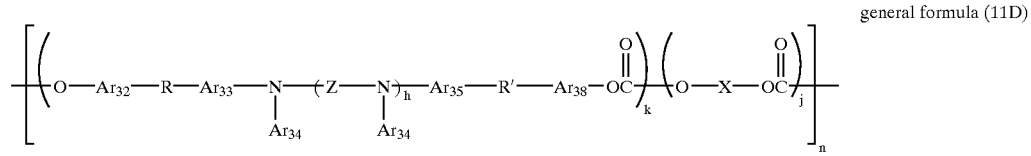

(in the formula (11D), each of $Ar_{32}$, $Ar_{33}$, $Ar_{35}$ and $Ar_{36}$ represents substituted or non-substituted arylene group; $Ar_{34}$ represents a substituted or non-substituted aryl group; Z represents arylene group or —$Ar_{37}$—Za—$Ar_{37}$—; $Ar_{37}$ represents substituted or non-substituted arylene group; Za represents O, S, or an alkylene group; each of R and R' represents a linear chain or branched alkylene group or —O—; h represents 0 or 1; each of k and j represents a composition which satisfies $0.1 \leq k \leq 1$ and $0 \leq j \leq 0.9$; n represents a repeating uint of 5 to 5000; X is one of a substituted or non-substituted aliphatic divalent group, a substituted or non-substituted ring aliphatic divalent group, a substituted or non-substituted aromatic series divalent group, a divalent group formed by bonding them, and a divalent group expressed by one of a general formula (A'), general formula (F), and general formula (G):

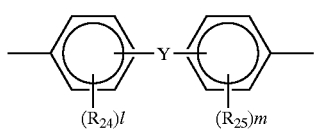
general formula (A')

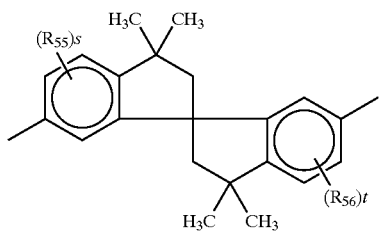
general formula (F)

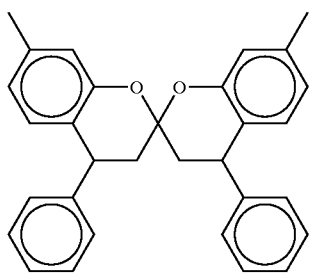
general formula (G)

(in the formulae (A'), (F) and (G), each of $R_{24}$, $R_{25}$, $R_{55}$ and $R_{56}$ may each independently represents a substituted or non-substituted alkyl group, a substituted or non-substituted aryl group or a halogen atom; l and m may each independently represents an integer of 0 to 4; each of s and t independently represents an integer of 0 to 3; When $R_{24}$, $R_{25}$, $R_{55}$ and $R_{56}$ respectively has a plurality of elements, they may be the same or may be different); Y represents one of a single bond, a linear chain having a carbon atom number of 1 to 12, a branched or a ring type alkylene group, a divalent group formed of at least one alkylene group having a carbon atom number of 1 to 10 and at least one oxygen atom and sulfur atom, —O—, —S—, —SO—, $SO_2$—, —CO—, —CO—O—, —CO—O—$Z_1$—O—CO—, —CO—$Z_2$—CO— (in the formula, each of $Z_1$ and $Z_2$ is a substituted or non-substituted aliphatic divalent group, or substituted or non-substituted arylene group), and one of a general formula (B) and general formulae (H) to (N).

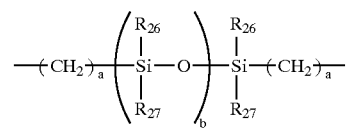
general formula (B)

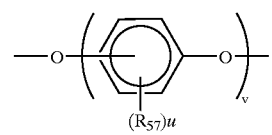
general formula (H)

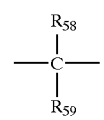
general formula (I)

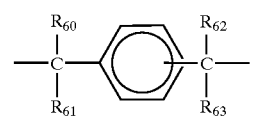
general formula (J)

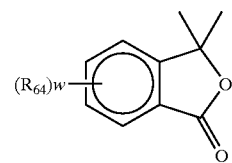
general formul (K)

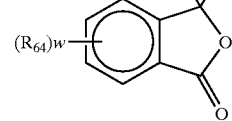
general formula (L)

general formula (M)

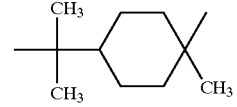
General formula (N)

[in the formulae (B), (H) to (N), each of $R_{26}$ and $R_{27}$ independently represents one of a substituted or non-substituted alkyl group, and a substituted or non-substituted aryl group; each of $R_{57}$, $R_{58}$ and $R_{64}$ represents a halogen atom, a substituted or non-substituted alkyl group, a substituted or non-substituted alkoxy group, and a substituted or non-substituted aryl group; each of $R_{59}$, $R_{60}$, $R_{61}$, $R_{62}$ and $R_{63}$ independently represents one of a hydrogen atom or halogen atom, a substituted or non-substituted alkyl group, a substituted or non-substituted alkoxy group, and a substituted or non-substituted aryl group; $R_{58}$ and $R_{59}$ can be combined and form a carbon ring having a carbon numbers of 5 to 12; each of $R_{65}$ and $R_{66}$ represents an edge bond or an alkylene group having a carbon number of 1 to 4; a represents an integer of 1 to 20; b represents an integer of 1 to 2000; each of u and w is an integer of 0 to 4; and v represents 1 or 2: when each of the $R_{26}$, $R_{27}$, $R_{57}$ and $R_{64}$ has a plurality of elements, they may be the same or may be different.]]

The present invention also provides a mode in which in the aforementioned electrophotographic photoconductor of the second aspect, the photoconductive layer further contains an acceptor compound.

The present invention also provides a mode in which in the aforementioned electrophotographic photoconductor of the second aspect, the acceptor compound is a 2,3-diphenyl indene compound expressed by a general formula <<18>>.

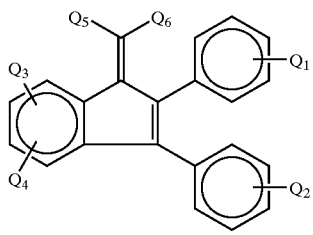

general formula <<18>>

(in the formula <<18>>, each of $Q_1$, $Q_2$, $Q_3$ and $Q_4$ is one of a hydrogen atom, a halogen atom, a substituted or non-substituted alkyl group, a cyano group, and a nitro group; each of $Q_5$ and $Q_6$ is a hydrogen atom substituted or non-substituted aryl group, a cyano group, an alkoxy carbonyl group, or aryl oxy carbonyl group.)

The present invention also provides a mode in which in the aforementioned electrophotographic photoconductor of the second aspect, the photoconductive layer further contains a phenol compound.

The present invention also provides a mode in which in the aforementioned electrophotographic photoconductor of the second aspect, the phenol compound is a phenol compound expressed by a general formula <<19>>.

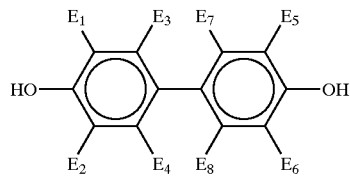

general formula <<19>>

(in general formula <<19>>, each $E_1$ to $E_4$ is one of a hydrogen atom, a substituted or non-substituted alkyl group, a substituted or non-substituted alkoxy carbonyl group, substituted or non-substituted aryl group, and a substituted or non-substituted alkoxy group.)

In the third aspect of the present invention, there is provided an electrophotographic photoconductor comprising a photoconductive layer which contains a charge generating substance and a charge transporting substance on a conductive support, wherein the charge generating substance is an azo compound expressed by a following general formula <<1>>.

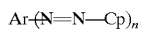

general formula <<1>>

(in the general formula <<1>>, Ar is a substituted or non-substituted aromatic series hydrocarbon group or an aromatic series heterocyclic ring group which can be bonded by way of a bonding group. Cp is a coupler residual group, n represents an integer of any one of 1, 2, 3, and 4. At least one of the Cp is a coupler residual group selected from one of a general formula <<2>>, general formula <<3>>, and general formula <<4>>.)

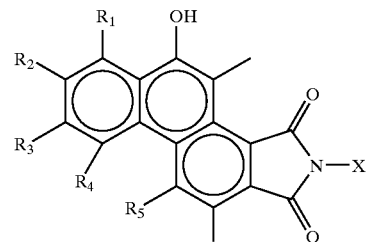

general formula <<2>>

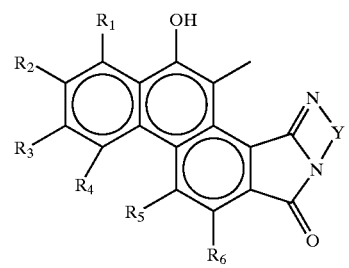

general formula <<3>>

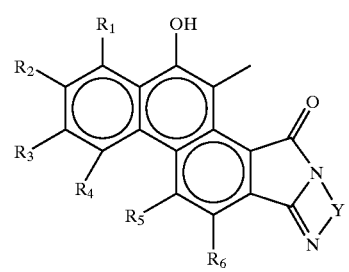

general formula <<4>>

(in the general formula <<2>>, the general formula <<3>>, and the general formula <<4>>, each of $R_1$, $R_2$, $R_3$, $R_4$, $R_5$, and $R_6$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group).)

In the fourth aspect of the present invention, there is provided an electrophotographic photoconductor comprising a photoconductive layer containing a charge generating substance and a charge transporting substance on a conductive support, wherein the charge generating substance is an azo compound expressed by a general formula <<101>>.

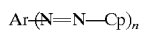

general formula <<101>>

(in general formula <<101>>, Ar is one of a substituted or non-substituted aromatic series hydrocarbon group, and an aromatic series heterocyclic ring group which can be bonded by way of a bonding group; Cp is a coupler residual group;

n represents an integer of any one of 1, 2, 3, and 4; more than one element of the Cp is a coupler residual group selected from a general formula <<102>>, general formula <<103>>, and general formula <<104>>):

general formula <<102>>

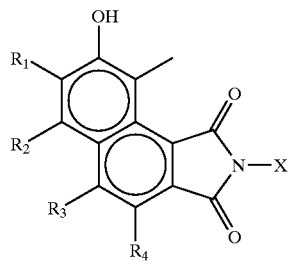

General formula <<103>>

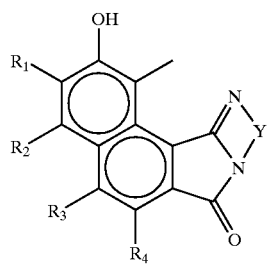

general formula <<104>>

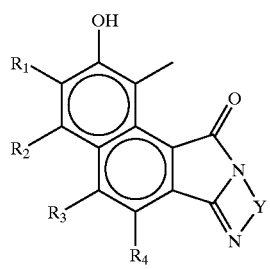

(in the general formulae <<102>>, <<103>>, and <<104>>, each of $R_1$, $R_2$, $R_3$, and $R_4$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and —CO—Z— carbonyl group containing divalent organic residual group (here, Z represents one of a substituted or non-substituted alkylene group, a substituted or non-substituted aromatic series divalent organic residual group, and a substituted or non-substituted heterocyclic ring aromatic series divalent organic residual group). Here, each of the alkyl groups $R_1$ and $R_2$ may form a ring).

In the fifth aspect of the present invention, there is provided an azo compound expressed by a general formula <<1'>>, wherein at least one of the Cp is a coupler residual group selected from following expressions <<2'>>, <<3'>> and <<4'>>.

Ar—(N=N—Cp)$_n$     general formula <<1'>>

(in the formula, Ar expresses one of a substituted or non-substituted aromatic carbon hydride group, and an heterocyclic ring aromatic group which can be combined by way of a bond group; Cp expresses a coupler residual group; n expresses an integer of any of 1, 2, 3, and 4.)

general formula <<2'>>

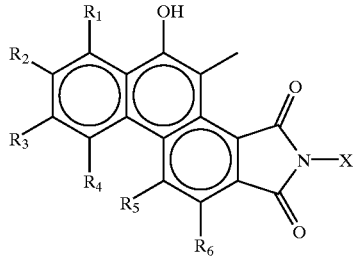

general formula <<3'>>

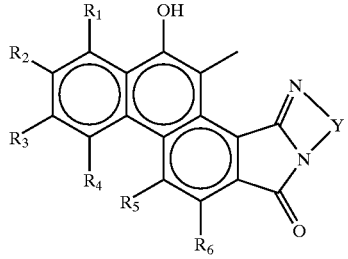

general formula <<4'>>

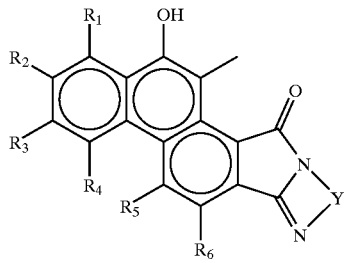

(in the formulae, each of $R_1$, $R_2$, $R_3$, $R_4$, $R_5$ and $R_6$ is one of a hydrogen atom, an alkyl group, an alkoxy group, and a halogen atom, X represents one of a hydrogen atom, a substituted or non-substituted alkyl group, a substituted or non-substituted aromatic series hydrocarbon group, and a substituted or non-substituted heterocyclic ring group; Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group (here, Z represents one of a substituted or non-substituted alkylene group, a substituted or non-substituted aromatic series divalent organic residual group, and a substituted or non-substituted heterocyclic ring aromatic series divalent organic residual group.))

The present invention also provides a mode in which in the aforementioned azo compound of the fifth aspect, at least one of the Cp is a coupler residual group expressed by a general formula <<5'>>.

general formula <<5'>>

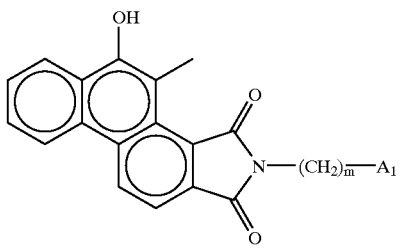

(in the general formula, $A_1$ represents one of a substituted or non-substituted aromatic series hydrocarbon group, and a substituted or non-substituted heterocyclic ring group; where m is an integer of 1 to 6.)

The present invention also provides a mode in which in the aforementioned azo compound of the fifth aspect, in the general formula <<1'>>, at least one of the Cp is a coupler residual group expressed by a general formula <<6'>> when n is one of 2,3 and 4.

general formula <<6'>>

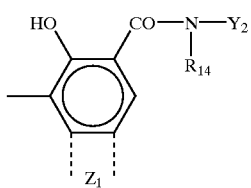

(in general formula, $Z_1$ represents one of a hydrocarbon ring or its substituent, and a heterocyclic ring group or its substituent; $R_{14}$ is one of hydrogen, an alkyl group or its substituent, and a phenyl group or its substituent; $Y_2$ represents one of a hydrocarbon ring group or its substituent, and a heterocyclic ring group or its substituent.)

The present invention also provides a mode in which in the aforementioned azo compound of the fifth aspect, in the general formula <<1'>>, at least one of the Cp is a coupler residual group selected by one of a general formulae <<7>> and <<8>>, when n is one of 2, 3, and 4.

general formula <<7>> general formula <<8>>

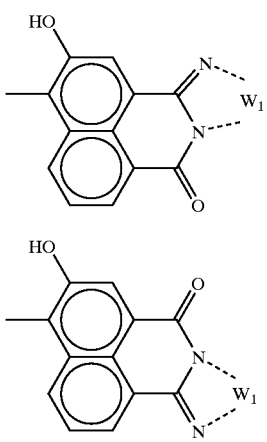

(in the general formula <<7>> and <<8>>, $W_1$ represents an aromatic series hydrogen divalent group or a heterocyclic ring divalent group including a nitrogen atom in a ring. These rings may be substituted or non-substituted.)

In the sixth aspect of the present invention, there is provided a phenanthrene compound comprising a phenanthrene compound expressed by a general formula <<20>>.

general formula <<20>>

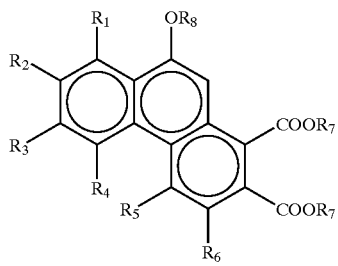

(in the formula, each of $R_1$, $R_2$, $R_3$, $R_4$, $R_5$ and $R_6$ is one of a hydrogen atom, an alkyl group, an alkoxy group, and a halogen atom; $R_7$ is a substituted or non-substituted alkyl group; $R_8$ represents one of a linear chain or a branched alkyl group, and a substituted alkyl group.)

In the seventh aspect of the present invention, there is provided a phenanthrene compound comprising a phenanthrene compound expressed by a general formula <<21>>.

general formula <<21>>

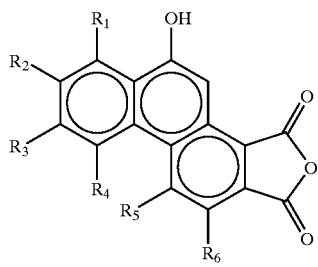

(in the formula, each of $R_1$, $R_2$, $R_3$, $R_4$, $R_5$ and $R_6$ is one of a hydrogen atom, an alkyl group, an alkoxy group, and a halogen atom.)

In the eighth aspect of the present invention, there is provided a coupler compound comprising a phenanthrene compound expressed by a general formula <<22>>.

general formula <<22>>

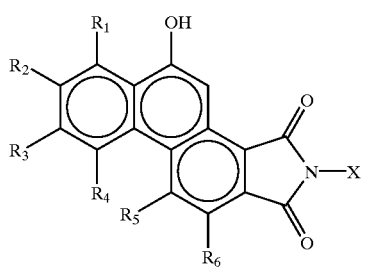

(in the formula, each of $R_1$, $R_2$, $R_3$, $R_4$, $R_5$ and $R_6$ represents one of a hydrogen atom, an alkyl group, an alkoxy group, and a halogen atom; X is a one of a hydrogen atom, a substituted or non-substituted alkyl group, substituted or non-substituted aromatic series hydrocarbon group, and substituted or non-substituted heterocyclic ring group.)

In the ninth aspect of the present invention, there is provided a coupler compound comprising a coupler expressed by a general formula <<23>>.

general formula <<23>>

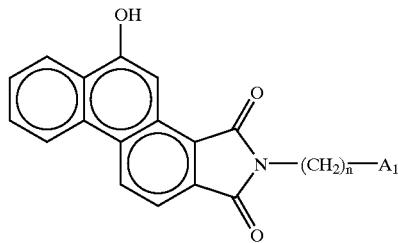

(in the general formula, $A_1$ represents one of a substituted or non-substituted aromatic series hydrocarbon group, a substituted or non-substituted heterocyclic ring group, where m is an integer of 1 to 6.)

In the tenth aspect of the present invention, there is provided a coupler compound comprising a coupler expressed by one of a general formula <<24>> and a general formula <<25>>.

general formula <<24>>

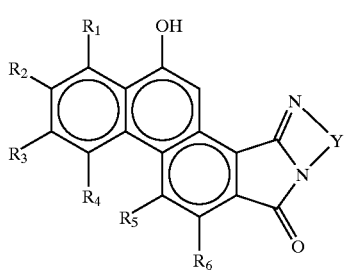

general formula <<25>>

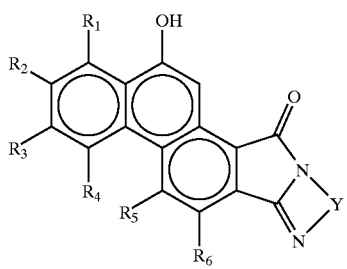

(in the formulae, each of $R_1$, $R_2$, $R_3$, R, $R_5$ and $R_6$ represents one of a hydrogen atom, an alkyl group, an alkoxy group, and a halogen atom; Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group [here, Z represents one of a substituted or non-substituted alkylene group, a substituted or non-substituted aromatic series divalent organic residual group, and a substituted or non-substituted heterocyclic ring aromatic series divalent organic residual group.])

In the eleventh aspect of the present invention, there is provided a method for producing an azo compound expressed by a general formula <<1'>>, wherein a diazonium salts compound expressed by a general formula <<15>> and a coupler compound expressed by a general formula <<16>> are reacted.

Ar—(N$_2^{\oplus}$Z$^{\ominus}$)$_n$  general formula <<15>>

H—Cp  general formula <<16>>

(in the formulae, Ar represents one of a substituted or non-substituted aromatic series hydrocarbon group, and an aromatic series heterocyclic ring group which may be combined by way of a bonding group, where n expresses an integer of any of 1, 2, 3or4.)

Ar—(N=N—Cp)$_n$  general formula <<1'>>

(in the formula, Ar represents one of a substituted or non-substituted aromatic series hydrocarbon group, and an aromatic series heterocyclic ring group which may be combined by way of a bonding group; Cp represents a coupler residual group, where n expresses an integer of any one of 1, 2, 3 and 4.)

general formula <<2'>>

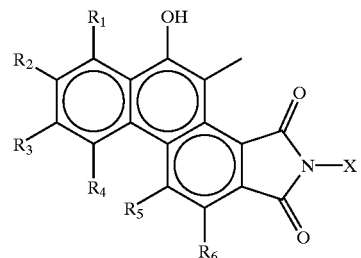

general formula <<3'>>

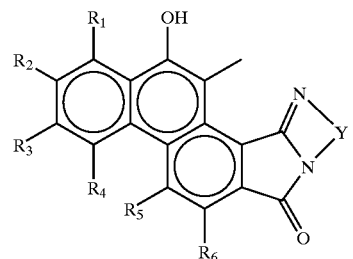

general formula <<4'>>

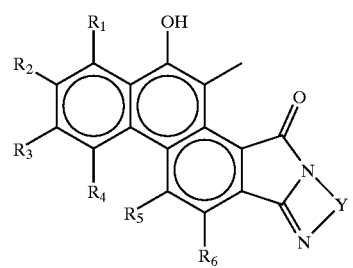

(in the formulae, each of $R_1$, $R_2$, $R_3$, $R_4$, $R_5$ and $R_6$ represents one of a hydrogen atom, an alkyl group, an alkoxy group, and a halogen atom; X represents one of a hydrogen atom, a substituted or non-substituted alkyl group, a substituted or non-substituted aromatic series hydrocarbon group, and substituted or non-substituted heterocyclic ring group; Y is one of a substituted or non-substituted alkylene group, a substituted or non-substituted aromatic series divalent organic residual group, a substituted or non-substituted heterocyclic ring aromatic series divalent organic residual group, and —CO—Z— carbonyl group containing divalent organic residual group [here, Z represents one of a substituted or non-substituted alkylene group, a substituted or non-substituted aromatic series divalent organic residual group, and a substituted or non-substituted heterocyclic ring aromatic series divalent organic residual group.])

In the twelfth aspect of the present invention, there is provided a method for producing a phenanthrene compound expressed by a general formula <<20>>, wherein a naphthalene compound expressed by a general formula <<26>> and an acetylene dicarboxylic acid ester compound expressed by a general formula <<27>> are reacted using nitrobenzene at a temperature of 100° C. to 160° C.

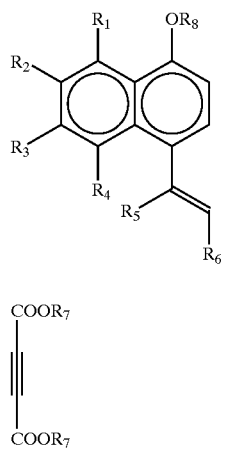

general formula <<26>>

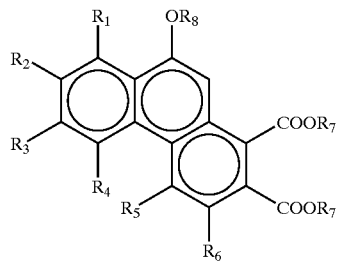

general formula <<27>>

(in the formulae, each of $R_1$, $R_2$, $R_3$, $R_4$, $R_5$ and $R_6$ is one of a hydrogen atom, an alkyl group, an alkoxy group, and a halogen atom; $R_7$ is a substituted or non-substituted alkyl group; $R_8$ represents one of a linear chain or a branched alkyl group, and a substituted alkyl group.)

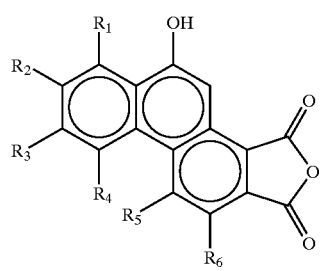

general formula <<20>>

(in the formulae, each of $R_1$, $R_2$, $R_3$, $R_4$, $R_5$ and $R_6$ is one of a hydrogen atom, an alkyl group, an alkoxy group, and a halogen atom; $R_7$ is a substituted or non-substituted alkyl group; $R_8$ represents one of a linear chain or a branched alkyl group, and a substituted alkyl group.)

In the thirteenth aspect of the present invention, there is provided a method for producing a phenanthrene compound expressed by a general formula <<21>>, wherein a phenanthrenes compound expressed by a general formula <<20>> is reacted in an existance of acid catalyst.

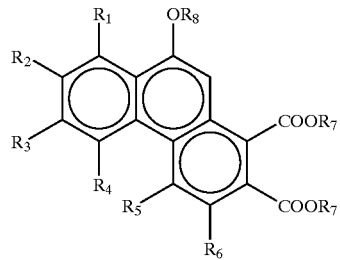

general formula <<20>>

(in the formula, each of $R_1$, $R_2$, $R_3$, $R_4$, $R_5$ and $R_6$ is one of a hydrogen atom, an alkyl group, an alkoxy group, and a halogen atom; $R_7$ is a substituted or non-substituted alkyl group; $R_8$ represents one of a linear chain or a branched alkyl group, and a substituted alkyl group.)

general formula <<21>>

(in the formulae, each of $R_1$, $R_2$, $R_3$, $R_4$, $R_5$ and $R_6$ is one of a hydrogen atom, an alkyl group, an alkoxy group, and a halogen atom.)

In the fourteenth aspect of the present invention, there is provided a method for producing a coupler compound expressed by a general formula <<2'>>, wherein a phenanthrenes compound expressed by a general formula <<21>> and an amine compound expressed by a general formula <<28>> are reacted in an existance of acid catalyst.

general formula <<21>>

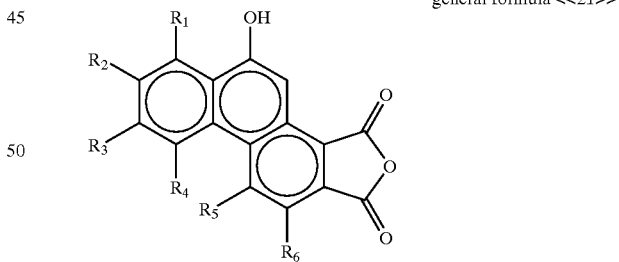

(in the formulae, each of $R_1$, $R_2$, $R_3$, $R_4$, $R_5$ $R_6$ is one of a hydrogen atom, an alkyl group, an alkoxy group, and a halogen atom.)

$H_2n$-X  general formula <<28>>

(in the formula, X represents one of a hydrogen atom, a substituted or non-substituted alkyl group, a substituted or non-substituted aromatic series hydrocarbon group, and a substituted or non-substituted aromatic series heterocyclic ring group.)

general formula <<2'>>

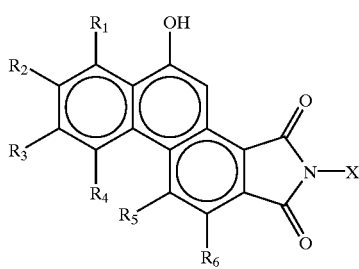

(in the formula, each of $R_1$, $R_2$, $R_3$, $R_4$, $R_5$ and $R_6$ represents one of a hydrogen atom, an alkyl group, an alkoxy group, and a halogen atom, X is one of a hydrogen atom, a substituted or non-substituted alkyl group, substituted or non-substituted aromatic series hydrocarbon group, and substituted or non-substituted heterocyclic ring group.)

In the fifteenth aspect of the present invention, there is provided a method for producing a coupler compound expressed by a general formula <<23>>, wherein a phenanthrenes compound expressed by a general formula <<21>> and an amine compound expressed by a general formula <<29>> are reacted in an existance of acid catalyst.

general formula <<21>>

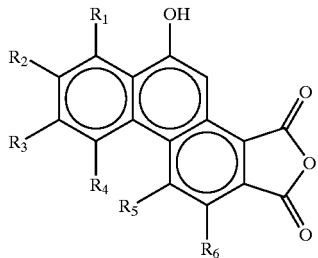

(in the formulae, each of $R_1$, $R_2$, $R_3$, $R_4$, $R_5$ $R_6$ is one of a hydrogen atom, an alkyl group, an alkoxy group, and a halogen atom.)

H2N—(CH2)$m$-A1  general formula <<29>>

(in the formula, $A_1$ represents one of a substituted or non-substituted aromatic series hydrocarbon group, and a substituted or non-substituted heterocyclic ring group; where m is an integer of 1 to 6.)

general formula <<23>>

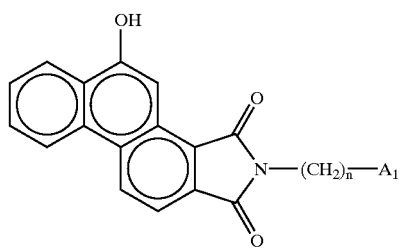

(in the formula, $A_1$ represents one of a substituted or non-substituted aromatic series hydrocarbon group, and a substituted or non-substituted heterocyclic ring group; m is an integer of 1 to 6.)

In the sixteenth aspect of the present invention, there is provided a method for producing a coupler compound expressed by one of a general formula <<24>> and a general formula <<25>>, wherein a naphthalene compound expressed by a general formula <<21>> and a diamine compound expressed by a general formula <<30>> are reacted in an existance of acid catalyst.

general formula <<21>>

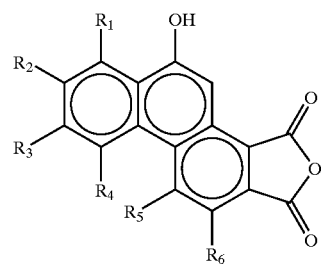

(in the formulae, each of $R_1$, $R_2$, $R_3$, $R_4$, $R_5$ and $R_6$ is one of a hydrogen atom, an alkyl group, an alkoxy group, and a halogen atom.)

$H_2N$—Y—$NH_2$  general formula <<30>>

(in the formula, Y represents one of a substituted or non-substituted alkylene group, a substituted or non-substituted aromatic series divalent organic residual group, a substituted or non-substituted heterocyclic ring aromatic series divalent organic residual group, and —CO—Z— carbonyl group containing divalent organic residual group [here, Z represents one of a substituted or non-substituted alkylene group, a substituted or non-substituted aromatic series divalent organic residual group, and a substituted or non-substituted heterocyclic ring aromatic series divalent residual group.])

general formula <<24>>

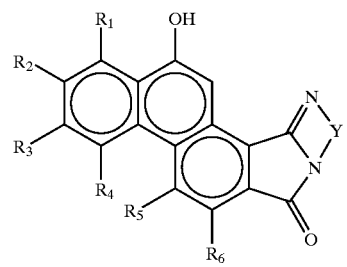

general formula <<25>>

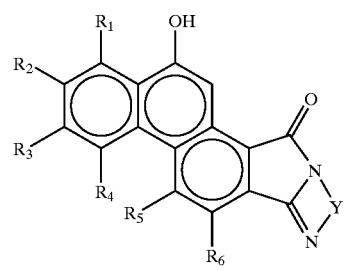

(in the formulae, each of $R_1$, $R_2$, $R_3$, $R_4$, and $R_6$ represents one of a hydrogen atom, an alkyl group, an alkoxy group, and a halogen atom; Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group [here, Z represents one of a substituted or non-substituted alkylene group, a substituted or non-substituted aromatic series divalent organic residual group, and a substituted or non-substituted heterocyclic ring aromatic series divalent organic residual group.])

In the seventeenth aspect of the present invention, there is provided an azo compound comprising an azo compound expressed by a general formula <<101'>>, wherein at least one of the Cp is a coupler residual group selected from one of the following general formulae <<102'>>, <<103'>> and <<04'>>.

Ar—(N=N—Cp)$_n$  general formula <<101'>>

(in the formula, Ar expresses one of a substituted or non-substituted aromatic carbon hydride group, and an heterocyclic ring aromatic group which can be combined by way of a bond group; Cp expresses a coupler residual group; n expresses an integer of any one of 1, 2, 3, and 4.)

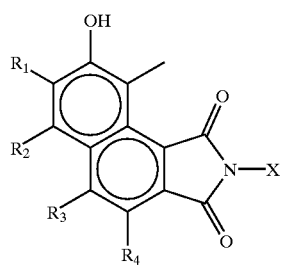

general formula <<102'>>

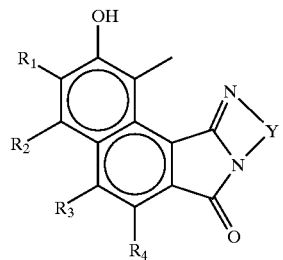

general formula <<103'>>

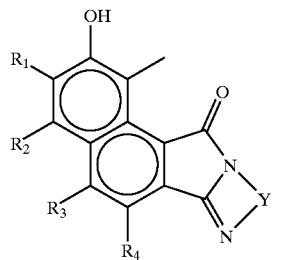

general formula <<104'>>

(in the formulae, each of $R_1$, $R_2$, $R_3$ and $R_4$ represents one of a hydrogen atom, an alkyl group, an alkoxy group, and a halogen atom. X represents one of a hydrogen atom, a substituted or non-substituted alkyl group, a substituted or non-substituted aromatic series hydrocarbon group, a substituted or non-substituted heterocyclic ring group, and a substituted or non-substituted amino group. Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group (here, Z is one of a substituted or non-substituted alkylene group, a substituted or non-substituted aromatic series divalent organic residual group, and a substituted or non-substituted heterocyclic ring aromatic series divalent organic residual group.))

In the eighteenth aspect of the present invention, there is provided an azo compound expressed by a general formula <<141>>, wherein at least one of the Cp is a coupler residual group selected from one of the general formulae <<102'>>, <<103'>> and <<104'>>.

general formula <<141>>

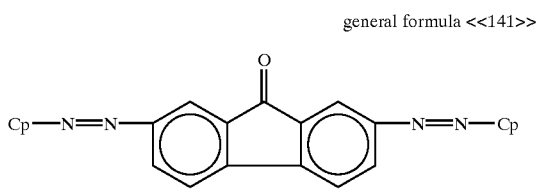

In the nineteenth aspect of the present invention, there is provided an azo compound expressed by a general formula <<142>>, wherein at least one of the Cp is a coupler residual group selected from one of the general formulae <<102'>>, <<103'>> and <<104'>>.

general formula <<142>>

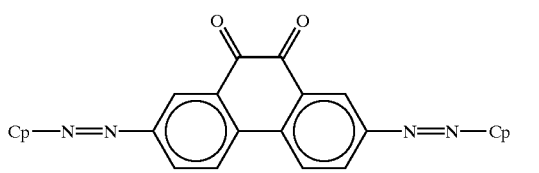

The present invention also provides a mode in which in the azo compound aforementioned in the seventeenth aspect, in the general formula <<101'>>, at least one of the Cp is a coupler residual group expressed by a following general formula <<6>>, when n is one of 2, 3 and 4.

general formula <<6>>

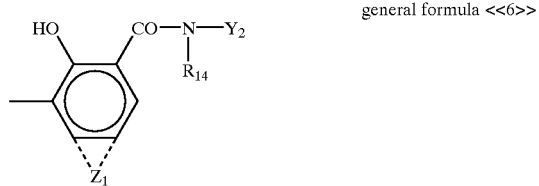

(in the formula, $Z_1$ represents one of a hydrocarbon ring or its substituent, and a heterocyclic ring group or its substituent; $R_{14}$ is one of a hydrogen, an alkyl group or its substituent, and a phenyl group or its substituent; $Y_2$ represents one of a hydrocarbon ring group or its substituent, and a heterocyclic ring group or its substituent.)

The present invention also provides a mode in which in the electrophotographic photoconductor aforementioned in the seventeenth aspect, in the general formula <<101'>>, at least one of the Cp is a coupler residual group selected from one of general formulae <<7>> and <<8>>, when n is one of 2,3, and 4.

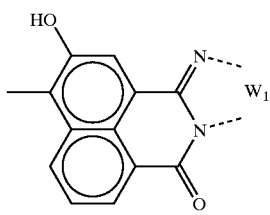

general formula <<7>>

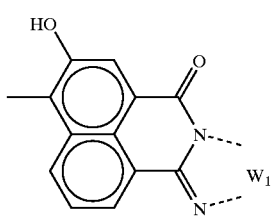

general formula <<8>>

(in the general formulae <<7>> and <<8>>, $W_1$ represents an aromatic series hydrogen divalent group or a heterocyclic ring divalent group including a nitrogen atom in a ring. These rings may be substituted or non-substituted.)

In the twentieth aspect of the present invention, there is provided a naphthalene compound comprising a naphthalene compound expressed by a general formula <<120>>.

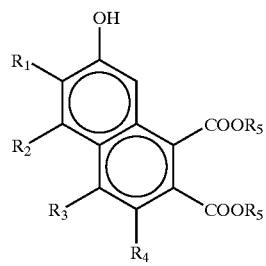

general formula <<120>>

(in the formula, each of $R_1$, $R_2$, $R_3$, and $R_4$ is one of a hydrogen atom, an alkyl group, an alkoxy group, and a halogen atom; $R_5$ is a substituted or non-substituted alkyl group; $R_6$ represents one of a linear chain or a branched alkyl group, and a substituted alkyl group.)

In the twenty first aspect of the present invention, there is provided a naphthalene compound comprising a naphthalene compound expressed by a general formula <<149>>.

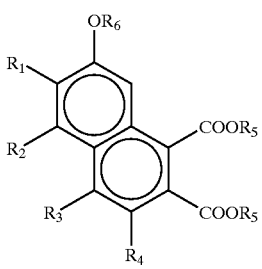

general formula <<149>>

(in the formula, each of $R_1$, $R_2$, $R_3$, and $R_4$ is one of a hydrogen atom, an alkyl group, an alkoxy group, and a halogen atom; $R_5$ is a substituted or non-substituted alkyl group.)

In the twenty second aspect of the present invention, there is provided a coupler compound comprising a coupler compound expressed by a general formula <<122>>.

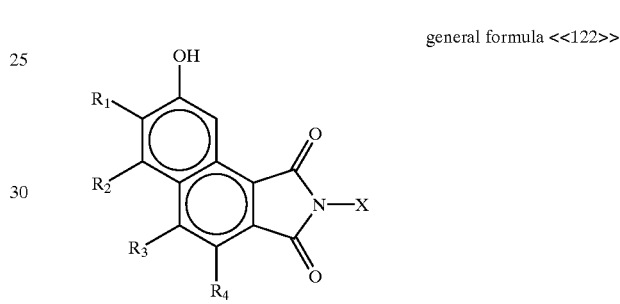

general formula <<122>>

(in the formula, each of $R_1$, $R_2$, $R_3$, and $R_4$ represents one of a hydrogen atom, an alkyl group, an alkoxy group, and a halogen atom; X is one of a hydrogen atom, a substituted or non-substituted alkyl group, substituted or non-substituted aromatic series hydrocarbon group, and substituted or non-substituted heterocyclic ring group.)

In the twenty third aspect of the present invention, there is provided a coupler compound comprising a coupler compound expressed by a general formula <<123>>.

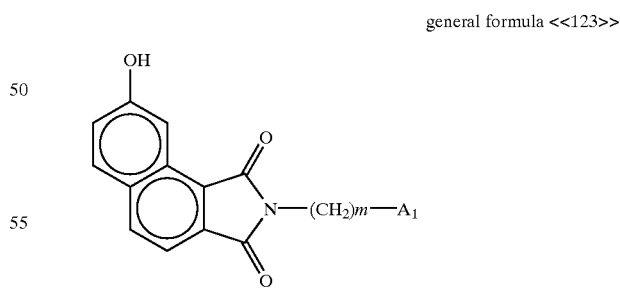

general formula <<123>>

(in the general formula, $A_1$ represents one of a substituted or non-substituted aromatic series hydrocarbon group, and a substituted or non-substituted heterocyclic ring group; and m is an integer of 1 to 6.)

In the twenty fourth aspect of the present invention, there is provided a coupler compound comprising a coupler compound expressed by one of a general formula <<124>> and a general formula <<125>>.

general formula <<124>>

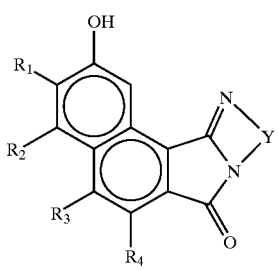

general formula <<125>>

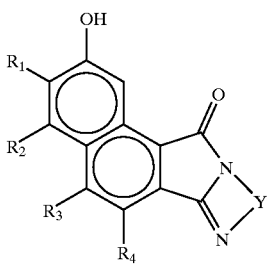

(in the formulae, each of $R_1$, $R_2$, $R_3$, and $R_4$ represents one of a hydrogen atom, an alkyl group, an alkoxy group, and a halogen atom; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— [here, Z represents one of a substituted or non-substituted alkylene group, a substituted or non-substituted aromatic series divalent organic residual group, and a substituted or non-substituted heterocyclic ring aromatic series divalent organic residual group.])

In the twenty fifth aspect of the present invention, there is provided a coupler compound comprising a coupler compound expressed by one of a general formula <<143>> and a general formula <<144>>.

general formula <<143>>

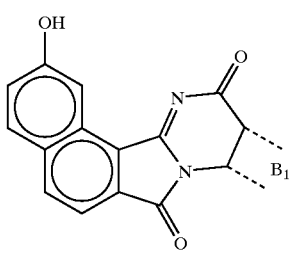

general formula <<144>>

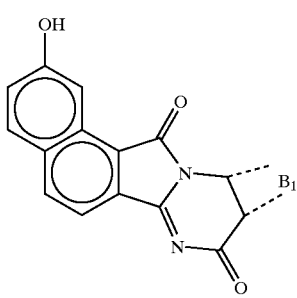

(in the formulae, $B_1$ represents one of a substituted or non-substituted aromatic series hydrocarbon ring divalent group, and a substituted or non-substituted aromatic series heterocyclic ring divalent group.)

In the twenty sixth aspect of the present invention, there is provided a coupler compound comprising a coupler compound expressed by one of a general formula <<145>> and a general formula <<146>>.

general formula <<145>>

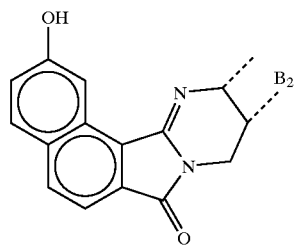

general formula <<146>>

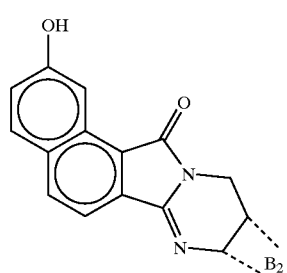

(in the formulae, $B_2$ represents one of a substituted or non-substituted aromatic series hydrocarbon ring divalent group, and a substituted or non-substituted aromatic series heterocyclic ring divalent group.)

In the twenty seventh aspect of the present invention, there is provided a method for producing an azo compound expressed by a general formula <<101>>, wherein a diazonium salts compound expressed by a general formula <<15>> and a coupler compound expressed by a general formula <<16>> are reacted.

$$Ar\text{-}(N_2^{\oplus 1} \ Z^{\ominus})_n \qquad \text{general formula <<15>>}$$

$$H\text{—}Cp \qquad \text{general formula <<16>>}$$

(in the formulae, Ar represents one of a substituted or non-substituted aromatic series hydrocarbon group, and an aromatic series heterocyclic ring group which may be combined by way of a bonding group; n expresses an integer of any one of 1, 2, 3 and 4.)

$$Ar\text{-}(N\text{=}N\text{—}Cp)_n \qquad \text{general formula <<101'>>}$$

(in the formula, Ar represents one of a substituted or non-substituted aromatic series hydrocarbon group, and an aromatic series heterocyclic ring group which may be combined by way of a bonding group; Cp represents a coupler residual group; n expresses an integer of any one of 1, 2, 3 and 4.)

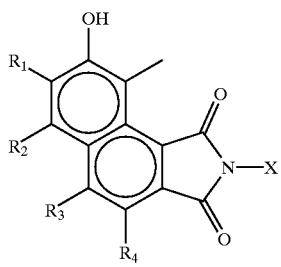

general formula <<102'>>

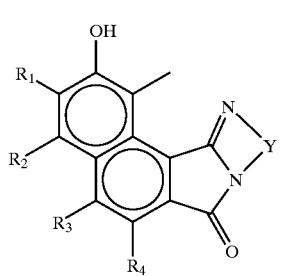

general formula <<103'>>

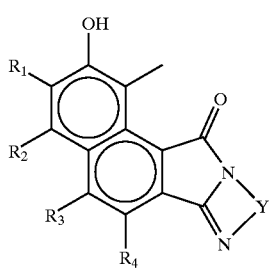

general formula <<104'>>

(in the formulae, each of $R_1$, $R_2$, $R_3$ and $R_4$ represents one of a hydrogen atom, an alkyl group, an alkoxy group, and a halogen atom; X is one of a hydrogen atom, a substituted or non-substituted alkyl group, a substituted or non-substituted aromatic series hydrocarbon group, a substituted or non-substituted heterocyclic ring group, and a substituted or non-substituted amino group; Y is one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group).)

In the twenty eighth aspect of the present invention, there is provided a method for producing a naphthalene compound expressed by a general formula <<120>>, wherein a styrene compound expressed by a general formula <<126>> and a acetylene dicarboxylic acid ester compound expressed by a general formula <<127>> are reacted using nitrobenzene at a temperature of 100° C. to 160° C.

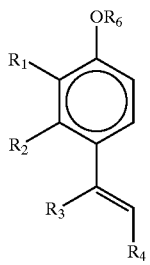

general formula <<126>>

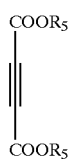

general formula <<127>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group; $R_6$ represents one of a linear chain or a branched alkyl group, and a substituted alkyl group.)

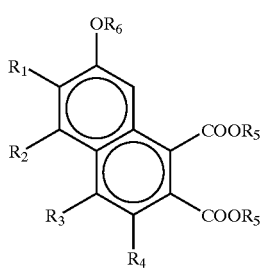

general formula <<120>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group; $R_6$ represents one of a linear chain or a branched alkyl group, and a substituted alkyl group.)

In the twenty ninth aspect of the present invention, there is provided a method for producing a naphthalene compound expressed by a general formula <<149>>, wherein a naphthalene compound expressed by a general formula <<120>> is reacted in an existance of acid catalysts at a temperature of 0° C. to 50° C.

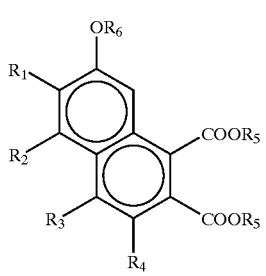

general formula <<120>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group; $R_6$ represents one of a linear chain or a branched alkyl group, and a substituted alkyl group.)

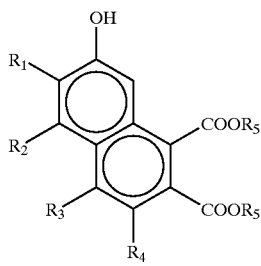

general formula <<149>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group.)

In the thirtieth aspect of the present invention, there is provided a method for producing a coupler compound expressed by a general formula <<102'>>, wherein an amine compound expressed by a general formula <<28>> and a naphthalene compound expressed by a general formula <<149>> are reacted in one of a glycol and in a group containing at least one element selected from glycerol solvent.

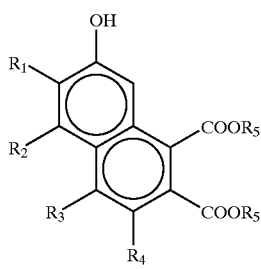

general formula <<149>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group.)

$H_2n\text{-}X$  general formula <<28>>

(in the formula, X represents one of a hydrogen atom, a substituted or non-substituted alkyl group, a substituted or non-substituted aromatic series hydrocarbon group, a substituted or non-substituted heterocyclic ring group, and a substituted or non-substituted amino group.)

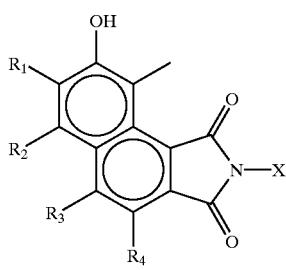

general formula <<102'>>

(in the formula, each of $R_1$, $R_2$, $R_3$, and $R_4$ represents one of a hydrogen atom, an alkyl group, an alkoxy group, and a halogen atom; X is one of a hydrogen atom, a substituted or non-substituted alkyl group, substituted or non-substituted aromatic series hydrocarbon group, and substituted or non-substituted heterocyclic ring group.)

In the thirty first aspect of the present invention, there is provided a method for producing a coupler compound expressed by one of a general formula <<124>> and a general formula <<125>>, wherein a naphthalene compound expressed by a general formula <<149>> and a diamine compound expressed by a general formula <<30>> are reacted in a glycol or in containing at least one element selected from a glycerol solvent.

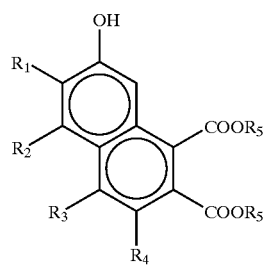

general formula <<149>>

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group.)

$H_2N\text{—}Y\text{—}NH_2$  general formula <<30>>

(in the formula, Y represents one of a substituted or non-substituted alkylene group, a substituted or non-substituted aromatic series divalent organic residual group, a substituted or non-substituted heterocyclic ring aromatic series divalent organic residual group, and carbonyl group containing divalent organic residual group expressed by —CO—Z— [here, Z represents one of a substituted or non-substituted alkylene group, a substituted or non-substituted aromatic series divalent organic residual group, and a substituted or non-substituted heterocyclic ring aromatic series divalent residual group.])

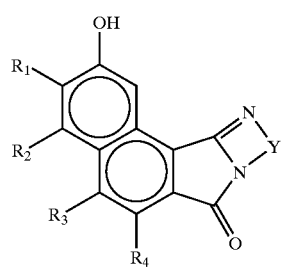

general formula <<124>>

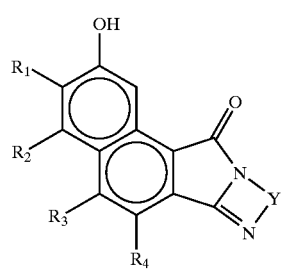

general formula <<125>>

(in the formulae, each of $R_1$, $R_2$, $R_3$, and $R_4$ represents one of a hydrogen atom, an alkyl group, an alkoxy group, and a halogen atom; Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group [here, Z represents one of a substituted or non-substituted alkylene group, a substituted or non-substituted aromatic series divalent organic residual group, and a substituted or non-substituted heterocyclic ring aromatic series divalent organic residual group.])

In the thirty second aspect of the present invention, there is provided a method for producing a coupler compound expressed by one of a general formula <<143>> and a general formula <<144>>, wherein a naphthalene compound expressed by a general formula <<149>> and a diamine compound expressed by a general formula <<147>> are reacted in a glycol or containing at least one element selected from a glycerol solvent.

general formula <<147>>

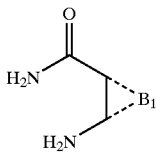

(in the formula, $B_1$ represents one of a substituted or non-substituted aromatic series hydrocarbon ring divalent group, and a substituted or non-substituted aromatic series heterocyclic ring divalent group.)

In the thirty third aspect of the present invention, there is provided a method for producing a coupler compound expressed by one of a general formula <<145>> and a general formula <<146>>, wherein a naphthalene compound expressed by a general formula <<149>> and a diamine compound expressed by a general formula <<148>> are reacted in a glycol or containing at least one element selected from a glycerol solvent.

general formula <<149>>

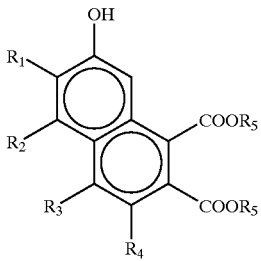

(in the formulae, each of $R_1$, $R_2$, $R_3$, and $R_4$ is one of a hydrogen atom, an alkyl group, an alkoxy group, and a halogen atom; $R_5$ is a substituted or non-substituted alkyl group.)

general formula <<148>>

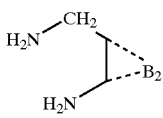

(in the formula, $B_2$ represents one of a substituted or non-substituted aromatic series hydrocarbon ring divalent group, and a substituted or non-substituted aromatic series heterocyclic ring divalent group.)

general formula <<145>>

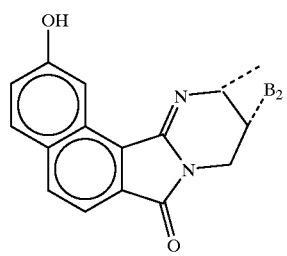

general formula <<146>>

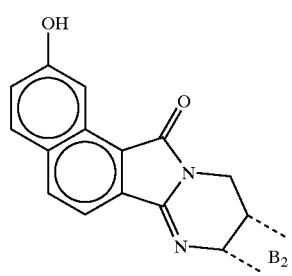

(in the formulae, $B_2$ represents one of a substituted or non-substituted aromatic series hydrocarbon ring divalent group, and a substituted or non-substituted aromatic series heterocyclic ring divalent group.)

In the thirty fourth aspect of the present invention, there is provided a process for forming an image comprising: a step for charging an electrophotographic photoconductor; a step for exposing the electrophotographic photoconductor charged in the step for charging with a light, and forming a latent electrostatic image; a step for developing the latent electrostatic image with a developing agent, visualizing the latent electrostatic image, and forming a developed image; and a step for transferring the developed image formed in the step for developing onto a transferring substance, wherein the electrophotographic photoconductor comprises a photoconductive layer which contains an azo compound expressed by a general formula <<1>> on a photoconductive layer.

Ar—(N=N—Cp)$_n$     general formula <<1>>

(in the general formula <<1>>, Ar expresses one of a substituted or non-substituted aromatic carbon hydride group, and heterocyclic ring aromatic group which can be combined by way of a bond group; Cp expresses a coupler residual group; n expresses an integer of any one of 1, 2, 3, or 4. At least one of the Cp is a coupler residual group selected from general formulae <<2>>, <<3>>, and <<4>>.)

general formula <<2>>

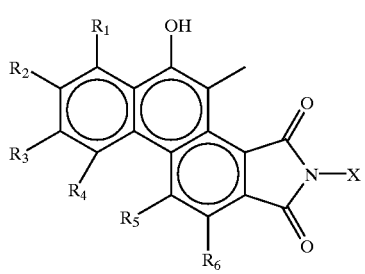

general formula <<3>>

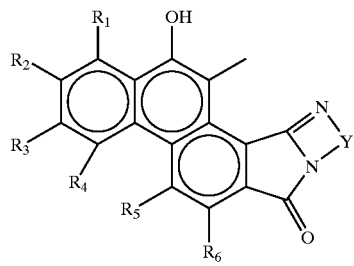

general formula <<4>>

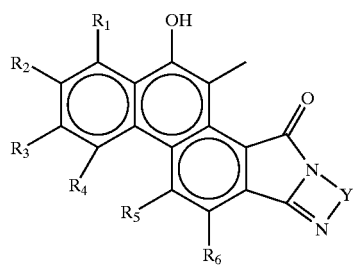

general formula <<102>>

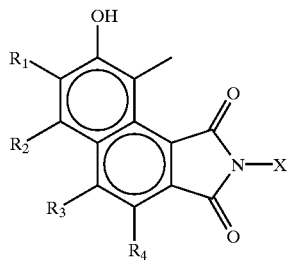

general formula <<103>>

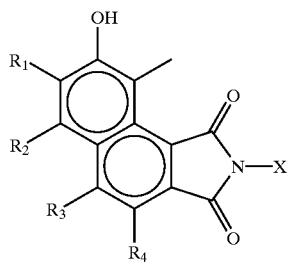

general formula <<104>>

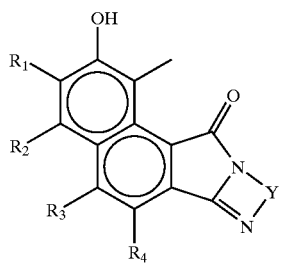

(in the general formulae <<2>>, <<3>>, and <<4>>, each of $R_1, R_2, R_3, R_4, R_5$ and $R_6$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group).)

In the thirty fifth aspect of the present invention, there is provided a process for forming an image comprising: a step for charging an electrophotographic photoconductor; a step for exposing the electrophotographic photoconductor charged by the step for charging with a light, and forming a latent electrostatic image; a step for developing the latent electrostatic image with a developing agent, visualizing the latent electrostatic image, and forming a developed image; and a step for transferring the developed image formed by the step for developing onto a transferring substance, wherein the electrophotographic photoconductor comprises a photoconductive layer which contains an azo compound expressed by a general formula <<101>> on a photoconductive layer.

$$Ar\text{-}(N=N-Cp)_n$$ general formula <<101>>

(in general formula <<101>>, Ar is one of a substituted or non-substituted aromatic series hydrocarbon group, and an aromatic series heterocyclic ring group which can be bonded by way of a bonding group; Cp is a coupler residual group; n represents an integer of any one of 1, 2, 3, and 4. At least one of the Cp is a coupler selected from a general formula <<102>>, general >, and general formula <<104>>.)

(in the general formulae <<102>>, <<103>>, and <<104>>, each of $R_1, R_2, R_3$ and $R_4$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group). Here, each of the alkyl groups $R_1$ and $R_2$ may form a ring.)

In the thirty sixth aspect of the present invention, there is provided an electrophotographic device comprising: an electrophotographic photoconductor; means for charging an electrophotographic photoconductor; means for exposing the electrophotographic photoconductor charged by the means for charging and forming a latent electrostatic image; means for developing the latent electrostatic image, visualizing the latent electrostatic image, and forming a developed image; and means for transferring the developed image formed by the means for developing onto a transferring substance, wherein the electrophotographic photoconductor comprises a photoconductive layer which contains an azo compound expressed by a general formula <<1>> on a photoconductive layer.

$$Ar\text{-}(N{=}N\text{-}Cp)_n \qquad \text{general formula <<1>>}$$

(in the general formula <<1>>, Ar expresses one of a substituted or non-substituted aromatic carbon hydride group, and an heterocyclic ring aromatic group which can be combined by way of a bond group; Cp expresses a coupler residual group; n expresses an integer of any one of 1, 2, 3, and 4. At least one of the Cp is a coupler residual group selected from general formulae <<2>>, <<3>>, and <<4>>.)

general formula <<2>>

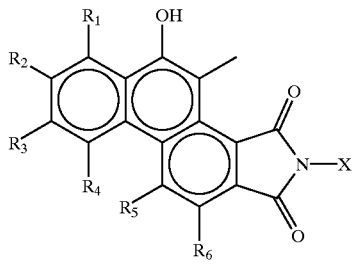

general formula <<3>>

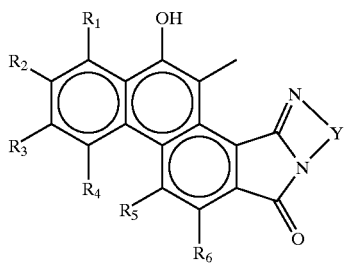

general formula <<4>>

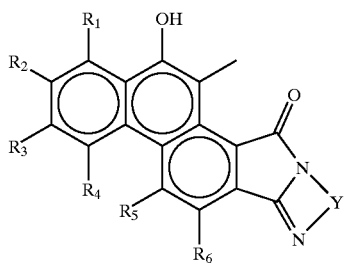

(in the general formulae <<2>>, <<3>>, and <<4>>, each of $R_1$, $R_2$, $R_3$, $R_4$, $R_5$ and $R_6$ is one of a hydrogen atom, an alkyl group, an alkoxy group, a halogen atom, an amino group, a hydroxy group, a nitro group, and a cyano group; X represents a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group).)

In the thirty seventh aspect of the present invention, there is provided an electrophotographic device comprising: an electrophotographic photoconductor; means for charging an electrophotographic photoconductor; means for exposing the electrophotographic photoconductor charged by the means for charging and forming a latent electrostatic image; means for developing the latent electrostatic image, visualizing the latent electrostatic image, and forming a developed image; and means for transferring the developed image formed by the means for developing onto a transferring substance, wherein the electrophotographic photoconductor comprises a photoconductive layer which contains an azo compound expressed by a general formula <<101>> on a photoconductive layer.

$$Ar\text{-}(N{=}N\text{-}Cp)_n \qquad \text{general formula <<101>>}$$

(in general formula <<101>>, Ar is one of a substituted or non-substituted aromatic series hydrocarbon group, and an aromatic series heterocyclic ring group which can be bonded by way of a bonding group; Cp is a coupler residual group; n represents an integer of any one of 1, 2, 3, and 4. At least one of the Cp is a coupler residual group selected from a general formula <<102>>, general formula <<103>>, and general formula <<104>>.)

general formula <<102>>

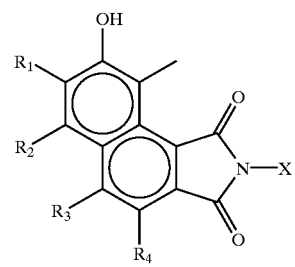

general formula <<103>>

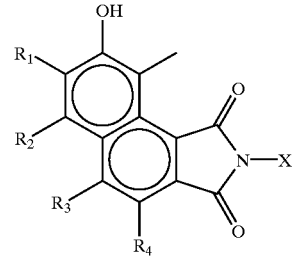

general formula <<104>>

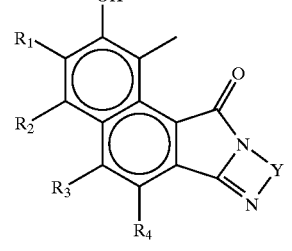

(in the general formulae <<102>>, <<103>>, and <<104>>, each of $R_1$, $R_2$, $R_3$, $R_4$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group). Here, each of the alkyl groups $R_1$ and $R_2$ may form a ring.)

In the thirty eighth aspect of the present invention, there is provided a process cartridge freely attachable and detachable to an electrophotographic device, comprising an electrophotographic photoconductor and at least one means selected from: means for charging; means for image exposing; means for developing; means for transferring; and means for cleaning, wherein the electrophotographic photoconductor comprises a photoconductive layer which contains an azo compound expressed by a general formula <<1>> formed on a conductive support.

Ar-(N=N—Cp)$_n$        general formula <<1>>

(in the general formula <<1>>, Ar expresses one of a substituted or non-substituted aromatic carbon hydride group, and an heterocyclic ring aromatic group which can be combined by way of a bond group; Cp expresses a coupler residual group; n expresses an integer of any one of 1, 2, 3, and 4. At least one of the Cp is a coupler residual group selected from general formulae <<2>>, <<3>>, and <<4>>.)

general formula <<2>>

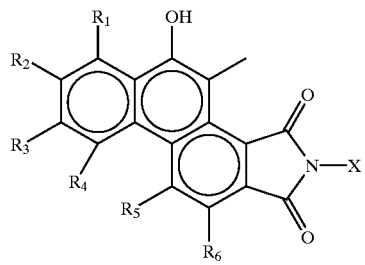

general formula <<3>>

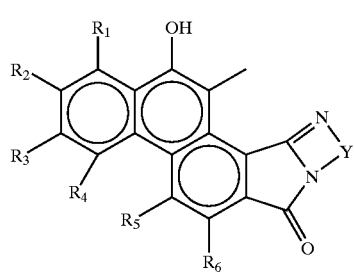

general formula <<4>>

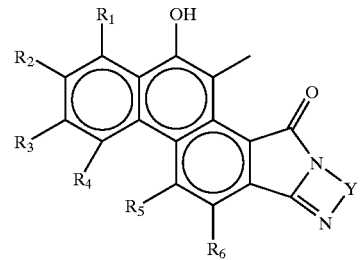

(in the general formulae <<2>>, <<3>>, and <<4>>, each of $R_1$, $R_2$, $R_3$, $R_4$, $R_5$ and $R_6$ is one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group).)

In the thirty ninth aspect of the present invention, there is provided a process cartridge freely attachable and detachable to an electrophotographic device, comprising an electrophotographic photoconductor and at least one means selected from: means for charging; means for image exposing; means for developing; means for transferring; and means for cleaning, wherein the electrophotographic photoconductor comprises a photoconductive layer which contains an azo compound expressed by a general formula <<101>> formed on a conductive support.

Ar-(N=N—Cp)$_n$        general formula <<101>>

(in the general formula <<101>>, Ar is one of a substituted or non-substituted aromatic series hydrocarbon group, and an aromatic series heterocyclic ring group which can be bonded by way of a bonding group; Cp is a coupler residual group; n represents an integer of any one of 1, 2, 3, and 4. At least one of the Cp is a coupler residual group selected from a general formula <102>>, general formula <<103>>, and general formula <<104>>.)

general formula <<102>>

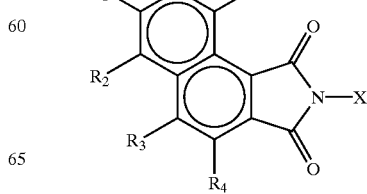

-continued general formula <<103>>

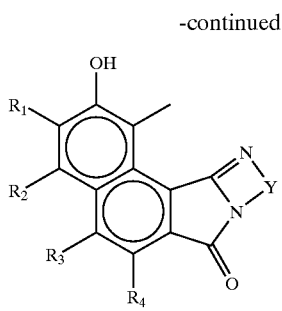

general formula <<104>>

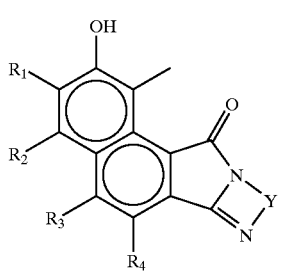

(in the general formulae <<102>>, <<103>>, and <<104>>, each of $R_1$, $R_2$, $R_3$ and $R_4$ is one of a hydrogen atom, an alkyl group, an alkoxy group, a halogen atom, an amino group, a hydroxy group, a nitro group, and a cyano group; X represents one of a hydrogen atom a substituted or non-substituted alkyl group, a substituted or non-substituted aromatic series hydrocarbon group, a substituted or non-substituted heterocyclic ring group, and a substituted or non-substituted amino group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z— (here, Z represents one of a substituted or non-substituted alkylene group, a substituted or non-substituted aromatic series divalent organic residual group, and a substituted or non-substituted heterocyclic ring aromatic series divalent organic residual group). Here, each of the alkyl groups $R_1$ and $R_2$ may form a ring.)

Such a photoconductor has satisfactory charge and sensitive properties, light resistance, durability, and excellent properties of copying at a wide speed ranging from a high speed to a low speed. Further, it is possible to apply it to such a wide field as an analog copying machine for monochrome or full color photographs and the photoconductor for a page printer using LD or LED for writing by using light.

Especially, the important thing of the photoconductor of the present invention is to contain the azo compound having a specific coupler residual group. Accordingly, it is made real to improve photoconductor sensitivity, electrostatic properties, light resistance, and durability. Although the reason why those properties have improved is not clear at this point, it is thought that a solid contribution, in which the azo group of the azo compound can be covered by a coupler residual group, and an electronic contribution, oxidation potential of the azo compound is increased, are made to the novel coupler compound used in the present invention and the molecular structure of the azo compound based on them and further intermolecular force interaction caused by its molecular structure affect efficient charge production in a photoconductive layer and also stability to light of the azo compound itself, an oxidation gas, and so forth.

Further, that makes it possible to transport a charge speedily by using a charge transport substance together, and thus it has been realized to hold high durability to charge properties, sensitivity, and electrostatic properties.

Further, a highly uniform charge mobility matrix is formed in a photoconductive layer by using a high polymer charge transport substance of the present invention, and thus the photoconductor, in which charge injection and charge mobility from a charge generating substance are smoother and mechanical strength are improved, is obtained. For them, it is considered that the high polymer charge transport substance of the present invention is a polymer of at least one of polycarbonate, polyurethane, polyester, and polyether, membranous capability is excellent, its mechanical strength is high, and excellent durability to friction is caused. Further, high mobility is attained since the high polymer charge transport substance of the present invention has an amine triaryl structure. For the high polymer charge transport substance of the present invention, it is effective to improve properties in the case that high polymer charge transport substance is polycarbonate having the triaryl amine structure. Further, it makes it possible to apply to a wet development process, to which it has been impossible to apply by a conventional single layer type photoconductor, by using the high polymer charge transport substance together.

Further, it comes to be possible to move a lot of electrons created by light irradiation to a side of an acceptor type compound by using the acceptor type compound together. Thus, it is realized to have durability to charge properties, sensitivities, and electrostatic properties in which there is no difficulty for utilizing the photoconductor. Further, it is made real to have durability to charge properties by using a phenol compound together since the phenol compound functions as an oxidizing inhibitor.

BRIEF DESCRIPTION OF THE DRAWINGS

FIG. 120 is a graph showing an example of an infrared spectrum of an azo compound.

FIG. 121 is a graph showing an example of an infrared spectrum of an azo compound.

FIG. 122 is a graph showing an example of an infrared spectrum of an azo compound.

FIG. 123 is a graph showing an example of an infrared spectrum of an azo compound.

FIG. 124 is a graph showing an example of an infrared spectrum of an azo compound.

FIG. 125 is a graph showing an example of an infrared spectrum of an azo compound.

FIG. 126 is a graph showing an example of an infrared spectrum of an azo compound.

FIG. 127 is a graph showing an example of an infrared spectrum of an azo compound.

FIG. 128 is a graph showing an example of an infrared spectrum of an azo compound.

FIG. 129 is a graph showing an example of an infrared spectrum of an azo compound.

FIG. 130 is a graph showing an example of an infrared spectrum of an azo compound.

FIG. 131 is a graph showing an example of an infrared spectrum of an azo compound.

Figure 132:
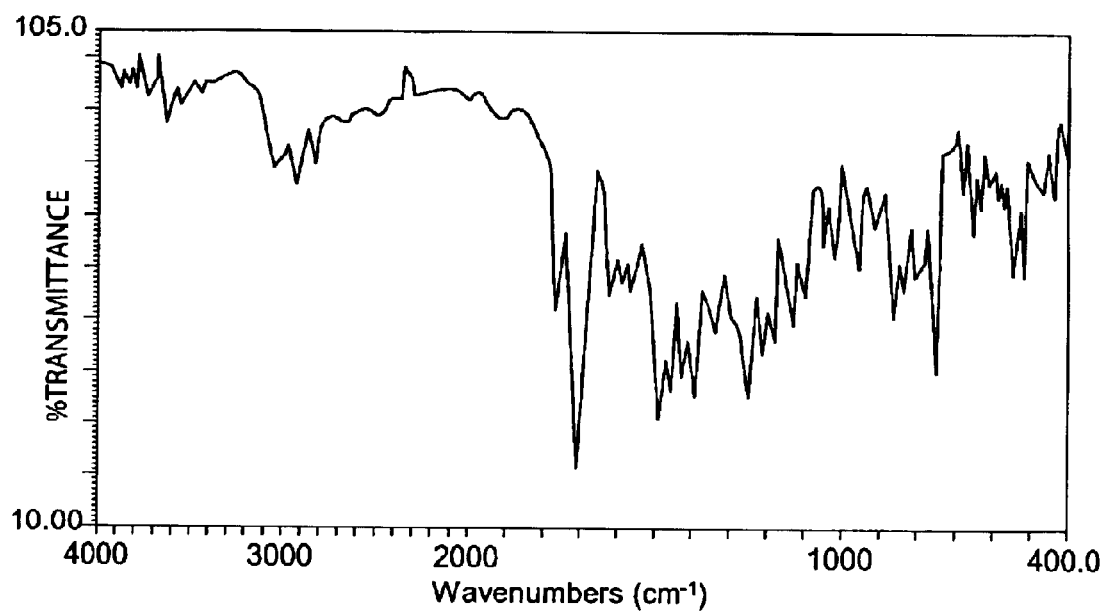

FIG. 132 is a graph showing an example of an infrared spectrum of an azo compound.

Figure 133:
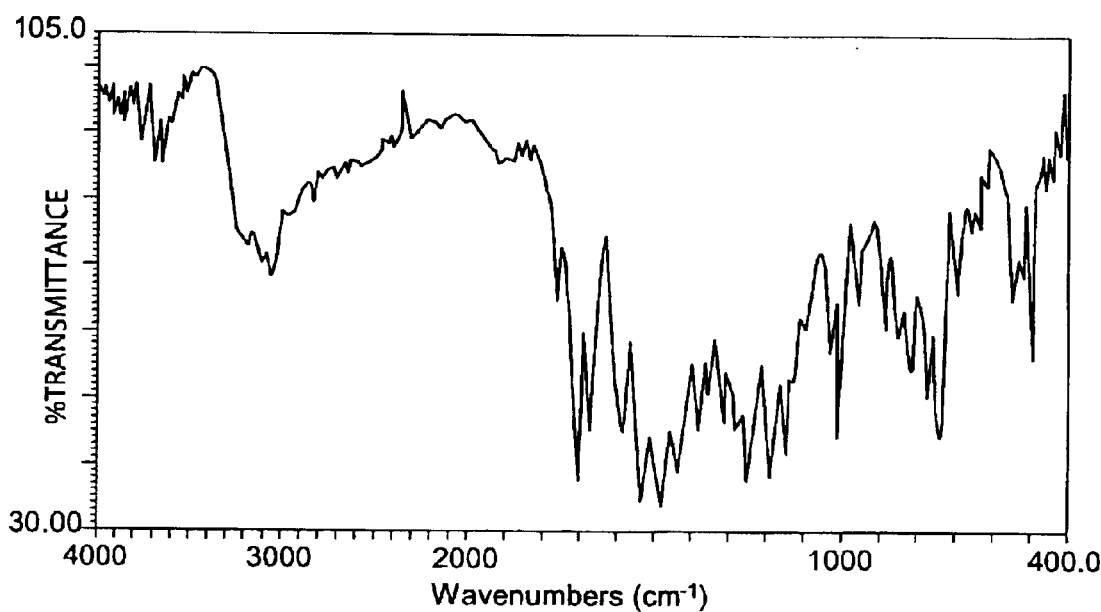

FIG. 133 is a graph showing an example of an infrared spectrum of an azo compound.

Figure 134:
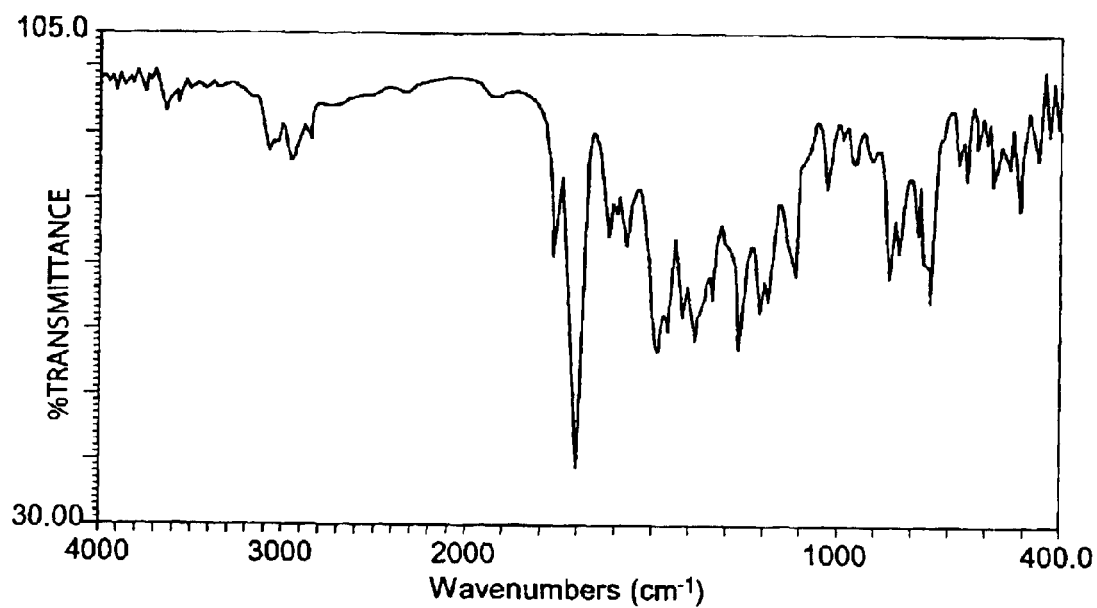

FIG. 134 is a graph showing an example of an infrared spectrum of an azo compound.

Figure 135:
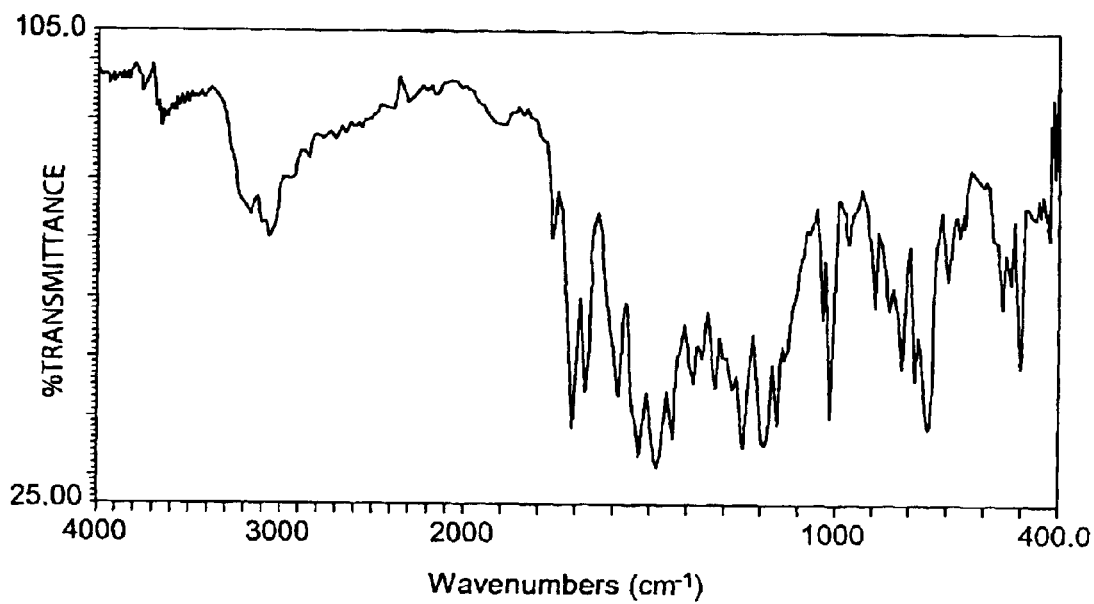

FIG. 135 is a graph showing an example of an infrared spectrum of an azo compound.

Figure 136:
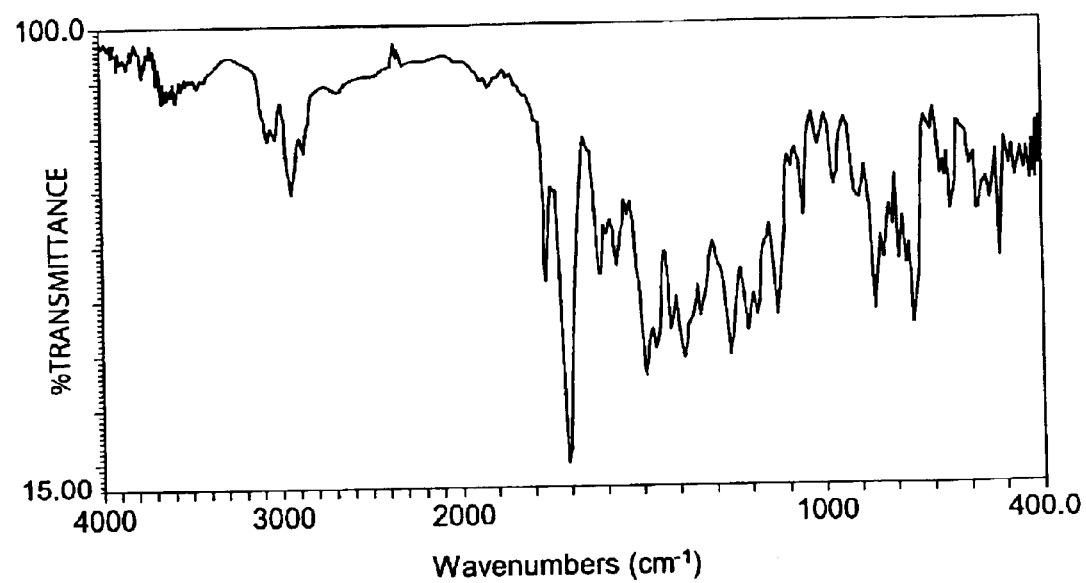

FIG. 136 is a graph showing an example of an infrared spectrum of an azo compound.

Figure 137:
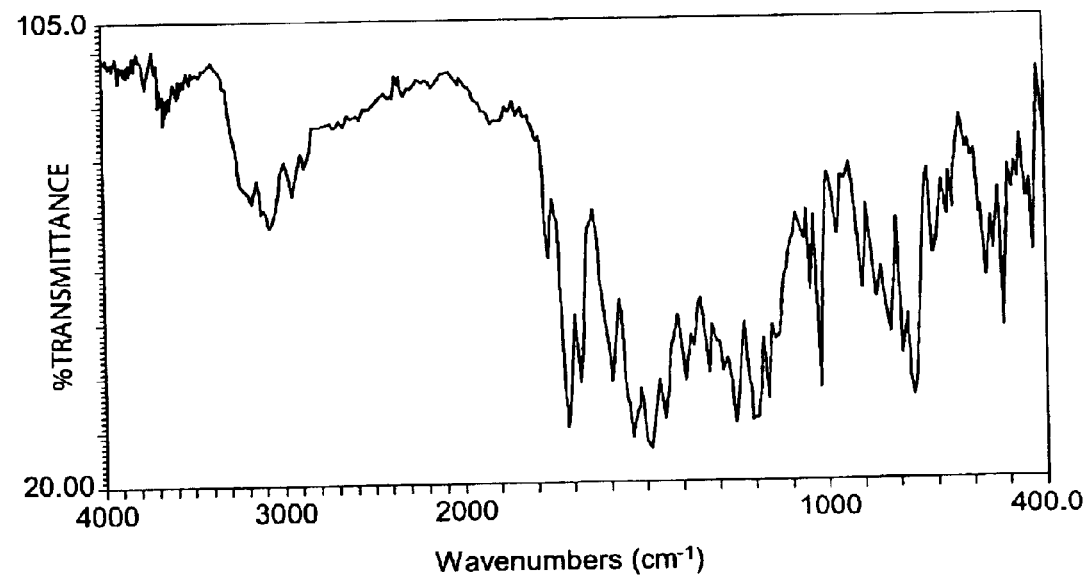

FIG. 137 is a graph showing an example of an infrared spectrum of an azo compound.

Figure 138:
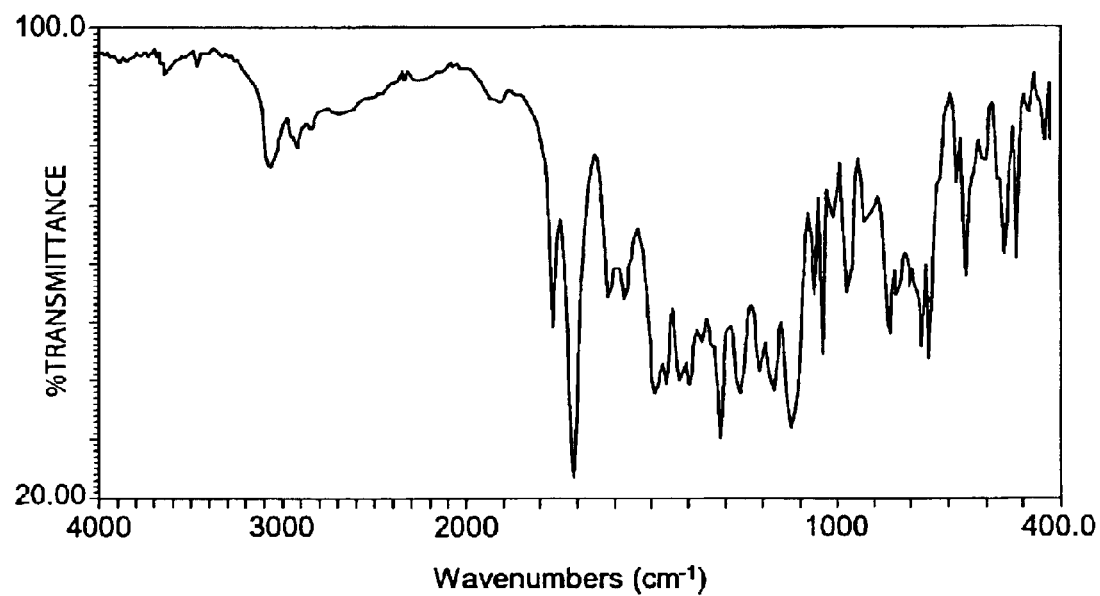

FIG. 138 is a graph showing an example of an infrared spectrum of an azo compound.

Figure 139:
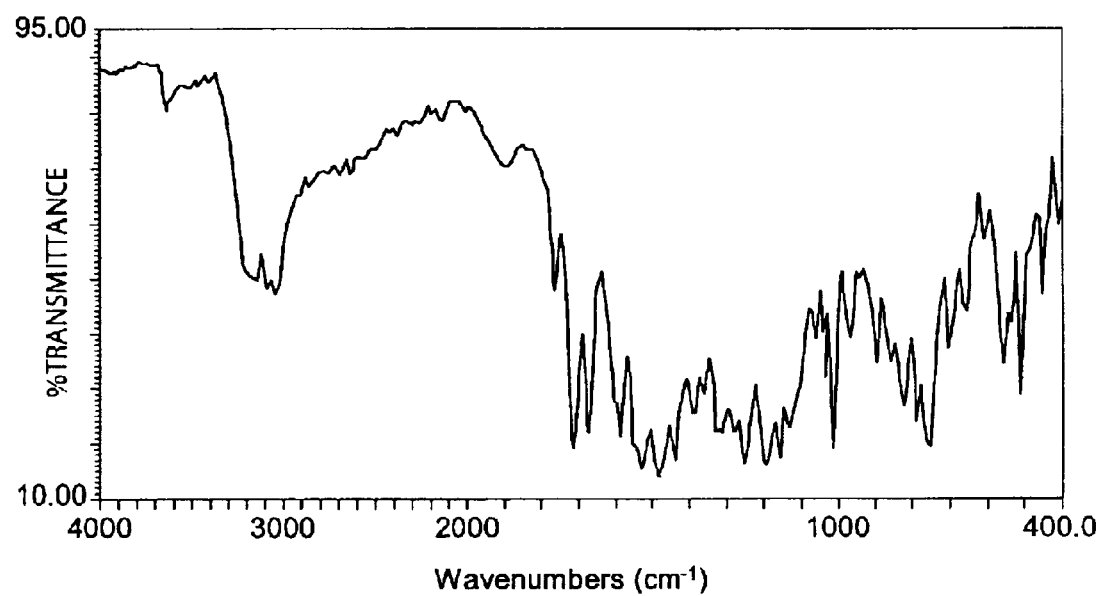

FIG. 139 is a graph showing an example of an infrared spectrum of an azo compound.

Figure 140:
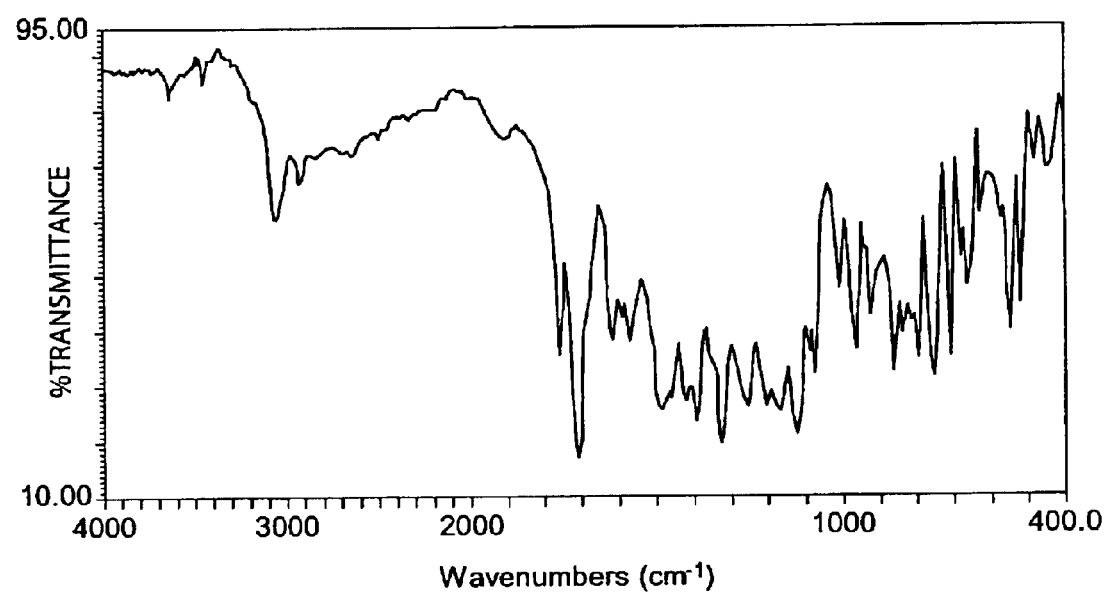

FIG. 140 is a graph showing an example of an infrared spectrum of an azo compound.

Figure 141:
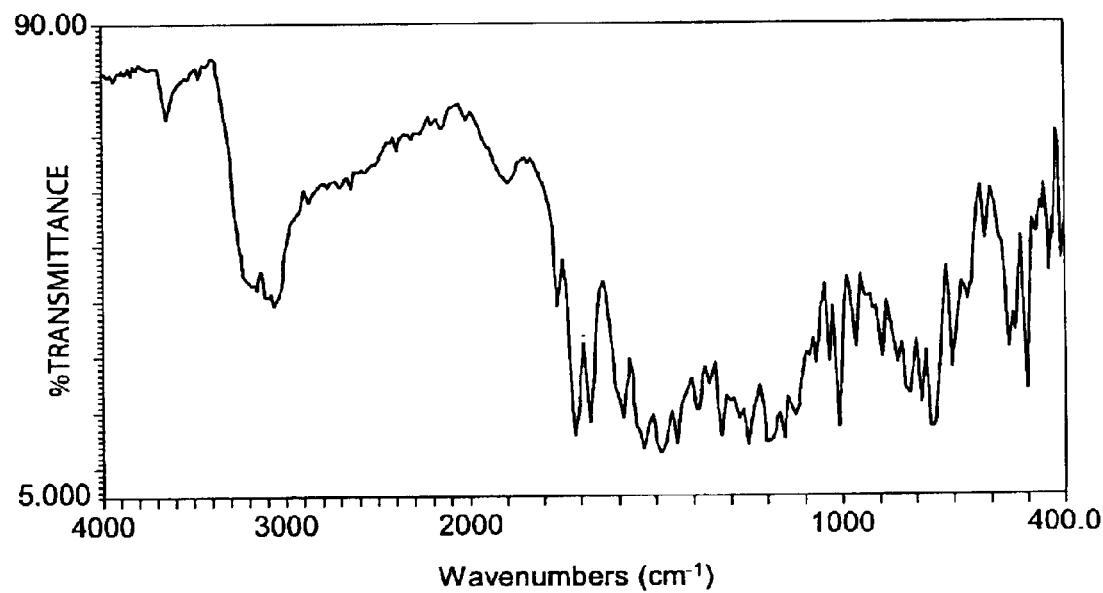

FIG. 141 is a graph showing an example of an infrared spectrum of an azo compound.

Figure 142:
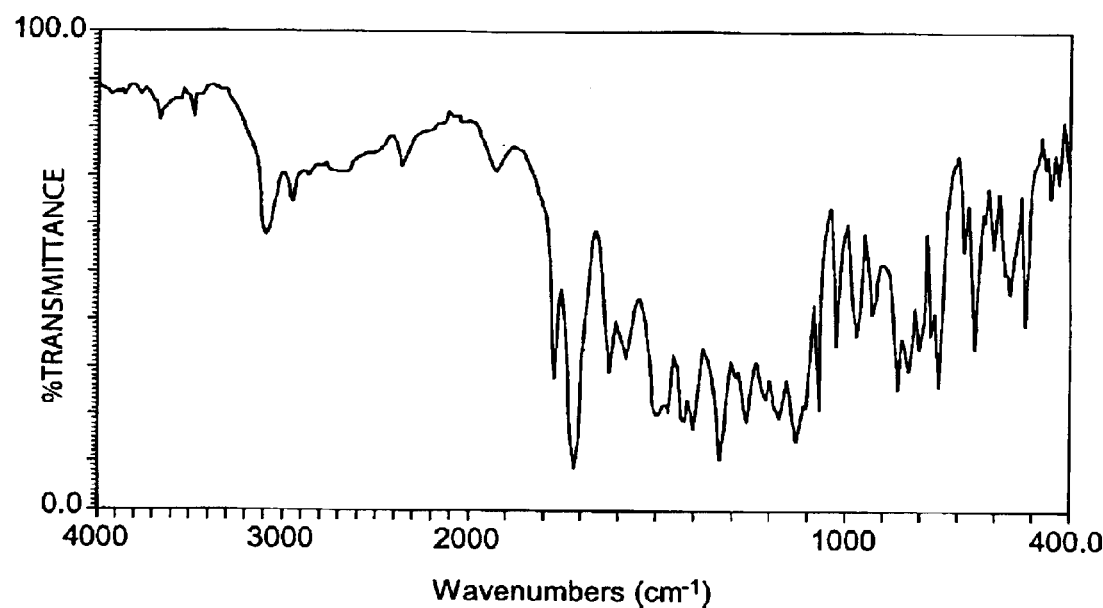

FIG. 142 is a graph showing an example of an infrared spectrum of an azo compound.

Figure 143:
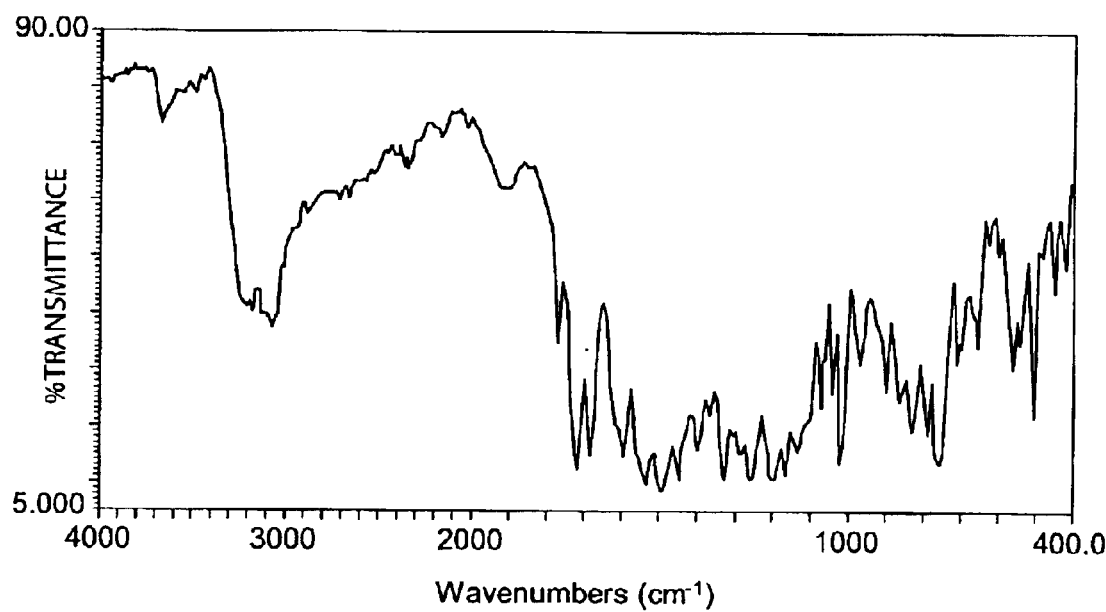

FIG. 143 is a graph showing an example of an infrared spectrum of an azo compound.

Figure 144:
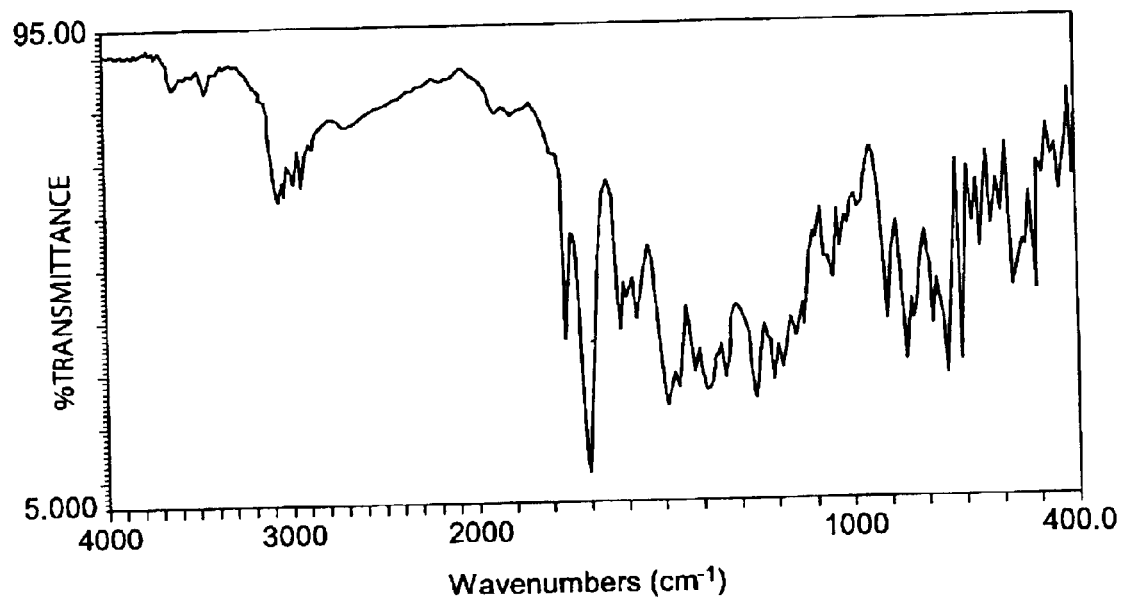

FIG. 144 is a graph showing an example of an infrared spectrum of an azo compound.

Figure 145:
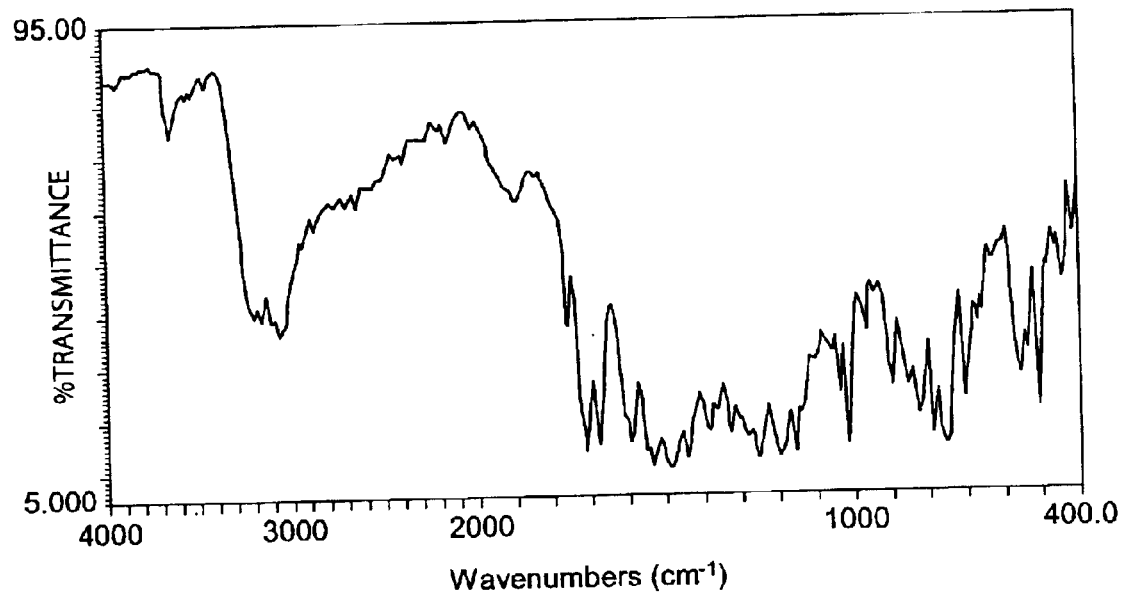

FIG. 145 is a graph showing an example of an infrared spectrum of an azo compound.

Figure 146:
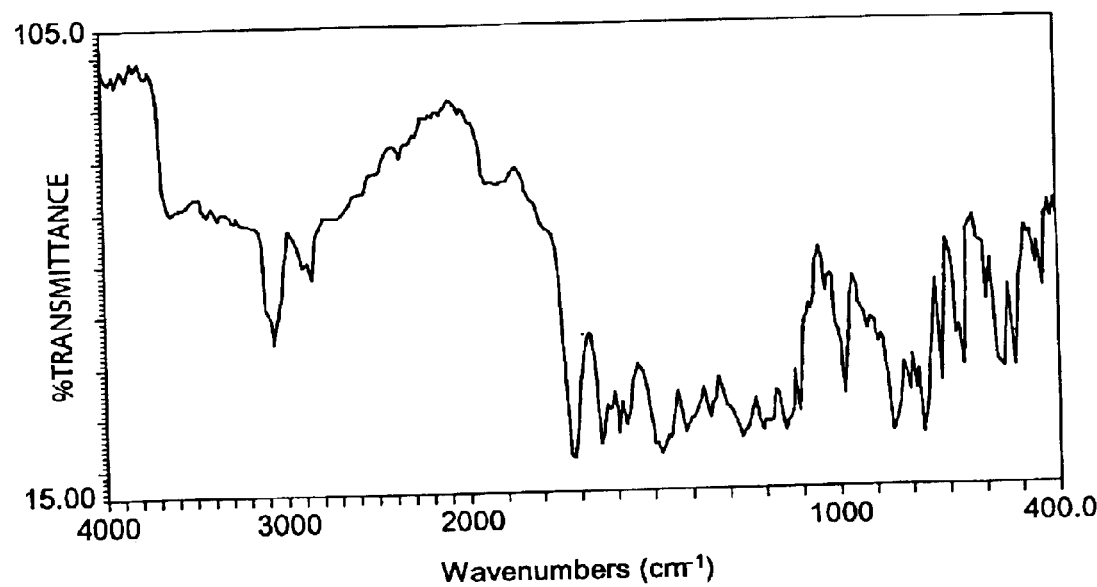

FIG. 146 is a graph showing an example of an infrared spectrum of an azo compound.

Figure 147:
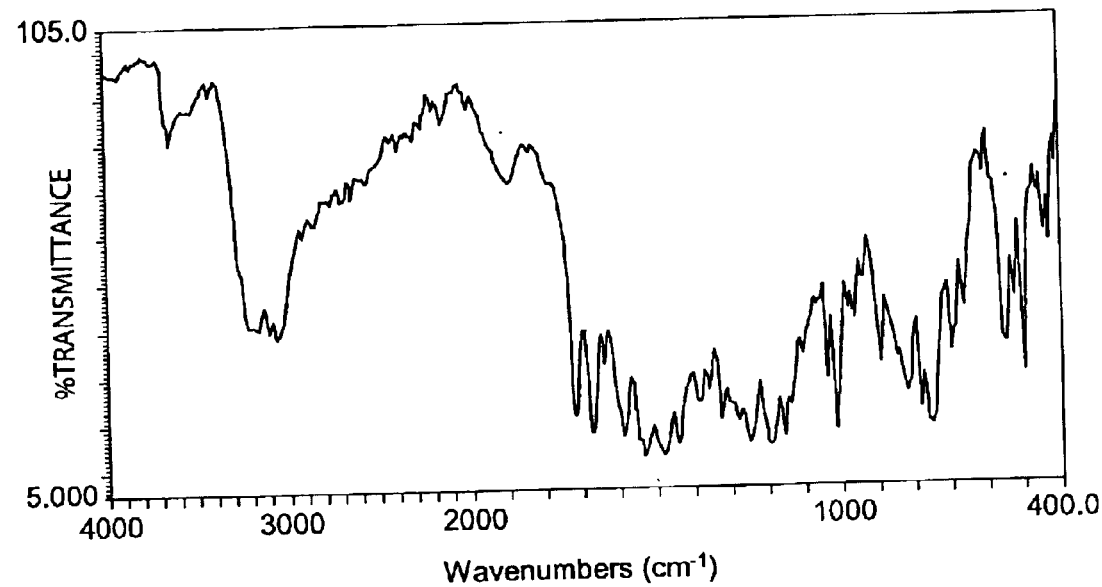

FIG. 147 is a graph showing an example of an infrared spectrum of an azo compound.

Figure 148:
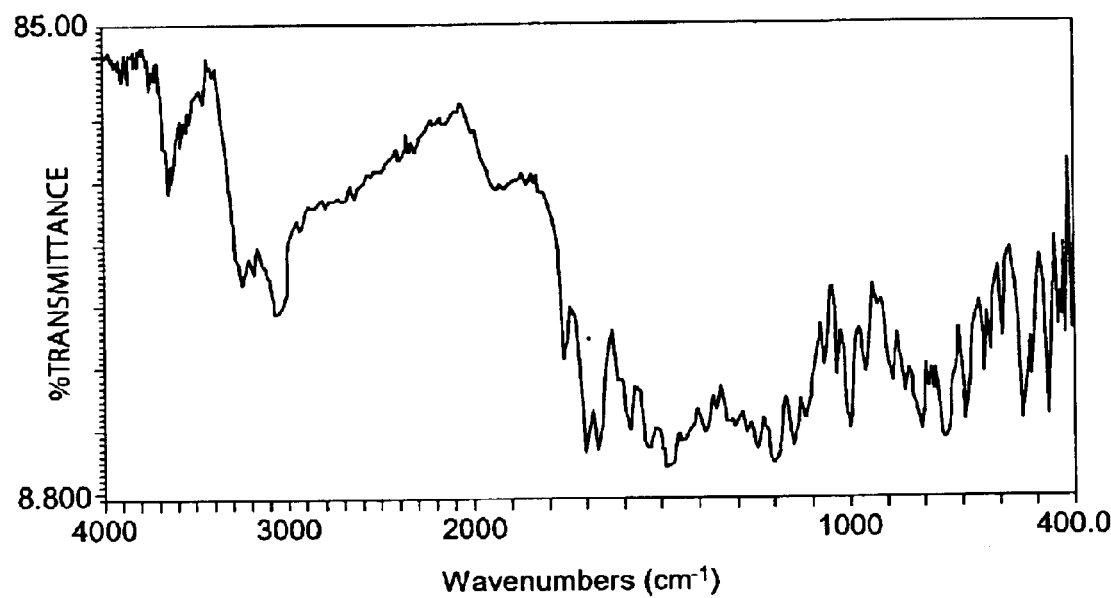

FIG. 148 is a graph showing an example of an infrared spectrum of an azo compound.

Figure 149:
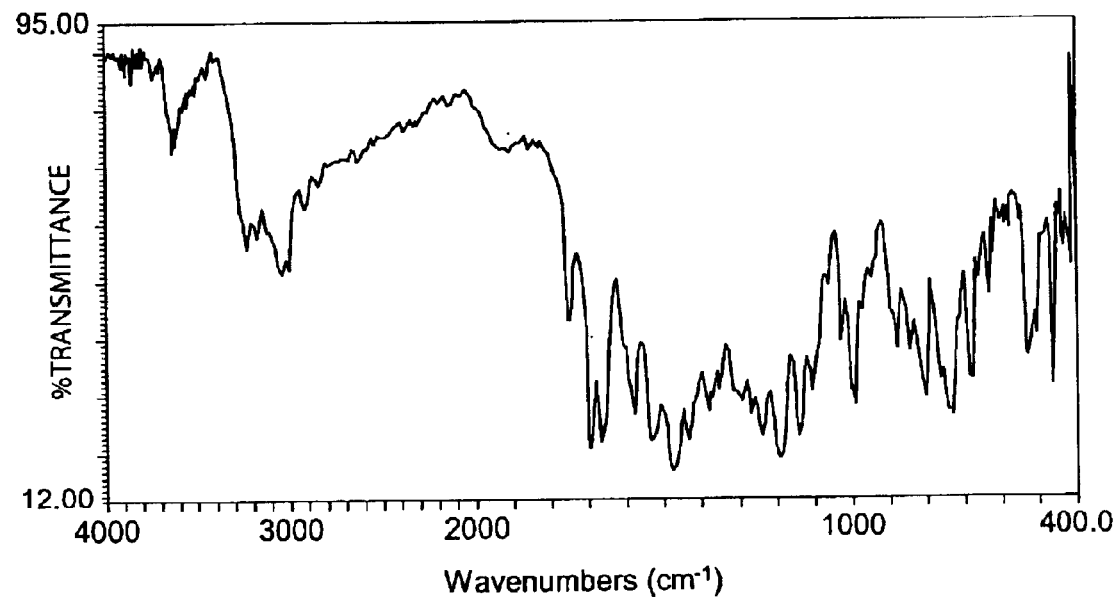

FIG. 149 is a graph showing an example of an infrared spectrum of an azo compound.

Figure 150:
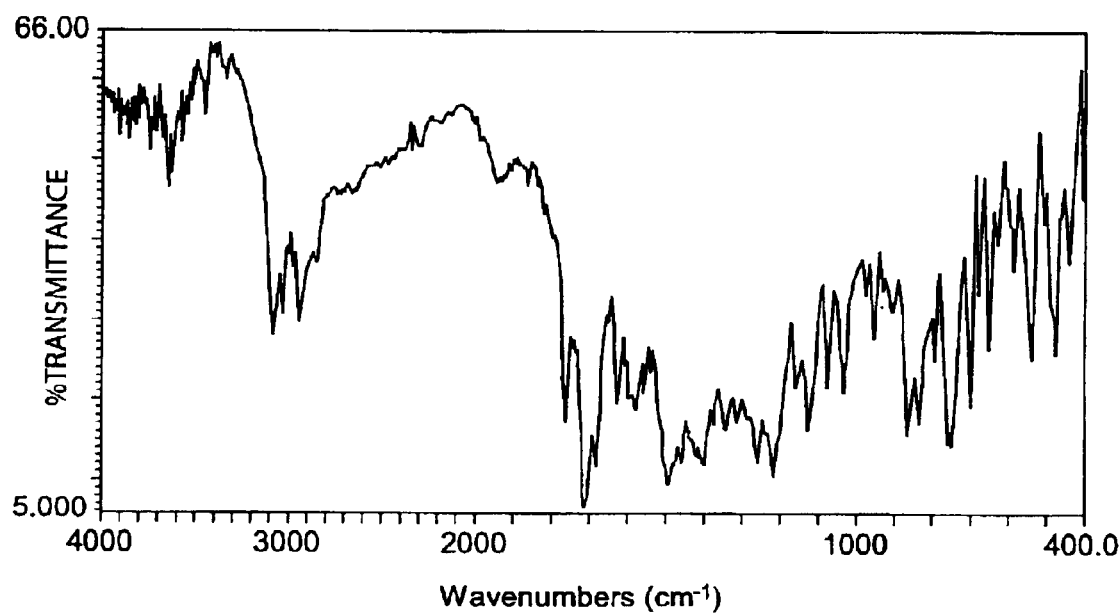

FIG. 150 is a graph showing an example of an infrared spectrum of an azo compound.

Figure 151:
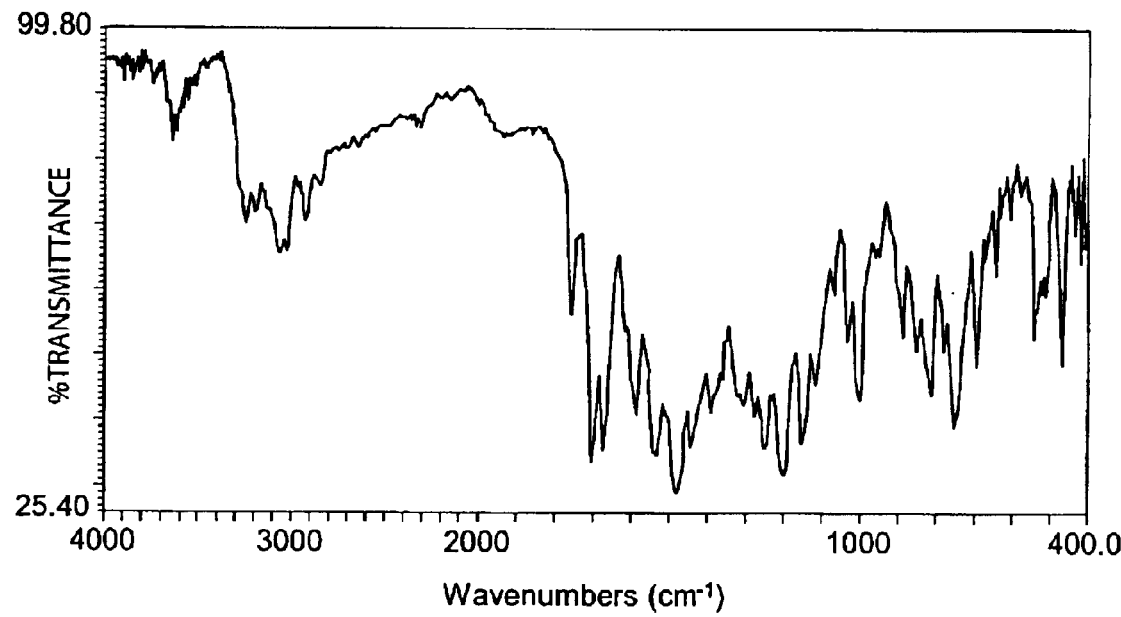

FIG. 151 is a graph showing an example of an infrared spectrum of an azo compound.

Figure 152:
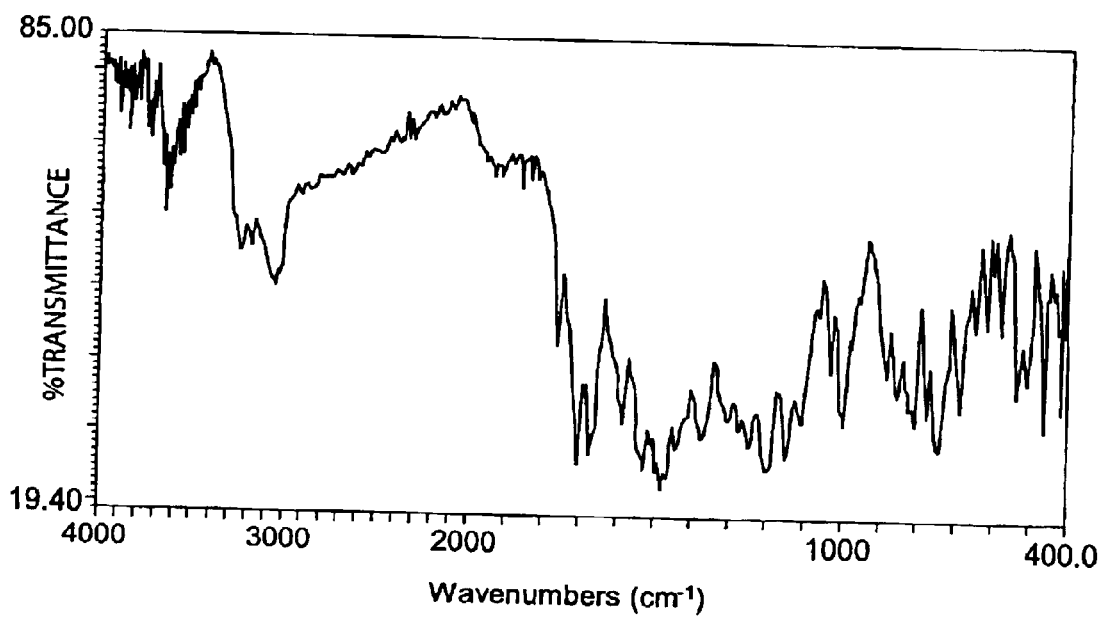

FIG. 152 is a graph showing an example of an infrared spectrum of an azo compound.

Figure 153:
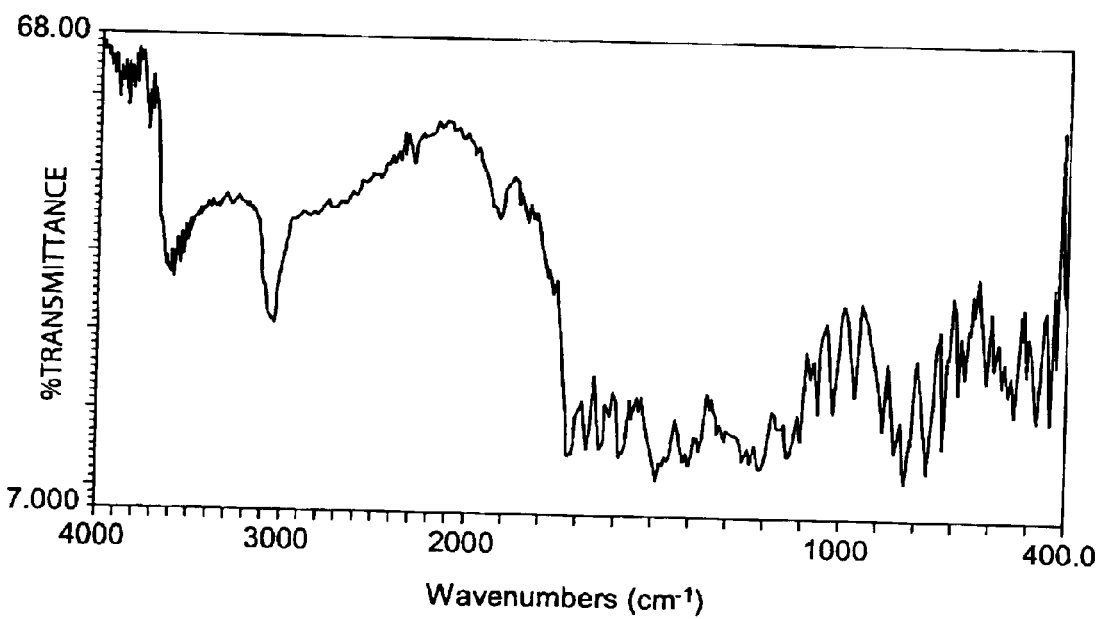

FIG. 153 is a graph showing an example of an infrared spectrum of an azo compound.

Figure 154:
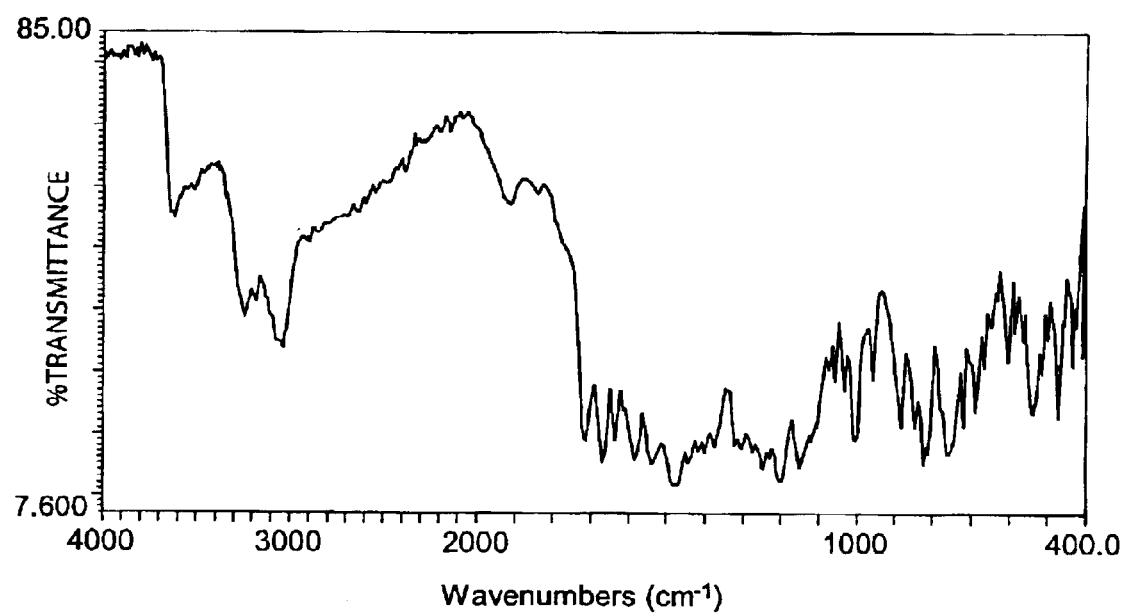

FIG. 154 is a graph showing an example of an infrared spectrum of an azo compound.

Figure 155:
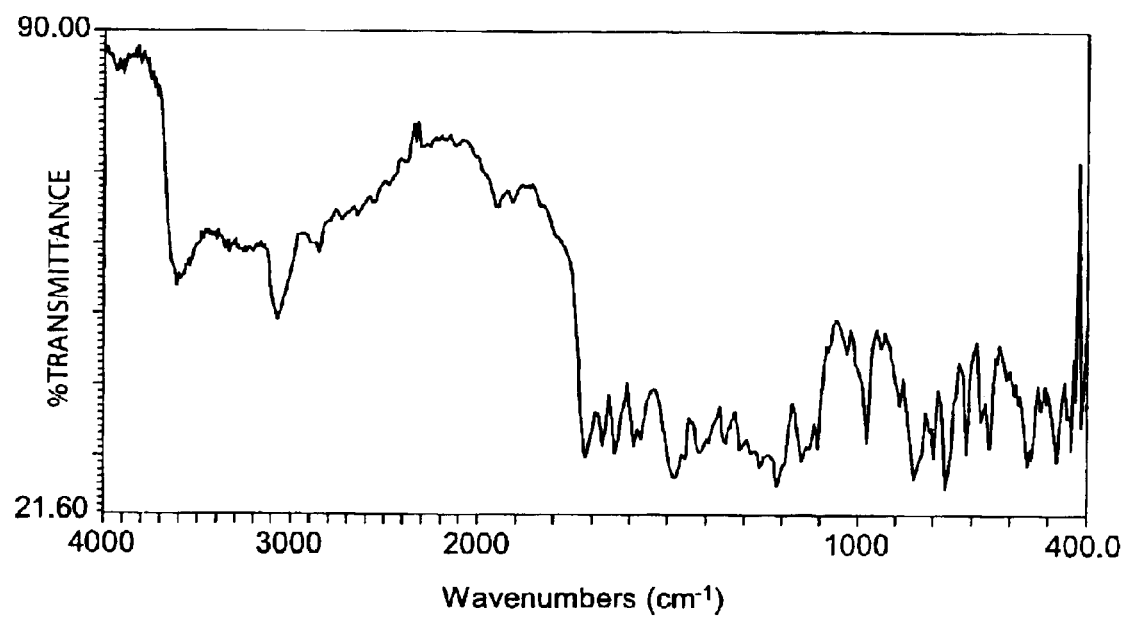

FIG. 155 is a graph showing an example of an infrared spectrum of an azo compound.

Figure 156:
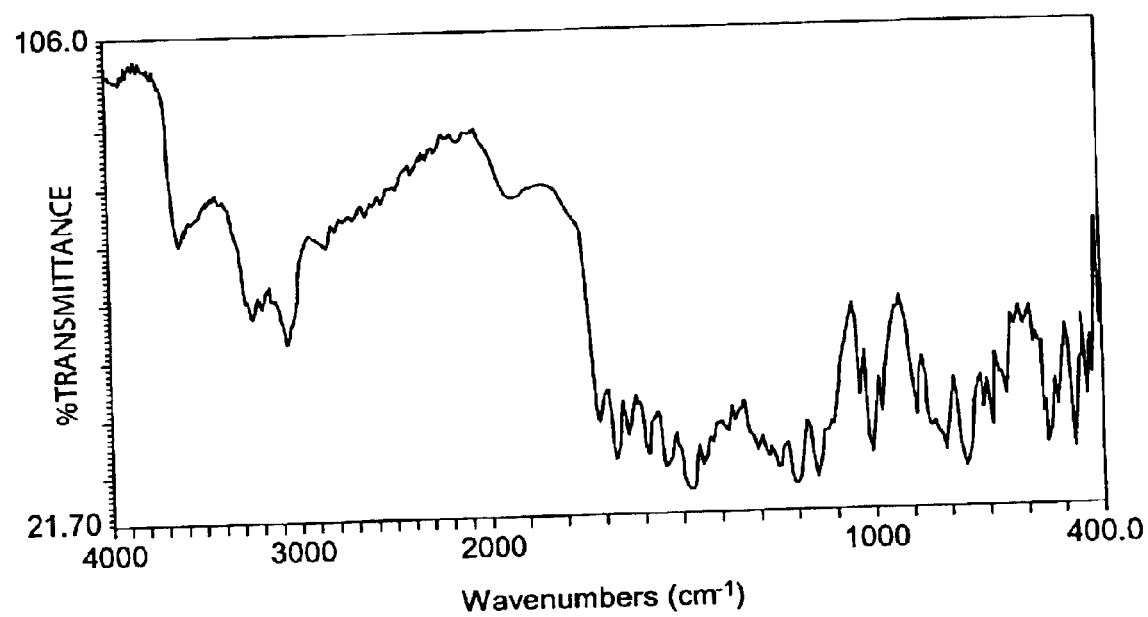

FIG. 156 is a graph showing an example of an infrared spectrum of an azo compound.

DESCRIPTION OF THE PREFERRED EMBODIMENTS

<Electrophotographic Photoconductor>

An electrophotographic photoconductor according to an embodiment of the present invention contains any of azo compounds represented by a general formula <<1>> in a photoconductive layer.

Now, the azo compounds will be explained in detail hereinafter.

In the present invention, among azo compounds indicated in the general formula <<1>> and to be contained in the photoconductive layer, examples of aromatic hydrocarbon groups which may have a substituent that may bond via a bond group indicated by Ar, include aromatic hydrocarbons such as benzene, naphthalene, fluorine, phenanthrene, anthracene, pyrene and the like, heterocycles such as furan, thiophene, pyridine, indole, benzothiazole, carbazole, acridone, dibenzothiophene, benzoxazole, benzotriazole, oxadiazole, thiadiazole and the like, and the compounds formed by bonding the above-mentioned aromatic rings directly or via aromatic groups or nonaromatic groups, for example, triphenylamine, diphenylamine, N-methyldiphenylamine, biphenyl, tarphenyl, binaphthyl, fluorenone, phenanthrenequinone, anthraquinone, benzanthrone, diphenyloxadiazole, phenylbenzoxazole, diphenylmethane, diphenylsulfone, diphenylether, benzophenone, stilbene, distilylbenzene, tetraphenyl-p-phenylenediamine, and tetraphenylbenzidinemonopyridilydiphenylamine and the like.

Among the above-mentioned main skeletons, fluorenon main skeletons indicated by the general formula <<10>>, the general formula <<13>>, and the general formula <<14>> are, in particular, preferable, because the azo compounds obtained by combining with a novel coupler residue of the present invention have high light sensitivity and better durability.

Examples of the substituents contained in the above-mentioned rings include alkyl groups such as a methyl group, an ethyl group, a propyl group, a butyl group, and the like, alkoxyl groups such as a methoxyl group an ethoxyl group, and the like, halogen atoms such as a fluorine atom, a chlorine atom, a bromine atom and the like, amino groups such as a dimethylamino group, a diethylamino group, and a diphenylamino group, a hydroxyl group, a nitro group, a cyano group, a halomethyl group and the like.

Now, examples of the main skeletons expressed by Ar will be shown in Table 1-1 and Table 1-2.

TABLE 1-1

| Main Skeleton (Ar) No. | Structure |
|---|---|
| A1 | —⟨benzene⟩—NO₂ |
| A2 | —⟨fluorene with H₃C, CH₃ at 9-position⟩— |
| A3 | —⟨Cl-phenyl⟩—⟨phenyl-Cl⟩— (biphenyl with Cl substituents) |
| A4 | —⟨phenyl⟩—⟨1,3,4-oxadiazole (N—N, O)⟩—⟨phenyl⟩— |
| A5 | —⟨phenyl⟩—⟨oxazole (N, O)⟩—⟨phenyl⟩— |
| A6 | —⟨phenyl⟩—⟨1,2,4-triazole (N—N, NH)⟩—⟨phenyl⟩— |

TABLE 1-1-continued

| Main Skeleton (Ar) No. | Structure |
|---|---|
| A7 | [structure: 1,4-phenylene–C≡C–1,4-phenylene] |
| A8 | [structure: 1,4-phenylene–N=N–1,4-phenylene] |
| A9 | [structure: fluorenone] |
| A10 | [structure: 9-ethylcarbazole] |
| A11 | [structure: dicyanomethylene fluorene] |
| A12 | [structure: dibenzothiophene S,S-dioxide] |
| A13 | [structure: dibenzothiophene] |
| A14 | [structure: phenyl–CH=CH–phenyl–CH=CH–phenyl] |
| A15 | [structure: phenyl–(CH=CH)$_2$–phenyl] |

TABLE 1-2

| Main Skeleton (Ar) No. | Structure |
|---|---|
| A16 | [structure: phenyl–(CH=CH)$_3$–phenyl] |
| A17 | [structure: benzoxazole–phenyl] |
| A18 | [structure: benzothiazole–phenyl] |
| A19 | [structure: anthraquinone (2,6-)] |
| A20 | [structure: anthraquinone (2,3-)] |
| A21 | [structure: xanthone] |
| A22 | [structure: acridone] |
| A23 | [structure: N(phenyl)$_3$] |
| A24 | [structure: phenanthrenequinone] |
| A25 | [structure: N(phenyl–CH=CH–phenyl)$_3$] |
| A26 | [structure: aceanthrylenone/benzanthrone-type] |

In the general formula <<2>>, the general formula <<3>>, the general formula <<4>>, the general formula <<9>>, the general formula <<11>>, the general formula <<12>>, the general formula <<10>>, the general formula <<13>>, and the general formula <<14>>, $R_1$, $R_2$, $R_3$, $R_4$, $R_5$, and $R_6$ indicate any one of alkoxyl groups such as a methyl group, an ethyl group, a propyl group, a butyl group, and the like; and hydrogen atoms such as a fluorine atom, a chlorine atom, a bromine atom and the like, amino groups such as a dimethylamino group, a diethylamino group, and a diphenylamino group, a hydroxyl group, a nitro group, a cyano group, an acetyl group, a benzoyl group which may have a substituent, an alkoxycarbonyl group, a phenoxycarbonyl group which may have a substituent, a carbamoyl group which may have a substituent, and the like.

In the general formula <<2>>, the general formula <<9>>, and the general formula <<10>>, X indicates any one of an alkyl groups such as a methyl group, an ethyl group, a propyl group, a butyl group, a pentyl group, a hexyl group, an octyl group, a decile group and the like, cyclic alkyl groups such as a cyclopentyl group, a cyclohexyl group and the like, aromatic hydrocarbon groups such as a phenyl group, a naphthyl group, an anthracenyl group, a phenanthrenyl group, a pyrenyl group and the like, heterocyclic groups such as a pyridyl group, a pyrazino group, a quinolino group, an oxazolyl group, a benzoxazolyl group, a thiazolyl group, a benzothiazolyl group, an imidazolyl group, a benzoimidazolyl group, an indolyl group and the like, alkylamino groups such as a methylamino group, an ethylamino group, and the like, aromatic amino groups such as a phenylamino group a naphthylamino group and the like, carboamino groups such as an acetylamino group, a benzoylamino group and the like.

Examples of the substituents for them include alkyl groups such as a methyl group, an ethyl group, a propyl group, a butyl group, and the like, substituent alkyl groups such as a benzyl group, a phenethyl group, a methoxymethyl group, and the like, alkoxyl groups such as a methoxyl group, an ethoxyl group, a phenoxyl group, a phenyl group which may have a substituent, a naphthyl group which may have a substituent, and the like, aromatic groups such as an anthracenyl group, a phenanthrenyl group, a pyrenyl group and the like, halogen atoms such as a fluorine atom, a chlorine atom, a bromine atom, and the like, a hydroxyl group, carboamino groups such as an amino group which may have a substituent, an acetylamino group, a benzoylamino group which may have a substituent, and the like, a nitro group, a cyano group, an acetyl group, a benzoyl group which may have a substituent, an alkoxycarbonyl group, a phenoxycarbonyl group which may have a substituent, a carbamoyl group which may have a substituent and the like.

Among the coupler residues represented in the general formula <<2>>, in particular, the residues represented in the general formula <<5>> are preferable because the residues enable the azo compounds obtained in the present invention to have high light sensitivity and better electrostatic stability.

In the general formula <<5>>, $A_1$ indicates any of aromatic hydrocarbon groups such as a phenyl group, a naphthyl group, an anthracenyl group, a phenanthrenyl group, a pyrenyl group and the like, heterocyclic groups such as a pyridyl group, a pyrazino group, a quinolino group, an oxazolyl group, a benzoxazolyl group, a thiazolyl group, a benzothiazolyl group, an imidazolyl group, a benzoimidazolyl group, an indolyl group, and the like and the substitu ents for them include alkyl groups such as a methyl group, an ethyl group, propyl group, a butyl group, and the like, substituent alkyl groups such as a benzyl group, a phenethyl group a methoxymethyl group, and the like, an alkoxyl groups such as a methoxyl group, an ethoxyl group and a phenoxyl group, and the like, a phenyl group which may have a substituent, halogen atoms such as a fluorine atom, a chlorine atom, a bromine atom, and the like, a trifluoromethyl group, a cyano group, an alkoxycarbonyl group, a carbamoyl group which may have a substituent, and the like.

In the general formula <<3>>, the general formula <<4>>, the general formula <<11>>, the general formula <<12>>, the general formula <<13>>, and the general formula <<14>>, Y indicates any one of a substituent or non-substituent alkylene group, bivalent organic residues having substituent or non-substituent aromaticity, bivalent organic residues having substituent or non-substituent heterocyclic aromaticity, and bivalent organic residues containing a carbonyl group represented by —CO—Z— (note that Z indicates a substituent or non-substituent alkylene group, any of bivalent organic residues having substituent or non-substituent aromaticity, and any of bivalent organic residues having substituent or non-substituent heterocyclic aromaticity). The alkylene group includes an ethylene group, a propylene group, a butylene group, a cyclopentyl group, a cyclohexyl group and the like. Note that the aromatic ring is formed via a carbon-carbon bond between the alkylene groups. The bivalent organic residues having aromaticity includes an o-phenylene group, a 1,8-naphtylene group, a 2,3-naphtylene group, a 1,2-anthrylene group, a 9,10-phenanthrylene group, and the like, the bivalent organic residue having heterocyclic aromaticity includes a 3,4-pyrimidyl group, 2,3-pyridinedyl group, 5,6-pyrimidinedyl group, a 6,7-benzimidadyl group, a 6,7-quinolidyl group, and the like, and the bivalent organic residue containing a carbonyl group includes a 2-benzoyl group, a 2-naphthylcarbonyl group, and the like. The substituents for them include alkyl groups such as a methyl group, an ethyl group, a propyl group, a butyl group, and the like, substituent alkyl groups such as a benzyl group, a phenethyl group, methoxymethyl group, and the like, alkoxyl groups such as a methoxyl group, an ethoxyl group, a phenoxyl group, and the like, a phenyl group which may have a substituent, a naphthyl group which may have a substituent, aromatic groups such as an anthracenyl group, a phenanthrenyl group, a pyrenyl group, and the like, halogen atoms such as a fluorine atom, a chlorine atom, a bromine atom, and the like, a hydroxyl group, carboamino groups such as an amino group which may have a substituent, an acetylamino group, a benzoylamino group which may have a substituent, a nitro group, a cyano group, an acetyl group, a benzoyl group which may have a substituent, an alkoxycarbonyl group, a phenoxycarbonyl group which may have a substituent, a carbamoyl group which may have a substituent, and the like.

Now, examples of the coupler compounds corresponding to the general formula <<2>>, the general formula <<3>>, and the general formula <<4>> are shown in Table 2-1 to 2-8 and in Table 3-1 to 3-.3

TABLE 2-1
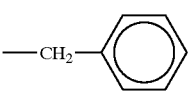
| Coupler (Cp) No. | R1 | R2 | R3 | R4 | R5 | R6 | X |
|---|---|---|---|---|---|---|---|
| C1 | H | H | H | H | H | H | —C$_6$H$_{13}$ |
| C2 | H | H | H | H | H | H | —C$_8$H$_{17}$ |
| C3 | —CH$_3$ | H | H | H | H | H | —C$_6$H$_{13}$ |
| C4 | H | —CH$_3$ | H | H | H | H | —C$_6$H$_{13}$ |
| C5 | H | H | H | H | H | H | —CH$_2$—C$_6$H$_5$ |
| C6 | H | —CH$_3$ | H | H | H | H | —CH$_2$—C$_6$H$_5$ |
| C7 | H | H | —CH$_3$ | H | H | H | —CH$_2$—C$_6$H$_5$ |
| C8 | H | H | H | H | H | —C$_2$H$_5$ | —CH$_2$—C$_6$H$_5$ |
| C9 | H | H | H | H | H | H | —CH$_2$—C$_6$H$_4$—CH$_3$ (p) |
| C10 | H | H | H | H | H | H | —CH$_2$—C$_6$H$_4$—OCH$_3$ (p) |
| C11 | H | H | H | H | H | H | —CH$_2$—C$_6$H$_4$—Cl (p) |
| C12 | H | H | H | H | H | H | —CH$_2$—C$_6$H$_4$—OCH$_3$ (m) |
| C13 | H | H | H | H | H | H | —CH$_2$—(1-naphthyl) |
| C14 | H | H | H | H | H | H | —CH$_2$CH$_2$—C$_6$H$_5$ |

TABLE 2-1-continued
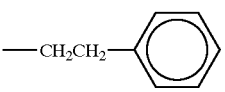
| Coupler (Cp) No. | R1 | R2 | R3 | R4 | R5 | R6 | X |
|---|---|---|---|---|---|---|---|
| C15 | —OCH$_3$ | H | H | H | H | H | —CH$_2$CH$_2$—C$_6$H$_5$ |
TABLE 2-2
| Coupler (Cp) No. | R1 | R2 | R3 | R4 | R5 | R6 | X |
|---|---|---|---|---|---|---|---|
| C16 | H | H | H | H | H | H | —CH$_2$CH$_2$—(C$_6$H$_4$)—CH$_3$ |
| C17 | H | H | H | H | H | H | —CH$_2$CH$_2$—(C$_6$H$_4$)—OCH$_3$ |
| C18 | H | H | H | H | H | H | —CH$_2$CH$_2$—(2,3-dimethylphenyl) |
| C19 | H | H | H | H | H | H | —CH$_2$CH$_2$—(2,5-dimethylphenyl) |
| C20 | H | H | H | H | H | H | —CH$_2$CH$_2$—C$_6$H$_4$—CH$_2$—C$_6$H$_5$ |
| C21 | H | H | H | H | H | H | —CH$_2$CH$_2$—(2-naphthyl) |
| C22 | H | H | H | H | H | H | —CH$_2$CH$_2$—(methoxynaphthyl) |
| C23 | H | H | H | H | H | H | —CH$_2$CH$_2$—(phenanthryl) |

TABLE 2-2-continued
| Coupler (Cp) No. | R1 | R2 | R3 | R4 | R5 | R6 | X |
|---|---|---|---|---|---|---|---|
| C24 | H | H | H | H | H | H | 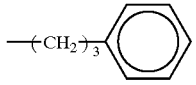 —(CH₂)₃—⌬ |
| C25 | H | —NO₂ | H | H | H | H | 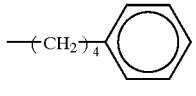 —(CH₂)₄—⌬ |
| C26 | H | H | H | H | H | H | —C₂H₄OCH₃ |
| C27 | H | H | H | H | H | H | —C₂H₄OCOCH₃ |
| C28 | H | H | H | H | H | H | 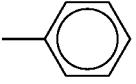 |
| C29 | —CH₃ | H | H | H | H | H |  |
| C30 | H | —OCH₃ | —CH₃ | H | H | H |  |
TABLE 2-3
| Coupler (Cp) No. | R1 | R2 | R3 | R4 | R5 | R6 | X |
|---|---|---|---|---|---|---|---|
| C31 | H | —Cl | H | H | H | H | 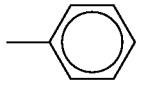 |
| C32 | H | H | H | H | H | H | 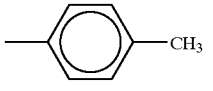 |
| C33 | H | H | H | H | H | H | 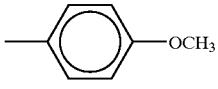 |
| C34 | H | H | H | H | H | H | 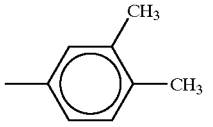 |
| C35 | H | H | —CH₃ | H | H | H | 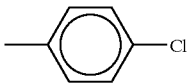 |
| C36 | H | H | H | H | H | H | 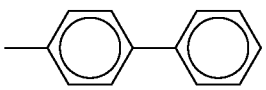 |
| C37 | H | H | H | H | H | H | 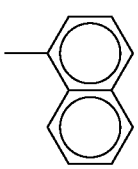 |

TABLE 2-3-continued

| Coupler (Cp) No. | R1 | R2 | R3 | R4 | R5 | R6 | X |
|---|---|---|---|---|---|---|---|
| C38 | H | H | H | H | H | H | 4-methoxynaphthalen-1-yl-methyl group |
| C39 | H | H | H | H | H | H | phenanthren-yl-methyl group |
| C40 | H | H | H | H | H | H | pyren-yl-methyl group |
| C41 | H | H | H | H | H | H | —CH$_2$-(pyridin-2-yl) |
| C42 | H | H | H | H | H | H | pyridin-2-yl-methyl group |
| C43 | H | H | H | H | H | H | pyridin-4-yl-methyl group |
| C44 | H | H | H | H | H | H | quinolin-2-yl-methyl group |
| C45 | H | H | H | H | H | H | quinolin-3-yl-methyl group |

TABLE 2-4

| Coupler (Cp) No. | R1 | R2 | R3 | R4 | R5 | R6 | X |
|---|---|---|---|---|---|---|---|
| C46 | H | H | H | H | H | H | H |
| C47 | H | H | H | H | H | H | —CH$_3$ |
| C48 | H | H | H | H | H | H | —C$_2$H$_5$ |
| C49 | H | H | H | H | H | H | 2-methoxybenzyl group (—CH$_2$-C$_6$H$_4$-OCH$_3$) |

TABLE 2-4-continued
| Coupler (Cp) No. | R1 | R2 | R3 | R4 | R5 | R6 | X |
|---|---|---|---|---|---|---|---|
| C50 | H | H | H | H | H | H | 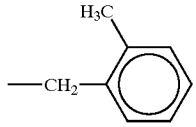 |
| C51 | H | H | H | H | H | H | 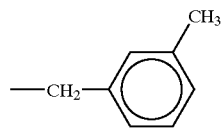 |
| C52 | H | H | H | H | H | H | 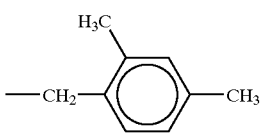 |
| C53 | H | H | H | H | H | H | 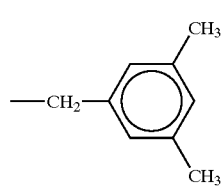 |
| C54 | H | H | H | H | H | H | 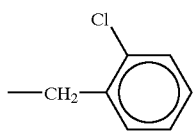 |
| C55 | H | H | H | H | H | H | 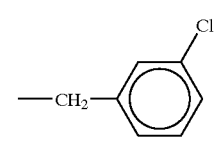 |
| C56 | H | H | H | H | H | H | 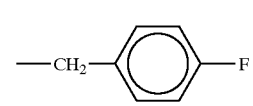 |
| C57 | H | H | H | H | H | H | 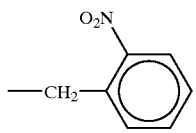 |
| C58 | H | H | H | H | H | H | 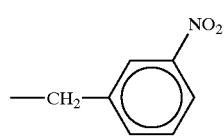 |
| C59 | H | H | H | H | H | H | 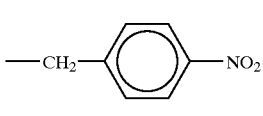 |
| C60 | H | H | H | H | H | H |  |

TABLE 2-5
| Coupler (Cp) No. | R1 | R2 | R3 | R4 | R5 | R6 | X |
|---|---|---|---|---|---|---|---|
| C61 | H | H | H | H | H | H | 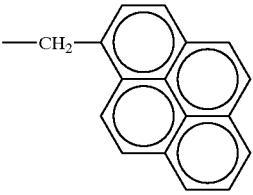 |
| C62 | H | H | H | H | H | H | 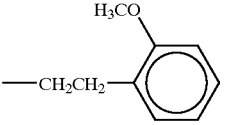 |
| C63 | H | H | H | H | H | H | 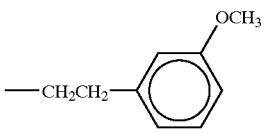 |
| C64 | H | H | H | H | H | H | 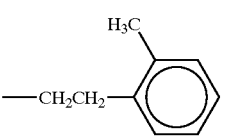 |
| C65 | H | H | H | H | H | H | 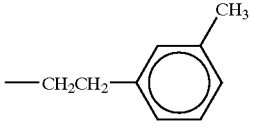 |
| C66 | H | H | H | H | H | H | 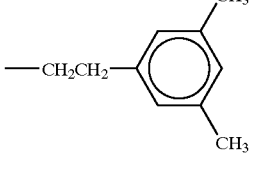 |
| C67 | H | H | H | H | H | H | 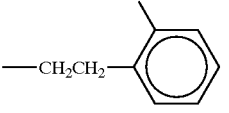 |
| C68 | H | H | H | H | H | H | 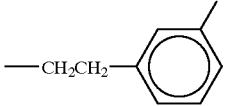 |
| C69 | H | H | H | H | H | H | 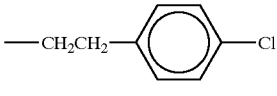 |
| C70 | H | H | H | H | H | H | 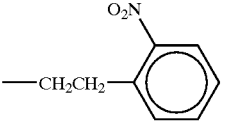 |

TABLE 2-5-continued
| Coupler (Cp) No. | R1 | R2 | R3 | R4 | R5 | R6 | X |
|---|---|---|---|---|---|---|---|
| C71 | H | H | H | H | H | H | 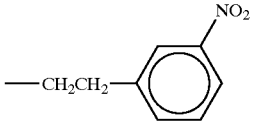 |
| C72 | H | H | H | H | H | H | 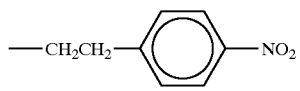 |
| C73 | H | H | H | H | H | H | 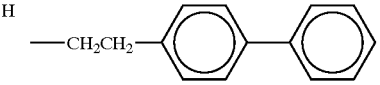 |
| C74 | H | H | H | H | H | H | —C$_3$H$_7$ |
| C75 | H | H | H | H | H | H | —C$_4$H$_9$ |
TABLE 2-6
| Coupler (Cp) No. | R1 | R2 | R3 | R4 | R5 | R6 | X |
|---|---|---|---|---|---|---|---|
| C76 | H | H | H | H | H | H | —C$_5$H$_{11}$ |
| C77 | H | H | H | H | H | H |  |
| C78 | H | H | H | H | H | H |  |
| C79 | H | H | H | H | H | H |  |
| C80 | H | H | H | H | H | H | 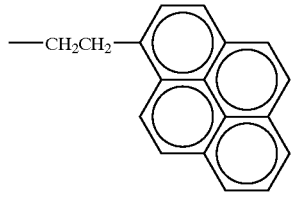 |
| C81 | H | H | H | H | H | H | 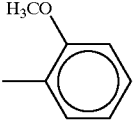 |
| C82 | H | H | H | H | H | H | 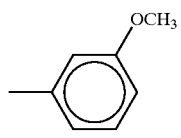 |

TABLE 2-6-continued
| Coupler (Cp) No. | R1 | R2 | R3 | R4 | R5 | R6 | X |
|---|---|---|---|---|---|---|---|
| C83 | H | H | H | H | H | H | 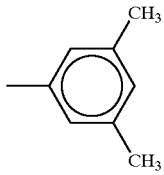 |
| C84 | H | H | H | H | H | H | 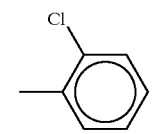 |
| C85 | H | H | H | H | H | H | 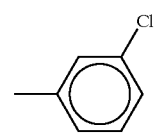 |
| C86 | H | H | H | H | H | H |  |
| C87 | H | H | H | H | H | H |  |
| C88 | H | H | H | H | H | H | 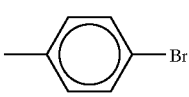 |
| C89 | H | H | H | H | H | H | 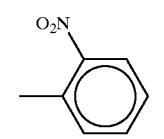 |
| C90 | H | H | H | H | H | H | 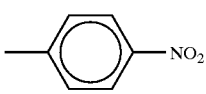 |
TABLE 2-7
| Coupler (Cp) No. | R1 | R2 | R3 | R4 | R5 | R6 | X |
|---|---|---|---|---|---|---|---|
| C91 | H | H | H | H | H | H | 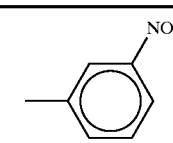 |
| C92 | H | H | H | H | H | H | 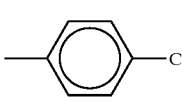 |
| C93 | H | H | H | H | H | H | 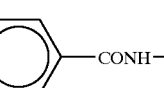 |
| C94 | H | H | H | H | H | H | 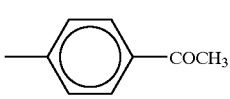 |

TABLE 2-7-continued

| Coupler (Cp) No. | R1 | R2 | R3 | R4 | R5 | R6 | X |
|---|---|---|---|---|---|---|---|
| C95 | H | H | H | H | H | H | -C6H4-NHCO-C6H5 |
| C96 | H | H | H | H | H | H | -NHCO-C6H5 |
| C97 | H | H | H | H | H | H | cyclohexyl |
| C98 | H | H | H | H | H | H | -CH2-cyclohexyl |
| C99 | H | H | H | H | H | H | -CH2CH2-cyclohexyl |
| C100 | H | H | H | H | H | H | 2-benzoxazolyl |
| C101 | H | H | H | H | H | H | 2-benzothiazolyl |
| C102 | H | H | H | H | H | H | 2-benzimidazolyl |
| C103 | H | H | H | H | H | H | -C6H4-OCO-C6H5 |

TABLE 2-8

| Coupler (Cp) No. | R1 | R2 | R3 | R4 | R5 | R6 | X |
|---|---|---|---|---|---|---|---|
| C104 | H | H | H | H | H | H | 2-indanyl |
| C105 | H | H | H | H | H | H | 1-indanyl |
| C106 | H | H | H | H | H | H | 1-tetralinyl |
| C107 | H | H | H | H | H | H | -CH2-C6H4(2-CF3) |
| C108 | H | H | H | H | H | H | -CH2-C6H4(3-CF3) |
| C109 | H | H | H | H | H | H | -CH2-C6H4(4-CF3) |

TABLE 2-8-continued

| Coupler (Cp) No. | R1 | R2 | R3 | R4 | R5 | R6 | X |
|---|---|---|---|---|---|---|---|
| C110 | H | H | H | H | H | H | 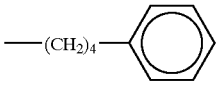 —(CH$_2$)$_4$—Ph |
| C111 | H | H | H | H | H | H | 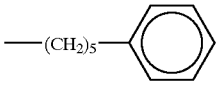 —(CH$_2$)$_5$—Ph |
| C112 | H | H | H | H | H | H | 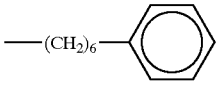 —(CH$_2$)$_6$—Ph |
| C113 | H | H | H | H | H | H | 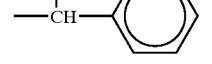 —CH(CH$_3$)—Ph |
| C114 | H | H | H | H | H | H | 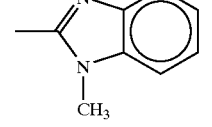 1,2-dimethylbenzimidazol-yl |

TABLE 3-1

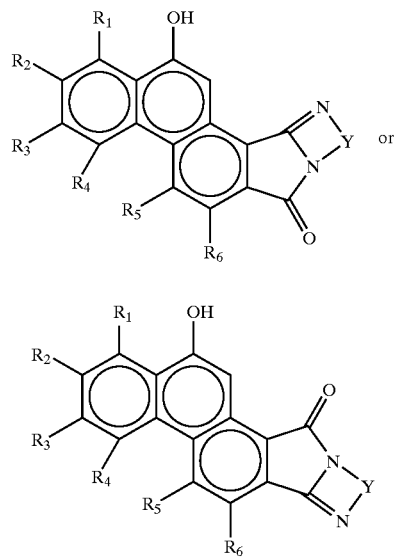

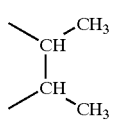

| Coupler (Cp) No. | R1 | R2 | R3 | R4 | R5 | R6 | Y |
|---|---|---|---|---|---|---|---|
| E1 | H | H | H | H | H | H | 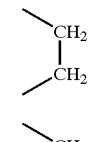 |
| E2 | H | —CH$_3$ | H | H | H | H |  |

TABLE 3-1-continued

| Coupler (Cp) No. | R1 | R2 | R3 | R4 | R5 | R6 | Y |
|---|---|---|---|---|---|---|---|
| E3 | H | H | H | H | H | H | 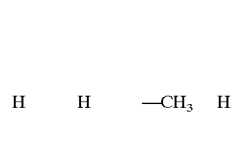 —CH(CH$_3$)$_2$ |
| E4 | H | H | H | H | H | H | 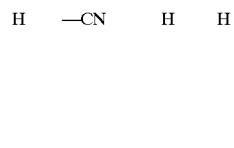 cyclohexyl |
| E5 | H | H | —CH$_3$ | H | H | H | 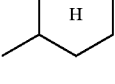 cyclohexyl |
| E6 | H | —CN | H | H | H | H |  |
| E7 | H | H | H | H | H | H | 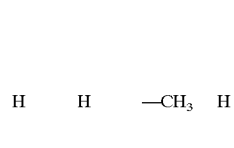 —CH$_2$CH$_2$CH$_2$— |
| E8 | H | H | —CH$_3$ | H | H | H | 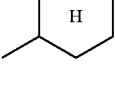 —CH$_2$CH$_2$CH$_2$— |
| E9 | H | —OCH$_3$ | H | H | H | H | 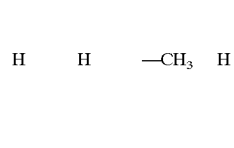 —CH$_2$CH$_2$CH$_2$— |

TABLE 3-1-continued

[Structure 1: Naphthalene-fused ring with OH, R1-R6 substituents, and N-Y-N-C(=O) heterocycle]

or

[Structure 2: Similar naphthalene-fused ring with OH, R1-R6, and C(=O)-N-Y-N heterocycle]

| Coupler (Cp) No. | R1 | R2 | R3 | R4 | R5 | R6 | Y |
|---|---|---|---|---|---|---|---|
| E10 | H | —CN | H | H | H | H | —CH(CH₃)—CH(CHCH₃)—CH(CH₃) (branched alkyl: —CH(CH₃)CH(CH₃)CH(CH₃)—) |

TABLE 3-2

| Coupler (Cp) No. | R1 | R2 | R3 | R4 | R5 | R6 | Y |
|---|---|---|---|---|---|---|---|
| E11 | H | —N(Et)₂ | H | H | H | H | decahydronaphthyl (trans-decalin, with two H shown) |
| E12 | H | H | H | H | H | H | o-phenylene (1,2-disubstituted benzene) |
| E13 | —CH₃ | H | H | H | H | H | o-phenylene |
| E14 | H | —OCH₃ | H | H | H | H | o-phenylene |

TABLE 3-2-continued
| Coupler (Cp) No. | R1 | R2 | R3 | R4 | R5 | R6 | Y |
|---|---|---|---|---|---|---|---|
| E15 | H | H | —CH₃ | H | H | H | 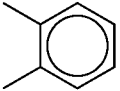 |
| E16 | H | H | H | H | H | —CH₃ | 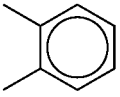 |
| E17 | H | H | H | H | H | H | 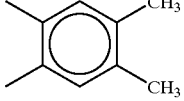 |
| E18 | H | —CH₃ | H | H | H | H | 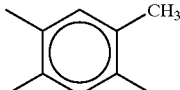 |
| E19 | H | H | H | H | H | H | 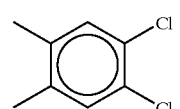 |
| E20 | H | H | H | H | H | H | 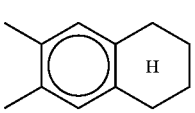 |
| E21 | H | H | H | H | H | H | 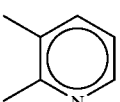 |
| E22 | H | —N(CH₃)₂ | H | H | H | H | 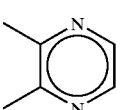 |
| E23 | H | H | H | H | H | H | 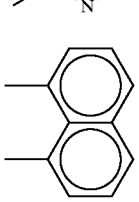 |
| E24 | —CH₃ | H | H | H | H | H | 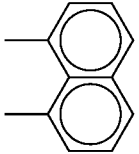 |
| E25 | H | H | —CH₃ | H | H | H | 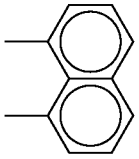 |

TABLE 3-3

| Coupler (Cp) No. | R1 | R2 | R3 | R4 | R5 | R6 | Y |
|---|---|---|---|---|---|---|---|
| E26 | H | H | H | H | H | H | 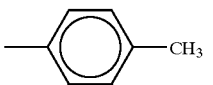 |
| E27 | H | H | H | H | H | H | 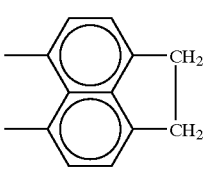 |
| E28 | H | H | H | H | H | H | 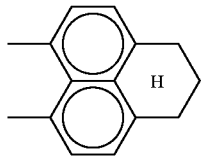 |
| E29 | H | H | H | H | H | H | 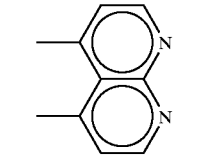 |
| E30 | H | H | H | H | H | H | 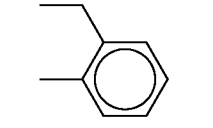 |
| E31 | H | H | H | H | H | H | 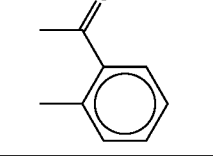 |

In addition to the coupler residues represented in the above-listed general formula <<2>>, general formula <<3>>, and general formula <<4>>, examples of the coupler residues (Cp') which may coexist include the compounds having a phenol hydroxyl group such as any of phenols and naphthols, aromatic amino compounds having an amino group, the compounds having any of amino groups such as any of amino naphthols, a phenol hydroxyl group, and the like, the compounds having any of fatty or aromatic enol-ketone (the compounds having an active methylene group) and the like. In particular, the preferable compounds are represented by the following general formulae (Cp1)-(Cp15).

General formula (Cp1)

General formula (Cp2)

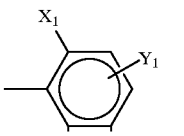

General formula (Cp3)

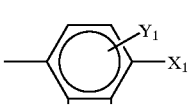

General formula (Cp4)

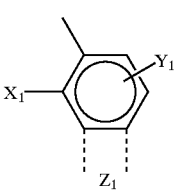

In the general formula <<Cp1>>, the general formula <<Cp2>>, the general formula <<Cp3>>, and the general formula <<Cp4>>, $X_1$, $Y_1$, $Z_1$, and m each indicates the followings.

$X_1$: —OH, —N($R_{11}$)($R_{12}$), or —NHSO$_2$—$R_{13}$($R_{11}$ and $R_{12}$ indicate a hydrogen atom, or a substituent or non-substituent alkyl group, and $R_{13}$ indicates a substituent or non-substituent alkyl group, or a substituent or non-substituent allyl group.)

$Y_1$: a hydrogen atom, a halogen atom, a substituent or non-substituent alkyl group, a substituent or non-substituent alkoxyl group, a carboxyl group, a sulfo group, a substituent or non-substituent sulfamoyle group, or —CON($R_{14}$)($Y_2$) [($R_{14}$ indicates a hydrogen, an alkyl group or a substitution product thereof, or a phenyl group or a substitution product thereof. $Y_2$ indicates a hydrocarbon cyclic group, or a substitution product thereof, a heterocyclic group, or a substitution product thereof, or —N=C($R_{15}$)($R_{16}$)(note that $R_{15}$ may indicate a hydrocarbon cyclic group, a substitution product thereof, a heterocyclic group or, a substitution product thereof, or a sterile group, a substitution product thereof, and $R_{16}$ may indicate a hydrogen atom, an alkyl group, a phenyl group or, a substitution product thereof, alternately, $R_{15}$ and $R_{16}$ may form a ring by binding to a hydrogen atom.))]. $Z_1$: a hydrocarbon ring or, a substitution product thereof, or heterocycle or, a substitution product thereof l: an integer of 1 or 2
m: an integer of 1 or 2

General formula (Cp5)

[In the general formula (Cp5), $R_{17}$ expresses a substituent or non-substituent hydrogen group and $X_1$ refers to the same as the mentioned above.]

[Formula structure 40]

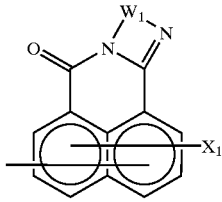

(Cp6)

[In the general formula (Cp6), $W_1$ expresses a bivalent group of an aromatic hydrocarbon or a bivalent group of a heterocycle containing a nitrogen atom in its ring. Alternately, these rings may be either substituents or non-substituents. $X_1$ refers to the same as the mentioned above.]

General formula (Cp7)

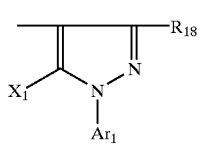

[In the general formula (Cp7), $R_{18}$ indicates an alkyl group, a carbamoyl group, or a carboxyl group or an ester thereof, $Ar_1$ indicates a hydrocarbon ring or a substitution product thereof, and $X_1$ is the same as that mentioned above.]

General formula (Cp8)

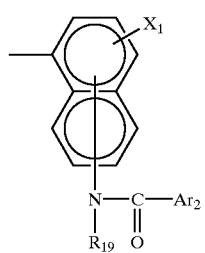

General formula (Cp9)

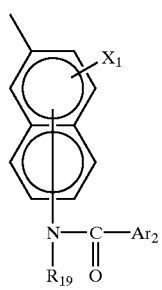

[In the general formula (Cp8) and the general formula (Cp9), $R_{19}$ indicates a hydrogen atom, or a substituent or non-substituent hydrocarbon group, and Ar2 indicates a hydrocarbon ring group or a substitution product thereof.]

In the general formula (Cp1) to the general formula (Cp4), examples of a hydrocarbon ring, $Z_1$ include a benzene ring, a naphthalene ring, and the like; examples of the heterocycle which may have a substituent include a dibenzofuran ring and the like; examples of the substituent in the ring, $Z_1$ include halogen atoms such as a chlorine atom, a bromine atom and the like.

Examples of hydrocarbon ring group groups corresponding to $Y_2$ or $R_{15}$ include a phenyl group, a naphtyl group, an anthryl group, a pyrenyl group and the like. Examples of heterocyclic groups include a pyridyl group, a thienyl group, a furyl group, an indoryl group, a benzofuranyl group, a carbazoryl group, a dibenzofuranyl group, and the like. Further a fluorene ring-may be given as an example of the ring formed by means of binding between $R_{15}$ and $R_{16}$.

Examples of the hydrocarbon ring groups, heterocyclic groups corresponding to $Y_2$ or $R_{15}$, and substituents for rings formed by $Y_2$ or $R_{15}$ include alkyl groups such as a methyl group, an ethyl group, a propyl group, a buthyl group and the like, alkoxyl groups such as a methoxyl group, an ethoxyl group, a propoxyl group, a butoxyl group and the like, halogen atoms such as a fluorine atom, a chlorine atom, and the like dialkylamino groups such as a dimethylamino group, a diethylamino group, and the like, halomethyl groups such as a trifluoromethyl, a nitro group, a cyano group, a carboxyl group or ester, a hydroxyl group, a sulfonic acid base such as —$SO_3Na$, and the like.

Examples of the substituents for the phenyl group include halogen atoms such as a chloride atom, a bromine atom and the like.

Typical examples of the hydrocarbon group corresponding to $R_{17}$ or $R_{19}$ include alkyl groups such as a methyl group, an ethyl group, a propyl group, a buthyl group and the like, aryl groups such as a phenyl group and the like, and substituents thereof.

Examples of the substituents corresponding to $R_{17}$ or $R_{19}$ include alkyl groups such as a methyl group, an ethyl group, a propyl group, and a buthyl group, and the like alkoxyl groups such as a methoxyl group, an ethoxyl group, a propoxyl group, a butoxyl group and the like, halogen atoms such as a chloride atom, a bromine atom, and the like a hydroxyl group, a nitro group and the like.

Typical examples of the hydrocarbon ring group corresponding to $Ar_1$ and $Ar_2$ include a phenyl group, a naphtyl group, and the like. A phenyl group and a naphtyl group may be given as typical examples of the hydrocarbon ring group corresponding to $Ar_1$ and $Ar_2$. Examples of the substituents include alkyl groups such as a methyl group, an ethyl group, a propyl group, and a butyl group, alkoxyl groups such as a methoxyl group, an ethoxyl group, a propoxyl group, a butoxyl group, and the like a nitro group, halogen atoms such as a chloride atom, a bromine atom, and the like, a cyano group, and dialkylamino groups such as a dimethylamino group, a diethylamino group, and the like.

In $X_1$, the hydroxyl group is particularly suitable.

Among the coupler residues mentioned above, those represented in the general formula (Cp2), the general formula (Cp5), the general formula (Cp6), the general formula (Cp7), the general formula (Cp8), and the general formula (Cp9) are preferable, and in particular, the residues, of which $X_1$ is a hydroxyl group, are more preferable. Among the coupler residues represented in the general formula (Cp2), in particular, those represented in the general formula (Cp10) are preferable, and General formula (Cp10)

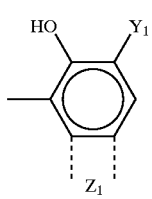

($Y_1$ and $Z_1$ are the same as those mentioned above.)

The coupler residues represented in the general formula (Cp11) are further more preferable.

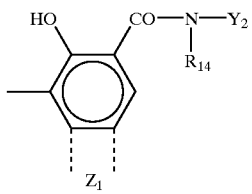

General formula (Cp11)

($Z_1$, $Y_2$, and $R_{14}$ are the same as those mentioned above.)

Further, among the preferable coupler residues mentioned above, those represented in the general formula (Cp12) or the general formula (Cp13) are suitable.

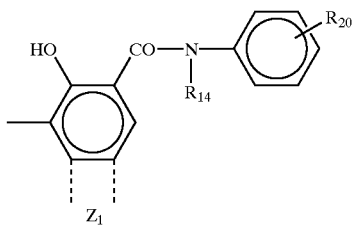

General formula (Cp12)

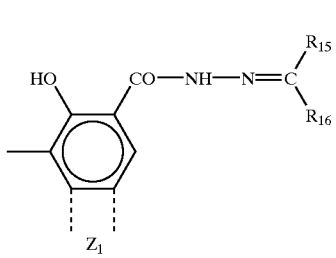

General formula (Cp13)

($Z_1$, $R_{14}$, $R_{15}$, and $R_{16}$ are the same as those mentioned above and the substituents for $Y_2$ may be given as examples of $R_{20}$.)

Among the coupler residues represented in the general formula (Cp6), in particular, those represented in the general formula (Cp14) or the general formula (Cp15) are preferable.

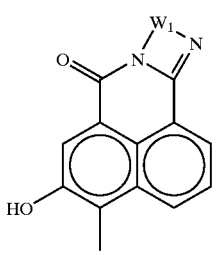

General formula (Cp14)

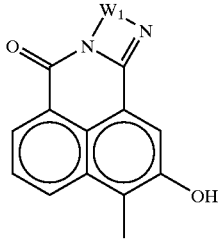

General formula (Cp15)

($W_1$ indicates a bivalent group of an aromatic hydrocarbon or a bivalent group of the heterocycle containing a nitrogen atom in its ring. These rings may be either substituents or non-substituents.

Among the preferable coupler residues mentioned above, in particular, those represented in the general formula <<6>>, the general formula <<7>>, and the general formula <<8>> are more preferable because the azo compounds obtained by combining a novel coupler residue of the present invention have high sensitivity and exhibit better electrostatic stability.

Now, examples of the coupler compounds are shown below in tables 4-1 through 19 corresponding to those represented in the general formula (Cp1) to the general formula (Cp15).

TABLE 4-1

| Coupler No. | $R^1$ | $(R^2)_n$ | Melting Point (° C.) |
|---|---|---|---|
| 1 | H | H | 243~244 |
| 2 | H | 2-$NO_2$ | 194~196 |
| 3 | H | 3-$NO_2$ | 246~247 |
| 4 | H | 4-$NO_2$ | 266~267.5 |
| 5 | H | 2-$CF_3$ | 178~179 |
| 6 | H | 3-$CF_3$ | 237.5~238.5 |
| 7 | H | 4-$CF_3$ | 279~281 |
| 8 | H | 2-CN | 221~222.5 |
| 9 | H | 3-CN | 256.5~258.5 |
| 10 | H | 4-CN | 274.5~277 |
| 11 | H | 2-I | 199~199.5 |
| 12 | H | 3-I | 258.5~259.5 |
| 13 | H | 4-I | 261.5~262 |
| 14 | H | 2-Br | 217~218 |
| 15 | H | 3-Br | 254~255 |
| 16 | H | 4-Br | 265~268 |
| 17 | H | 2-Cl | 228~230 |
| 18 | H | 3-Cl | 256.5~257 |

TABLE 4-2

| Coupler No. | $R^1$ | $(R^2)_n$ | Melting Point (° C.) |
|---|---|---|---|
| 19 | H | 4-Cl | 264~266 |
| 20 | H | 2-F | 223.0~224.0 |
| 21 | H | 3-F | 250.0~251.0 |
| 22 | H | 4-F | 265.0~267.0 |

TABLE 4-2-continued

| Coupler No. | R¹ | (R²)ₙ | Melting Point (° C.) |
|---|---|---|---|
| 23 | H | 2-CH₃ | 195.5~198.0 |
| 24 | H | 3-CH₃ | 214.5~216.5 |
| 25 | H | 4-CH₃ | 227.0~229.0 |
| 26 | H | 2-C₂H₅ | 168.5~169.5 |
| 27 | H | 4-C₂H₅ | 203.0~204.5 |
| 28 | H | 2-OCH₃ | 167~168 |
| 29 | H | 3-OCH₃ | 195.5~198.0 |
| 30 | H | 4-OCH₃ | 229~230 |
| 31 | H | 2-OC₂H₅ | 157~158 |
| 32 | H | 3-OC₂H₅ | 188.5~189.0 |
| 33 | H | 4-OC₂H₅ | 225.0~225.5 |
| 34 | H | 4-N(CH₃)₂ | 232.0~233.5 |
| 35 | —CH₃ | H | 189.5~190.5 |
| 36 | 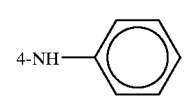 | H | 182.0~183.0 |
| 37 | H | 2-OCH₃, 5-OCH₃ | 186.0~188.0 |
| 38 | H | 2-OC₂H₅, 5-OC₂H₅ | 173.0~173.5 |
| 39 | H | 2-CH₃, 5-CH₃ | 207.0~208.5 |
| 40 | H | 2-Cl, 5-Cl | 253.5~254.5 |

TABLE 4-3

| Coupler No. | R¹ | (R²)ₙ | Melting Point (° C.) |
|---|---|---|---|
| 41 | H | 2-CH₃, 5-Cl | 245~247 |
| 42 | H | 2-OCH₃, 4-OCH₃ | 151.0~152.0 |
| 43 | H | 2-CH₃, 4-CH₃ | 226~228 |
| 44 | H | 2-CH₃, 4-Cl | 244~245 |
| 45 | H | 2-NO₂, 4-OCH₃ | 179.5~181.0 |
| 46 | H | 3-OCH₃, 5-OCH₃ | 180.5~182.0 |
| 47 | H | 2-OCH₃, 5-Cl | 219.0~220.0 |
| 48 | H | 2-OCH₃, 5-OCH₃, 4-Cl | 193.5~195.5 |
| 49 | H | 2-OCH₃, 4-OCH₃, 5-Cl | 193~194 |
| 50 | H | 3-Cl, 4-Cl | 272.5~273.5 |
| 51 | H | 2-Cl, 4-Cl, 5-Cl | 257.5~258.5 |
| 52 | H | 2-CH₃, 3-Cl | 227.5~228.5 |
| 53 | H | 3-Cl, 4-CH₃ | 259.5~260.5 |
| 54 | H | 2-F, 4-F | 246.0~246.5 |
| 55 | H | 2-F, 5-F | 259.0~260.0 |
| 56 | H | 2-Cl, 4-NO₂ | 283.0~284.0 |
| 57 | H | 2-NO₂, 4-Cl | 226.5~227.5 |
| 58 | H | 2-Cl, 3-Cl, 4-Cl, 5-Cl | 280.0~281.5 |
| 59 | H | 4-OH | 268 |

TABLE 5-1

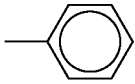

| Coupler No. | R¹ | (R²)ₙ | Melting Point (° C.) |
|---|---|---|---|
| 60 | H | H | >300 |
| 61 | H | 2-NO₂ | 283~284 |
| 62 | H | 3-NO₂ | >300 |
| 63 | H | 4-NO₂ | >300 |
| 64 | H | 2-Cl | >300 |
| 65 | H | 3-Cl | >300 |
| 66 | H | 4-Cl | >300 |
| 67 | H | 2-CH₃ | >300 |
| 68 | H | 3-CH₃ | >300 |
| 69 | H | 4-CH₃ | >300 |
| 70 | H | 2-C₂H₅ | 271~273 |
| 71 | H | 4-C₂H₅ | >300 |
| 72 | H | 2-OCH₃ | 276~278 |
| 73 | H | 3-OCH₃ | >300 |
| 74 | H | 4-OCH₃ | >300 |
| 75 | H | 2-OC₂H₅ | 273.5~275.0 |
| 76 | H | 4-OC₂H₅ | >300 |
| 77 | H | 2-CH₃, 4-OCH₃ | 296 |

TABLE 5-2

| Coupler No. | R¹ | (R²)ₙ | Melting Point (° C.) |
|---|---|---|---|
| 78 | H | 2-CH₃, 4-CH₃ | >300 |
| 79 | H | 2-CH₃, 5-CH₃ | 274.0~276.0 |
| 80 | H | 2-CH₃, 6-CH₃ | >300 |
| 81 | H | 2-OCH₃, 4-OCH₃ | 296.5~298.5 |
| 82 | H | 2-OCH₃, 5-OCH₃ | 284.5~286.5 |
| 83 | H | 3-OCH₃, 5-OCH₃ | 300.5~302.0 |
| 84 | H | 2-CH₃, 3-Cl | 296.0~297.5 |
| 85 | H | 2-CH₃, 4-Cl | >300 |
| 86 | H | 2-CH₃, 5-Cl | 290.5~292.0 |
| 87 | H | 4-NH—⌬ | 304 |
| 88 | H | 2-CH(CH₃)₂ | 239.0~240.0 |

TABLE 6-1

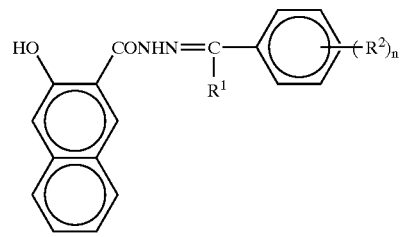

| Coupler No. | R¹ | (R²)ₙ | Melting Point (° C.) |
|---|---|---|---|
| 89 | H | H | 228.0~230.0 |
| 90 | H | 4-N(CH₃)₂ | 238.5~240.0 |
| 91 | H | 2-OCH₃ | 218.0~222.0 |
| 92 | H | 3-OCH₃ | 186.5~188.5 |
| 93 | H | 4-OCH₃ | 224.5~225.0 |
| 94 | H | 4-OC₂H₅ | 236.0~237.5 |
| 95 | H | 2-CH₃ | 227.0~228.0 |
| 96 | H | 3-CH₃ | 212.5~214.0 |
| 97 | H | 4-CH₃ | 233.0~236.0 |
| 98 | H | 2-F | 233.0~233.5 |
| 99 | H | 3-F | 248.5 |
| 100 | H | 4-F | 239.5~240.0 |
| 101 | H | 2-Cl | 254.0~255.0 |
| 102 | H | 3-Cl | 226.5~230.0 |
| 103 | H | 4-Cl | 265.5~269.0 |
| 104 | H | 2-Br | 243.0 |
| 105 | H | 3-Br | 231.0~231.5 |
| 106 | H | 4-Br | 259.0 |

TABLE 6-2

| Coupler No. | R¹ | (R²)ₙ | Melting Point (° C.) |
|---|---|---|---|
| 107 | H | 2-Cl, 4-Cl | 251.5~252.0 |
| 108 | H | 3-Cl, 4-Cl | 260.0~261.0 |
| 109 | H | 2-CN | 175.0~176.5 |
| 110 | H | 4-CN | 267.5~268.0 |
| 111 | H | 2-NO₂ | 240.0 |
| 112 | H | 3-NO₂ | 255.5~257.0 |
| 113 | H | 4-NO₂ | 260.0~261.0 |
| 114 | H | 2-CH₃, 4-CH₃ | 234.5~236.5 |
| 115 | H | 2-OCH₃, 5-OCH₃ | 221.5~222.0 |
| 116 | H | 2-OCH₃, 3-OCH₃, 4-OCH₃ | 191.0~192.0 |
| 117 | —CH₃ | H | 248.5~250.0 |
| 118 | —CH₂—C₆H₅ | H | 182.5~185.0 |
| 119 | —C₆H₄—CH₃ | H | 213.0~214.5 |
| 120 | H | 4-N(C₆H₅)₂ | 237.0~237.5 |

TABLE 7

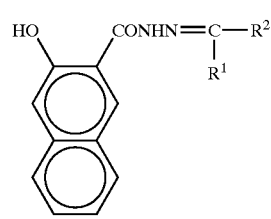

| Coupler No. | R¹ | R² | Melting Point (° C.) |
|---|---|---|---|
| 121 | —CH₃ | —CH₃ | 232.5~233.0 |
| 122 | H | —CH=CH—C₆H₅ | 208.5~209.0 |
| 123 | H | —CH=C(CH₃)—C₆H₅ | 224.0~224.5 |
| 124 | H | 2-methylfuryl | 197.5~199.0 |
| 125 | H | 4-methylpyridyl | 188.0~188.5 |
| 126 | H | 2-methylthienyl | 227.0~228.0 |
| 127 | —CH₃ | 2-methylthienyl | 225.5~226.0 |
| 128 | H | methylnaphthyl | 212.5~214.0 |
| 129 | H | methylanthryl | 257 |

TABLE 7-continued

Structure: 2-hydroxy-naphthalene-CONHN=C(R¹)-R²

| Coupler No. | R¹ | R² | Melting Point (° C.) |
|---|---|---|---|
| 130 | H | (pyrene group) | 250 |
| 131 | H | (N-ethyl carbazole group) | 232.5~236.0 |
| 132 | H | (pyridyl group) | 240.5~241.5 |

TABLE 8

Structure: hydroxy-carbazole-naphthalene-CONHN=CH-phenyl-(R)ₙ

| Coupler No. | (R)ₙ | Melting Point (° C.) |
|---|---|---|
| 133 | H | >300 |
| 134 | 2-OCH₃ | 268 |
| 135 | 3-OCH₃ | 281.0~283.0 |
| 136 | 4-OCH₃ | 293 |
| 137 | 2-CH₃ | 297 |
| 138 | 3-CH₃ | 296 |
| 139 | 4-CH₃ | >300 |
| 140 | 4-Cl | >300 |
| 141 | 2-NO₂ | >300 |
| 142 | 4-NO₂ | >300 |
| 143 | 2-OH | >300 |
| 144 | 2-OH, 3-NO₂ | >300 |
| 145 | 2-OH, 5-NO₂ | >300 |
| 146 | 2-OH, 3-OCH₃ | >300 |

TABLE 9

Structure: HO-anthracene-CONH-phenyl-(R)ₙ

| Coupler No. | (R)ₙ | Melting Point (° C.) |
|---|---|---|
| 147 | 4-Cl | >300 |
| 148 | 2-NO₂ | 268~274 |
| 149 | 3-NO₂ | >300 |
| 150 | 4-NO₂ | >300 |
| 151 | 4-NH-phenyl | 296 |
| 152 | H | 300~307 |
| 153 | 2-OCH₃ | 242~248 |
| 154 | 3-OCH₃ | 269~275 |
| 155 | 4-OCH₃ | 312 |
| 156 | 2-CH₃ | 265~270 |
| 157 | 3-CH₃ | 270~278 |
| 158 | 4-CH₃ | 304 |
| 159 | 2-Cl | 283~288 |
| 160 | 3-Cl | 281~287 |

TABLE 10

Structure: HO-naphthalene(R¹)-CONH-phenyl-(R²)ₙ

| Coupler No. | R¹ | (R²)ₙ | Melting Point (° C.) |
|---|---|---|---|
| 161 | H | 2-OCH₃, 4-Cl, 5-CH₃ | 208.0~208.5 |
| 162 | —OCH₃ | H | 230.5~231.5 |
| 163 | —OCH₃ | 2-CH₃ | 205.5~206.0 |
| 164 | —OCH₃ | 2-OCH₃, 5-OCH₃, 4-Cl | 245.5~246.0 |

TABLE 11

| Coupler No. | X | Melting Point (° C.) |
| --- | --- | --- |
| 165 | cyclohexyl | 207.0~209.0 |
| 166 | fluorenyl | 257.0~259.0 |
| 167 | nitro-fluorenyl | 290 |

TABLE 12

| Coupler No. | R$^1$ | Melting Point (° C.) |
| --- | --- | --- |
| 168 | naphthyl | >300 |

TABLE 12-continued

| Coupler No. | R$^1$ | Melting Point (° C.) |
| --- | --- | --- |
| 169 | anthracenyl | >300 |
| 170 | N-ethylcarbazolyl | >300 |
| 171 | methylthienyl | 298 |

TABLE 13

| Coupler No. | X | R | Melting Point (° C.) |
| --- | --- | --- | --- |
| 172 | bromo-dimethylphenyl | methoxy-methylphenyl | 180~183 |
| 173 | dimethylphenyl | methoxy-methyl-dibenzofuranyl | 228.5~229.5 |

TABLE 13-continued

[Structure: 2-hydroxy-benzamide with fused ring containing X, CONH—R]

| Coupler No. | X | R | Melting Point (° C.) |
|---|---|---|---|
| 174 | [2,3-dimethyl indoline, HN] | [4-chlorophenyl] | >262 |
| 175 | [2,3-dimethyl benzofuran, O] | [2,5-dimethoxyphenyl, OCH₃/OCH₃] | 226.5~227.0 |
| 176 | [2,3-dimethyl benzofuran, O] | [naphthyl] | 308~310 |
| 177 | [dimethyl phenyl] | [methyl naphthyl] | 222~223 |

TABLE 14

[Structure: 3-hydroxy-2-naphthamide with CON(R¹)(R²)]

| Coupler No. | R¹ | R² | Melting Point (° C.) |
|---|---|---|---|
| 178 | H | H | 220.5~221.5 |
| 179 | —CH₃ | H | 190.5~192.5 |
| 180 | —CH₃ | —CH₃ | 196.0~198.0 |
| 181 | H | [4-methylphenyl-NH-phenyl] | 222.0~223.0 |

TABLE 15-1

| Coupler No. | Structure | Melting Point (° C.) |
|---|---|---|
| 182 | [3-hydroxy-2-naphthamide linked via CONH to 2-mercaptobenzimidazole] | >300 |

TABLE 15-1-continued

| Coupler No. | Structure | Melting Point (° C.) |
|---|---|---|
| 183 | 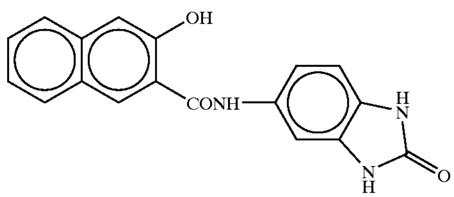 | >300 |
| 184 | 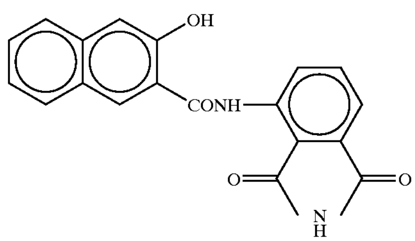 | >300 |
| 185 | 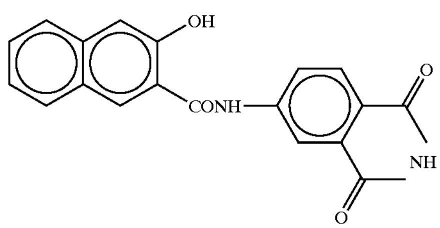 | >300 |
| 186 | 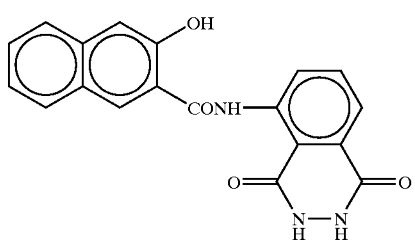 | >300 |
| 187 | 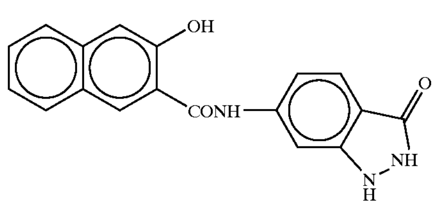 | >300 |
| 188 | 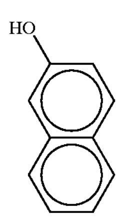 | 122.0~122.5 |

TABLE 15-2

| Coupler No. | Structure | Melting Point (° C.) |
|---|---|---|
| 189 | HO-naphthalene-COOH | 222.5~224.0 |
| 190 | HO-naphthalene-COOCH₃ | 74.5~75.5 |
| 191 | HO-naphthalene fused with N-CH₃ imide | 275.5~276.5 |
| 192 | HO-naphthalene-COO-phenyl | 130.5~131.5 |
| 193 | HO-naphthalene fused with NH imide | >300 |
| 194 | HO-naphthalene fused with N-phenyl imide | >300 |
| 195 | HO-naphthalene fused with benzimidazole carbonyl | >300 |

TABLE 15-2-continued

| Coupler No. | Structure | Melting Point (° C.) |
|---|---|---|
| 196 | 3-hydroxy-2-(1-phenyl-1H-benzimidazol-2-yl)naphthalene | 172.5~173.5 |

TABLE 15-3

| Coupler No. | Structure | Melting Point (° C.) |
|---|---|---|
| 197 | HO, CONH-phenyl, N-CH₃ carbazole-fused naphthalene | 262.5~265.5 |
| 198 | HO, CONH-phenyl, NH carbazole-fused naphthalene | >300 |
| 199 | HO, CONH-phenyl, NH carbazole-fused naphthalene (isomer) | >300 |

TABLE 15-3-continued

| Coupler No. | Structure | Melting Point (° C.) |
|---|---|---|
| 200 | (pyrazolone with CH3, N-phenyl) | 128.0~129.0 |

TABLE 16-1

(Structure: HO-naphthalene-CONH-phenyl(R²)ₙ fused with carbazole bearing R¹)

| Coupler No. | R¹ | (R²)ₙ | Melting Point (° C.) |
|---|---|---|---|
| 201 | Cl | H | >300 |
| 202 | Cl | 2-OCH₃ | >300 |
| 203 | Cl | 3-OCH₃ | >300 |
| 204 | Cl | 4-OCH₃ | >300 |
| 205 | Cl | 2-CH₃ | >300 |
| 206 | Cl | 3-CH₃ | >300 |
| 207 | Cl | 4-CH₃ | >300 |
| 208 | Cl | 2-Cl | >300 |
| 209 | Cl | 3-Cl | >300 |
| 210 | Cl | 4-Cl | >300 |
| 211 | Cl | 2-NO₂ | >300 |
| 212 | Cl | 3-NO₂ | >300 |
| 213 | Cl | 4-NO₂ | >300 |
| 214 | Cl | 2-CH₃, 4-Cl | >300 |
| 215 | Cl | 2-CH₃, 4-CH₃ | >300 |
| 216 | Cl | 2-C₂H₅ | 299.0~301.0 |
| 217 | CH₃ | H | >300 |

TABLE 16-2

| Coupler No. | R¹ | (R²)ₙ | Melting Point (° C.) |
|---|---|---|---|
| 218 | CH₃ | 2-OCH₃ | 297 |
| 219 | CH₃ | 3-OCH₃ | >300 |
| 220 | CH₃ | 4-OCH₃ | >300 |
| 221 | CH₃ | 2-CH₃ | >300 |
| 222 | CH₃ | 3-CH₃ | >300 |
| 223 | CH₃ | 4-CH₃ | >300 |
| 224 | CH₃ | 2-Cl | >300 |
| 225 | CH₃ | 3-Cl | >300 |
| 226 | CH₃ | 4-Cl | >300 |
| 227 | CH₃ | 2-NO₂ | >300 |
| 228 | CH₃ | 3-NO₂ | >300 |
| 229 | CH₃ | 4-NO₂ | >300 |
| 230 | CH₃ | 2-CH₃, 4-Cl | >300 |
| 231 | CH₃ | 2-CH₃, 4-CH₃ | >300 |

TABLE 16-2-continued

| Coupler No. | R¹ | (R²)ₙ | Melting Point (° C.) |
|---|---|---|---|
| 232 | CH₃ | 2-C₂H₅ | 268.5~270.0 |
| 233 | OCH₃ | H | 289.0 |
| 234 | OCH₃ | 2-OCH₃ | 268.0~270.0 |
| 235 | OCH₃ | 3-OCH₃ | >300 |
| 236 | OCH₃ | 4-OCH₃ | >300 |
| 237 | OCH₃ | 2-CH₃ | 284.5~285.5 |
| 238 | OCH₃ | 3-CH₃ | >300 |
| 239 | OCH₃ | 4-CH₃ | >300 |

TABLE 16-3

| Coupler No. | R¹ | (R²)ₙ | Melting Point (° C.) |
|---|---|---|---|
| 240 | OCH₃ | 2-Cl | >300 |
| 241 | OCH₃ | 3-Cl | >300 |
| 242 | OCH₃ | 4-Cl | >300 |
| 243 | OCH₃ | 2-NO₂ | >300 |
| 244 | OCH₃ | 3-NO₂ | >300 |
| 245 | OCH₃ | 4-NO₂ | >300 |
| 246 | OCH₃ | 2-C₂H₅ | 264.5~266.5 |

TABLE 17-1

| Coupler No. | Structure |
|---|---|
| 247 | (HO-naphtho-benzimidazole fused ketone) |
| 248 | (as 247 with CH₃ substituent) |
| 249 | (as 247 with OCH₃ substituent) |
| 250 | (as 247 with two CH₃ substituents) |

TABLE 17-1-continued

| Coupler No. | Structure |
|---|---|
| 251 | 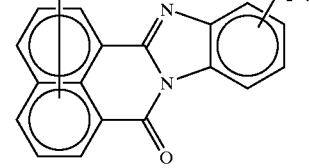 |
| 252 | 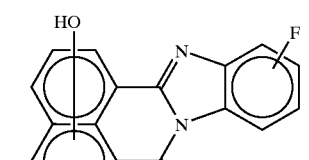 |
| 253 | 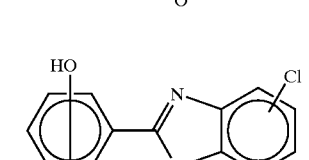 |

TABLE 17-2

| Coupler No. | Structure |
|---|---|
| 254 | 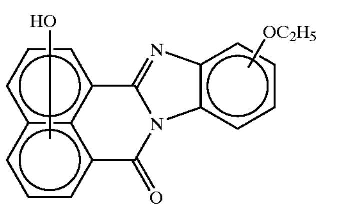 |
| 255 | 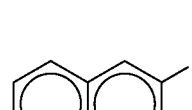 |
| 256 | 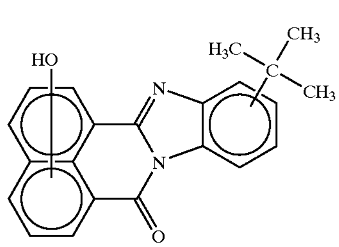 |

TABLE 17-2-continued

| Coupler No. | Structure |
|---|---|
| 257 | 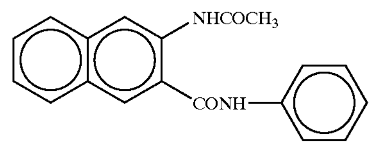 |
| 258 | 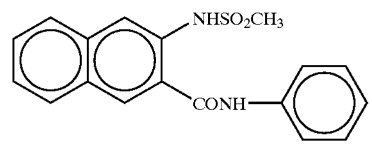 |

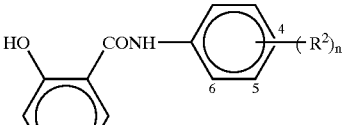

TABLE 18

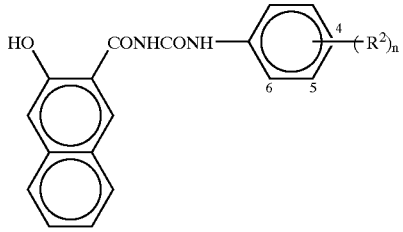

| Coupler No. | $(R^2)_n$ |
|---|---|
| 259 | 2-Cl, 3-Cl |
| 260 | 2-Cl, 4-Cl |
| 261 | 3-Cl, 5-Cl |

TABLE 19

| Coupler No. | $(R^2)_n$ |
|---|---|
| 262 | 4-CH$_3$ |
| 263 | 3-NO$_2$ |
| 264 | 2-Cl |
| 265 | 3-Cl |
| 266 | 4-Cl |
| 267 | 2-Cl, 3-Cl |
| 268 | 2-Cl, 4-Cl |
| 269 | 3-Cl, 5-Cl |
| 270 | 2-Cl, 5-Cl |
| 271 | 3-Cl, 4-Cl |

The azo compounds represented in the general formula <<1>> of the present invention can be manufactured by using the amino compounds corresponding to the main skeleton (Ar portion) as starting materials, isolating as diazonium salt represented in the general formula <<15>> after diazotizating the starting materials, then cpoupling-reacting the isolated material in a proper organic solvent (N,N-dimethylformamide or the like) under the condition having the corresponding coupler compounds to those represented in the general formula <<16>> and alkali. Among the azo compounds represented in the general formula <<1>> of the present invention, the azo compounds with n=2 or more can utilize 2 or more types of coupler compounds. In that case, an diazonium compound indicated by the general formula <<15>> can be obtained either by reacting with the coupler compound corresponding to that represented in the general formula <<2>>, <<3>>, or <<4>> and the coupler compound represented in any of the general formulae mentioned below (Cp1)-(Cp15) in two-stage manner and in turn, or by reacting the corresponding coupler compounds to each general formula after isolating the diazonium salt compound obtained through the first coupling reaction.

Now, embodiments of the above-mentioned azo compounds represented in the general formula <<1>> are shown below and for simplification, only n, the main skeleton (Ar portion), and coupler compound (Cp) are illustrated to explain the azo compounds by means of combination of numbers for them. The azo compounds of the present invention are not limited only to the embodiments.

TABLE 20-1

| Azo Compound No. | n | Main Skeleton (Ar) No. | Coupler (Cp) No. | |
|---|---|---|---|---|
| P1 | 1 | A1 | C1 | |
| P2 | 1 | A1 | C5 | |
| P3 | 1 | A1 | C14 | |
| P4 | 1 | A1 | C28 | |
| P5 | 1 | A1 | E23 | |
| P6 | 1 | A2 | C5 | |
| P7 | 1 | A2 | E23 | |
| P8 | 2 | A3 | C5 | |
| P9 | 2 | A3 | C5 | 1 |
| P10 | 2 | A3 | C18 | |
| P11 | 2 | A4 | C5 | |
| P12 | 2 | A4 | C5 | 247 |
| P13 | 2 | A4 | C21 | |
| P14 | 2 | A4 | E23 | 247 |
| P15 | 2 | A8 | C14 | |
| P16 | 2 | A8 | C71 | |
| P17 | 2 | A9 | C1 | |
| P18 | 2 | A9 | C1 | 17 |
| P19 | 2 | A9 | C5 | |
| P20 | 2 | A9 | C5 | 17 |
| P21 | 2 | A9 | C10 | |
| P22 | 2 | A9 | C13 | |
| P23 | 2 | A9 | C14 | |
| P24 | 2 | A9 | C14 | 17 |
| P25 | 2 | A9 | C18 | |
| P26 | 2 | A9 | C20 | |
| P27 | 2 | A9 | C28 | |
| P28 | 2 | A9 | C28 | 17 |
| P29 | 2 | A9 | C30 | |
| P30 | 2 | A9 | C35 | |
| P31 | 2 | A9 | C36 | |
| P32 | 2 | A9 | C44 | |
| P33 | 2 | A9 | E4 | |
| P34 | 2 | A9 | E12 | |
| P35 | 2 | A9 | E12 | 17 |
| P36 | 2 | A9 | E12 | 152 |
| P37 | 2 | A9 | E17 | |
| P38 | 2 | A9 | E23 | |
| P39 | 2 | A9 | E23 | 17 |
| P40 | 2 | A9 | E26 | |

TABLE 20-2

| Azo Compound No. | n | Main Skeleton (Ar) No. | Coupler (Cp) No. | |
|---|---|---|---|---|
| P41 | 2 | A10 | C14 | |
| P42 | 2 | A10 | C14 | 4 |
| P43 | 2 | A10 | E23 | |
| P44 | 2 | A11 | C5 | |
| P45 | 2 | A11 | C14 | |
| P46 | 2 | A11 | E23 | |
| P47 | 2 | A14 | C1 | |
| P48 | 2 | A14 | C1 | 43 |
| P49 | 2 | A14 | C5 | |
| P50 | 2 | A14 | C5 | 43 |
| P51 | 2 | A14 | C10 | |
| P52 | 2 | A14 | C14 | |
| P53 | 2 | A14 | C14 | 43 |
| P54 | 2 | A14 | C19 | |
| P55 | 2 | A14 | C21 | |
| P56 | 2 | A14 | C27 | |
| P57 | 2 | A14 | C28 | |
| P58 | 2 | A14 | C28 | 43 |
| P59 | 2 | A14 | C28 | 17 |
| P60 | 2 | A14 | C36 | |
| P61 | 2 | A14 | C42 | |
| P62 | 2 | A14 | E4 | |
| P63 | 2 | A14 | E11 | |
| P64 | 2 | A14 | E12 | |
| P65 | 2 | A14 | E12 | 43 |
| P66 | 2 | A14 | E23 | |
| P67 | 2 | A14 | E23 | 43 |
| P68 | 2 | A14 | E26 | |
| P69 | 2 | A19 | C14 | |
| P70 | 2 | A19 | E24 | |
| P71 | 2 | A20 | C14 | |
| P72 | 2 | A20 | E24 | |
| P73 | 3 | A23 | C1 | |
| P74 | 3 | A23 | C5 | |
| P75 | 3 | A23 | C7 | |
| P76 | 3 | A23 | C7 | 70 |
| P77 | 3 | A23 | C14 | |
| P78 | 3 | A23 | C14 | 70 |
| P79 | 3 | A23 | C20 | |
| P80 | 3 | A23 | C25 | |

TABLE 20-3

| Azo Compound No. | n | Main Skeleton (Ar) No. | Coupler (Cp) No. | |
|---|---|---|---|---|
| P81 | 3 | A23 | C28 | |
| P82 | 3 | A23 | C28 | 70 |
| P83 | 3 | A23 | C34 | |
| P84 | 3 | A23 | E12 | |
| P85 | 3 | A23 | E12 | 70 |
| P86 | 3 | A23 | E23 | |
| P87 | 3 | A23 | E23 | 70 |
| P88 | 2 | A24 | C5 | |
| P89 | 2 | A24 | C14 | |
| P90 | 2 | A24 | C21 | |
| P91 | 2 | A24 | C28 | |
| P92 | 2 | A24 | E12 | |
| P93 | 2 | A24 | E23 | |
| P94 | 2 | A26 | C5 | |
| P95 | 2 | A26 | C5 | 216 |
| P96 | 2 | A26 | C13 | |
| P97 | 2 | A26 | C14 | |
| P98 | 2 | A26 | C28 | 216 |
| P99 | 2 | A26 | E12 | |
| P100 | 2 | A26 | E24 | |
| P101 | 2 | A26 | E24 | 216 |
| P102 | 2 | A9 | C9 | |
| P103 | 2 | A9 | C9 | 17 |
| P104 | 2 | A9 | C10 | 17 |
| P105 | 2 | A9 | C13 | 17 |
| P106 | 2 | A9 | C54 | |
| P107 | 2 | A9 | C54 | 17 |

TABLE 20-3-continued

| Azo Compound No. | n | Main Skeleton (Ar) No. | Coupler (Cp) No. | |
|---|---|---|---|---|
| P108 | 2 | A9 | C55 | |
| P109 | 2 | A9 | C55 | 17 |
| P110 | 2 | A9 | C56 | |
| P111 | 2 | A9 | C56 | 17 |
| P112 | 2 | A9 | C59 | |
| P113 | 2 | A9 | C59 | 17 |
| P114 | 2 | A9 | C60 | |
| P115 | 2 | A9 | C60 | 17 |
| P116 | 2 | A9 | C61 | |
| P117 | 2 | A9 | C61 | 17 |
| P118 | 2 | A9 | C82 | |
| P119 | 2 | A9 | C82 | 17 |
| P120 | 2 | A9 | C83 | |

TABLE 20-4

| Azo Compound No. | n | Main Skeleton (Ar) No. | Coupler (Cp) No. | |
|---|---|---|---|---|
| P121 | 2 | A9 | C83 | 17 |
| P122 | 2 | A9 | C92 | |
| P123 | 2 | A9 | C92 | 17 |
| P124 | 2 | A9 | C95 | |
| P125 | 2 | A9 | C95 | 17 |
| P126 | 2 | A9 | C96 | |
| P127 | 2 | A9 | C96 | 17 |
| P128 | 2 | A9 | C101 | |
| P129 | 2 | A9 | C101 | 17 |
| P130 | 2 | A9 | C102 | |
| P131 | 2 | A9 | C102 | 17 |
| P132 | 2 | A9 | E31 | |
| P133 | 2 | A9 | E31 | 17 |
| P134 | 2 | A9 | C11 | |
| P135 | 2 | A9 | C11 | 17 |
| P136 | 2 | A9 | C24 | |
| P137 | 2 | A9 | C24 | 17 |

TABLE 20-5

| Azo Compound No. | n | Main Skeleton (Ar) No. | Coupler (Cp) No. | |
|---|---|---|---|---|
| P138 | 2 | A9 | C40 | |
| P139 | 2 | A9 | C40 | 17 |
| P140 | 2 | A9 | C37 | |
| P141 | 2 | A9 | C37 | 17 |
| P142 | 2 | A9 | C110 | |
| P143 | 2 | A9 | C110 | 17 |
| P144 | 2 | A9 | C50 | |
| P145 | 2 | A9 | C50 | 17 |
| P146 | 2 | A9 | C5 | 195 |
| P147 | 2 | A9 | C12 | |
| P148 | 2 | A9 | C12 | 17 |
| P149 | 2 | A9 | C49 | |
| P150 | 2 | A9 | C49 | 17 |
| P151 | 2 | A9 | C51 | |
| P152 | 2 | A9 | C51 | 17 |
| P153 | 2 | A9 | C104 | |
| P154 | 2 | A9 | C104 | 17 |
| P155 | 2 | A9 | C105 | |
| P156 | 2 | A9 | C105 | 17 |
| P157 | 2 | A9 | C106 | |
| P158 | 2 | A9 | C106 | 17 |
| P159 | 2 | A9 | C107 | |
| P160 | 2 | A9 | C107 | 17 |
| P161 | 2 | A9 | C108 | |
| P162 | 2 | A9 | C108 | 17 |
| P163 | 2 | A9 | C109 | |
| P164 | 2 | A9 | C109 | 17 |
| P165 | 2 | A9 | C111 | |
| P166 | 2 | A9 | C111 | 17 |

TABLE 20-5-continued

| Azo Compound No. | n | Main Skeleton (Ar) No. | Coupler (Cp) No. | |
|---|---|---|---|---|
| P167 | 2 | A9 | C112 | |
| P168 | 2 | A9 | C112 | 17 |
| P169 | 2 | A9 | C113 | |
| P170 | 2 | A9 | C113 | 17 |
| P171 | 2 | A9 | C114 | |
| P172 | 2 | A9 | C114 | 17 |
| P173 | 2 | A9 | E30 | |
| P174 | 2 | A9 | E30 | 17 |
| P175 | 2 | A9 | C14 | 195 |
| P176 | 2 | A9 | C24 | 195 |
| P177 | 2 | A9 | C110 | 195 |
| P178 | 2 | A9 | E30 | 195 |
| P179 | 2 | A9 | E31 | 195 |

TABLE 20-6

| Azo Compound No. | n | Main Skeleton (Ar) No. | Coupler (Cp) No. | |
|---|---|---|---|---|
| P180 | 2 | A24 | C5 | 1 |
| P181 | 2 | A24 | C14 | 1 |
| P182 | 2 | A24 | C24 | |
| P183 | 2 | A24 | C24 | 1 |
| P184 | 2 | A24 | C28 | 1 |
| P185 | 2 | A24 | E23 | |
| P186 | 2 | A24 | E23 | 1 |
| P187 | 2 | A24 | E30 | |
| P188 | 2 | A24 | E30 | 1 |

Further, in a different aspect of the Electrophotographic photoconductor of the present invention, the photoconductive layer contains the azo compound represented in the general formula <<101>>.

Now, the azo compounds will be explained below in detail.

In the present invention, among azo compounds to be contained in the photoconductive layer, which may be represented by the general formula <<1>>, aromatic hydrocarbon groups, which may have a substituent, to which they may bind via a bond group represented by Ar, include aromatic hydrocarbons such as benzene, naphthalene, fluorine, phenanthrene, anthracene, pyrene, and the like, heterocycles such as furan, thiophene, pyridine, indole, benzothiazole, carbazole, acridone, dibenzothiophene, benzoxazole, benzotriazole, oxadiazole, thiadiazole, and the like, and the compounds formed by bonding the above-mentioned aromatic rings directly or via an aromatic group or nonaromatic group, for example, triphenylamine, diphenylamine, N-methyldiphenylamine, biphenyl, tarphenyl, binaphthyl, fluorenone, phenanthrenequinone, anthraquinone, benzanthrone, diphenyloxadiazole, phenylbenzoxazole, diphenylmethane, diphenylsulfone, diphenylether, benzophenone, stilbene, distilylbenzene, tetraphenyl-p-phenylenediamine, tetraphenylbenzidinemonopyridilydiphenylamine, and the like.

Among the above-mentioned main skeletons, fluorenon main skeletons represented in the general formula <<110>>, the general formula <<113>>, and the general formula <<114>> and the phenanthrenquinone main skeletons represented in the general formula <<135>>, the general formula <<136>>, and the general formula <<137>> are, in particular, preferable because the azo compounds obtained by combining the novel coupler residue of the present invention have high sensitivity and better durability.

The substituents contained in the above-mentioned rings include alkyl groups such as a methyl group, an ethyl group, a propyl group, a butyl group, and the like, alkoxyl groups such as a methoxyl group, an ethoxyl group, and the like, halogen atoms such as a fluorine atom, a chlorine atom, a bromine atom, and the like, amino groups such as a dimethylamino group, a diethylamino group, a diphenylamino group, and the like, a hydroxyl group, a nitro group, a cyano group, a halomethyl group, and the like.

Examples of a main skeletone Ar are the same as those (Table 1) of the main skeletone represented by the general formula <<1>>.

In the general formula <<102>>, the general formula <<103>>, the general formula <<104>>, the general formula <<109>>, the general formula <<111>>, the general formula <<112>>, the general formula <<110>>, the general formula <<135>>, the general formula <<113>>, the general formula <<114>>, the general formula <<136>>, and the general formula <<137>>, $R_1$, $R_2$, $R_3$, and $R_4$ indicate any of hydrogen atoms, alkyl groups such as a methyl group, an ethyl group, a propyl group, a butyl group, and the like, alkoxyl groups such as a methoxyl group, an ethoxyl group, and the like, halogen atoms such as a fluorine atom, a chlorine atom, a bromine atom, and the like, amino groups such as a dimethylamino group, a diethylamino group, a diphenylamino group, and the like, a hydroxyl group, a nitro group, a cyano group, an acetyl group, a benzoyl group which may have a substituent, an alkoxycarbonyl group, a phenoxycarbonyl group which may have a substituent, and a carbamoyl group which may have a substituent. Alternately, $R_1$ and $R_2$ may form a ring together by means of bivalent alkyl groups such as a propylene group, a buthylene group, a penthylene group, and the like.

In the general formula <<102>>, the general formula <<109>>, the general formula <<110>>, and the general formula <<135>>, X indicates any of a hydrogen atom, alkyl groups such as a methyl group, an ethyl group, a propyl group, a butyl group, a pentyl group, a hexyl group, an octyl group, a decile group, and the like, cyclic alkyl groups such as a cyclopentyl group, a cyclohexyl group, and the like, aromatic hydrocarbon groups such as a phenyl group, a naphthyl group, an anthracenyl group, a phenanthrenyl group, a pyrenyl group, and the like, heterocyclic compound groups such as a pyridyl group, a pyrazino group, a quinolino group, an oxazolyl group, a benzoxazolyl group, a thiazolyl group, a benzothiazolyl group, an imidazolyl group, a benzoimidazolyl group, an indolyl group, and the like, alkylamino groups such as a methylamino group, an ethylamino group, and the like, aromatic amino groups such as a phenylamino group, a naphthylamino group, and the like, carboamino groups such as an acetylamino group, a benzoylamino group, and the like. The substituents for them include alkyl groups such as a methyl group, an ethyl group, a propyl group, a butyl group, and the like, substituent alkyl groups such as a benzyl group, a phenethyl group, a methoxymethyl group, and the like, alkoxyl groups such as a methoxyl group, an ethoxyl group, a phenoxyl group, and the like, a phenyl group which may have a substituent, a naphthyl group which may have a substituent, aromatic groups such as an anthracenyl group, a phenanthrenyl group, a pyrenyl group, and the like, halogen atoms such as a fluorine atom, a chlorine atom, a bromine atom, and the like, a hydroxyl group, carboamino groups such as an amino group which may have a substituent, an acetylamino group, a benzoylamino group which may have a substituent, and the like, a nitro group, a cyano group, an acetyl group, a benzoyl group which may have a substituent, an alkoxycarbonyl group, a phenoxycarbonyl group which may have a substituent, a carbamoyl group which may have a substituent, and the like.

Among the residues represented in the general formula <<102>>, the coupler residues, of which X is a substituent or nonsubsituent alkyl group, or a substituent or non-substituent cyclic alkyl group, and in particular, among them, the coupler residues represented in the general formula <<105>> are more preferable because the azo compounds obtained according to the present invention have high sensitivity and better light sensitivity. In the general formula <<105>>, $A_1$ indicates any of aromatic hydrocarbon groups such as a phenyl group, a naphthyl group, an anthracenyl group, a phenanthrenyl group, a pyrenyl group, and the like, heterocyclic groups such as a pyridyl group, a pyrazino group, a quinolino group, an oxazolyl group, a benzoxazolyl group, a thiazolyl group, a benzothiazolyl group, an imidazolyl group, a benzoimidazolyl group, an indolyl group, and the like, and the substituents for them include alkyl groups such as a methyl group, an ethyl group, a propyl group, a butyl group, and the like, substituent alkyl groups such as a benzyl group, a phenethyl group, a methoxymethyl group, and the like, alkoxyl groups such as a methoxyl group, an ethoxyl group, a phenoxyl group, and the like, a phenyl group which may have a substituent, halogen atoms such as a fluorine atom, a chlorine atom, a bromine atom, and the like, a trifluoromethyl group, a cyano group, an alkoxycarbonyl group, a carbamoyl group which may have a substituent, and the like.

In the general formula <<103>>, the general formula <<104>>, the general formula <<111>>, the general formula <<112>>, the general formula <<110>>, the general formula <<135>>, the general formula <<113>>, the general formula <<114>>, the general formula <<136>>, and the general formula <<137>>, Y indicates any of a substituent or non-substituent alkylene group, bivalent organic residues having substituent or non-substituent aromaticity, bivalent organic residues having substituent or non-substituent heterocyclic aromaticity, and bivalent organic residues containing a carbonyl group represented by —CO—Z— (note that Z indicates a substituent or non-substituent alkylene group, any of bivalent organic residues having substituent or non-substituent aromaticity, and any of bivalent organic residues having substituent or non-substituent heterocyclic aromaticity). The alkylene group includes an ethylene group, a propylene group, a butylene group, a cyclopentyl group, and a cyclohexyl group. Note that the aromatic ring is formed via a carbon-carbon bond between the alkylene groups. The bivalent organic residues having aromaticity includes an o-phenylene group, a 1,8-naphtylene group, a 2,3-naphtylene group, a 1,2-anthrylene group, a 9,10-phenanthrylene group, and the like, the bivalent organic residue having heterocyclic aromaticity includes a 3,4-pyrimidyl group, 2,3-pyridinedyl group, 5,6-pyrimidinedyl group, a 6,7-benzimidadyl group, a 6,7-quinolidyl group, and the like. The bivalent organic residue containing a carbonyl group includes a 2-benzoyl group and a 2-naphthylcarbonyl group, and the like. The substituents for them include alkyl groups such as a methyl group, an ethyl group, a propyl group, a butyl group, and the like, substituent alkyl groups such as a benzyl group, a phenethyl group methoxymethyl group, and the like, alkoxyl groups such as a methoxyl group, an ethoxyl group and a phenoxyl group, and the like, a phenyl group which may have a substituent, a naphthyl group which may have a substituent, aromatic groups such as an anthracenyl group, a phenanthrenyl group, a pyrenyl group, and the like, halogen atoms such as a fluorine atom, a chlorine atom, a bromine atom, and the like, a hydroxyl group, carboamino groups such as an amino group which may have a substituent, an acetylamino group, a benzoylamino group which may have a substituent, and the like, a nitro group, a cyano group, an acetyl group, a benzoyl group which may have a substituent, an alkoxycarbonyl group, a phenoxycarbonyl group which may have a substituent, a carbamoyl group which may have a substituent, and the like.

Among the coupler residues represented in the general formula <<103>> and the general formula <<104>>, the coupler residues, of which Y contains a substituent or non-substituent bivalent organic residue containing a substituent or non-substituent alkylene group or a substituent or non-substituent carbonyl group, and among them, in particular, the coupler residues represented in the general formula <<131>> and the general formula <<132>> and the coupler residues represented in the general formula <<133>> and the general formula <<134>> are preferable because the azo compounds obtained according to the present invention have high sensitivity and exhibit better electrostatic stability. $B_1$ represented in the general formula <<131>> and in the general formula <<132>>, and $B_2$ represented in the general formula <<133>> and the general formula <<134>> indicate bivalent groups of the aromatic hydrocarbon ring such as an o-phenylene group, a 2,3-naphthylene group, and the like, 2,3-pyrinly group, a 3,4-pyrazoyl group, a 2,3-pyridinyl group, a 4,5-pyridinyl group, and a 4,5-imidazolyl group, and the substituents for them include alkyl groups such as a methyl group, an ethyl group, a propyl group, a buthyl group, and the like, alkoxyl groups such as a methoxyl group, an ethoxyl group, a phenoxyl group, and the like, halogen atoms such as a fluorine atom, a chlorine atom, a bromine atom, and the like, a nitro group and the like.

The examples of the coupler residues Cp and Cp' in the azo compounds represented in the general formula <<101>>, the general formula <<109>>, the general formula <<111>>, the general formula <<112>>, the general formula <<110>>, the general formula <<135>>, the general formula <<113>>, the general formula <<114>>, the general formula <<136>>, and the general formula <<137>> are shown in Tables 21-1 through 21-8 and Tables 22-1 through 22-3.

TABLE 21-1

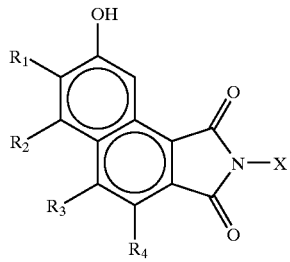

general formula <<102>>

| Coupler (Cp) No. | R1 | R2 | R3 | R4 | X |
|---|---|---|---|---|---|
| C1 | H | H | H | H | —$C_6H_{13}$ |
| C2 | H | H | H | H | —$C_8H_{17}$ |
| C3 | —$CH_3$ | H | H | H | —$C_6H_{13}$ |
| C4 | H | —$CH_3$ | H | H | —$C_6H_{13}$ |
| C5 | H | H | H | H | —$CH_2$—⌬ |
| C6 | H | —$CH_3$ | H | H | —$CH_2$—⌬ |
| C7 | —$CH_2CH_2CH_2CH_2$— | —$CH_3$ | H | | —$CH_2$—⌬ |
| C8 | H | H | H | —$C_2H_5$ | —$CH_2$—⌬ |
| C9 | H | H | H | H | —$CH_2$—⌬—$CH_3$ |
| C10 | H | H | H | H | —$CH_2$—⌬—$OCH_3$ |

TABLE 21-1-continued general formula <<102>>

| Coupler (Cp) No. | R1 | R2 | R3 | R4 | X |
|---|---|---|---|---|---|
| C11 | H | H | H | H | —CH₂—C₆H₄—Cl (4-chlorobenzyl) |
| C12 | H | H | H | H | —CH₂—C₆H₄—OCH₃ (3-methoxybenzyl) |
| C13 | H | H | H | H | —CH₂-(1-naphthyl) |
| C14 | H | H | H | H | —CH₂CH₂—C₆H₅ |
| C15 | —OCH₃ | H | H | H | —CH₂CH₂—C₆H₅ |

TABLE 21-2

| Coupler (Cp) No. | R1 | R2 | R3 | R4 | X |
|---|---|---|---|---|---|
| C16 | H | H | H | H | —CH₂CH₂—C₆H₄—CH₃ (4-methylphenethyl) |
| C17 | H | H | H | H | —CH₂CH₂—C₆H₄—OCH₃ (4-methoxyphenethyl) |
| C18 | H | H | H | H | —CH₂CH₂—C₆H₃(CH₃)₂ (3,4-dimethylphenethyl) |
| C19 | H | H | H | H | —CH₂CH₂—C₆H₃(CH₃)₂ (2,4-dimethylphenethyl) |

TABLE 21-2-continued
| Coupler (Cp) No. | R1 | R2 | R3 | R4 | X |
|---|---|---|---|---|---|
| C20 | H | H | H | H | 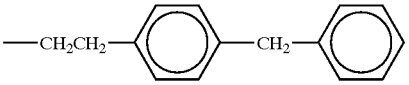 |
| C21 | H | H | H | H | 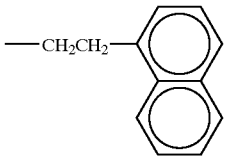 |
| C22 | H | H | H | H | 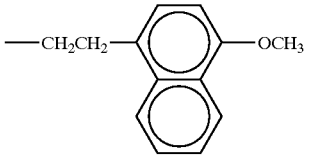 |
| C23 | H | H | H | H | 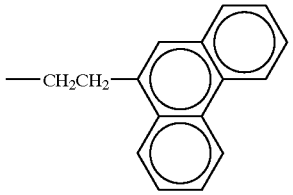 |
| C24 | H | H | H | H | 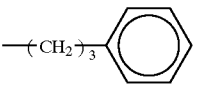 |
| C25 | H | —NO$_2$ | H | H | 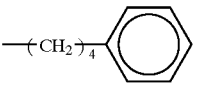 |
| C26 | H | H | H | H | —C$_2$H$_4$OCH$_3$ |
| C27 | H | H | H | H | —C$_2$H$_4$OCOCH$_3$ |
| C28 | H | H | H | H | 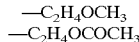 |
| C29 | —CH$_3$ | H | H | H | 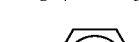 |
| C30 | H | —OCH$_3$ | —CH$_3$ | H | 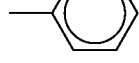 |
TABLE 21-3
| Coupler (Cp) No. | R1 | R2 | R3 | R4 | X |
|---|---|---|---|---|---|
| C31 | H | —Cl | H | H | 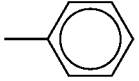 |
TABLE 21-3-continued
| Coupler (Cp) No. | R1 | R2 | R3 | R4 | X |
|---|---|---|---|---|---|
| C32 | H | H | H | H |  |

TABLE 21-3-continued
| Coupler (Cp) No. | R1 | R2 | R3 | R4 | X |
|---|---|---|---|---|---|
| C33 | H | H | H | H | 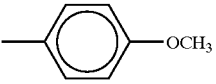 |
| C34 | H | H | H | H | 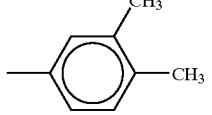 |
| C35 | H | H | —CH₃ | H |  |
| C36 | H | H | H | H | 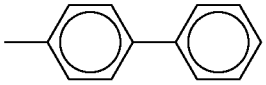 |
| C37 | H | H | H | H | 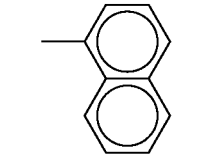 |
| C38 | H | H | H | H | 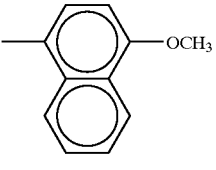 |
| C39 | H | H | H | H | 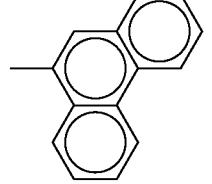 |
| C40 | H | H | H | H | 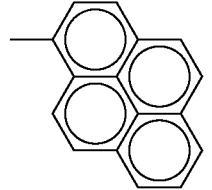 |
| C41 | H | H | H | H | 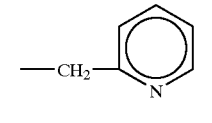 |
| C42 | H | H | H | H | 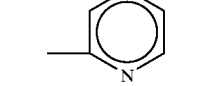 |
| C43 | H | H | H | H | 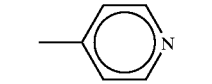 |
TABLE 21-3-continued
| Coupler (Cp) No. | R1 | R2 | R3 | R4 | X |
|---|---|---|---|---|---|
| C44 | H | H | H | H |  |
| C45 | H | H | H | H | 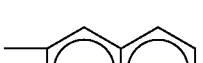 |
TABLE 21-4
| Coupler (Cp) No. | R1 | R2 | R3 | R4 | X |
|---|---|---|---|---|---|
| C46 | H | H | H | H | H |
| C47 | H | H | H | H | —CH₃ |
| C48 | H | H | H | H | —C₂H₅ |
| C49 | H | H | H | H | 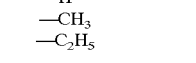 |
| C50 | H | H | H | H | 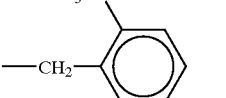 |
| C51 | H | H | H | H | 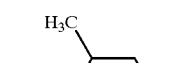 |
| C52 | H | H | H | H |  |
| C53 | H | H | H | H |  |
| C54 | H | H | H | H | 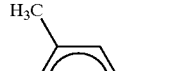 |
| C55 | H | H | H | H |  |

TABLE 21-4-continued

| Coupler (Cp) No. | R1 | R2 | R3 | R4 | X |
|---|---|---|---|---|---|
| C56 | H | H | H | H | —CH$_2$—C$_6$H$_4$—F (para) |
| C57 | H | H | H | H | —CH$_2$—C$_6$H$_4$—NO$_2$ (ortho) |
| C58 | H | H | H | H | —CH$_2$—C$_6$H$_4$—NO$_2$ (meta) |
| C59 | H | H | H | H | —CH$_2$—C$_6$H$_4$—NO$_2$ (para) |
| C60 | H | H | H | H | —CH$_2$—C$_6$H$_4$—C$_6$H$_5$ (biphenyl) |

TABLE 21-5

| Coupler (Cp) No. | R1 | R2 | R3 | R4 | X |
|---|---|---|---|---|---|
| C61 | H | H | H | H | —CH$_2$—(pyrene) |
| C62 | H | H | H | H | —CH$_2$CH$_2$—C$_6$H$_4$—OCH$_3$ (ortho) |
| C63 | H | H | H | H | —CH$_2$CH$_2$—C$_6$H$_4$—OCH$_3$ (meta) |
| C64 | H | H | H | H | —CH$_2$CH$_2$—C$_6$H$_4$—CH$_3$ (ortho) |
| C65 | H | H | H | H | —CH$_2$CH$_2$—C$_6$H$_4$—CH$_3$ (meta) |

TABLE 21-5-continued

| Coupler (Cp) No. | R1 | R2 | R3 | R4 | X |
|---|---|---|---|---|---|
| C66 | H | H | H | H | —CH$_2$CH$_2$—C$_6$H$_3$(CH$_3$)$_2$ (3,5-dimethyl) |
| C67 | H | H | H | H | —CH$_2$CH$_2$—C$_6$H$_4$—Cl (ortho) |
| C68 | H | H | H | H | —CH$_2$CH$_2$—C$_6$H$_4$—Cl (meta) |
| C69 | H | H | H | H | —CH$_2$CH$_2$—C$_6$H$_4$—Cl (para) |
| C70 | H | H | H | H | —CH$_2$CH$_2$—C$_6$H$_4$—NO$_2$ (ortho) |
| C71 | H | H | H | H | —CH$_2$CH$_2$—C$_6$H$_4$—NO$_2$ (meta) |
| C72 | H | H | H | H | —CH$_2$CH$_2$—C$_6$H$_4$—NO$_2$ (para) |
| C73 | H | H | H | H | —CH$_2$CH$_2$—C$_6$H$_4$—C$_6$H$_5$ (biphenyl) |
| C74 | H | H | H | H | —C$_3$H$_7$ |
| C75 | H | H | H | H | —C$_4$H$_9$ |

TABLE 21-6

| Coupler (Cp) No. | R1 | R2 | R3 | R4 | X |
|---|---|---|---|---|---|
| C76 | H | H | H | H | —C$_5$H$_{11}$ |
| C77 | H | H | H | H | —CH$_2$CH$_2$—(pyrene) |

TABLE 21-6-continued

| Coupler (Cp) No. | R1 | R2 | R3 | R4 | X |
|---|---|---|---|---|---|
| C78 | H | H | H | H | 2-methoxyphenyl |
| C79 | H | H | H | H | 3-methoxyphenyl |
| C80 | H | H | H | H | 2-methylphenyl |
| C81 | H | H | H | H | 3-methylphenyl |
| C82 | H | H | H | H | 2,4-dimethylphenyl |
| C83 | H | H | H | H | 3,5-dimethylphenyl |
| C84 | H | H | H | H | 2-chlorophenyl |
| C85 | H | H | H | H | 3-chlorophenyl |
| C86 | H | H | H | H | 4-chlorophenyl |
| C87 | H | H | H | H | 4-fluorophenyl |
| C88 | H | H | H | H | 4-bromophenyl |
| C89 | H | H | H | H | 2-nitrophenyl |
| C90 | H | H | H | H | 4-nitrophenyl |

TABLE 21-7

| Coupler (Cp) No. | R1 | R2 | R3 | R4 | X |
|---|---|---|---|---|---|
| C91 | H | H | H | H | 3-nitrophenyl |
| C92 | H | H | H | H | 4-carbamoylphenyl |
| C93 | H | H | H | H | 4-(phenylcarbamoyl)phenyl |
| C94 | H | H | H | H | 4-acetylphenyl |
| C95 | H | H | H | H | 4-(phenylcarbonylamino)phenyl |
| C96 | H | H | H | H | phenylcarbonylamino |
| C97 | H | H | H | H | cyclohexyl |
| C98 | H | H | H | H | —CH$_2$—cyclohexyl |
| C99 | H | H | H | H | —CH$_2$CH$_2$—cyclohexyl |
| C100 | H | H | H | H | 2-benzoxazolyl |
| C101 | H | H | H | H | 2-benzothiazolyl |

TABLE 21-7-continued
| Coupler (Cp) No. | R1 | R2 | R3 | R4 | X |
|---|---|---|---|---|---|
| C102 | H | H | H | H | 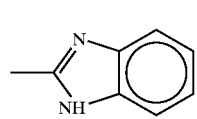 |
| C103 | H | H | H | H |  |
TABLE 21-8
| Coupler (Cp) No. | R1 | R2 | R3 | R4 | X |
|---|---|---|---|---|---|
| C104 | H | H | H | H | 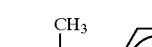 |
| C105 | H | H | H | H | 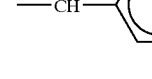 |
| C106 | H | H | H | H | 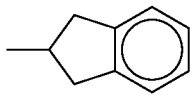 |
| C107 | H | H | H | H | 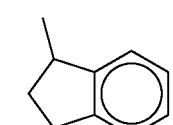 |
| C108 | H | H | H | H | 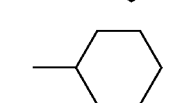 |
| C109 | H | H | H | H | 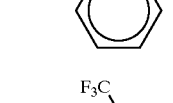 |
| C110 | H | H | H | H | —(CH$_2$)$_4$—⟨phenyl⟩ |
| C111 | H | H | H | H | —(CH$_2$)$_5$—⟨phenyl⟩ |
| C112 | H | H | H | H | —(CH$_2$)$_6$—⟨phenyl⟩ |
TABLE 21-8-continued
| Coupler (Cp) No. | R1 | R2 | R3 | R4 | X |
|---|---|---|---|---|---|
| C113 | H | H | H | H | 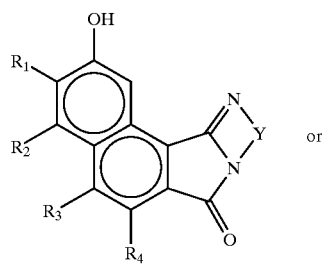 |
| C114 | H | H | H | H | 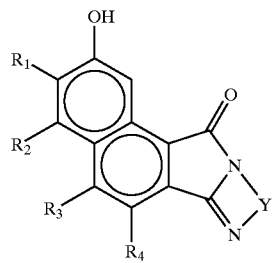 |
TABLE 22-1
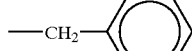
general formula <<103>>
general formula <<104>>
| Coupler (Cp) No. | R1 | R2 | R3 | R4 | Y |
|---|---|---|---|---|---|
| E1 | H | H | H | H |  |
| E2 | H | —CH$_3$ | H | H | 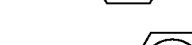 |
| E3 | —CH$_2$CH$_2$CH$_2$— | H | H | 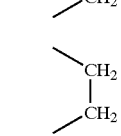 |
| E4 | H | H | H | H | 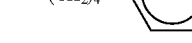 |

TABLE 22-1-continued
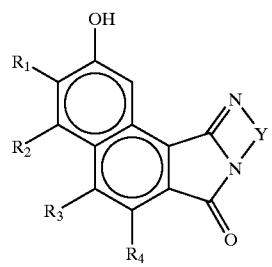
general formula <<103>>
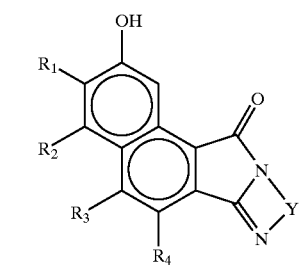
general formula <<104>>
| Coupler (Cp) No. | R1 | R2 | R3 | R4 | Y |
|---|---|---|---|---|---|
| E5 | H | H | —CH$_3$ | H | 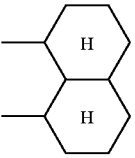 |
| E6 | H | —CN | H | H | 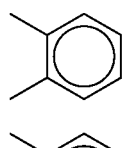 |
| E7 | H | H | H | H | 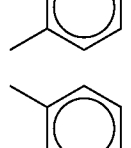 |
| E8 | H | H | —CH$_3$ | H | 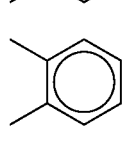 |
| E9 | H | —OCH$_3$ | H | H | 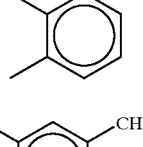 |
| E10 | H | —CN | H | H | 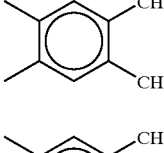 |
TABLE 22-2
| Coupler (Cp) No. | R1 | R2 | R3 | R4 | Y |
|---|---|---|---|---|---|
| E11 | H | —N(C$_2$H$_5$)$_2$ | H | H | 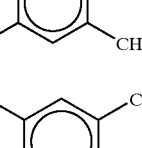 |
| E12 | H | H | H | H | 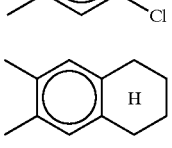 |
| E13 | —CH$_3$ | H | H | H | 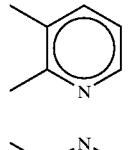 |
| E14 | H | —OCH$_3$ | H | H | 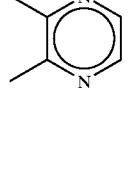 |
| E15 | H | H | —CH$_3$ | H |  |
| E16 | H | H | H | —CH$_3$ | 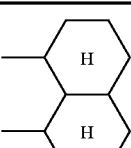 |
| E17 | H | H | H | H | 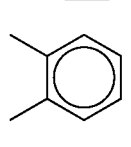 |
| E18 | H | —CH$_3$ | H | H | 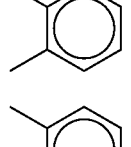 |
| E19 | H | H | H | H | 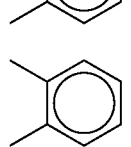 |
| E20 | H | H | H | H | 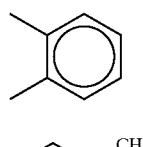 |
| E21 | H | H | H | H | 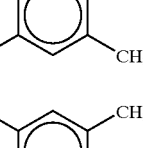 |
| E22 | H | —N(CH$_3$)$_2$ | H | H | 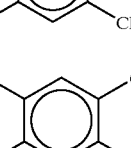 |

TABLE 22-2-continued

| Coupler (Cp) No. | R1 | R2 | R3 | R4 | Y |
|---|---|---|---|---|---|
| E23 | H | H | H | H | 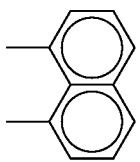 |
| E24 | —CH$_3$ | H | H | H | 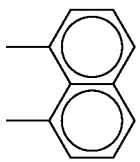 |
| E25 | H | H | —CH$_3$ | H | 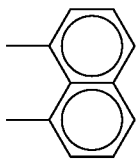 |

TABLE 22-3

| Coupler (Cp) No. | R1 | R2 | R3 | R4 | Y |
|---|---|---|---|---|---|
| E26 | H | H | H | H | 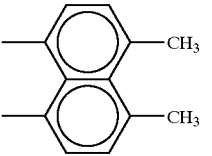 |
| E27 | H | H | H | H | 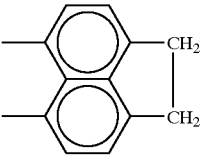 |
| E28 | H | H | H | H | 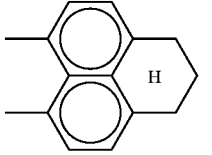 |
| E29 | H | H | H | H | 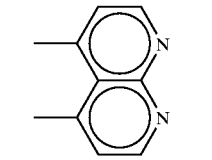 |
| E30 | H | H | H | H | 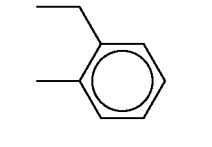 |

TABLE 22-3-continued

| Coupler (Cp) No. | R1 | R2 | R3 | R4 | Y |
|---|---|---|---|---|---|
| E31 | H | H | H | H | 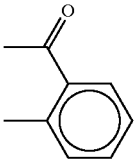 |

Further, in addition to the coupler residues expressed in the general formula <<102>>, the general formula <<103>>, and the general formula <<104>>, those (Cp'), which may coexist, include the coupler residues expressed in the above-mentioned general formula <<2>>, the general formula <<3>>, and the general formula <<4>>, as well as the coupler residues (Cp'), of which the description that they may coexist can be found.

To manufacture the azo compounds expressed in the general formula <<101>> of the present invention, for example, the amino compounds corresponding to the main skeleton (Ar portion) can be used as initial materials, isolated as diazonium salt expressed in the general formula <<15>> through diazotization, and then coupling-reacted with their associated coupler compounds expressed in the general formula <<16>> under the presence of alkali in an appropriate organic solvent (N,N-dimethylformamide or the like). Among the azo compounds expressed in the general formula <<101>> of the present invention, for those with n=2 or larger, two or more kinds of coupler compounds can be used and in this case, these azo compounds can be manufactured by reacting the coupler compound corresponding to that expressed in the following general formula <<122>>, <<124>>, or <<125>>,

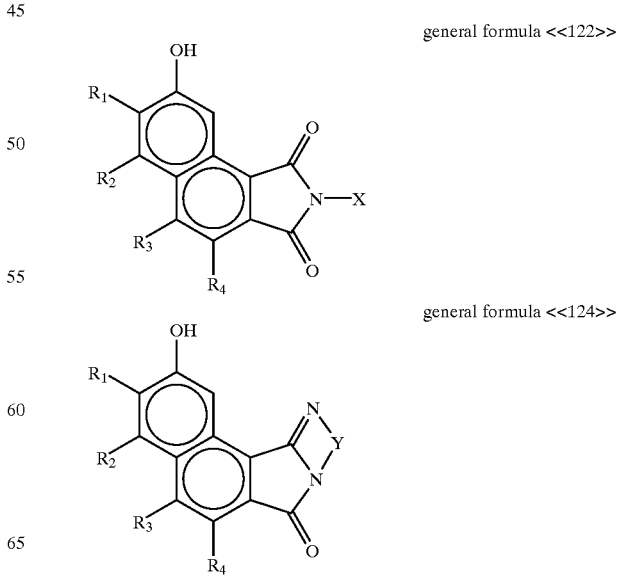

general formula <<122>> general formula <<124>>

-continued general formula <<125>>

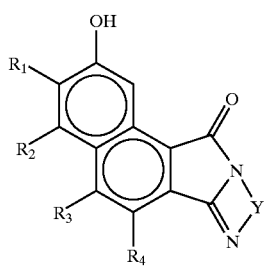

and the coupler compound expressed in any of the general formula mentioned below (Cp1)-(Cp15) with the diazonium compound expressed in the general formula <<15>> at two stages in that order, alternately, by isolating the diazonium salt compound obtained through the first coupling reaction and then reacting with the associated coupler compound.

Now, embodiments of the above-mentioned azo compounds expressed in the general formula <<101>> are shown below in table 23-1 to table 23-6 and for simplification, only n, the main skeleton (Ar portion), and coupler compound (Cp) are illustrated to explain the azo compounds by means of combination of numbers for them. The azo compounds of the present invention are not limited only to the embodiments.

TABLE 23-1

| Azo Compound No. | n | Main Skeleton (Ar) No. | Coupler (Cp) No. | |
|---|---|---|---|---|
| P1 | 1 | A1 | C1 | |
| P2 | 1 | A1 | C5 | |
| P3 | 1 | A1 | C14 | |
| P4 | 1 | A1 | C28 | |
| P5 | 1 | A1 | E23 | |
| P6 | 1 | A2 | C5 | |
| P7 | 1 | A2 | E23 | |
| P8 | 2 | A3 | C5 | |
| P9 | 2 | A3 | C5 | 1 |
| P10 | 2 | A3 | C18 | |
| P11 | 2 | A4 | C5 | |
| P12 | 2 | A4 | C5 | 247 |
| P13 | 2 | A4 | C21 | |
| P14 | 2 | A4 | E23 | 247 |
| P15 | 2 | A8 | C14 | |
| P16 | 2 | A8 | C71 | |
| P17 | 2 | A9 | C1 | |
| P18 | 2 | A9 | C1 | 17 |
| P19 | 2 | A9 | C5 | |
| P20 | 2 | A9 | C5 | 17 |
| P21 | 2 | A9 | C10 | |
| P22 | 2 | A9 | C13 | |
| P23 | 2 | A9 | C14 | |
| P24 | 2 | A9 | C14 | 17 |
| P25 | 2 | A9 | C18 | |
| P26 | 2 | A9 | C20 | |
| P27 | 2 | A9 | C28 | |
| P28 | 2 | A9 | C28 | 17 |
| P29 | 2 | A9 | C30 | |
| P30 | 2 | A9 | C35 | |
| P31 | 2 | A9 | C36 | |
| P32 | 2 | A9 | C44 | |
| P33 | 2 | A9 | E4 | |
| P34 | 2 | A9 | E12 | |
| P35 | 2 | A9 | E12 | 17 |
| P36 | 2 | A9 | E12 | 152 |
| P37 | 2 | A9 | E17 | |
| P38 | 2 | A9 | E23 | |
| P39 | 2 | A9 | E23 | 17 |
| P40 | 2 | A9 | E26 | |

TABLE 23-2

| Azo Compound No. | n | Main Skeleton (Ar) No. | Coupler (Cp) No. | |
|---|---|---|---|---|
| P41 | 2 | A10 | C14 | |
| P42 | 2 | A10 | C14 | 4 |
| P43 | 2 | A10 | E23 | |
| P44 | 2 | A11 | C5 | |
| P45 | 2 | A11 | C14 | |
| P46 | 2 | A11 | E23 | |
| P47 | 2 | A14 | C1 | |
| P48 | 2 | A14 | C1 | 43 |
| P49 | 2 | A14 | C5 | |
| P50 | 2 | A14 | C5 | 43 |
| P51 | 2 | A14 | C10 | |
| P52 | 2 | A14 | C14 | |
| P53 | 2 | A14 | C14 | 43 |
| P54 | 2 | A14 | C19 | |
| P55 | 2 | A14 | C21 | |
| P56 | 2 | A14 | C27 | |
| P57 | 2 | A14 | C28 | |
| P58 | 2 | A14 | C28 | 43 |
| P59 | 2 | A14 | C28 | 17 |
| P60 | 2 | A14 | C36 | |
| P61 | 2 | A14 | C42 | |
| P62 | 2 | A14 | E4 | |
| P63 | 2 | A14 | E11 | |
| P64 | 2 | A14 | E12 | |
| P65 | 2 | A14 | E12 | 43 |
| P66 | 2 | A14 | E23 | |
| P67 | 2 | A14 | E23 | 43 |
| P68 | 2 | A14 | E26 | |
| P69 | 2 | A19 | C14 | |
| P70 | 2 | A19 | E24 | |
| P71 | 2 | A20 | C14 | |
| P72 | 2 | A20 | E24 | |
| P73 | 3 | A23 | C1 | |
| P74 | 3 | A23 | C5 | |
| P75 | 3 | A23 | C7 | |
| P76 | 3 | A23 | C7 | 70 |
| P77 | 3 | A23 | C14 | |
| P78 | 3 | A23 | C14 | 70 |
| P79 | 3 | A23 | C20 | |
| P80 | 3 | A23 | C25 | |

TABLE 23-3

| Azo Compound No. | n | Main Skeleton (Ar) No. | Coupler (Cp) No. | |
|---|---|---|---|---|
| P81 | 3 | A23 | C28 | |
| P82 | 3 | A23 | C28 | 70 |
| P83 | 3 | A23 | C34 | |
| P84 | 3 | A23 | E12 | |
| P85 | 3 | A23 | E12 | 70 |
| P86 | 3 | A23 | E23 | |
| P87 | 3 | A23 | E23 | 70 |
| P88 | 2 | A24 | C5 | |
| P89 | 2 | A24 | C14 | |
| P90 | 2 | A24 | C21 | |
| P91 | 2 | A24 | C28 | |
| P92 | 2 | A24 | E12 | |
| P93 | 2 | A24 | E23 | |
| P94 | 2 | A26 | C5 | |
| P95 | 2 | A26 | C5 | 216 |
| P96 | 2 | A26 | C13 | |
| P97 | 2 | A26 | C14 | |
| P98 | 2 | A26 | C28 | 216 |
| P99 | 2 | A26 | E12 | |
| P100 | 2 | A26 | E24 | |
| P101 | 2 | A26 | E24 | 216 |
| P102 | 2 | A9 | C9 | |
| P103 | 2 | A9 | C9 | 17 |
| P104 | 2 | A9 | C10 | 17 |
| P105 | 2 | A9 | C13 | 17 |
| P106 | 2 | A9 | C54 | |
| P107 | 2 | A9 | C54 | 17 |

TABLE 23-3-continued

| Azo Compound No. | n | Main Skeleton (Ar) No. | Coupler (Cp) No. | |
|---|---|---|---|---|
| P108 | 2 | A9 | C55 | |
| P109 | 2 | A9 | C55 | 17 |
| P110 | 2 | A9 | C56 | |
| P111 | 2 | A9 | C56 | 17 |
| P112 | 2 | A9 | C59 | |
| P113 | 2 | A9 | C59 | 17 |
| P114 | 2 | A9 | C60 | |
| P115 | 2 | A9 | C60 | 17 |
| P116 | 2 | A9 | C61 | |
| P117 | 2 | A9 | C61 | 17 |
| P118 | 2 | A9 | C82 | |
| P119 | 2 | A9 | C82 | 17 |
| P120 | 2 | A9 | C83 | |

TABLE 23-4

| Azo Compound No. | n | Main Skeleton (Ar) No. | Coupler (Cp) No. | |
|---|---|---|---|---|
| P121 | 2 | A9 | C83 | 17 |
| P122 | 2 | A9 | C92 | |
| P123 | 2 | A9 | C92 | 17 |
| P124 | 2 | A9 | C95 | |
| P125 | 2 | A9 | C95 | 17 |
| P126 | 2 | A9 | C96 | |
| P127 | 2 | A9 | C96 | 17 |
| P128 | 2 | A9 | C101 | |
| P129 | 2 | A9 | C101 | 17 |
| P130 | 2 | A9 | C102 | |
| P131 | 2 | A9 | C102 | 17 |
| P132 | 2 | A9 | E31 | |
| P133 | 2 | A9 | E31 | 17 |
| P134 | 2 | A9 | C11 | |
| P135 | 2 | A9 | C11 | 17 |
| P136 | 2 | A9 | C24 | |
| P137 | 2 | A9 | C24 | 17 |

TABLE 23-5

| Azo Compound No. | n | Main Skeleton (Ar) No. | Coupler (Cp) No. | |
|---|---|---|---|---|
| P138 | 2 | A9 | C40 | |
| P139 | 2 | A9 | C40 | 17 |
| P140 | 2 | A9 | C37 | |
| P141 | 2 | A9 | C37 | 17 |
| P142 | 2 | A9 | C110 | |
| P143 | 2 | A9 | C110 | 17 |
| P144 | 2 | A9 | C50 | |
| P145 | 2 | A9 | C50 | 17 |
| P146 | 2 | A9 | C5 | 195 |
| P147 | 2 | A9 | C12 | |
| P148 | 2 | A9 | C12 | 17 |
| P149 | 2 | A9 | C49 | |
| P150 | 2 | A9 | C49 | 17 |
| P151 | 2 | A9 | C51 | |
| P152 | 2 | A9 | C51 | 17 |
| P153 | 2 | A9 | C104 | |
| P154 | 2 | A9 | C104 | 17 |
| P155 | 2 | A9 | C105 | |
| P156 | 2 | A9 | C105 | 17 |
| P157 | 2 | A9 | C106 | |
| P158 | 2 | A9 | C106 | 17 |
| P159 | 2 | A9 | C107 | |
| P160 | 2 | A9 | C107 | 17 |
| P161 | 2 | A9 | C108 | |
| P162 | 2 | A9 | C108 | 17 |
| P163 | 2 | A9 | C109 | |
| P164 | 2 | A9 | C109 | 17 |
| P165 | 2 | A9 | C111 | |
| P166 | 2 | A9 | C111 | 17 |

TABLE 23-5-continued

| Azo Compound No. | n | Main Skeleton (Ar) No. | Coupler (Cp) No. | |
|---|---|---|---|---|
| P167 | 2 | A9 | C112 | |
| P168 | 2 | A9 | C112 | 17 |
| P169 | 2 | A9 | C113 | |
| P170 | 2 | A9 | C113 | 17 |
| P171 | 2 | A9 | C114 | |
| P172 | 2 | A9 | C114 | 17 |
| P173 | 2 | A9 | E30 | |
| P174 | 2 | A9 | E30 | 17 |
| P175 | 2 | A9 | C14 | 195 |
| P176 | 2 | A9 | C24 | 195 |
| P177 | 2 | A9 | C110 | 195 |
| P178 | 2 | A9 | E30 | 195 |
| P179 | 2 | A9 | E31 | 195 |

TABLE 23-6

| Azo Compound No. | n | Main Skeleton (Ar) No. | Coupler (Cp) No. | |
|---|---|---|---|---|
| P180 | 2 | A24 | C5 | 1 |
| P181 | 2 | A24 | C14 | 1 |
| P182 | 2 | A24 | C24 | |
| P183 | 2 | A24 | C24 | 1 |
| P184 | 2 | A24 | C28 | 1 |
| P185 | 2 | A24 | E23 | |
| P186 | 2 | A24 | E23 | 1 |
| P187 | 2 | A24 | E30 | |
| P188 | 2 | A24 | E30 | 1 |

Now, the electrophotographic photoconductor made of other compounds than the above-mentioned azo compounds will be explained below in detail.

In the present invention, single-layer or laminated (function-separated) electrophotographic photoconductors can be manufactured from a charge generating substance alone or by means of combination with a charge transporting substance. In the layer composition of the single-layer type, the photoconductive layer, in which the charge generating substance is dispersed alone or by means of combination with the charge transporting substance, is disposed on a conductive substratum. In the layer composition of the laminated type, the charge generating layer containing the charge generating substance is formed on the conductive substratum and the charge transporting layer containing the charge transporting substance is formed thereon, alternately, the charge generating layer may be inversely laminated on the charge transporting layer. Further, to improve adhesion and charge blocking performance, an interlayer may be disposed between the photoconductive layer and the conductive substratum. Furthermore, to improve mechanical durability such as wear resistance, a protective layer may be disposed on the top of the photoconductive layer.

Solvents to be used in adjusting a dispersion liquid or a solution of the photoconductive layer include, for example, N,N-dimethylhormamido, toluene, xylene, monochlorbenzene, 1,2-dichlorethane, 1,1,1-trichlorethane, dichlormethane, 1,1,2-trichlorethane, trichlorethylene, tetrahydrofuran, methyl ethyl ketone, methyl isobuthyl ketone, cyclohexanone, ethyl acetate, butyl acetate, dioxin, dioxsolan, and the like.

Adheisves used in a process of manufacturing the photoconductive layser may be preferably selected from any of adhesives for electrophotographic photoconductors having better insulation performance, which have conventionally been known, and no special limitations are applied. For example, addition polymerized resins such as polyethylene, polyvinylbutyral, polyvinylformar, polystyrene, phenoxy resin, polypropylene, acrylic resin, methacrylate resin, vinylchloride resin, vinylacetate resin, epoxy resin, polyurethane resin, phenol resin, polyester, alkyd resin, polycarbonate, polyamido, silicone resin, and melamine resin, polyaddition resins, polycondensation resins, and copolymer resins containing two out of repetitive units of these resins, and insulating resins, for example, vinyl chloride-vinyl acetate copolymer, styrene-acrylic copolymer, and vinyl chloride-vinyl acetate-anhydrous maleic acid copolymer, as well as semi-conductive organic polymer such as poly-N-vinylcarbazole and the like may be given as examples. These adhesives can be used alone or as a mixture of two or more.

In addition to the azo compounds expressed in the general formula <<1>> and <<101>>, combinations of the azo compounds with an organic or an inorganic charge generating substance can be used for the charge generating substance of the present invention in a mixture or dispersion form.

Organic charge generating substances include, for example, C.I. pigment blue 25 (color index CI 21180), C.I. pigment red 41 (CI 21200), C.I. acid red 52 (CI 45100), C.I. basic red 3 (CI 45210), azo pigments such as azo pigment having a carbazole skeleton (JP-A No. 53-95033), azo pigment having a distilylbenzene skeleton (JP-A No. 53-133445), azo pigment having a triphenylamine skeleton (JP-A No. 53-132347), azo pigment having a dibenzothiophene skeleton (JP-A No. 54-21728), azo pigment having an oxadiazole skeleton (JP-A NO. 54-12742), azo pigment having a fluorenon skeleton (JP-A No. 54-22834), dia pigment having a bis stilbene skeleton (JP-A No. 54-17733), azo pigment having a distilyloxadiazole skeleton (JP-A No. 54-2129), and azo pigment having a distilylcarbazole skeleton (JP-A No. 54-14967), phthalocyanine pigments such as C.I. pigment blue 16 (CI 74100), and the like, indigo pigments such as C.I. vat brown 5 (CI 73410), C.I. vat dye (CI), and the like, and perylene pigments such as argo scarlet B (Buyer) 73030, INDO F.BR Scarlet R (Buyer).

The inorganic charge generating substances include, for example, selenium, selenium-tellurium, cadmium sulfide, cadmium-selenium, α-silicone, and the like. Note that these charge generating substances may be used alone or by combination of two or more.

Alternately, the charge generating substances for the present invention may be used after they undergo a crystal conversion process, which may include, for example, solvent treatment, mechanical treatment, and heat treatment. Solvent treatment means that pigment is suspended and stirred in a solvent at room temperature or under a heating condition, while milling treatment is performed by any milling equipment such as a sand mill and a ball mill using, for example, glass beads, steel beads, or aluminum balls at constant temperature or under a heating condition. Milling treatment may be performed in a system, in which a solvent is added together with any of the above-mentioned milling medium. The solvents to be used in these treatments include, for example, N,N-dimethylformamide, N-methylpyrolidone, 1,3-dimethyl-2-imidazolydine, dimethylsulfoxide, toluene, xylene, monochlorbenzene, 1,2-dichlorethane, 1,1,1-trichlorethane, dichlormethane, 1,1,2-trichlorethane, trichlorethylene, tetrahydrofuran, dioxane, dioxysolan, methyl ethyl ketone, methyl isobuthyl ketone, cyclohexanone, ethyl acetate, butyl acetate, methanol, ethanol, isopropanol, butanol, 2-methoxyethanol, and the like.

The charge generating substances can be disposed by adding a binder resin to an appropriate solvent, if necessary, for dissolution or dispersion, coating, and then drying.

The method for dispersing the charge generating substances include, for example, ball mill dispersion, ultrasonic dispersion, and homomixer dispersion. The methods for coating the substances include dip coating, blade coating, spray coating, and the like.

If the photoconductive layer is formed by dispersing a charge generating substance, it is preferable that the charge generating substance has an average particle size equal to or smaller than 2 $\mu$m, in particular, equal to or smaller than 1 $\mu$m to improve dispensability into the photoconductive layer. Note that too small particle sizes mentioned above cause the substance to easily aggregate, leading to increased resistance of the layer and increased defects in crystal, which may deteriorate sensitivity and repeatability of the layer. Considering the limitations in micro-fabrication, it is preferable that the lower limit of the average particle size is 0.01 $\mu$m.

In the photoconductive layer of the present invention, the charge transporting substances are used, if necessary. The charge transporting substances to be used according to the present invention are largely divided into two types, one being the hole transporting substance and the other being the electron transporting substance. For the hole transporting substance, for example, poly-N-carbazole and its derivatives, poly-γ-carbazolylethylglutamate and its derivatives, pyrene-formaldehyde condensate and its derivatives, polyvinylpyrene, polyvinylphenanthrene, oxazole derivatives, imidazole derivatives, triphenylamine derivatives, and the compounds expressed by the general formula shown below are preferably used.

The examples of the hole transporting substance are shown below but the hole transporting substances according to the present invention are not limited only to them.

The Hole Transporting Substances Disclosed in JP-A No.55-154955 and JP-A No. 55-156954

General Formula (T1)

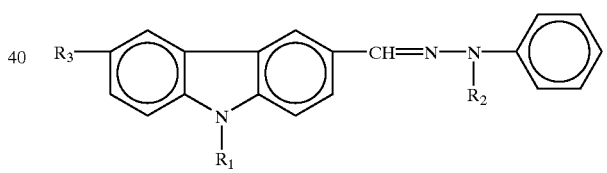

(In the general formula (T1), $R_1$ represents a methyl group, an ethyl group, a 2-hydroxyethyl group, or a 2-chlorethyl group, $R_2$ represents a methyl group, an ethyl group, a benzyl group, or a phenyl group, and $R_3$ represents a hydrogen atom, a chlorine atom, a bromine atom, an alkyl group having 1, 2, 3, or 4 carbon atoms, an alkoxyl group having 1, 2, 3, or 4 carbon atoms, a dialkylamino group, or a nitro group.)

The Hole Transporting Substances Disclosed in JP-A No.55-52063.

General Formula (T2)

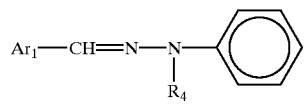

(In the general formula (T2), $Ar_1$ represents a naphthalene ring, an anthracene ring, a stilyl ring, and their constituents, a pyridine ring, a furan ring, or a thiophene ring, and $R_4$ represents an alkyl group or a benzyl group.)

The Hole Transporting Substances Disclosed in JP-A No.56-81850.

General Formula (T3)

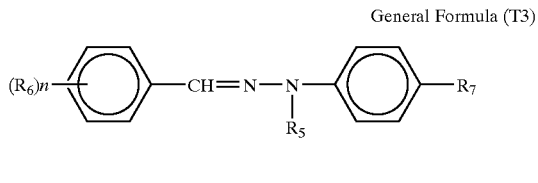

(In the general formula (T3), $R_5$ represents an alkyl group, a benzyl group, a phenyl group, or a naphthyl group, $R_6$ represents a hydrogen atom, an alkyl group having 1, 2, or 3 carbon atoms, a alkoxyl group having 1, 2, or 3 carbon atoms, a dialkylamino group, a diaralkylamino group or diallylamino group, and n represents any integer of 1, 2, 3, and 4 and when n=2 or larger, $R_6$ may be the same as or different from any of those mentioned above. $R_7$ represents a hydrogen atom or a methoxyl group.)

The Hole Transporting Substances Disclosed in the Japanese Patent Application Publication (JP-B) No.51-10983.

General Formula (T4)

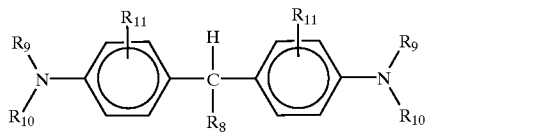

(In the general formula (T4), $R_8$ represents an alkyl group having 1, 2,3, 4, 5, 6, 7, 8, 9, 10, or 11 carbon atoms, a substituted or nonsubstituted phenyl group, or a heterocyclic group, and $R_9$ and $R_{10}$, which may be the same between or different from one another, represent hydrogen atoms, alkyl groups having 1, 2, 3, or 4 carbon atoms, hydroxyalkyl groups, chloralkyl groups, or substituted or nonsubstituted aralkyl groups and may bind between one another to form a heterocycle containing a nitrogen atom. Two $R_{11}$s, which may be the same between or different from one another, represent hydrogen atoms, alkyl groups having 1, 2, 3, or 4 carbon atoms, alkoxyl groups, or halogen atoms.)

The Hole Transporting Substances Disclosed in JP-A No.51-94829.

General Formula (T 5)

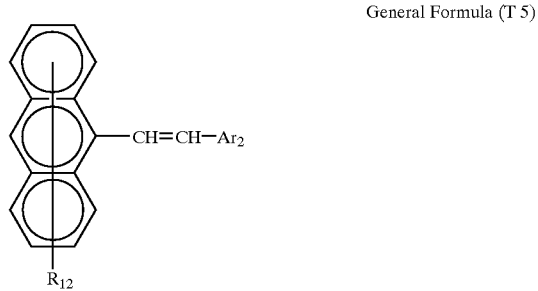

(In the general formula (T5), $R_{12}$ represents a hydrogen atom, or a halogen atom and $Ar_2$ represents a substituted or nonsubstituted phenyl group, a naphthyl group, an antholyl group, or a carbazolyl group.)

The Hole Transporting Substances Disclosed in JP-A No.52-128373.

General Formula (T6)

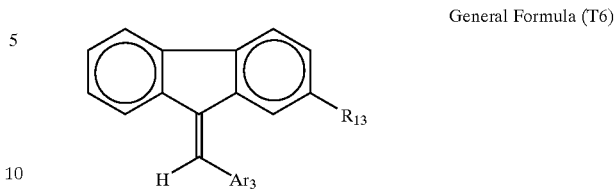

(In the general formula (T6), $R_{13}$ represents a hydrogen atom, a halogen atom, a cyano group, an alkoxyl group having 1, 2, 3, or 4 carbon atoms, or an alkyl group having 1, 2, 3, or 4 carbon atoms, and $Ar_3$ represents General Formula (T6')

General Formula (T6")

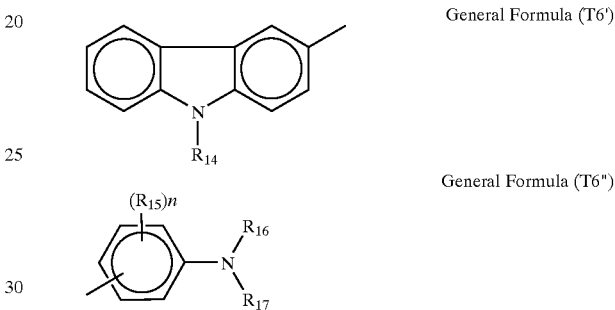

in the formular T6' and T6", $R_{14}$ represents an alkyl group having 1, 2, 3, or 4 carbon atoms, $R_{15}$ represents a hydrogen atom, a halogen atom, an alkyl group having 1, 2, 3, or 4 carbon atoms, an alkoxyl group having 1, 2, 3, or 4 carbon atoms, or a dialkylamino group, n is an integer of 1 or 2 and when n=2, $R_{15}$ may be the same or different, and $R_{16}$ and $R_{17}$ represent hydrogen atoms, substituted or nonsubstituted alkyl groups having 1, 2, 3, or 4 carbon atoms, or substituted or nonsubstituted benzyl groups.)

The Hole Transporting Substances Disclosed in JP-A No.56-29245.

General Formula (T7)

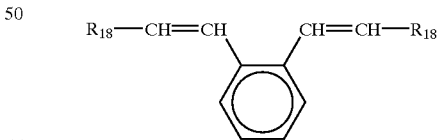

(In the general formula (T7), $R_{18}$ represents a carbazolyl group, a pyridilyl group, a thienyl group, an indolyl group, a furyl group, or a substituted or nonsubstituted phenyl group, stilyl group, naphthyl group, or anthoryl group and the substituents for them selected from a group of a dialkylamino group, a alkyl group, an alkoxyl group, a carboxyl group or its ester, a halogen atom, a cyano group, an aralkylanimo group, a N-alkyl-N-aralkylamino group, an amino group, nitoro group,and acetylamino group.)

The Hole Transporting Substances Disclosed in JP-A No.58-58552.

General Formula (T8)

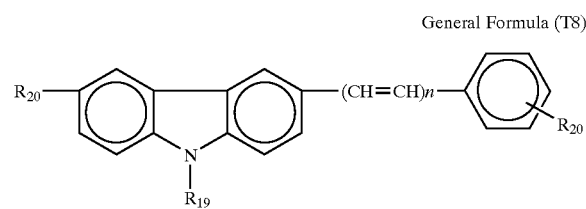

(In the general formula (T8), $R_{19}$ represents a low class of alkyl group, a substituted or nonsubstituted phenyl group, or benzyl group, $R_{20}$ represents a hydrogen atom, a low class of alkyl group, a low class of alkoxyl group, a halogen atom, a nitro group, an amino group, or an amino group substituted by a low class of alkyl group or a benzyl group, and n represents an integer of 1 or 2.

The Hole Transporting Substances Disclosed in JP-A No.57-73075.

General Formula (T9)

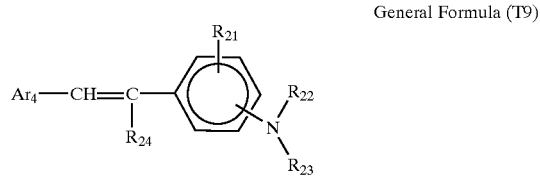

(In the general formula (T9), $R_{21}$ represents a hydrogen atom, an alkyl group, an alkoxyl group, or a halogen atom, $R_{22}$ and $R_{23}$ represent an alkyl group, a substituted or nonsubstituted aralkyl group, or a substituted or nonsubstituted aryl group, $R_{24}$ represents a hydrogen atom, a low class alkyl group, or a substituted or nonsubstituted phenyl group, and $Ar_4$ represents a substituted or nonsubstituted phenyl group or a naphthyl group.)

The Hole Transporting Substances Disclosed in JP-A No.58-198043.

General Formula (T10)

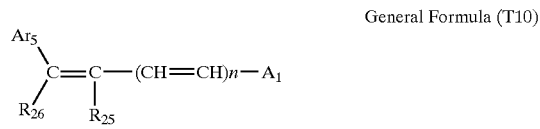

(In the general formula (T10), n represents an integer of 0 or 1, $R_{25}$ represents a hydrogen atom, an alkyl group, or a substituted or nonsubstituted phenyl group, $Ar_5$ represents a substituted or nonsubstituted aryl group, $R_{26}$ represents an alkyl group including a substituted alkyl group or a substituted or nonsubstituted aryl group, and A1 represents General Formula (T10')

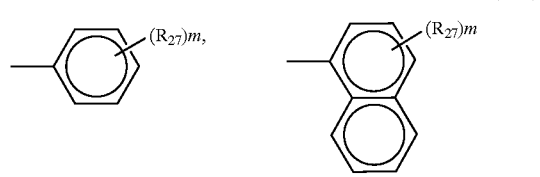

a 9-antholyl group or a substituted or nonsubstituted carbazole group, wherein $R_{27}$ represents a hydrogen atom, an alkyl group, an alkoxyl group, a halogen atom, or General Formula (T10")

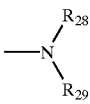

(note that $R_{28}$ and $R_{29}$ represent an alkyl group, a substituted or nonsubstituted aralkyl group, or a substituted or nonsubstituted aryl group and they may be the same between or different from one another, and $R_{29}$ may form a ring.) m represents an integer of 1, 2, or 3 and when m=2 or larger, $R_{27}$s may be the same between or different from one another. Alternately, when n=0, $A_1$ and $R_{25}$ may form a ring in cooperation.)

The Hole Transporting Substances Disclosed in JP-A No.49-105537.

General Formula (T11)

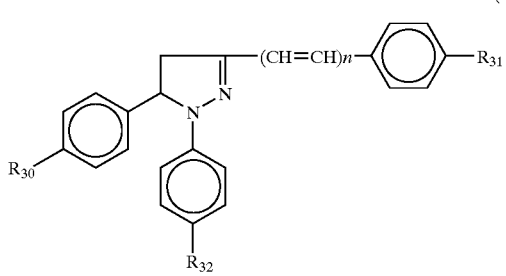

(In the general formula (T11), $R_{30}$, $R_{31}$, and $R_{32}$ represent a hydrogen atom, a low class of alkyl group, a low class of alkoxyl group, a halogen atom or a dialkylamino group and n represents an integer of 0 or 1.)

The Hole Transporting Substances Disclosed in JP-A No.52-139066.

General Formula (T12)

(In the general formula (T12), $R_{33}$ and $R_{34}$ represent an alkyl group including a substituted or nonsubstituted alkyl group, or a substituted or nonsubstituted aryl group, and $A_2$ represents a substituted amino group, a substituted or nonsubstituted aryl group, or an aryl group.)

The Hole Transporting Substances Disclosed in JP-A No.52-139065.

General Formula (T13)

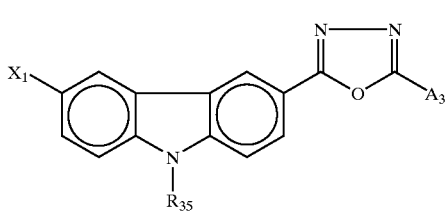

(In the general formula (T13), $X_1$ represents a hydrogen atom, a low class of alkyl group, or a halogen atom, $R_{35}$ represents an alkyl group including a substituted alkyl group or a substituted or nonsubstituted aryl group, and $A_3$ represents is a substituted amino group or a substituted or nonsubstituted aryl group.)

The Hole Transporting Substances Disclosed in JP-A No.58-32372.

General Formula (T14)

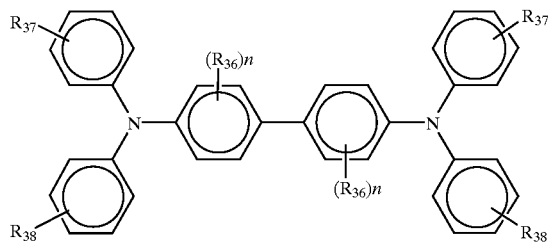

(In the general formula (T14), $R_{36}$ represents a low class of alkyl group, a low class of alkoxyl group or a halogen atom, n represents an integer of 1, 2,3, or 4, $R_{37}$ and $R_{38}$ may be the same between or different from one another and represent an hydrogen atom, a low class of alkyl group, a low class of alkoxyl group or a halogen atom.)

The Hole Transporting Substances Disclosed in JP-A No.2-178669.

General Formula (T15)

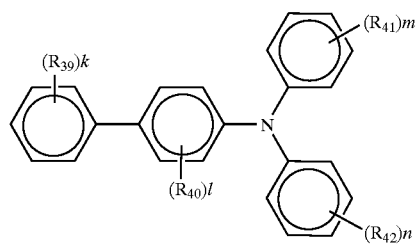

(In the general formula (T15), $R_{39}$, $R_{41}$, and $R_{42}$ represent a hydrogen atom, an amino group, an alkoxyl group, a thioalkoxyl group, an aryloxyl group, a methylenedioxyl group, a substituted or nonsubstituted alkyl group, a halogen atom, or a substituted or nonsubstituted aryl group and $R_{40}$ represents a hydrogen atom, alkoxyl group, a substituted or nonsubstituted alkyl group, or a halogen atom. Note that if all of $R_{39}$, $R_{40}$, $R_{41}$ and $R_{42}$ are hydrogen atoms, the above-mentioned conditions are not applicable. k, l, m, and n are any integer of 1, 2, 3, or 4, respectively and when they are any of 2, 3, or 4, respectively, the above-mentioned $R_{39}$, $R_{40}$, $R_{41}$, and $R_{42}$ may be the same among or different from each other.)

The Hole Transporting Substances Disclosed in JP-A No.3-285960.

General Formula (T16)

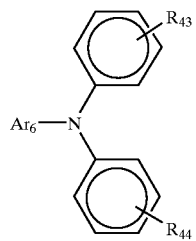

(In the general formula (T16), Ar6 represents a condensation polycyclic hydrocarbon group having 18 carbon atoms or less, $R_{43}$ and $R_{44}$ represent a hydrogen atom, a halogen atom, a substituted or nonsubstituted alkyl group, alkoxyl group, or a substituted or nonsubstituted phenyl group, respectively and may be the same among or different from each other.)

The Hole Transporting Substances Disclosed in JP-A No.1-25748.

$$A_4\text{—}CH\text{=}CH\text{—}Ar_7\text{—}CH\text{=}CH\text{—}A_4 \quad \text{General Formula (T17)}$$

(In the general formula (T17), $Ar_7$ represents a substituted or nonsubstituted aromatic hydrocarbon group and $A_4$ represents:

General Formula (T17')

Note that in the formula T17', $Ar_8$ represents a substituted or nonsubstituted aromatic hydrocarbon group and $R_{45}$ and $R_{46}$ represent a substituted or nonsubstituted alkyl group or a substituted or nonsubstituted aryl group.)

The Hole Transporting Substances Disclosed in JP-A No.4-230764.

General Formula (T18)

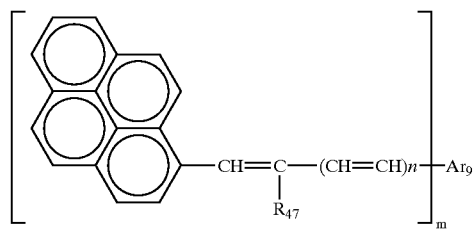

(In the general formula (T18), $Ar_9$ represents a substituted or nonsubstituted aromatic hydrocarbon group and $R_{47}$ represents a hydrogen atom, a substituted or nonsubstituted alkyl group or a substituted or nonsubstituted aryl group. n is an integer of 0 or 1 and m is an integer of 1 or 2, and when n=0 and m=1, $Ar_9$ and $R_{47}$ may form a ring in cooperation.)

The compounds expressed by the general formula (T1) include, for example, 9-ethylcarbazole-3-aldehyde-1-methyl-1-phenylhydrazone, 9-ethylcarbazole-3-aldehyde-1-benzyl-1-phenylhydrazone, 9-ethylcarbazole-3-aldehyde-1, 1-diphenylhydrazone, and the like.

The compounds expressed by the general formula (T2) include 4-diethylaminostilil-β-aldehyde-1-methyl-1-phenylhydrazone, 4-methoxynaphthalene-1-aldehyde-1-benzyl-1-phenylhydrazone, and the like.

The compounds expressed by the general formula (T3) include 4-methoxybenzaldehyde-1-methyl-1-phenylhydrazone, 2,4-dimethoxybenzaldehyde-1-benzyl-1-phenylhydrazone, 4-diethylaminobenzaldehyde-1,1-diphenylhydrazone, 4-methoxybenzaldehyde-1-(4-methoxy) phenylhydrazone, 4-diphenylaminobenzaldehyde-1-benzyl-1-phenylhydrazone, 4-dibenzylaminobenzaldehyde-1,1-diphenylhydrazone, and the like.

The compounds expressed by the general formula (T4) include 1,1-bis(4-dibenzylaminophenyl)propane, tris(4-diethylaminophenyl)methane, 1,1-bis(4-dibenzylaminophenyl)propane, 2,2'dimethyl-4,4'-bis (diethylamino)-triphenylmethane, and the like.

The compounds expressed by the general formula (T5) include 9-(4-diethylaminostilil)anthracene 9-bromine-10-(4-diethylaminostilil)anthracene, and the like.

The compounds expressed by the general formula (T6) include 9-(4-dimethylaminobenzlidene)fluorine, 3-(9-fluorenilidene)-9-ethylcarbazole, and the like.

The compounds expressed by the general formula (T7) include 1,2-bis(4-diethylaminostilil)benzene 1,2-bis(2,4-dimethoxystilil)benzene, and the like.

The compounds expressed by the general formula (T8) include 3-stilil-9-ethylcarbazole and 3-(4-methoxystilyl)-9-ethylcarbazole, and the like.

The compounds expressed by the general formula (T9) include 4-diphenylaminostilbezene, 4-dibenzylaminostilbene, 4-ditolylaminostilbene, 1-(4-diphenylaminostilil)naphthalene, and 1-(4-diethylaminostilil)naphthalene, and the like.

The compounds expressed by the general formula (T10) include 4'-diphenylamino-α-phenylstilbene and 4'-bis(4-methylphenyl)amino-α-phenylstilbene, and the like.

The compounds expressed by the general formula (T11) include 1-phenyl-3-(4-diethylaminostilil)-5-(4-diethylaminophenyl)pyrazoline, and the like.

The compounds expressed by the general formula (T12) include, for example, 2,5-bis(4-diethylaminophenyl)-1,3,4-oxadiazole, 2-N,N-diphenylamino-5-(4-diethylaminophenyl)-1,3,4-oxadiazole, 2-(4-dimethylaminophenyl)-5-(4-diethylaminophenyl)-1,3,4-oxadiazole, and the like.

The compounds expressed by the general formula (T13) include, for example, 2-N,N-diphenylamino-5-(N-ethylcarbazole-3-yl)-1,3,4-oxadiazole, 2-(4-diethylaminophenyl)-5-(N-ethylcarbazole-3-yl)-1,3,4-oxadiazole, and the like.

The benzidine compounds expressed by the general formula (T14) include, for example, N-N'-diphenyl-N-N'-bis(3-methylphenyl)-[1,1'-biphenyl]-4,4'-diamine 3,3'-dimethyl-N-N-N'-N'tetrakyls(4-methylphenyl)-[1,1'-biphenyl]-4,4'-diamine, and the like.

The biphenylamine compounds expressed by the general formula (T15) include, for example, 4-methoxy-N,N-diphenyl-[1,1'-biphenyl]-4-amine, 4'-methyl-N,N-bis(4-methylphenyl)-[1,1'-biphenyl]-4-amine, 4'-methoxy-N,N-bis(4-methylphenyl)-[1,1'-biphenyl]4-amine, and the like.

The triarylamine compounds expressed by the general formula (T16) include, for example, 1-diphenylaminopyrene, 1-di(p-tolylamino) pyrene, and the like.

The diolefin aromatic compounds expressed by the general formula (T17) include, for example, 14-bis(4-diphenylaminostilil)benzene, 1,4-bis[4-di(p-tolyl)aminostilyl]benzene, and the like.

The stilylpyrene compounds expressed by the general formula (T14) include, for example, 1-(4-diphenylaminostilyl)pyrene, 1-[4-di(p-tolyl)aminostilyl] pyrene, and the like.

Among the above-mentioned hole transporting substances, the compounds expressed by the general formula (T1), the general formula (T10), and the general formula (T11) are in particular preferable because they have high charge transporting ability and the combination of them with the new azo compounds of the present invention exhibit better electrostatic properties.

The electron transporting substances include, for example, chloranyl, bromineanyl, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-on, 1,3,7-trinitrodibenzothiophene-5,5-dioxide,, and the like, and (2,3-diphenyl-1-indenylidene) malononitryl expressed by the following general formula (A1) and the electron transporting substances expressed by the general formula (A2) and the general formula (A3) may be preferably used.

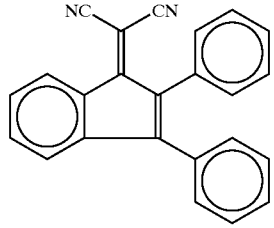

General Formula (A1)

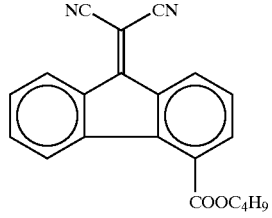

General Formula (A2)

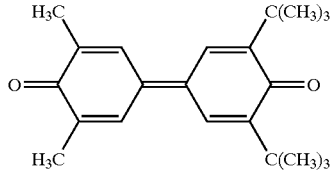

General Formula (A3)

These materials for charge transporting substances can be either alone or in combination of two or more.

In manufacturing the photoconductors using the composition and substances of the layer above mentioned, a preferable scope is applicable to the film thickness and the ratio of substances. With respect to the function-separated (conductive substratum/charge generating layer/charge transporting layer) photoconductors, an adhesive is used in the charge generating layer, if necessary, wherein preferably, the ratio of the charge generating substance to a 100 dead weight of adhesive content (hereafter, simply referred to as the "dead-weight content") is the 20 dead-weight content or more and the film thickness is 0.01–5 μm. With respect to the charge transporting layer, it is preferable that the ratio of the 100 dead-weight of adhesive content to the substance of the charge transporting substance is the 20–200 dead-weight content and the film thickness is 5–100 μm. Alternately, if any polymer charge-transporting substance is used, it alone may form the charge transporting layer. Further, it is preferable that the charge transporting substance is contained in the charge generating layer, which is usable for controlling any residual potential and improving the sensitivity. In this case, it is preferable that a 20–200 dead-weight content of charge transporting substance is contained when 100 dead-weight content of adhesive is applied.

With respect to the single-layer photoconductors, the ratio of weight of the azo compound expressed by the general formula <<1>> and the general formula <<101>> used in the prevent invention to the whole photoconductive layer is preferably 0.1–40% by weight and in particular, 0.3–25% by weight is more preferable.

The ratio of the charge generating substance to the 100 weight content of adhesive in the photoconductive layer is preferably 5–95 weight content and the ratio of the charge generating substance to the photoconductive layer is preferably 0.1–40% by weight, and more preferably 0.3–25% by weight.

From an aspect of electrostatic property, the film thickness is preferably 5 μm and from an aspect of sensitivity, it is preferably equal to or less than 100 μm.

10–100 μm is more preferable and 10–40 μm is further more preferable.

When the charge generating substance is used together with the charge transporting substance, the ratio of the charge transporting substance to 100 dead-weight content of adhesive is preferably a 30–200 dead-weight content. Alternately, the photoconductor may be formed using the polymer charge transporting substance and the charge generating substance, wherein it is preferable that the ratio of the charge generating substance to the 100 dead-weight of polymer charge transporting substance is a 5–95 dead-weight content and the ratio of the charge transporting substance to the whole photoconductive layer is 15–60% by weight, in particular, more preferably 20–40% by weight.

Note that in the mode of the prevent invention where said polymer charge transporting substance is used, the ratio of the polymer transporting substance to the whole photoconductive layer is preferably 20–95% by weight and in particular, 30–80% by weight is more preferable.

With respect to the electrophotographic photoconductors according to the prevent invention, the single layer electrophotographic photoconductors, which use the single-type of photoconductive layer among the above-mentioned photoconductive layers, are preferable from an aspect of reduction in cost of manufacture by means of simplification of the manufacturing process. The above-mentioned hole transporting substance is preferably used as the charge transporting substance for the photoconductive layer of the single-layer electrophotographic photoconductor.

With respect to the single layer of electrophotographic photoconductors according to the prevent invention, the use of the high polymer charge transporting substance is preferable because a highly homogeneous charge mobility matrix is induced, charge injection into and charge movement from the charge generating substance can be performed with no difficulty, and the photoconductors with its mechanical strength improved can be obtained. These better characteristics seem to be achieved using for the polymer charge transporting substance of the prevent invention at least one of polymers such as polycarbonate, polyurethane, polyester, and polyester, resulting in better film formation performance, high mechanical strength, and high wear-resistance.

The use of the polymer transporting substance having a triarylamine structure is preferable from an aspect of achievement of high mobility and in particular, the polycarbonate having a triarylamine structure has an effect on improvement in the properties of the layer. In addition, the combination with high polymer charge transporting substance can achieve the compatibility with the wet-development process, which is difficult for the conventional single layer of photoconductors.

The polymer charge transporting substance, said polycarbonate having the triarylamine structure, includes the polymer charge transporting substances expressed by the general formula (1D), the general formula (2D), the general formula (3D), the general formula (4D), the general formula (5D), the general formula (6D), the general formula (7D), the general formula (8D), the general formula (9D), the general formula (10D), and the general formula (11D) and they are explained below in detail.

The polymer charge transporting substances expressed by the following general formula (1D) are described.

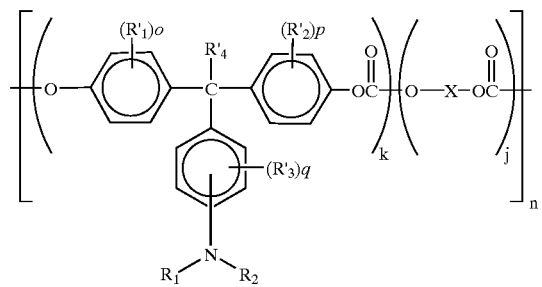

General Formula (1D)

{In the general formula, R'$_1$, R'$_2$, and R'$_3$ represent a substituted or nonsubstituted alkyl group or a halogen atom independently of each other and R'$_4$ represents a hydrogen atom or a substituted or nonsubstituted alkyl group. R$_1$ and R$_2$ represent a substituted or nonsubstituted aryl group. o, p, and q represent an integer of 1, 2, 3, or 4 independent of each other. k and j represent a composition, between which a relationship, $0.1 \leq k \leq 1$ and $0 \leq j \leq 0.9$ is established, and n represents the time number of repetitions, which is any integer of 5–5000. A is a fatty bivalent group, a cyclic fatty bivalent, or a bivalent expressed by the following general formula (A):

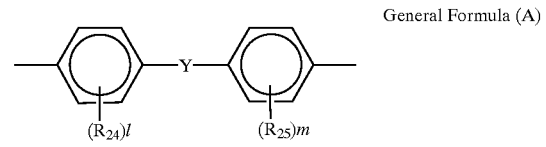

General Formula (A)

[in the formula, R$_{24}$ and R$_{25}$ represent a substituted or nonsubstituted alkyl group, an aryl group, or a halogen atom independent of each other and l and m represent any integer of 1, 2, 3, or 4. Y represents a single bond, linear, branched-chain cyclic alkylene containing 1–12 carbon atoms, —O—, —S—, —SO—, —SO$_2$—, —CO—, —CO—O—Z—O—CO— (in the formula, Z represents a fatty bivalent group.) or the general formula (B)

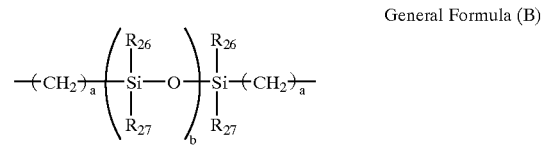

General Formula (B)

(in the formula, a represents an integer of 1–20 and b represents an integer of 1–2000. R$_{26}$ and R$_{27}$ represent a substituted or nonsubstituted alkyl group or aryl group.). Pairs of R$_{24}$ and R$_{25}$ and R$_{26}$ and R$_{27}$ may be the same between and difference from one another in each pair.)}.

The alkyl groups for R'$_1$, R'$_2$ and R'$_3$ are preferably C$_1$–C$_{12}$, in particular, C$_1$–C$_8$, further preferably C$_1$–C$_4$ linear or branched-chain alkyl groups and these alkyl groups may further contain a fluorine atom, a hydroxyl group, a cyano group, a C$_1$–C$_4$ alkoxyl group, a phenyl group, or a phenyl group with substituted with a halogen atom, a C$_1$–C$_4$ alkyl group or a C$_1$–C$_4$ alkoxyl group. Specifically, a methyl group, an ethyl group, a n-propyl group, an i-propyl group, a t-butyl group, a s-butyl group, a n-butyl group, an i-butyl group, a trifluoromethyl group, a 2-hydroxyethyl group, a 2-cyanoethyl group, a 2-ethoxyethyl group, a 2-methoxyethyl group, a benzyl group, a 4-chlorobenzyl group, a 4-methylbenzyl group, a 4-methoxybenzyl group, and 4-phenylbenzyl group may be given as examples. Halogen atoms include a fluorine atom, a chlorine atom, a bromine atom, and an iodine atom. Substituted or nonsubstituted $R'_4$ alkyl groups include the same groups as those given for $R'_1$, $R'_2$, and $R'_3$ mentioned above.

The aryl groups for $R'_1$, $R'_2$ include aromatic hydrocarbon group such as a phenyl group, condensation polycyclic groups such as a naphthyl group, pirenyl group, 2-fluorenyl group, 9,9-dimethyl-2-fluorenyl group, azulenyl group, antholyl group, triphenylenyl group, chrysenyl group, fluorenilidenphenyl group, and 5H-dibenzo[a,d]cycloheptenilidenphenyl group, noncondensation polycyclic groups such as a biphenylyl group and tarphenylyl group, heterocyclic groups such as a thienyl group, benzothieyl group, furil group, benzo group, benzofuranyl group, and carbazolyl group.

The above-mentioned aryl groups may have the groups listed blow as the substituents for themselves.

(1) halogen atom, trifluoromethyl group, cyano group, nitro group (2) alkyl group: the same as those given for above-mentioned $R_1$, $R_2$, and $R_3$ (3) alkoxy group (—$OR_{41}$): $R_{41}$ represents the alkyl group given in the above-mentioned (2). Specifically, it includes a methoxyl group, an ethoxyl group, a n-propoxyl group, an i-propoxyl group, a t-butoxyl group, a n-butoxyl group, a s-butoxyl group, an i-butoxyl group, a 2-hydroxyethoxyl group, a 2-cyanoethoxyl group, a benzyloxyl group, a 4-methylbenzyloxyl group, and a trifluoromethoxyl group are given as examples.

(4) aryloxyl group: the aryl group includes a phenyl group and a naphthyl group. They may contain a $C_1$–$C_4$ alkoxy group, a $C_1$–$C_4$ alkyl group or a halogen atom as its substituent. Specifically, a phenoxyl group, a 1-naphthyloxy group, a 2-naphthyloxy group, a 4-methylphenoxy group, a 4-methoxyphenoxy group, a 4-chlorophenoxy group, and a 6-methyl-2-naphthyloxy group are given as examples.

(5) substituted mercapto group or arylmercapto group: specifically, a methylthio group, an ethylthio group, a phenylthio group, and a p-methylphenylthio group are given as examples.

(6) alkyl substituted amino group: an alkyl group indicats the alkyl group given in the above mentioned (2), specifically, a dimethylamino group, a diethylamino group, a N-methyl-N-propylamino group, and a N,N-dibenzylamino group are given as examples.

(7) acyl group: specifically, an acetyl group, a propionyl group, a butyryl group, a malonyl group, and a benzoyl group are given as examples.

X is introduced into the main chain by combining the diole compound expressed by the following general formula (C) in polymerizing the diole compound having a triarylamino group expressed by the following general formula (1D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (1D') and bischloroformate induced from the following general formula (C). In this case, the obtained polycarbonate resin is an alternating copolymer.

General Formula (1D')

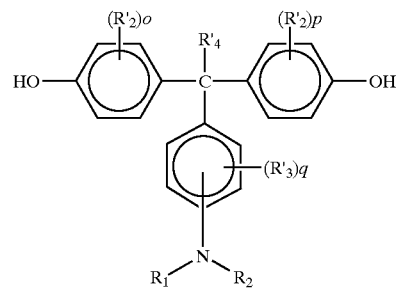

General Formula (C)

HO—X—OH

Examples of the diole compound expressed by the general formula (C) are given as follows. They include fatty dioles such as 1,3-propanediol, 1,4-butanediol, 1,5-pentanediol, 1,6-hexanediol, 1,8-octanediol, 1,10-decanediol, 2-methyl-1,3-propanediol, 2,2-dimetyl-1,3-propanediol, 2-ethyl-1,3-propanediol, diethylenglycol, triethylenglycol, polyethylenglycol, and polytetramethylenetherglycol, and cyclic fatty dioles such as 1,4-cyclohexanediol, 1,3-cyclohexanediol, cyclohexane-1,4-dimethanol. The dioles having a aromatic ring include 4,4'-dihydroxydiphenyl, bis(4-hydroxyphenyl)methane, 1,1-bis(4-hydroxyphenyl)ethane, 1,1bis(4-hydroxyphenyl)-1-phenylethane, 2,2-bis(4-hydroxyphenyl)propane, 2,2-bis(3-methyl-4-hydroxyphenyl)propane, 1,1-bis(4-hydroxyphenyl)cyclohexane, 1,1-bis(4-hydroxyphenyl)cyclopentane, 2,2-bis(3-phenyl-4-hydroxyphenyl)propane, 2,2-bis(3-isopropyl-4-hydroxyphenyl)propane, 2,2-bis(4-hydroxyphenyl)butane, 2,2-bis(3,5-dimethyl-4-hydroxyphenyl)propane, 2,2-bis(3,5-dibromo-4-hydroxyphenyl)propane, 4,4'-dihydroxydiphenylsulfone, 4,4'-dihydroxydiphenylsulfoxide, 4,4'-dihydroxydiphenylsulfydo, 3,3'-dimethyl-4,4'-dihydroxydiphenylsulfydo, 4,4'-dihydroxydiphenyloxide, 2,2-bis(4-hydroxyphenyl)hexafluoropropane, 9,9-bis(4-hydroxyphenyl)fluorine, 9,9-bis(4-hydroxyphenyl)xanthen, ethyleneglycol-bis(4-hydroxybenzoate), diethyleneglycol-bis(4-hydroxybenzoate), triethyleneglycol-bis(4-hydroxybenzoate), 1,3-bis(4-hydroxyphenyl)-tetramethyldisiloxane, and phenol-degenerated silicone oil.

Now, the polymer transporting substances expressed by the following general formula (2D) will be explained.

General Formula (2D)

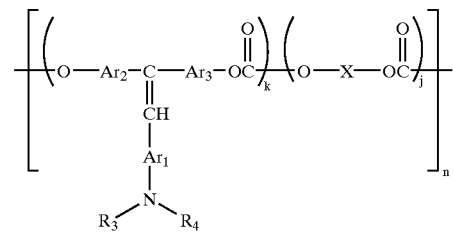

[In the formula, $R_3$ and $R_4$ represent a substituted or nonsubstituted aryl group and $Ar_1$, $Ar_2$, and $Ar_3$ represent the same or different allylene group. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

The aryl groups for $R_3$ and $R_4$ include aromatic hydrocarbon groups such as a phenyl group, condensation polycyclic groups such as a naphthyl group, a pyrenyl group, a 2-fluorenyl group, a 9,9-dimethyl-2-fluorenyl group, an azulenyl group, an antholyl group, a triphenylenyl group, a chrysenyl group, a fluorenylidenphenyl group, a 5H-dibenzo[a,d]cycloheptenylidenphenyl group, a heterocyclic groups such as a thienyl group, a benzothienyl group, a furil group, a benzofuranyl group, a carbazolyl group, or noncondensation polycyclic groups expressed by the following general formula (a) such as a biphenylyl group, and a tarphenylyl group.

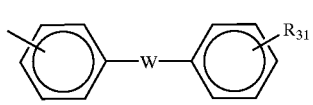

General Formula (a)

In the formula, W represents —O—, —S—, —SO—, —SO$_2$—, —CO— and a bivalent expressed by the following general formulae (b), (c), (d), and

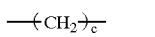

General formula (b)

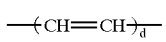

General formula (c)

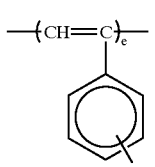

General formula (d)

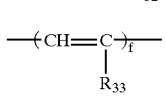

General formula (e)

(in the formula, c represents any of integers 1–12 and d, e, and f represent an integer of 1, 2, or 3.).

The allylene groups for $Ar_1$, $Ar_2$, and $Ar_3$ include bivalent groups of the aryl groups given for $R_3$ and $R_4$.

The aryl groups for $R_3$ and $R_4$ and the allylene groups $Ar_1$, $Ar_2$, and $Ar_3$ may contain the groups shown below as the substituents for them. These substituents are the examples of $R_{31}$, $R_{32}$, and $R_{33}$ in the above-mentioned general formula (a), the general formula (d), the general formula (e).

(1) halogen atom, trifluoromethyl group, cyano group, nitro group (2) Alkyl group: preferably, $C_1$–$C_2$, in particular $C_1$–$C_8$, further preferably, $C_1$–$C_4$ linear or branched-chain alkyl groups and these alkyl groups may further contain a fluorine atom, a hydroxyl group, a cyano group, a $C_1$–$C_4$ alkoxy group, a phenyl group, or a halogen atom, a $C_1$–C4 alkyl group or a phenyl group substituted with $C_1$–$C_4$ alkoxy group. Specifically, a methyl group, an ethyl group, a n-propyl group, an i-propyl group, a t-butyl group, a s-butyl group, a n-butyl group, an i-butyl group, a trifluoromethyl group, a 2-hydroxyethyl group, a 2-syanoethyl group, a 2-ethoxyethyl group, a 2-methoxyethyl group, a benzyl group, a 4-chlorobenzyl group, a 4-methylbenzyl group, a 4-methoxybenzyl group, and a 4-phenylbenzyl group are given as examples.

(3) alkoxy group (—$OR_{41}$): $R_{41}$ represents the alkyl group given in the above-mentioned (2). Specifically, it includes a methoxyl group, an ethoxyl group, a n-propoxyl group, an i-propoxyl group, a t-butoxyl group, a n-butoxyl group, a s-butoxyl group, an i-butoxyl group, a 2-hydroxyethoxyl group, a 2-cyanoethoxyl group, a benzyloxyl group, a 4-methylbenzyloxyl group, and a trifluoromethoxyl group are given as examples.

(4) aryloxyl group: the aryl group includes a phenyl group and a naphthyl group. They may contain a $C_1$–$C_4$ alkoxy group, a $C_1$–$C_4$ alkyl group or a halogen atom as its substituent. Specifically, a phenoxyl group, a 1-naphthyloxy group, a 2-naphthyloxy group, a 4-methylphenoxy group, a 4-methoxyphenoxy group, a 4-chlorophenoxy group, and a 6-methyl-2-naphthyloxy group are given as examples.

(5) substituted mercapto group or arylmercapto group: specifically, a methylthio group, an ethylthio group, a phenylthio group, and a p-methylphenylthio group are given as examples.

(6) substituted amino groups expressed by the general formula —$N(R_{42})(R_{43})$ (In the formula, $R_{42}$ and $R_{43}$ represent the alkyl groups shown in the above-mentioned (2) or the aryl groups shown in the above-mentioned $R_3$ and $R_4$ and preferable aryl groups include, for example, a phenyl group, a biphenyl group, and a naphthyl group, which may contain a $C_1$–$C_4$ alkoxyl group, a $C_1$–$C_4$ alkyl group, or a halogen atom as the substituents for them. They and carbon atoms of aryl groups may form a ring in corporation. Specifically, a diethylamino group, a N-methyl-N-phenylamino group, a N,N-diphenylamino group, a N,N-di(p-tolyl) amino group, a dibenzylamino group, a piperidino group, a morpholino group, and a eurolysil group are given as examples.

(7) A methylenedioxy group, an alkylenedioxyl groups such as an methylenedioxide or an alkylenedithio group.

X is introduced into the main chain by combining the diole compound expressed by the following general formula (C) in polymerizing the diole compound having a triarylamino group expressed by the following general formula (2D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (2D') and bischloroformate induced from the following general formula (C). In this case, the obtained polycarbonate resin is an alternating copolymer.

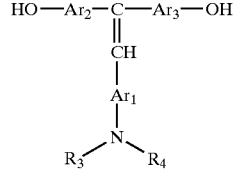

General Formula (2 D')

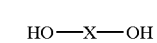

General Formula (C)

Examples of the diole compound expressed by the general formula (C) include those given in the explanation of the above-mentioned general formula (1D).

Now, the polymer transporting substances expressed by the following general formula (3D) will be explained.

General Formula (3D)

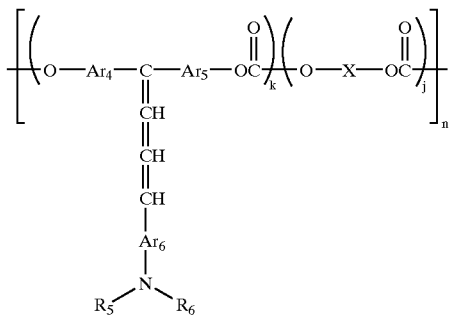

[In the formula, $R_5$ and $R_6$ represent a substituted or nonsubstituted aryl group and $Ar_4$, $Ar_5$, and $Ar_6$ represent the same or different allylene group. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

The aryl groups for $R_5$ and $R_6$ include aromatic hydrocarbon groups such as a phenyl group, and the like, condensation polycyclic groups such as a naphthyl group, a pyrenyl group, a 2-fluorenyl group, a 9,9-dimethyl-2-fluorenyl group, an azulenyl group, an antholyl group, a triphenylenyl group, a chrysenyl group, a fluorenylidenphenyl group, a 5H-dibenzo[a,d]cycloheptenylidenphenyl group, and the like noncondensation polycyclic groups such as a biphenylyl group, a tarphenylyl group, and the like, and a heterocyclic groups such as a thienyl group, a benzothienyl group, a furil group, a benzo group, a benzofuranyl group, a carbazolyl group, and the like.

Alternately, The allylene groups for $Ar_4$, $Ar_5$, and $Ar_6$ include bivalent groups of the aryl groups shown for $R_5$ and $R_6$. The aryl groups for $R_5$ and $R_6$ and the allylene groups for $Ar_4$, $Ar_5$, and $Ar_6$ may contain the groups shown below as the substituents for them.

(1) halogen atom, trifluoromethyl group, cyano group, nitro group (2) Alkyl group: preferably, $C_1$–$C_{12}$, in particular $C_1$–$C_8$, further preferably, $C_1$–$C_4$ linear or branched-chain alkyl groups and these alkyl groups may further contain a fluorine atom, a hydroxyl group, a cyano group, a $C_1$–$C_4$ alkoxy group, a phenyl group, or a halogen atom, a $C_1$–$C_4$ alkyl group or a $C_1$–$C_4$ alkoxy group. Specifically, a methyl group, an ethyl group, a n-propyl group, an i-propyl group, a t-butyl group, a s-butyl group, a n-butyl group, an i-butyl group, a trifluoromethyl group, a 2-hydroxyethyl group, a 2-cyanoethyl group, a 2-ethoxyethyl group, a 2-methoxyethyl group, a benzyl group, a 4-chlorobenzyl group, a 4-methylbenzyl group, a 4-methoxybenzyl group, a 4-phenylbenzyl group, and the like are given as examples.

(3) alkoxy group (—$OR_{41}$): $R_{41}$ represents the alkyl group given in the above-mentioned (2). Specifically, it includes a methoxyl group, an ethoxyl group, a n-propoxyl group, an i-propoxyl group, a t-butoxyl group, a n-butoxyl group, a s-butoxyl group, an i-butoxyl group, a 2-hydroxyethoxyl group, a 2-cyanoethoxyl group, a benzyloxyl group, a 4-methylbenzyloxyl group, a trifluoromethoxyl group, and the like are given as examples.

(4) aryloxyl group: the aryl group includes a phenyl group and a naphthyl group. They may contain a $C_1$–$C_4$ alkoxy group, a $C_1$–$C_4$ alkyl group or a halogen atom as its substituent. Specifically, a phenoxyl group, a 1-naphthyloxy group, a 2-naphthyloxy group, a 4-methylphenoxy group, a 4-methoxyphenoxy group, a 4-chlorophenoxy group, a 6-methyl-2-naphthyloxy group, and the like are given as examples.

(5) substituted mercapto group or arylmercapto group: specifically, a methylthio group, an ethylthio group, a phenylthio group, a p-methylphenylthio group, and the like are given as examples.

(6) alkyl substituted amino group: alkyl group represemts the alkyl group in the above mentioned (2). Specifically, a dimethylamino group, a diethylamino group, a N-methyl-N-propylamino group, a N,N-dibenzylamino group, and the like are given as examples.

(7) acyl group: specifically, an acetyl group, a propionyl group, a butyryl group, a malonyl group, a benzoyl group, and the like are given as examples.

X is introduced into the main chain by combining the diole compound expressed by the following general formula (C) in polymerizing the diole compound having a triarylamino group expressed by the following general formula (3D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (3D') and bischloroformate induced from the following general formula (C). In this case, the obtained polycarbonate resin is an alternating copolymer.

General Formula (3D')

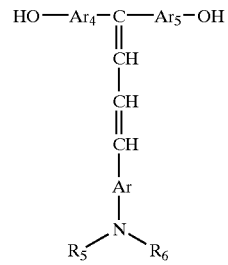

General Formula (C)

HO—X—OH

Examples of a diole compound expressed by the general formula (C) are the same as those given in the explanation of the above-mentioned general formula (1D).

Now, the polymer transporting substances expressed by the following general formula (4D) will be explained.

General Formula (4D)

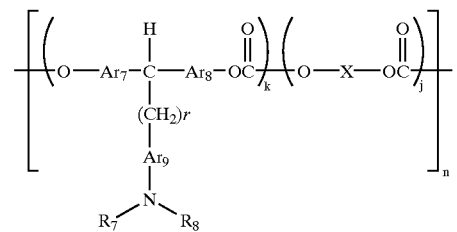

[In the formula, $R_7$ and $R_8$ represent a substituted or nonsubstituted aryl group and $Ar_7$, $Ar_8$, and $Ar_9$ represent the same or different allylene group. k and j represent a composition, wherein a relationship, $0.1 \leq k \leq 1$ and $0 \leq j \leq 0.9$ is established between them and n represents the time number of repetitions, which is any integer of 5–5000.

r represents any of integers 1 to 5. X represents the same group expressed by the above-mentioned general formula (1D).]

Examples of the aryl groups for $R_7$ and $R_8$ is the same as those given for the aryl group for $R_5$ and $R_6$ in the explanation of the general formula (3D) and examples of the allylene groups for $Ar_7$, $Ar_8$, and $Ar_9$ include bivalent groups of these aryl groups. In addition, examples of the substituents for these allylene groups and aryl groups are the same as those give as the substituents for the aryl group and the allylene group in the explanation of the general formula (3D).

X is introduced into the main chain by combining the diole compound expressed by the following general formula (C) in polymerizing the diole compound having a triarylamino group expressed by the following general formula (4D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (4D') and bischloroformate induced from the following general formula (C). In this case, the obtained polycarbonate resin is an alternating copolymer.

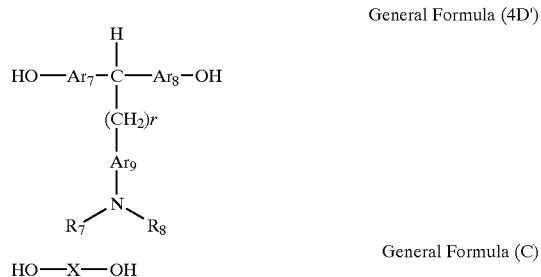

General Formula (4D')

HO—X—OH

General Formula (C)

Examples of the diole compound expressed by the general formula (C) include those given in the explanation of the above-mentioned general formula (1D).

Now, the charge transporting polymeric substances expressed by the following general formula (5D) will be explained.

allylene groups for $Ar_{10}$, $Ar_{11}$, and $Ar_{12}$ include bivalent groups of these aryl groups. In addition, examples of the substituents for these allylene groups and aryl groups are the same as those give as the substituents for the aryl group and the allylene group in the explanation of the general formula (3D). The substituents for the ethylene groups or the vinylene groups for $X_1$ and $X_2$ include a cyano group, a halogen atom, a nitro group, the aryl groups given as examples of aryl groups for $R_5$ and $R_6$ in the general formula (3D), or the allylene groups given as examples of the substituents for aryl groups and allylene groups in the explanation of the general formula (3D).

X is introduced into the main chain by combining the diole compound expressed by the following general formula (C) in polymerizing the diole compound having a triarylamino group expressed by the following general formula (5D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (5D') and bischloroformate induced from the following general formula (C). In this case, the obtained polycarbonate resin is an alternating copolymer.

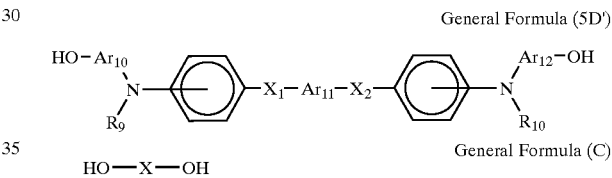

General Formula (5D')

HO—X—OH

General Formula (C)

Examples of the diole compound expressed by the general formula (C) include those given in the explanation of the above-mentioned general formula (1D).

Now, the polymer transporting substances expressed by the following general formula (6D) will be explained.

General Formula (5D)

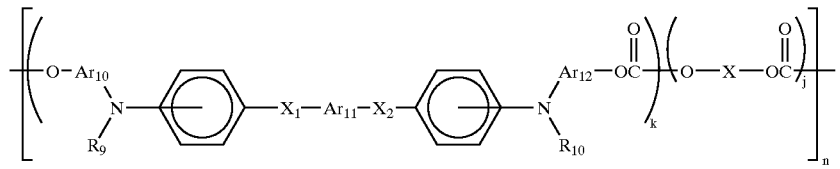

[In the formula, $R_9$ and $R_{10}$ rpresent a substituted or nonsubstituted aryl group and $Ar_{10}$, $Ar_{11}$, and $Ar_{12}$ represent the same or different allylene group. $X_1$ and $X_2$ represent a substituted or nonsubstituted ethylene group, or a substituted or nonsubstituted vinylene group. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

Examples of the aryl groups for $R_9$ and $R_{10}$ is the same as those given for the aryl group for $R_5$ and $R_6$ in the explanation of the general formula (3D) and examples of the General Formula (6D)

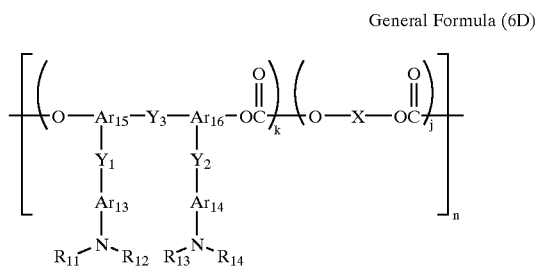

[In the formula, $R_{11}$, $R_{12}$, $R_{13}$, and $R_{14}$ represent substituted or non substituted aryl groups and $Ar_{13}$, $Ar_{14}$, $Ar_{15}$, and $Ar_{16}$ represent the same or different allylene groups. $Y_1$, $Y_2$, and $Y_3$ represent a single bond, a substituted or nonsubstituted alkylene group, a substituted or nonsubstituted cycloalkylene group, a substituted or nonsubstituted alkylene ether group, an oxygen atom sulfur atom, or a vinylene group, which may be the same among or different from each other. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

Examples of the aryl groups for $R_{11}$, $R_{12}$, $R_{13}$, and $R_{14}$ is the same as those given for the aryl group for $R_5$ and $R_6$ in the explanation of the general formula (3D) and examples of the allylene groups for $Ar_{13}$, $Ar_{14}$, $Ar_{15}$, and $Ar_{16}$ include bivalent groups of these aryl groups. In addition, examples of the substituents for these allylene groups and aryl groups are the same as those give as the substituents for the aryl group and the allylene group in the explanation of the general formula (3D).

The alkylene groups for $Y_1$, $Y_2$, and $Y_3$ represent the bivalent groups induced from the alkyl groups given as examples of the substituents for the aryl group or allylene group in the explanation of the general formula (3D). Specifically, a methylene group, an ethylene group, a 1,3-propylene group, 1,4-butylene group, a 2-methyl-1, a 3-propylene group, a difluoromethylene group, a hydroxyethylene group, a cyanoethylene group, a methoxyethylene group, a phenylmethylene group, a 4-methylphenylmethylene group, a 2,2-propylene group, a 2,2-butylene group, and a diphenylmethylene group are given as examples. The cycloalkylene group includes a 1,1-cyclopentylene group, a 1,1-cyclohexylene group, and a 1,1-cyclooctylene group. The aklylene ether group includes a dimethylene ether group, a diethylene ether group, an ethylenemethylene ether group, a bis(triethylene) ether group, a polytetramethylene ether group, and the like.

X is introduced into the main chain by combining the diole compound expressed by the following general formula (C) in polymerizing the diole compound having a triarylamino group expressed by the following general formula (6D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (6D') and bischloroformate induced from the following general formula (C). In this case, the obtained polycarbonate resin is an alternating copolymer.

General Formula (6D')

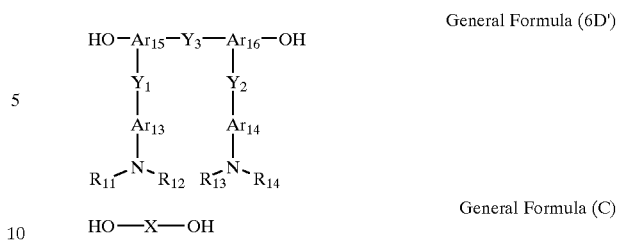

General Formula (C)

HO—X—OH

Examples of the diole compound expressed by the general formula (C) include those given in the explanation of the above-mentioned general formula (1D).

Now, the polymer transporting substances expressed by the following general formula (7D) will be explained.

General Formula (7D)

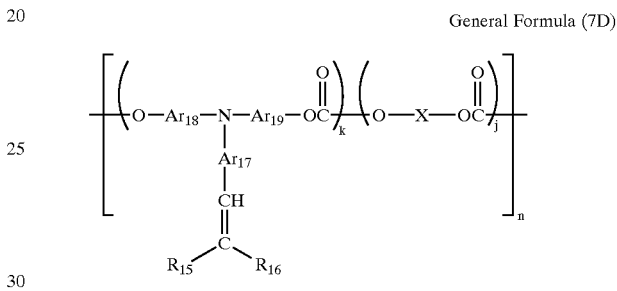

[In the formula, $R_{15}$ and $R_{16}$ represent a hydrogen atom, or a substituted or nonsubstituted aryl group, which may form a ring. $Ar_{17}$, $Ar_{18}$, and $Ar_{19}$ represent the same or different allylene groups. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

Examples of the aryl group for $R_{15}$ and $R_{16}$ include those of the aryl group for $R_5$ and $R_6$ given in the explanation of the general formula (3D) and when $R_{15}$ and $R_{16}$ form a ring, they include 9-fluorinidene, 5H-dibenzo[a,d] cycloheptenylidene and the like. Examples of the allylene groups for $Ar_{17}$, $Ar_{18}$, and $Ar_{19}$ include the bivalent groups for these aryl groups, and the like. Examples of the substituents for these aryl groups and allylene groups include those for the aryl group and allylene group given in the general formula (3D).

X is introduced into the main chain by combining the diole compound expressed by the following general formula (C) in polymerizing the diole compound having a triarylamino group expressed by the following general formula (1D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (1D') and bischloroformate induced from the following general formula (C). In this case, the obtained polycarbonate resin is an alternating copolymer.

General Formula (7D')

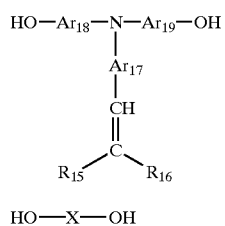

General Formula (C)

HO—X—OH

Examples of the diole compound expressed by the general formula (C) include those given in the explanation of the above-mentioned general formula (1D).

Now, the polymer transporting substances expressed by the following general formula (8D) will be explained.

General Formula (8D)

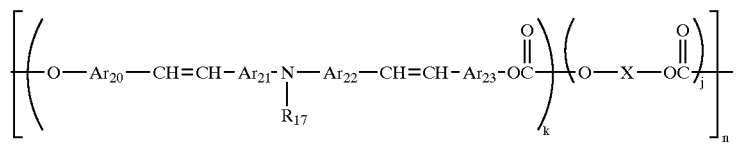

[In the formula, $R_{17}$ represents a substituted or nonsubstituted aryl group and $Ar_{20}$, $Ar_{21}$, $Ar_{22}$ and $Ar_{23}$ represent the same or different allylene group. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

Examples of the aryl groups for $R_{17}$ is the same as those given for the aryl group for $R_5$ and $R_6$ in the explanation of the general formula (3D) and examples of the allylene groups for $Ar_{20}$, $Ar_{21}$, $Ar_{22}$ and $Ar_{23}$ include bivalent groups of these aryl groups. In addition, examples of the substituents for these allylene groups and aryl groups are the same as those give as the substituents for the aryl group and the allylene group in the explanation of the general formula (3D).

X is introduced into the main chain by combining the diole compound expressed by the following general formula (C) in polymerizing the diole compound having a triarylamino group expressed by the following general formula (8D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (8D') and bischloroformate induced from the following general formula (C). In this case, the obtained polycarbonate resin is an alternating copolymer.

General Formula (8D')

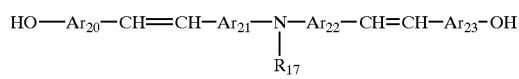

HO—X—OH  General Formula (C)

Examples of the diole compound expressed by the general formula (C) include those given in the explanation of the above-mentioned general formula (1D).

Now, the polymer transporting substances expressed by the following general formula (9D) will be explained.

General Formula (9D')

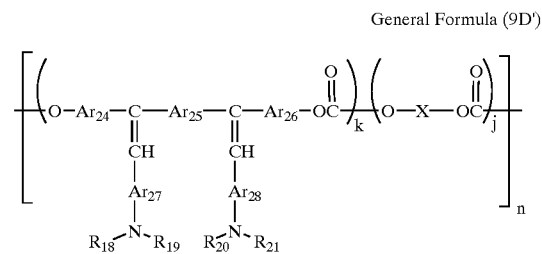

HO—X—OH  General Formula (C)

Examples of the diole compound expressed by the general formula (C) include those given in the explanation of the above-mentioned general formula (1D).

Now, the polymer transporting substances expressed by the following general formula (10D) will be explained.

General Formula (10D)

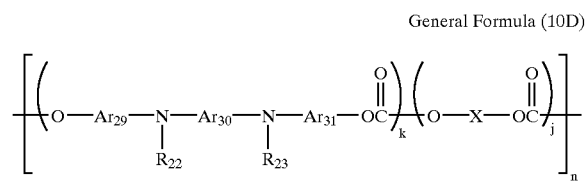

[In the formula, $R_{22}$, and $R_{23}$ represent a substituted or nonsubstituted aryl group and $Ar_{29}$, $Ar_{30}$, and $Ar_{31}$ represent the same or different allylene group. k and j represent a composition, wherein a relationship, $0.1 \leq k \leq 1$ and $0 \leq j \leq 0.9$, is established between them and n represents the time number of repetitions, which is any integer of 5–5000. X represents the same group expressed by the above-mentioned general formula (1D).]

Examples of the aryl groups for $R_{22}$, and $R_{23}$ is the same as those given for the aryl group for $R_5$ and $R_6$ in the explanation of the general formula (3D) and examples of the allylene groups for $Ar_{29}$, $Ar_{30}$, and $Ar_{31}$ include bivalent groups of these aryl groups. In addition, examples of the substituents for these allylene groups and aryl groups are the same as those give as the substituents for the aryl group and the allylene group in the explanation of the general formula (3D).

X is introduced into the main chain by combining the diole compound expressed by the following general formula (C) in polymerizing the diole compound having a triarylamino group expressed by the following general formula (10D') using any method such as the phosgene method and the ester conversion method. In this case, the obtained polycarbonate resin is a random copolymer or block copolymer. Alternately, X may be repetitively introduced in the main chain by polymerizing the diole compound having triaryamino group expressed by the following general formula (10D') and bischloroformate induced from the following general formula (C). In this case, the obtained polycarbonate resin is an alternating copolymer.

General Formula (10D')

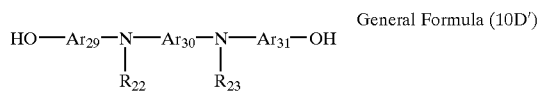

General Formula (C)

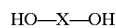

Examples of the diole compound expressed by the general formula (C) include those given in the explanation of the above-mentioned general formula (1D).

Now, the polymer transporting substances expressed by the following general formula (11D) will be explained.

General Formula (11D)

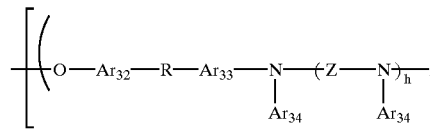

(In the general formula (11D), $Ar_{32}$, $Ar_{33}$, $Ar_{35}$, and $Ar_{36}$ represent a substituted or nonsubstituted allylene group and $Ar_{34}$ represents a substituted or nonsubstituted aryl group. Z represents an allylene group or —$Ar_{37}$—Za—$Ar_{37}$— and $Ar_{37}$ represents a substituted or nonsubstituted allylene group. Za represents O, S, or an allylene group. h is an integer of 0 or 1. k and j represent the composition, wherein a relationship, $0.1 \leq k \leq 1$ and $0 \leq j \leq$, is established between them, and n represents the time number of repetition, which is any integer of 5–5000. X represents a substituted or nonsubstituted fatty bivalent group, a substituted or nonsubstituted cyclic fatty bivalent group, a substituted or nonsubstituted aromatic bivalent group, or the bivalent groups expressed by the following general formula (A7), the general formula (F), and the general formula (G).

General Formula (A')

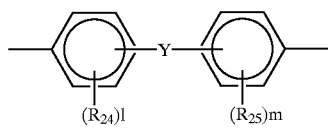

General Formula (F)

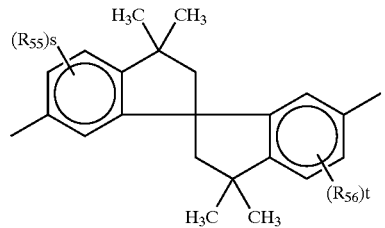

General Formula (G)

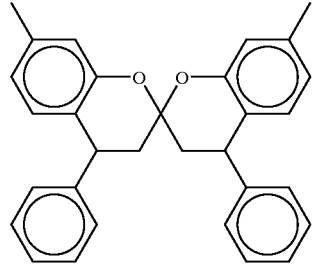

(In the general formula (A'), the general formula (F), and general formula (G), $R_{24}$, $R_{25}$, $R_{55}$, and $R_{56}$ represent a substituted or nonsubstituted alkyl group, a substituted or nonsubstituted aryl group, or a halogen atom independently of each other. l and m represent any integer of 1, 2, 3, or 4 independently of one another and a and t represent any integer of 1, 2, or 3 independently of one another. When more than one $R_{24}$, $R_{25}$, $R_{55}$, and/or $R_{56}$ coexist, they may be the same among or different from each other.). Y represents a single bond, a linear, branched-chain, or cyclic alkylene group containing 1–12 carbon atoms, a bivalent group composed of one or more alkylene groups containing 1–10 carbon atoms and one or more oxygen atoms and sulfur atoms, —O—, —S—, —SO—, —SO$_2$—, CO—, —COO—, —CO—O—Z$_1$—O—CO—, —CO—Z$_2$—CO— (in the formulae, Z$_1$ and Z$_2$ represent a substituted or nonsubstituted fatty bivalent group or a substituted or nonsubstituted allylene group), or the following general formula (B) and general formula (H), the general formula (I), the general formula (J), the general formula (K), general formula (L), the general formula (M), and the general formula (N).

General Formula (B)

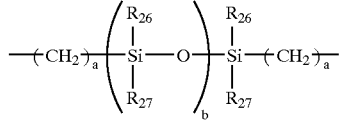

General Formula (H)

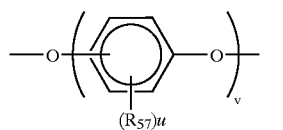

General Formula (I)

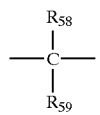

General Formula (J)

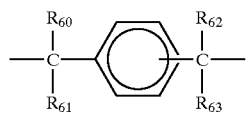

General Formula (K)

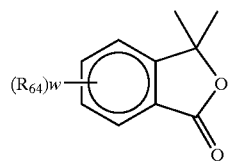

General Formual (L)

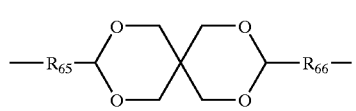

(In the general formula (B), the general formula (H), the general formula (I), the general formula (J), the general formula (K), the general formula (L), the general formula (M), and the general formula (N), $R_{26}$ and $R_{27}$ represent a substituted or nonsubstituted alkyl group independently of one another, or a substituted or nonsubstituted aryl group. $R_{57}$, $R_{58}$, and $R_{64}$ represent a halogen atom, a substituted or nonsubstituted alkyl group, a substituted or nonsubstituted alkoxyl group, or a substituted or nonsubstituted aryl group. $R_{58}$ and $R_{59}$ may bind together to form a carbon ring containing 5–12 carbon atoms. $R_{65}$ and $R_{66}$ represent a single bond or an alkylene group containing 1–4 carbon atoms. a represents any integer of 1–20, b represents any integer of 1–2000, u and w represent any integer of 0–4, and v represents an integer of 1 or 2. When more than one $R_{26}$, $R_{27}$, $R_{57}$, and/or $R_{64}$ coexist, they may be the same among or different from each other.))

Examples of the aryl groups for $R_{34}$ is the same as those given for the aryl group for $R_5$ and $R_6$ in the explanation of the general formula (3D) and examples of the allylene groups for $Ar_{32}$, $Ar_{33}$, $Ar_{35}$ and $Ar_{36}$ include bivalent groups of these aryl groups. In addition, examples of the substituents for these allylene groups and aryl groups are the same as those give as the substituents for the aryl group and the allylene group in the explanation of the general formula (3D).

The represented X is introduced by combining the diole compound expressed by the following general formula (C) when the diole compound expressed in the following general formula (11D') is polymerized by any of methods such as the phosgene method and the ester conversion method. In this case, the obtained polycarbonate resin is a random polymer or a block polymer. Alternately, X is repetitively introduced by polymerizing the diole compound expressed by the general formula (11D') and the bischloroformate induced from the general formula (C). In this case, the obtained polycarbonate resin is an alternating copolymer.

General Formula (11D')

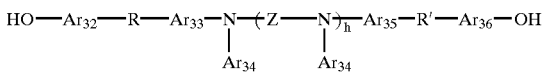

HO—X—OH            General Formula (C)

In the general formula (C), examples of the diole compound include those given in the explanation of the general formulae (1D) through (1J).

The example compounds expressed by the general formula (1D) through (1J), the general formula (2D) through (2Q), the general formula (3D) through (3F), the general formula (4D) through (4F), the general formula (5D) through (5G), the general formula (6D) through (6F), the general formula (7D) through (7E), the general formula (8D) through (8F), the general formula (9D) through (9F), the general formula (10D) through (10E), and the general formula (11D) through (11H) are shown in the following general formulae but the compounds of the present invention are not limited only to them. Examples of polymer charge transporting substances:

General Formula 1D

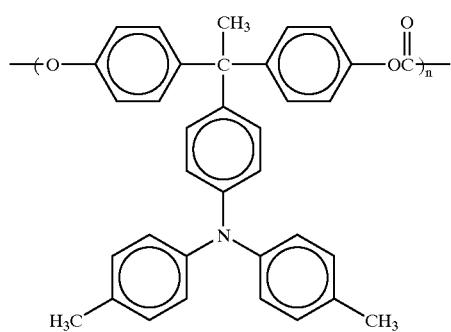

-continued
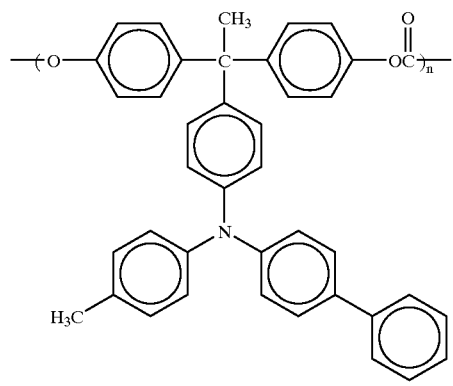
General Formula 1E
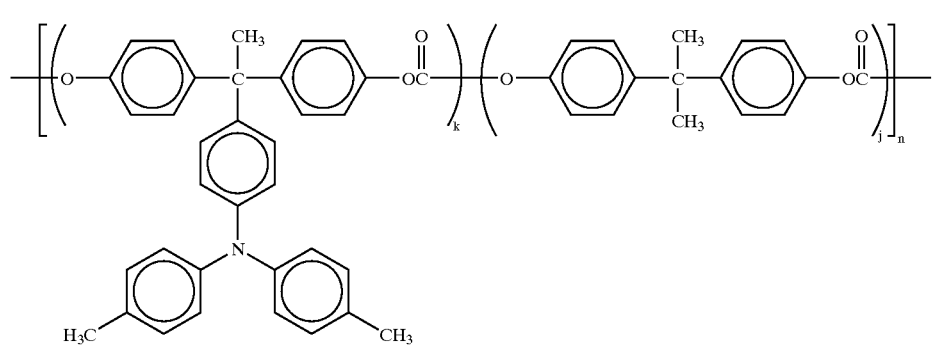
General Formula 1F
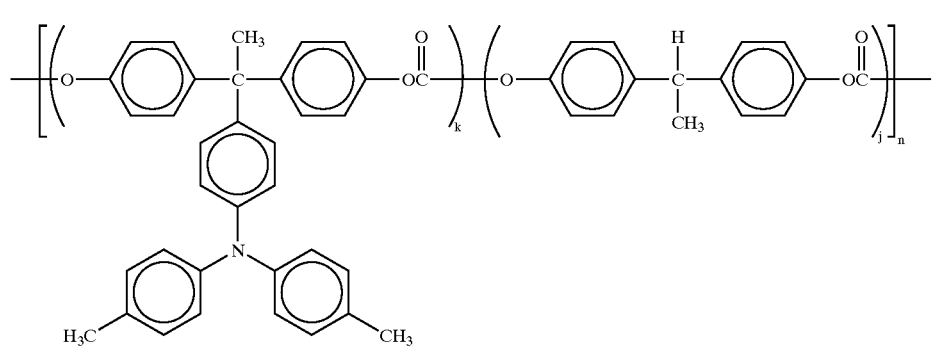
General Formula 1G
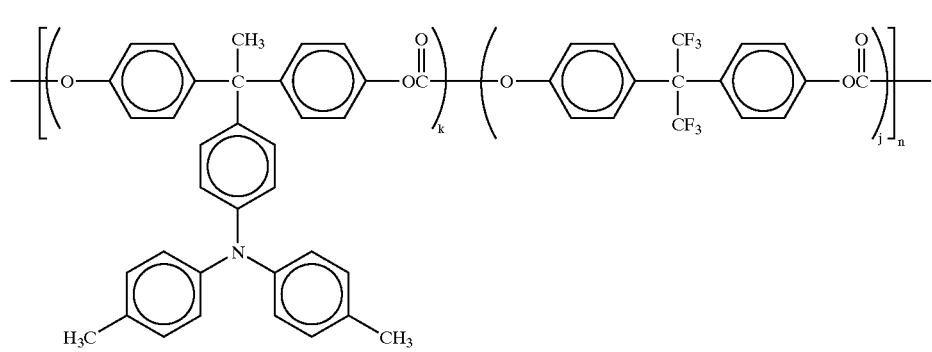
General Formula 1H General Formula 1I
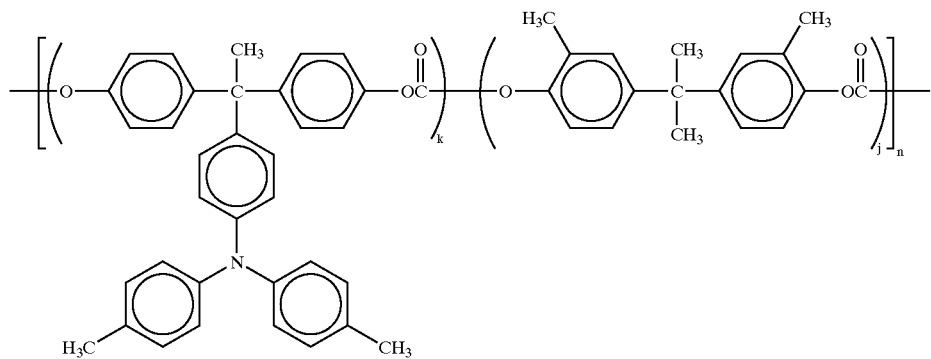
General Formula 1J
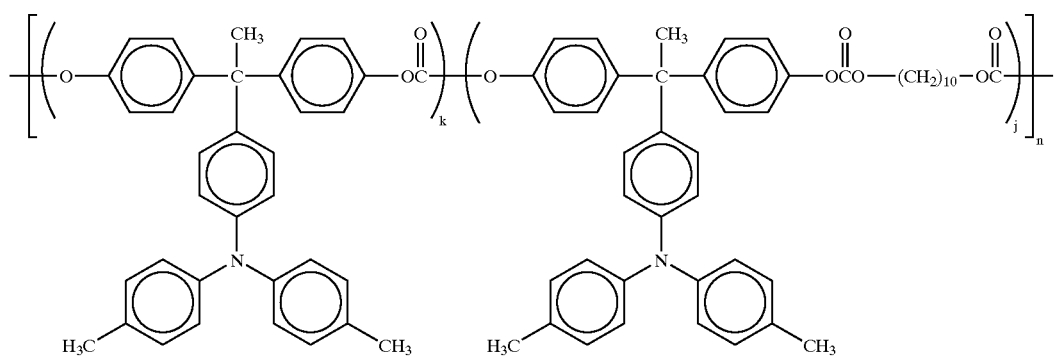
General Formula 2D
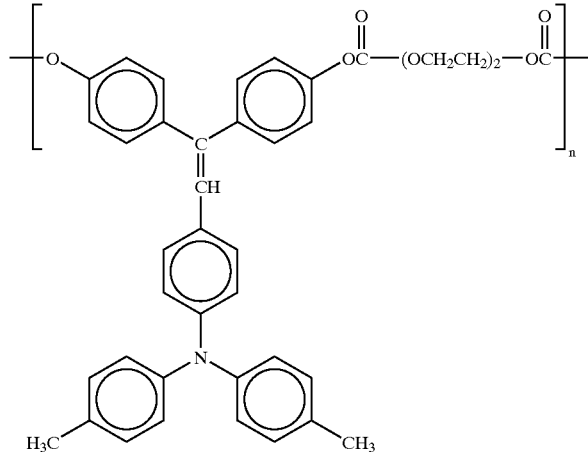
General Formula 2E
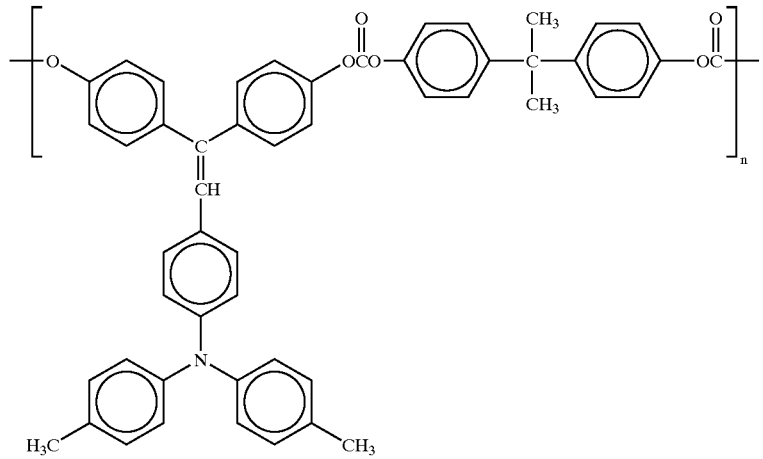

-continued
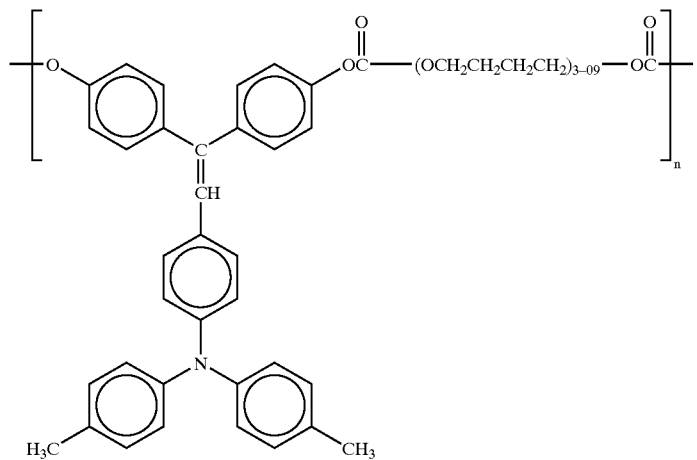
General Formula 2F
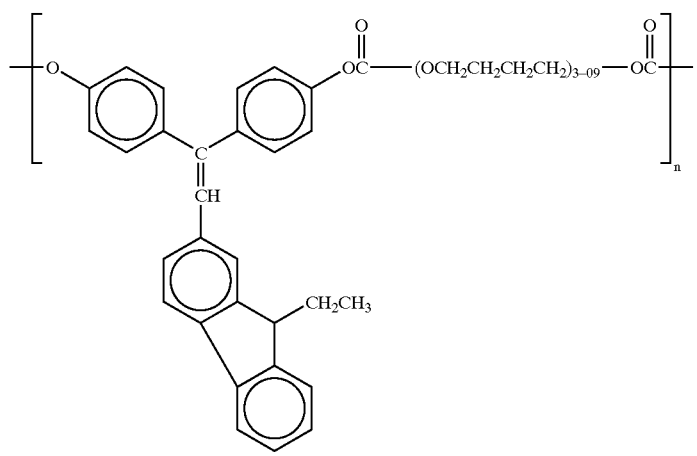
General Formula 2G
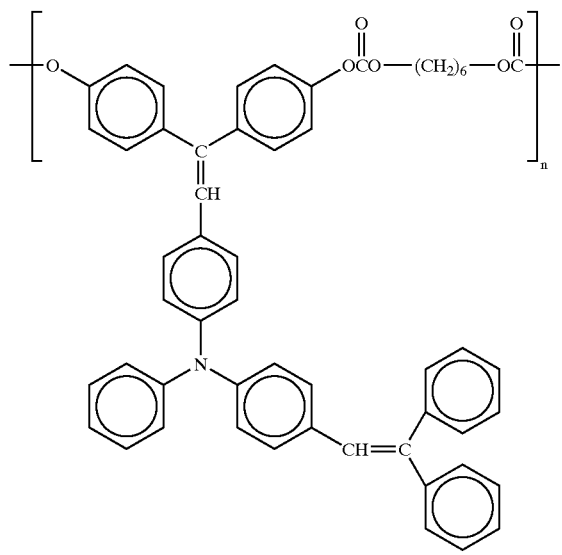
General Formula 2H -continued
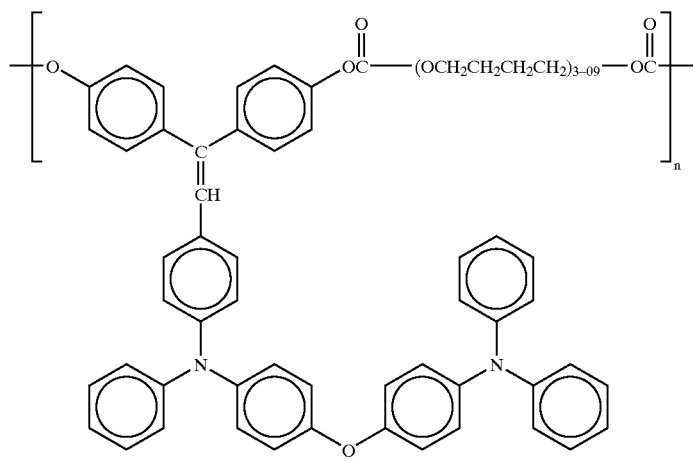
General Formula 2I
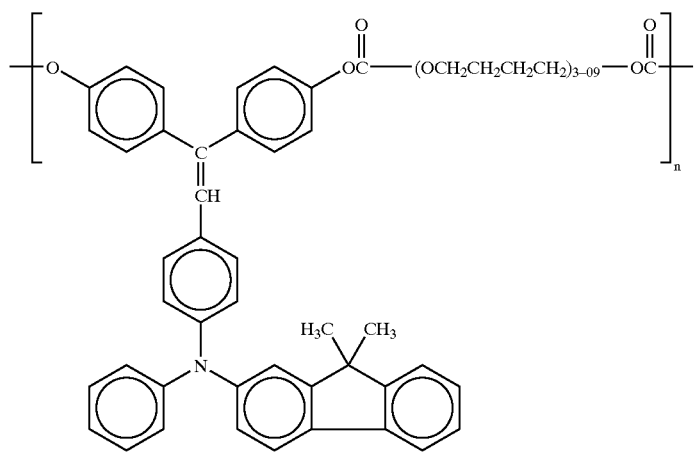
General Formula 2J
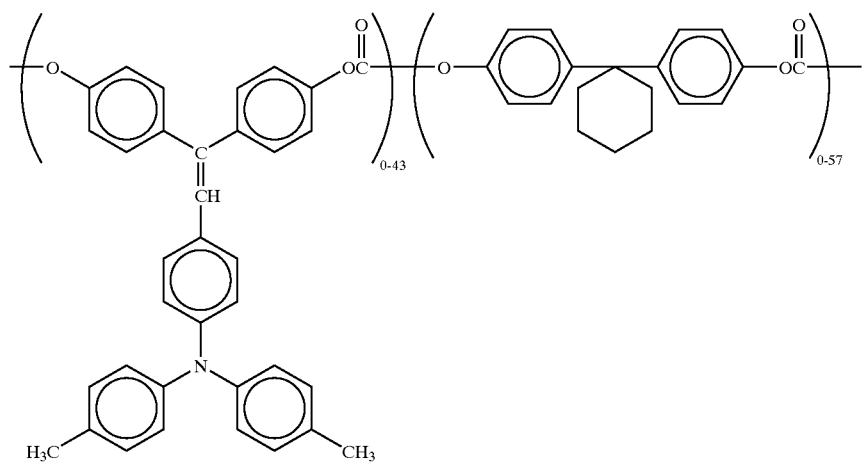
General Formula 2K

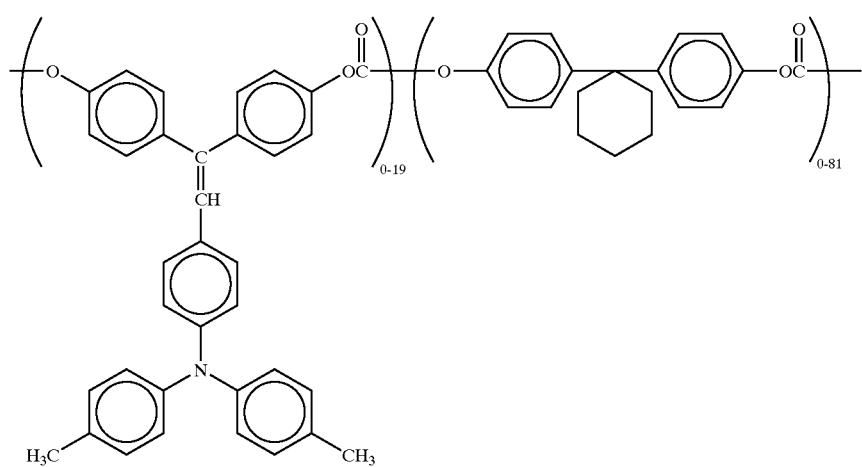
General Formula 2L
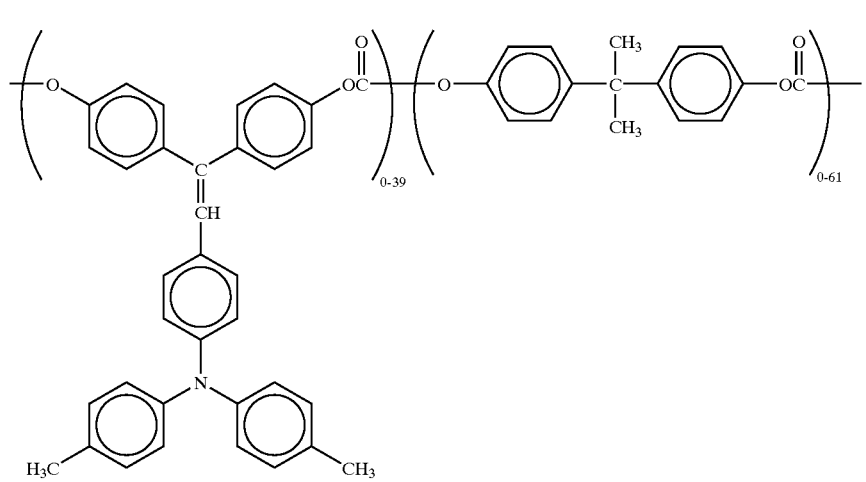
General Formula 2M
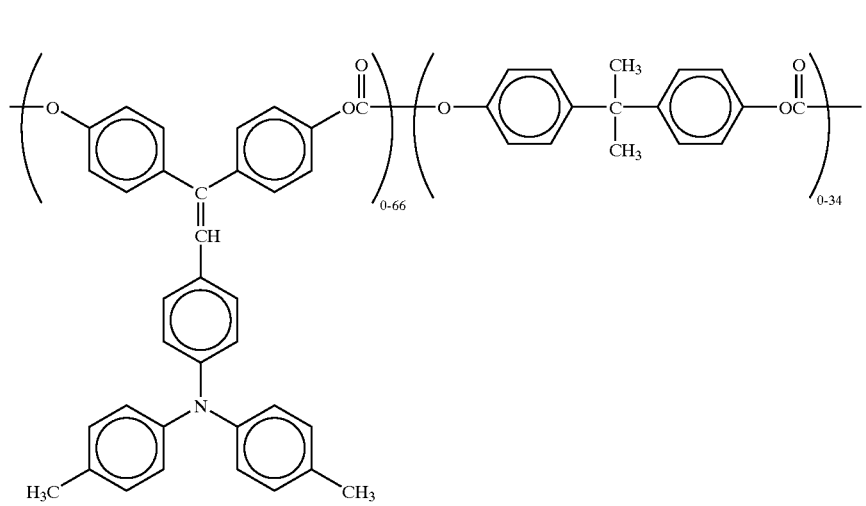
General Formula 2N

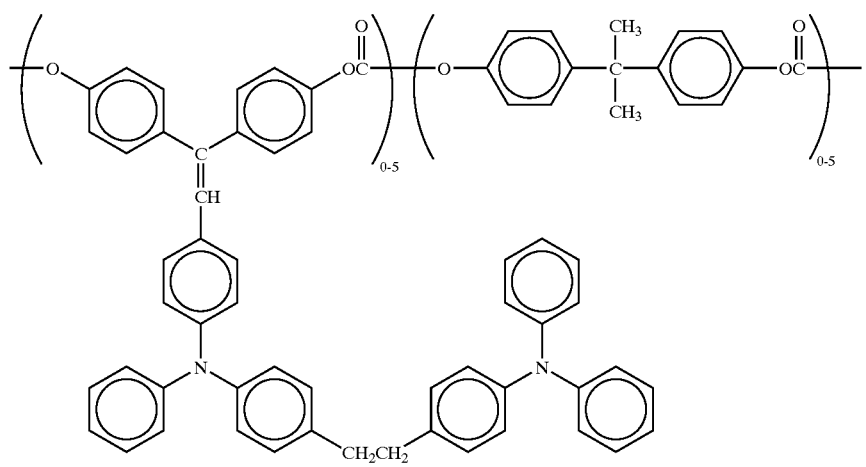
General Formula 2O
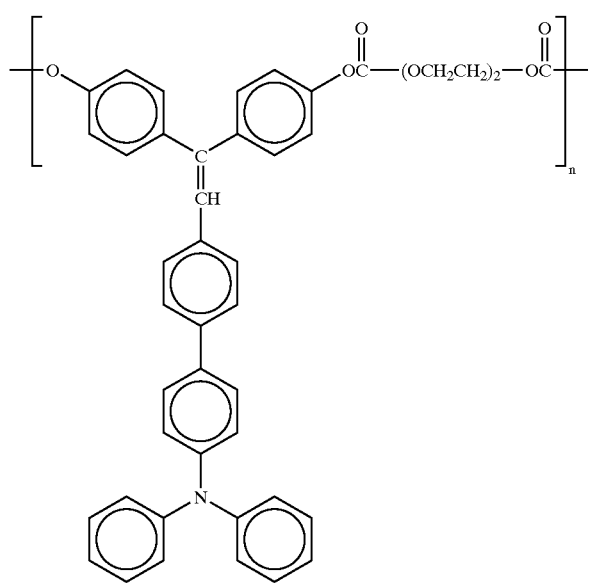
General Formula 2P
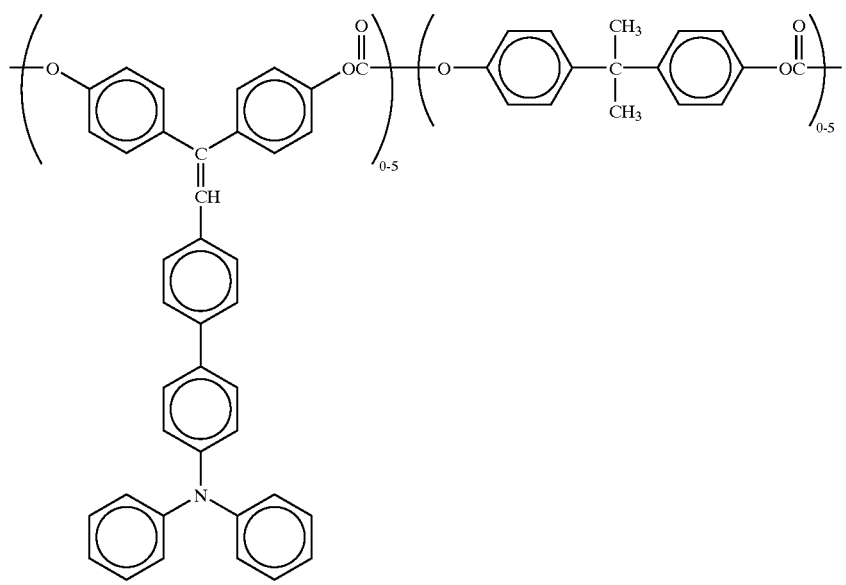
General Formula 2Q

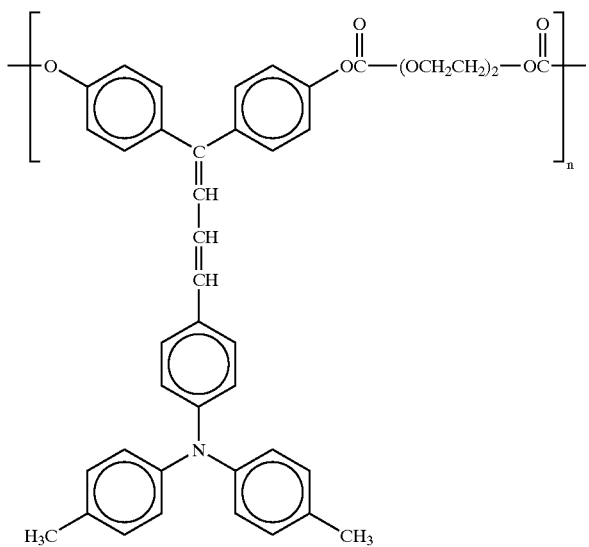
General Formula 3D
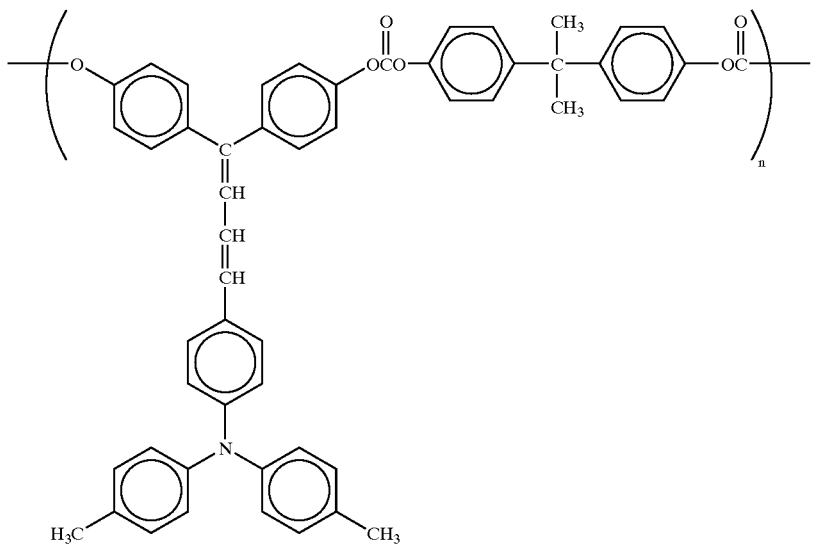
General Formula 3E
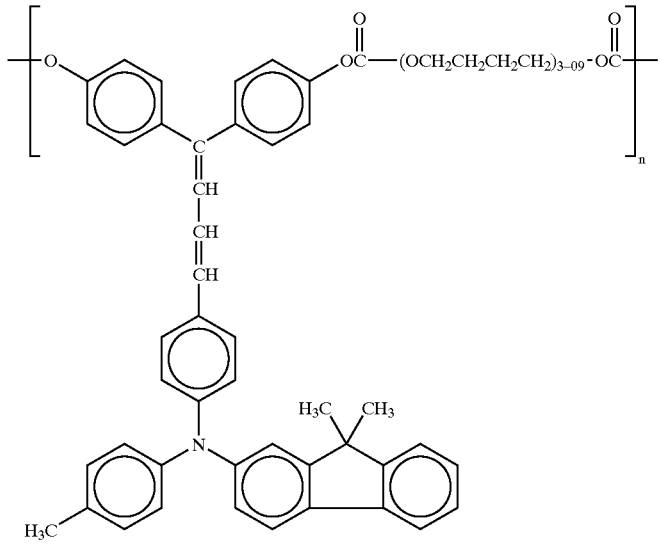
General Formula 3F -continued
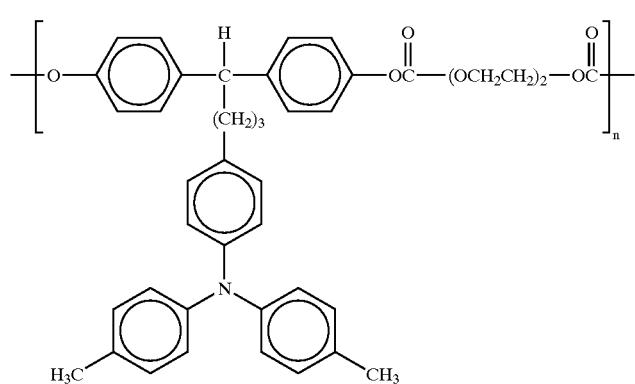
General Formula 4D
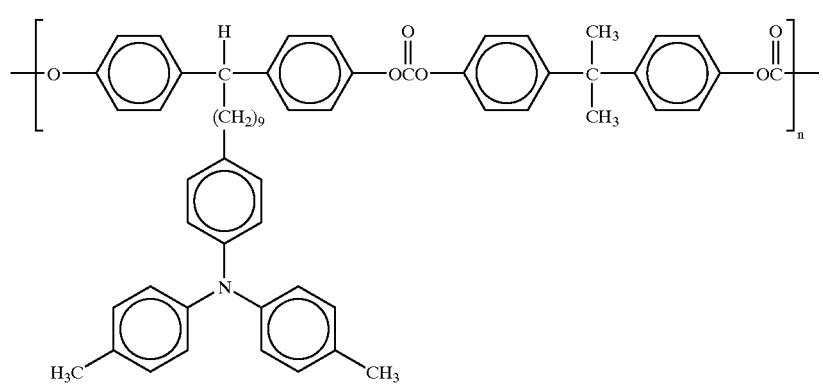
General Formula 4E
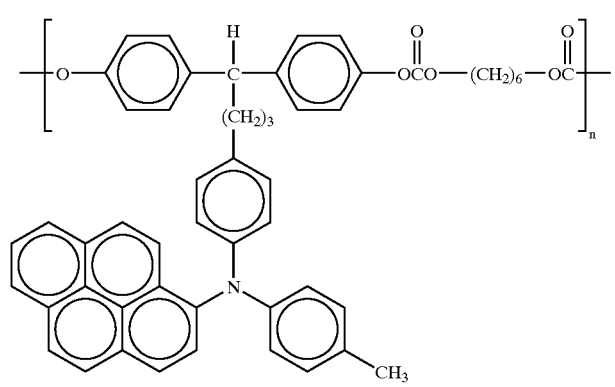
General Formula 4F
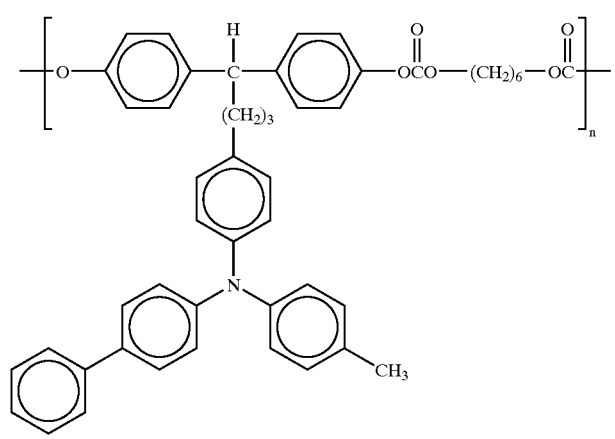
General Formula 4G -continued
General Formula 5D
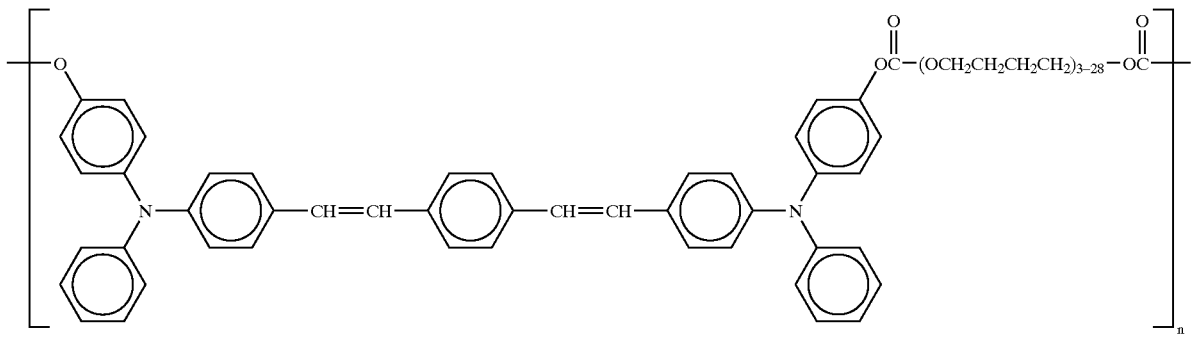
General Formula 5E
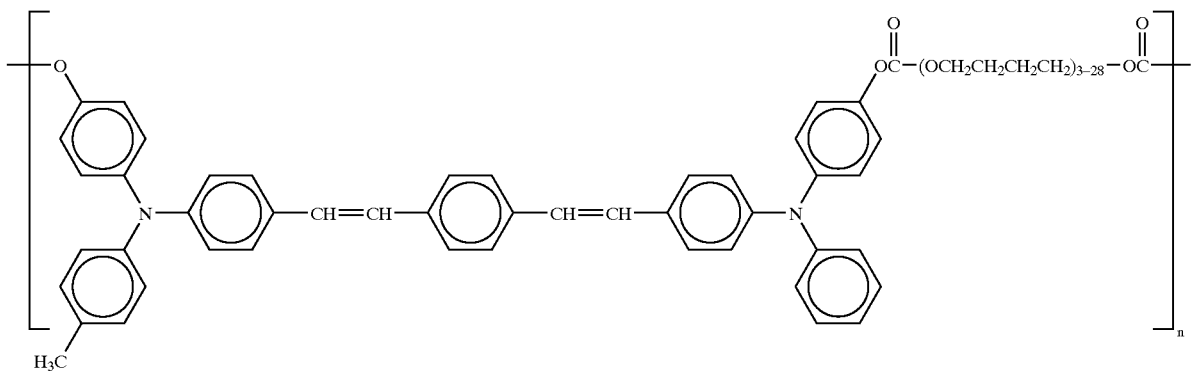
General Formula 5F
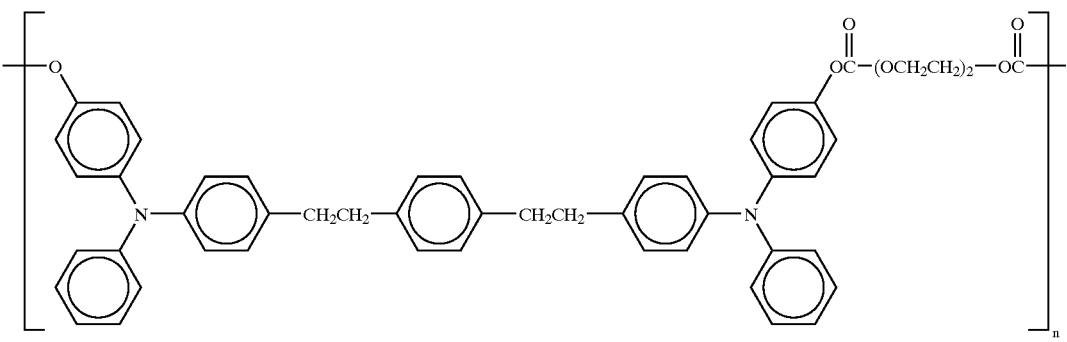
General Formula 5G
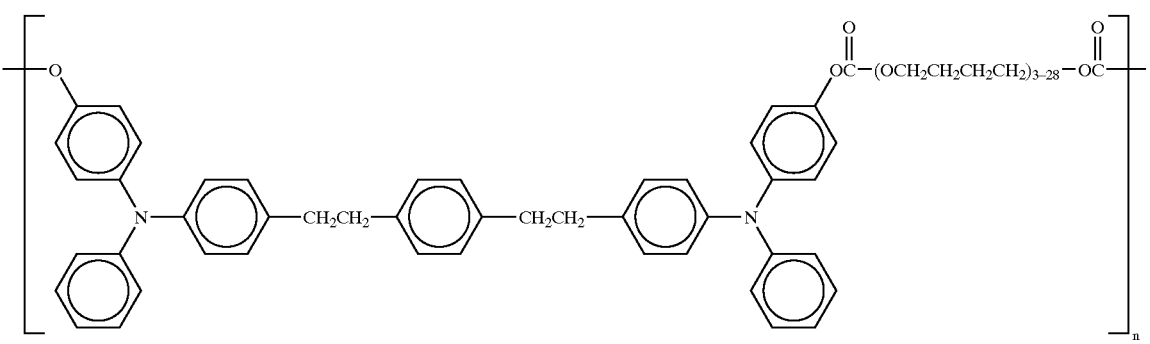

-continued
General Formula 6D
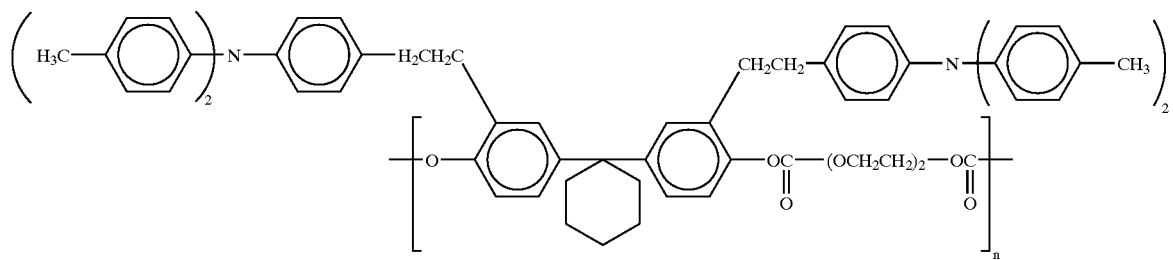
General Formula 6E
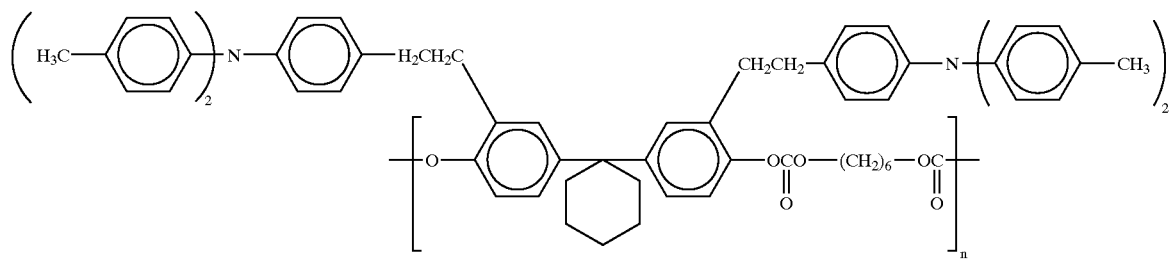
General Formula 6F
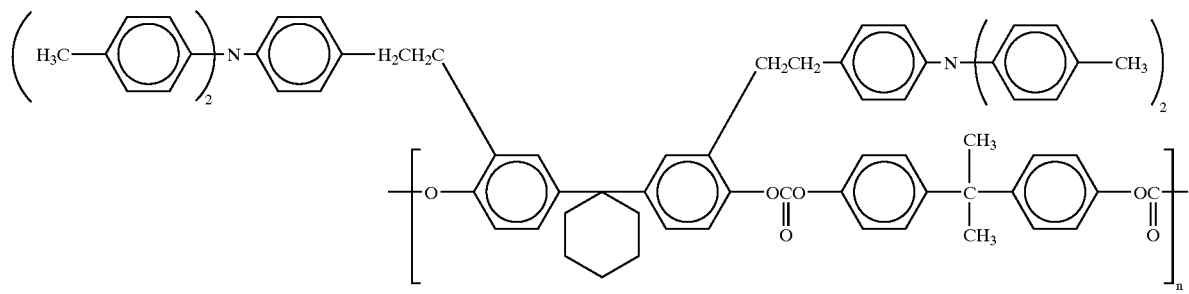
General Formula 7D
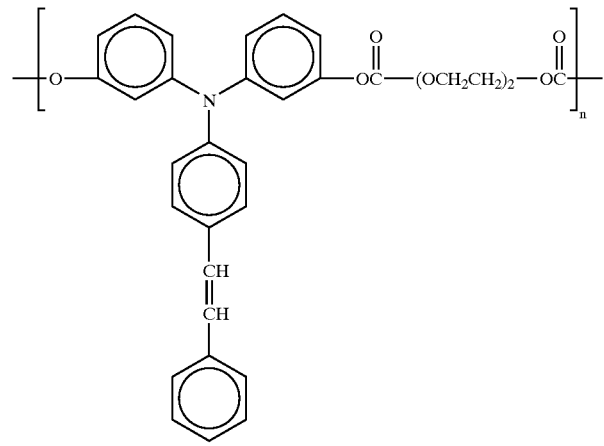

-continued
General Formula 7E
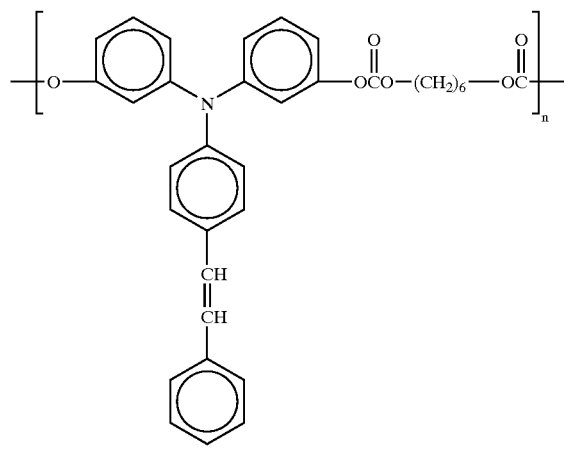
General Formula 8D
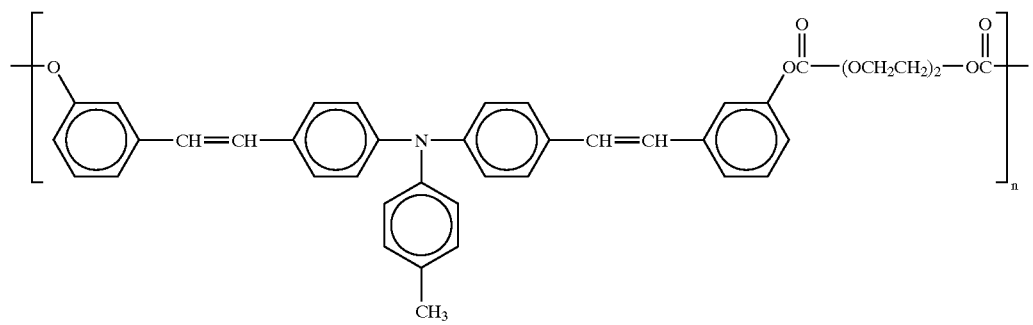
General Formula 8E
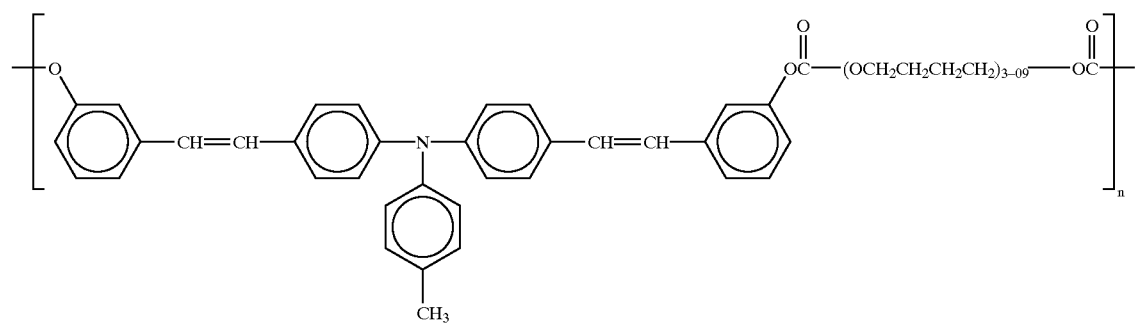
General Formula 8F
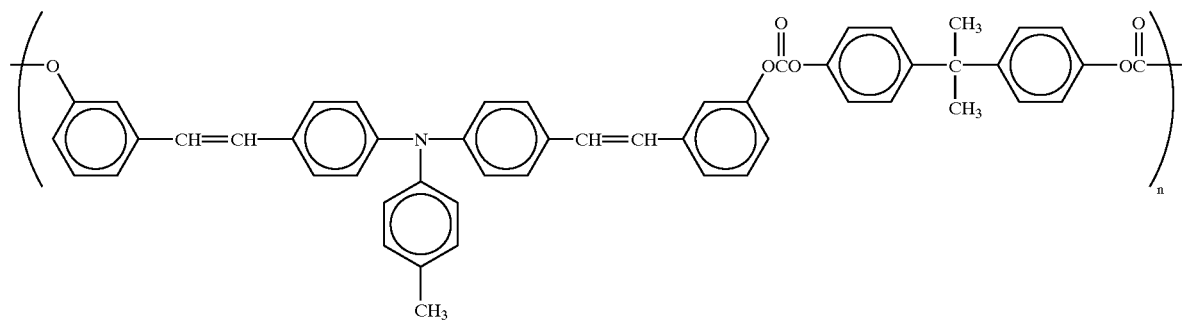

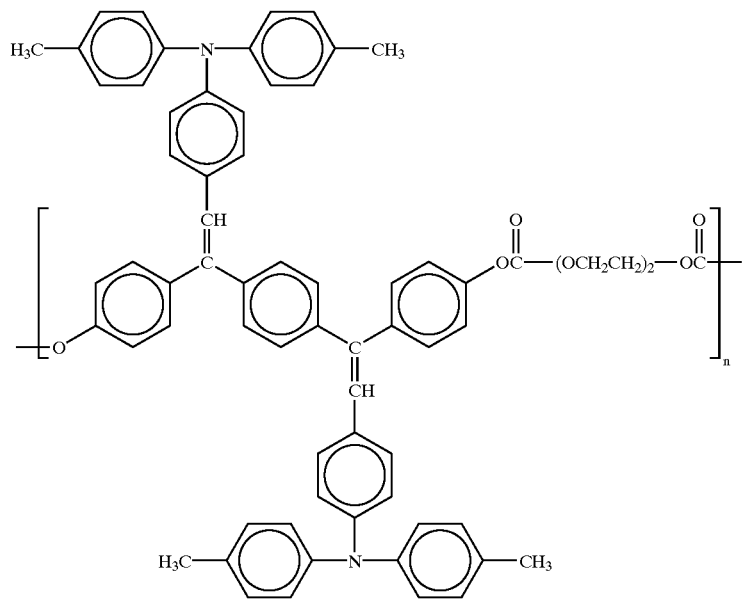
General Formula 9D
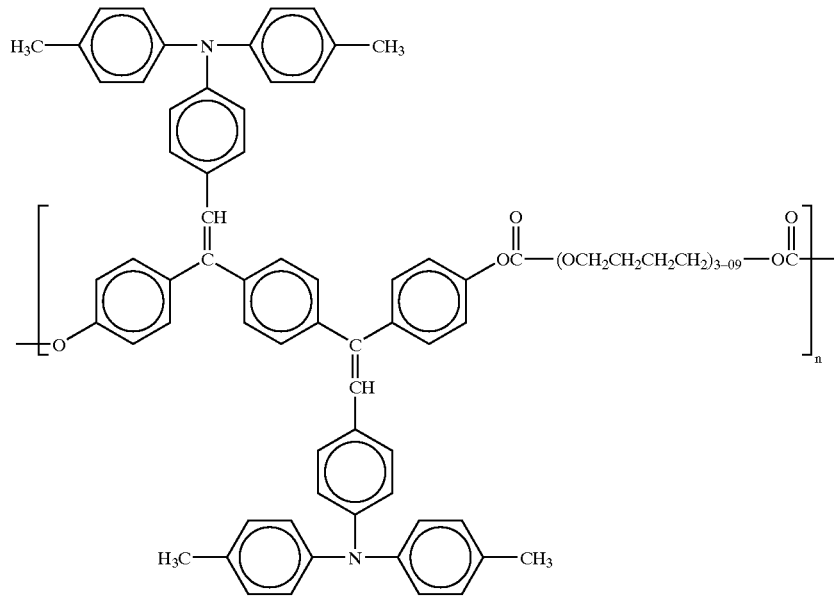
General Formula 9E

General Formula 9F
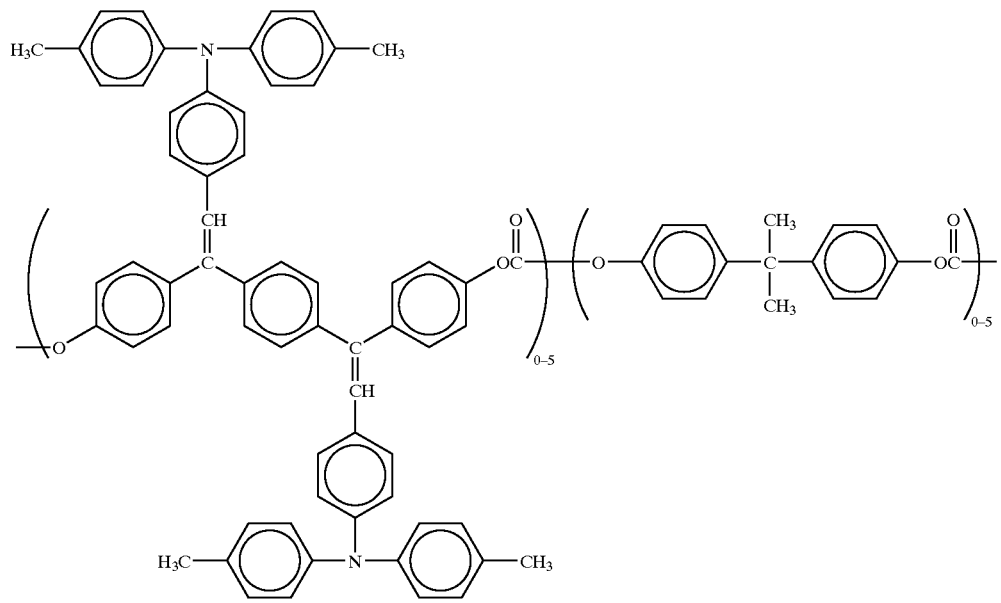
General Formula 10D
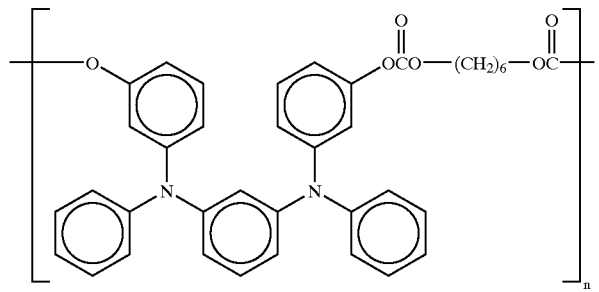
General Formula 10E
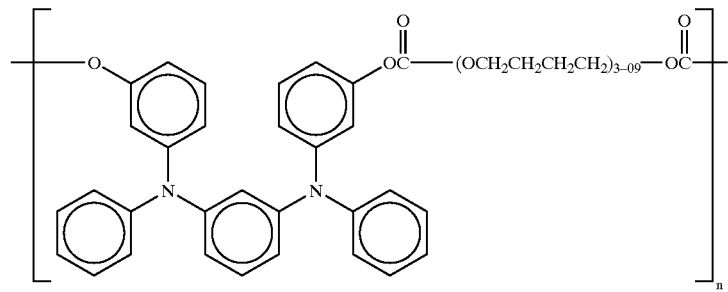
General Formula 11D
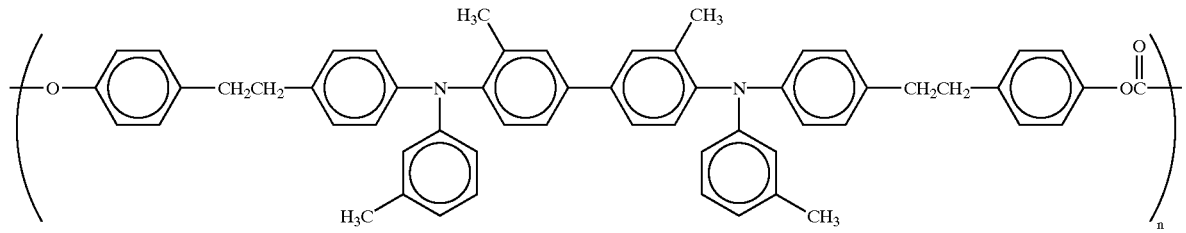

General Formula 11E
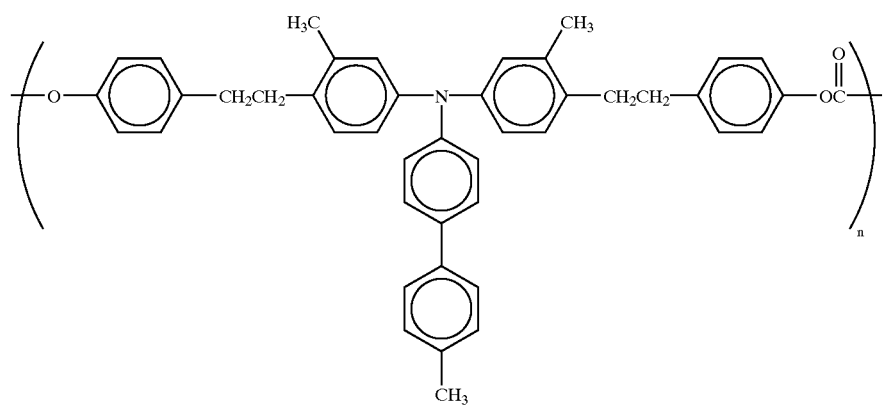
General Formula 11F
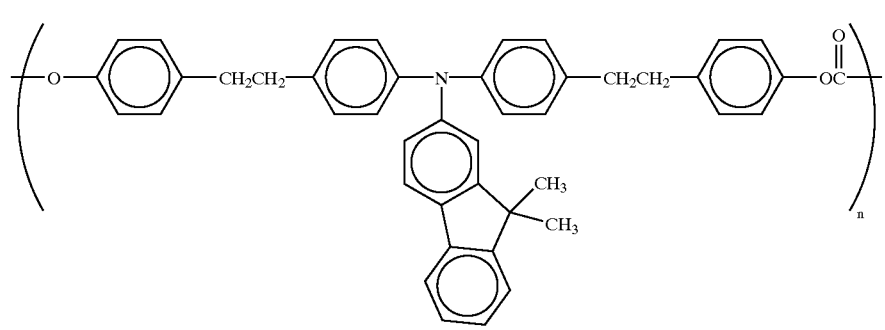
General Formula 11G
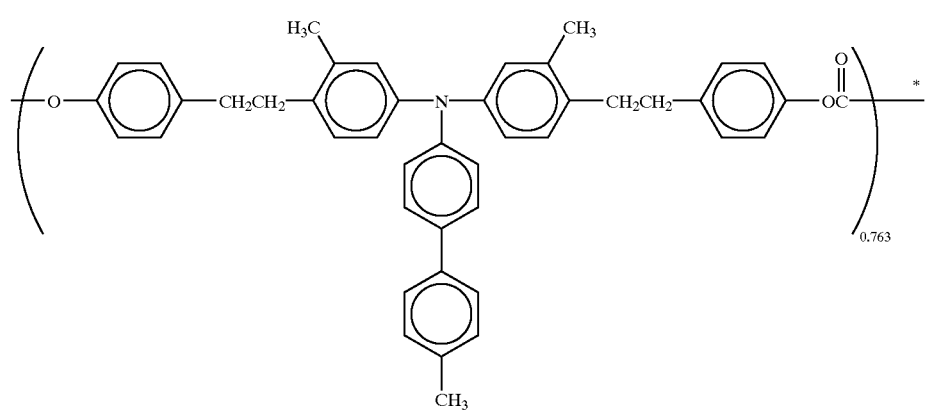
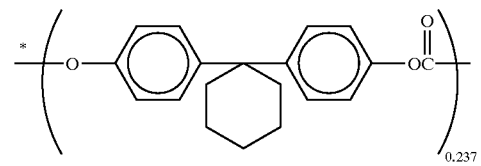
General Formula 11H
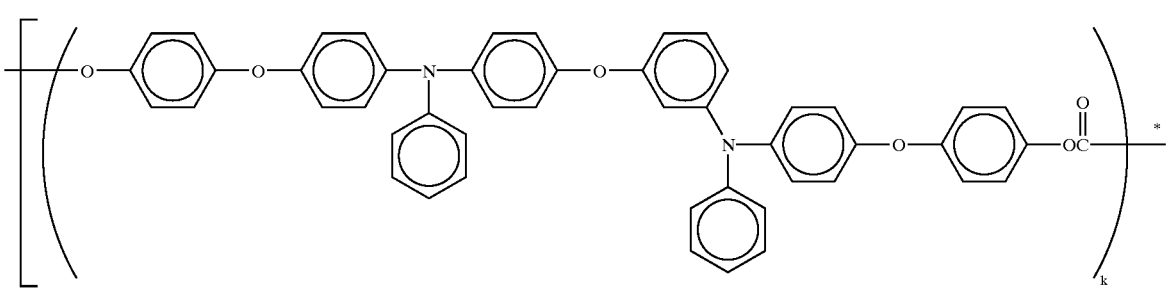

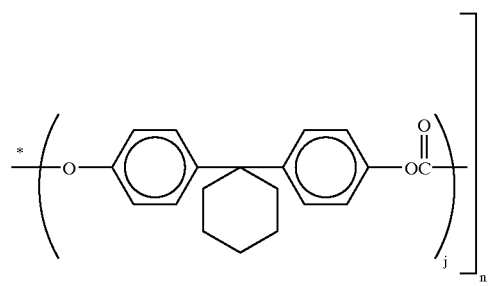

For the photoconductive layer of the single layer of the electrophotographic photoconductor of the present invention, an acceptor compound is used, if necessary. The use of the acceptor compound is preferable from an aspect of possible mobility of a large number of electrons generated by light irradiation to the acceptor compound side, resulting in better electrostatic property, high sensitivity, and high durability with no sacrifice of the practical use of the photoconductor.

The acceptor compound to be used in the present invention includes, for example, chloranyl, bromanyl, tetracyanoethylene, tetracyanoquinodimethan, 2,4,7-trinitro-9-fluorenone, 2,4,5,7-tetranitro-9-fluorenone, 2,4,5,7-tetranitroxanthone, 2,4,8-trinitrothioxantone, 2,6,8-trinitro-indeno4H-indeno[1,2-b]thiophene4-on, 1,3,7-trinitrodibenzothiophene-5,5-dioxide, and the acceptor compounds expressed by the following chemical formulae (Q-1) and (Q-2).

Chemical Formula (Q-1)

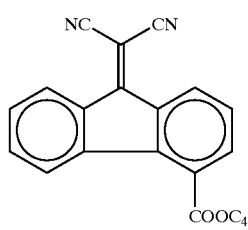

Chemical Formula (Q-2)

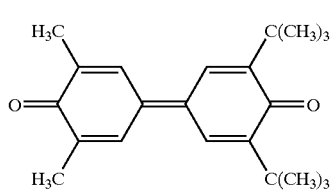

In addition, a 2,3-diphenylindine compound expressed by the general formula <<18>> is preferably used because it has better compatibility with a polymer matrix and high electron transporting ability.

General Formula <<18>>

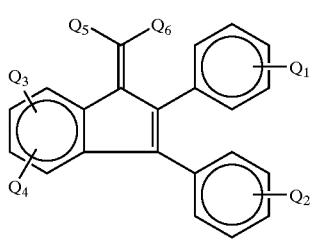

In the general formula <<18>>, Q1, Q2, Q3, and Q4 represent any of halogen atoms such as hydrogen atom, fluorine atom, and chlorine atom, an alkyl groups such as a methyl group, an ethyl group, a n-propyl group, iso-propyl group, an n-buthyl group, and a t-buthyl group, substituted alkyl groups such as a benzyl group, a methoxylmethyl group, and a methoxyethyl group, alkoxycarbonyl groups such as a cyano group, a methoxycarbonyl group, an ethoxycarbonyl group, and the like, substituted alkylcarbonyl groups such as a benzyloxycarboxyl group and an ethoxyethylcarbonyl group, and aryl groups such as a phenyl group and a naphtyl group, and the substituent for them include alkyl groups such as a methyl group and a ethyl group, and phenyl group, ethoxyl group, a phenoxyl group, and halogen atoms such as a fluorine atom and a chlorine atom. In the general formula <<18>>, in particular, (2,3-diphenyl-1-indene)malononitryl expressed by the following chemical formula (Q-3) is preferably used.

Chemical formula (Q-3)

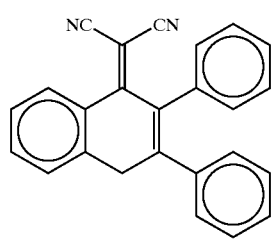

These acceptor compounds may be used alone or by means of combination with one or more other acceptor compounds. The ratio of the acceptor compound to the whole photoconductive layer is 1–40% by weight and in particular, 5–40% by weight is preferable.

In the photoconductive layer of the present invention, an adhesive may be added, if necessary. Any of known substances for electrophotographic photoconductors with better insulation performance may be used as the adhesive in forming the photoconductive layer and no special limitations are applicable. For example, addition polymerized resins such as polyethylene, poly vinyl butyral, poly vinyl formar, polystyrene, phenoxyl resin, polypropylene, acrylic resin, methacrylate resin, vinyl chloride resin, vinyl acetate resin, epoxy resin, polyurethane, phenol resin, polyester, alkyd resin, polycarbonate, polyamido, silicone resin, and melamine resin, polyaddition resins, polycondensation resins, and copolymer resins containing two out of repetitive units of these resins, and insulating resins, for example, vinyl chloride-vinyl acetate copolymer, styrene-acrylic copolymer, and vinyl chloride-vinyl acetate-anhydrous maleic acid copolymer, as well as semiconductive organic polymer such as poly-N-vinylcarbazole may be given as examples. These adhesives may be used alone or as a mixture by means of combination with one or more other compounds. The ratio of the adhesive to the photoconductive layer is 30–95% by weight and in particular, 40–7% by weight is preferable.

Furthermore, in the photoconductive layer of the present invention, any additives such as a plasticizer, an antioxidant, a photo-stablilizer, a thermo-stabilizer, and a lubricant may be used. The plasticizer includes halogenated paraffin, dimethylnaphthalene, and dibutylphthalete, and the antioxidant and the photo-stabilizer include phenol compounds, hydroquinon compounds, hindered phenol compounds, hindered amine compounds, and the compounds with hindered amine and hindered phenol coexisting in the same molecule.

Among the phenol compounds, those expressed by the general formula <<19>> are, in particular, preferable because they improve electrostatic properties when the photoconductor is repeatedly used.

General formula <<19>>

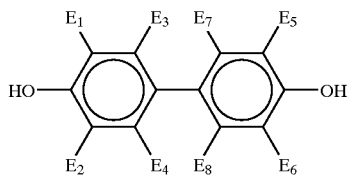

In the general formula <<19>>, $E_1$, $E_2$, $E_3$, $E_4$, $E_5$, $E_6$, and $E_8$ represent a hydrogen atom, alkyl groups such as a methyl group, an ethyl group, n-propyl group, iso-propyl group, n-butyl group, and t-butyl group, substituted alkyl groups such as a benzyl group, a methoxymethyl group, and a methoxyethyl group, alkoxycarbonyl groups such as a methoxycarbonyl group and a ethoxycarbonyl group, substituted alkylcarbonyl groups such as a benzyloxycarbonyl group and a methoxyethylcarbonyl group, and aryl groups such as a phenyl group and naphthyl group, and the substituents for them include alkyl groups such as methyl groups and a ethyl group, and phenyl groups, metoxyl groups, ethoxyl groups, phenoxyl groups, halogen atoms such as a fluorine atom and a chlorine atom. The content of the any of these phenol compounds in the photoconductive layer is 0.1–50% by weight, and preferably it is within a range of 0.1–30% by weight. The content of the phenol compound less than 0.1% by weight has no sufficient effect on improvement in durability when the photoconductive layer is repetitively used while the content more than 50% by weight leads to deterioration in mechanical durability and sensitivity. Examples of the phenol compounds expressed by the general formula <<19>> are shown below in general formulae 19A through 19 H, however the phenol compounds of the present invention are not limited to these.

General Formula 19A

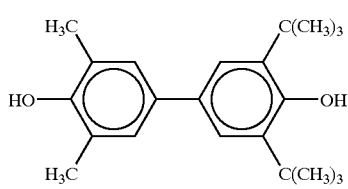

General Formula 19B

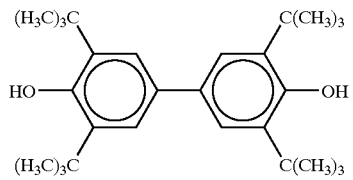

General Formula 19C

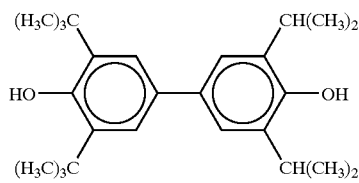

General Formula 19D

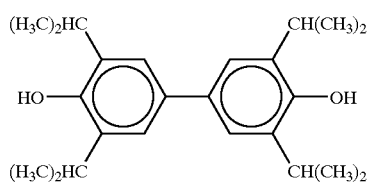

General Formula 19E

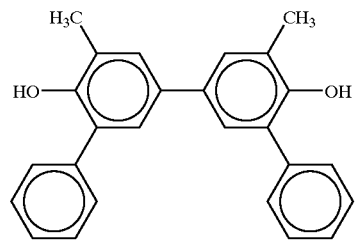

General Formula 19F

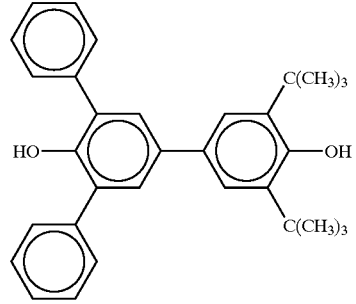

General Formula 19G

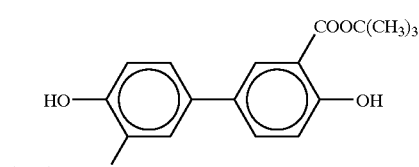

General Formula 19H

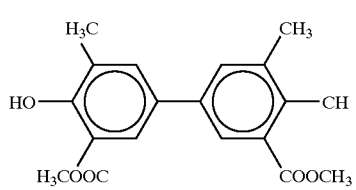

The conductive support, which can be used in the present invention, include metal plates, metal drums, or thin films made of any of aluminum, nickel, copper, titanium, gold, stainless, and the like, plastic films, on which any of aluminum, nickel, copper, titanium, gold, tin oxide, indium oxide, and the like has been evaporated, or paper, plastic films, or drums, on which any of photoconductive substances has been coated.

If necessary, an interlayer may be disposed on the conductive support. The interlayer generally comprises any of resins and it is desirable that these resins have higher resistance to standard organic solvents. These resins include water-soluble resins such as polyvinyl alcohol, casein, and polyacrylic sodium, alcohol-soluble resins such as copolymer nylon and methoxymethylated nylon, curable resins with a 3D network structure formed such as polyurethane resin, melamine resin, phenol resin, alkyd-melamine resin, epoxy resin, and the like. Fine pigment powders of any of metal oxides such as titanium oxide, silica, aluminuma, zirconium oxide, tin oxide, and indium oxide may be added to the interlayer to prevent moire from occurring and minimize residual potential. These types of interlayer can be formed using an appropriate solvent and the coating method as shown in the above-mentioned explanation of the photoconductive layer. In addition, a silane coupling agent, a titanium coupling agent, and a chromium coupling agent may be used for the interlayer of the present invention. Besides these, those which have been made by anodizing $Al_2O_3$, and the interlayer, which has been made of any of organic substances such as polyparaxylene (parylene) or of any of inorganic substances such as $SiO_2$, $SnO_2$, $TiO_2$, ITO, and $CeO_2$ by the vacuum thin-film formation method may be preferably used. The appropriate film thickness of the interlayer is 0–5 µm.

Further, to improve mechanical durability such as wear-resistance, a protective layer may be disposed on the photoconductive layer, if necessary.

The materials to be used in the protective layer include ABS resin, olefin-vinyl monomer copolymer resin, polyamido resin, polyamidoimido resin, polyacylate resin, polyacrylsulfone resin, polybutylene resin, polubutylene terephthalete resin, polyimido resin, acrylic resin, polypropylene resin, polyphenylene oxide resin, polysulfone resin, polystyrene resin, AS resin, butadiene-styrene copolymer resin, polyurethane resin, polyvinyl chloride resin, polyvinylidene chloride resin, and epoxy resin. To improve wear-resistance, fluororesin such as polytetrafluoroethylene, silicone resin, and the above-mentioned resins with any of organic materials such as titanium oxide, tin oxide, and potassium titanate dispersed may be added to the protective layer. To form the protective layer, the commonly used coating method may be applied. Note that the appropriate thickness of the protective layer is about 0.1–10 µm. Alternatively, known materials such as a-C and a-SiC formed by vacuum thin-film formation method may be used for the protective layer in addition to the above-mentioned materials.

(Process for Forming an Image, Apparatus for Forming an Image, and Process Cartridge for Apparatus for Forming an Image)

Now, the process for forming an image, apparatus for forming an image, and process cartridge for apparatus for forming an image of the present invention will be explained hereinafter.

Figure 1:
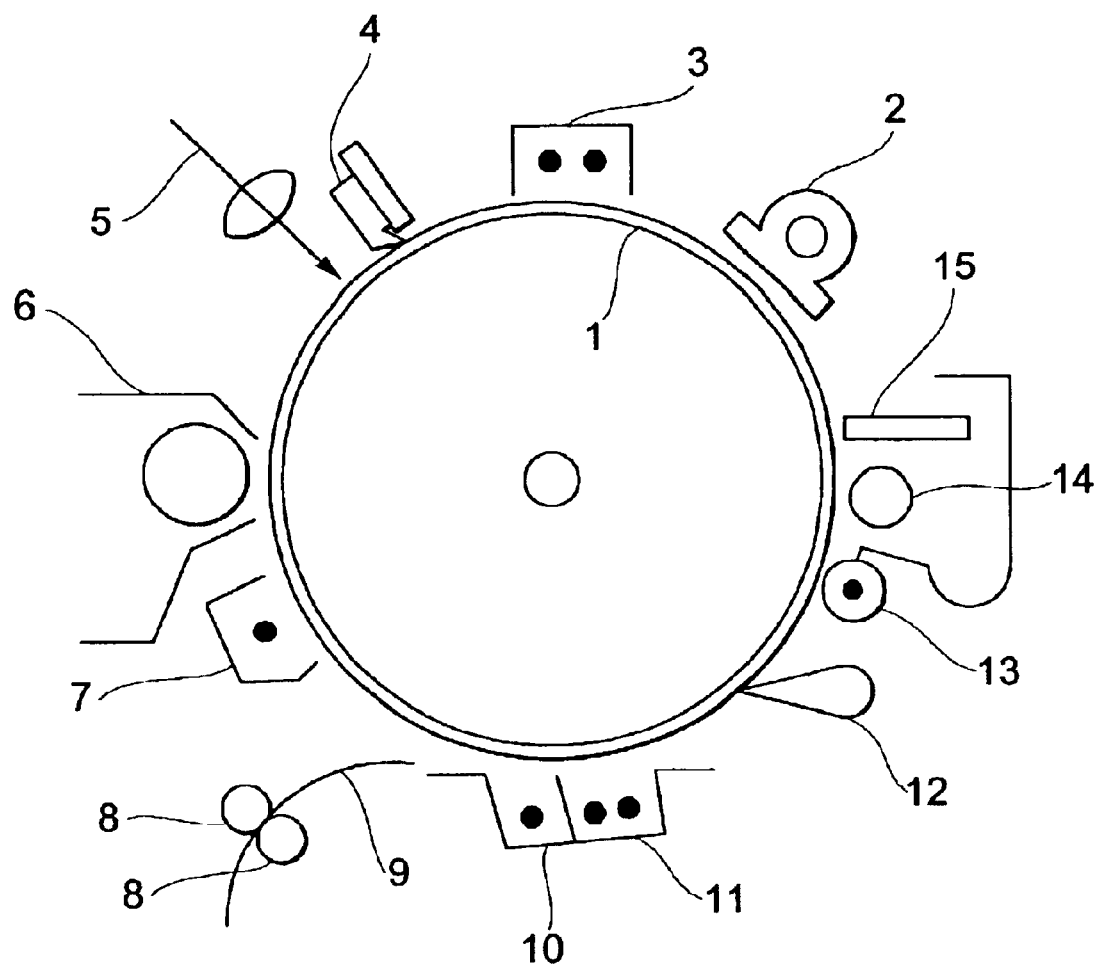
FIG. 1 is a schematic view showing an example of an apparatus for forming an image of the present invention.

FIG. 1 is a schematic view for explaining the process for forming an image, apparatus for forming an image, and process cartridge for apparatus for forming an image of the present invention which includes variations as described below within its scope.

In FIG. 1, a photoconductor (1) has a photoconductive layer disposed having a charge generating layer and a charge transporting layer disposed alternatively thereon on the support. The photoconductor (1) shown has a shape of drum, however, in a shape of sheet or endless belt may also be used. Any of the known means such as Colotoron, Scolotoron, a solid-state charger, and an electrostatic roller are used for a electrostatic charger (3), a pre-transfer charger (7), a transfer charger (10), a separation charger (11), and a pre-cleaning charger (13).

The above-mentioned electrostatic apparatus can be generally used but a combination of a transfer charger and a separation charger as shown in FIG. 1 has higher effect.

Any of all the light-emitting bodies such as a fluorescent light, a tungsten lamp, a halogen lamp, a mercury lamp, a sodium lamp, a light-emitting diode (LED), a semiconductor laser (LD), and an electroluminescent lamp can be used for light sources for a image exposing means (5), a charge neutralizer (2), and the like. To irradiate only light with a desired wavelength band, various types of filters such as a sharp-cut filter, a band-pass filter, a near-infrared-cut filter, a dichroic filter, an interference filter, and a color conversion filter can be used. The light sources of the present invention can irradiate light onto the photoreceptor using the transfer step, the neutralization step, cleaning step, or pre-exposure step in combination with a light irradiation feature in addition to the steps shown in FIG. 1.

Toner developed on the photoconductor (1) by a development unit (6) is transferred onto a transfer paper (9) but all toner is not always transferred on the paper and some of it may remain not transferred on the photoconductor (1). This remaining toner can be removed away from the photoreceptor using a fur brash (14) and a blade brash (15). In some cases, only a cleaning brash is used for cleaning and any of known brushes including a fur brash and a magfur brash is used for the cleaning brash. In FIG. 1, (4) indicates an eraser, (8) indicates a resist roller, and (12) indicate a separation claw.

By positively (or negatively) charging the electrophotography and then exposing images, positive (or negative) latent electrostatic images are formed on the surface of the photoreceptor. By developing these images using the negative-polarity (or positive-polarity) toner (charge-detection fine powder), positive images can be obtained, while by developing them using the positive-polarity (or negative-polarity) toner, negative images can be obtained. Any of known methods is applicable to the development method of the present invention and any of known methods is used for the neutralization method of the present invention.

Figure 2:
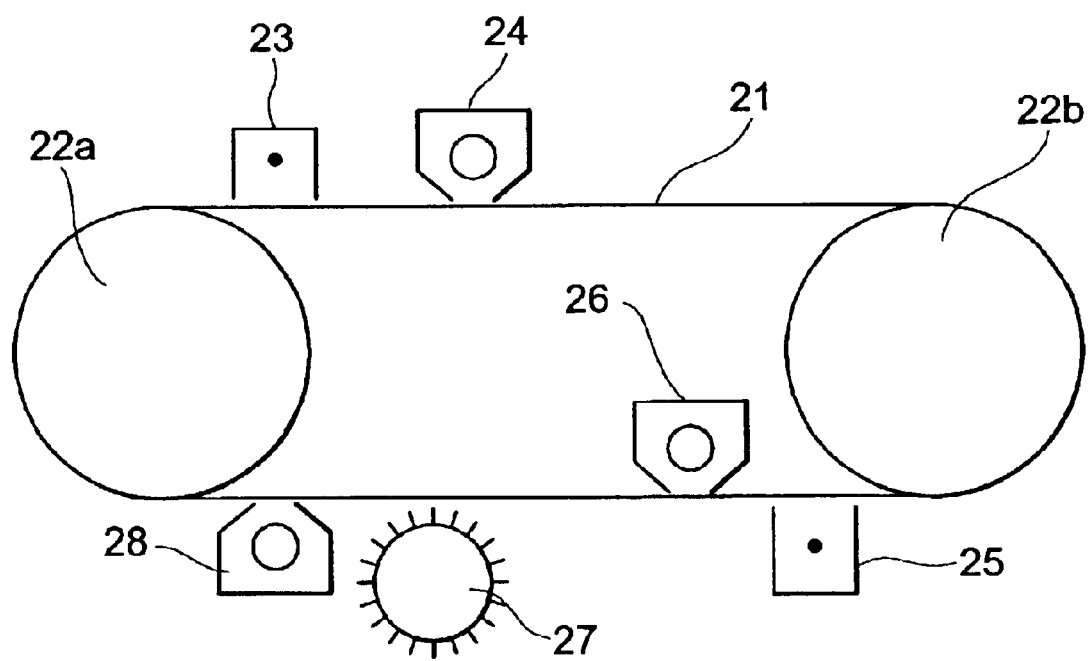
FIG. 2 is a schematic view showing an example of other apparatus for forming an image of the present invention.

In FIG. 2, another example of the image formation step according to the present invention is shown. In the step, a photoreceptor (21) having the photoconductive layer of the present invention is driven by driving rollers (22a) and (22b), charged by a electrostatic charger (23), exposed to a light source (24) to form image on it, and the images are developed (not shown in the figure) and transferred to the paper using a electrostatic charger (25), and the photoreceptor is pre-cleaning exposes to light, cleaned using a brash (27), and neutralized using the light source and this step is repeated. In FIG. 2, light is irradiated onto a photoreceptor (21) from the support side (of cause, in this case, the support is of transparent type) for pre-cleaning exposure.

The electrophotographic image-forming step shown in the figure is only an example of an embodiment of present invention and it is assumed that any other embodiments may be applicable. For example, in FIG. 2, pre-cleaning exposure is performed from the support side but this step may be done from the photoconductive layer side, and light may be irradiated from the support side for image formation and neutralization.

On the other hand, in the light irradiation step, pre-transfer exposure, pre-exposure for image formation, and any other known light-irradiation step may be used for irradiating the photoreceptor in addition to the steps of light exposure for image formation, pre-cleaning exposure, and neutralization exposure shown in the figure.

Figure 3:
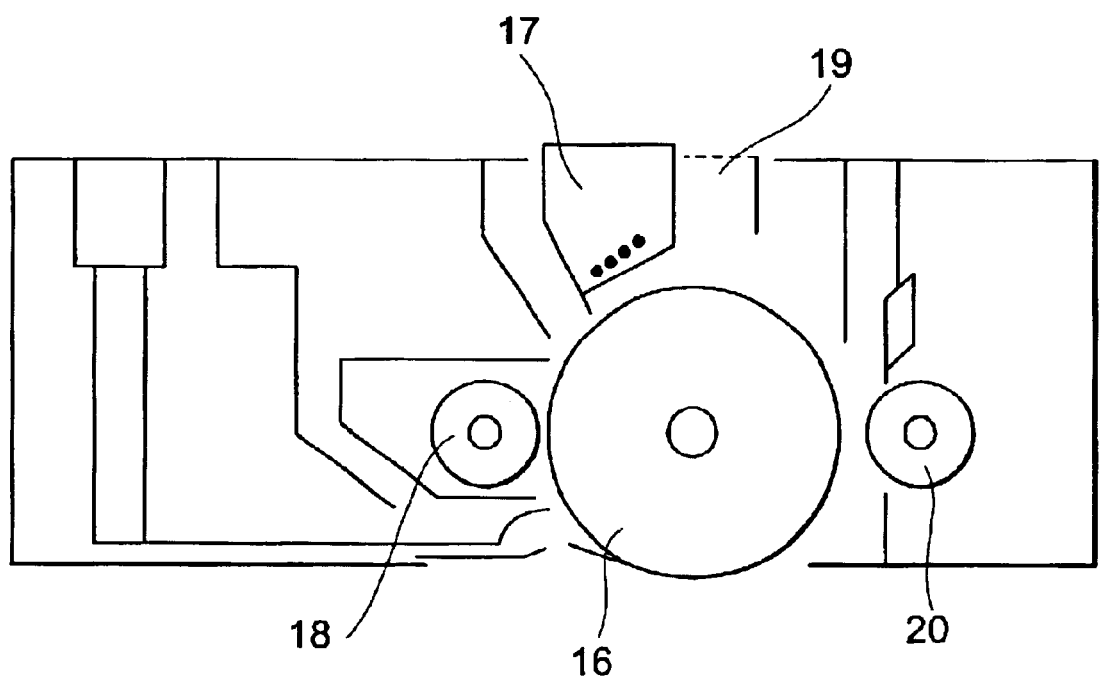
FIG. 3 is a schematic view showing an example of a process cartridge of the present invention.

The image formation means explained above may be fixedly incorporated in a copier, a facsimile, or a printer and may be incorporated in an apparatus in form of a process cartridge. The process cartridge is an independent device (component) including the photoreceptor and such means as charging, light exposure, development, transfer, cleaning, and neutralization. Various shapes for the process cartridge can be given and in FIG. 3, a general type of process cartridge is shown. A photoreceptor (16) has the photoconductive layer disposed so that the charge generating layer and the charge transporting layer are deposited Alternatively on the photoconductive support. In FIG. 3, (17) indicates the electrostatic charger, (18) indicates the cleaning brash, (19) indicates the image exposure unit, and (20) indicates the developing roller.

(Azo Compounds, Materials for Manufacturing the Same, and Method for Producing Both of them According to the Present Invention)

Now, the azo compounds, the materials for manufacturing the azo compounds, and method for producing them will be explained below. In other words, a mode of the azo compounds of the present invention is expressed by the general formula <<1'>> and at least one of said Cps is a coupler residue selected from those expressed by the following general formulae <<2'>>, <<3'>>, and <<4'>>.

Ar—(N=N—Cp)$_n$  general formula <<1'>>

(In the formula, Ar indicates a substituent or nonsubstituent aromatic hydrocarbon group or a aromatic heterocyclic group, which may bind via a bond group, Cp indicates the coupler residue, and n indicates any integer of 1, 2, 3, or 4.)

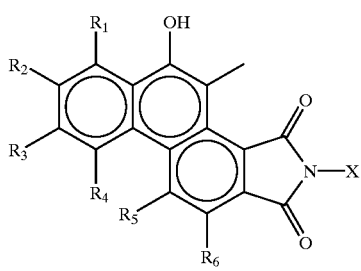

General formula <<2'>>

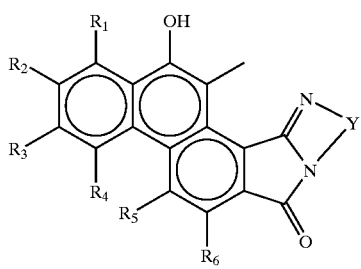

General formula <<3'>>

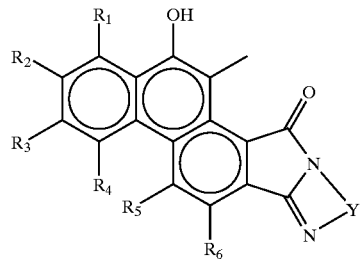

General formula <<4'>>

(In the formulae, $R_1$, $R_2$, $R_3$, $R_5$, and $R_6$ indicate a hydrogen atom, an alkyl group, an alkoxyl group, or a halogen atom, X indicates a hydrogen atom, a substituent or nonsubstituent alkyl group, a substituent or nonsubstituent aromatic hydrocarbon group, or a substituent or nonsubstituent heterocyclic group, and Y indicates a substituent or nonsubstituent alkylene group, a substituent or nonsubstituent bivalen organic residue with aromaticity, a substituent or nonsubstituent bivalent organic residue with heterocyclic aromaticity, or bivalent organic residue containing a carbonyl group expressed by —CO—Z— [note that Z indicates a substituent or nonsubstituent alkylene group, a substituent or nonsubstituent bivalent organic residue having aromaticity, or a substituent or nonsubstituent bivalent organic residue having heterocyclic aromaticity.].)

One mode of the azo compounds of the present invention and the materials for manufacturing said azo compound can be manufactured by the following method.

In other words, a naphthalene compound expressed by the general formula <<20>> can be obtained by reacting styrene compound expressed by the general formula <<26>> and an acetylene carboxylic acid ester compound expressed by the general formula <<27>> as shown below (Diels-Alder reaction).

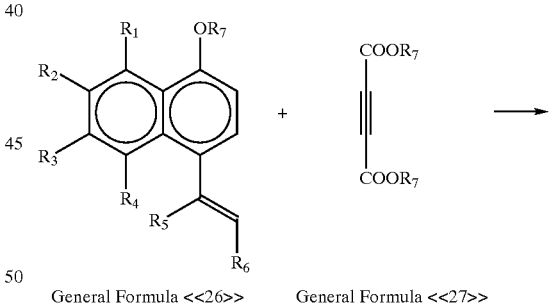

General Formula <<26>>    General Formula <<27>>

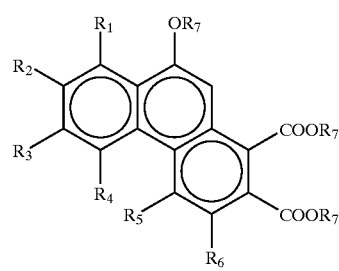

General Formula <<20>>

Note that the reaction is the Diels-Alder reaction involving an oxidization reaction and the reaction between any of hydroquinons and iodine is described in Liebigs Ann.Chem., 595, 1(1955) and the reaction by anhydrous maleic acid in a nitrobenzene solution is described in Ber.,69,1686(1936) .In the present invention, it was found that by controlling the reaction by acetylene dicarboxylic acid ester in the nitrobenzene solution at a reaction temperature of 100–160° C., and in particular, preferably at a reaction temperature of 130–150° C., the phenanthrene compound expressed by the general formula <<20>> at a high yield during only one stage reaction.

Now, the phenanthrene compound expressed by the general formula <<21>> can be obtained by removing (protective group removal) $R_7$ and $R_8$, which are protecting groups for the phenanthrene compound obtained as mentioned above, which are expressed by the general formula <<20>> as shown below.

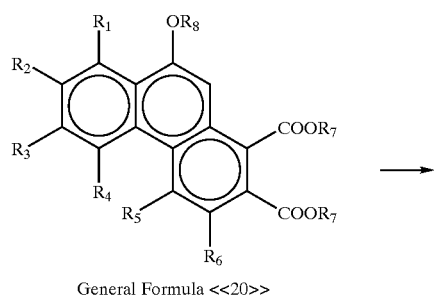

General Formula <<20>>

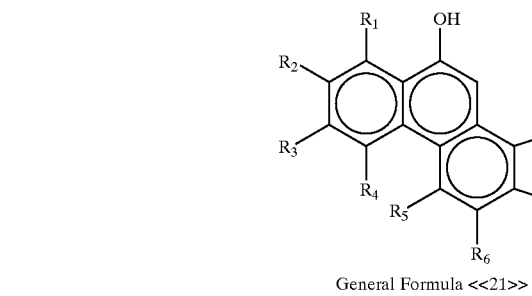

General Formula <<21>>

No special limitations are applicable to $R_6$ assuming that it is protecting group for OH groups, while the preferable examples of $R_6$ include a methyl group, an iso-propyl group, a t-butyl group, a benzyl group, an aryl group, a methoxymethyl group, a tetrahydropiranyl, a pyranyl group, and a trimethylcylyl group and further preferable examples include a methyl group, an iso-propyl group, a t-butyl group, and a methoxymethyl group which can be removed under the presence of acid catalytic agent at room temperature. The acid catalytic agent includes sulfuric acid, trifluoro acetic acid, hydrobromic acid, tribromo boron, methane sulfonic acid, and trifluoro methane sulfonic acid.

Next, the coupler compound expressed by the structural <<22>> can be obtained through the imidization reaction between the phenanthrene compound expressed by the general formula <<21>> and the amine compound expressed by the general formula <<28>> as shown below.

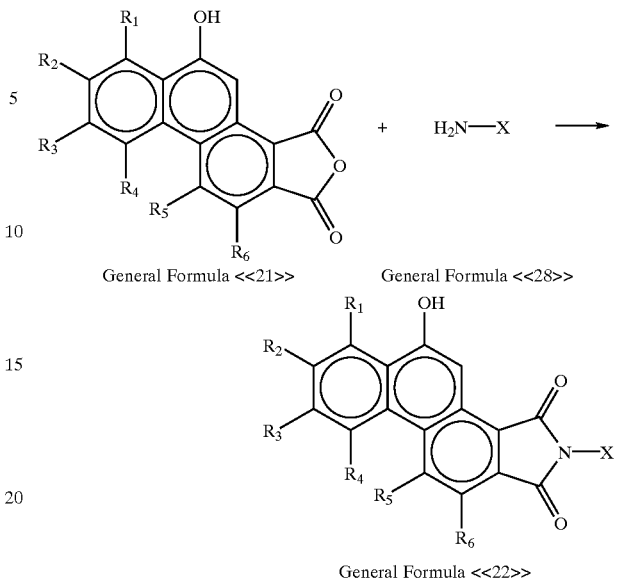

General Formula <<21>>   General Formula <<28>>

General Formula <<22>>

Generally, this type of imide reaction can be induced under the presence of a high-boiling point solvent. The reaction catalytic agents include toluene, xylene, chlorobenzene, o-dichlorobenzene, nitrobenzene, α-chloronaphthalene, quinoline, diphenyl ether, N-methyl pyrrolidone, ethylene glycol, acetic acid, and propionic acid and if necessary, removal of water produced from the reaction system can further improve the efficiency of the reaction. In addition, to facilitate the reaction, any acid catalytic agent may be used. The acid catalytic agent includes acetic acid, propionic acid, sulfuric acid, and p-toluenesulfonic acid and in particular, organic acid such as acetic acid and propionic acid are preferably used. It was found that the coupler compound expressed by the general formula <<22>> could be obtained at a high yield by controlling the reaction temperature within 100–170° C., preferably within 100–150° C.

Next, the coupler compound expressed by the general formula <<24>> or the general formula <<25>> are manufactured from the naphtharene compound expressed by the general formula <<21>> and obtained from the above-mentioned synthesizing process and the diaminized compound expressed by the general formula <<30>>,

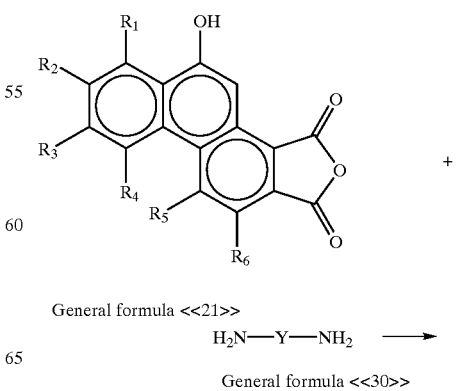

General formula <<21>>

$H_2N-Y-NH_2$

General formula <<30>>

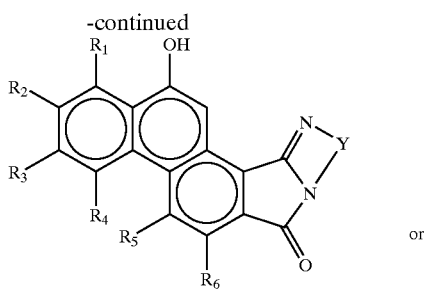

General formula <<24>>

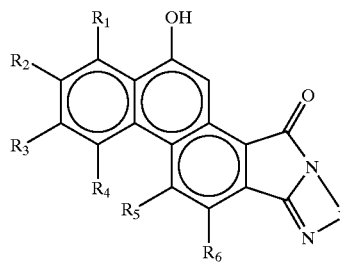

General formula <<25>>

The imidization reaction (including the dehydrated ring reaction) can be used in the same manner as shown in manufacturing the coupler compound expressed by the general formula <<22>>. Note that the reaction temperature is 100–180° C., preferably, 100–170° C.

Alternatively, the coupler compounds expressed by the general formula <<22>>, <<23>>, <<24>>, and <<25>> also can be manufactured by the following method (another synthesizing method).

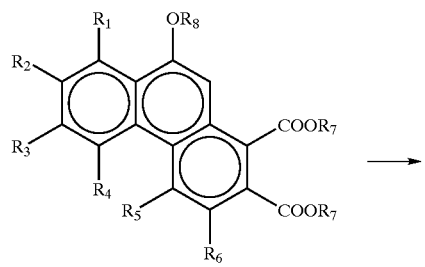

General formula <<20>>

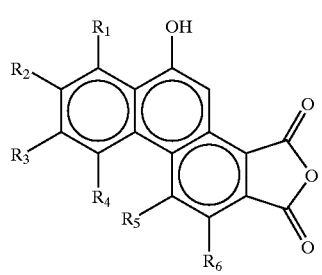

General formula <<5'>>

In other word, the phenanthrene compound expressed by the general formula <<5'>> is obtained by removing $R_8$, which is a protecting group for the phenanthrene compound expressed by the general formula <<5>>, in the manner as shown below (removal of protecting group). No special limitations are applied to $R_8$ assuming that it is a protecting group for OH groups but $R_8$ preferably indicates a methyl group, an iso-propyl group, a t-butyl group, a benzyl group, an allyl group, a methoxymethyl group, a tetrahydropyranyl group, and a torimethylcylyl group and more preferable examples include an iso-propyl group, a t-butyl group, and a methoxymethyl group, which may be removed under the presence of an acid catalytic agent at room temperature. The acid catalytic agent includes sulfuric acid, trifluoroacetic acid, hydrobromic acid, methansulfonic acid, and trifluoromethansulfonic acid.

Next, the coupler compound expressed by the general formula <<22>> can be obtained by inducing the ester-imido conversion reaction between the phenanthrene compound expressed by the general formula <<5'>> and obtained from the above-mentioned synthesizing process and the amine compound expressed by the general formula <<28>>, that is by inducing the reaction in the reaction system containing at least one kind of solvent selected from glycolic or glyceryl solvents at a reaction temperature of 100–170° C., preferably, 110–150° C.

Next, the coupler compound expressed by the general formula <<24>> or the general formula <<25>> can be obtained by inducing the ester/imido reaction between the phenanthrene compound expressed by the general formula <<5'>> and obtained from the above-mentioned synthesizing process and the diamine compound expressed by the general formula <<30>> in the same manner as for the coupler compound expressed by the general formula <<22>>.

Next, the azo compound expressed by the general formula <<1'>> can be manufactured from the reaction General formula below.

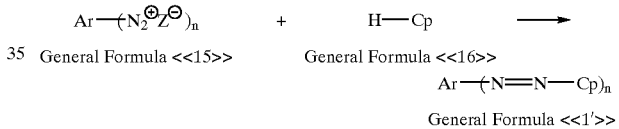

for example, the amino compound corresponding to the main skeleton (Ar portion) is used as a starting material and diazotized to isolated as diazonium salt expressed by the general formula <<15>>, and the obtained diazonuim salt is coupling-reacted with the coupler compound expressed by the general formula <<16>> and corresponding to each of the above-mentioned pigments under the presence of alkali. Among the azo compounds expressed by the general formula <<1'>> according to the present invention, two kinds or more coupler compounds <<16>> may be used in the azo compounds with n=2 or larger and in this case, the diazonium compound expressed by the general formula <<15>> is reacted with the coupler compound expressed by the above-mentioned general formula <<22>>, <<23>>, <<24>>, or <<25>> and any of the coupler compounds expressed by the later-mentioned general formulae (Cp1)-(Cp13) at two stages or the diazonium compound is isolated by the first coupling reaction and then reacted with corresponding coupler compound to obtain the azo compound.

In the general formula <<1'>> of the present invention, aromatic hydrocarbon groups, which may bind via a bond group in Ar, include a benzene, naphthalene, fluorine, phenanthrene, anthracene, and pyrene, heterocycls such as a furan, thiophene, pyridine, indole, benzothiazole, carbazole, acrydone, dibenzothiophene, benzooxazole, benzotrisole, oxadiazole and thiadiazole, and the above-mentioned aromatic rings binding directly to or via an aromatic group or a nonaromatic group, for example, triphenylamine, diphenylamine, N-methyldiphenylamine, biphenyl, tarphenyl, binaphthyl, fluorenone, phenanthrenequinone, anthraquinone, benzanthrone, anthraquinone, diphenyloxadiazole, phenylbenzooxazole, diphenylmethane, diphenylsulfone, diphenylether, benzophenone, stilbene, distilbenebenzene, tetraphenyl-p-phenylenediamine, and tetraphenylbenzidinemonopyridyldiphenylamine.

The substituents contained in the above-mentioned rings include alkyl groups such as a methyl group, an ethyl group, a propyl group, and a butyl group, alkoxyl groups such as a methoxyl group and an ethoxyl group, halogen atoms such as a fluorine atom, a chlorine atom, and a bromine atom, amino groups such as a dimethylamino group, a diethylamino group, and a diphenylamino group, a hydroxyl group, a nitro group, a cyano group, and a halomethyl group.

Examples of main skeleton (Ar) include those listed in Table 1 above-mentioned.

$R_1$, $R_2$, $R_3$, $R_4$, $R_5$, and $R_6$ in the general formula <<2'>>, the general formula <<3'>>, the general formula <<4'>>, the general formula <<20>>, the general formula <<21>>, the general formula <<22>>, the general formula <<24>>, the general formula <<25>>, the general formula <<26>>, and the general formula <<5'>> include a hydrogen atom, alkyl groups such as a methyl group, an ethyl group, a propyl group, and a butyl group, alkoxyl groups such as a methoxyl group and an ethoxyl group, halogen atoms such as a fluorine atom, a chlorine atom, and a bromine atom, amino groups such as a dimethylamino group, a diethylamino group, and a diphenylamino group, a hydroxyl group, a nitro group, a cyano group, and a halomethyl group.

Further, $R_7$ in the general formula <<20>>, the general formula <<21>>, the general formula <<27>>, and the general formula <<5'>> indicates a methyl group, an ethyl group, a propyl group, alkyl groups such as a butyl group, substituent alkyl groups such as a benzyl group and a 2-methoxyethyl group.

Further, $R_8$ in the general formula <<20>> and the general formula <<26>> indicates a methyl group, an iso-propyl group, a t-butyl group, a benzyl group, an allyl group, a methoxymethyl group, a tetrahydropiranyl group, and a trimethylcylyl and preferably includes an iso-propyl group and a t-butyl group.

In the general formula <<2'>>, the general formula <<22>>, and the general formula <<28>>, X indicates any of a hydrogen atom, alkyl groups such as a methyl group, an ethyl group, a propyl group, a butyl group, a pentyl group, a hexyl group, an octyl group and a decile group, cyclic alkyl groups such as a cyclopentyl group and a cyclohexyl group, aromatic hydrocarbon groups such as a phenyl group, a naphthyl group, an anthracenyl group, a phenanthrenyl group, and a pyrenyl group, heterocyclic compound groups such as a pyridyl group, a pyrazino group, a quinolino group, an oxazolyl group, a benzoxazolyl group, a thiazolyl group, a benzothiazolyl group, an imidazolyl group, a benzoimidazolyl group, and an indolyl group, alkylamino groups such as a methylamino group, and an ethylamino group, aromatic amino groups such as a phenylamino group and a naphthylamino group, carboamino groups such as an acetylamino group and a benzoylamino group. The substituents for them include alkyl groups such as a methyl group, an ethyl group, a propyl group, and a butyl group, substituent alkyl groups such as a benzyl group, a phenethyl group, and a methoxymethyl group, alkoxyl groups such as a methoxyl group, an ethoxyl group, and a phenoxyl group, a phenyl group, which may have a substituent, a naphthyl group, which may have a substituent, aromatic groups such as an anthracenyl group, a phenanthrenyl group, and a pyrenyl group, halogen atoms such as a fluorine atom, a chlorine atom, and a bromine atom, a hydroxyl group, an amino group, which may have a substituent, a nitro group, a cyano group, an acetyl group, a benzoyl group, which may have a substituent, an alkoxycarbonyl group, a phenoxycarbonyl group, which may have a substituent, and a carbamoyl group, which may have a substituent.

Further, in the general formula <<5'>>, $A_1$ indicates aromatic hydrocarbon groups such as a phenyl group, a naphthyl group, an anthracenyl group, phenanthrenyl group, and a pyrenyl group, a heterocyclic compound groups such as a pyrizyl group, a pyrazino group, a quinolino group, an oxazolyl group, a benzoxazolyl group, a thiazolyl group, a benzothiazolyl group, an imidazolyl group, a benzoimidazolyl group, and an indolyl group, and the substituents for them include alkyl groups such as a methyl group, an ethyl group, a propyl group, and a butyl group, substituent alkyl groups such as a benzyl group, a phenethyl group and a methoxymethyl group, alkoxyl groups such as a methoxyl group, an ethoxyl group and a phenoxyl group, a phenyl group, which may have a substituent, halogen atoms such as a fluorine atom, a chlorine atom, and a bromine atom, a trifluoromethyl group, a cyano group, an alkoxycarbonyl group, and a carbamoyl group, which may have a substituent.

In the general formula <<3'>>, the general formula <<4'>>, the general formula <<24>>, the general formula <<25>>, and the general formula <<30>>, Y indicates any of a substituent or nonsubstituent alkylene group, bivalent organic residues having substituent or nonsubstituent aromaticity, bivalent organic residues having substituent or nonsubstituent heterocyclic aromaticity, and bivalent organic residues containing a carbonyl group expressed by —CO—Z— (note that Z indicates a substituent or nonsubstituent alkylene group, any of bivalent organic residues having substituent or nonsubstituent aromaticity, and any of bivalent organic residues having substituent or nonsubstituent heterocyclic aromaticity). The alkylene group includes an ethylene group, a propylene group, a butylene group, a cyclopentyl group, and a cyclohexyl group. Note that the aromatic ring is formed via a carbon-carbon bond between the alkylene groups. The bivalent organic residues having aromaticity includes an o-phenylene group, a 1,8-naphtylene group, a 2,3-naphtylene group, a 1,2-anthrylene group, and a 9,10-phenanthrylene group, the bivalent organic residue having heterocyclic aromaticity includes a 3,4-pyrimidyl group, 2,3-pyridinedyl group, 5,6-pyrimidinedyl group, a 6,7-benzimidadyl group, a 6,7-quinolidyl group, and the bivalent organic residue containing a carbonyl group includes a 2-benzoyl group and a 2-naphthylcarbonyl group. The substituents for them include alkyl groups such as a methyl group, an ethyl group, a propyl group, and a butyl group, substituent alkyl groups such as a benzyl group, a phenethyl group and methoxymethyl group, alkoxyl groups such as a methoxyl group, an ethoxyl group and a phenoxyl group, a phenyl group, which may have a substituent, a naphthyl group, which may have a substituent, aromatic groups such as an anthracenyl group, a phenanthrenyl group, and a pyrenyl group, halogen atoms such as a fluorine atom, a chlorine atom, and a bromine atom, a hydroxyl group, carboamino groups such as an amino group, which may have a substituent, an acetylamino group, and a benzoylamino group, which may have a substituent, a nitro group, a cyano group, an acetyl group, a benzoyl group, which may have a substituent, an alkoxycarbonyl group, a phenoxycarbonyl group, which may have a substituent, and a carbamoyl group, which may have a substituent.

The substituents for them include alkyl groups such as a methyl group, an ethyl group, a propyl group, and a butyl group, substituent alkyl groups such as a benzil group, a phenethyl group and a methoxymethyl group, aromatic groups such as a phenyl group, which may have a substituent, naphthyl group, which may have a substituent, an anthracenyl group, a phenanthrenyl group, and a pyrenyl group, alkoxyl groups such as a methoxyl group, an ethoxyl group, and a phenoxyl group, halogen atoms such as a fluorine atom, chlorine atom, and a bromine atom, amino groups, which may have a substituent, such as a hydroxyl group, an dimethylamino group, an diethylamino group, and a diphenylamino group, carboamino groups such as an acetylamino group, and a benzoylamino group, a nitro group, a cyano group, an acetyl group, a benzoyl group, which may have a substituent, and a carbamoyl group, which may have a substituent.

Examples of the coupler compounds corresponding to those expressed by the general formula <<2'>>, the general formula <<3'>>, and the general formula <<4'>> include those given in Table 2 and Table 3 above mentioned.

With respect to Cp in the general formula <<1'>>, examples of the coupler residues, which may coexist in addition to the coupler residues expressed by the general formula <<2'>>, <<3'>>, and <<4'>> include for example, the compounds having any of phenol hydroxyl groups such as phenols or naphthols, the aromatic amino compounds having an amino group, amononaphthols having a amino group and a naphthol group, or the compounds having a fatty or aromatic enol ketone (compounds having an active methylene group) and preferably, include the coupler residues expressed by the general formula (1), the general formulae (Cp1)-(Cp15), of which it has been described in the above-mentioned general formula <<1>> that they may coexist in addition to the coupler residues expressed by the general formula <<2>>, <<3>>, and <<4>>.

Thus, Examples of the azo compounds of the present invention include those listed in table 20 above-mentioned. note that the azo compounds of the present invention are not limited only to the embodiments.

Another mode of the azo compound is expressed by the general formula <<101'>> and at least one of said Cps is the coupler residues selected from those expressed by the following general formulae <<102'>>, <<103'>>, and <<104'>>.

Ar─(N=N─Cp)$_n$   General formula <<101'>>

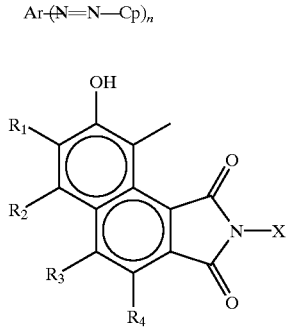

General formula <<102'>>

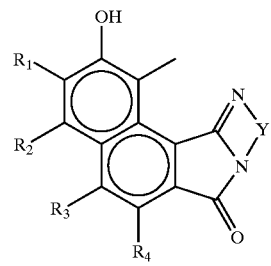

General formula <<103'>>

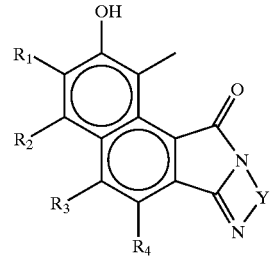

General formula <<104'>>

(In the formulae, $R_1$, $R_2$, $R_3$, and $R_4$ indicate a hydrogen atom, an alkyl group, an alkoxyl group, a halogen atom, X indicates a hydrogen atom, a substituent or nonsubstituent alkyl group, a substituent or nonsubstituent aromatic hydrocarbon group, a substituent or nonsubstituent heterocyclc group, or a substituent or nonsubstituent amino group, and Y indicates a substituent or nonsubstituent alkylene group, a substituent or nonsubstituent bivalent organic residues having aromaticity, a substituent or nonsubstituent bivalent organic residues having heterocyclic aromaticity, or bivalent organic residues containing a carbonyl group expressed by —CO—Z—. [note that Z indicates a substituent or nonsubstituent alkylene group, a substituent or nonsubstituent bivalent organic residue having aromaticity, or a substituent or nonsubstituent bivalent organic residue having heterocyclic aromaticity.].)

The said azo compounds and the materials for manufacturing said azo compounds can be manufactured in the following manner.

In other words, a naphthalene compound expressed by the general formula <<120>> can be obtained by reacting styrene compound expressed by the general formula <<126>> and an acetylene carboxylic acid ester compound expressed by the general formula <<127>> as shown below (Diels-Alder reaction).

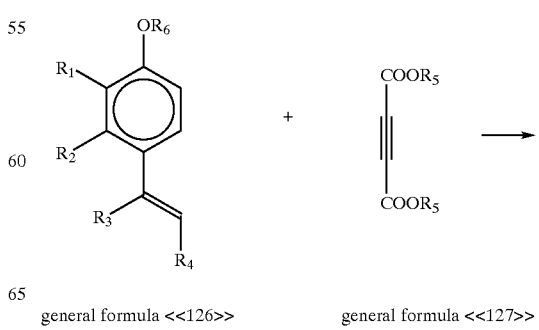

general formula <<126>>   general formula <<127>>

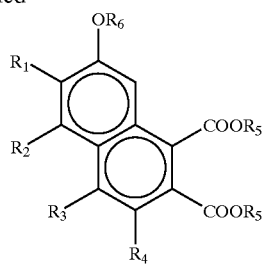

general formula <<120>>

Note that the reaction is the Diels-Alder reaction involving an oxidization reaction and the reaction between any of hydroquinons and iodine is described in Liebigs Ann.Chem., 595, 1(1955) and the reaction by anhydrous maleic acid in a nitrobenzene solution is described in Ber.,69,1686(1936). In the present invention, it was found that by controlling the reaction by acetylene dicarboxylic acid ester in the nitrobenzene solution at a reaction temperature of 100–160° C., and in particular, preferably at a reaction temperature of 130–150° C., the phenanthrene compound expressed by the general formula <<120>> at a high yield during only one stage reaction.

Next, the naphthalene compound expressed by the general formula <<149>> can be obtained by removing $R_6$, which is a preventing group for the naphthalene compound expressed by the general formula <<120>> and obtained from the above-mentioned process, in the following manner (removal of preventive group).

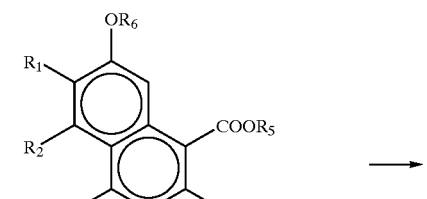

general formula <<120>>

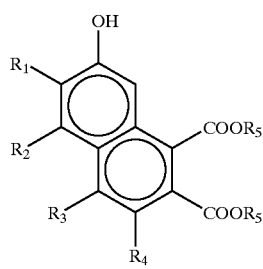

general formula <<149>>

No special limitations are applicable to $R_6$ assuming that it is a preventive group for OH groups, but preferably it include a methyl group, an iso-propyl group, a t-butyl group, a benzyl group, an aryl group, a methoxymethyl group, a tetrahydropiranyl group, and a trimethylsylyl group, and more preferably includes the iso-propyl group, the t-butyl group, and the methoxymethyl group, which can be removed under the presence of an acid catalytic agent at room temperature. The acid catalytic agent includes sulfuric acid, trifluoroacetic acid, hydrobromic acid, methansulfonic acid, and trifluoromethansulfonic acid.

Next, the coupler compound expressed by the general formula <<122>> by inducing the ester/amido conversion reaction between the naphthalene compound expressed by the general formula <<149>> and the amine compound expressed by the general formula <<28>> as shown below.

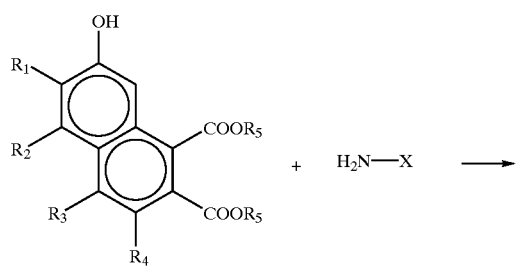

general formula <<149>>    general formula <<28>>

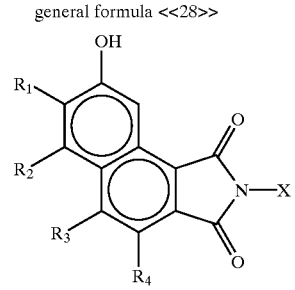

general formula <<122>>

Generally, it is described that presence of a basic catalytic agent or addition of glycol, water-soluble, or glycerol solvent is effective in the ester/ amido reaction in J.Am.Chem., Soc.,71, 1245 (1945). In the present invention, it was found that by controlling the reaction between the naphthalene compound expressed by the general formula <<149>> and the amine compound expressed by the formula <<28>> in the reaction system containing at least glycol or glycerol solvent at a reaction temperature of 100–170° C., and in particular, preferably at a reaction temperature of 110–150° C., the coupler compound expressed by the general formula <<122>> can be obtained at a high yield.

Next, the coupler compound expressed by the general formula <<124>> or the general formula <<125>> can be manufactured from the naphthalene compound expressed by the general formula <<149>> and obtained from the above-mentioned synthesizing process and the diamine compound expressed by the general formula <<30>> as shown in the following general formulae,

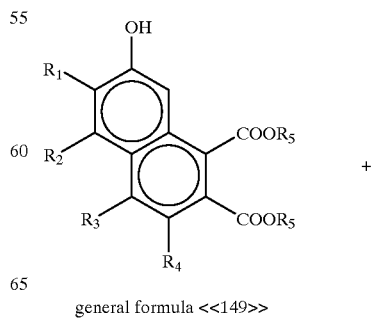

general formula <<149>>

-continued $H_2N-Y-NH_2$ ⟶ general formula <<30>>

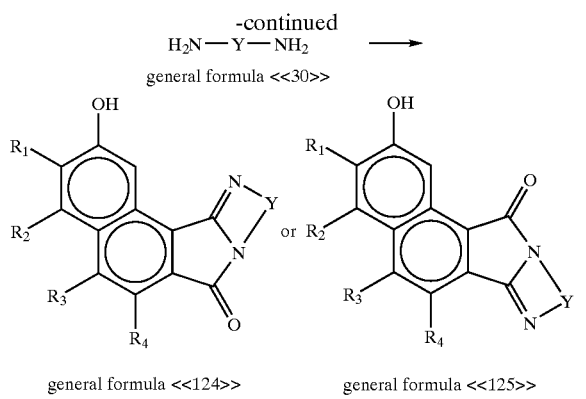

general formula <<124>>     general formula <<125>> and in this case, the same ester/ imido conversion reaction (including two cyclization reaction) as for manufacturing the coupler compound expressed by the general formula <<122>> mentioned above may be used. note that the reaction temperature is 130–180° C. and preferably, 140–170° C.

The coupler compounds expressed by the general formula <<122>>, the general formula <<123>>, the general formula <<124>>, the general formula <<125>>, the general formula <<143>>, the general formula <<144>>, the general formula <<145>>, and the general formula <<146>> also may be manufacture by the method described below.

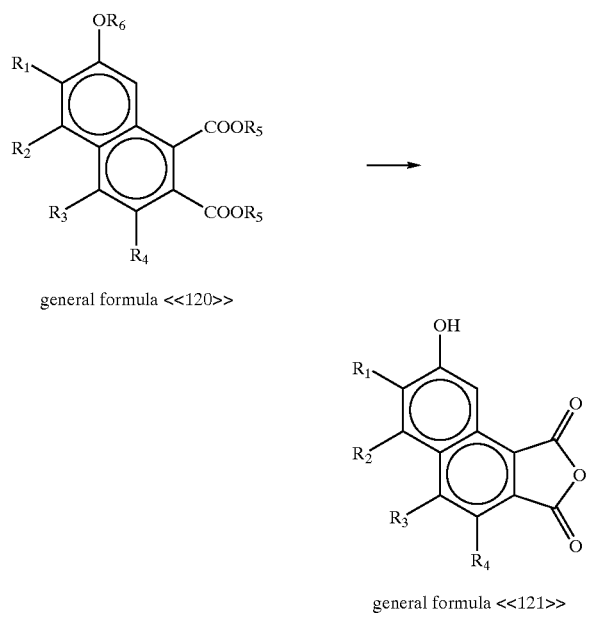

general formula <<120>> general formula <<121>>

In other words, by reacting the naphthalene compound under the presence of an acid catalytic agent, the naphthalene compound expressed by the general formula <<121>> can be obtained. In this case, no special limitations are applicable to $R_6$ assuming that it is a protecting group and a methyl group, a iso-propyl group, and the like can be used but preferably a methyl group is used. The acid catalytic agent includes hydrobromic acid and tribromoboron.

Next, by reacting the naphthalene compound expressed by the general formula <<121>> and obtained the above-mentioned synthesizing process and the amine compound expressed by the general formula <<28>> under the presence of the acid catalytic agent, the coupler compounds expressed by the general formula <<122>> and the general formula <<123>> can be obtained.

The acid catalytic agent includes acetic acid and sulfuric acid and by removing water produced during the reaction out of the reaction system, if necessary, further improvement in efficiency of the reaction may be achieved.

Next, The coupler compounds expressed by the general formula <<124>>, the general formula <<125>>, the general formula <<143>>, the general formula <<144>>, and the general formula <<155>> can be obtained by reacting the naphthalene compound expressed by the general formula <<121>> and obtained from the above-mentioned synthesizing process and the diamine compound expressed by the general formula <<30>> under the presence of the acid catalytic agent. The acid catalytic agent includes acetic acid and sulfuric acid and by removing water produced during the reaction out of the reaction system, if necessary, further improvement in efficiency of the reaction may be achieved.

Next, the azo compound expressed by the general formula <<101'>> also may be manufacture from the following general formulae;

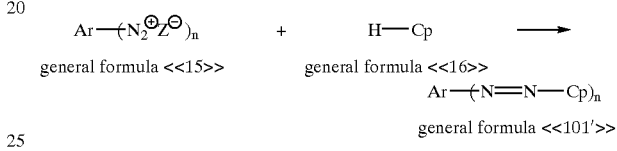

general formula <<15>>     general formula <<16>>

$Ar-(N=N-Cp)_n$ general formula <<101'>> for example, the amino compound corresponding to the main skeleton (Ar portion) is used as a starting material and diazotized to isolated as diazonium salt expressed by the general formula <<15>>, and the obtained diazonuim salt is coupling-reacted with the coupler compound expressed by the general formula <<16>> and corresponding to each of the above-mentioned pigments under the presence of alkali in the of an organic solvent(N,N-dimethylformaldehyde). Among the azo compounds expressed by the general formula <<101'>> according to the present invention, two kinds or more coupler compounds <<16>> may be used in the azo compounds with n=2 or larger and in this case, the diazonium compound expressed by the general formula <<15>> is reacted with the coupler compound expressed by the above-mentioned general formulae <<122>>, <<123>>, <<124>>, or <<125>> and any of the coupler compounds expressed by the later-mentioned general formulae (Cp1)-(Cp13) at two stages or the diazonium compound is isolated by the first coupling reaction and then reacted with corresponding coupler compound to obtain the azo compound.

In the general formula <<101'>> of the present invention, aromatic hydrocarbon groups, which may bind via a bond group in Ar, include a benzene, naphthalene, fluorine, phenanthrene, anthracene, and pyrene, heterocycls such as a furan, thiophene, pyridine, indole, benzothiazole, carbazole, acrydone, dibenzothiophene, benzooxazole, benzotrisole, oxadiazole and thiadiazole, and the above-mentioned aromatic rings binding directly to or via an aromatic group or a nonaromatic group, for example, triphenylamine, diphenylamine, N-methyldiphenylamine, biphenyl, tarphenyl, binaphthyl, fluorenone, phenanthrenequinone, anthraquinone, benzanthrone, anthraquinone, diphenyloxadiazole, phenylbenzooxazole, diphenylmethane, diphenylsulfone, diphenylether, benzophenone, stilbene, distilbenebenzene, tetraphenyl-p-phenylenediamine, and tetraphenylbenzidinemonopyridyldiphenylamine.

The substituents contained in the above-mentioned rings include alkyl groups such as a methyl group, an ethyl group, a propyl group, and a butyl group, alkoxyl groups such as a methoxyl group and an ethoxyl group, halogen atoms such as a fluorine atom, a chlorine atom, and a bromine atom, amino groups such as a dimethylamino group, a diethylamino group, and a diphenylamino group, a hydroxyl group, a nitro group, a cyano group, and a halomethyl group.

Examples of main skeleton (Ar) include those listed in Table 1 above-mentioned.

$R_1$, $R_2$, $R_3$, and $R_4$ in the general formula <<102'>>, the general formula <<103'>>, the general formula <<104'>>, the general formula <<120>>, the general formula <<149>>, the general formula <<122>>, the general formula <<124>>, the general formula <<125>>, and the general formula <<126>> include a hydrogen atom, alkyl groups such as a methyl group, an ethyl group, a propyl group, and a butyl group, alkoxyl groups such as a methoxyl group and an ethoxyl group, halogen atoms such as a fluorine atom, a chlorine atom, and a bromine atom, amino groups such as a dimethylamino group, a diethylamino group, and a diphenylamino group, a hydroxyl group, a nitro group, a cyano group, and a halomethyl group.

In the general formula <<120>>, the general formula <<149>>, the general formula <<127>>, $R_5$ indicates alkyl groups such as a methyl group, an ethyl group, a propyl group, and a butyl group, or substituent alkyl groups such as a benzil group and a 2-methoxyethyl group.

In the general formula <<120>> and the general formula <<126>>, preferably, $R_6$ indicates a methyl group, an isopropyl group, a t-butyl group, a benzil group, an allyl group, a methoxymethyl group, a tetrahydropiranyl group, or a trimethylcylyl group.

In addition, In the general formula <<102'>>, the general formula <<122>>, and the general formula <<28>>, X indicates a hydrogen atom, alkyl groups such as a methyl group, an ethyl group, a propyl group, a butyl group, a pentyl group, a hexyl group, an octyl group, and a decyl group, cyclic alkyl groups such as a cyclopentyl group, and a cyclohexyl group, aromatic hydrocarbon groups such as a phenyl group, a naphthyl group, an anthracenyl group, a phenanthrenyl group, and a pyrenyl group, heterocyclic compound groups such as a pyrizyl group, a pyrazino group, a quinolino group, an oxazolyl group, a benzoxazolyl group, a thiazolyl group, a benzothiazolyl group, an imidazolyl group, a benzoimidazolyl group, and an indolyl group, alkylamino groups such as a methylamino group and an ethylamino group, aromatic amino groups such as a phenylamino group, and naphthylamino group, or carboamino groups such as a acetylamino group and a benzoylamino group. The substituents for them include alkyl groups such as a methyl group, an ethyl group, a propyl group, and a butyl group, substituent alkyl groups such as a benzil group, a phenethyl group and a methoxymethyl group, alkoxyl groups such as a methoxyl group, an ethoxyl group and phenoxyl group, phenyl group, which may have a substituent, naphthyl group, which may have a substituent, aromatic groups such as an anthracenyl group, a phenanthrenyl group, and a pyrenyl group, halogen atoms such as a fluorine atom, a chlorine atom, and a bromine atom, carboamino groups such as a hydroxyl group, amino group, which may have a substituent, an acetylamino group, a benzoylamino group, nitro group, a cyano group, an acetyl group, benzoyl group, which may have a substituent, an alkoxycarbonyl group, a phenoxycarbonyl group, which may have a substituent, or a carbamoyl group, which may have a substituent.

In the general formula <<123>>, $A_1$ indicates any of aromatic hydrocarbon groups such as a phenyl group, a naphthyl group, an anthracenyl group, a phenanthrenyl group, and a pyrenyl group, heterocyclic groups such as a pyridyl group, a pyrazino group, a quinolino group, an oxazolyl group, a benzoxazolyl group, a thiazolyl group, a benzothiazolyl group, an imidazolyl group, a benzoimidazolyl group, and an indolyl group, and the substituents for them include alkyl groups such as a methyl group, an ethyl group, propyl group, and a butyl group, substituent alkyl groups such as a benzyl group, a phenethyl group and a methoxymethyl group, an alkoxyl groups such as a methoxyl group, an ethoxyl group and a phenoxyl group, a phenyl group, which may have a substituent, halogen atoms such as a fluorine atom, a chlorine atom, and a bromine atom, a trifluoromethyl group, a cyano group, an alkoxycarbonyl group, and a carbamoyl group, which may have a substituent.

In the general formula <<103'>>, the general formula <<104'>>, the general formula <<124>>, the general formula <<125>>, and the general formula <<30>>, Y indicates any of a substituent or nonsubstituent alkylene group, bivalent organic residues having substituent or nonsubstituent aromaticity, bivalent organic residues having substituent or nonsubstituent heterocyclic aromaticity, and bivalent organic residues containing a carbonyl group expressed by —CO—Z— (note that Z indicates a substituent or nonsubstituent alkylene group, any of bivalent organic residues having substituent or nonsubstituent aromaticity, and any of bivalent organic residues having substituent or nonsubstituent heterocyclic aromaticity). The alkylene group includes an ethylene group, a propylene group, a butylene group, a cyclopentyl group, and a cyclohexyl group. Note that the aromatic ring is formed via a carbon-carbon bond between the alkylene groups. The bivalent organic residues having aromaticity includes an o-phenylene group, a 1,8-naphtylene group, a 2,3-naphtylene group, a 1,2-anthrylene group, and a 9,10-phenanthrylene group, the bivalent organic residue having heterocyclic aromaticity includes a 3,4-pyrimidyl group, 2,3-pyridinedyl group, 5,6-pyrimidinedyl group, a 6,7-benzimidadyl group, a 6,7-quinolidyl group, and the bivalent organic residue containing a carbonyl group includes a 2-benzoyl group and a 2-naphthylcarbonyl group. The substituents for them include alkyl groups such as a methyl group, an ethyl group, a propyl group, and a butyl group, substituent alkyl groups such as a benzyl group, a phenethyl group and methoxymethyl group, alkoxyl groups such as a methoxyl group, an ethoxyl group and a phenoxyl group, a phenyl group, which may have a substituent, a naphthyl group, which may have a substituent, aromatic groups such as an anthracenyl group, a phenanthrenyl group, and a pyrenyl group, halogen atoms such as a fluorine atom, a chlorine atom, and a bromine atom, a hydroxyl group, carboamino groups such as an amino group, which may have a substituent, an acetylamino group, and a benzoylamino group, which may have a substituent, a nitro group, a cyano group, an acetyl group, a benzoyl group, which may have a substituent, an alkoxycarbonyl group, a phenoxycarbonyl group, which may have a substituent, and a carbamoyl group, which may have a substituent.

$B_1$ in the general formula <<143>> and the general formula <<144>> and $B_2$ in the general formula <<145>> and the general formula <<146>> indicate a bivalent group of an aromatic hydrocarbon ring such as a o-phenylene group and a 2,3-naphthylene group, a bivalent group of a aromatic heterocycle such as a 2,3-pilinyl group, a 3,4-pyrazoleyl group, a 2,3-pyridineyl group, and a 3,4-imidazoleyl group, and the substituents fort hem include alkyl groups such as a methyl group, an ethyl group, a propyl group, and a butyl group, alkoxyl groups such as a methoxyl group, an ethoxyl group, and a phenoxyl group, halogen atoms such as a fluorine atom, a chlorine atom, and a bromine atom, and nitro group.

Examples of the new couplers (Cr) include those listed in Table 21 and Table 22 mentioned above.

With respect to Cr in the general formula <<101'>> examples of the coupler residues, which may coexist in addition to the coupler residues expressed by the general formula <<102'>>, the general formula <<103'>>,and the general formula <<104'>> include, for example, the compounds having a phenolhydroxyl group such as phenols and naphthols, an aromatic amino compound having an amino group, or aminonaphthols having an amino group and a phenol hydroxyl group, the compounds having a fatty or aromatic enol ketone(compound having an active methylene group) and preferably include the coupler residues expressed by the general formulae (cp1)-(Cp15), of which it is described that they may coexist in addition to the coupler compounds expressed by the general formula <<2>>, the general formula <<3>>, and the general formula <<4>> in the above-mentioned general formula <<1>>.

Actual examples of the above-mentioned azo compounds include those listed Table 23 mentioned above.

EXAMPLES

In the following, although the Synthetic Examples, the manufacturing examples, and the embodiments for an electrophotographic photoconductor having a photoconductive layer containing an azo compound expressed by the general formula <<1>> are explained, the present invention is not limited thereto.

Synthetic Example I-1

Synthesizing 9-methoxy phenanthrene-1,2-dicarboxylic acid dimethyl ester.

Figure 4:
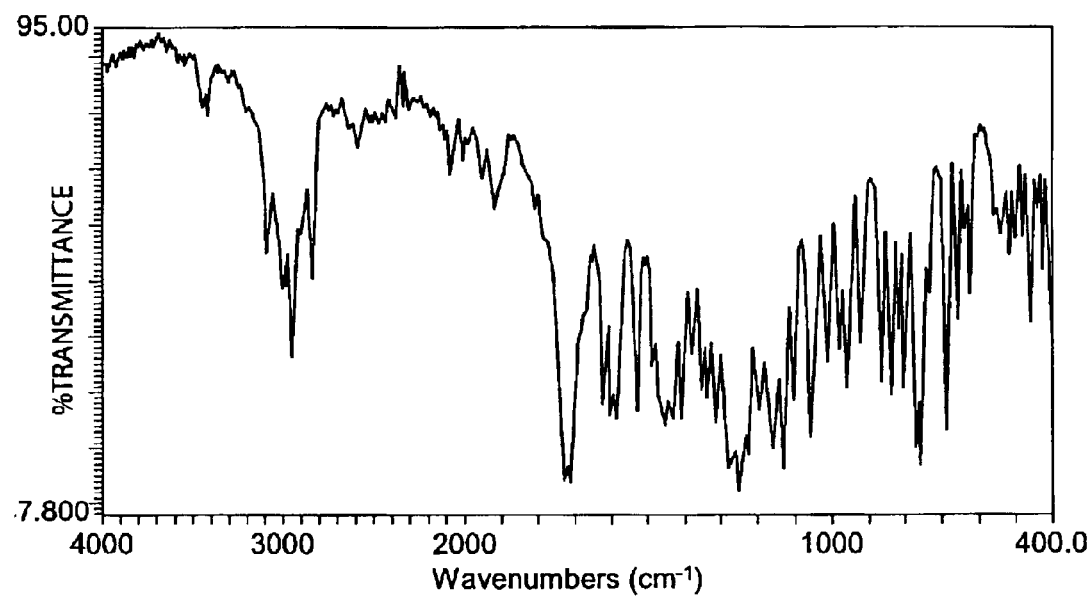
FIG. 4 is a graph showing an example of an infrared absorption spectrum of a phenanthrene compound obtained in Synthetic Example 1-1 of the present invention.

1-methoxy-4-vinyl naphthalene 18.42 g (0.1 mol) and acetylene dicarboxylic acid dimethyl ester 28.42 g (0.2 mol) were dissolved in nitrobenzene, 200 ml, and they were reacted for 7 hours at the temperature of 130° C. After cooling, nitrobenzene was escaped in vapor under a reduced pressure condition, silica gel column chromatography (developing solvent n-hexane: an acetic acid ethyl=9:1) process was performed to residual elements, crude material, 23.08 g, was obtained. Further, objective phenanthrene compounds, 19.85 g (yield 61.2%) was obtained by recrystallizing from n-butanol. A melting point was 150.2 to 151.0° C. An infrared absorption spectrum of this phenanthrene compound is shown in FIG. 4.

TABLE 24

| Elemental Analysis Value | C (%) | H (%) |
|---|---|---|
| Actual Measurement Value | 70.39 | 4.93 |
| Calculation Value | 70.36 | 4.97 |

Synthetic Example I-2

Synthesizing 9-hydroxy phenanthrene-1,2-dicarboxylic acid anhydride.

Figure 5:
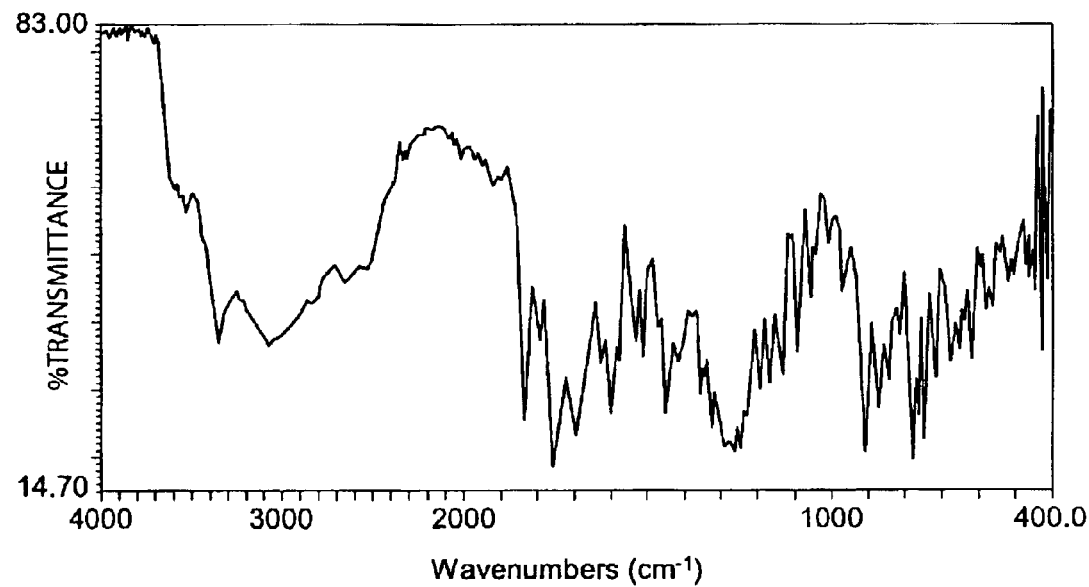
FIG. 5 is a graph showing an example of an infrared absorption spectrum of a phenanthrene compound obtained in Synthetic Example 1-2 of the present invention.

9-methoxy phenanthrene-1,2-dicarboxylic acid dimethyl ester 8.11 g (0.025 mol) obtained in the example I-1 was dissolved in chloride methylene 100 ml, by ice-cooling and mixing under nitrogen gas airstreams, 1M 3 bromide boron/chloride methylene solution 100 ml (0.1 mol) was dropped for 60 minutes, and further a mixing reaction was performed for 5 hours under a room temperature. Then, reactants were poured into an ice, water was added, and further hydrogen carbonate sodium 8.4 g (0.1 mol) was added and mixed sufficiently, accordingly extracted crystals were filtered. Then, they were washed twice by 500 ml ion exchange water and dried under reduced pressure at the temperature of 60° C., thus 5.84 g (yield 88.4%) objective phenanthrene compound was obtained. An infrared absorption spectrum of this phenanthrene compound is shown in FIG. 5.

TABLE 25

| Elemental Actual Value | C (%) | H (%) |
|---|---|---|
| Actual Measurement Value | 72.54 | 3.19 |
| Calculation Value | 72.73 | 3.05 |

Synthetic Example I-3

Synthesizing Coupler Compound No. C5.

Figure 6:
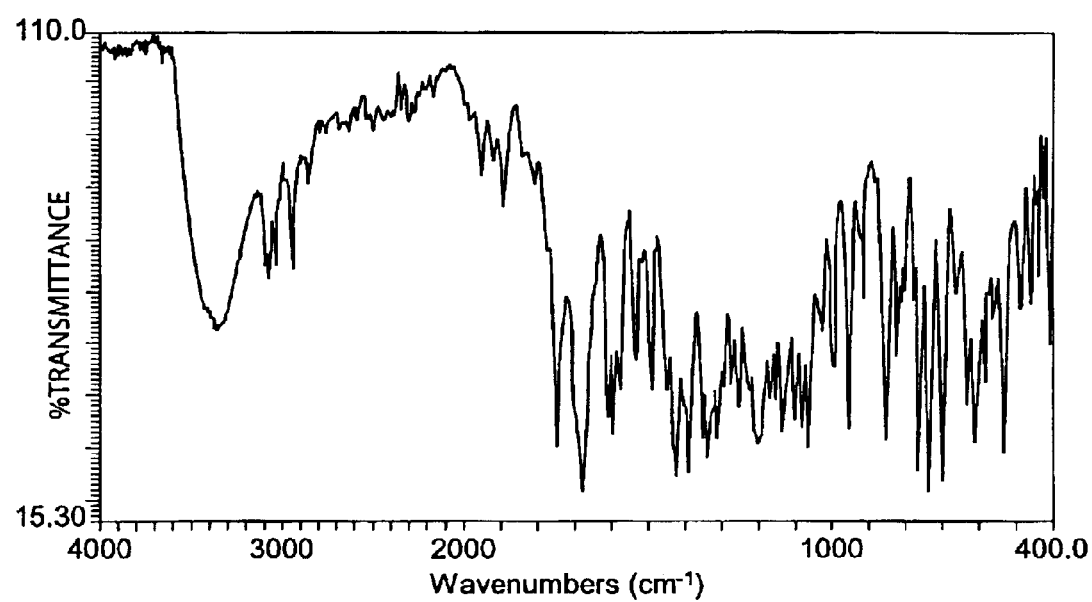
FIG. 6 is a graph showing an example of infrared absorption spectrum of a coupler compound obtained in Synthetic Example 1-3 of the present invention.

9-hydroxy phenanthrene-1,2-dicarboxylic acid anhydride 5.28 g (0.02 mol) obtained in Synthetic Example I-2 and benzyl amine 4.29 g (0.04 mol) were mixed and reacted for 12 hours using acetic acid, 100 ml, under a circulating condition. After cooling, reactants were poured into an ice, and extracted crystals were filtered. Then, they were washed by 500 ml ion exchange water, dried under reduced pressure at the temperature of 60° C., thus 6.68 g crude material was obtained. Obtained crude material was recrystallized by n-butanol/dioxane mixed solvent, 5.58 g (yield 79.0%) coupler compounds <No. C5> were obtained. The melting point was 307.9 to 321.8° C. The infrared absorption spectrum for a coupler compound is shown in FIG. 6.

TABLE 26

| Elemental Analysis Value | C (%) | H (%) | N (%) |
|---|---|---|---|
| Actual Measurement Value | 78.29 | 4.26 | 3.89 |
| Calculation Value | 78.18 | 4.28 | 3.96 |

Manufacturing Example 1

Manufacturing Azo Compounds No. P19

Figure 7:
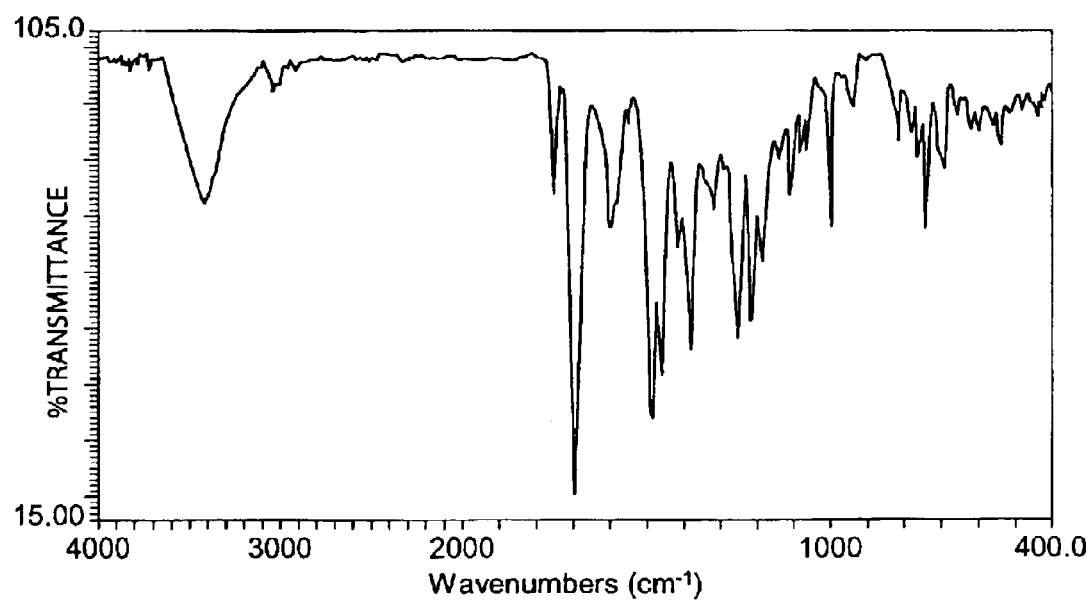
FIG. 7 is a graph showing an example of infrared absorption spectrum of an azo compound obtained in Manufacturing Example 1 of the present invention (KBr tablet method).

N-benzyl-9-hydroxy-1,2-phenanthrene dicarboxylic acid imido (coupler No. C5 compounds) 1.06 g (3 mmol) was dissolved in DMF 100 ml, and then 9-fluorenone2,7-bis diazonium tetra fluoro borate 0.61 g (1.5 mol) which was synthesized by 2,7-diamino-9-fluorenone in advance was added at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P19) 0.62 g (yield 44.0%) was obtained by drying at the temperature of 70° C. under a reduced pressure condition. This azo compound's infrared absorption spectrum (KBr tablet method) is shown in FIG. 7.

TABLE 27

| Elemental Analysis Value | C (%) | H (%) | N (%) |
|---|---|---|---|
| Actual Measurement Value | 75.26 | 3.53 | 8.76 |
| Calculation Value | 75.47 | 3.65 | 8.95 |

Manufacturing Example 2

Manufacturing Azo Compounds No. P20

Figure 8:
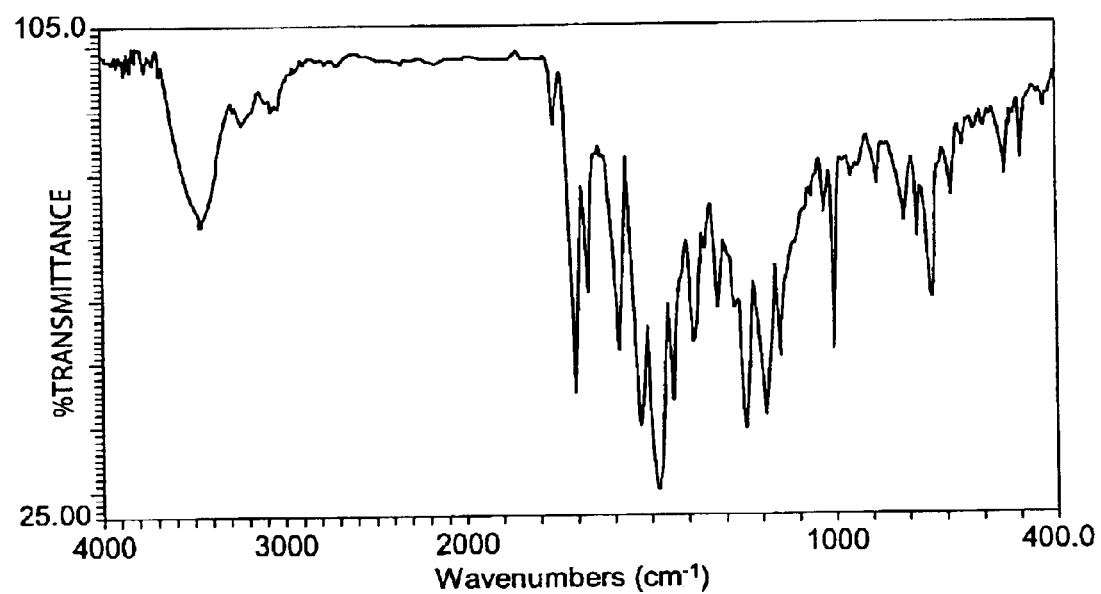
FIG. 8 is a graph showing an example of an infrared absorption spectrum of an azo compound obtained in Manufacturing Example 2 of the present invention (KBr tablet method).

N-benzyl-9-hydroxy-1,2-phenanthrene dicarboxylic acid imido (coupler No. C5 compound) 0.53 g (1.5 mmol) was dissolved in DMF 60 ml, 9-fluorenone-2,7-bis diazonium tetra fluoro borate 0.61 g (1.5 mmol) which was synthesized by 2,7-diamino-9-fluorenone in advance was added and mixed for 10 minutes at a room temperature. Then, 2-hydroxy-3-(2-chlorophenyl carbamoyl)naphthalene (coupler No. 17 compound) 0.45 g (1.5 mmol) and DMF 40 ml solution were added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P20) 0.62 g (yield 49.3%) was obtained by drying at the temperature of 70° C. under a reduced pressure condition. This azo compound's infrared absorption spectrum (KBr tablet method) is shown in FIG. 8.

TABLE 28

| Elemental Analysis Value | C (%) | H (%) | N (%) |
|---|---|---|---|
| Actual Measurement Value | 71.81 | 3.32 | 9.51 |
| Calculation Value | 72.07 | 3.54 | 9.51 |

Example I-1

Azo compounds (No. P19) 7.5 volumes, which were obtained by manufacturing example 1, and polyester resin (VYLON® 200: TOYOBO Co., Ltd.) 0.5% tetra hydro furan solution 500 volumes were crushed and mixed in a ball mill and obtained. Then dispersion liquid was coated by a doctor blade on an aluminium evaporation polyester film and a charge generating layer was formed, a thickness of which was more or less 1 $\mu$m, by drying naturally. Then, as charge transport substance, 1-phenyl-3-(4-diethyl amino styryl)-5-(4-diethyl amino phenyl) pyrazoline (charge transport substance No. D1), 1 volume, polycarbonate resin (Panlite® K1300; TEJIN KASEI Co., Ltd.), 1 volume, tetrahydrofuran, 8 volumes, and charge transporting layer coating liquid were conditioned, coated by the doctor blade on the aforementioned charge generating layer, dried for 2 minutes at the temperature of 80° C. and for 5 minutes at the temperature of 120° C., thus a charge transporting layer having the thickness of more or less 20 $\mu$m was formed, and a photoconductor was formed.

Examples I-2 to I-20

Except that azo compound and charge transporting substance, each of which is indicated in Table 29, were used instead of the azo compound and charge transporting substance which were used in the example I-1, the photoconductor was manufactured in the same way as the example I-1.

(Electrostatic Properties Evaluation)

For thus obtained electrophotographic photoconductor, 6 KV corona discharge was performed for 20 seconds in a dark place in order to take a charge using an electrostatic copying paper test device EPA-8200 (KAWAGUCHI DENKI SEISAKUSHO) under 25° C./55% RH condition. Further, after it was put in the dark place for 20 seconds, surface electrokinetic potential $V_0$ (V) was measured. Then, a tungsten lamp was used for irradiation in order for an illumination unit of the photoconductor's surface to be 5.3 luxes, time (sec) till its surface electrokinetic potential became a half of $V_0$ was obtained, as sensitivity in a visible region, 50 percent exposing volume $E_{1/2}$ (lux·sec) was calculated. The result is shown in Table 29.

Charge transporting substance No. D1: 1-phenyl-3-(4-ethyl amino styryl)-5-(4-ethyl amino phenyl)pyrazoline Charge transporting substance No. D2: 9-ethyl carbazole-3-aldehyde-1-methyl-1-phenyl hydrazone Charge transporting substance No. D3: α-phenyl-4'-bis (4-methyl phenyl)amino stilbene Charge transporting substance No. D4: α-pheny-1-4'-diphenyl amino stilbene

TABLE 29

| | Azo Compound No. | Charge transporting substance No. | Vo | E1/2 |
|---|---|---|---|---|
| Ex. I-1 | P19 | D1 | 727 | 1.95 |
| Ex. I-2 | P20 | D3 | 1140 | 1.05 |
| Ex. I-3 | P20 | D4 | 1214 | 1.32 |
| Ex. I-4 | P23 | D1 | 1354 | 3.30 |
| Ex. I-5 | P24 | D2 | 1246 | 2.20 |
| Ex. I-6 | P24 | D3 | 1298 | 1.43 |
| Ex. I-7 | P27 | D2 | 1055 | 8.87 |
| Ex. I-8 | P28 | D3 | 1097 | 0.83 |
| Ex. I-9 | P28 | D4 | 1304 | 1.28 |
| Ex. I-10 | P38 | D4 | 601 | 6.83 |
| Ex. I-11 | P11 | D2 | 1233 | 2.34 |
| Ex. I-12 | P53 | D3 | 1192 | 1.57 |
| Ex. I-13 | P74 | D2 | 1084 | 2.51 |
| Ex. I-14 | P94 | D3 | 1206 | 2.20 |
| Ex. I-15 | P107 | D3 | 1245 | 0.85 |
| Ex. I-16 | P133 | D3 | 1221 | 0.81 |
| Ex. I-17 | P146 | D3 | 689 | 1.50 |
| Ex. I-18 | P146 | D4 | 1102 | 2.56 |
| Ex. I-19 | P181 | D3 | 1185 | 0.97 |
| Ex. I-20 | P183 | D3 | 1231 | 1.13 |

Comparative Example I-1

Except that azo compound and charge transporting substance No. D3, each of which is indicated by the following structural formula (CGM-1), were used instead of azo compound and charge transporting substance which were used in the example I-1, the photoconductor was manufactured in the same way as the example I-1.

Structural formula (CGM-1)

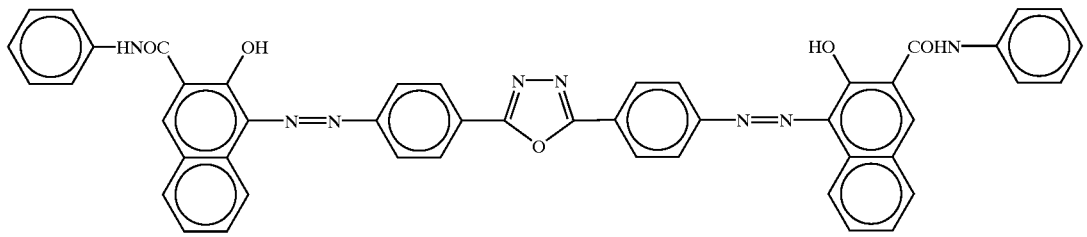

Comparative Example I-2

Except that azo compound and charge transporting substance No. D3, each of which is indicated by the following structural formula (CGM-2), were used instead of azo compound and charge transporting substance which were used in the example I-1, the photoconductor was manufactured in the same way as the example I-1.

Example I-21

Polyamide resin (CM-8000; TORAY Co., Ltd.) liquid solution, which was dissolved in a mixture solvent having methanol/n-butanol=4/1 (vol ratio) on an aluminium evaporation polyester film, was coated by a doctor blade and dried at the temperature of 100° C., thus a middle layer having the thickness of 0.5 μm was formed. Then, designated azo Structural formula (CGM-2)

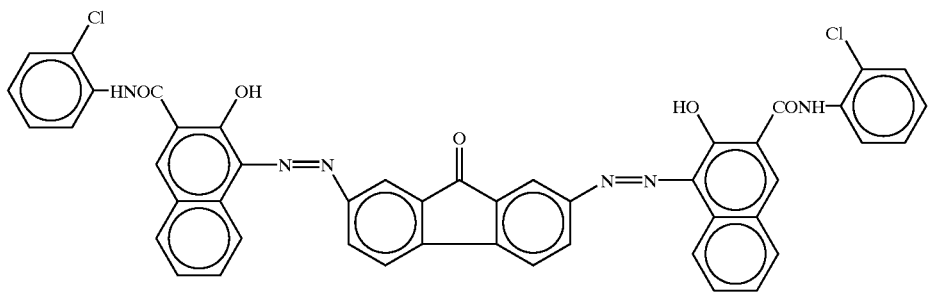

(Chemical Endurance Test)

The electrophotographic photoconductor which was manufactured by the example I-2, example I-6, example I-8, example I-19, comparative example I-1, and comparative example I-2 was left as it was for 40 hours at a room temperature in a NOx gas (NO=40 ppm/NO$_2$=10 ppm) exposure tester. Then, for thus obtained electrophotographic photoconductor, in the same way as the case that the NOx gas was not been used, electrostatic properties were evaluated and the changing rate (surface electrokinetic potential after NOx gas was exposed/surface electrokinetic potential before NOx gas was exposed) of surface electrokinetic potential $V_0$ before and after NOx gas exposure was calculated. The result is indicated in Table 30.

TABLE 30

|  | surface electro kinetic potential $V_0$ |
|---|---|
| Ex. I-2 | 0.97 |
| Ex. I-6 | 0.99 |
| Ex. I-8 | 0.96 |
| Ex. I-19 | 0.94 |
| Comp. Ex. I-1 | 0.51 |
| Comp. Ex. I-2 | 0.62 |

From the result of Table 30, the photoconductor of the present invention designates the stable charge properties in which the fluctuation surface electrokinetic potential after NOx gas was exposed was small.

compounds (No. P24) 7.5 volumes and polyvinyl butyral resin (XYHL; UNION CARBIDE Co., Ltd.) 0.5% tetra hydro furan liquid solution 500 volumes were crushed and mixed in a ball mill, and then obtained dispersion liquid was coated on the aforementioned middle layer by the doctor blade and then dried naturally, thus a charge generating layer having the thickness of more or less 1 μm was formed. Then, as the charge transporting substance, α-phenyl-4'-bis(4-dimethyl phenyl)amino stilbene 1 volume, polycarbonate resin (PCX-5; TEIJIN KASEI Co., Ltd.) 1 volume, silicon oil (KF-50; SHINETSU KAGAKU Co., Ltd.) 0.001 volume, and tetrahydrofuran 8 volumes charge transporting layer coating liquid were prepared, they were coated on the aforementioned charge generating layer by the doctor blade, and dried at the temperature of 80° C. for 2 minutes and at the temperature of 120° C. for 5 minutes, thus the photoconductor was made by forming the charge transporting layer having the thickness of 20 μm.

Comparative Example I-3

Except that the azo compound which was expressed by a structural formula (CGM-1) was used instead of the azo compound which has been used in the example I-21, the photoconductor was made in the same way as the example I-21.

(Repeating Properties Evaluation)

Electrophotographic photoconductor which was made in the example I-21 and comparative example I-3 was mounted on a drum having a line speed of 260 mm/s, then minus charge, white color exposing, and light quenching were repeated for 3000 times. Then, the initial and charge potential Vd (V) after 3000 times and post-exposing electrokinetic potential Vl (V) were measured. The result is designated in Table 31.

TABLE 31

|  | Initial | | After Repeated for 3000 times | |
|---|---|---|---|---|
|  | Vd (V) | Vl (V) | Vd (V) | Vl (V) |
| Ex. I-21 | 855 | 110 | 845 | 125 |
| Comp. Ex. I-3 | 845 | 145 | 690 | 205 |

From the result of Table 31, the photoconductor of the present invention designates the stable repeating properties in which the fluctuation electrokinetic potential was small even after 3000 times.

Therefore, obviously in the detailed and concrete explanation, it is possible to provide the high sensitive electrophotographic photoconductor, the process for forming an image, the Apparatus for Forming An Image, and the processor for a formed image by utilizing a novel azo compound.

Example II-1

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 μm was formed. Next, after an azo compound (designated compound No. P19) 0.5 g was ball-milling-dispersed with liquid solution composed of a polycarbonate resin (PCX-5, TEIJIN KASEI Co., Ltd.) 0.5 g and tetra hydro furan 19 g, charge transporting substance, acceptor compound, tetra hydro furan, and silicon oil were added in order that percentage composition might be azo compound 2% by weight, polycarbonate resin 50% by weight, charge transporting substance 30% by weight indicated in the following structural formula (CTM-1), acceptor compound 18% by weight indicated in the aforementioned structural formula (Q-3), silicon oil (KF50: SHINETSU CHEMICAL INDUSTRY Co., Ltd.) 0.001% by weight, and then solid content 20% by weight photoconductor coating liquid was adjusted. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example II-2 to II-11

Except that azo compound, charge transporting substance, and acceptor compound indicated in Table 32 were used instead of azo compound, charge transporting substance, and acceptor compound used in the example II-1, the photoconductor was manufactured in the same way as the example II-1.

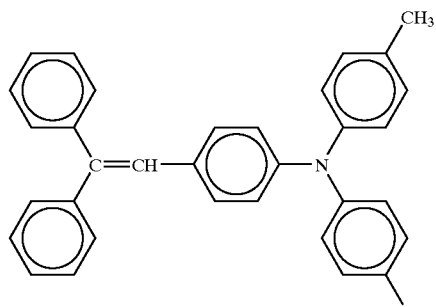

Structural formula (CTM-1)

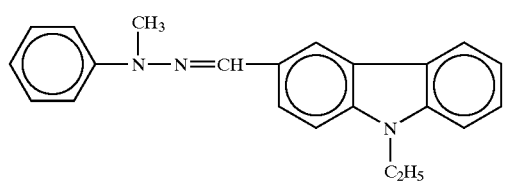

Structural formula (CTM-2)

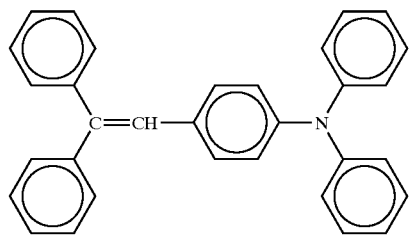

Structural formula (CTM-3)

TABLE 32

|  | Azo Compound | Charge transporting substance | acceptor compound |
|---|---|---|---|
| Ex. II-1 | P19 | CTM-1 | Q-3 |
| Ex. II-2 | P20 | CTM-1 | Q-3 |
| Ex. II-3 | P23 | CTM-2 | Q-3 |
| Ex. II-4 | P24 | CTM-1 | Q-3 |
| Ex. II-5 | P27 | CTM-2 | Q-1 |
| Ex. II-6 | P28 | CTM-1 | Q-3 |
| Ex. II-7 | P38 | CTM-3 | Q-3 |
| Ex. II-8 | P107 | CTM-1 | Q-2 |
| Ex. II-9 | P117 | CTM-1 | Q-1 |
| Ex. II-10 | P133 | CTM-1 | Q-3 |
| Ex. II-11 | P146 | CTM-1 | Q-3 |

Example I-12

Polyamide resin (CM-8000: TORAY Co., Ltd.) liquid solution which was dissolved in methanol/butanol mixture solvent was coated by the doctor blade on an aluminium evaporation polyester film, dried at the temperature of 100° C. for 5 minutes, and then a middle layer having the thickness of 0.5 μm was provided. Next, after azo compound (designated compound No. P20) 0.5 g was ball-milling-dispersed with liquid solution made of a polycarbonate resin (PCX-5, TEIJIN KASEI Co., Ltd.) 0.5 g and tetra hydro furan 19 g, a charge transporting substance, an acceptor compound, a phenol compound, tetra hydro furan, and silicon oil were added in order that percentage composition might become azo compound 2% by weight, polycarbonate resin 47.5% by weight, charge transporting substance 30% by weight indicated by the aforementioned structural formula (CTM-1), acceptor compound 18% by weight indicated by the aforementioned structural formula (Q-3), phenol compound 2.5% by weight indicated by the aforementioned structural formula (E-2), and silicon oil (KF50: SHINETSU CHEMICAL INDUSTRY Co., Ltd.) 0.001% by weight, and then solid content 20% by weight photoconductor coating liquid was adjusted. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example II-13

Except that the designated azo compound (No. P181) was used instead of azo compound used in the example II-12, the photoconductor was manufactured in the same way as the example II-12.

Example II-14

Except that the designated azo compound (No. P183) was used instead of azo compound used in the example II-12, the photoconductor was manufactured in the same way as the example II-12.

Comparative Example II-1

Except that azo compound, which is indicated by the following structural formula (CGM-1), were used instead of azo compound which were used in the example II-1, the photoconductor was manufactured in the same way as the example II-1.

TABLE 33

|  | Vo (V) | E½ (lux · sec) |
|---|---|---|
| Ex. II-1 | 1001 | 1.44 |
| Ex. II-2 | 1132 | 0.72 |
| Ex. II-3 | 1365 | 2.00 |
| Ex. II-4 | 1323 | 0.90 |
| Ex. II-5 | 1154 | 2.15 |
| Ex. II-6 | 1306 | 0.53 |
| Ex. II-7 | 1017 | 1.71 |
| Ex. II-8 | 1189 | 0.89 |
| Ex. II-9 | 1238 | 1.03 |
| Ex. II-10 | 1245 | 0.67 |
| Ex. II-11 | 1224 | 1.21 |
| Ex. II-12 | 1097 | 0.61 |
| Ex. II-13 | 1226 | 0.87 |
| Ex. II-14 | 1264 | 1.02 |
| Comp. Ex. II-1 | 974 | 1.82 |

(Evaluation 2)

The single layer type electrophotographic photoconductor of example II-4, example II-12, and comparative example II-1 was installed on a drum having the speed of 260 mm/s, then plus charging, exposing, and optical quenching were repeated for 5000 times, and charge electrokinetic potential Vd (V) after the initial and 5000 times and electrokinetic potential Vl (V) after exposing were measured. The result is indicated in Table 34.

Structural formula (CGM-1)

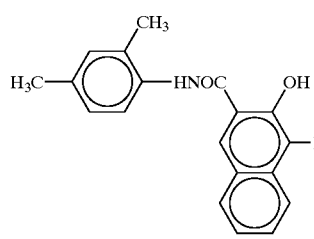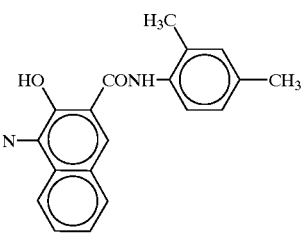

(Evaluation 1)

For the single layer type electrophotographic photoconductor of examples II-1-14 and comparative example II-1, +6 KV corona discharge was performed for 20 seconds in a dark place so as to charge using an electrostatic copying paper tester EPA-8200 (KAWAGUCHI ELECTRIC Co., Ltd.) under the condition, 25° C./55% RH. Further, after it was left as it was for 20 seconds in the dark place, surface electrokinetic potential $V_0$ (V) was measured. Next, a tungsten lamp was used for irradiation in order for photoconductor's surface illumination strength to become 5.3 luxes, time (sec) till its surface electrokinetic potential became a half of $V_0$ was required, then 50 percent exposing volume $E_{1/2}$ (lux·sec) was calculated as sensitivity for a visual range. The result is indicated in Table 33.

TABLE 34

|  | Initially | | After 5000 operation | |
|---|---|---|---|---|
|  | Vd (V) | Vl (V) | Vd (V) | Vl (V) |
| Ex. II-4 | 865 | 34 | 830 | 45 |
| Ex. II-12 | 873 | 29 | 858 | 31 |
| Comp. Ex. II-1 | 740 | 45 | 620 | 93 |

Accordingly, obviously in the detail and concrete explanation, the single layer type electrophotographic photoconductor of the present invention has excellent charge properties and sensitivity. Further, the present invention has excellent light resistance and durability, thus excellent electrostatic properties are attained even if a copying process is repeated. Further, the excellent electrophotographic photoconductor, process for forming an image, apparatus for forming an image, and process cartridge for apparatus for forming an image can be provided by the present invention.

Example III-1

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 µm was formed. Next, an azo compound (designated compound No. P19) 0.5 g was ball-milling-dispersed with liquid solution composed of high polymer charge transporting substance (designated compound 1D-01) 0.5 g and tetra hydro furan 19 g, then high polymer charge transporting substance, acceptor compound, tetra hydro furan, and silicon oil were added in order that percentage composition might become azo compound 2% by weight, high polymer charge transporting substance 80% by weight, acceptor compound (designated compound Q-3) 18% by weight, and silicon oil (KF50: SHINETSU CHEMICAL INDUSTRY Co., Ltd.) 0.001% by weight, thus solid content 20% by weight photoconductor coating liquid was prepared. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 µm was manufactured.

Example III-2 to 11

Except that azo compound, high polymer charge transporting substance, and acceptor compound indicated in Table 35 were used instead of azo compound, high polymer charge transporting substance, and acceptor compound used in the example III-1, the single layer type electrophotographic photoconductor was manufactured in the same way as the example III-1.

TABLE 35

| | Azo Compound | High polymer charge transporting substance | acceptor compound |
|---|---|---|---|
| Ex. III-1 | P19 | 1D-01 | Q-3 |
| Ex. III-2 | P20 | 7D-01 | Q-3 |
| Ex. III-3 | P23 | 10D-01 | Q-1 |
| Ex. III-4 | P24 | 2D-08 | Q-3 |
| Ex. III-5 | P27 | 4D-01 | Q-3 |
| Ex. III-6 | P28 | 5D-03 | Q-2 |
| Ex. III-7 | P38 | 3D-01 | Q-3 |
| Ex. III-8 | P107 | 9D-01 | Q-2 |
| Ex. III-9 | P117 | 6D-01 | Q-1 |
| Ex. III-10 | P133 | 8D-01 | Q-3 |
| Ex. III-11 | P146 | 11D-01 | Q-3 |

Example III-12

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 µm was formed. Next, azo compound (designated compound No. P20) 0.5 g was ball-milling-dispersed with liquid solution composed of a high polymer charge transporting substance (designated compound 11D-02) 0.5 g and tetra hydro furan 19 g, then high polymer charge transporting substance, acceptor compound, phenol compound, tetra hydro furan, and silicon oil were added in order for percentage composition to become azo compound 2% by weight, high polymer charge transporting substance 77.5% by weight, acceptor compound (designated compound Q-3) 18% by weight, phenol compound (designated compound E-2) 2.5% by weight, and silicon oil (KF50: SHIN-ETSU CHEMICAL INDUSTRY Co., Ltd.) 0.001% by weight, thus solid content 20% by weight photoconductor coating liquid was prepared. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 µm was manufactured.

Example III-13

Except that the designated azo compound (No. P181) was used instead of azo compound used in the example III-12, the photoconductor was manufactured in the same way as the example III-12.

Example III-14

Except that the designated azo compound (No. P183) was used instead of azo compound used in the example III-12, the photoconductor was manufactured in the same way as the example III-12.

Comparative Example III-1

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 µm was formed. Next, a charge generating substance 0.5 g indicated by the following structural formula (CGM-1) was ball-milling-dispersed with liquid solution composed of polycarbonate resin (PCX-5: TEIJIN KASEI Co., Ltd.) 0.5 g and tetra hydro furan 19 g, then the charge transporting substance, acceptor compound, tetra hydro furan, and silicon oil were added in order for percentage composition to become charge generating substance 2% by weight, polycarbonate resin 50% by weight, charge transporting substance 30% by weight indicated by the following structural formula (CTM-1), acceptor compound 18% by weight indicated by the aforementioned structural formula (Q-3), and silicon oil (KF50: SHINETSU CHEMICAL INDUSTRY Co., Ltd.) 0.001% by weight, thus solid content 20% by weight photoconductor coating liquid was prepared. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 µm was manufactured.

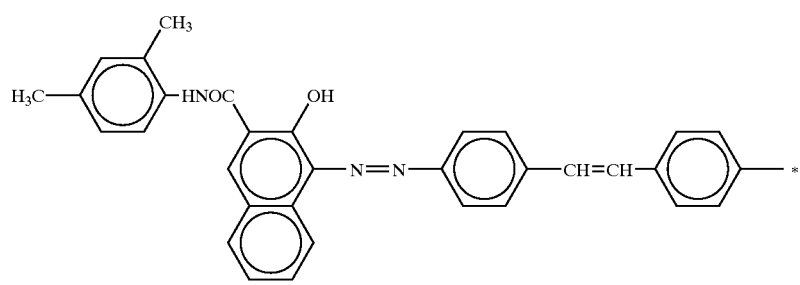

Structural formula (CGM-1)

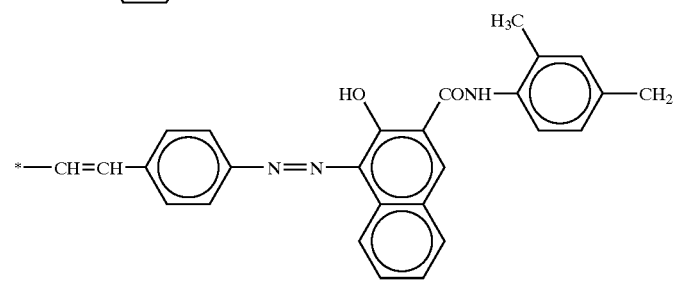

Structural formula (CTM-1)

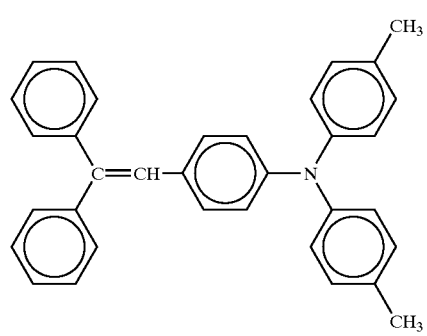

(Evaluation 1)

For the single layer type electrophotographic photoconductor of examples III-1-14 and comparative example III-1, +6KV corona discharge was performed for 20 seconds in a dark place so as to charge using an electrostatic copying paper tester EPA-8200 (KAWAGUCHI ELECTRIC Co., Ltd.) under the condition, 25° C./55% RH. Further, after it was left as it was for 20 seconds in the dark place, surface electrokinetic potential $V_0$ (V) was measured. Next, a tungsten lamp was used for irradiation in order for photoconductor's surface illumination strength to become 5.3 luxes, time (sec) till its surface electrokinetic potential became a half of $V_0$ was required, then 50 percent exposing volume $E_{1/2}$ (lux·sec) was calculated as sensitivity for a visual range. Succeedingly, a photoconductor surface was abrasion-tested with 3000 revolutions and weight 1 Kg using a CS-5 abrasion wheel for a taper abrasion test (TOYO SEIKI Co., Ltd.) in accordance with Japanese Industrial Standard JIS K7204 (1995), then abrasion volume was measured. The result is indicated in Table 36.

TABLE 36

| | Vo (V) | E1/2 (lux · sec) | Abrasion Volume (mg) |
|---|---|---|---|
| Ex. III-1 | 1026 | 1.46 | 5.7 |
| Ex. III-2 | 1148 | 0.73 | 4.0 |
| Ex. III-3 | 1371 | 1.98 | 4.5 |
| Ex. III-4 | 1302 | 0.92 | 6.0 |
| Ex. III-5 | 1254 | 2.11 | 5.1 |

TABLE 36-continued

| | Vo (V) | E1/2 (lux · sec) | Abrasion Volume (mg) |
|---|---|---|---|
| Ex. III-6 | 1315 | 0.51 | 3.7 |
| Ex. III-7 | 1003 | 1.77 | 5.6 |
| Ex. III-8 | 1234 | 0.89 | 2.8 |
| Ex. III-9 | 1183 | 1.07 | 7.2 |
| Ex. III-10 | 1207 | 0.69 | 3.4 |
| Ex. III-11 | 1250 | 1.14 | 3.6 |
| Ex. III-12 | 1357 | 0.60 | 2.0 |
| Ex. III-13 | 1250 | 0.88 | 2.1 |
| Ex. III-14 | 1281 | 1.10 | 2.4 |
| Comp. Ex. III-1 | 974 | 1.82 | 9.0 |

(Evaluation 2)

The single layer type electrophotographic photoconductor of example III-4, example III-12, and comparative example III-1 was installed on a drum having the speed of 260 mm/s, then plus charging, exposing, and optical quenching were repeated for 5000 times, and charge electrokinetic potential Vd (V) after the initial and 5000 times and electrokinetic potential Vl (V) after exposing were measured. The result is indicated in Table 37.

TABLE 37

|  | Initially | | After 5000 operation | |
|---|---|---|---|---|
|  | Vd (V) | VI (V) | Vd (V) | VI (V) |
| Ex. III-4 | 880 | 30 | 853 | 42 |
| Ex. III-12 | 871 | 26 | 860 | 31 |
| Comp. Ex. III-1 | 740 | 45 | 620 | 93 |

From the results of the abovementioned evaluation 1 and evaluation 2, the photoconductor containing azo compound and the high polymer charge transporting substance of the present invention have excellent sensitivity for the visual range and the abrasion volume of the photoconductor surface was small. Excellent light resistance and durability were attained, and stable electrostatic properties were attained even if the copying process for charging, exposing, and optical quenching and so forth was repeated.

The single layer electrophotographic photoconductor of the present invention has excellent charge properties and sensitivity. Further, excellent light resistance and durability were attained, and stable electrostatic properties were attained even if the copying process was repeated. Further, the excellent electrophotographic photoconductor, process for forming an image, apparatus for forming an image, and process cartridge for the apparatus for forming an image can be provided by the present invention.

Then, concrete explanation is made using embodiments for azo compounds, azo compound manufacturing raw material, and their methods for producing indicated by the general formula <<1>> of the present invention. However, the embodiments of the present invention are not limited thereto.

Example IV-1

Manufacturing 9-methoxy phenanthrene-1,2-dicarboxylic acid dimethyl ester
[$R_1=R_2=R_3=R_4=R_5=R_6$=H and $R_7=R_8$=$CH_3$ Compound of the General Formula <<20>>]

This is the same as the Synthetic Example I-1 of the embodiment (embodiment I) of the electrophotographic photoconductor having the photoconductive layer containing the azo compound indicated by the aforementioned general formula <<1>>.

Example IV-2

Manufacturing 9-hydroxy phenanthrene-1,2-dicarboxylic acid anhydride
[$R_1=R_2=R_3=R_4=R_5=R_6$=H Compound of the General Formula <<21>>]

This is the same as the aforementioned example I-2.

Example IV-3

Manufacturing n-benzyl-9-hydroxy phenanthrenes-1,2-dicarboxylic acid imido
[$R_1=R_2=R_3=R_4=R_5=R_6$=H, X=—$CH_2$—$C_6H_5$ <Coupler No. C5> Compound of the General Formula <<22>>]

This is the same as the example I-3 of the aforementioned compound.

Example IV-4

Manufacturing coupler No.-C14 Compounds>

In the embodiment IV-3, benzyl amine 4.29 g (0.04 mol) was reacted/purified in the same way as the embodiment IV-3 instead of 2-ethyl amine 4.85 g (0.04 mol), then 5.31 g (yield 72.3%) coupler compound <coupler No. C14> was obtained. Melt points, element analysis values, and the infrared absorption spectrum chart of these coupler compounds thereof are shown in Table 38.

Example IV-5

Manufacturing Coupler No-C28 Compounds

The same reaction/purification as the embodiment IV-3 was performed using benzyl amine 4.29 g (0.04 mol) instead of 3.73 g (0.04 mol) in the embodiment IV-3, then the 4.60 g (yield 67.8%) coupler compound <coupler No. C28> was obtained. Melt points, element analysis values, and the infrared absorption spectrum chart of these coupler compounds thereof are shown in Table 38.

Example IV-6

Manufacturing Coupler No-C61 Compounds

In the embodiment IV-3, benzyl amine 4.29 g (0.04 mol) was reacted and purified in the same way as the embodiment IV-3 instead of 1-pyrene dimethyl amine hydrochlorid 10.71 g (0.04 mol), 5.37 g(yield 56.2%) coupler compounds <No. C61> were obtained. Melt points, element analysis values, and the infrared absorption spectrum chart of these coupler compounds thereof are shown in Table 38.

Example IV-7

Manufacturing Coupler No.-E23 Compounds

In the embodiment IV-3, benzyl amine 4.29 g (0.04 mol) was reacted and purified in the same way as the embodiment IV-3 instead of 1,8-naphthalene amine6.33 g (0.04 mol), then 6.51 g (yield 84.2%) coupler compounds <No. E14> were obtained. Melt points, element analysis values, and the infrared absorption spectrum chart of these coupler compounds thereof are shown in Table 38.

TABLE 38

Figure 9:
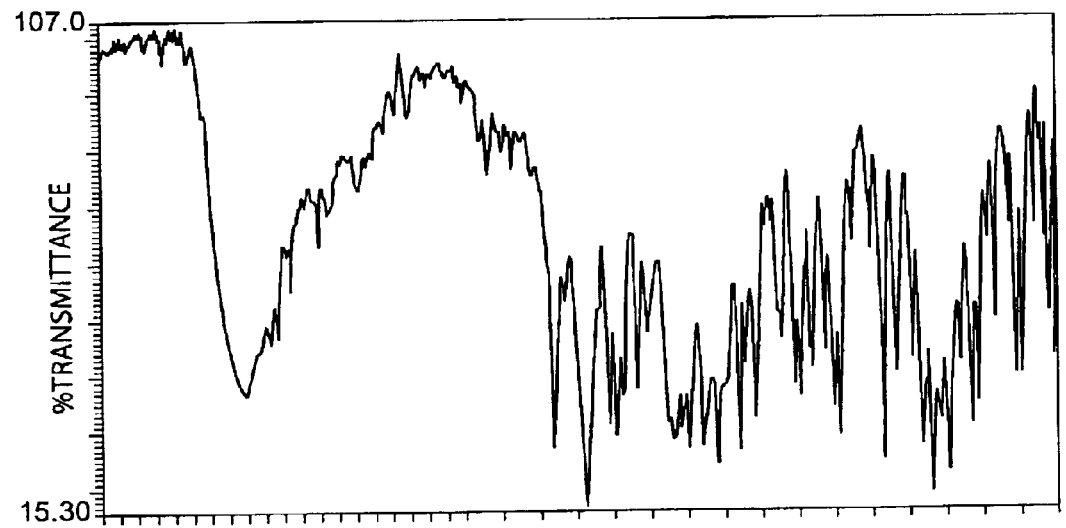
FIG. 9 is a graph showing an example of an infrared spectrum of a coupler compound.

| Ex. | Coupler (Cp) No. | Melting Point (° C.) <Dissolving point (° C.)> | Actual measurement value C (Calculation value C) | Actual measurement value H (Calculation value H) | Actual measurement value N (Calculation value N) | Infrared absorption spectrum Fig. |
|---|---|---|---|---|---|---|
| Ex. IV-4 | C14 | 322.5~324.8 | 18.44 (78.46) | 4.54 (4.66) | 3.84 (3.81) | FIG. 9 |

TABLE 38-continued

Figure 10:
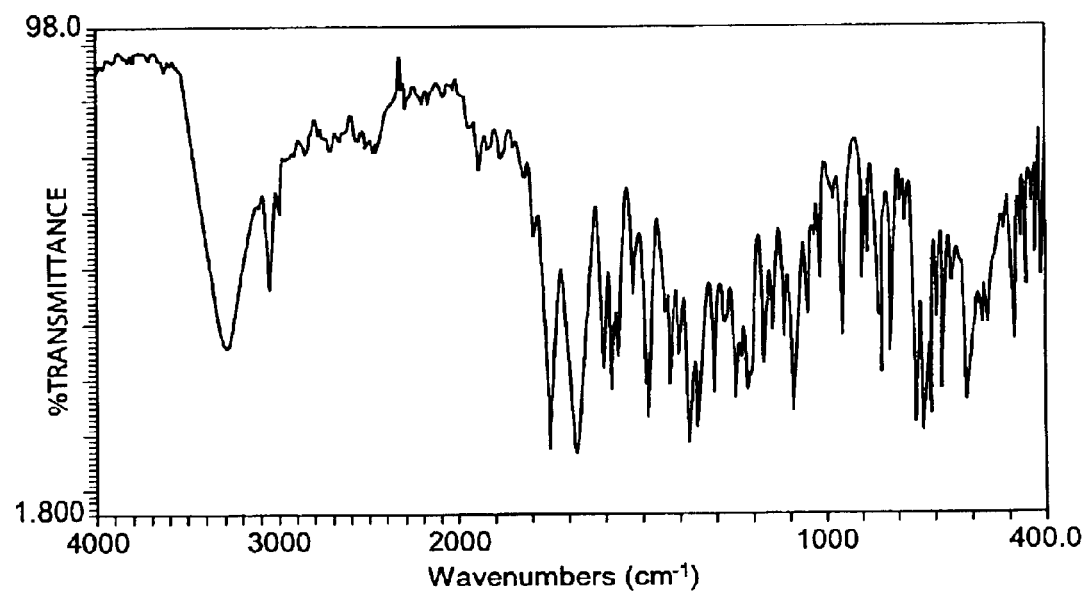
FIG. 10 is a graph showing an example of an infrared spectrum of a coupler compound.
Figure 11:
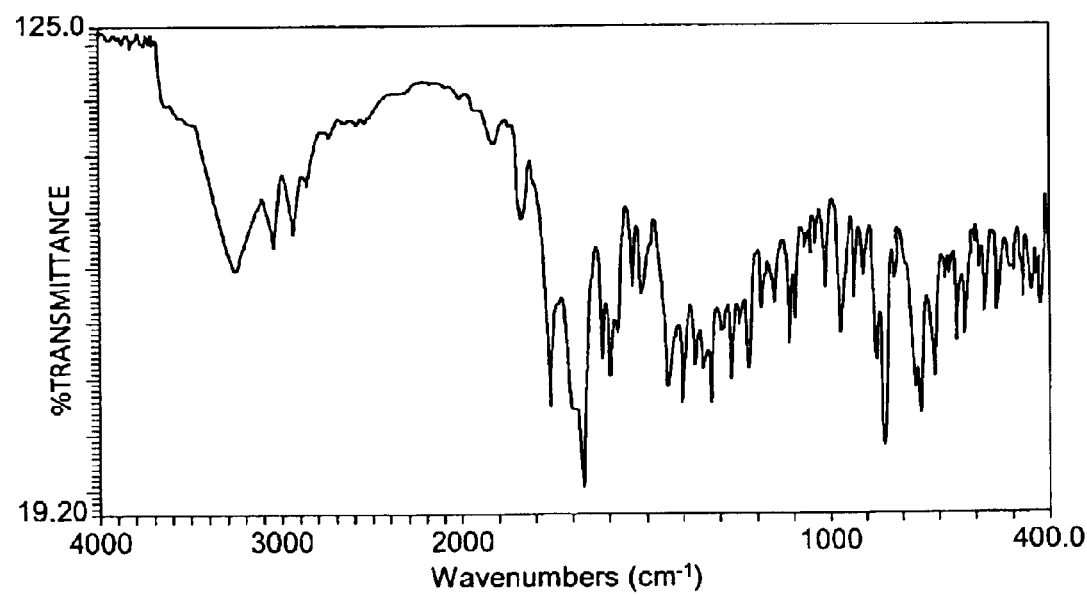
FIG. 11 is a graph showing an example of an infrared spectrum of a coupler compound.
Figure 12:
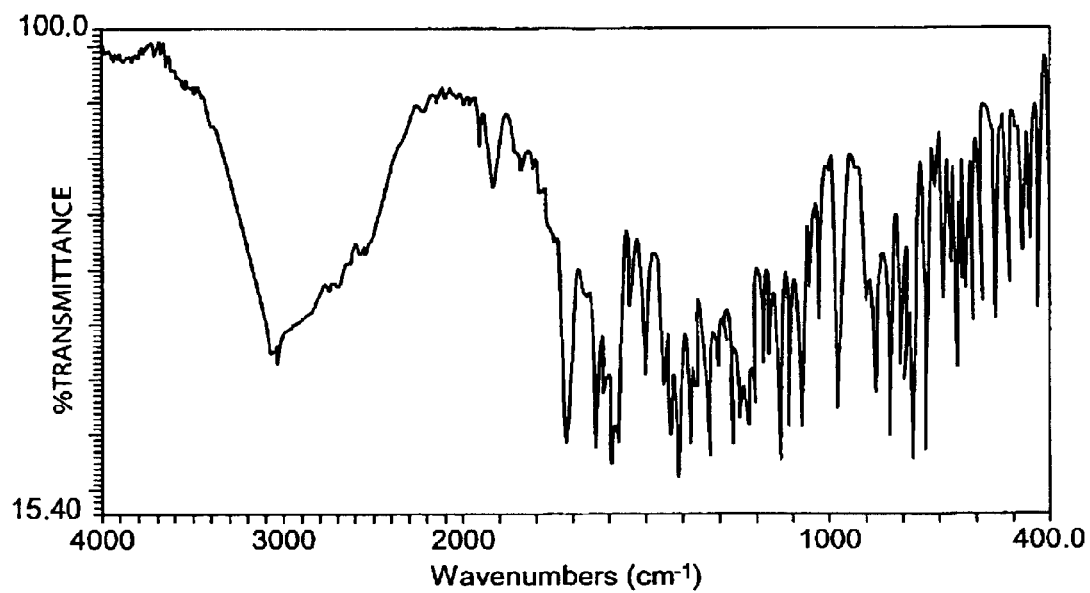
FIG. 12 is a graph showing an example of an infrared spectrum of a coupler compound.

| Ex. | Coupler (Cp) No. | Melting Point (° C.) <Dissolving point (° C.)> | Elemental analysis (%) | | | Infrared absorption spectrum Fig. |
| --- | --- | --- | --- | --- | --- | --- |
| | | | Actual measurement value C (Calculation value C) | Actual measurement value H (Calculation value H) | Actual measurement value N (Calculation value N) | |
| Ex. IV-5 | C28 | 313.5~316.6 | 77.80 (77.87) | 3.79 (3.86) | 4.03 (4.13) | FIG. 10 |
| Ex. IV-6 | C61 | 396.3~399.2 | 82.87 (83.01) | 4.18 (4.01) | 2.71 (2.93) | FIG. 11 |
| Ex. IV-7 | E23 | 450.5~454.2 | 80.84 (80.82) | 3.56 (3.65) | 7.44 (7.25) | FIG. 12 |

Manufacturing Example 1

Manufacturing Azo Compounds (Azo Compounds No. P19)

This was manufactured in the same way as the aforementioned embodiment I manufacturing example 1.

Manufacturing Example 2

Manufacturing Azo Compounds (Azo Compounds No. P20)

This was manufactured in the same way as the aforementioned embodiment I manufacturing example 2.

Manufacturing Example 3

Manufacturing Azo Compounds (Azo Compounds No. P23)

In the manufacturing example 1, except that the coupler compounds (coupler No. C14) 1.10 g (3 mmol), which were manufactured in the embodiment IV-4, were used instead of n-benzyl-9-hydroxy phenanthrene-1,2-dicarboxylic acid imido (coupler No. C5 compounds) 1.06 g (3 mmol), azo compound (azo compound No. P23) was obtained by manufacturing in the same way as the manufacturing example 1. The volume (yield), an infrared absorption spectrum, and element analysis results are indicated in Table 39.

Manufacturing Example 4

Manufacturing Azo Compounds (Azo Compounds No. P24)

In the manufacturing example 2, except that the coupler compounds (coupler No. C14) 0.55 g (1.5 mmol), which were manufactured in the embodiment IV-4, were used instead of n-benzyl-9-hydroxy phenanthrene-1,2-dicarboxylic acid imido (coupler No. C5 compounds) 0.53 g (1.5 mmol), azo compound (azo compound No. P24) was obtained by manufacturing in the same way as the manufacturing example 1. The volume (yield), an infrared absorption spectrum, and element analysis results are indicated in Table 39.

Manufacturing Example 5

Manufacturing Azo Compounds (Azo Compounds No. P27)

In the manufacturing example 1, except that the coupler compounds (coupler No. C28) 1.02 g (3 mmol), which were manufactured in the embodiment IV-5, were used instead of n-benzyl-9-hydroxy phenanthrene-1,2-dicarboxylic acid imido (coupler No. C5 compounds) 1.06 g (3 mmol), azo compound (azo compound No. P27) was obtained by manufacturing in the same way as the manufacturing example 1. The volume (yield), an infrared absorption spectrum, and element analysis results are indicated in Table 39.

Manufacturing Example 4

Manufacturing Azo Compounds (Azo Compounds No. P24)

In the manufacturing example 2, except that the coupler compounds (coupler No. C28) 0.51 g (1.5 mmol), which were manufactured in the embodiment IV-5, were used instead of n-benzyl-9-hydroxy phenanthrene-1,2-dicarboxylic acid imido (coupler No. C5 compounds) 0.53 g (1.5 mmol), azo compound (azo compound No. P24) was obtained by manufacturing in the same way as the manufacturing example 1. The volume (yield), an infrared absorption spectrum, and element analysis results are indicated in Table 39.

Manufacturing Example 7

Manufacturing Azo Compounds (Azo Compounds No. P38)

Coupler compounds (coupler No. E23 compounds) 1.16 g (3 mmol) manufactured in the embodiment IV-7 were dissolved in dimethyl sulfoxide (DMSO) 100 ml, then 9-2,7-bis diazonium tetra fluoro borate 0.61 g (1.5 mmol) synthesized by 2,7-diamino-9-fluore in advance was added at a room temperature. Then, 10% by weight acetic acid sodium solution 4.13 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P38) was obtained by drying at the temperature of 70° C. under a reduced pressure condition. The volume (yield), an infrared absorption spectrum, and element analysis results are indicated in Table 39.

Manufacturing Example 8

Manufacturing Azo Compounds (Azo Compounds No. P146)

N-benzyl-2-hydroxy phenanthrene-1,2-dicarboxylic acid imido (coupler No.C5 compound) 0.53 g (1.5 mmol) was dissolved in dimethyl sulfoxide (DMSO) 60 ml, 9-fluorenone-2,7-bis diazonium tetra fluoro borate 0.61 g (1.5 mmol) synthesized by 2,7-diamino-9-fluorene in advance was added at a room temperature, and mixing was performed for 30 minutes. Then, liquid solution composed of 2(5)-hydroxy-7H-benzimidado[2,1-a]benzisoquinoline-7 (coupler No.195 compound) 0.43 g (1.5 mmol) and DMSO 40 ml was added. Then, 10% by weight acetic acid sodium solution 4.13 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P146) was obtained by drying at the temperature of 70° C. under a reduced pressure condition. The volume (yield), an infrared absorption spectrum, and element analysis results are indicated in Table 39.

TABLE 39

Figure 13:
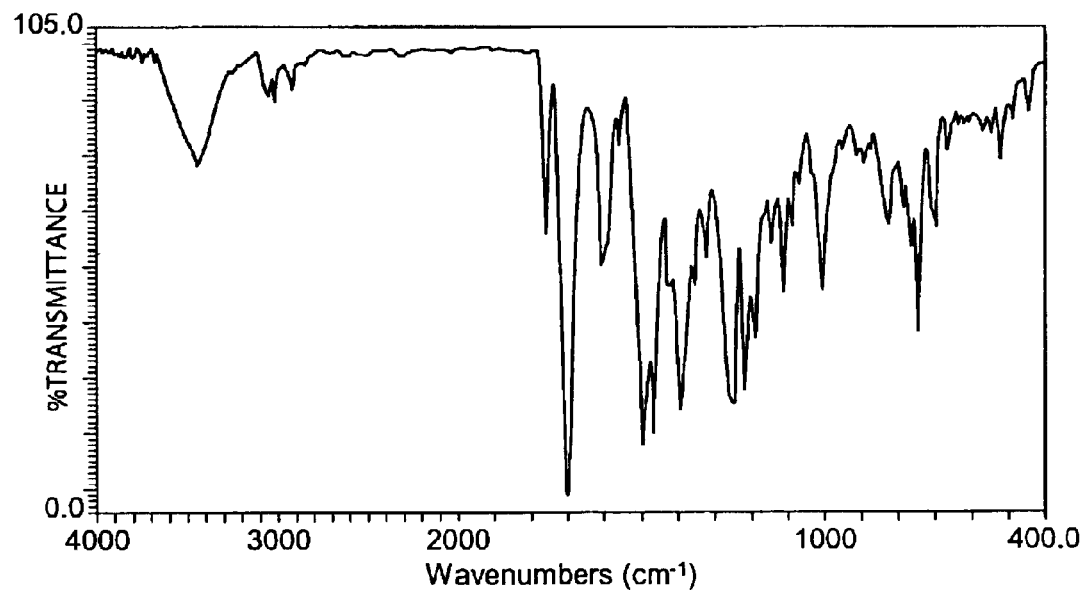
FIG. 13 is a graph showing an example of an infrared spectrum of an azo compound.
Figure 14:
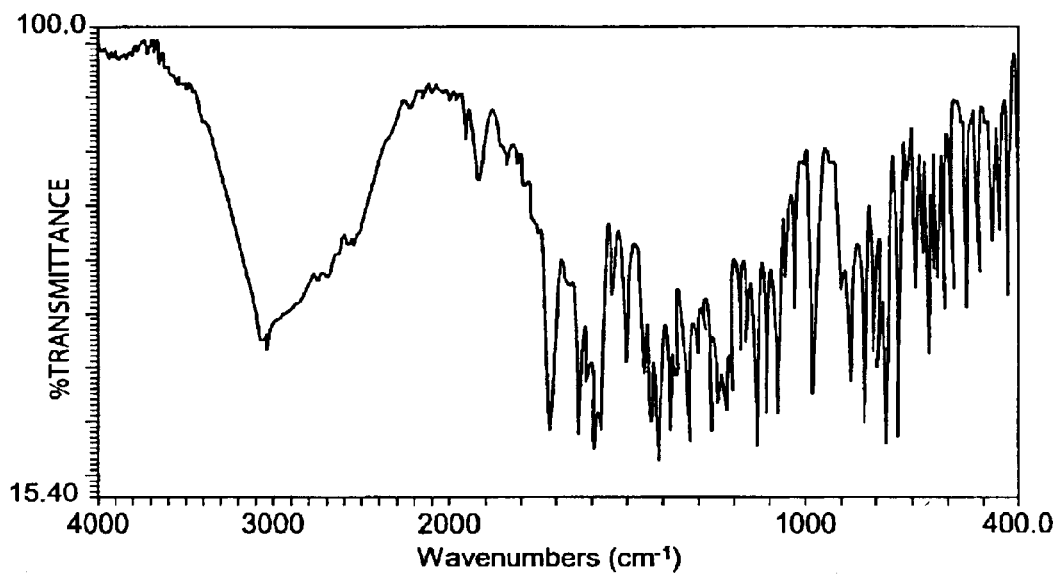
FIG. 14 is a graph showing an example of an infrared spectrum of an azo compound.
Figure 15:
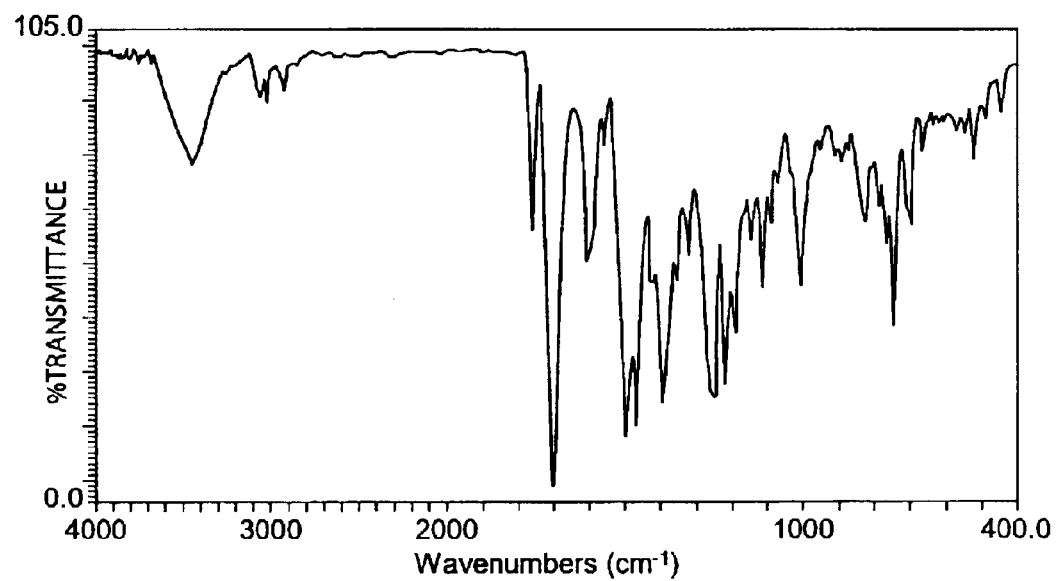
FIG. 15 is a graph showing an example of an infrared spectrum of an azo compound.
Figure 16:
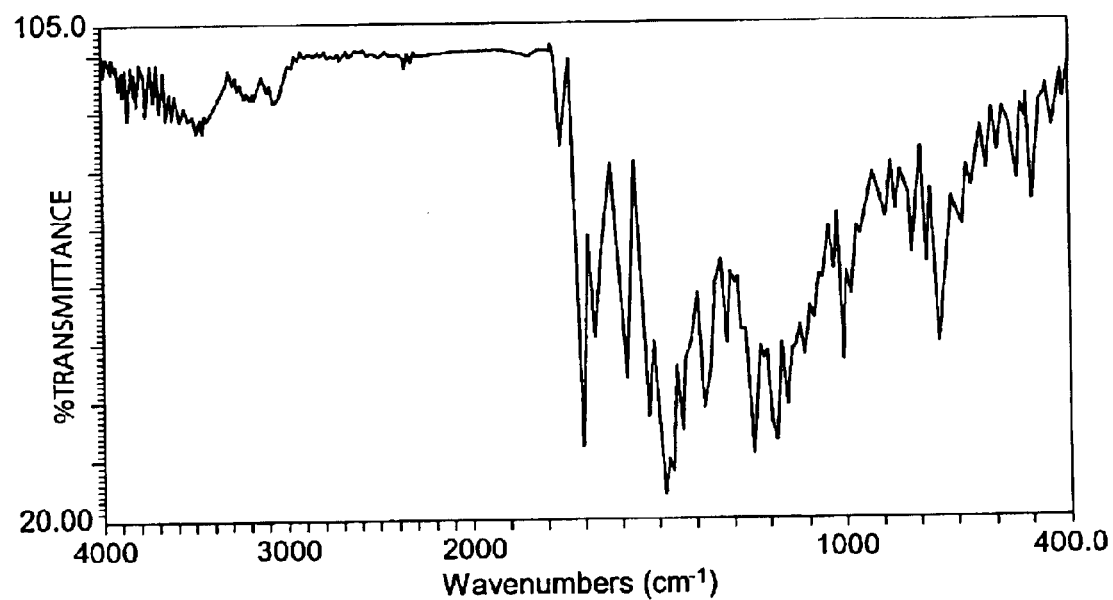
FIG. 16 is a graph showing an example of an infrared spectrum of an azo compound.
Figure 17:
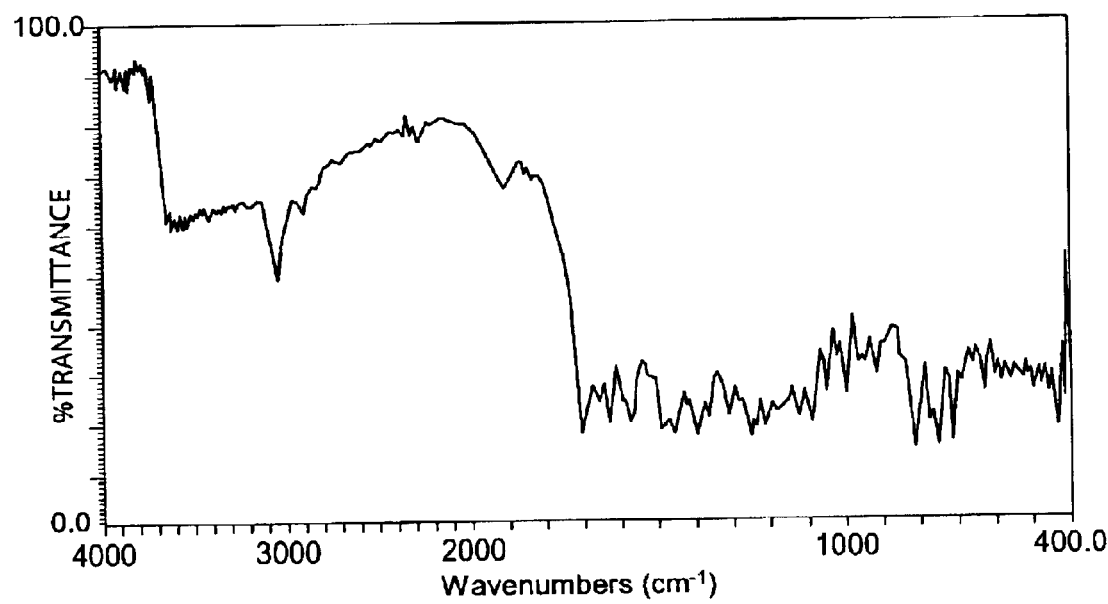
FIG. 17 is a graph showing an example of an infrared spectrum of an azo compound.
Figure 18:
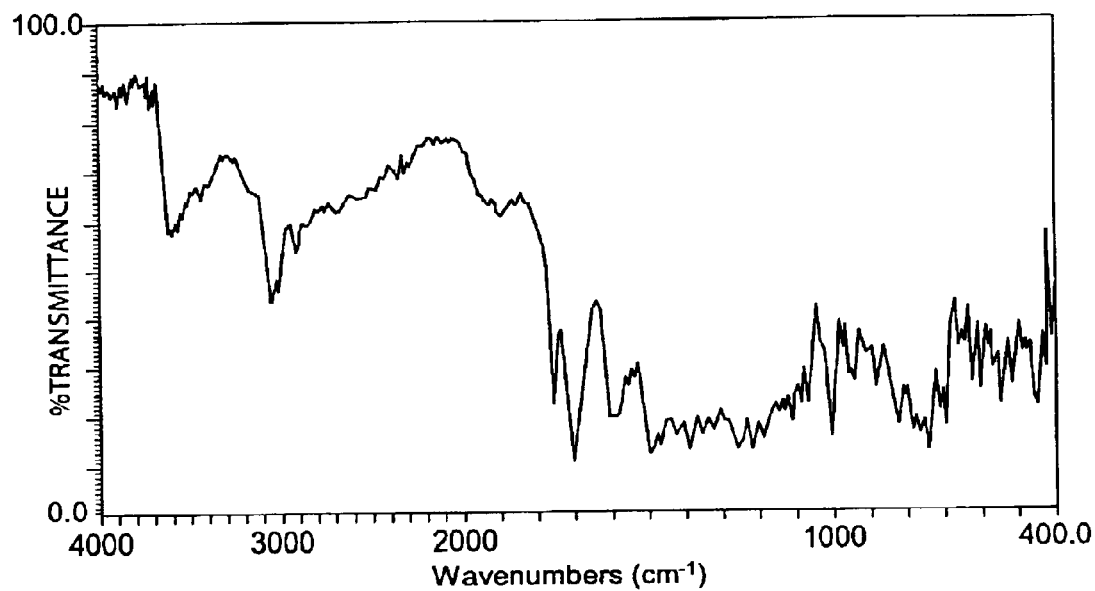
FIG. 18 is a graph showing an example of an infrared spectrum of an azo compound.
Figure 19:
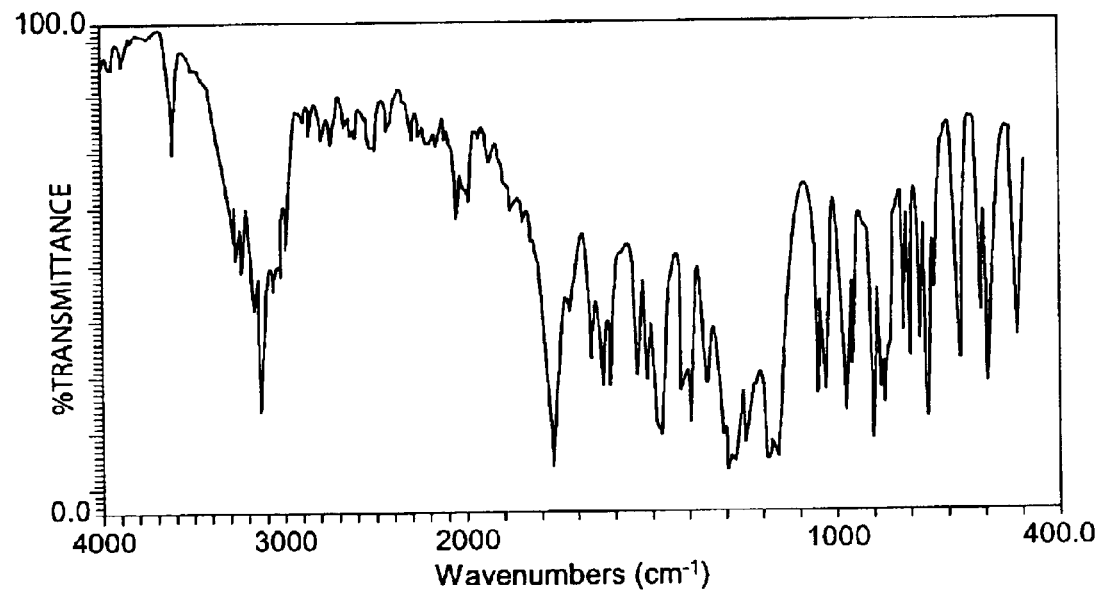
FIG. 19 is a graph showing an example of an infrared absorption spectrum of a naphthalene compound obtained in Synthetic Example V-1 of the present invention.
Figure 20:
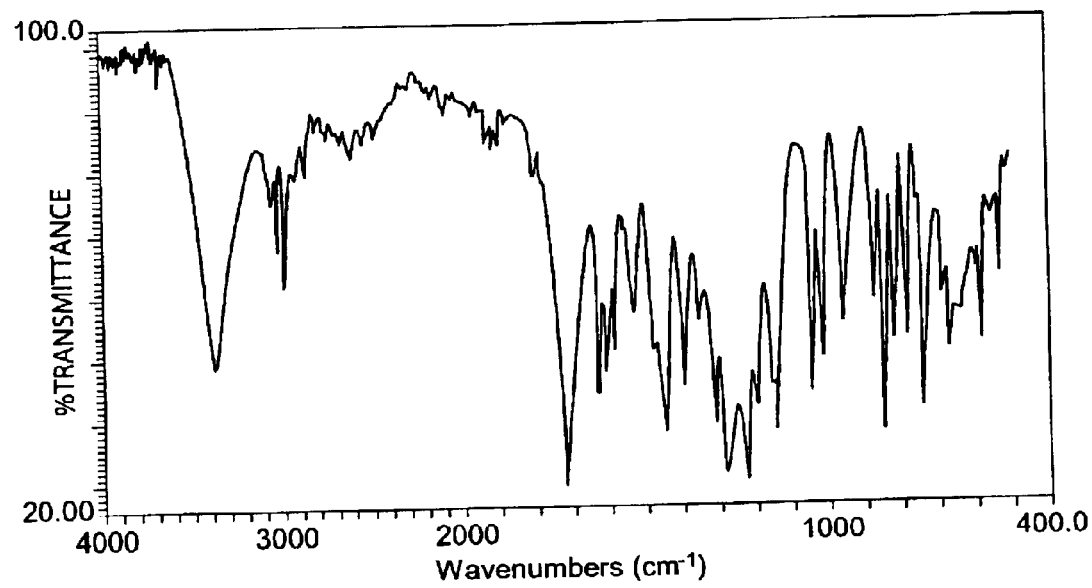
FIG. 20 is a graph showing an example of an infrared absorption spectrum of a naphthalene compound obtained in Synthetic Example V-2 of the present invention.
Figure 21:
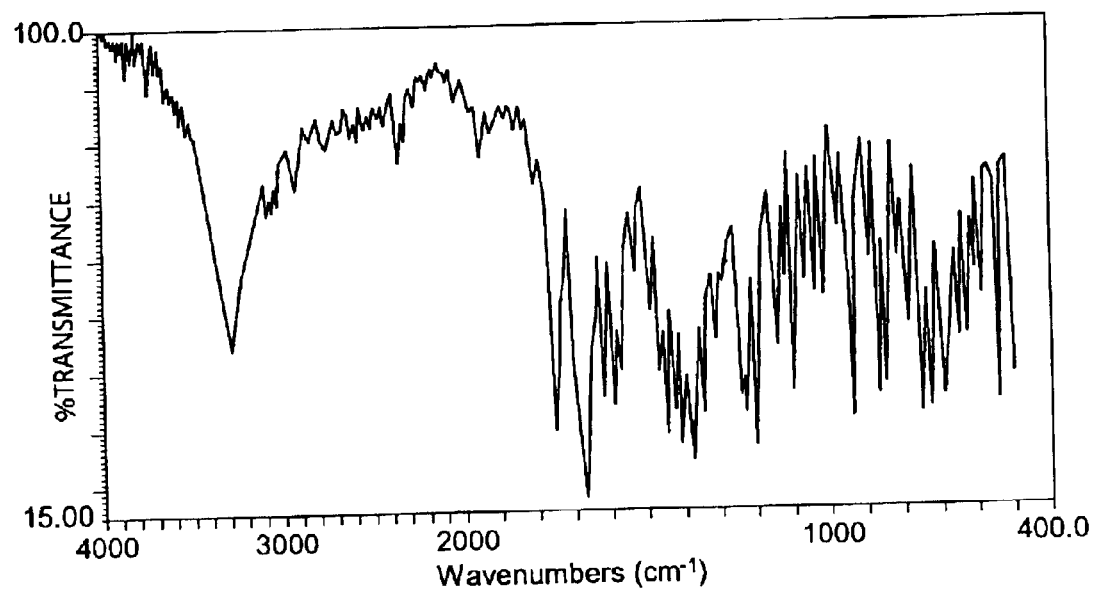
FIG. 21 is a graph showing an example of an infrared absorption spectrum of a naphthalene compound obtained in Synthetic Example V-3 of the present invention.
Figure 22:
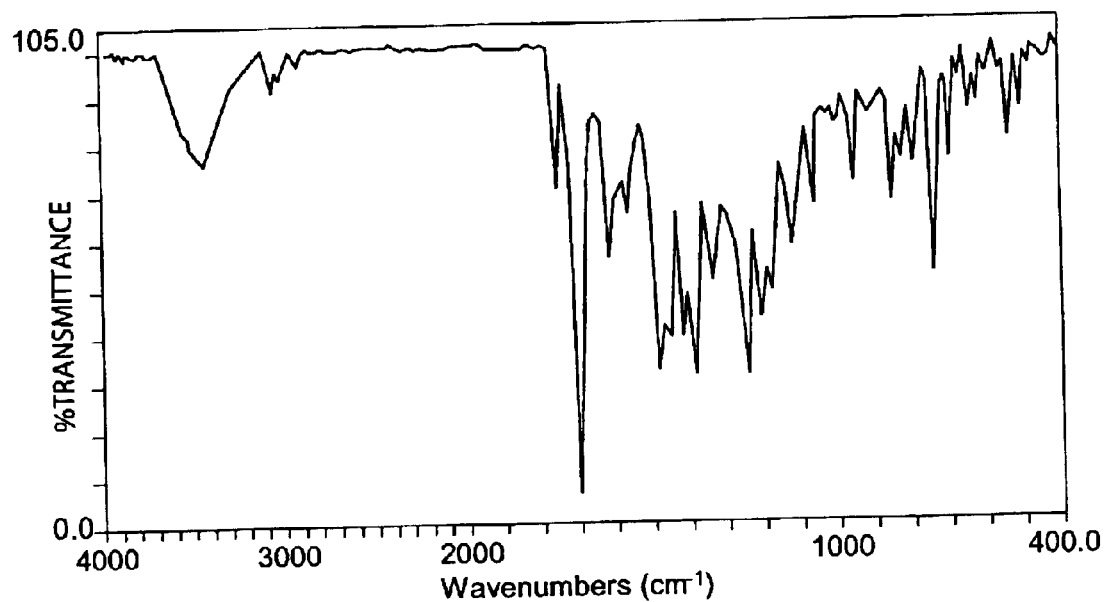
FIG. 22 is a graph showing an example of an infrared absorption spectrum of an azo compound obtained in Manufacturing Example 1 of the present invention (KBr tablet method).
Figure 23:
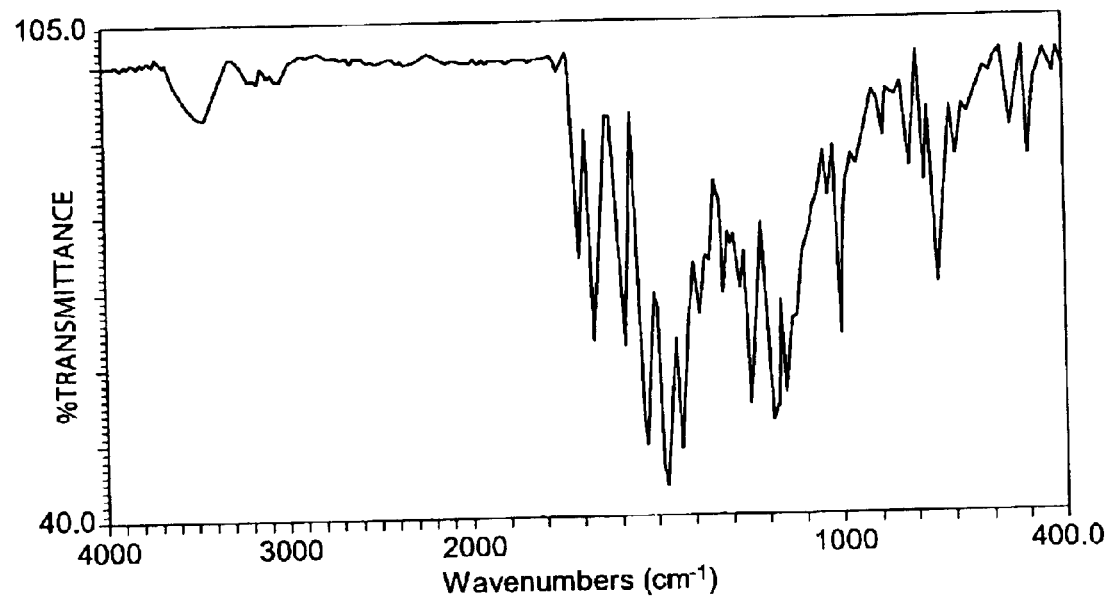
FIG. 23 is a graph showing an example of an infrared absorption spectrum of an azo compound obtained in Manufacturing Example 2 of the present invention (KBr tablet method).
Figure 24:
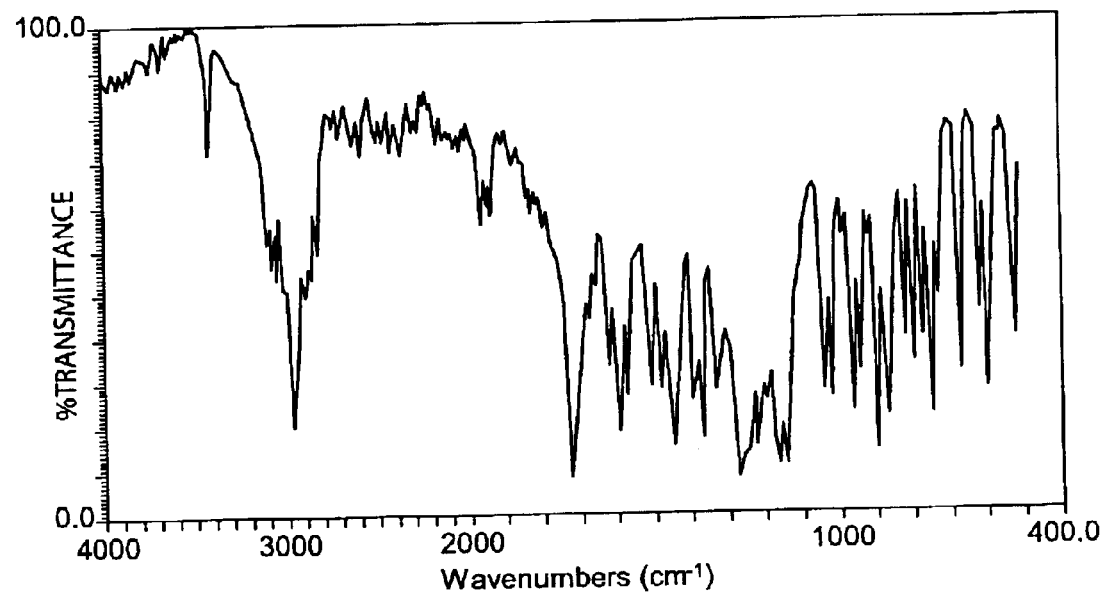
FIG. 24 is a graph showing an example of an infrared spectrum of a naphthalene compound.
Figure 25:
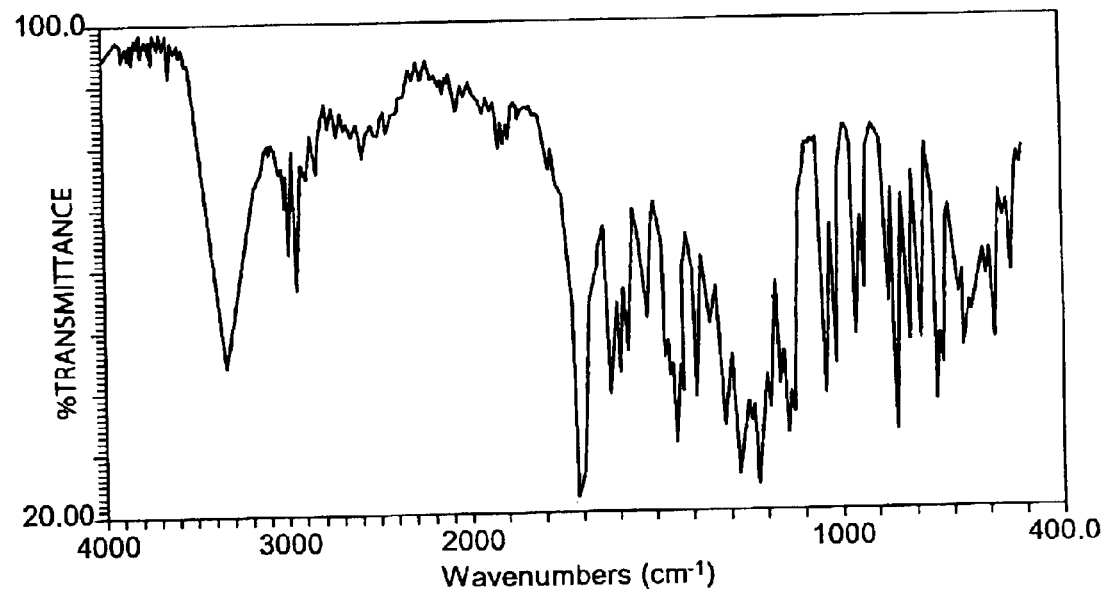
FIG. 25 is a graph showing an example of an infrared spectrum of a naphthalene compound.
Figure 26:
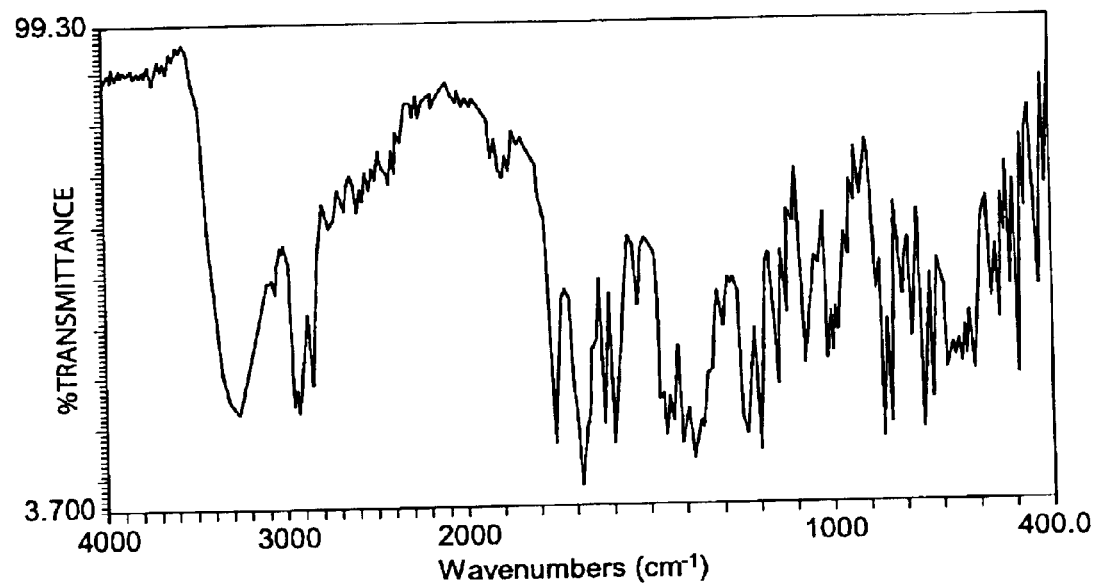
FIG. 26 is a graph showing an example of an infrared spectrum of a coupler compound.
Figure 27:
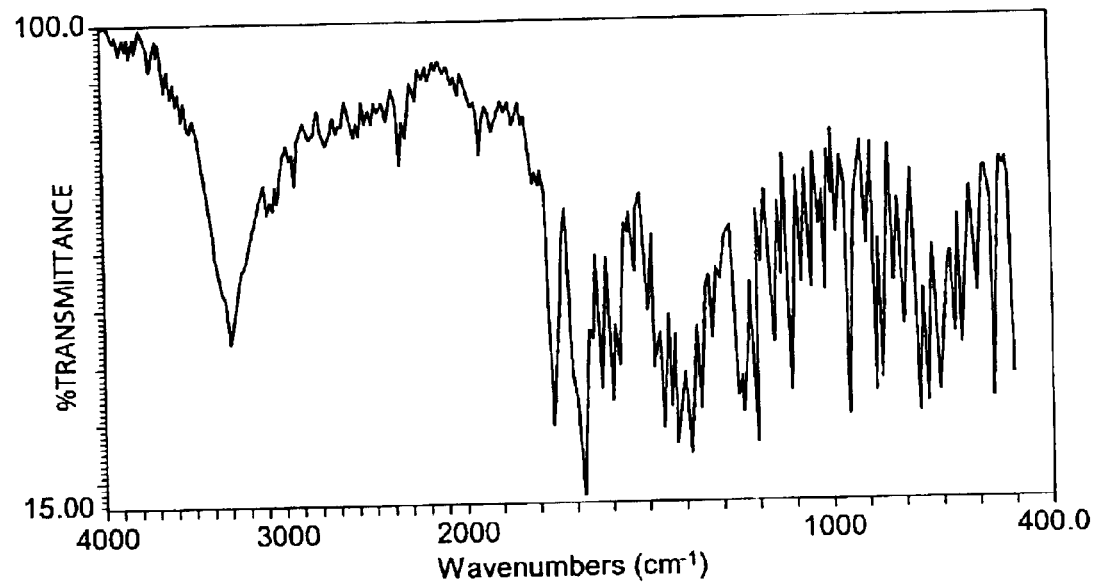
FIG. 27 is a graph showing an example of an infrared spectrum of a coupler compound.
Figure 28:
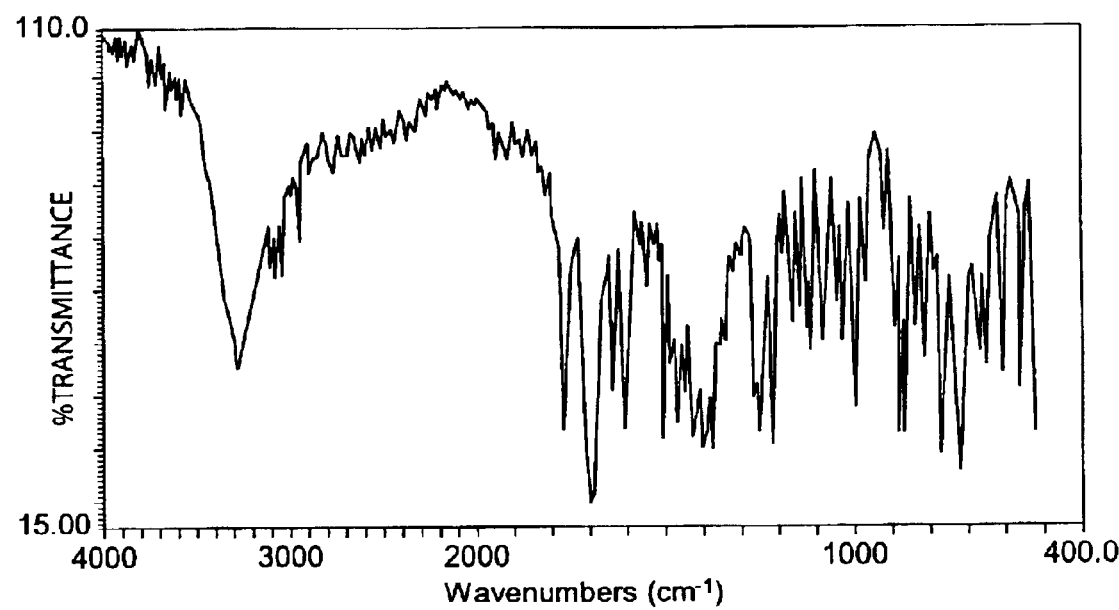
FIG. 28 is a graph showing an example of an infrared spectrum of a coupler compound.
Figure 29:
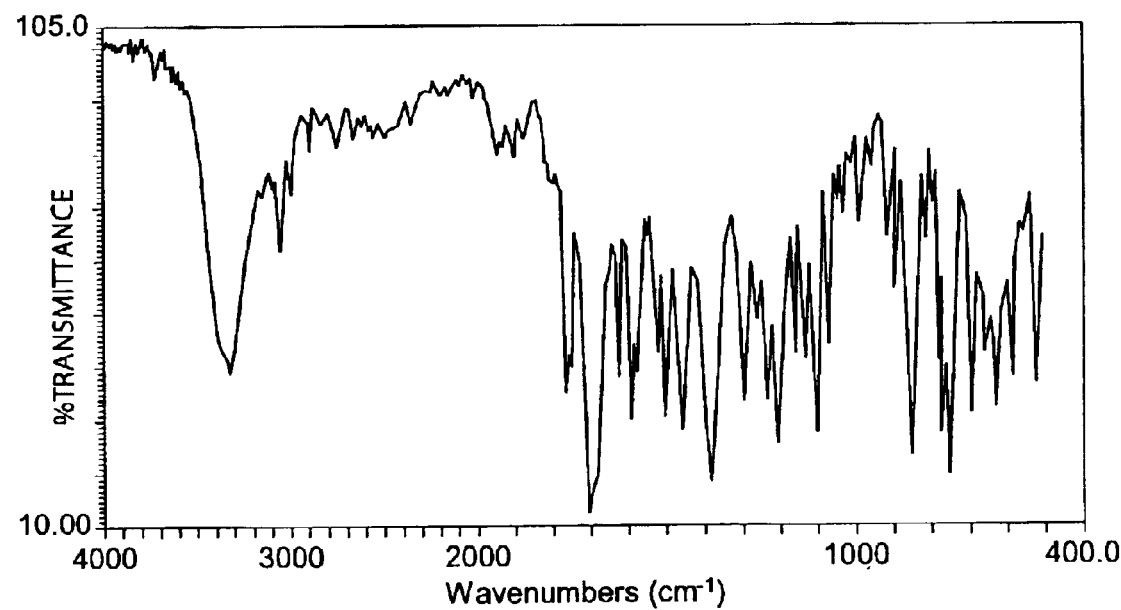
FIG. 29 is a graph showing an example of an infrared spectrum of a coupler compound.
Figure 30:
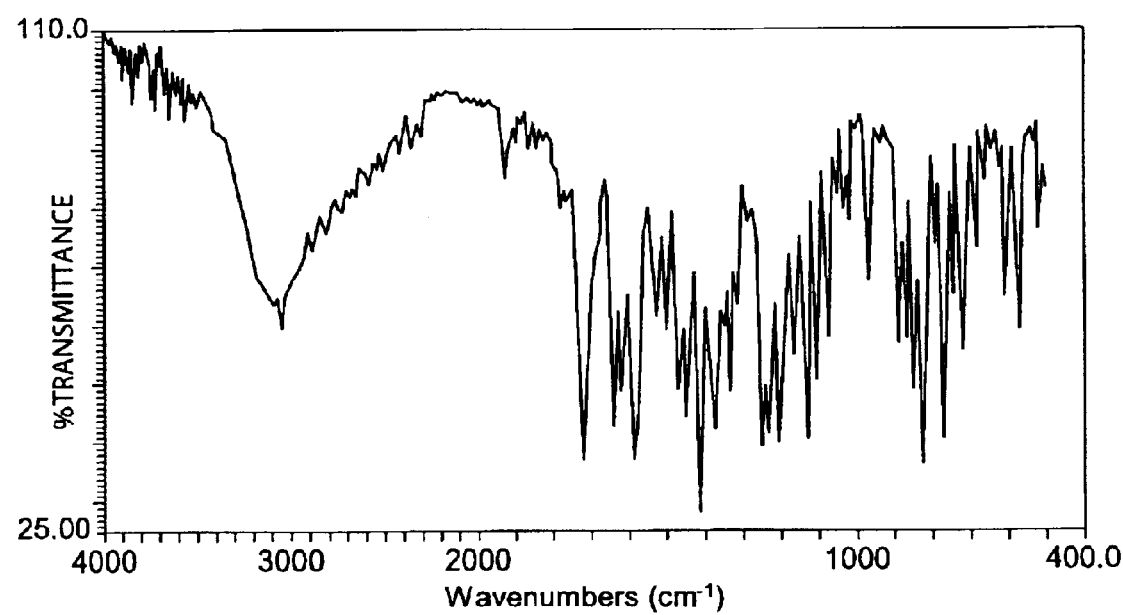
FIG. 30 is a graph showing an example of an infrared spectrum of a coupler compound.

| Mfg. Ex. | Azo Compound No. | Yield amount (g) (Yield ratio (%)) | Elemental analysis (%) | | | Infrared absorption spectrum Fig. |
| --- | --- | --- | --- | --- | --- | --- |
| | | | Actual measurement value C (Calculation value C) | Actual measurement value H (Calculation value H) | Actual measurement value N (Calculation value N) | |
| Mfg. Ex. IV-1 | P19 | 0.62 (44.0) | 75.26 (75.47) | 3.53 (3.65) | 8.76 (8.95) | FIG. 7 |
| Mfg. Ex. IV-2 | P20 | 0.62 (49.3) | 71.81 (72.07) | 3.32 (3.54) | 9.51 (9.51) | FIG. 8 |
| Mfg. Ex. IV-3 | P23 | 1.30 (89.6) | 76.04 (75.77) | 3.79 (3.69) | 8.48 (8.69) | FIG. 13 |
| Mfg. Ex. IV-4 | P24 | 0.99 (73.5) | 71.99 (72.28) | 3.49 (3.71) | 9.53 (9.36) | FIG. 14 |
| Mfg. Ex. IV-5 | P27 | 1.17 (85.9) | 74.90 (75.16) | 3.11 (3.32) | 9.06 (9.23) | FIG. 15 |
| Mfg. Ex. IV-6 | P28 | 0.95 (72.8) | 71.57 (71.85) | 3.16 (3.36) | 9.58 (9.67) | FIG. 16 |
| Mfg. Ex. IV-7 | P38 | 0.66 (44.2) | 77.29 (77.68) | 3.03 (3.21) | 11.05 (11.15) | FIG. 17 |
| Mfg. Ex. IV-8 | P146 | 0.78 (59.6) | 74.24 (74.39) | 3.14 (3.35) | 10.98 (11.25) | FIG. 18 |

Further, the present invention is explained in detail using the following examples. However, the embodiments of the present invention are not limited thereto.

Example 1

Azo compound 7.5 volumes and polyester resin (VYLON® 200: TOYOBO Co., Ltd.) 0.5% by weight tetra hydro furan liquid solution 500 volumes of the manufacturing example 4 (azo compound No. P20) of the present invention were crushed and mixed in a ball, obtained dispersion liquid was coated by the doctor blade on an aluminium evaporation polyester film, and a charge generating layer having the thickness of more or less 1 μm was formed by drying naturally.

Then, charge transporting substance 1 volume, polycarbonate resin (K1300: TEJIN KASEI Co., Ltd.) 1 volume, and tetra hydro furan 8 volume charge transporting layer coating liquid, which were indicated by the following structural formula (D-1), were conditioned, coated on the aforementioned charge generating layer by the doctor blade, then dried at the temperature of 80° C .for 2 minutes and at the temperature of 120° C. for 5 minutes, thus a charge transporting layer having the thickness of 20 μm was formed.

Structural Formula (D-1)

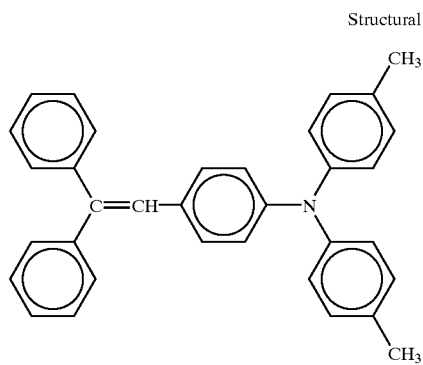

For thus obtained electrophotographic photoconductor, under the condition of 25° C./55% RH, −6 KV corona discharge was performed for 20 seconds in a dark place and the photoconductor was charged using the electrostatic copying paper tester EPA-8100 (KAWAGUCHI ELECTRIC Co., Ltd.), succeedingly it was left as it was for 20 seconds in the dark place, and surface electrokinetic potential $V_0$ (V) at this time was measured. Then, light was given as irradiation by a tungsten lamp in order for illumination unit of the photoconductor surface to become 5.3 luxes, time till its surface electro kinetic potential reached a half of $V_0$ was obtained, and exposing volume $E_{1/2}$ (lux·second) was calculated. As a result, $V_0 = -1140$ volts and $E_{1/2} = 1.05$ luxes·second were obtained.

Thus, obviously in the detailed and concrete example, azo compound manufacturing raw material (coupler compound) of the present invention can be manufactured easily compared with a conventional coupler compound, high sensitive electrophotographic photoconductor can be provided by utilizing azo compound using this manufacturing raw material (coupler compound) as a charge generating substance. Further, the novel coupler of the present invention affects advanced points in which it is very useful to be azo compound manufacturing pigments as an organic optical conductor.

Then, the Synthetic Examples, the manufacturing examples, and the embodiments for the electrophotographic photoconductor having azo compound containing photoconductive layer expressed by the general formula <<101>> of the present invention are listed and explained. However, the present invention is not limited thereto.

Synthetic Example V-1

Synthesizing 2-(t-butoxy)-7,8-naphthalic acid dimethyl ester p-t-butoxy styrene 35.25 g (0.2 mol) and acetylene dicarboxylic acid dimethyl ester 56.84 g (0.4 mol) were dissolved in nitrobenzene, 200 ml, and then reacted at the temperature of 140° C. for 5 hours. After cooling, nitro benzene was removed under a reduced pressure, silica gel column chromatography (developing solvent n-hexane:acetic acid ethyl= 9:1) was performed to the residual, thus 40.78 g crude material was obtained. Further, 36.63 g (yield 57.9%) objective naphthalene compounds were obtained by recrystalliz ing through diisopropyl ether. Melt points were 82.0–83.0° C. This naphthalene compound's infrared absorption spectrum is indicated in FIG. 4.

TABLE 40

| | Elemental analysis value (%) | |
|---|---|---|
| | C | H |
| Actual measurement value | 68.32 | 6.46 |
| Calculation value | 68.34 | 6.37 |

Synthetic Example V-2

Synthesizing 2-hydroxy-7,8-naphthalic acid dimethyl ester 2-(t-butoxy)-7,8-naphthalic acid dimethyl ester 31.63 g (0.1 mol) obtained in the Synthetic Example V-1 was dissolved in chloride methylene 120 ml and mixed at a room temperature, then trifluoro acetic acid 57.01 g (0.5 mol) was dropped for 10 minutes, and reaction was performed for 3 hours under the same condition. Succeedingly, reacted material was poured on ice, phase splitting was performed by adding water, then chloride methylene phase was washed twice and dehydraded by sulfuric anhydride magnesium. Sulfuric magnesium was removed by filtering, then the objective naphthalene compound, 24.31 g (yield 93.4%), was obtained by recrystallizing the residual material from which chloride methylene was removed through toluene. Melt points were 139.0–139.8° C. This naphthalene compound's infrared absorption spectrum is indicated in FIG. 5.

TABLE 41

| | Elemental analysis value (%) | |
|---|---|---|
| | C | H |
| Actual measurement value | 64.60 | 4.56 |
| Calculation value | 64.61 | 4.65 |

Synthetic Example V-3

Synthesizing Coupler Compound No. C5

2-hydroxy-7,8-naphthalic acid dimethyl ester 10.41 g (0.04 mol) and benzyl amine 8.57 g (0.08 mol) obtained by the Synthetic Example V-2 was mixed and reacted through ethylene glycol 100 ml under a nitrogen gas air stream at the temperature of 140° C. for 8 hours. After cooling, methanol 400 ml was added to reacted material and mixed for 1 hour at a room temperature, then extracted crystal was filtered and dried under a reduced pressure at the temperature of 60° C., thus crude material 10.21 g was obtained. Obtained crude material was recrystallized by n-butanol, thus 9.57 g (yield 78.9%) orange color coupler compound <coupler No. C5> was obtained. Melt points were 258.0–259.5° C. This naphthalene compound's infrared absorption spectrum is indicated in FIG. 6.

TABLE 42

| | Elemental analysis value (%) | | |
|---|---|---|---|
| | C | H | N |
| Actual measurement value | 75.30 | 4.29 | 4.60 |
| Calculation value | 75.24 | 4.32 | 4.62 |

Manufacturing Example 1

Manufacturing Azo Compounds No. P19

N-benzyl-2-hydroxy-7,8-naphthalic acid imido (coupler No.C5 compound) 0.91 g (3 mmol) was dissolved in DMF 100ml, then 9-fluorenone-2,7-bis diazonium tetra fluoro borate 0.61 g (1.5 mmol) synthesized by 2,7-diamino-9-fluorenone in advance was added at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P19) 0.64 g (yield 50.8%) was obtained by drying at the temperature of 70° C. under a reduced pressure condition. This azo compound's infrared absorption spectrum (KBr tablet method) is shown in FIG. 7.

TABLE 43

| | Elemental analysis value (%) | | |
|---|---|---|---|
| | C | H | N |
| Actual measurement value | 72.91 | 3.51 | 9.94 |
| Calculation value | 73.02 | 3.60 | 10.02 |

Manufacturing Example 2

Manufacturing Azo Compounds No. P20

N-benzyl-9-hydroxy-1,2-phenanthrene dicarboxylic acid imido (coupler No. C5 compound) 0.53 g (1.5 mmol) was dissolved in DMF 60 ml, 9-fluorenone-2,7-bis diazonium tetra fluoro borate 0.61 g (1.5 mmol) which was synthesized by 2,7-diamino-9-fluorenone in advance was added and mixed for 10 minutes at a room temperature. Then, 2-hydroxy-3-(2-chlorophenyl carbamoyl)naphthalene (coupler No. 17 compound) 0.45 g (1.5 mmol) and DMF 40 ml solution were added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P20) 0.68 g (yield 54.4%) was obtained by drying at the temperature of 70° C. under a reduced pressure condition. This azo compound's infrared absorption spectrum (KBr tablet method) is shown in FIG. 8.

TABLE 44

| | Elemental analysis value (%) | | |
|---|---|---|---|
| | C | H | N |
| Actual measurement value | 70.55 | 3.35 | 9.93 |
| Calculation value | 70.63 | 3.51 | 10.08 |

Example V-1

Azo compounds (No. P19) 7.5 volumes, which were obtained by manufacturing example 1, and polyester resin (VYLON® 200: TOYOBO Co., Ltd.) 0.5% tetra hydro furan solution 500 volumes were crushed and mixed in a ball mill and obtained. Then dispersion liquid was coated by a doctor blade on an aluminium evaporation polyester film and a charge generating layer was formed, a thickness of which was more or less 1 μm, by drying naturally. Then, α-phenyl-4'-bis(4-methyl phenyl)amino stilbene 1 volume, polycarbonate resin(K1300; TEIJIN KASEI Co., Ltd.) 1 volume, tetra hydro furan 8 volumes charge transporting layer coating liquid were prepared as charge transporting substances and coated by the doctor blade on the aforementioned charge generating layer, then dried at the temperature of 80° C. for 2 minutes and at the temperature of 120° C. for 5 minutes and a charge transporting layer having the thickness of 20 μm was formed, thus the photoconductor was manufactured.

Examples V-2 to 102

Except that azo compound and charge transporting substance, each of which is indicated in Table 45, were used instead of the azo compound and charge transporting substance which were used in the example V-1, the photoconductor was manufactured in the same way as the example V-1.

(Electrostatic Properties Evaluation)

For thus obtained electrophotographic photoconductor, 6 KV corona discharge was performed for 20 seconds in a dark place in order to take a charge using an electrostatic copying paper test device EPA-8200 (KAWAGUCHI DENKI SEISAKUSHO) under 25° C./55% RH condition. Further, after it was put in the dark place for 20 seconds, surface electrokinetic potential $V_0$ (V) was measured. Then, a tungsten lamp was used for irradiation in order for an illumination unit of the photoconductor's surface to be 5.3 luxes, time (sec) till its surface electrokinetic potential became a half of $V_0$ was obtained, as sensitivity in a visible region, 50 percent exposing volume $E_{1/2}$ (lux·sec) was calculated. The result is shown in Table 45.

Charge transporting substance No. D1: 1-phenyl-3-(4-ethyl amino styryl)-5-(4-ethyl amino phenyl)pyrazoline Charge transporting substance No. D2: 9-ethyl carbazole-3-aldehyde-1-methyl-1-phenyl hydrazone Charge transporting substance No. D3: α-phenyl-4'-bis(4-methyl phenyl)amino stilbene Charge transporting substance No. D4: α-pheny-1-4'-diphenyl amino stilbene

TABLE 45-1

| | Azo Compound No. | Charge transporting substance No. | Vo | E1/2 |
|---|---|---|---|---|
| Ex. V-1 | P19 | D3 | 938 | 2.04 |
| Ex. V-2 | P19 | D4 | 1108 | 3.66 |
| Ex. V-3 | P20 | D3 | 630 | 1.23 |
| Ex. V-4 | P20 | D4 | 709 | 1.57 |
| Ex. V-5 | P1 | D1 | 1510 | 11.41 |
| Ex. V-6 | P11 | D2 | 1001 | 2.02 |
| Ex. V-7 | P17 | D1 | 1344 | 3.45 |
| Ex. V-8 | P21 | D2 | 1235 | 2.30 |
| Ex. V-9 | P22 | D3 | 1449 | 3.69 |
| Ex. V-10 | P23 | D1 | 1005 | 7.79 |
| Ex. V-11 | P24 | D4 | 709 | 1.12 |
| Ex. V-12 | P27 | D3 | 794 | 4.84 |
| Ex. V-13 | P28 | D4 | 776 | 1.17 |

TABLE 45-1-continued

| | Azo Compound No. | Charge transporting substance No. | Vo | E1/2 |
|---|---|---|---|---|
| Ex. V-14 | P38 | D2 | 651 | 3.01 |
| Ex. V-15 | P39 | D3 | 1168 | 2.61 |
| Ex. V-16 | P41 | D2 | 888 | 3.76 |
| Ex. V-17 | P44 | D2 | 953 | 3.48 |
| Ex. V-18 | P49 | D1 | 1180 | 5.48 |
| Ex. V-19 | P50 | D3 | 1032 | 2.58 |
| Ex. V-20 | P52 | D1 | 988 | 8.29 |
| Ex. V-21 | P53 | D3 | 940 | 2.10 |
| Ex. V-22 | P57 | D1 | 936 | 4.98 |
| Ex. V-23 | P58 | D3 | 962 | 1.80 |
| Ex. V-24 | P59 | D1 | 731 | 2.59 |
| Ex. V-25 | P66 | D4 | 1235 | 9.75 |
| Ex. V-26 | P67 | D3 | 1164 | 6.80 |
| Ex. V-27 | P74 | D4 | 737 | 9.99 |
| Ex. V-28 | P77 | D1 | 622 | 4.57 |
| Ex. V-29 | P81 | D1 | 1093 | 10.53 |
| Ex. V-30 | P86 | D2 | 899 | 10.33 |
| Ex. V-31 | P88 | D3 | 766 | 1.95 |
| Ex. V-32 | P94 | D3 | 912 | 2.72 |
| Ex. V-33 | P102 | D1 | 1198 | 4.13 |
| Ex. V-34 | P103 | D3 | 1117 | 1.54 |
| Ex. V-35 | P104 | D3 | 1081 | 1.41 |
| Ex. V-36 | P105 | D4 | 1111 | 2.00 |
| Ex. V-37 | P112 | D2 | 963 | 3.36 |
| Ex. V-38 | P113 | D4 | 1065 | 3.12 |
| Ex. V-39 | P114 | D1 | 1322 | 2.56 |
| Ex. V-40 | P115 | D3 | 1181 | 2.15 |
| Ex. V-41 | P134 | D3 | 1371 | 2.09 |
| Ex. V-42 | P135 | D4 | 1066 | 1.34 |

TABLE 45-2

| | Azo Compound No. | Charge transporting substance No. | Vo | E½ |
|---|---|---|---|---|
| Ex. V-43 | P35 | D3 | 829 | 1.08 |
| Ex. V-44 | P106 | D2 | 1431 | 8.12 |
| Ex. V-45 | P107 | D3 | 1155 | 0.89 |
| Ex. V-46 | P108 | D1 | 1230 | 3.44 |
| Ex. V-47 | P109 | D3 | 1423 | 2.67 |
| Ex. V-48 | P110 | D1 | 1400 | 10.01 |
| Ex. V-49 | P111 | D3 | 1153 | 2.08 |
| Ex. V-50 | P116 | D2 | 1252 | 1.45 |
| Ex. V-51 | P117 | D3 | 1336 | 1.30 |
| Ex. V-52 | P120 | D1 | 1037 | 2.76 |
| Ex. V-53 | P121 | D3 | 1207 | 1.95 |
| Ex. V-54 | P122 | D2 | 1448 | 9.33 |
| Ex. V-55 | P123 | D4 | 1303 | 1.20 |
| Ex. V-56 | P132 | D2 | 1152 | 8.11 |
| Ex. V-57 | P133 | D3 | 981 | 0.79 |
| Ex. V-58 | P133 | D4 | 1076 | 1.06 |
| Ex. V-59 | P136 | D1 | 1517 | 5.22 |
| Ex. V-60 | P137 | D3 | 1269 | 1.30 |
| Ex. V-61 | P138 | D4 | 694 | 7.60 |
| Ex. V-62 | P139 | D4 | 1208 | 1.47 |
| Ex. V-63 | P140 | D1 | 884 | 2.01 |
| Ex. V-64 | P141 | D2 | 1314 | 1.38 |
| Ex. V-65 | P142 | D1 | 1498 | 5.52 |
| Ex. V-66 | P143 | D3 | 1258 | 1.49 |
| Ex. V-67 | P144 | D1 | 1056 | 1.74 |
| Ex. V-68 | P145 | D3 | 1246 | 1.52 |
| Ex. V-69 | P146 | D3 | 912 | 1.65 |

TABLE 45-3

| | Azo Compound No. | Charge transporting substance No. | Vo | E½ |
|---|---|---|---|---|
| Ex. V-70 | P89 | D1 | 608 | 8.40 |
| Ex. V-71 | P91 | D1 | 638 | 8.24 |
| Ex. V-72 | P124 | D4 | 629 | 6.00 |
| Ex. V-73 | P125 | D3 | 1398 | 1.34 |
| Ex. V-74 | P147 | D2 | 1631 | 9.52 |
| Ex. V-75 | P148 | D3 | 1135 | 1.26 |
| Ex. V-76 | P149 | D1 | 1114 | 1.73 |
| Ex. V-77 | P150 | D3 | 1110 | 0.86 |
| Ex. V-78 | P153 | D3 | 1782 | 3.14 |
| Ex. V-79 | P154 | D3 | 1387 | 1.11 |
| Ex. V-80 | P155 | D1 | 1261 | 1.66 |
| Ex. V-81 | P156 | D3 | 1222 | 1.38 |
| Ex. V-82 | P157 | D1 | 1314 | 1.26 |
| Ex. V-83 | P158 | D3 | 1243 | 2.59 |
| Ex. V-84 | P159 | D1 | 993 | 3.28 |
| Ex. V-85 | P160 | D4 | 1213 | 1.56 |
| Ex. V-86 | P161 | D3 | 1196 | 3.71 |
| Ex. V-87 | P162 | D3 | 1134 | 0.80 |
| Ex. V-88 | P163 | D4 | 1426 | 3.30 |
| Ex. V-89 | P164 | D3 | 1138 | 1.51 |
| Ex. V-90 | P169 | D1 | 1210 | 3.17 |
| Ex. V-91 | P170 | D3 | 1187 | 1.11 |
| Ex. V-92 | P173 | D3 | 1465 | 5.93 |
| Ex. V-93 | P174 | D3 | 1255 | 0.92 |
| Ex. V-94 | P180 | D3 | 1274 | 1.62 |
| Ex. V-95 | P181 | D3 | 1116 | 0.88 |
| Ex. V-96 | P182 | D2 | 1353 | 5.79 |
| Ex. V-97 | P183 | D4 | 1308 | 0.94 |
| Ex. V-98 | P184 | D3 | 1042 | 0.84 |
| Ex. V-99 | P185 | D2 | 1104 | 8.62 |
| Ex. V-100 | P186 | D3 | 1123 | 1.31 |
| Ex. V-101 | P187 | D2 | 1205 | 4.82 |
| Ex. V-102 | P188 | D3 | 1187 | 0.89 |

Comparative Example V-1

Except that azo compound, which is indicated by the following structural formula (CGM-1), were used instead of azo compound which were used in the example V-1, the photoconductor was manufactured in the same way as the example V-1.

Structural Formula (CGM-1)

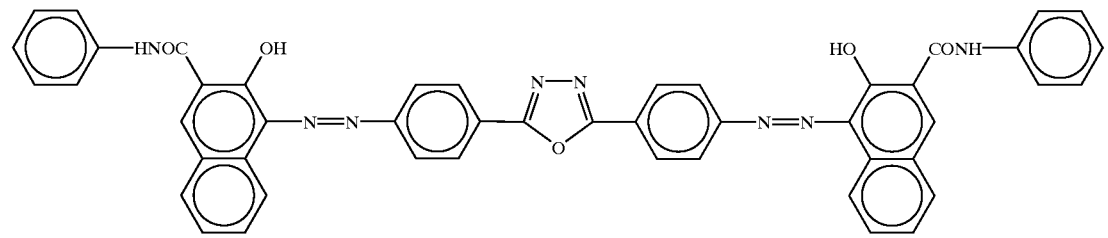

Comparative example V-2

Except that azo compound, which is indicated by the following structural formula (CGM-2), were used instead of azo compound which were used in the example V-1, the photoconductor was manufactured in the same way as the example V-1.

Structural Formula (CGM-2)

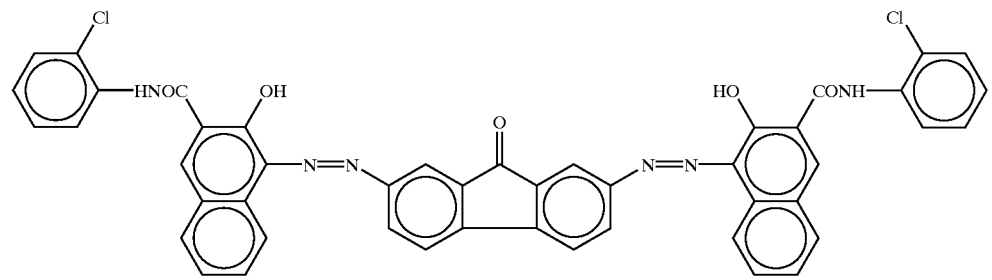

(Chemical Endurance Test)

The electrophotographic photoconductor which was manufactured by the example V-1, example V-3, example V-60, example V-69, example V-93, example V-95, comparative example 1, and comparative example V-2 was left as it was for 40 hours at a room temperature in a NOx gas (NO =40 ppm/ $NO_2$=10 ppm) exposure tester. Then, for thus obtained electrophotographic photoconductor, in the same way as the case that the NOx gas was not been used, electrostatic properties were evaluated and the changing rate (surface electrokinetic potential after NOx gas was exposed/ surface electrokinetic potential before NOx gas was exposed) of surface electrokinetic potential $V_0$ before and after NOx gas exposure was calculated. The result is indicated in Table 46.

TABLE 46

|  | Vo |
| --- | --- |
| Ex. V-1 | 0.94 |
| Ex. V-3 | 0.98 |
| Ex. V-60 | 0.99 |
| Ex. V-69 | 0.92 |
| Ex. V-93 | 0.95 |
| Ex. V-95 | 0.99 |
| Comp. Ex. V-1 | 0.51 |
| Comp. Ex. V-2 | 0.62 |

From the result of Table 46, the photoconductor of the present invention designates the stable charge properties in which the fluctuation surface electrokinetic potential after NOx gas was exposed was small.

Example V-103

Polyamide resin (CM-8000; TORAY Co., Ltd.) liquid solution, which was dissolved in a mixture solvent having methanol/n-butanol=4/1 (vol ratio) on an aluminium evaporation polyester film, was coated by a doctor blade and dried at the temperature of 100° C., thus a middle layer having the thickness of 0.5 μm was formed. Then, designated azo compounds (No. P137) 7.5 volumes and polyvinyl butyral resin (XYHL; UNION CARBIDE Co., Ltd.) 0.5% tetra hydro furan liquid solution 500 volumes were crushed and mixed in a ball mill, and then obtained dispersion liquid was coated on the aforementioned middle layer by the doctor blade and then dried naturally, thus a charge generating layer having the thickness of more or less 1 μm was formed. Then, as the charge transporting substance, α-phenyl-4'-bis(4-dimethyl phenyl) amino stilbene 1 volume, polycarbonate resin (PCX-5; TEIJIN KASEI Co., Ltd.) 1 volume, silicon oil (KF-50; SHINETSU KAGAKU Co., Ltd.) 0.001 volume, and tetrahydrofuran 8 volumes charge transporting layer coating liquid were prepared, they were coated on the aforementioned charge generating layer by the doctor blade, and dried at the temperature of 80° C. for 2 minutes and at the temperature of 120° C. for 5 minutes, thus the photoconductor was made by forming the charge transporting layer having the thickness of 20 μm.

Example V-104

Except that the designated azo compound (No. P181) was used instead of azo compound used in the example V-103, the photoconductor was manufactured in the same way as the example V-103.

Comparative Example V-3

Except that azo compound, which is indicated by the following structural formula (CGM-1), were used instead of azo compound which were used in the example V-103, the photoconductor was manufactured in the same way as the example V-103.

(Repeating Properties Evaluation)

Electrophotographic photoconductor which was made in the example V-103, example V-104 and comparative example V-3 was mounted on a drum having a line speed of 260 mm/s, then minus charge, white color exposing, and light quenching were repeated for 3000 times. Then, the initial and charge potential Vd (V) after 3000 times and post-exposing electrokinetic potential VI (V) were measured. The result is designated in Table 47.

TABLE 47

|  | Initially | | After 3000 operation | |
| --- | --- | --- | --- | --- |
|  | Vd (V) | VI (V) | Vd (V) | VI (V) |
| Ex. V-103 | 855 | 105 | 845 | 125 |
| Ex. V-104 | 850 | 100 | 845 | 130 |
| Comp. Ex. V-3 | 845 | 145 | 690 | 205 |

From the result of Table 47, the photoconductor of the present invention designates the stable repeating properties in which the fluctuation electrokinetic potential was small even after 3000 times.

Accordingly, obviously as indicated in the detailed and concrete explanation, the present invention affects excellent advantageous points in which high sensitive electrophotographic photoconductors, processes for forming an image, apparatus for forming an image, and process cartridges for the apparatus for forming an image can be provided by utilizing the novel azo compound.

Example VI-1

Polyamide resin (CM-8000: TORAY Co., Ltd.) liquid solution which was dissolved in methanol/butanol mixture solvent was coated on an aluminium evaporation polyester film was coated by the doctor blade, dried at the temperature of 100° C. for 5 minutes, thus a middle layer having the thickness of 0.5 μm was formed. Next, after an azo compound (Table 23 No. P58) 0.5 g was ball-milling-dispersed with liquid solution composed of a polycarbonate resin (PCX-5, TEIJIN KASEI Co., Ltd.) 0.5 g and tetra hydro furan 19 g, charge transporting substance, acceptor compound, tetra hydro furan, and silicon oil were added in order that percentage composition might be azo compound 2% by weight, polycarbonate resin 50% by weight, charge transporting substance 30% by weight indicated in the following structural formula (CTM-1), acceptor compound 18% by weight indicated in the aforementioned structural formula (A-1), silicon oil (KF50: SHINETSU CHEMICAL INDUSTRY Co., Ltd.) 0.001% by weight, and then solid content 20% by weight photoconductor coating liquid was adjusted.

Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

[Chemical Structure 190]

Example VI-2 to 10

Except that azo compound, charge transporting substance, and acceptor compound indicated in Table 48 were used instead of azo compound, charge transporting substance, and acceptor compound used in the example VI-1, the photoconductor was manufactured in the same way as the example VI-1. In Table, azo compound is indicated by No. in Table 23.

TABLE 48

|  | Azo Compound | Charge transporting substance | acceptor compound |
| --- | --- | --- | --- |
| Ex. VI-1 | P58 | CTM-1 | A-1 |
| Ex. VI-2 | P53 | CTM-2 | A-2 |
| Ex. VI-3 | P19 | CTM-1 | A-1 |
| Ex. VI-4 | P20 | CTM-1 | A-1 |
| Ex. VI-5 | P24 | CTM-1 | A-1 |
| Ex. VI-6 | P28 | CTM-3 | A-1 |
| Ex. VI-7 | P103 | CTM-1 | A-3 |
| Ex. VI-8 | P104 | CTM-1 | A-1 |
| Ex. VI-9 | P134 | CTM-1 | A-1 |
| Ex. VI-10 | P135 | CTM-1 | A-1 |

Comparative Example VI-1

Except that azo compound, which is indicated by the following structural formula (CGM-1), were used instead of azo compound (Table 23 No. P58) which were used in the example VI-1, the photoconductor was manufactured in the same way as the example VI-1.

TABLE 49

|  | $V_0$ (V) | $E^{1/2}$ (lux · sec) |
| --- | --- | --- |
| Ex. VI-1 | 887 | 1.40 |
| Ex. VI-2 | 870 | 1.35 |
| Ex. VI-3 | 938 | 1.21 |
| Ex. VI-4 | 630 | 0.93 |
| Ex. VI-5 | 993 | 1.63 |
| Ex. VI-6 | 792 | 1.28 |
| Ex. VI-7 | 1117 | 0.99 |
| Ex. VI-8 | 1081 | 0.95 |
| Ex. VI-9 | 1066 | 1.16 |
| Ex. VI-10 | 756 | 0.83 |
| Comp. Ex. VI-1 | 974 | 1.82 |

(Evaluation 2)

The single layer type electrophotographic photoconductor of example VI-4, example VI-10, and comparative example VI-1 was installed on a drum having the speed of 260 mm/s, then plus charging, exposing, and optical quenching were repeated for 5000 times, and charge electrokinetic potential Vd (V) after the initial and 5000 times and electrokinetic potential VI (V) after exposing were measured. The result is indicated in Table 50.

Structural Formula (CGM-1)

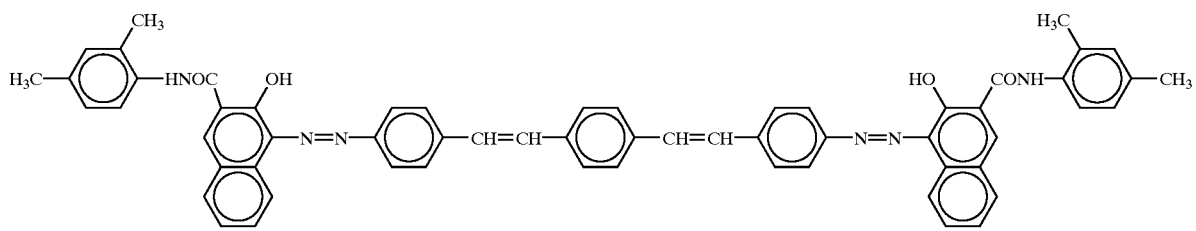

(Evaluation 1)

For the examples VI-1 -10 and comparative example VI-1 single layer type electrophotographic photoconductor, the following evaluation was made using the electrostatic copying paper tester EPA-8200 (KAWAGUCHI ELETRIC Co., Ltd.) under the condition of 25° C./55% RH. The result is indicated in Table 49.

(1)+6 KV corona discharge was performed for 20 seconds in a dark place, further, after it was left as it was for 20 seconds in the dark place, surface electrokinetic potential $V_0$ (V) was measured.

(2) A tungsten lamp was used for irradiation in order for photoconductor's surface illumination strength to become 5.3 luxes, time (sec) till its surface electro kinetic potential became a half of $V_0$ was required, then 50 percent exposing volume $E^{1/2}$ (lux·sec) was calculated as sensitivity for a visual range.

TABLE 50

|  | Initially | | After 5000 operation | |
| --- | --- | --- | --- | --- |
|  | Vd (V) | VI (V) | Vd (V) | VI (V) |
| Ex. VI-4 | 703 | 41 | 691 | 48 |
| Ex. VI-10 | 797 | 33 | 786 | 42 |
| Comp. Ex. VI-1 | 740 | 45 | 620 | 93 |

Example VI-11

Polyamide resin (CM-8000: TORAY Co., Ltd.) was dissolved in methanol/butanol mixture solvent, liquid solution was coated on aluminium plate supporter by the doctor blade, and dried at the temperature of 100° C. for 5 minutes, thus a middle layer having the thickness of 0.5 μm was formed.

Azo compound (Table 23 No. P58) 0.5 g and a high polymer charge transporting substance (the abovementioned chemical expression 2D-08) 0.5 g were ball-millingdispersed in tetra hydro furan 19 g. The high polymer charge transporting substance, an acceptor compound, tetra hydro furan, and silicon oil were added to dispersion liquid in order for percentage composition to become azo compound 2% by weight, high polymer charge transporting substance 80% by weight, acceptor compound 18% by weight expressed by the abovementioned structural formula (A-1), and silicon oil (KF-50: SHINETSU CHEMICAL INDUSTRY Co., Ltd.) 0.001% by weight, thus solid content 20% by weight photoconductor coating liquid was prepared.

Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 µm was manufactured.

Example VI-12 to 20

Except that azo compound, high polymer charge transporting substance, and acceptor compound indicated in Table 51 were used instead of azo compound, high polymer charge transporting substance, and acceptor compound used in the example VI-11, the photoconductor was manufactured in the same way as the example VI-1.

TABLE 51

|  | Azo Compound | High polymer charge transporting substance | acceptor compound |
|---|---|---|---|
| Ex. VI-11 | P58 | 2D-08 | A-1 |
| Ex. VI-12 | P53 | 5D-03 | A-2 |
| Ex. VI-13 | P19 | 1D-01 | A-1 |
| Ex. VI-14 | P20 | 4D-01 | A-1 |
| Ex. VI-15 | P24 | 9D-01 | A-1 |
| Ex. VI-16 | P28 | 6D-01 | A-1 |
| Ex. VI-17 | P103 | 3D-01 | A-3 |
| Ex. VI-18 | P104 | 8D-01 | A-1 |

TABLE 51-continued

|  | Azo Compound | High polymer charge transporting substance | acceptor compound |
|---|---|---|---|
| Ex. VI-19 | P134 | 10D-01 | A-1 |
| Ex. VI-20 | P135 | 7D-01 | A-1 |

Comparative Example VI-2

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 µm was formed.

Next, a charge generating substance 0.5 g indicated by the following structural formula (CGM-1) was ball-milling-dispersed with liquid solution composed of polycarbonate resin (PCX-5: TEIJIN KASEI Co., Ltd.) 0.5 g and tetra hydro furan 19 g, then the charge transporting substance, acceptor compound, tetra hydro furan, and silicon oil were added in order for percentage composition to become charge generating substance 2% by weight, polycarbonate resin 50% by weight, charge transporting substance 30% by weight indicated by the following structural formula (CTM-1), acceptor compound 18% by weight indicated by the aforementioned structural formula (A-1), and silicon oil (KF50: SHINETSU CHEMICAL INDUSTRY Co., Ltd.) 0.001% by weight, thus solid content 20% by weight photoconductor coating liquid was prepared. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 µm was manufactured.

Structural Formula (CGM-1)

Structural Formula (CTM-1)

(Evaluation 3)

For the examples VI-11-20 and comparative example VI-2 single layer type electrophotographic photoconductor, the following evaluation was made using the electrostatic copying paper tester EPA-8200 (KAWAGUCHI ELETRIC Co., Ltd.) under the condition of 25° C./55% RH. The result is indicated in Table 52.

(1)+6 KV corona discharge was performed for 20 seconds in a dark place, further, after it was left as it was for 20 seconds in the dark place, surface electrokinetic potential $V_0$ (V) was measured.

(2) A tungsten lamp was used for irradiation in order for photoconductor's surface illumination strength to become 5.3 luxes, time (sec) till its surface electrokinetic potential became a half of $V_0$ was required, then 50 percent exposing volume E½ (lux·sec) was calculated as sensitivity for a visual range.

(3) Abrasion test was performed to a photoconductor surface, according to Japanese Industrial Standard JISK7204 (1995). That is to say, an abrasion test, weight 1 Kg, 3000 revolutions, was performed using a CS-5 abrasion wheel for taper abrasion test (TOYO SEIKI Co., Ltd.), and its abrasion volume was measured.

TABLE 52

|  | Vo (V) | E½ (lux · sec) | (mg) |
|---|---|---|---|
| Ex. VI-11 | 1016 | 1.41 | 6.2 |
| Ex. VI-12 | 918 | 1.28 | 3.6 |
| Ex. VI-13 | 1108 | 1.12 | 5.3 |
| Ex. VI-14 | 709 | 0.95 | 4.9 |
| Ex. VI-15 | 1146 | 1.56 | 2.9 |
| Ex. VI-16 | 840 | 1.32 | 6.9 |
| Ex. VI-17 | 1218 | 1.15 | 5.5 |
| Ex. VI-18 | 1012 | 1.03 | 3.0 |
| Ex. VI-19 | 1255 | 1.24 | 4.5 |
| Ex. VI-20 | 1066 | 0.90 | 4.0 |
| Comp. Ex. VI-2 | 974 | 1.82 | 9.0 |

(Evaluation 4)

The single layer type electrophotographic photoconductor of example VI-14, example VI-20, and comparative example VI-2 was installed on a drum having the speed of 260 mm/s, then plus charging, exposing, and optical quenching were repeated for 5000 times, and charge electrokinetic potential Vd (V) after the initial and 5000 times and electrokinetic potential VI (V) after exposing were measured. The result is indicated in Table 53.

TABLE 53

|  | Initially | | After 5000 operation | |
|---|---|---|---|---|
|  | Vd (V) | VI (V) | Vd (V) | VI (V) |
| Ex. VI-14 | 712 | 49 | 695 | 56 |
| Ex. VI-20 | 836 | 37 | 807 | 45 |
| Comp. Ex. VI-2 | 740 | 45 | 620 | 93 |

Example VI-21

Polyamide resin(CM-8000: TORAY Co., Ltd.) dissolved in a methanol/butanol mixture solvent was coated on an aluminium evaporation polyester film using the doctor blade, and dried at the temperature of 100° C. for 5 minutes, thus a middle layer having the thickness of 0.5 μm was formed.

Then, azo compound (No. P133) 0.5 g and the high polymer charge transporting substance (the aforementioned chemical expression 11D-02) 0.5 g were ball-milling-dispersed in tetra hydro furan 19 g. After dispersion, solid content 20% by weight photoconductor coating liquid was prepared in order for percentage composition to become azo compound 2% by weight, high polymer charge transporting substance 80% by weight, acceptor compound (designated compound A-1) 18% by weight, and silicon oil (KF-50: SHINETSU CHEMICAL INDUSTRY Co., Ltd.) 0.001% by weight, then high polymer charge transporting substance, acceptor compound, tetra hydro furan and silicon oil were added.

Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example VI-22, 23

Except that azo compound, high polymer charge transporting substance, and acceptor compound indicated in Table 54 were used instead of azo compound, high polymer charge transporting substance, and acceptor compound used in the example VI-21, the photoconductor was manufactured in the same way as the example VI-21.

TABLE 54

|  | Azo Compound | High polymer charge transporting substance | acceptor compound |
|---|---|---|---|
| Ex. VI-21 | P133 | 11D-02 | A-1 |
| Ex. VI-22 | P137 | 11D-02 | A-1 |
| Ex. VI-23 | P35 | 11D-04 | A-1 |

Example VI-24

Polyamide resin(CM-8000: TORAY Co., Ltd.) dissolved in a methanol/butanol mixture solvent was coated on an aluminium evaporation polyester film using the doctor blade, and dried at the temperature of 100° C. for 5 minutes, thus a middle layer having the thickness of 0.5 μm was formed.

Then, azo compound (No. P107) 0.5 g and the high polymer charge transporting substance (the aforementioned chemical expression 11D-02) 0.5 g were ball-milling-dispersed in tetra hydro furan 19 g. After dispersion, solid content 20% by weight photoconductor coating liquid was prepared in order for percentage composition to become azo compound 2% by weight, high polymer charge transporting substance 77.5% by weight, acceptor compound (designated compound A-1) 18% by weight, phenol compound (designated compound E-2) 2.5% by weight, and silicon oil (KF-50: SHINETSU CHEMICAL INDUSTRY Co., Ltd.) 0.001% by weight, then high polymer charge transporting substance, acceptor compound, phenol compound, tetra hydro furan and silicon oil were added.

Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example VI-25

Except that high polymer charge transporting substances, each of which was indicated by respective No. P146 azo compound and the abovementioned chemical expression 11D-01, were used instead of azo compound and high polymer charge transporting substance used in the example VI-24, the photoconductor was manufactured in the same way as the example VI-24.

(Evaluation 5)

For the examples VI-21 -25 and comparative example VI-2 single layer type electrophotographic photoconductor, the following evaluation was made using the electrostatic copying paper tester EPA-8200 (KAWAGUCHI ELETRIC Co., Ltd.) under the condition of 25° C./55% RH. The result is indicated in Table 55.

(1)+6 KV corona discharge was performed for 20 seconds in a dark place, further, after it was left as it was for 20 seconds in the dark place, surface electrokinetic potential $V_0$ (V) was measured.

(2) A tungsten lamp was used for irradiation in order for photoconductor's surface illumination strength to become 5.3 luxes, time (sec) till its surface electrokinetic potential became a half of $V_0$ was required, then 50 percent exposing volume E½ (lux·sec) was calculated as sensitivity for a visual range.

(3) Abrasion test was performed to a photoconductor surface, according to Japanese Industrial Standard JISK7204 (1995). That is to say, an abrasion test, weight 1 Kg, 3000 revolutions, was performed using a CS-5 abrasion wheel for taper abrasion test (TOYO SEIKI Co., Ltd.), and its abrasion volume was measured.

TABLE 55

|  | Vo (V) | E½ (lux · sec) | (mg) |
| --- | --- | --- | --- |
| Ex. VI-21 | 1076 | 0.63 | 2.0 |
| Ex. VI-22 | 1220 | 1.09 | 2.0 |
| Ex. VI-23 | 1043 | 0.88 | 3.2 |
| Ex. VI-24 | 1164 | 0.71 | 2.2 |
| Ex. VI-25 | 1114 | 1.32 | 3.8 |

(Evaluation 6)

The single layer type electrophotographic photoconductor of example VI-21, example VI-22, and example VI-24 was installed on a drum having the speed of 260 mm/s, then plus charging, exposing, and optical quenching were repeated for 5000 times, and charge electrokinetic potential Vd (V) after the initial and 5000 times and electrokinetic potential VI (V) after exposing were measured. The result is indicated in Table 56.

TABLE 56

|  | Initially | | After 5000 operation | |
| --- | --- | --- | --- | --- |
|  | Vd (V) | VI (V) | Vd (V) | VI (V) |
| Ex. VI-21 | 872 | 30 | 849 | 40 |
| Ex. VI-22 | 890 | 26 | 871 | 35 |
| Ex. VI-24 | 884 | 29 | 873 | 34 |

Example VI-26

Polyamide resin (CM-8000: TORAY Co., Ltd.) liquid solution which was dissolved in methanol/butanol mixture solvent was coated by the doctor blade on an aluminium evaporation polyester film, dried at the temperature of 100° C. for 5 minutes, and then a middle layer having the thickness of 0.5 μm was provided. Next, after azo compound (designated compound No. P150) 0.5 g was ball-milling-dispersed with liquid solution made of a polycarbonate resin (PCX-5, TEIJIN KASEI Co., Ltd.) 0.5 g and tetra hydro furan 19 g, a charge transporting substance, an acceptor compound, a phenol compound, tetra hydro furan, and silicon oil were added in order that percentage composition might become azo compound 2% by weight, polycarbonate resin 47.5% by weight, charge transporting substance 30% by weight indicated by the aforementioned structural formula (CTM-1), acceptor compound 18% by weight indicated by the aforementioned structural formula (A-1), phenol compound 2.5% by weight indicated by the aforementioned structural formula (E-2), and silicon oil (KF50: SHINETSU CHEMICAL INDUSTRY Co., Ltd.) 0.001% by weight, and then solid content 20% by weight photoconductor coating liquid was adjusted. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example VI-27

Except that azo compound expressed by the designated compound No. P174 instead of azo compound used in the example VI-26 was used, the photoconductor was manufactured in the same way as the embodimentVI-26.

Example VI-28

Except that azo compound expressed by the designated compound No. P183 instead of azo compound used in the example VI-26 was used, the photoconductor was manufactured in the same way as the embodimentVI-26.

Example VI-29

Except that azo compound expressed by the designated compound No. P186 instead of azo compound used in the example VI-26 was used, the photoconductor was manufactured in the same way as the embodimentVI-26.

Example VI-30

Polyamide resin (CM-8000: TORAY Co., Ltd.) liquid solution dissolved in methanol/butanol mixture solvent was coated by the doctor blade on an aluminium evaporation polyester film, dried at the temperature of 100° C. for 5 minutes, thus a middle layer having the thickness of 0.5 μm was formed.

Next, an azo compound (designated compound No. P162) 0.5 g was ball-milling-dispersed with liquid solution composed of high polymer charge transporting substance (designated compound 11D-02) 0.5 g and tetra hydro furan 19 g, then high polymer charge transporting substance, acceptor compound, phenol compound, tetra hydro furan, and silicon oil were added in order that percentage composition might become azo compound 2% by weight, high polymer charge transporting substance 77.5% by weight, acceptor compound (designated compound A-1) 18% by weight, phenol compound (designated compound E-2) 2.5% by weight, and silicon oil (KF50: SHINETSU CHEMICAL INDUSTRY Co., Ltd.) 0.001% by weight, thus solid content 20% by weight photoconductor coating liquid was prepared. Photoconductor coating liquid which was adjusted in this way was coated by the doctor blade on the aforementioned middle layer at the temperature of 120° C. for 20 minutes, and the single layer type electrophotographic photoconductor having the photoconductive layer having the thickness of 20 μm was manufactured.

Example VI-31

Except that azo compound expressed by the designated compound No. P181 instead of azo compound used in the example VI-30 was used, the photoconductor was manufactured in the same way as the embodimentVI-30.

Example VI-32

Except that azo compound expressed by the designated compound No. P188 instead of azo compound used in the example VI-30 was used, the photoconductor was manufactured in the same way as the embodimentVI-30.
(Evaluation 7)

For the examples VI-21 -25 and comparative example VI-2 single layer type electrophotographic photoconductor, the following evaluation was made using the electrostatic copying paper tester EPA-8200 (KAWAGUCHI ELETRIC Co., Ltd.) under the condition of 25° C./55% RH. The result is indicated in Table 57.

(1)+6 KV corona discharge was performed for 20 seconds in a dark place, further, after it was left as it was for 20 seconds in the dark place, surface electrokinetic potential $V_0$ (V) was measured.

(2) A tungsten lamp was used for irradiation in order for photoconductor's surface illumination strength to become 5.3 luxes, time (sec) till its surface electro kinetic potential became a half of $V_0$ was required, then 50 percent exposing volume E½ (lux·sec) was calculated as sensitivity for a visual range.

TABLE 57

|  | Vo (V) | E½ (lux · sec) |
| --- | --- | --- |
| Ex. VI-26 | 1132 | 0.69 |
| Ex. VI-27 | 1250 | 0.72 |
| Ex. VI-28 | 1167 | 0.73 |
| Ex. VI-29 | 1109 | 0.80 |
| Ex. VI-30 | 1144 | 0.64 |
| Ex. VI-31 | 1186 | 0.69 |
| Ex. VI-32 | 1392 | 0.77 |

Obviously in the above explanation, single layer type electrophotographic photoconductor can be provided by the present invention which affects excellent advantageous points in which charge properties, sensitivity, light resistance and durability are excellent, and stable electrostatic properties are attained even if a coping process is repeated.

Further, excellent electrophotographic photoconductor, process for forming an image, apparatus for forming an image, and process cartridge for the apparatus for forming an image can be provided.

Then, concrete explanation is made using embodiments for azo compounds, azo compound manufacturing raw material, and their methods for producing indicated by the general formula <<101>> of the present invention. However, the embodiments of the present invention are not limited thereto.

Example VII-1

Manufacturing 2-(t-butoxy)7,8-naphthalic acid dimethyl ester [$R_1=R_2=R_3=R_4=H$, $R_5=CH_3$, $R_6=t-C_4H_9$ Compound of the General Formula <<120>>]

P-t-butoxy styrene 35.25 g (0.2 mol) and acetylene carboxylic acid dimethyl ester 56.84 g (0.4 mol) were dissolved in nitrobenzene 200 ml, then reacted and cooled at the temperature of 140° C. for 5 hours. Further, nitrobenzene was removed under reduced pressure, then silica gel column chromatography (n-hexane: acetic acid ethyl=9: 1 as developing solvent) was performed to the residual, then 40.78 g objective crude material was obtained.

Further, 36.63 g (yield 57.9%) objective naphthalene compounds were obtained by recrystallizing through diisopropyl ether. Melt points were 82.0 –83.0° C. This naphthalene compound's infrared absorption spectrum is indicated in FIG. 1.

TABLE 58

|  | Elemental analysis value (%) | |
| --- | --- | --- |
|  | C | H |
| Actual measurement value | 68.32 | 6.46 |
| Calculation value | 68.34 | 6.37 |

Example VII-2

Manufacturing 2-hydroxy-7,8-naphthalic acid dimethyl ester [$R_1=R_2=R_3=R_4=H$, $R_5=CH_3$ Compound of the General Formula <<149>>]

2-(t-butoxy)7,8-naphthalic acid dimethyl ester 31.63 g (0.1 mol) obtained in the example VII-1 was dissolved in 120 ml chloride methylene, mixed at a room temperature, then trifluoro acetic acid 57.01 g (0.5 mol) was dropped for 10 minutes. Further, mixing reaction was continued for 3 hours under the same condition (room temperature). After reaction, reacted material was poured on an ice, water was added, and then phase splitting was performed. A chloride methylene phase was further washed twice using water and dehydrated through sulfuric anhydride magnesium. Sulfuric magnesium was removed by filtering, then the objective naphthalene compound, 24.31 g (yield 93.4%), was obtained by recrystallizing the residual material from which chloride methylene was removed through toluene. Melt points were 139.0 –139.8° C. This naphthalene compound's infrared absorption spectrum is indicated in FIG. 2.

TABLE 59

|  | Elemental analysis value (%) | |
| --- | --- | --- |
|  | C | H |
| Actual measurement value | 64.60 | 4.56 |
| Calculation value | 64.61 | 4.65 |

Example VII-3

Manufacturing N-n-hexyl-2-hydroxy-7,8-naphthalic acid imido [$R_1=R_2=R_3=R_4=H$, $X=C_6H_{13}$-n <coupler No. C1> Compound of the General Formula <<122>>]

2-hydroxy-7,8-naphthalic acid dimethyl ester 10.41 g (0.04 mol) and n-hexyl amine 12.14 g (0.12 mol) obtained in the example VII-2 were mixed and reacted in ethylene glycol 100 ml for 2 hours under a nitrogen gas air stream at the temperature of 120° C. for 4 hours. After reaction ended and cooled, after reacted material was poured on an ice, hydrochlorix acid was made, extracted crystal was filtered and washed using 500 ml ion exchange water, then dried under reduced pressure at the temperature of 60° C., thus crude objects 9.73 g were obtained.

Obtained crude material was processed by silica gel column chromatography (toluene: acetic acid ethyl =4: 1 as developing solvent) and recrystallized by toluene, thus 7.12 g (yield 59.9%) yellow coupler compound <coupler No. C1> was obtained. Melt points were 165.5 –166.5° C. The infrared absorption spectrum of this coupler compound <coupler No. C1> is shown in FIG. 3.

TABLE 60

| | Elemental analysis value (%) | | |
|---|---|---|---|
| | C | H | N |
| Actual measurement value | 72.84 | 6.51 | 4.68 |
| Calculation value | 72.71 | 6.44 | 4.71 |

Example VII-4

N-benzyl-2-hydroxy-7,8-naphthalic acid imido [$R_1$=$R_2$=$R_3$=$R_4$=H,X=

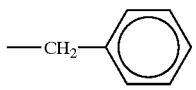

of the General Formula <<122>>]

Manufacturing <Coupler No. C5> Compounds 2-hydroxy-7,8-naphthalic acid dimethyl ester 10.41 g (0.04 mol) and benzyl amine 8.57 g (0.08 mol) obtained in the example VII-2 were mixed and reacted for 6 hours using ethylene glycol 100 ml under a nitrogen gas air stream at the temperature of 140° C. After reaction and cooling, reacted material was poured on a ice, hydrochlorid acid was made, then extracted crystal was filtered, it was washed by 500 ml ion exchange water, by drying at the temperature of 60° C. under reduced pressure, thus objective crude material 10.21 g was obtained. Obtained crude material was recrystallized by n-butanol, and 9.57 g (yield 78.9%) orange color coupler compound <coupler No. C5> was obtained. Melt points were 255.2 –259.0 ° C. This coupler compound <coupler No. C5> infrared absorption spectrum is shown in FIG. 4.

TABLE 61

| | Elemental analysis value (%) | | |
|---|---|---|---|
| | C | H | N |
| Actual measurement value | 75.30 | 4.29 | 4.60 |
| Calculation value | 75.24 | 4.32 | 4.62 |

Example VII-5

N-(2-phenyl ethyl)-2-hydroxy-7,8-naphthalic acid imido [$R_1$=$R_2$=$R_3$=$R_4$=H,X=

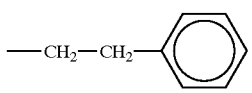

of the General Formula <<122>>]

Manufacturing <Coupler No. C14> Compounds

Except that benzyl amine 8.57 g (0.08 mol) was used in phenethyl amine 9.69 g (0.08 mol), crude object material 10.48 g was obtained in the same reaction as the example VII-4. Obtained crude material was recrystallized by n-butanol, and 9.95 g (yield 78.4%) yellow color coupler compound <coupler No. C14> was obtained. Melt points were 233.5 –236.5° C. This coupler compound <coupler No. C14> infrared absorption spectrum is shown in FIG. 5.

TABLE 62

| | Elemental analysis value (%) | | |
|---|---|---|---|
| | C | H | N |
| Actual measurement value | 75.78 | 4.71 | 4.36 |
| Calculation value | 75.70 | 4.77 | 4.41 |

Example VII-6

N-pheny-1,2-hydroxy-7,8-naphthalic acid imido [$R_1$=$R_2$=$R_3$=$R_4$=H,X=

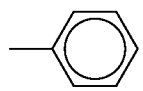

of the General Formula <<122>>]

Manufacturing <Coupler No. C28> Compound

Except that Benzyl amine 8.57 g (0.08 mol) was used in aniline 7.45 g (0.08 mol), the objective crude material 12.04 g was obtained in the same reaction as the example VII-4. Obtained crude material was recrystallized by n-butanol/toluene (1/1 vol), and 8.15 g (yield 69.7%) orange color coupler compound <coupler No. C28> was obtained. Melt points were 245.5 –248.9 ° C. This coupler compound <coupler No. C28> infrared absorption spectrum is shown in FIG. 6.

TABLE 63

| | Elemental analysis value (%) | | |
|---|---|---|---|
| | C | H | N |
| Actual measurement value | 74.79 | 3.88 | 4.83 |
| Calculation value | 74.73 | 3.83 | 4.84 |

Example VII-7

12-hydroxy-benzo[6,7]isoindole[2,1-a]perimysin-14-on or 9-hydroxy-benzo[4,5]isoindole[2,1-a]perimysin-14-on [$R_1$=$R_2$=$R_3$=$R_4$=H,Y=

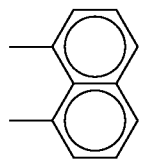

of the General Formula <<124>>]

Manufacturing <Coupler No. E23> Compound 2-hydroxy-7,8-naphthalic acid dimethyl ester 10.41 g (0.04 mol) and 1,8-diamino naphthalene 12.66 g (0.08 mol) obtained in the example VII-2 were mixed and reacted in ethylene glycol 100 ml under a nitrogen gas air stream at the temperature of 160° C. for 8 hours. After reaction and cooling, reacted material was poured on a ice, hydrochlorid acid was made, then extracted crystal was filtered, it was washed by 500 ml ion exchange water, by drying at the temperature of 60° C. under reduced pressure, thus objective crude material 9.96 g was obtained. Obtained crude material was recrystallized by nitrobenzene, and 8.80 g (yield 65.4%) orange color coupler compound <coupler No. E23> was obtained. The decomposition point was 398° C. This coupler compound <coupler uNo.E23> infrared absorption spectrum is shown in FIG. 7.

TABLE 64

|  | Elemental analysis value (%) | | |
| --- | --- | --- | --- |
|  | C | H | N |
| Actual measurement value | 78.50 | 3.57 | 8.32 |
| Calculation value | 78.56 | 3.60 | 8.33 |

Example VII-8–Example VII-13

Except that benzyl amine was used instead of various amine compounds expressed by the general formula <<28>> in the example VII-4, the same reaction was performed, and the following compound was obtained. Melt points, element analysis values, and infrared absorption spectrum chart therefor are shown in Table 65.

TABLE 65

Figure 31:
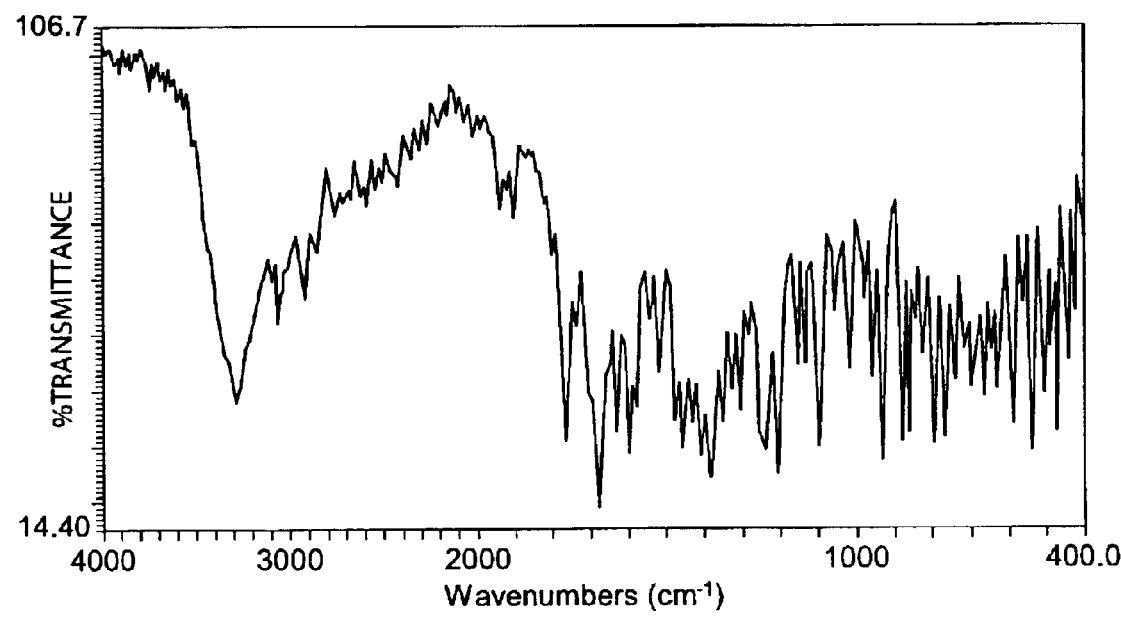
FIG. 31 is a graph showing an example of an infrared spectrum of a coupler compound.
Figure 32:
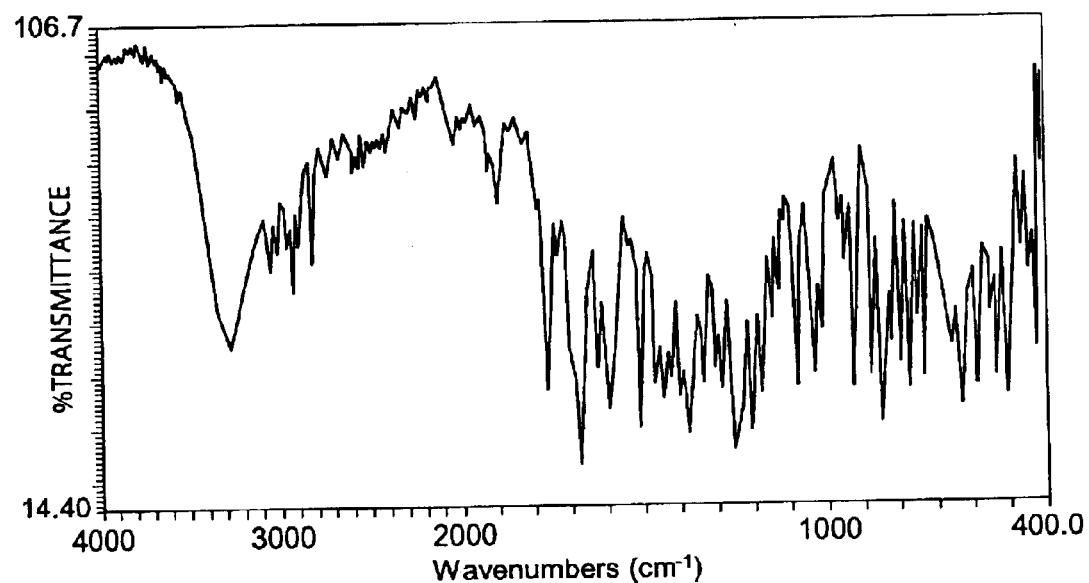
FIG. 32 is a graph showing an example of an infrared spectrum of a coupler compound.
Figure 33:
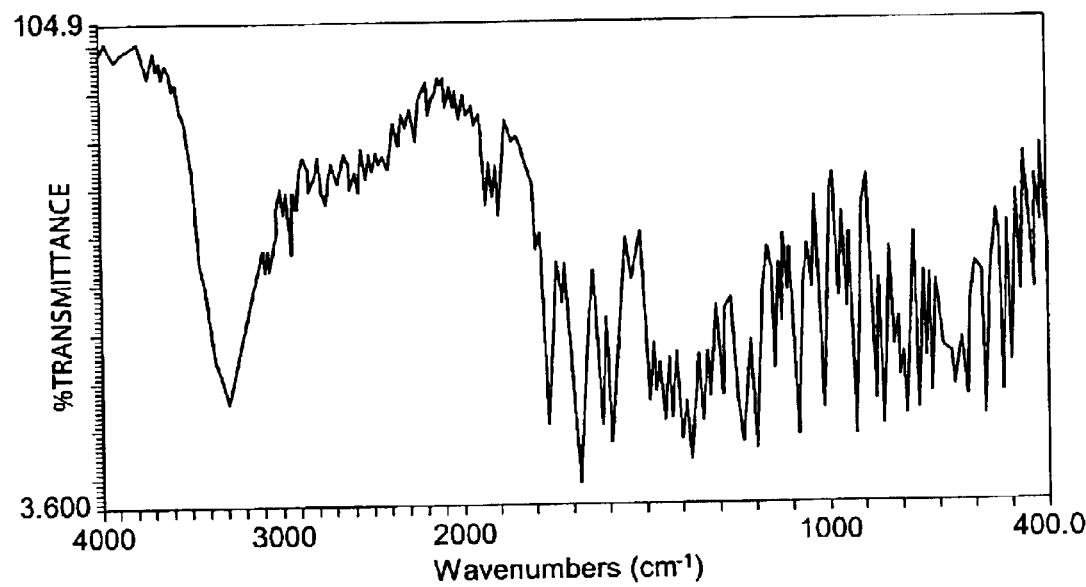
FIG. 33 is a graph showing an example of an infrared spectrum of a coupler compound.
Figure 34:
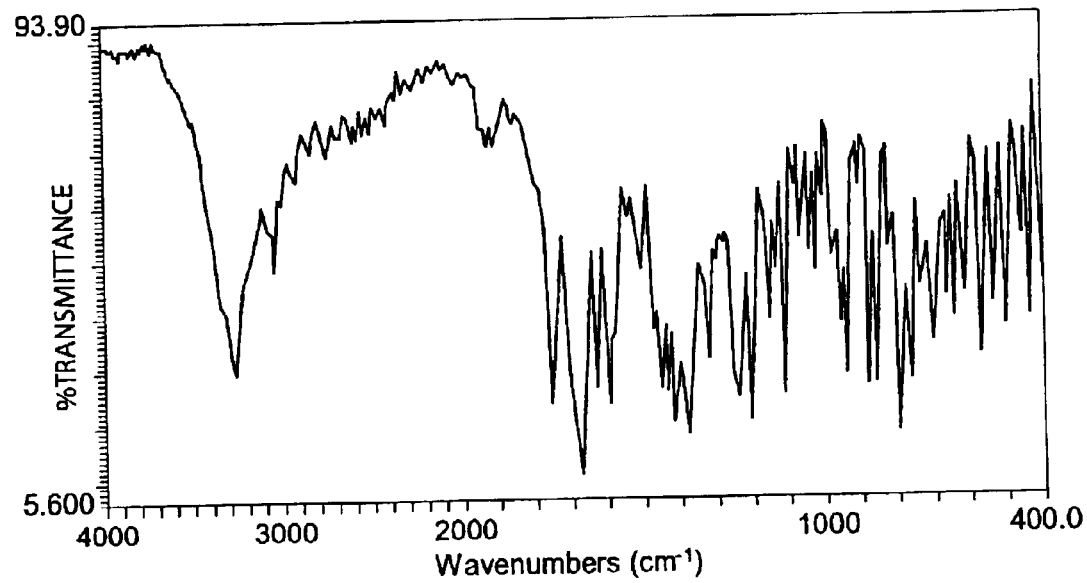
FIG. 34 is a graph showing an example of an infrared spectrum of a coupler compound.
Figure 35:
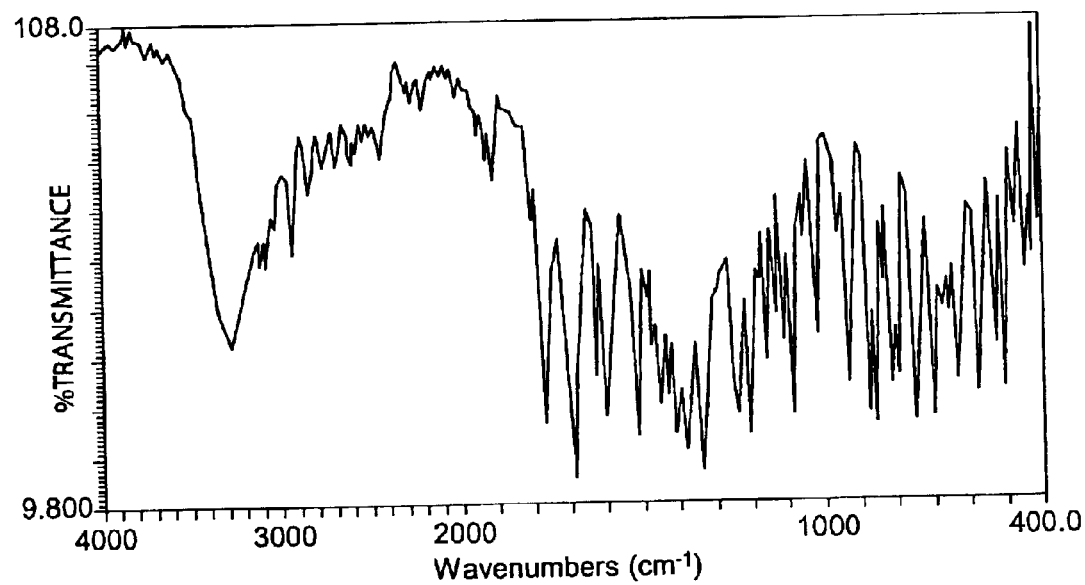
FIG. 35 is a graph showing an example of an infrared spectrum of a coupler compound.
Figure 36:
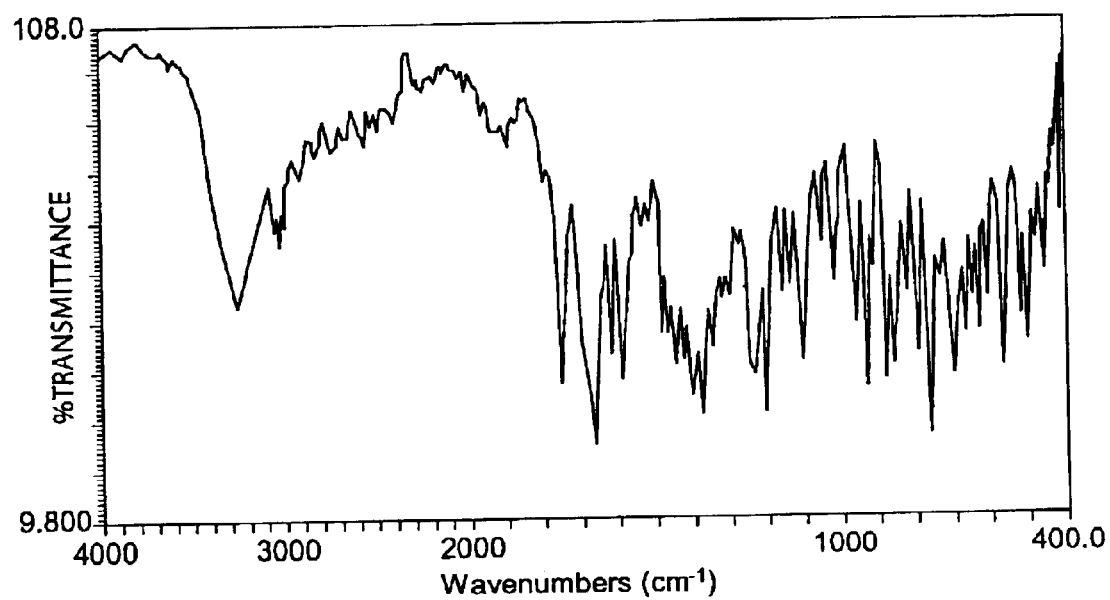
FIG. 36 is a graph showing an example of an infrared spectrum of a coupler compound.

| Ex. | Coupler (Cp) No. | Melting Point (° C.) <Dissolving point (° C.)> | Actual measurement value C (Calculation value C) | Actual measurement value H (Calculation value H) | Actual measurement value N (Calculation value N) | Infrared absorption spectrum Fig. |
| --- | --- | --- | --- | --- | --- | --- |
| Ex. VII-8 | C9 | 238.3~243.1 | 75.82 (75.70) | 4.71 (4.77) | 4.32 (4.41) | FIG. 31 |
| Ex. VII-9 | C10 | 212.9~219.0 | 72.13 (72.06) | 4.40 (4.54) | 4.11 (4.20) | FIG. 32 |
| Ex. VII-10 | C11 | 239.3~244.0 | 67.66 (67.57) | 3.38 (3.58) | 4.11 (4.15) | FIG. 33 |
| Ex. VII-11 | C13 | 258.8~263.2 | 78.23 (78.18) | 4.25 (4.28) | 3.93 (3.96) | FIG. 34 |
| Ex. VII-12 | C59 | 254.0~256.2 | 65.56 (65.52) | 3.39 (3.47) | 7.96 (8.04) | FIG. 35 |
| Ex. VII-13 | C60 | 263.1~267.2 | 79.21 (79.14) | 4.50 (4.52) | 3.59 (3.69) | FIG. 36 |

Example VII-14–Example VII-35

Except that benzyl amine was used instead of various amine compounds expressed by the general formula <<28>> in the example VII-4, the same reaction was performed, and the following compound was obtained. Melt points, element analysis values, and infrared absorption spectrum chart therefor are shown in Table 65.

TABLE 66-1

Figure 73:
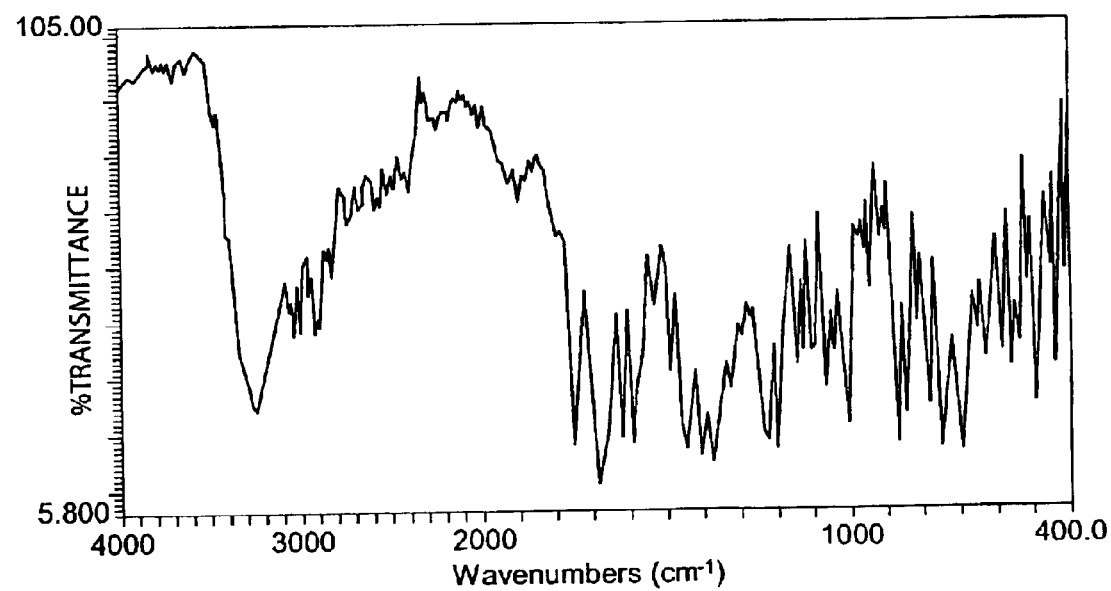
FIG. 73 is a graph showing an example of an infrared spectrum of a coupler compound.
Figure 74:
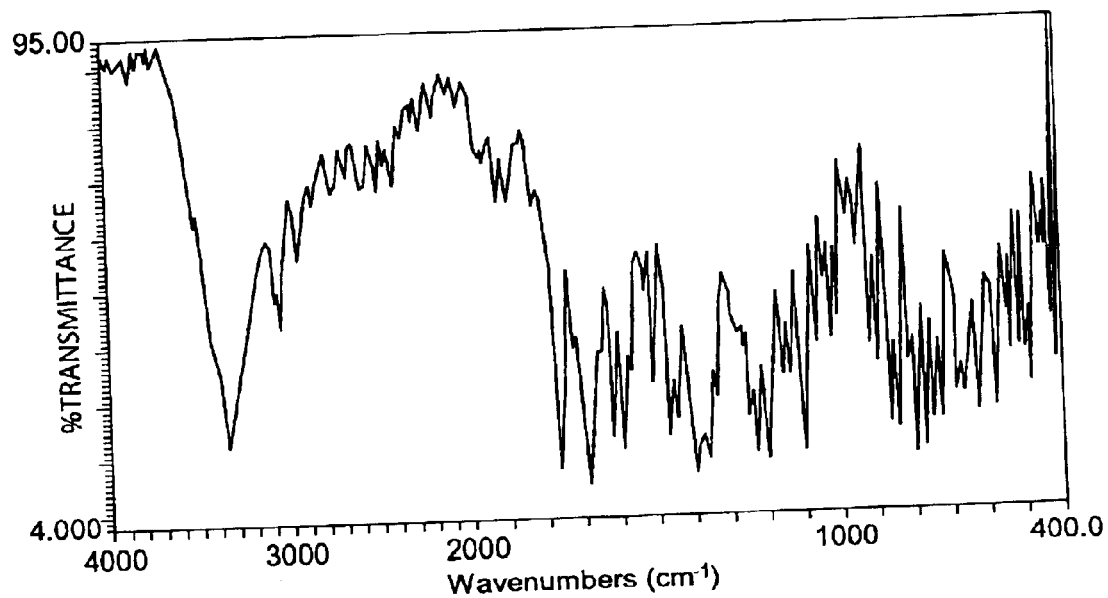
FIG. 74 is a graph showing an example of an infrared spectrum of a coupler compound.

| Ex. | Coupler (Cp) No. | Melting Point (° C.) <Dissolving point (° C.)> | Actual measurement value C (Calculation value C) | Actual measurement value H (Calculation value H) | Actual measurement value N (Calculation value N) | Infrared absorption spectrum Fig. |
| --- | --- | --- | --- | --- | --- | --- |
| Ex. VII-14 | C12 | 225.0~229.1 | 72.27 (72.06) | 4.46 (4.54) | 4.12 (4.20) | FIG. 72 |
| Ex. VII-15 | C24 | 206.9~212.0 | 76.20 (76.12) | 5.33 (5.17) | 4.21 (4.23) | FIG. 73 |
| Ex. VII-16 | C37 | 285.9~288.6 | 77.51 (77.87) | 3.89 (3.86) | 4.11 (4.13) | FIG. 74 |

TABLE 66-1-continued

Figure 75:
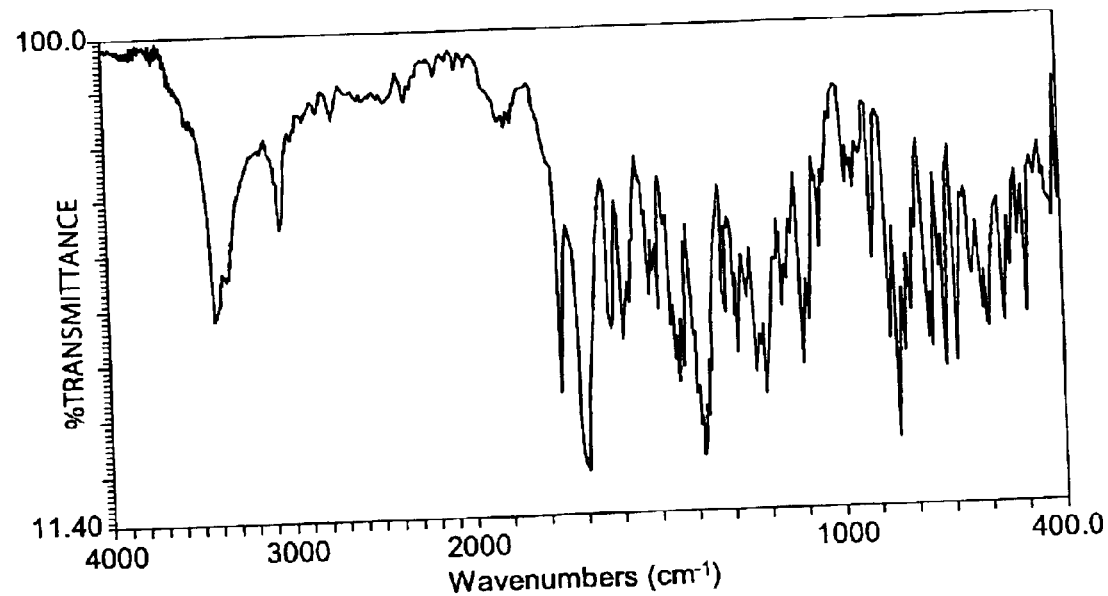
FIG. 75 is a graph showing an example of an infrared spectrum of a coupler compound.
Figure 76:
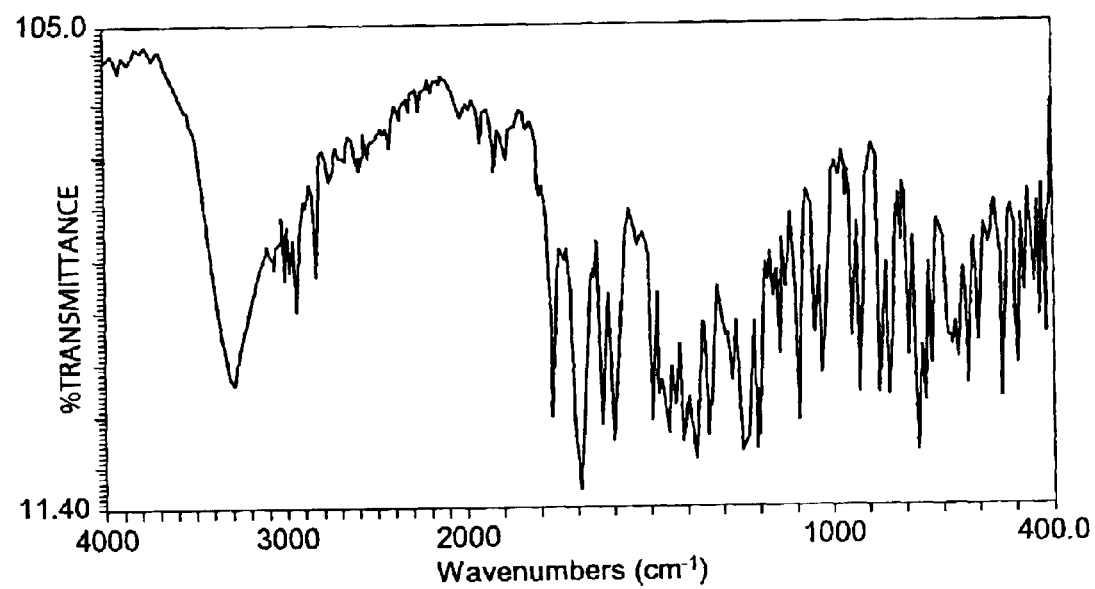
FIG. 76 is a graph showing an example of an infrared spectrum of a coupler compound.
Figure 77:
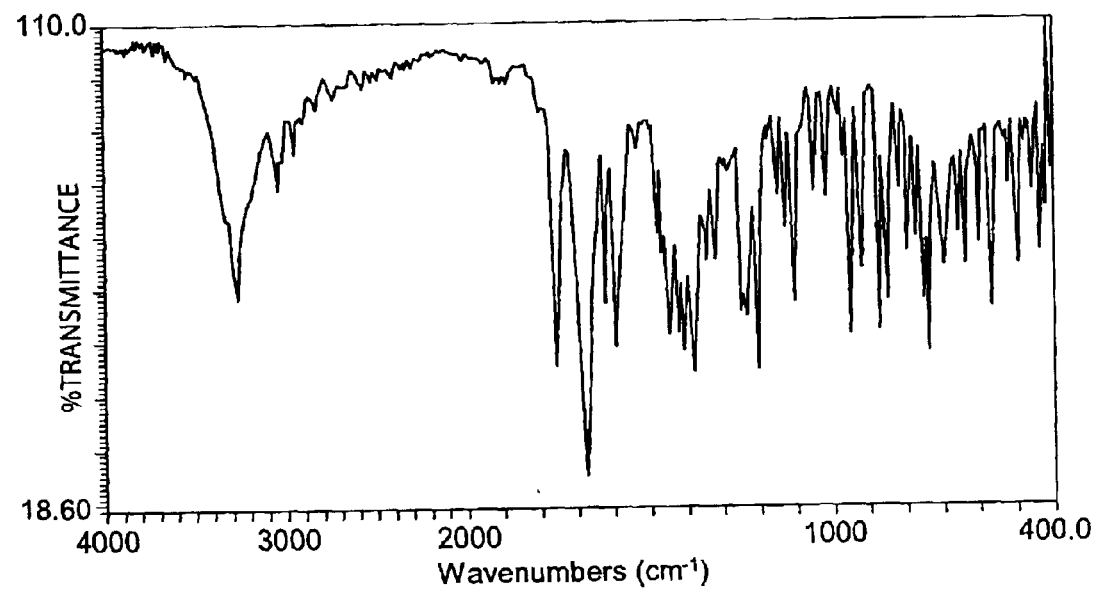
FIG. 77 is a graph showing an example of an infrared spectrum of a coupler compound.
Figure 78:
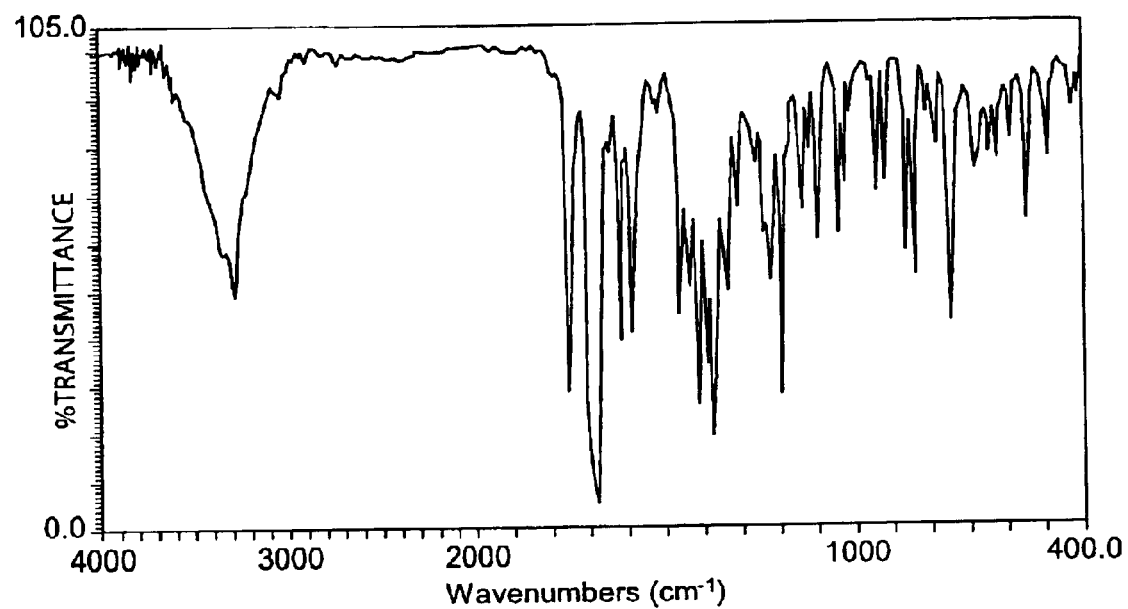
FIG. 78 is a graph showing an example of an infrared spectrum of a coupler compound.
Figure 79:
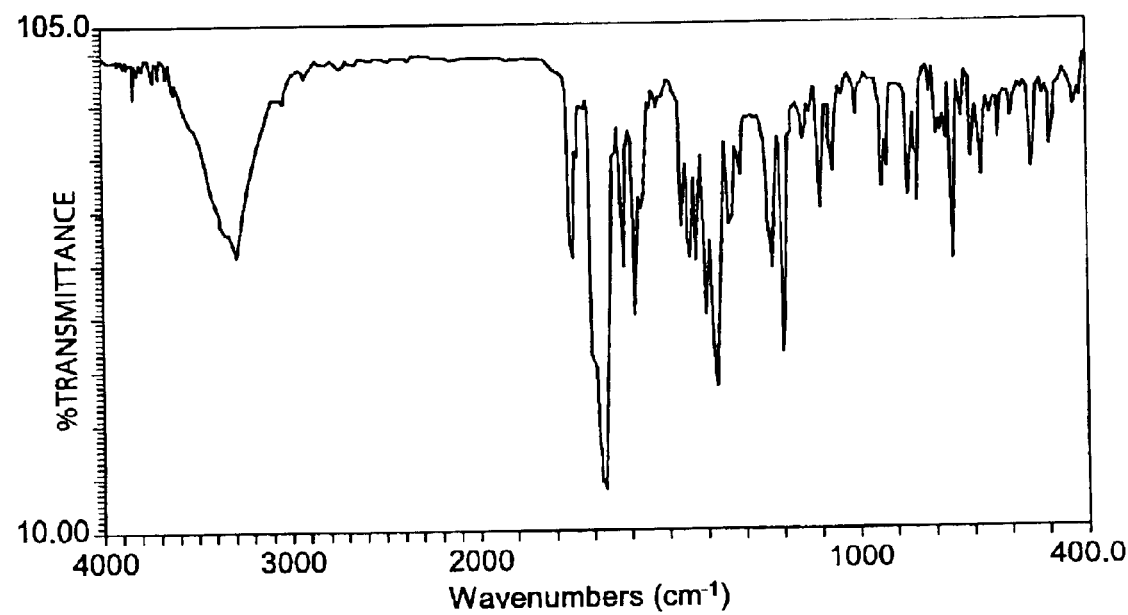
FIG. 79 is a graph showing an example of an infrared spectrum of a coupler compound.
Figure 80:
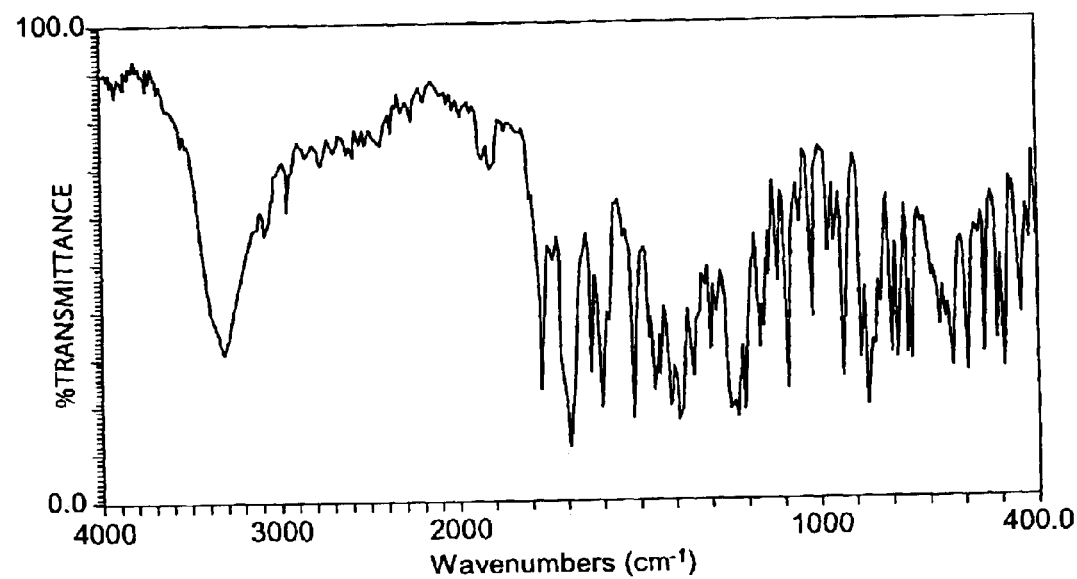
FIG. 80 is a graph showing an infrared spectrum of a coupler compound.
Figure 81:
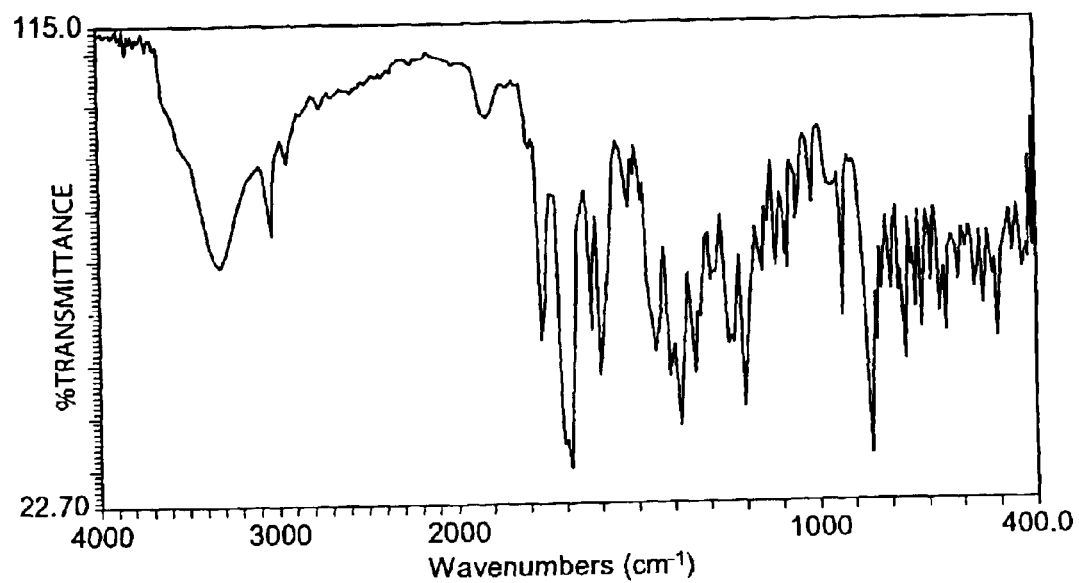
FIG. 81 is a graph showing an example of an infrared spectrum of a coupler compound.
Figure 82:
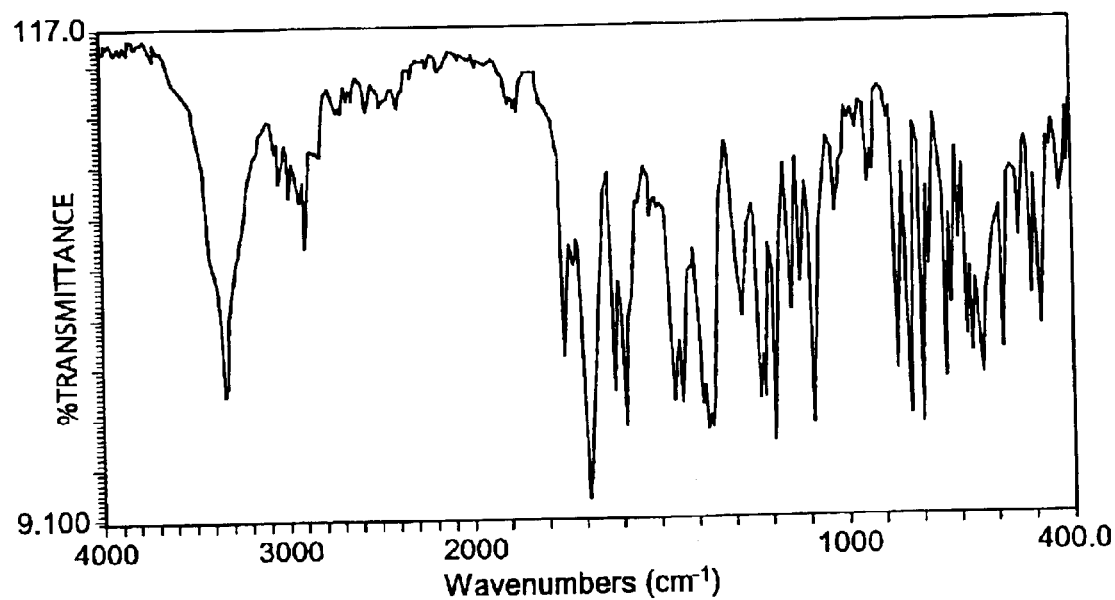
FIG. 82 is a graph showing an example of an infrared spectrum of a coupler compound.
Figure 83:
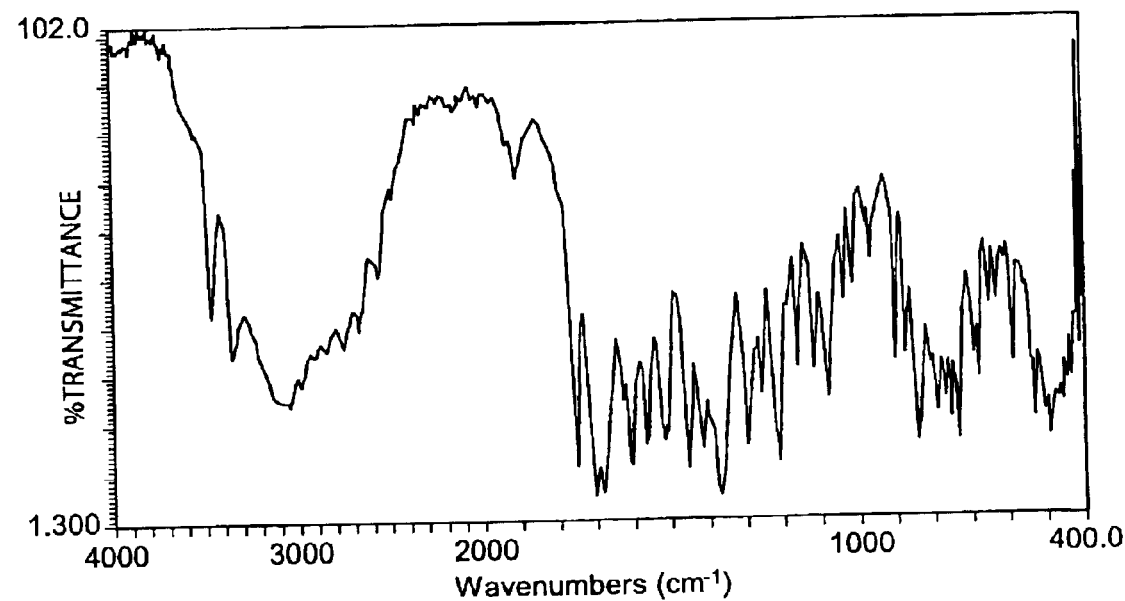
FIG. 83 is a graph showing an example of an infrared spectrum of a coupler compound.

| Ex. | Coupler (Cp) No. | Melting Point (° C.) <Dissolving point (° C.)> | Elemental analysis (%) | | | Infrared absorption spectrum Fig. |
| | | | Actual measurement value C (Calculation value C) | Actual measurement value H (Calculation value H) | Actual measurement value N (Calculation value N) | |
|---|---|---|---|---|---|---|
| Ex. VII-17 | C40 | 353.3~356.0 | 81.38 (81.35) | 3.51 (3.66) | 3.47 (3.39) | FIG. 75 |
| Ex. VII-18 | C49 | 236.9~241.9 | 72.17 (72.06) | 4.57 (4.54) | 4.09 (4.20) | FIG. 76 |
| Ex. VII-19 | C50 | 255.9~257.9 | 75.48 (75.70) | 4.67 (4.77) | 4.29 (4.41) | FIG. 77 |
| Ex. VII-20 | C54 | 253.7~258.2 | 67.49 (67.56) | 3.49 (3.58) | 4.24 (4.15) | FIG. 78 |
| Ex. VII-21 | C55 | 235.9~239.4 | 67.37 (67.56) | 3.48 (3.58) | 4.24 (4.15) | FIG. 79 |
| Ex. VII-22 | C56 | 262.9~266.6 | 70.90 (71.02) | 3.59 (3.76) | 4.36 (4.36) | FIG. 80 |
| Ex. VII-23 | C61 | 304.4~310.9 | 81.63 (81.49) | 3.95 (4.01) | 3.12 (3.28) | FIG. 81 |
| Ex. VII-24 | C83 | 263.8~265.8 | 75.53 (75.70) | 4.67 (4.77) | 4.48 (4.41) | FIG. 82 |
| Ex. VII-25 | C92 | 254.5~258.4 | 68.85 (68.67) | 3.66 (3.64) | 8.41 (8.42) | FIG. 83 |

TABLE 66-2

Figure 84:
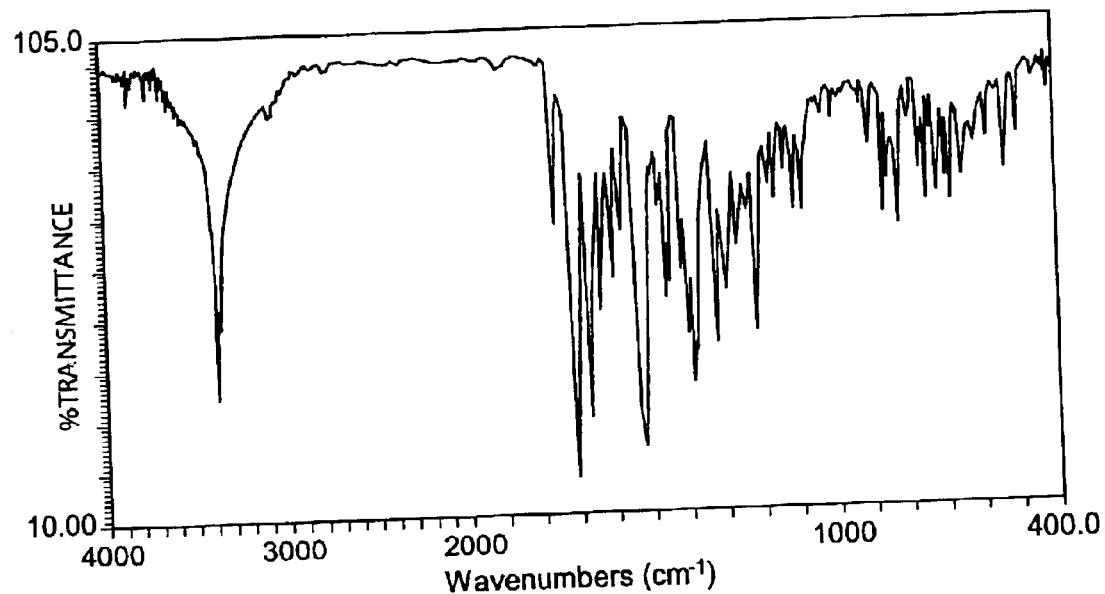
FIG. 84 is a graph showing an example of an infrared spectrum of a coupler compound.
Figure 85:
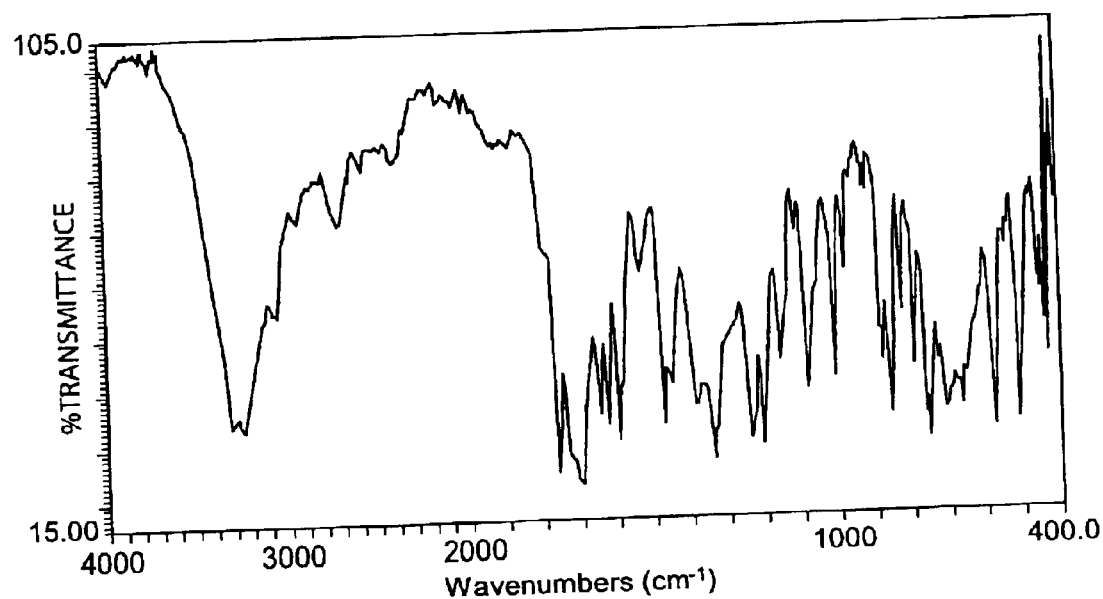
FIG. 85 is a graph showing an example of an infrared spectrum of a coupler compound.
Figure 86:
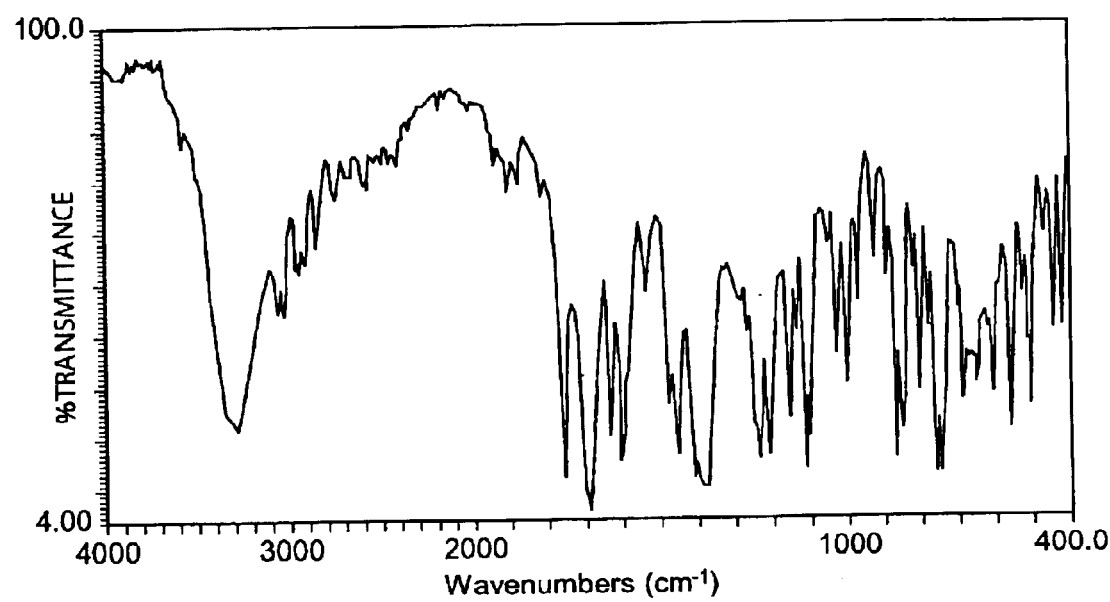
FIG. 86 is a graph showing an example of an infrared spectrum of a coupler compound.
Figure 87:
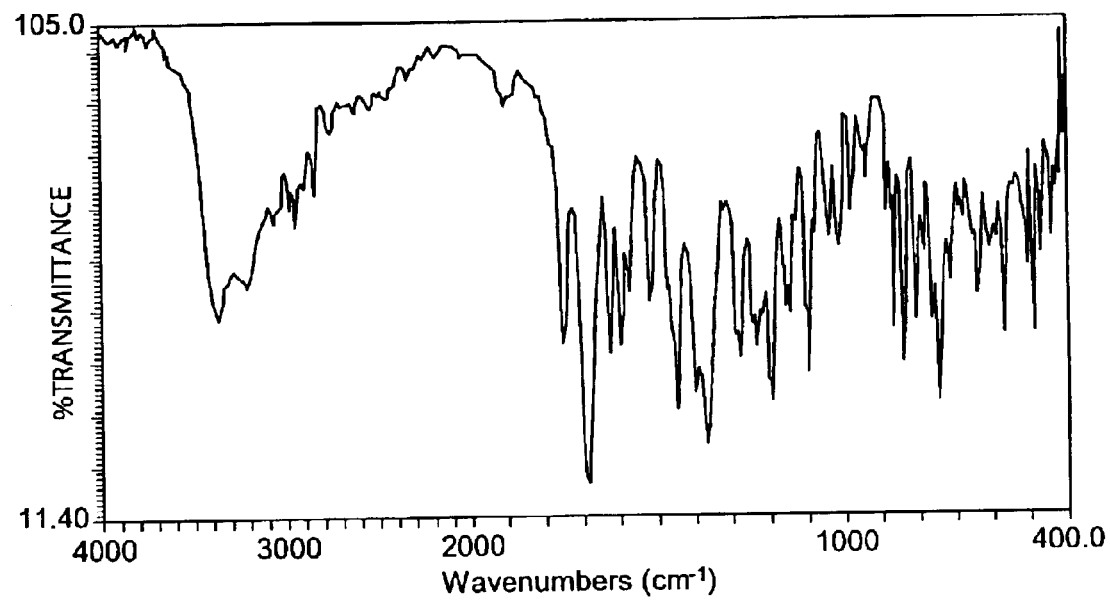
FIG. 87 is a graph showing an example of an infrared spectrum of a coupler compound.
Figure 88:
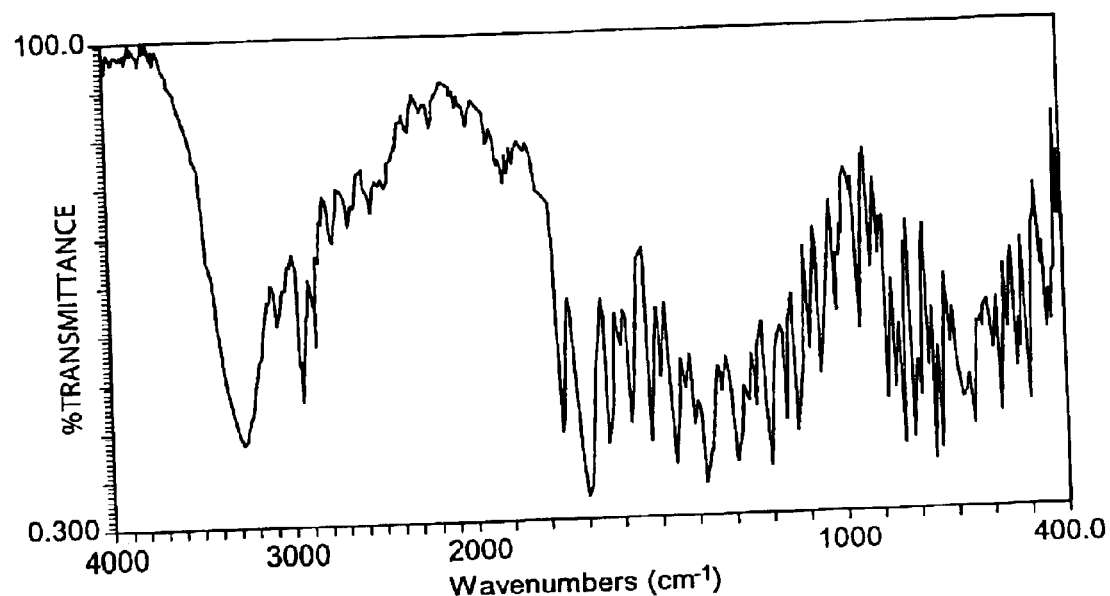
FIG. 88 is a graph showing an example of an infrared spectrum of a coupler compound.
Figure 89:
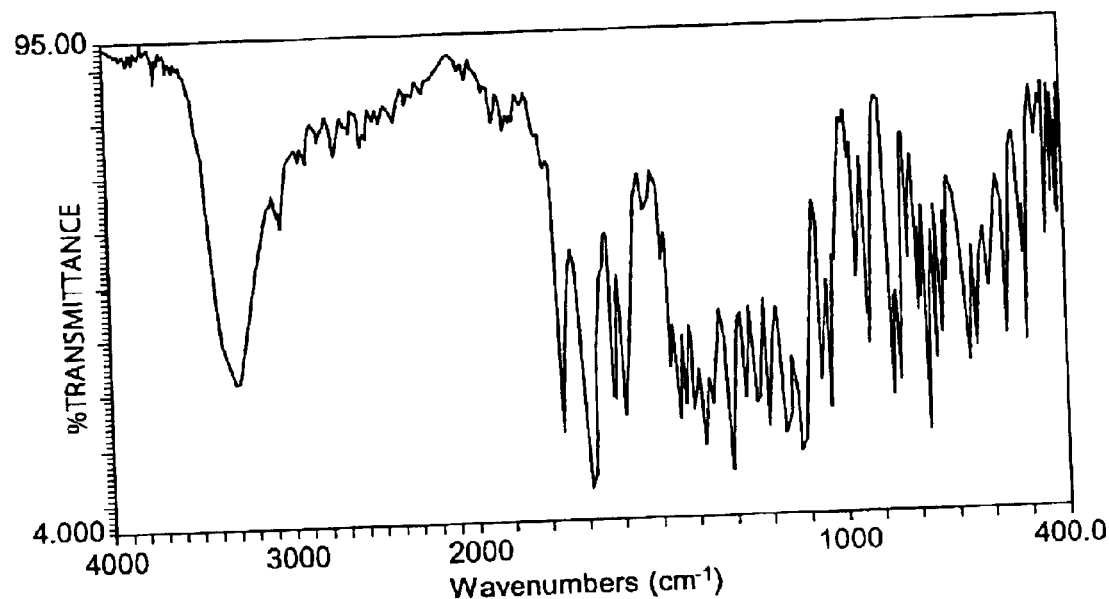
FIG. 89 is a graph showing an example of an infrared spectrum of a coupler compound.
Figure 90:
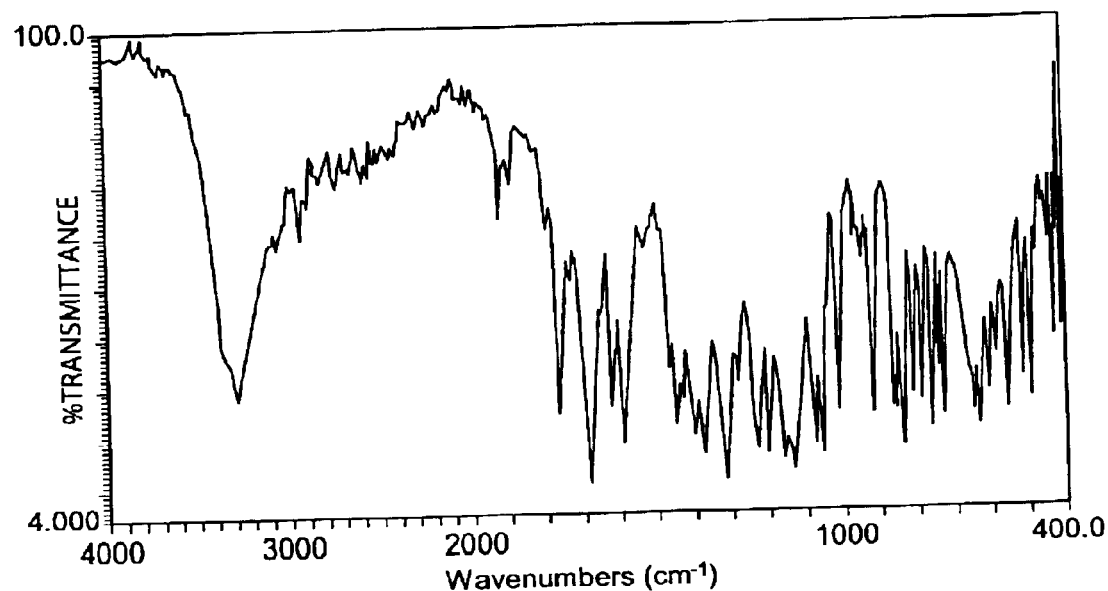
FIG. 90 is a graph showing an example of an infrared spectrum of a coupler compound.
Figure 91:
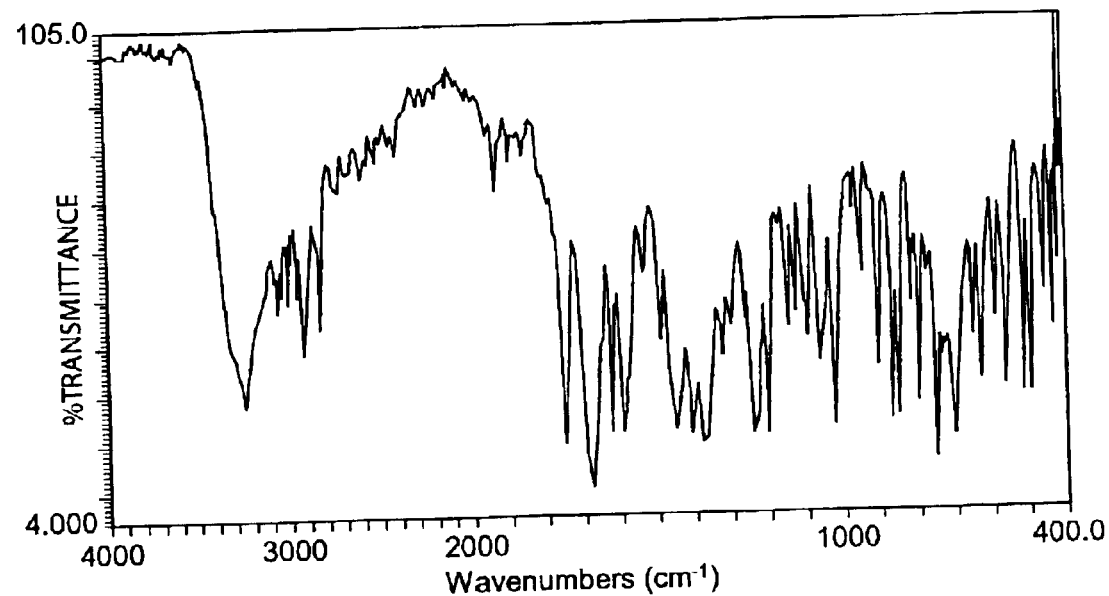
FIG. 91 is a graph showing an example of an infrared spectrum of a coupler compound.
Figure 92:
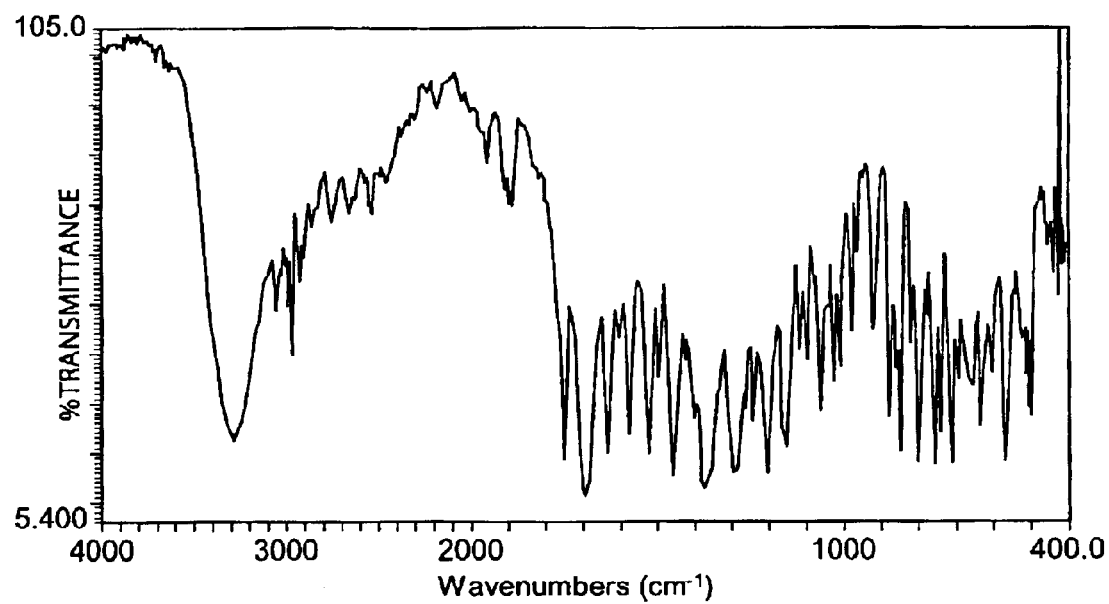
FIG. 92 is a graph showing an example of an infrared spectrum of a coupler compound.
Figure 93:
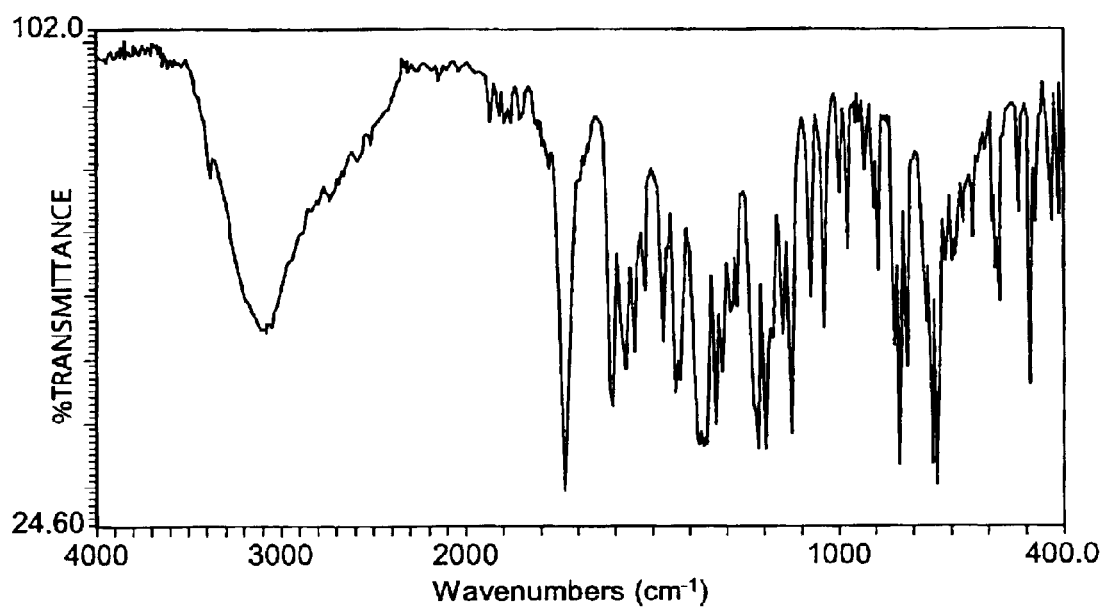
FIG. 93 is a graph showing an example of an infrared spectrum of a coupler compound.
Figure 94:
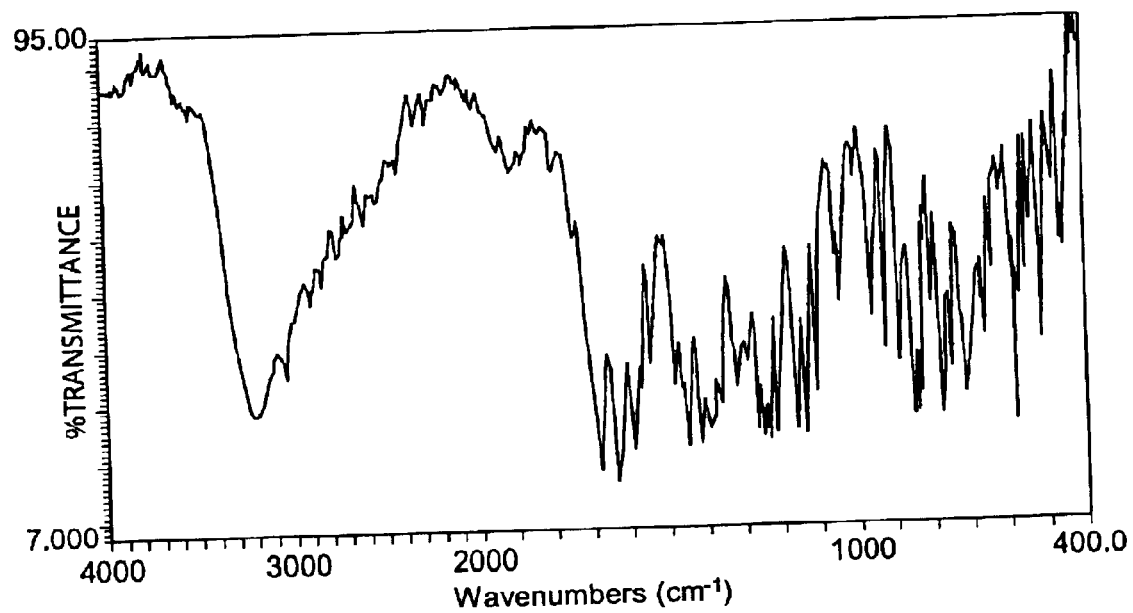
FIG. 94 is a graph showing an example of an infrared spectrum of a coupler compound.
Figure 95:
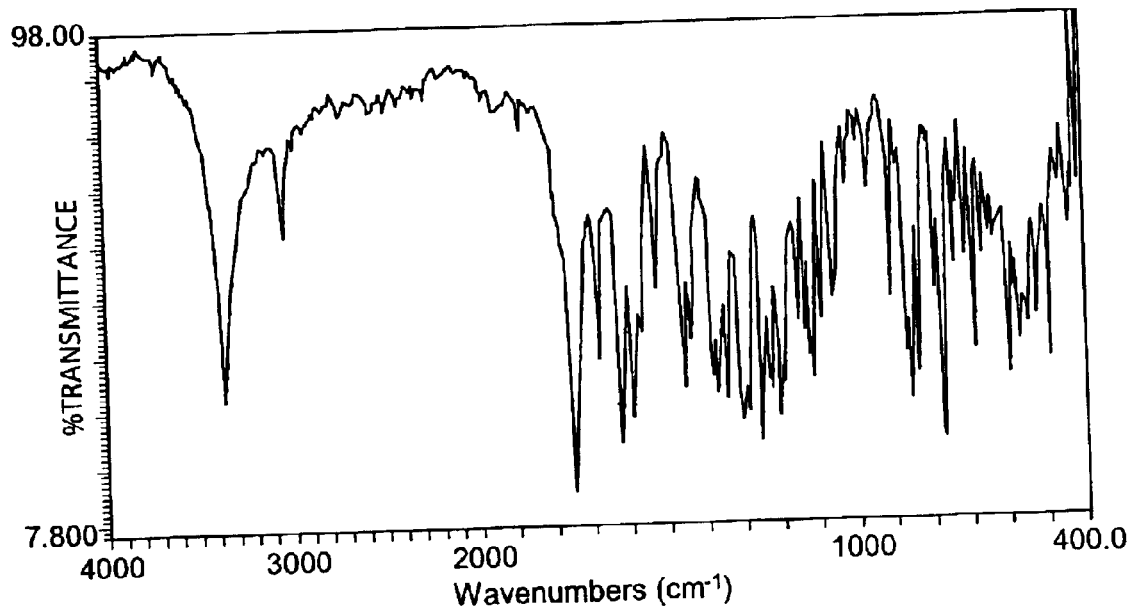
FIG. 95 is a graph showing an example of an infrared spectrum of a coupler compound.
Figure 124:
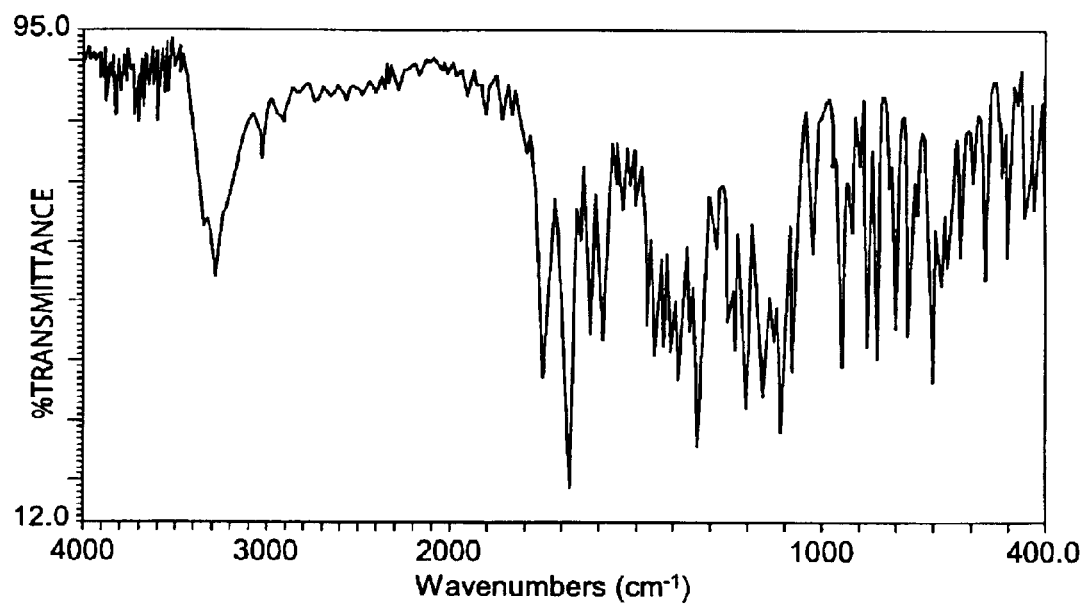

| Ex. | Coupler (Cp) No. | Melting Point (° C.) <Dissolving point (° C.)> | Elemental analysis (%) | | | Infrared absorption spectrum Fig. |
| | | | Actual measurement value C (Calculation value C) | Actual measurement value H (Calculation value H) | Actual measurement value N (Calculation value N) | |
|---|---|---|---|---|---|---|
| Ex. VII-26 | C95 | 323.0~325.0 | 73.44 (73.52) | 3.88 (3.95) | 6.79 (6.86) | FIG. 84 |
| Ex. VII-27 | C101 | 235.2~242.5 | 65.72 (65.89) | 3.09 (2.91) | 7.98 (8.09) | FIG. 85 |
| Ex. VII-28 | C104 | 275.8~278.3 | 76.40 (76.58) | 4.49 (4.59) | 4.29 (4.25) | FIG. 86 |
| Ex. VII-29 | C105 | 229.5~232.8 | 76.47 (76.58) | 4.49 (4.59) | 4.21 (4.25) | FIG. 87 |
| Ex. VII-30 | C106 | 230.6~234.6 | 76.95 (76.95) | 4.95 (4.99) | 4.09 (4.08) | FIG. 88 |
| Ex. VII-31 | C107 | 243.7~246.4 | 64.63 (64.70) | 3.22 (3.26) | 3.71 (3.77) | FIG. 89 |
| Ex. VII-32 | C109 | 263.1~265.7 | 64.84 (64.70) | 3.21 (3.26) | 3.81 (3.77) | FIG. 90 |
| Ex. VII-33 | C110 | 165.2~167.8 | 76.65 (76.50) | 5.69 (5.54) | 4.00 (4.06) | FIG. 91 |
| Ex. VII-34 | C113 | 198.3~203.5 | 75.62 (75.70) | 4.65 (4.77) | 4.38 (4.41) | FIG. 92 |
| Ex. VII-35 | C108 | 228.2~239.5 | 64.79 (64.70) | 3.09 (3.26) | 3.63 (3.77) | FIG. 124 |

Example VII-36
Manufacturing <Coupler No.E12> Compound

Figure 70:
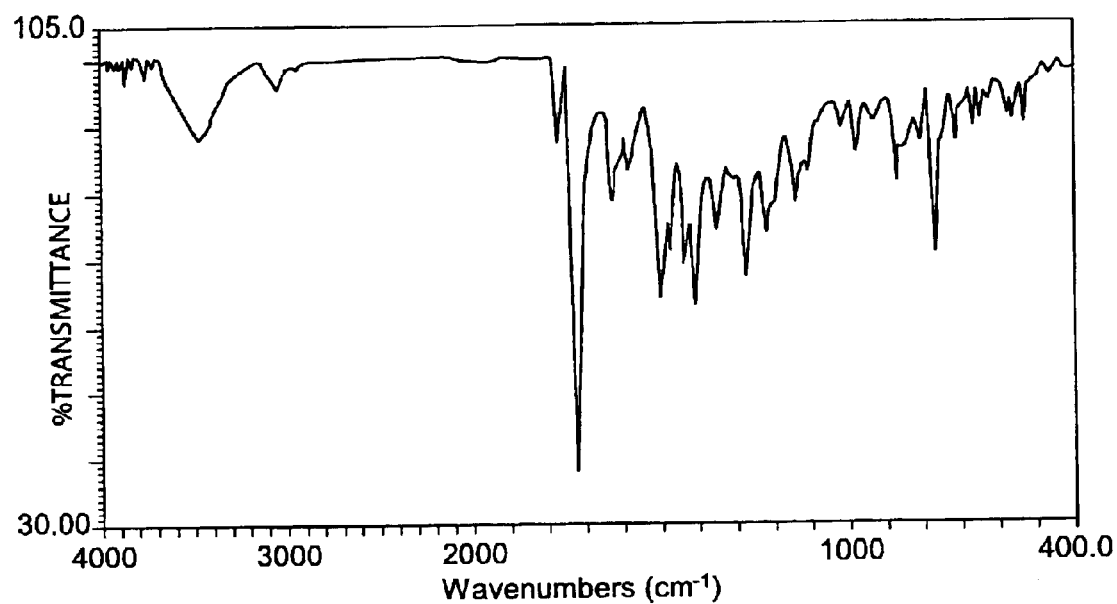
FIG. 70 is a graph showing an example of an infrared spectrum of an azo compound.

Except that 1,8-diamino naphthalene 12.66 g (0.08 mol) was used in o-phenylene diamine 8.65 g (0.08 mol), reaction was performed in the same way as the example VII-7, thus objective crude material 6.70 g was obtained. Obtained crude material was recrystallized by n-butanol, thus 4.07 g (33.5%) objective <coupler No. E12> was obtained. Melt points were 338.1 –340.9° C. An infrared absorption spectrum for the coupler compound <coupler No. E12> therefor is shown in FIG. 70.

Example VII-37
Manufacturing <Coupler No. E30> Compound

Figure 71:
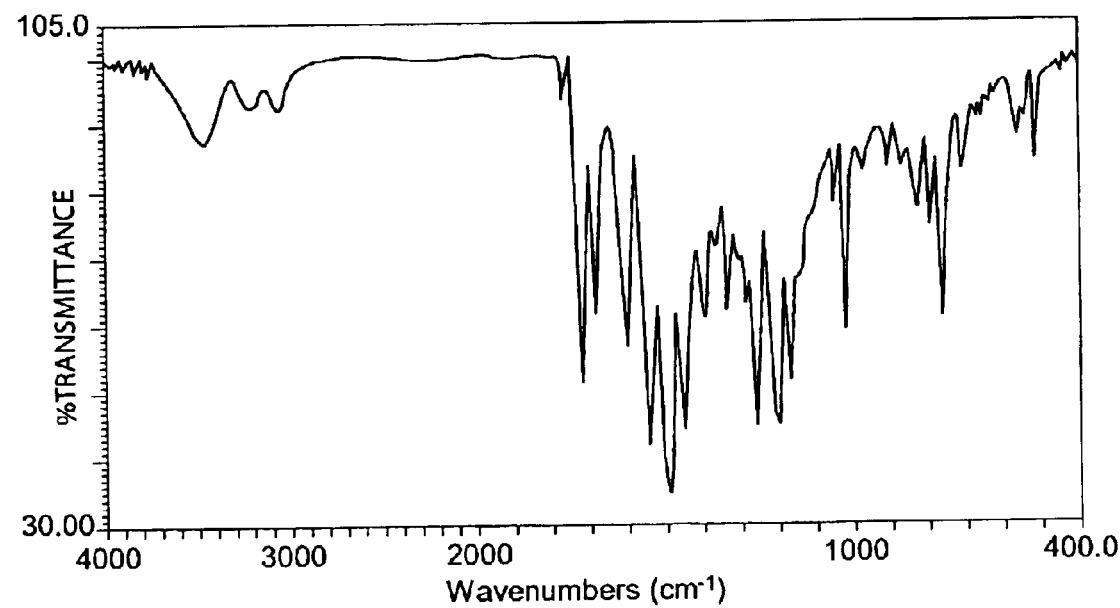
FIG. 71 is a graph showing an example of an infrared spectrum of an azo compound.

Except that 1,8-diamino naphthalene 12.66 g (0.08 mol) was used in o-amino benzyl amine 9.77 g (0.08 mol), reaction was made in the same way as the example VII-7, thus objective crude material 12.06 g was obtained. Obtained crude material was recrystallized by cyclo hexanoate/dimethyl formamide, thus objective material <coupler No. E30>9.19 g (76.5%) was obtained. Melt points were 347.0 –361.1° C. An infrared absorption spectrum for the coupler compound <coupler No. E30> therefor is shown in FIG. 71.

Example VII-38
Manufacturing <Coupler No. E31> Compound

Figure 72:
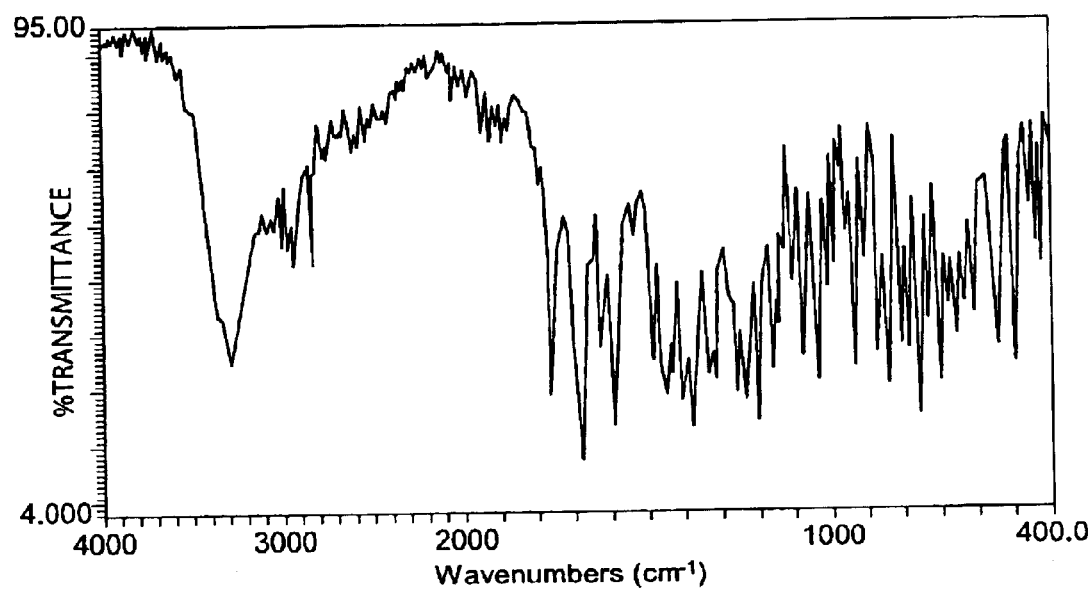
FIG. 72 is a graph showing an example of an infrared spectrum of a coupler compound.

Except that 1,8-diamino naphthalene 12.66 g (0.08 mol) was used in o-amino benzamide 10.89 g (0.08 mol), reaction was performed in the same way as the example VII-7, thus objective crude material 9.15 g was obtained. Obtained crude material was recrystallized by cyclo hexanoate/ dimethyl formamide, thus objective material <No. E31 >7.09 g (56.4%) was obtained. Melt points were 369.6 –372.9° C. An infrared absorption spectrum for coupler compound <coupler No. E31> is shown in FIG. 72.

Manufacturing Example 1
Manufacturing Azo Compound (Azo Compound No. P1
N-n-hexyl-2-hydroxy-7,8-naphthalic acid imido (coupler No. C1 compound) 0.89 g (3 mmol) was dissolved in DMF 80 ml, and 4-nitrobenzene diazonium tetra fluoro borate 0.71 g (3 mmol) was added thereto at a room temperature. Then, 10% by weight acetic acid sodium liquid solution 4.92 g was dropped for 10 minutes, reacted material, in which mixing reaction was performed for 6 hours at a room temperature, was poured on ice, then water was added thereto. After mixing was performed for more or less 1 hour, extracted crystal was filtered, then it was dried at the temperature of 50° C., thus objective material composition 1.03 g was obtained. Obtained composition material was processed by a silicagel column chromatography (toluene:acetic acid ethyl=4:1 as developing solvent) and recrystallized by toluene/ethanol, thus orange color azo compound (azo compound No. P1) was obtained. Obtained volume (yield), infrared absorption spectrum, and element analysis results are shown together in Table 67.

Manufacturing Example 2
Manufacturing Azo Compounds (Azo Compounds No. P17)
Except that 9-fluorenone-2,7-bis diazonium tetra fluoro borate 0.61 g (1.5 mmol) synthesized by 2,7-diamino-9-fluorenone in advance was used instead of 4-nitrobenzene diazonium tetra fluoro borate 0.71 g (3 mmol) in the example VII-1, objective material was manufactured in the same way as the example VII-1. Obtained volume (yield), an infrared absorption spectrum, and element analysis results are shown together in Table 67.

Manufacturing Example 3
Manufacturing Azo Compounds (Azo Compounds No. P19)
N-benzyl-2-hydroxy-7,8-naphthalic acid imido (coupler No. C5 compound) 0.91 g (3 mmol) manufactured in the example VII-4 was dissolved in DMF 100 ml, then at a room temperature, 9-fluorenone-2,7-bis diazonium tetra fluoro borate 0.61 g (1.5 mmol) compounded by 2,7-diamino-9-fluorenone in advance was added thereto. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P19) was obtained by drying at the temperature of 70° C. under a reduced pressure condition. The volume (yield), an infrared absorption spectrum, and element analysis results are indicated in Table 67.

Manufacturing Example 4
Manufacturing Azo Compounds (Azo Compounds No. P49)
Except that 1,4-dis tirril benzene-4',4"-diil-4',4"-bis diazonium tetra fluoro borate 0.77 g (1.5 mmol) synthesized by 4',4"-diamino-1,4-distirril benzene-4',4"-diil in advance was used instead of 9-fluorenone-2,7-bis diazonium tetra fluoro borate 0.61 g (1.5 mmol) in the example VII-10, objective material was manufactured in the same way as the embodiment 10. The volume (yield), an infrared absorption spectrum, and element analysis results are indicated in Table 67.

Manufacturing Example 5
Manufacturing Azo Compounds (Azo Compounds No. P74)
Except that triphenyl amine-4,4',4"-tris diazonium tetra fluoro borate 0.59 g (1.0 mmol) synthesized by -4,4',4"-triaminotriphenyl amine in advance was used instead of 9-fluorenone-2,7-bis diazonium tetra fluoro borate 0.61 g (1.5 mmol) in the example VII-10, objective material was manufactured in the same way as the example VII-10. The volume (yield), an infrared absorption spectrum, and element analysis results are indicated in Table 39.

Manufacturing Example 6
Manufacturing Azo Compounds (Azo Compounds No. P20)
N-benzyl-2-hydroxy-7,8-naphthalic acid imido (coupler No. C5 compound) 0.46 g (1.5 mmol) was dissolved in DMF 60 ml, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at a room temperature. Then, liquid solution composed of 2-hydroxy-3-(2-chloro phenyl carbamoyl)naphthalene (coupler No. 17 compound) 0.45 g (1.5 mmol) and DMF 40 ml were added thereto. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P20) was obtained by drying at the temperature of 70° C. under a reduced pressure condition. The volume (yield), an infrared absorption spectrum, and element analysis results are indicated in Table 67.

Manufacturing Example 7
Manufacturing Azo Compound (Azo Compound No. P50)
Except that 2-hydroxy-3-(2,4-dimethyl phenyl carbamoyl) naphthalene (coupler No. 43 compound) 0.44 g (1.5 mmol) was used instead of 9-fluorenone-2,7-bis diazonium tetra fluoro borate 0.61 g (1.5 mmol) in the example VII-13, 1,4-dis tirril benzene-4',4"-diil-4',4"-bis diazonium tetra fluoro borate 0.77 g (1.5 mmol), and 2-hydroxy-3-(2-chloro phenyl carbamoyl)naphthalene (coupler No.17 compound) 0.45 g (1.5 mmol) synthesized by 4',4"-diamino-1,4-dis tirril benzene4',4"-diil in advance, objective material was manufactured in the same way as the example VII-13. The volume (yield), an infrared absorption spectrum, and element analysis results are indicated in Table 67.

Manufacturing Example 8
Manufacturing Azo Compounds (Azo Compounds No. P23)
N-(2-phenyl, ethyl)-2-hydroxy-7,8-naphthalic acid imido (coupler No. C14 compound) 0.95 g (3 mmol) manufactured in the example VII-5 was dissolved in DMF 100 m, then 9-fluorenone-2,7-bis diazonium tetra fluoro borate 0.61 g (1.5 mmol) synthesized by 2,7-diamino-9-fluorenone in advance was added thereto at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P23) was obtained by drying at the temperature of 70° C. under a reduced pressure condition. The volume (yield), an infrared absorption spectrum, and element analysis results are indicated in Table 67.

Manufacturing Example 9
Manufacturing Azo Compounds (Azo Compounds No. P52)

Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance was used instead of 9-fluorenone-2,7-bis diazonium tetra fluoro borate 0.61 g (1.5 mmol) in the example 8, objective material was manufactured in the same way as the embodiment 8. The volume (yield), an infrared absorption spectrum, and element analysis results are indicated in Table 67.

Manufacturing Example 10
Manufacturing Azo Compounds (Azo Compound No. P77)

Except that triphenyl amine-4,4',4"-tris diazonium tetra fluoro borate 0.59 g (1.0 mmol) synthesized by 4,4',4"-triaminotriphenyl amine in advance was used instead of 9-fluorenone-2,7-bis diazonium tetra fluoro borate 0.61 g (1.5 mmol) in the example 8, objective material was manufactured in the same way as the embodiment 8. The volume (yield), an infrared absorption spectrum, and element analysis results are indicated in Table 67.

Manufacturing Example 11
Manufacturing Azo Compounds (Azo Compounds No. P24)

N-(2-phenyl ethyl)-2- hydroxy-7,8-naphthalic acid imido (coupler No. C14 compound) 0.48 g (1.5 mmol) manufactured in the example VII-5 was dissolved in DMF 60 ml, 9-fluorenone-2,7-bis diazonium tetra fluoro borate 0.61 g (1.5 mmol) synthesized by 2,7-diamino-9-fluorenone in advance was added at a room temperature, then mixing was performed for 30 minutes. Then, liquid solution composed of 2-hydroxy-3-(2-chloro phenyl carbamoyl) naphthalene (coupler No. 17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P24) was obtained by drying at the temperature of 70° C. under a reduced pressure condition. The volume (yield), an infrared absorption spectrum, and element analysis results are indicated in Table 67.

Manufacturing Example 12
Manufacturing Azo Compounds (Azo Compounds No. P53)

In the manufacturing example 11, instead of 9-fluorenone-2,7-bis diazonium tetra fluoro borate 0.61 g (1.5 mmol), 2-hydroxy-3-(2,4-dimethyl phenyl carbamoyl) naphthalene (coupler No. 43 compound) 0.44 g (1.5 mmol) was used instead of 1,4-dis tirril benzene-4',4"-diil-4',4"-bis diazonium tetra fluoro borate 0.77 g (1.5 mmol) and 2-hydroxy-3-(2-chloro phenyl carbamoyl)naphthalene (coupler No. 17 compound) 0.45 g (1.5 mmol) synthesized by 4',4"-diamino-1,4-dis tirril benzene4',4"-diil in advance, objective material was manufactured in the same way as the manufacturing example 11. The volume (yield), an infrared absorption spectrum, and element analysis results are indicated in Table 67.

Manufacturing Example 13
Manufacturing Azo Compounds (Azo Compounds No. P27)

N-phenyl-2-hydroxy-7,8-naphthalic acid imido (coupler No. C28 compound) 0.87 g (3 mmol) manufactured in the example VII-6 was dissolved in DMF 100 ml, and 9-fluorenone-2,7-bis diazonium tetra fluoro borate 0.61 g (1.5 mmol) synthesized by 2,7-diamino-9-fluorenone in advance was added at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P27) was obtained by drying at the temperature of 70° C. under a reduced pressure condition. The volume (yield), an infrared absorption spectrum, and element analysis results are indicated in Table 67.

Manufacturing Example 14
Manufacturing Azo Compounds (Azo Compounds No. P57)

Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance in the manufacturing example 13 was used instead of 9-fluorenone-2,7-bis diazonium tetra fluoro borate 0.61 g (1.5 mmol) in the manufacturing example 13, objective material was manufactured in the same way as the manufacturing example 13. The volume (yield), an infrared absorption spectrum, and element analysis results are indicated in Table 67.

Manufacturing Example 15
Manufacturing Azo Compounds (Azo Compounds No. P81)

Except that triphenyl amine-4,4',4"-tris diazonium tetra fluoro borate 0.59 g (1.0 mmol) synthesized by 4,4',4"-triamino triphenyl amine in advance was used instead of 9-fluorenone-2,7-bis diazonium tetra fluoro borate 0.61 g (1.5 mmol) in the manufacturing example 13, objective material was manufactured in the same way as the manufacturing example 13. The volume (yield), an infrared absorption spectrum, and element analysis results are indicated in Table 67.

Manufacturing Example 16
Manufacturing Azo Compounds (Azo Compounds No. P28)

N-phenyl-2-hydroxy-7,8-naphthalic acid imido (coupler No. C28 compound) 0.43 g (1.5 mmol) was dissolved in DMF 60 ml at a room temperature, 9-fluorenone-2,7-bis diazonium tetra fluoro borate 0.61 g (1.5 mmol) synthesized by 2,7-diamino-9-fluorenone in advance was added, then mixing was performed thereto for 30 minutes at a room temperature. Then, liquid solution composed of 2-hydroxy-3-(2-chloro phenyl carbamoyl)naphthalene (coupler No. 17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P28) was obtained by drying at the temperature of 70° C. under a reduced pressure condition. The volume (yield), an infrared absorption spectrum, and element analysis results are indicated in Table 67.

Manufacturing Example 17
Manufacturing Azo Compounds (Azo Compounds No. P58)

In the manufacturing example 16, instead of 9-fluorenone-2,7-bis diazonium tetra fluoro borate 0.61 g (1.5 mmol), 2-hydroxy-3-(2,4-dimethyl phenyl carbamoyl) naphthalene (coupler No.43 compound) 0.44 g (1.5 mmol) was used instead of 1,4-dis tirril benzene-4',4"-diil-4',4"-bis diazonium tetra fluoro borate 0.77 g (1.5 mmol) and 2-hydroxy-3-(2-chloro phenyl carbamoyl)naphthalene (coupler No. 17 compound) 0.45 g (1.5 mmol) synthesized by 4',4"-diamino-1,4-dis tirril benzene4',4"-diil in advance, objective material was manufactured in the same way as the manufacturing example 16. The volume (yield), an infrared absorption spectrum, and element analysis results are indicated in Table 67.

Manufacturing Example 18
Manufacturing Azo Compounds (Azo Compounds No. P59)
Except that 1,4-dis tirril benzene-4',4"-diil-4',4"-bis diazonium tetra fluoro borate 0.77 g (1.5 mmol) synthesized by 4',4"-diamino-1,4-dis tirril benzene4',4"-diil in advance in the manufacturing example 16 was used instead of 9-fluorenone-2,7-bis diazonium tetra fluoro borate 0.61 g (1.5 mmol) in the manufacturing example 13, objective material was manufactured in the same way as the manufacturing example 16. The volume (yield), an infrared absorption spectrum, and element analysis results are indicated in Table 67.

Manufacturing Example 19
Manufacturing Azo Compounds (Azo Compounds No. P38)
12-hydroxy-benzo[6,7]isoindole[2,1-a]perimysin-14-on, or 9-hydroxy-benzo[4,5]isoindole[2,1-a]perimysin-14-on [coupler No. E23 compound] 1.01 g (3 mmol) manufactured in the example VII-7 was dissolved in DMSO 100 ml at the temperature of 80° C., after cooling at a room temperature, 9-fluorenone-2,7-bis diazonium tetra fluoro borate 0.61 g (1.5 mmol) synthesized by 2,7-diamino-9-fluorenone in advance was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P38) was obtained by drying at the temperature of 70° C. under a reduced pressure condition. The volume (yield), an infrared absorption spectrum, and element analysis results are indicated in Table 67.

Manufacturing Example 20
Manufacturing Azo Compounds (Azo Compounds No. P66)
Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance in the manufacturing example 19 was used instead of 9-fluorenone-2,7-bis diazonium tetra fluoro borate 0.61 g (1.5 mmol) in the manufacturing example 13, objective material was manufactured in the same way as the manufacturing example 19. The volume (yield), an infrared absorption spectrum, and element analysis results are indicated in Table 67.

Manufacturing Example 21
Manufacturing Azo Compounds (Azo Compounds No. P86)
Except that triphenyl amine4,4',4"-tris diazonium tetra fluoro borate 0.59 g (1.0 mmol) synthesized by 4,4',4"-triamino triphenyl amine in advance was used instead of 9-fluorenone-2,7-bis diazonium tetra fluoro borate 0.61 g (1.5 mmol) in the manufacturing example 19, objective material was manufactured in the same way as the manufacturing example 19. The volume (yield), an infrared absorption spectrum, and element analysis results are indicated in Table 67.

Manufacturing Example 22
Manufacturing Azo Compounds (Azo Compounds No. P39)
12-hydroxy-benzo[6,7]isoindole[2,1-a]perimysin-14-on, or 9-hydroxy-benzo[4,5]isoindole[2,1-a]perimysin-14-on [coupler No. E23 compound] 0.50 g (1.5 mmol) manufactured in the example VII-7 was dissolved in DMSO 60 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at a room temperature. Then, liquid solution Composed of 2-hydroxy-3-(2-chloro phenyl carbamoyl)naphthalene (coupler No.17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P39) was obtained by drying at the temperature of 70° C. under a reduced pressure condition. The volume (yield), an infrared absorption spectrum, and element analysis results are indicated in Table 67.

Manufacturing Example 23
Manufacturing Azo Compounds (Azo Compounds No. P67)
Instead of 9-fluorenone-2,7-bis diazonium tetra fluoro borate 0.61 g (1.5 mmol) in the example VII-29, except that 2-hydroxy-3-(2,4-dimethyl phenyl carbamoyl)naphthalene (coupler No. 43 compound) 0.44 g (1.5 mmol) was used instead of 1,4-dis tirril benzene-4',4"-diil-4',4"-bis diazonium tetra fluoro borate 0.77 g (1.5 mmol) and 2-hydroxy-3-(2-chloro phenyl carbamoyl)naphthalene (coupler No. 17 compound) 0.45 g (1.5 mmol) synthesized by 4',4"-diamino-1,4-dis tirril benzene-4',4"-diil in advance, objective material was manufactured in the same way as the example VII-29. The volume (yield), an infrared absorption spectrum, and element analysis results are indicated in Table 30.

Manufacturing Example 24
Manufacturing Azo Compounds (Azo Compounds No. 102)
Except that n-(4-dimethyl benzyl)-2-hydroxy-7,8-naphthalic acid imido (coupler No. C9 compound) 0.95 g (3 mmol) manufactured in the example VII-8 was used instead of N-benzyl-2-hydroxy-7,8-naphthalic acid imido 0.91 g (3 mmol) in the manufacturing example 3, objective material was manufactured in the same way as the manufacturing example 3. The volume (yield), an infrared absorption spectrum, and element analysis results are indicated in Table 30.

Manufacturing Example 25
Manufacturing Azo Compounds (Azo Compounds No. 103)
Except that n-(4-dimethyl benzyl)-2-hydroxy-7,8-naphthalic acid imido (coupler No. C9 compound) 0.48 g (1.5 mmol) manufactured in the example VII-8 was used instead of N-benzyl-2-hydroxy-7,8-naphthalic acid imido 0.46 g (1.5 mmol) in the manufacturing example 6, objective material was manufactured in the same way as the manufacturing example 6. The volume (yield), an infrared absorption spectrum, and element analysis results are indicated in Table 67.

Manufacturing Example 26
Manufacturing Azo Compounds (Azo Compounds No.P21)
Except that n-(4-methoxy benzyl)-2-hydroxy-7,8-naphthalic acid imido (coupler No. C10 compound) 1.00 g (3 mmol) manufactured in the example VII-9 was used instead of n-benzyl-2-hydroxy-7,8-naphthalic acid imido 0.91 g (3 mmol) in the manufacturing example 3, objective

Manufacturing Example 27
Manufacturing Azo Compounds (Azo Compounds No.P104)

Except that n-(4-methoxy benzyl)-2-hydroxy-7,8-naphthalic acid imido (coupler No. C10 compound) 0.50 g (1.5 mmol) manufactured in the example VII-9 was used instead of n-benzyl-2-hydroxy-7,8-naphthalic acid imido 046 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 28
Manufacturing Azo Compounds (Azo Compounds No. P134)

Except that n-(4-chloro dibenzyl)-2-hydroxy-7,8-naphthalic acid imido (coupler No. C11 compound) 1.01 g (3 mmol) manufactured in the example VII-10 was used instead of n-benzyl-2-hydroxy-7,8-naphthalic acid imido 0.91 g (3 mmol) in the manufacturing example 3, objective material was manufactured in the same way as the manufacturing example 3. Obtained volume (yield), an infrared absorption spectrum, and element analysis results are shown together in Table 67.

Manufacturing Example 29
Manufacturing Azo Compounds (Azo Compounds No. P135)

Except that n-(4-chloro dibenzyl)-2-hydroxy-7,8-naphthalic acid imido (coupler No. C11 compound) 0.51 g (1.5 mmol) manufactured in the example VII-10 was used instead of n-benzyl-2-hydroxy-7,8-naphthalic acid imido 0.46 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 30
Manufacturing Azo Compounds (Azo Compounds No.P22)

Except that n-(1-naphthyl dimethyl)-2-hydroxy-7,8-naphthalic acid imido (coupler No. C13 compound) 1.06 g (3 mmol) manufactured in the example VII-11 was used instead of n-benzyl-2-hydroxy-7,8-naphthalic acid imido 0.91 g (3 mmol) in the example 3, objective material was manufactured in the same way as the manufacturing example 3. Obtained volume (yield), an infrared absorption spectrum, and element analysis results are shown together in Table 67.

Manufacturing Example 31
Manufacturing Azo Compounds (Azo Compounds No.P105)

Except that n-(1-naphthyl dimethyl)-2-hydroxy-7,8-naphthalic acid imido (coupler No. C13 compound) 0.53 g (1.5 mmol) manufactured in the example VII-11 was used instead of n-benzyl-2-hydroxy-7,8-naphthalic acid imido 0.46 g (1.5 mmol) in the example 6, objective material was manufactured in the same way as the manufacturing example 6. Obtained volume (yield), an infrared absorption spectrum, and element analysis results are shown together in Table 67.

Manufacturing Example 32
Manufacturing Azo Compounds (Azo Compounds No. P11)

Except that n-(4-nitrobenzyl)-2-hydroxy-7,8-naphthalic acid imido (coupler No. C59 compound) 1.05 g (3 mmol) manufactured in the example VII-12 was used instead of n-benzyl-2-hydroxy-7,8-naphthalic acid imido 0.91 g (3 mmol) in the manufacturing example 3, objective material was manufactured in the same way as the manufacturing example 3. Obtained volume (yield), an infrared absorption spectrum, and element analysis results are shown together in Table 67.

Manufacturing Example 33
Manufacturing Azo Compounds (Azo Compounds No. P113)

Except that n-(4-nitrobenzyl)-2-hydroxy-7,8-naphthalic acid imido (coupler No. C59 compound) 0.52 g (1.5 mmol) manufactured in the example VII-12 was used instead of n-benzyl-2-hydroxy-7,8-naphthalic acid imido 0.46 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 34
Manufacturing Azo Compounds (Azo Compounds No. P11)

Except that n-(4-biphenyl dimethyl)-2-hydroxy-7,8-naphthalic acid imido (coupler No. C60 compound) 1.14 g (3 mmol) manufactured in the example VII-12 was used instead of n-benzyl-2-hydroxy-7,8-naphthalic acid imido 0.91 g (3 mmol) in the manufacturing example 3, objective material was manufactured in the same way as the manufacturing example 3. Obtained volume (yield), an infrared absorption spectrum, and element analysis results are shown together in Table 67.

Manufacturing Example 35
Manufacturing Azo Compounds (Azo Compounds No. P115)

Except that n-(4-biphenyl dimethyl)-2-hydroxy-7,8-naphthalic acid imido (coupler No. C60 compound) 0.57 g (1.5 mmol) manufactured in the example VII-13 was used instead of n-benzyl-2-hydroxy-7,8-naphthalic acid imido 0.46 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 36
Manufacturing Azo Compounds (Azo Compounds No. P35)

Except that coupler compound (coupler No. E12) 0.43 g (1.5 mmol) manufactured in the example VII-35 was used instead of n-benzyl-2-hydroxy-7,8-naphthalic acid imido 0.46 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 37
Manufacturing Azo Compounds (Azo Compounds No. P106)

Except that coupler compounds (coupler No. C54) 1.01 g (3 mmol) manufactured in the example VII-20 was used instead of N-benzyl-2-hydroxy-7,8-naphthalic acid imido 0.91 g (3 mmol) in the manufacturing example 3, objective

Manufacturing Example 38
Manufacturing Azo Compounds (Azo Compounds No. P107)

Except that coupler compounds (coupler No. C54) 0.51 g (1.5 mmol) manufactured in the example VII-20 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 39
Manufacturing Azo Compounds (Azo Compounds No. P108)

Except that coupler compounds (coupler No. C55) 1.01 g (3 mmol) manufactured in the example VII-21 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 40
Manufacturing Azo Compounds (Azo Compounds No. P109)

Except that coupler compounds (coupler No. C55) 0.51 g (1.5 mmol) manufactured in the example VII-21 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 41
Manufacturing Azo Compounds (Azo Compounds No. P110)

Except that coupler compounds (coupler No. C56) 0.96 g (3 mmol) manufactured in the example VII-22 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 42
Manufacturing Azo Compounds (Azo Compounds No. P111)

Except that coupler compounds (coupler No. C56) 0.48 g (1.5 mmol) manufactured in the example VII-22 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 43
Manufacturing Azo Compounds (Azo Compounds No. P116)

Except that coupler compounds (coupler No. C61) 1.28 g (3 mmol) manufactured in the example VII-23 was used instead of N-benzyl-2-hydroxy-7,8-naphthalene acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 44
Manufacturing Azo Compounds (Azo Compounds No. P117)

Except that coupler compounds (coupler No. C61) 0.64 g (1.5 mmol) manufactured in the example VII-23 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 45
Manufacturing Azo Compounds (Azo Compounds No. P120)

Except that coupler compounds (coupler No. C83) 0.95 g (3 mmol) manufactured in the example VII-24 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 46
Manufacturing Azo Compounds (Azo Compounds No. P121)

Except that coupler compounds (coupler No. C83) 0.48 g (1.5 mmol) manufactured in the example VII-24 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 47
Manufacturing Azo Compounds (Azo Compounds No. P122)

Except that coupler compounds (coupler No. C92) 1.00 g (3 mmol) manufactured in the example VII-25 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 48
Manufacturing Azo Compounds (Azo Compounds No. P123)

Except that coupler compounds (coupler No. C92) 0.50 g (1.5 mmol) manufactured in the example VII-25 was used instead of N-benzyl-2-hydroxy-7,8-naphthalic acid imido 0.46 g (1.5 mmol) in the manufacturing example 6, objective material was manufactured in the same way as the manu-

Manufacturing Example 49
Manufacturing Azo Compounds (Azo Compounds No. P132)

Except that coupler compounds (coupler No. E31) 0.94 g (3 mmol) manufactured in the example VII-37 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 50
Manufacturing Azo Compounds (Azo Compounds No. P133)

Except that coupler compounds (coupler No. E31) 0.47 g (1.5 mmol) manufactured in the example VII-37 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 51
Manufacturing Azo Compounds (Azo Compounds No. P136)

Except that coupler compounds (coupler No. C24) 0.99 g (3 mmol) manufactured in the example VII-15 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 52
Manufacturing Azo Compounds (Azo Compounds No. P137)

Except that coupler compounds (coupler No. C24) 0.50 g (1.5 mmol) manufactured in the example VII-15 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 53
Manufacturing Azo Compounds (Azo Compounds No. P138)

Except that coupler compounds (coupler No. C40) 1.24 g (3 mmol) manufactured in the example VII-22 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 54
Manufacturing Azo Compounds (Azo Compounds No. P139)

Except that coupler compounds (coupler No. C40) 0.62 g (1.5 mmol) manufactured in the example VII-17 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 55
Manufacturing Azo Compounds (Azo Compounds No. P140)

Except that coupler compounds (coupler No. C37) 1.02 g (3 mmol) manufactured in the example VII-16 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 56
Manufacturing Azo Compounds (Azo Compounds No. P141)

Except that coupler compounds (coupler No. C37) 0.62 g (1.5 mmol) manufactured in the example VII-16 was used instead of N-benzyl-2-hydroxy-7,8-naphthalic acid imido 0.51 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 57
Manufacturing Azo Compounds (Azo Compounds No. P142)

Except that coupler compounds (coupler No. C110) 1.04 g (3 mmol) manufactured in the example VII-33 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 58
Manufacturing Azo Compounds (Azo Compounds No. P143)

Except that coupler compounds (coupler No. C11) 0.52 g (1.5 mmol) manufactured in the example VII-33 was used instead of N-benzyl-2-hydroxy-7,8-naphthalic acid imido 0.51 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 59
Manufacturing Azo Compounds (Azo Compounds No. P144)

Except that coupler compounds (coupler No. C50) 0.95 g (3 mmol) manufactured in the example VII-19 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 60
Manufacturing Azo Compounds (Azo Compounds No. P145)

Except that coupler compounds (coupler No. C50) 0.48 g (1.5 mmol) manufactured in the example VII-19 was used instead of N-benzyl-2-hydroxy-7,8-naphthalic acid imido 0.51 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 61
Manufacturing Azo Compounds (Azo Compounds No. P14)

Except that 2(5)-hydroxy-7H-benzimidazo [2,1-a] benzisoquinoline-7 (coupler No. 195 compound) 0.43 g (1.5 mmol) was used instead of 2-hydroxy-3-(2-chloro phenyl carbamoyl)naphthalene (coupler No.17 compound) 0.45 g (1.5 mmol) in the manufacturing example 6, objective material was manufactured in the same way as the manufacturing example 6. Obtained volume (yield), an infrared absorption spectrum, and element analysis results are shown together in Table 67.

Manufacturing Example 62
Manufacturing Azo Compounds (Azo Compounds No. P153)

Except that coupler compounds (coupler No. C104) 0.99 g (3 mmol) manufactured in the example VII-28 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 63
Manufacturing Azo Compounds (Azo Compounds No. P154)

Except that coupler compounds (coupler No. C104) 0.49 g (1.5 mmol) manufactured in the example VII-28 was used instead of N-benzyl-2-hydroxy-7,8-naphthalic acid imido 0.51 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 64
Manufacturing Azo Compounds (Azo Compounds No. P88)

N-benzyl-2-hydroxy-7,8-naphthalic acid imido (coupler No. C5 compound) 0.91 g (3 mmol) in the example VII-4 was dissolved in DMF 100 ml, then 9,10-phenanthrene quinone 2,7-bis diazonium tetra fluoro borate 0.70 g (1.5 mmol) synthesized by 2,7-diamino-9,10-phenanthrene quinone at a room temperature in advance was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P88) were obtained. Obtained volume (yield), infrared absorption spectrum, and element analysis results are shown together in Table 67.

Manufacturing Example 65
Manufacturing Azo Compounds (Azo Compounds No. P89)

Except that coupler compounds (coupler No. C14) 0.95 g (3 mmol) manufactured in the example VII-5 was used instead of N-benzyl-2-hydroxy-7,8-naphthalic acid imido 0.91 g (3 mmol) in the manufacturing example 64, objective material was manufactured in the same way as the manufacturing example 64. Obtained volume (yield), infrared absorption spectrum, and element analysis results are shown together in Table 67.

Manufacturing Example 66
Manufacturing Azo Compounds (Azo Compounds No. P91)

Except that coupler compounds (coupler No. C28) 0.87 g (3 mmol) manufactured in the example VII-6 was used instead of N-benzyl-2-hydroxy-7,8-naphthalic acid imido 0.91 g (3 mmol) in the manufacturing example 64, objective material was manufactured in the same way as the manufacturing example 64. Obtained volume (yield), infrared absorption spectrum, and element analysis results are shown together in Table 67.

Manufacturing Example 67
Manufacturing Azo Compounds (Azo Compounds No. P124)

Except that coupler compounds (coupler No. C95) 1.23 g (3 mmol) manufactured in the example VII-26 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 68
Manufacturing Azo Compounds (Azo Compounds No. P125)

Except that coupler compounds (coupler No. C95) 0.61 g (1.5 mmol) manufactured in the example VII-26 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 69
Manufacturing Azo Compounds (Azo Compounds No. P147)

Except that coupler compounds (coupler No. C12) 1.00 g (3 mmol) manufactured in the example VII-14 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 70
Manufacturing Azo Compounds (Azo Compounds No. P148)

Except that coupler compounds (coupler No. C12) 0.50 g (1.5 mmol) manufactured in the example VII-14 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 71
Manufacturing Azo Compounds (Azo Compounds No. P149)

Except that coupler compounds (coupler No. C49) 1.00 g (3 mmol) manufactured in the example VII-18 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 72
Manufacturing Azo Compounds (Azo Compounds No. P150)

Except that coupler compounds (coupler No. C49) 0.50 g (1.5 mmol) manufactured in the example VII-18 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 73
Manufacturing Azo Compounds (Azo Compounds No. P155)

Except that coupler compounds (coupler No. C105) 0.99 g (3 mmol) manufactured in the example VII-29 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 74
Manufacturing Azo Compounds (Azo Compounds No. P156)

Except that coupler compounds (coupler No. C105) 0.49 g (1.5 mmol) manufactured in the example VII-29 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 75
Manufacturing Azo Compounds (Azo Compounds No. P157)

Except that coupler compounds (coupler No. C106) 1.03 g (3 mmol) manufactured in the example VII-30 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 76
Manufacturing Azo Compounds (Azo Compounds No. P158)

Except that coupler compounds (coupler No. C106) 0.52 g (1.5 mmol) manufactured in the example VII-30 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 77
Manufacturing Azo Compounds (Azo Compounds No. P159)

Except that coupler compounds (coupler No. C107) 1.11 g (3 mmol) manufactured in the example VII-31 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 78
Manufacturing Azo Compounds (Azo Compounds No. P160)

Except that coupler compounds (coupler No. C107) 0.56 g (1.5 mmol) manufactured in the example VII-31 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 79
Manufacturing Azo Compounds (Azo Compounds No. P161)

Except that coupler compounds (coupler No. C108) 1.11 g (3 mmol) manufactured in the example VII-35 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 80
Manufacturing Azo Compounds (Azo Compounds No. P162)

Except that coupler compounds (coupler No. C108) 0.56 g (1.5 mmol) manufactured in the example VII-35 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 81
Manufacturing Azo Compounds (Azo Compounds No. P163)

Except that coupler compounds (coupler No. C109) 1.11 g (3 mmol) manufactured in the example VII-32 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 82
Manufacturing Azo Compounds (Azo Compounds No. P164)

Except that coupler compounds (coupler No. C109) 0.56 g (1.5 mmol) manufactured in the example VII-32 was used

Manufacturing Example 83
Manufacturing Azo Compounds (Azo Compounds No. P169)

Except that coupler compounds (coupler No. C113) 0.95 g (3 mmol) manufactured in the example VII-34 was used instead of N-benzyl-2-hydroxy-7,8-naphthalic acid imido 0.91 g (3 mmol) in the manufacturing example 3, objective material was manufactured in the same way as the manufacturing example 3. Obtained volume (yield), infrared absorption spectrum, and element analysis results are shown together in Table 67.

Manufacturing Example 84
Manufacturing Azo Compounds (Azo Compounds No. P170)

Except that coupler compounds (coupler No. C113) 0.48 g (1.5 mmol) manufactured in the example VII-34 was used instead of N-benzyl-2-hydroxy-7,8-naphthalic acid imido 0.46 g (1.5 mmol) in the manufacturing example 6, objective material was manufactured in the same way as the manufacturing example 6. Obtained volume (yield), infrared absorption spectrum, and element analysis results are shown together in Table 67.

Manufacturing Example 85
Manufacturing Azo Compounds (Azo Compounds No. P173)

Coupler compound (coupler No. E30) 0.90 g (3 mmol) manufactured in the example VII-37 was dissolved in DMF 100 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone at a room temperature in advance was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P173) were obtained. Obtained volume (yield), infrared absorption spectrum, and element analysis results are shown together in Table 67.

Manufacturing Example 86
Manufacturing Azo Compounds (Azo Compounds No. P174)

Coupler compound (coupler No. E30) 0.45 g (1.5 mmol) manufactured in the example VII-37 was dissolved in DMF 60 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at the room temperature. Then, liquid solution composed of 2-hydroxy-3-(2-chloro phenyl carbamoyl)naphthalene (coupler No. 17 compound) 0.45 g (1.5 mmol) and DMF 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P174) were obtained. Obtained volume (yield), infrared absorption spectrum, and element analysis results are shown together in Table 67.

Manufacturing Example 87
Manufacturing Azo Compounds (Azo Compounds No. P180)

N-benzyl-2-hydroxy-7,8-naphthalic acid imido(coupler No. C5 compound) 0.46 g (1.5 mmol) manufactured in the example VII-4 was dissolved in DMF 60 ml, then 9,10-phenanthrene quinone-2,7-bis diazonium tetra fluoro borate 0.70 g (1.5 mmol) synthesized by 2,7-diamino-9,10-phenanthrene quinone in advance at a room temperature was added, further mixing was performed for 30 minutes at the room temperature. Then, liquid solution composed of 2-hydroxy-3-phenyl carbamoyl naphthalene (No.1 compound) 0.39 g (1.5 mmol) and DMF 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P180) were obtained. Obtained volume (yield), infrared absorption spectrum, and element analysis results are shown together in Table 67.

Manufacturing Example 88
Manufacturing Azo Compounds (Azo Compounds No. P181)

Except that coupler compounds (coupler No. C14) 0.48 g (1.5 mmol) manufactured in the example VII-5 was used instead of N-benzyl-2-hydroxy-7,8-naphthalic acid imido 0.46 g (1.5 mmol) in the manufacturing example 87, objective material was manufactured in the same way as the manufacturing example 87. Obtained volume (yield), infrared absorption spectrum, and element analysis results are shown together in Table 67.

Manufacturing Example 89
Manufacturing Azo Compounds (Azo Compounds No. P182)

Except that coupler compounds (coupler No. C24) 0.99 g (3 mmol) manufactured in the example VII-15 was used instead of N-benzyl-2-hydroxy-7,8-naphthalic acid imido 0.91 g (3 mmol) in the manufacturing example 64, objective material was manufactured in the same way as the manufacturing example 64. Obtained volume (yield), infrared absorption spectrum, and element analysis results are shown together in Table 67.

Manufacturing Example 90
Manufacturing Azo Compounds (Azo Compounds No. P183)

Except that coupler compounds (coupler No. C24) 0.50 g (1.5 mmol) manufactured in the example VII-15 was used instead of N-benzyl-2-hydroxy-7,8-naphthalic acid imido 0.46 g (1.5 mmol) in the manufacturing example 87, objective material was manufactured in the same way as the manufacturing example 87. Obtained volume (yield), infrared absorption spectrum, and element analysis results are shown together in Table 67.

Manufacturing Example 91
Manufacturing Azo Compounds (Azo Compounds No. P184)

Except that coupler compounds (coupler No. C28) 0.43 g (1.5 mmol) manufactured in the example VII-6 was used instead of N-benzyl-2-hydroxy-7,8-naphthalic acid imido 0.46 g (1.5 mmol) in the manufacturing example 87, objective material was manufactured in the same way as the manufacturing example 87. Obtained volume (yield), infrared absorption spectrum, and element analysis results are shown together in Table 67.

Manufacturing Example 92
Manufacturing Azo Compounds (Azo Compounds No. P185)

12-hydroxy-benzo[6,7]isoindole[2,1-a]perimysin-14-on, or 9-hydroxy-benzo[4,5]isoindole[2,1-a]perimysin-14-on [coupler No.E23 compound] 1.01 g (3 mmol) manufactured in the example VII-7 was dissolved in DMSO 100 ml at the temperature of 80° C., after cooling it till it reached a room temperature, then 9,10-phenanthrene quinone-2,7-bis diazonium tetra fluoro borate 0.70 g (1.5 mmol) synthesized by 2,7-diamino-9,10-phenanthrene quinone in advance at a room temperature was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P185) were obtained. Obtained volume (yield), infrared absorption spectrum, and element analysis results are shown together in Table 67.

Manufacturing Example 93
Manufacturing Azo Compounds (Azo Compounds No. P186)

12-hydroxy-benzo[6,7]isoindole[2,1-a]perimysin-14-on, or 9-hydroxy-benzo[4,5]isoindole[2,1-a]perimysin-14-on (coupler No.E23 compound) 0.50 g (1.5 mmol) manufactured in the example VII-7 was dissolved in DMSO 60 ml at the temperature of 80° C., after cooling it till it reached a room temperature, 9,10-phenanthrene quinone-2,7-bis diazonium tetra fluoro borate 0.70 g (1.5 mmol) synthesized by 2,7-diamino-9,10-phenanthrene quinone in advance at a room temperature was added, then mixing was performed for 30 minutes at the room temperature. Then, liquid solution composed of 2-hydroxy-3-phenyl carbamoyl naphthalene (coupler No.1 compound) 0.39 g (1.5 mmol) and DMSO 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P186) were obtained. Obtained volume (yield), infrared absorption spectrum, and element analysis results are shown together in Table 67.

Manufacturing Example 34
Manufacturing Azo Compounds (Azo Compounds No. P187)

Except that coupler compound (coupler No. E30) 0.90 g (3 mmol) manufactured in the example VII-37 was used instead of 12-hydroxy benzo[6,7]isoindole[2,1-a]perimysin-14-on, or 9-hydroxy-benzo[4,5]isoindole[2,1-a]perimysin-14-on (coupler No. E23 compound) 1.01 g (3 mmol) in the manufacturing example 92, objective material was manufactured in the same way as the manufacturing example 92. Obtained volume (yield), an infrared absorption spectrum, and element analysis results are shown together in Table 67.

Manufacturing Example 95
Manufacturing Azo Compounds (Azo Compounds No. P188)

Except that coupler compounds (coupler No. E30) 0.45 g (1.5 mmol) manufactured in the example VII-37 were used instead of benzo[6, 7]isoindole[2, 1-a]perimidine-14-on, or 9-hydroxybenzo 4, 5] isoindole 2, 1-a]perimidine-14-on (coupler No. E23 compound) 0.50 g (1.5 mmol) in manufacturing example 93, objective material was manufactured in the same way as the manufacturing example 93. Obtained volume (yield), infrared absorption spectrum, and element analysis results are shown together in Table 67.

TABLE 67-1

Figure 37:
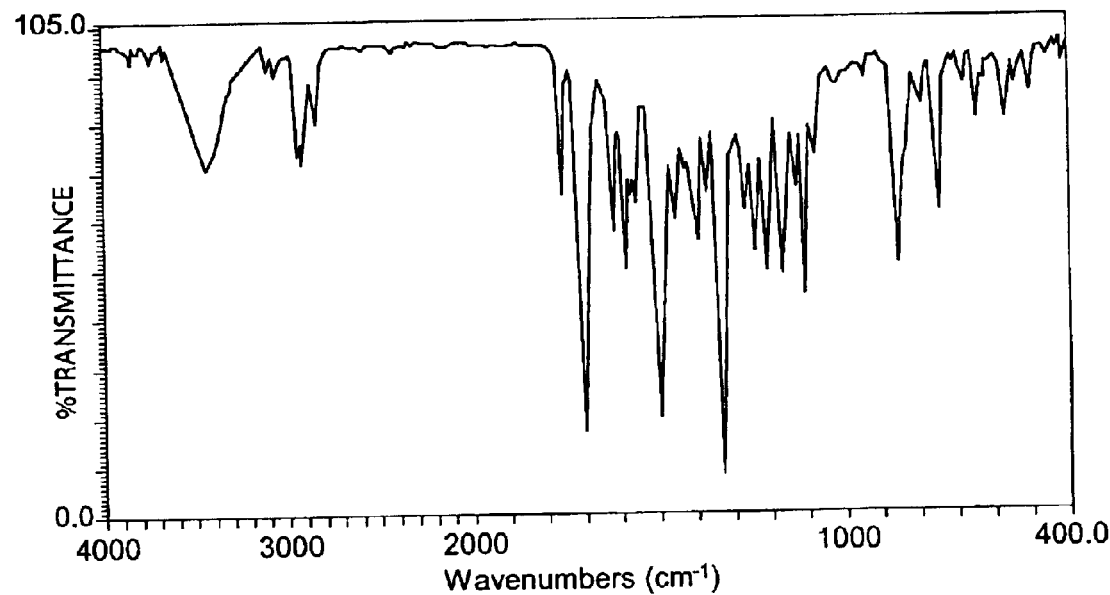
FIG. 37 is a graph showing an example of an infrared spectrum of an azo compound.
Figure 38:
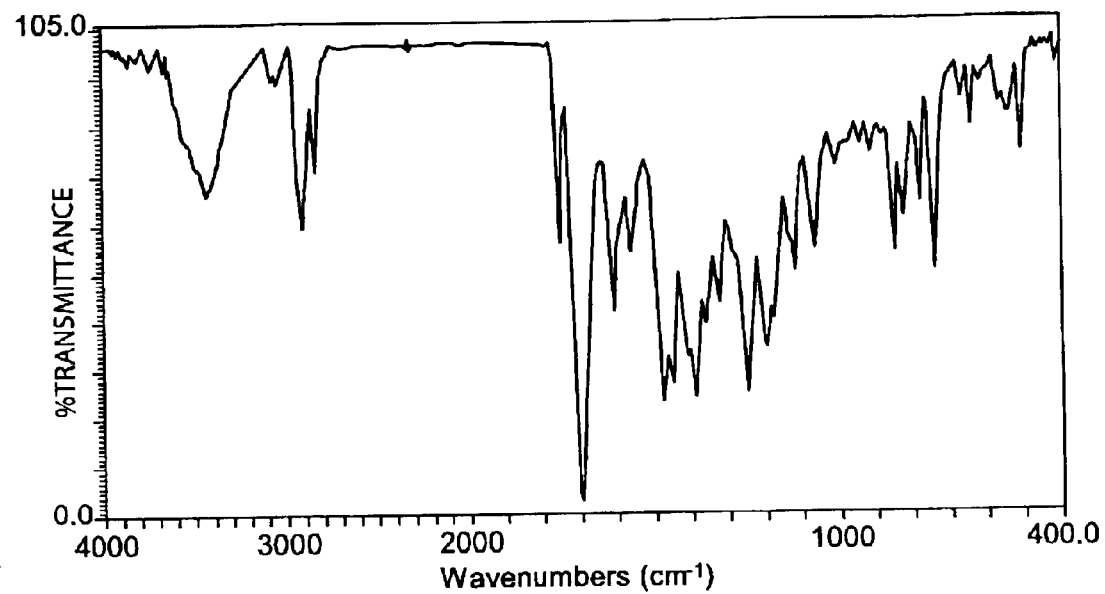
FIG. 38 is a graph showing an example of an infrared spectrum of an azo compound.
Figure 39:
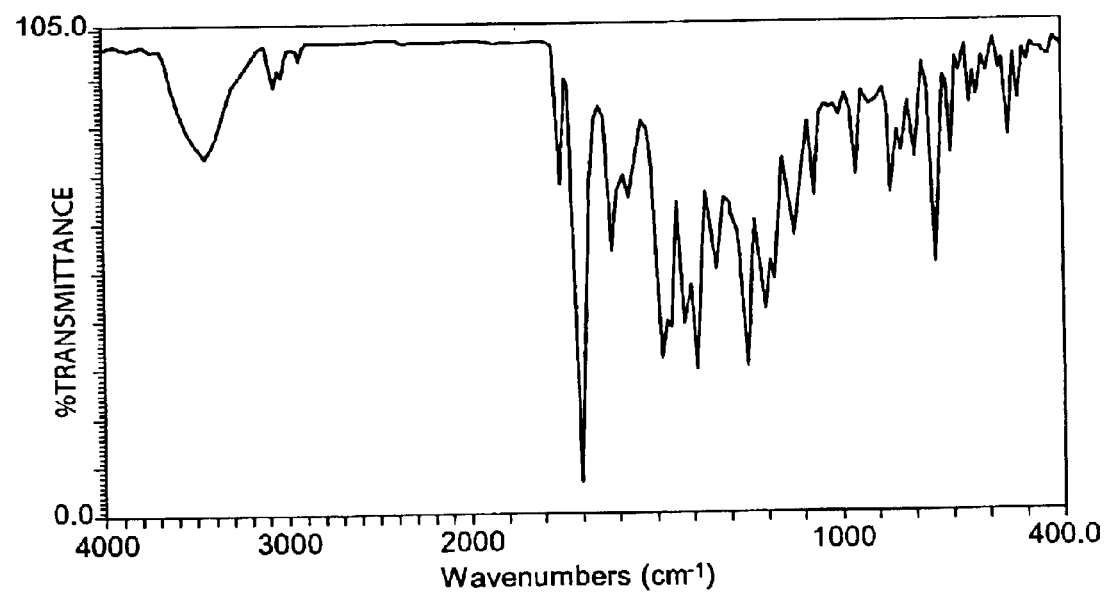
FIG. 39 is a graph showing an example of an infrared spectrum of an azo compound.
Figure 40:
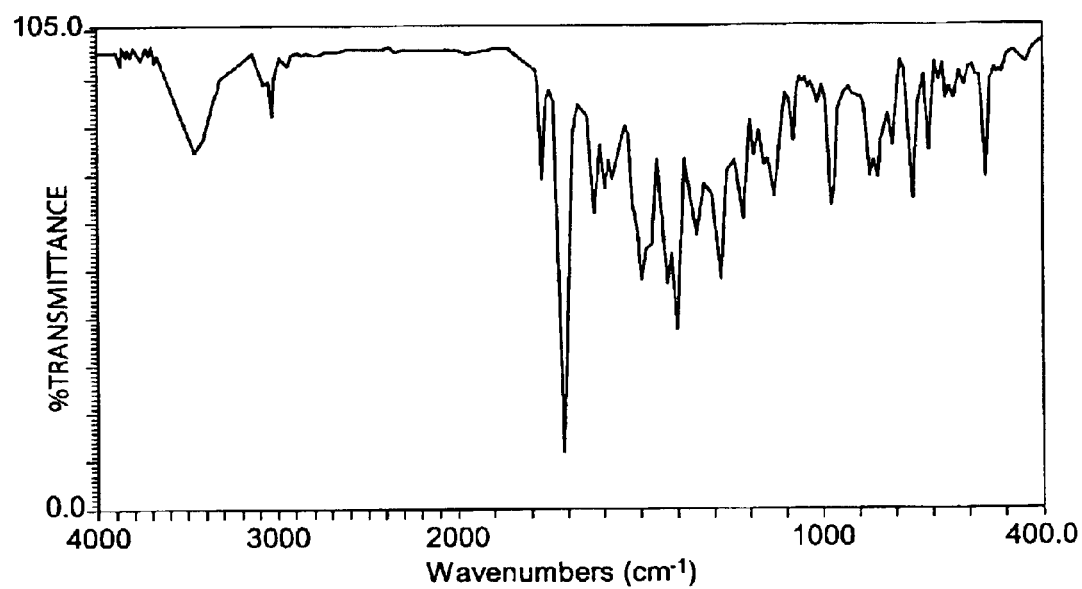
FIG. 40 is a graph showing an example of an infrared spectrum of an azo compound.
Figure 41:
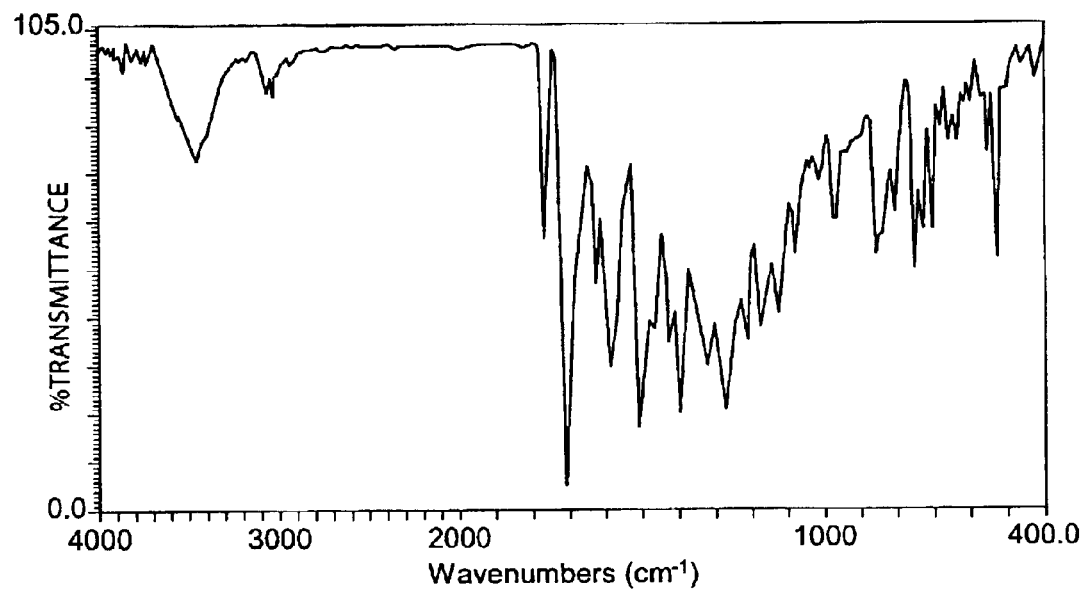
FIG. 41 is a graph showing an example of an infrared spectrum of an azo compound.
Figure 42:
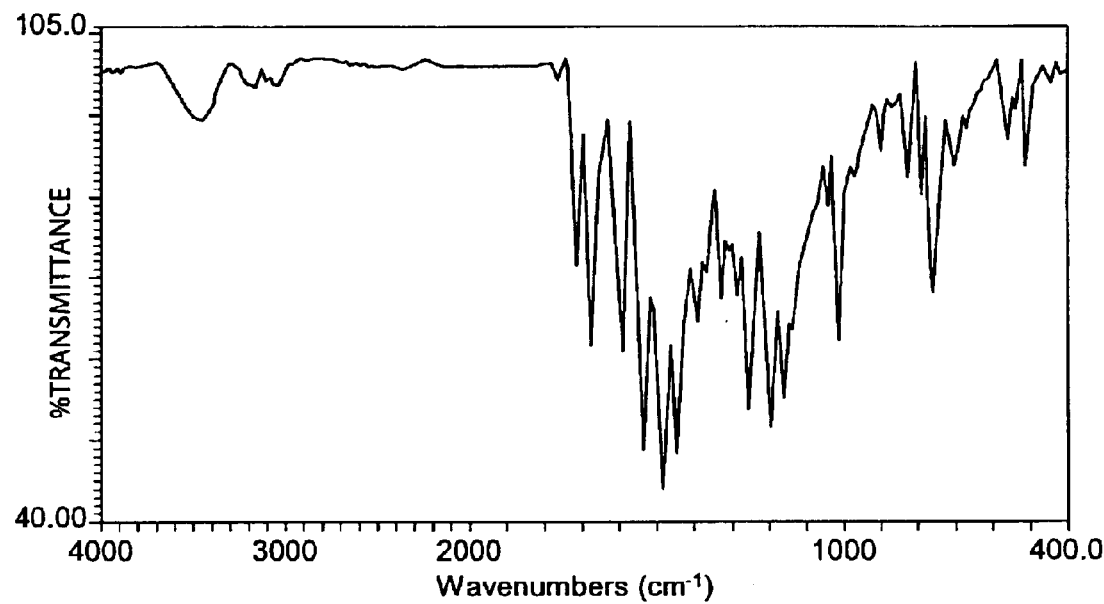
FIG. 42 is a graph showing an example of an infrared spectrum of an azo compound.
Figure 43:
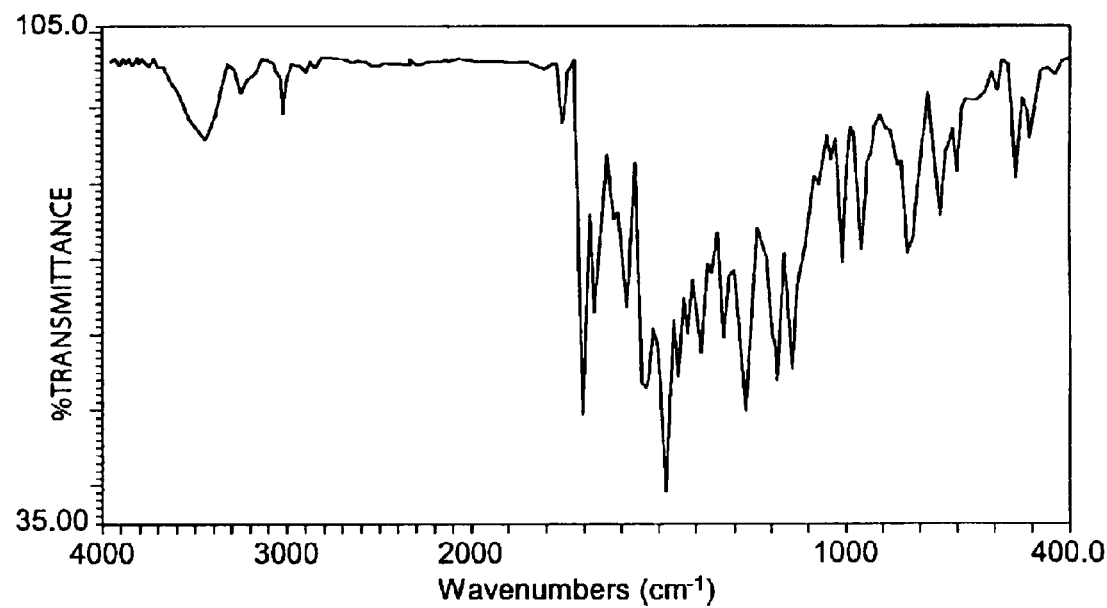
FIG. 43 is a graph showing an example of an infrared spectrum of an azo compound.
Figure 44:
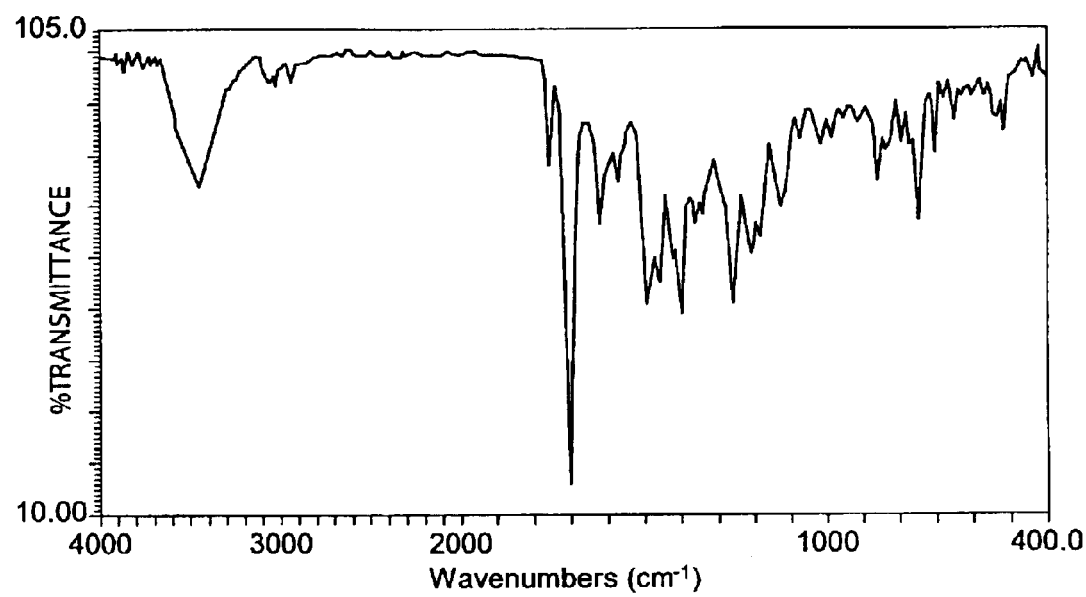
FIG. 44 is a graph showing an example of an infrared spectrum of an azo compound.

| | | | Elemental analysis (%) | | | |
| --- | --- | --- | --- | --- | --- | --- |
| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
| Mfg. Ex. VII-1 | P1 | 0.86 (64.2) | 64.45 (64.57) | 5.01 (4.97) | 12.53 (12.55) | FIG. 37 |
| Mfg. Ex. VII-2 | P17 | 0.87 (70.1) | 70.99 (71.17) | 5.07 (5.12) | 10.15 (10.16) | FIG. 38 |
| Mfg. Ex. VII-3 | P19 | 0.64 (50.8) | 72.91 (73.02) | 3.51 (3.60) | 9.94 (10.02) | FIG. 39 |
| Mfg. Ex. VII-4 | P49 | 1.21 (86.0) | 76.43 (76.58) | 4.16 (4.28) | 8.84 (8.93) | FIG. 40 |
| Mfg. Ex. VII-5 | P74 | 0.68 (55.2) | 72.88 (73.04) | 3.87 (3.92) | 11.27 (11.36) | FIG. 41 |
| Mfg. Ex. VII-6 | P20 | 0.68 (54.4) | 70.55 (70.63) | 3.35 (3.51) | 9.93 (10.08) | FIG. 42 |
| Mfg. Ex. VII-7 | P50 | 0.98 (70.0) | 77.75 (77.57) | 4.71 (4.77) | 8.93 (9.05) | FIG. 43 |
| Mfg. Ex. VII-8 | P23 | 0.74 (56.9) | 73.32 (73.43) | 3.77 (3.95) | 9.55 (9.69) | FIG. 44 |

TABLE 67-1-continued

Figure 45:
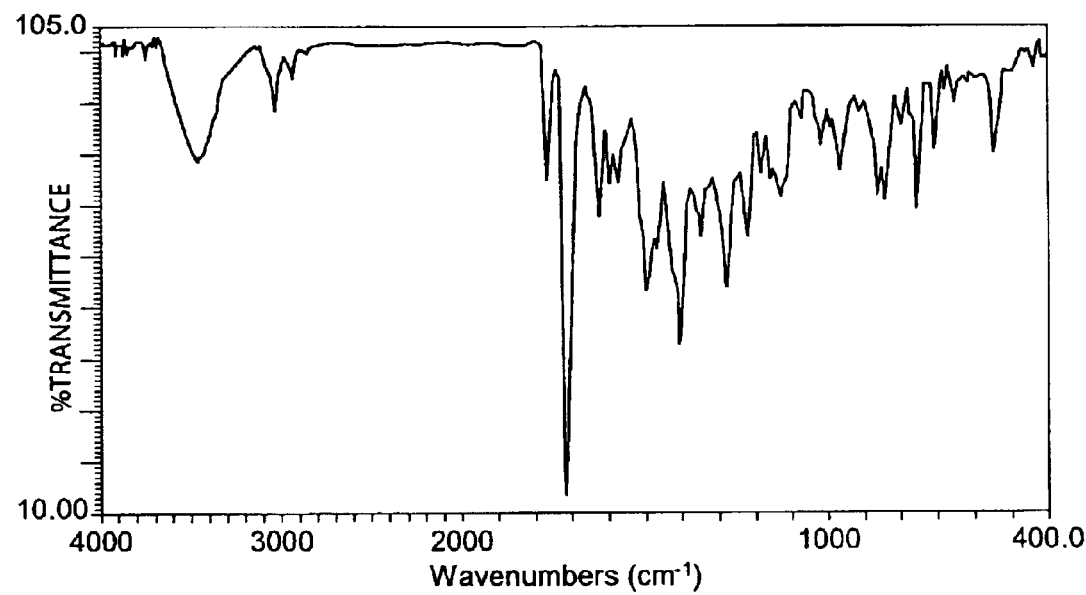
FIG. 45 is a graph showing an example of an infrared spectrum of an azo compound.
Figure 46:
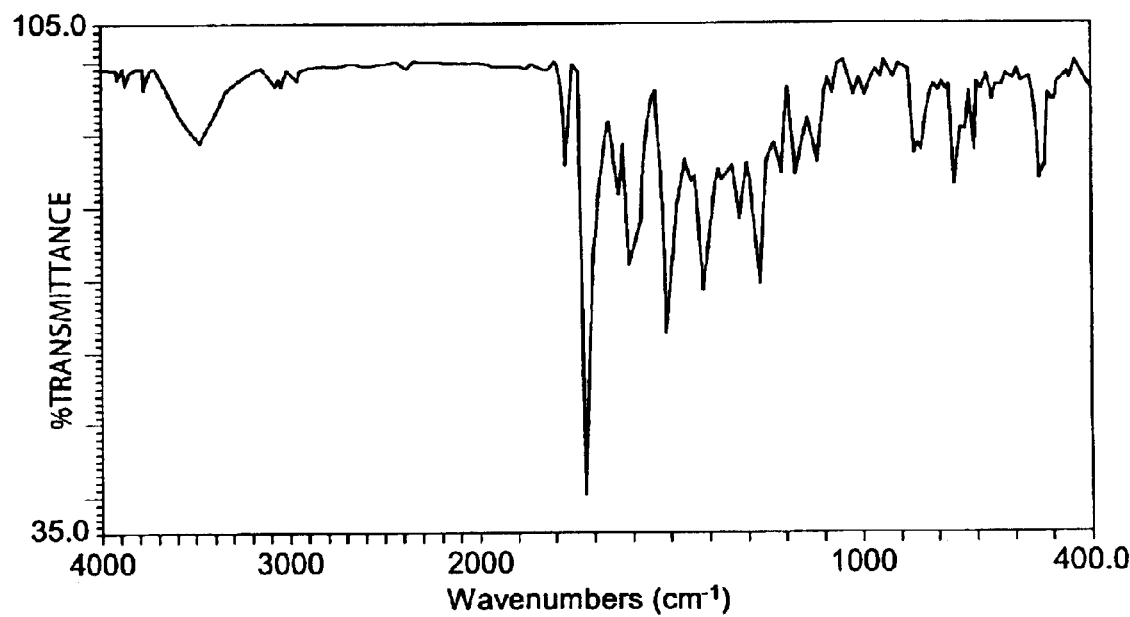
FIG. 46 is a graph showing an example of an infrared spectrum of an azo compound.
Figure 47:
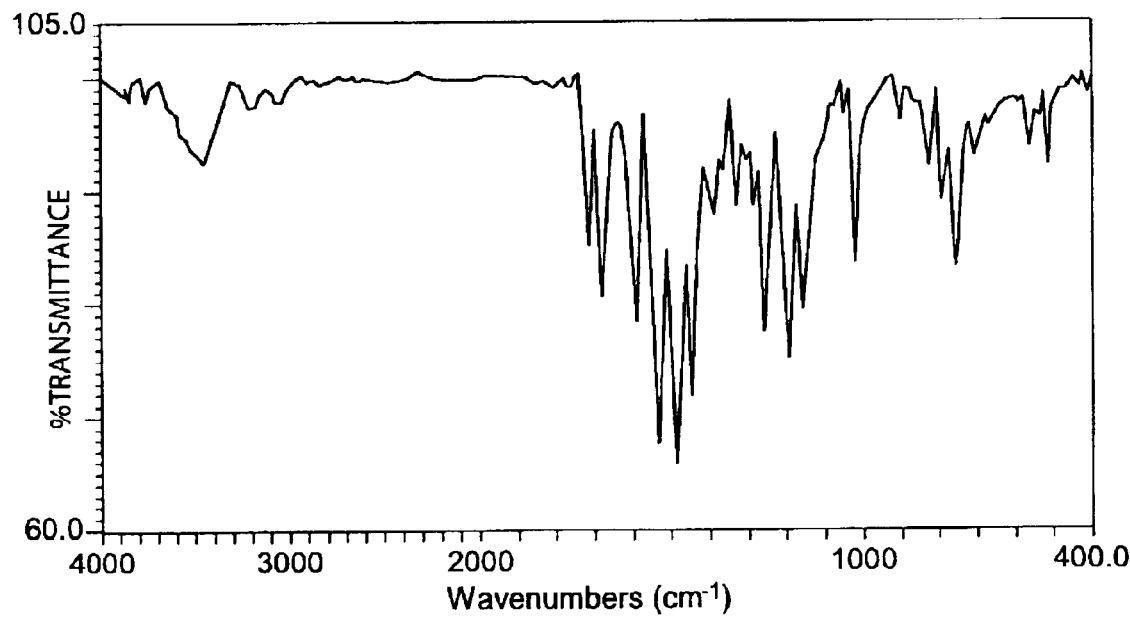
FIG. 47 is a graph showing an example of an infrared spectrum of an azo compound.
Figure 48:
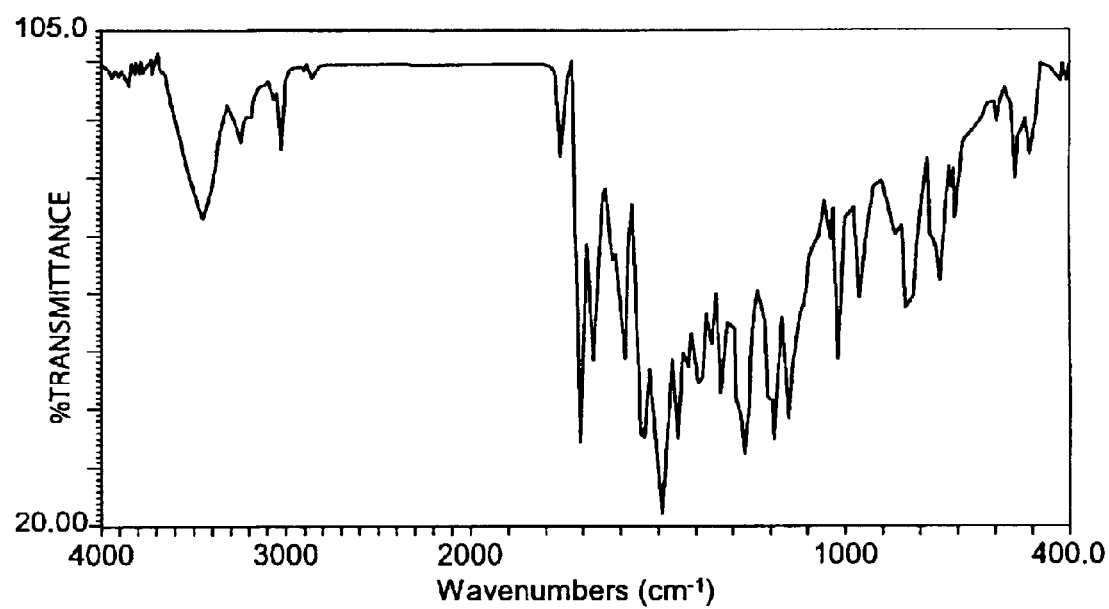
FIG. 48 is a graph showing an example of an infrared spectrum of an azo compound.
Figure 49:
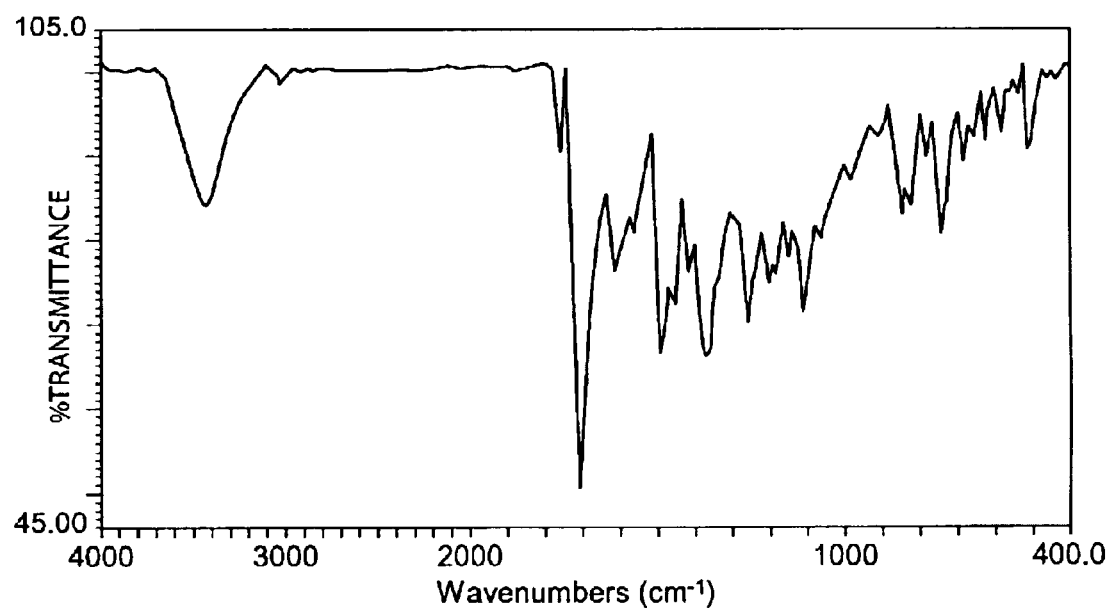
FIG. 49 is a graph showing an example of an infrared spectrum of an azo compound.
Figure 50:
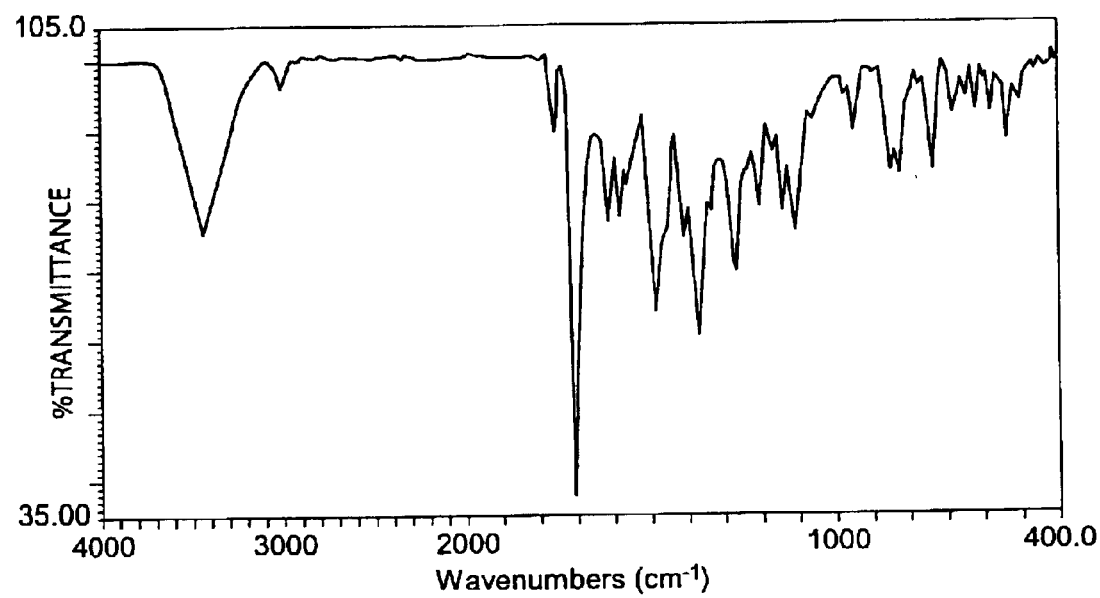
FIG. 50 is a graph showing an example of an infrared spectrum of an azo compound.
Figure 51:
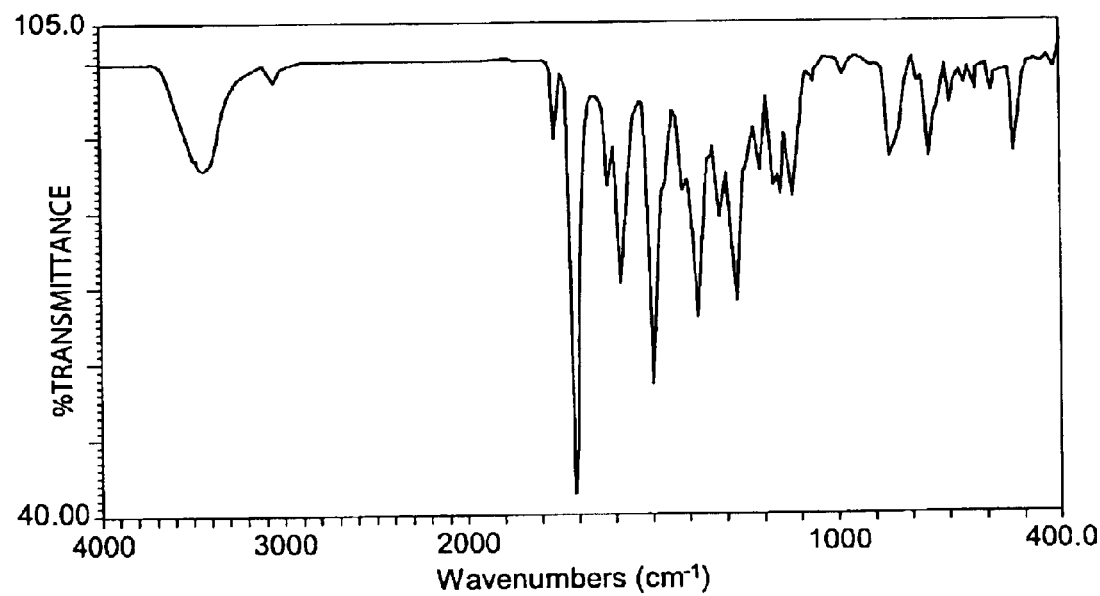
FIG. 51 is a graph showing an example of an infrared spectrum of an azo compound.
Figure 52:
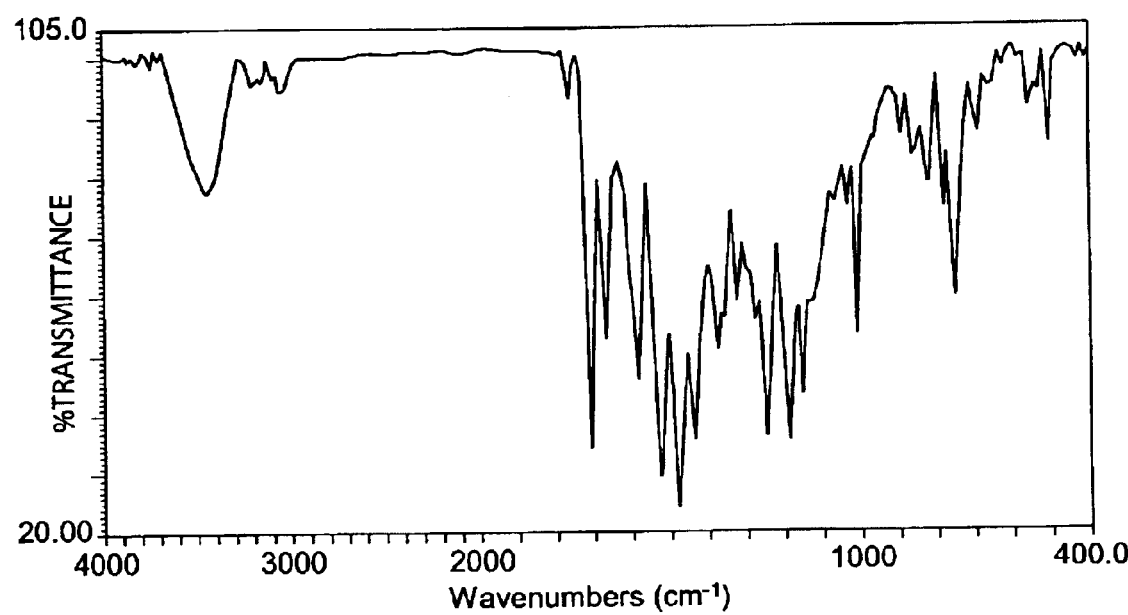
FIG. 52 is a graph showing an example of an infrared spectrum of an azo compound.
Figure 53:
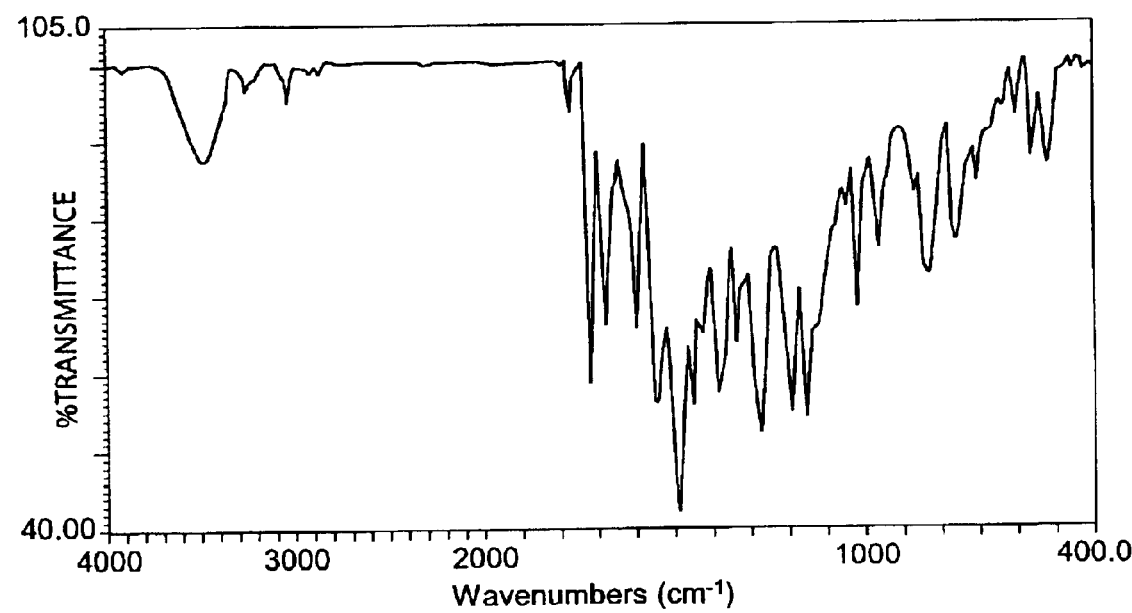
FIG. 53 is a graph showing an example of an infrared spectrum of an azo compound.
Figure 54:
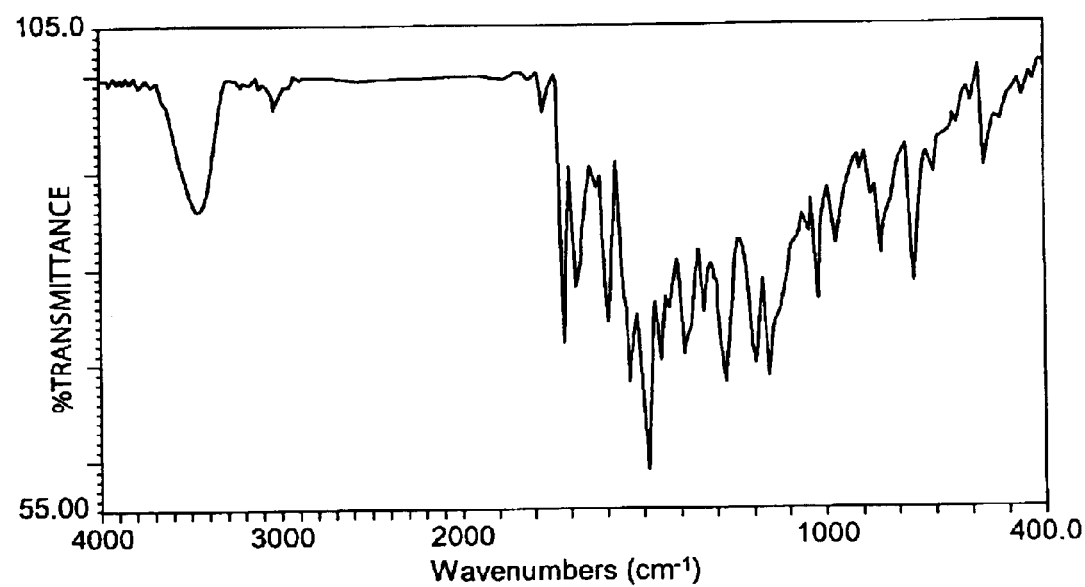
FIG. 54 is a graph showing an example of an infrared spectrum of an azo compound.
Figure 55:
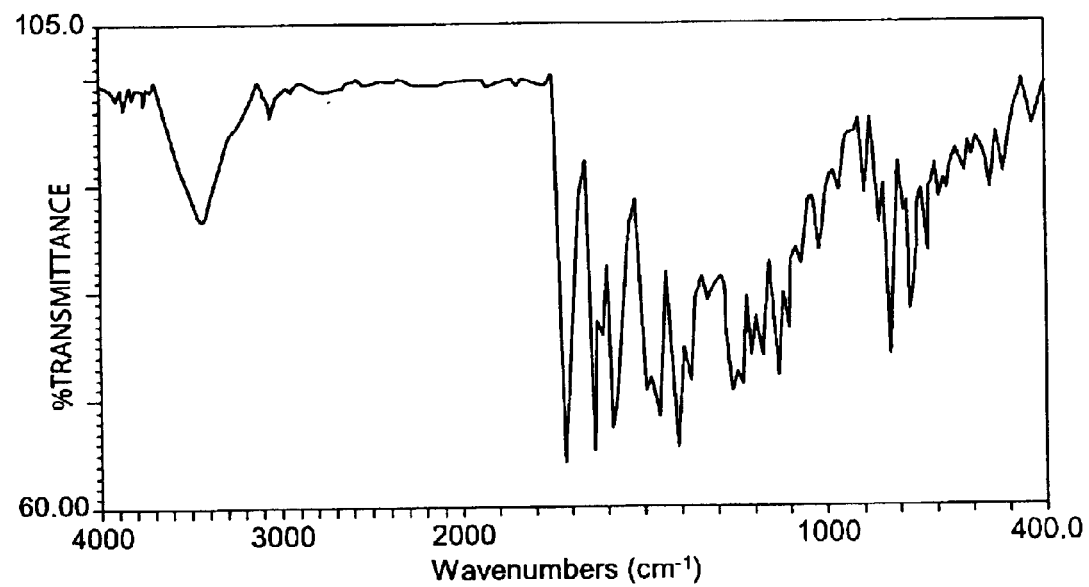
FIG. 55 is a graph showing an example of an infrared spectrum of an azo compound.
Figure 56:
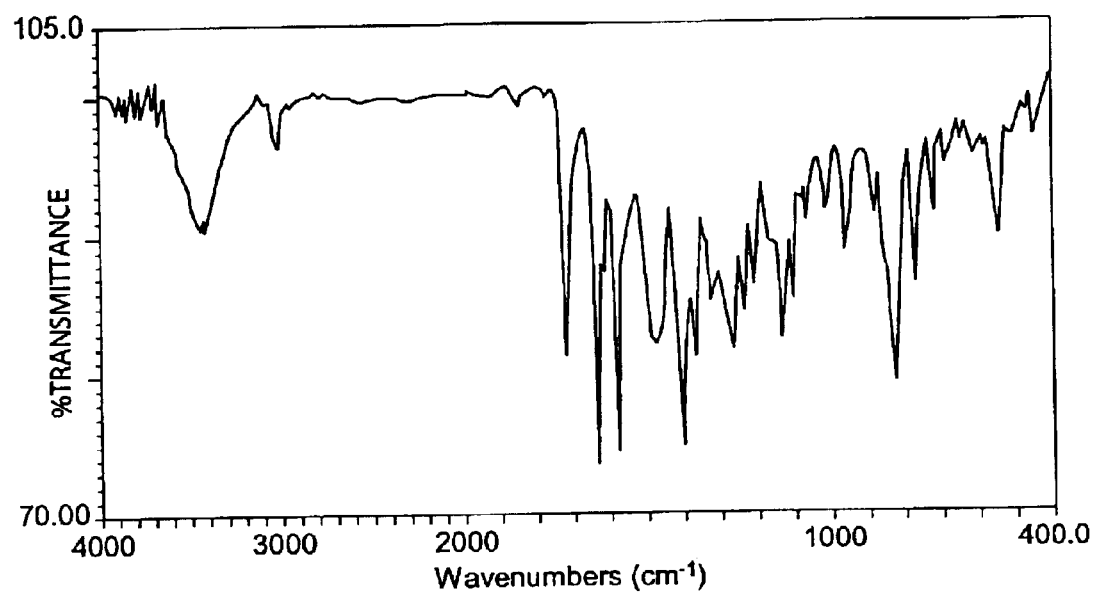
FIG. 56 is a graph showing an example of an infrared spectrum of an azo compound.
Figure 57:
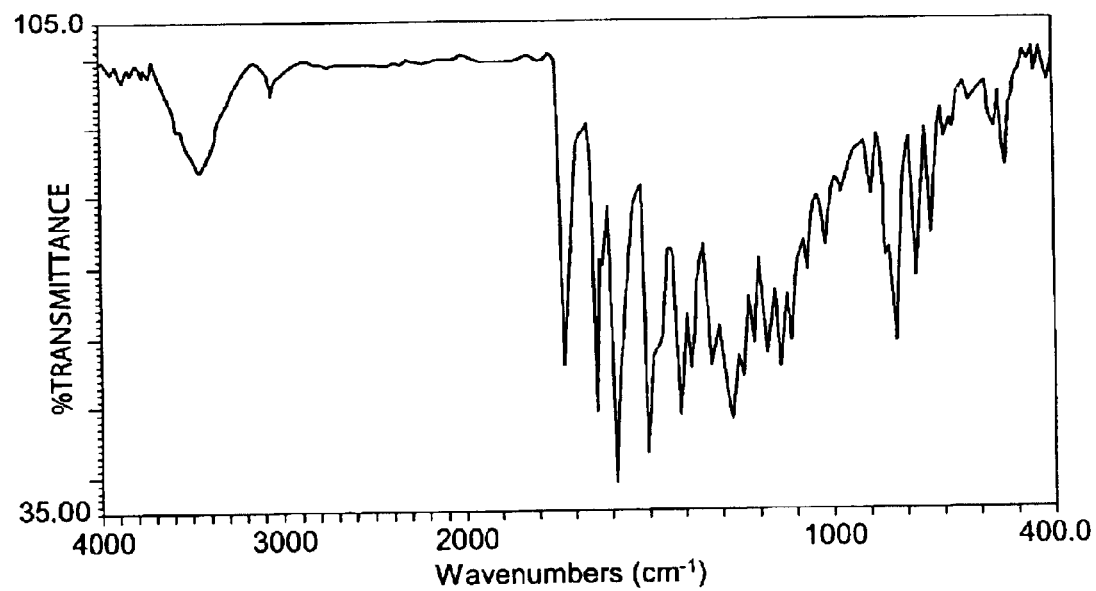
FIG. 57 is a graph showing an example of an infrared spectrum of an azo compound.
Figure 58:
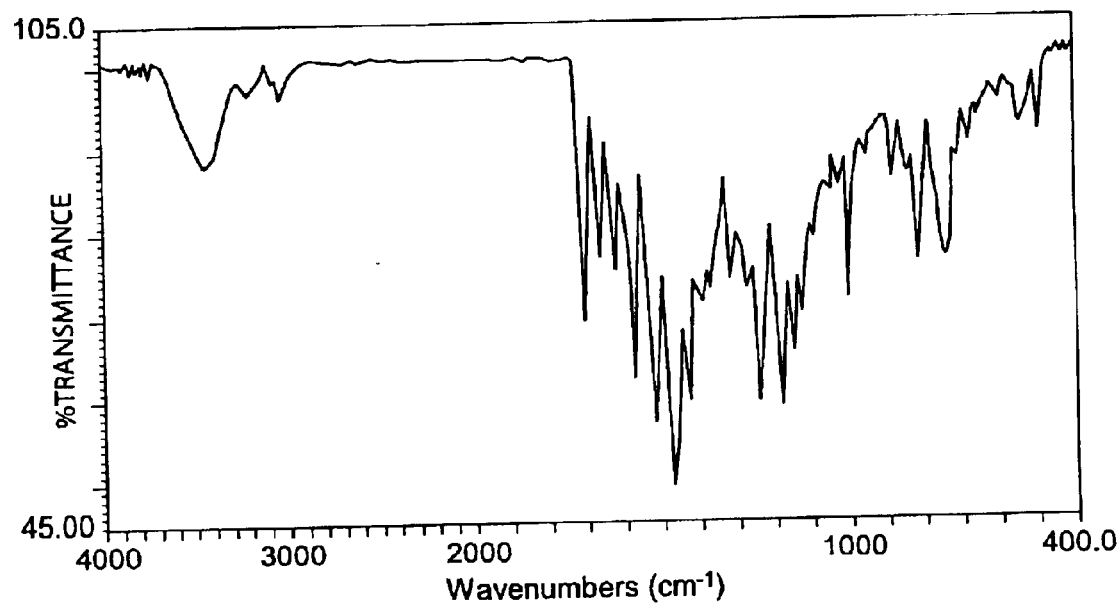
FIG. 58 is a graph showing an example of an infrared spectrum of an azo compound.
Figure 59:
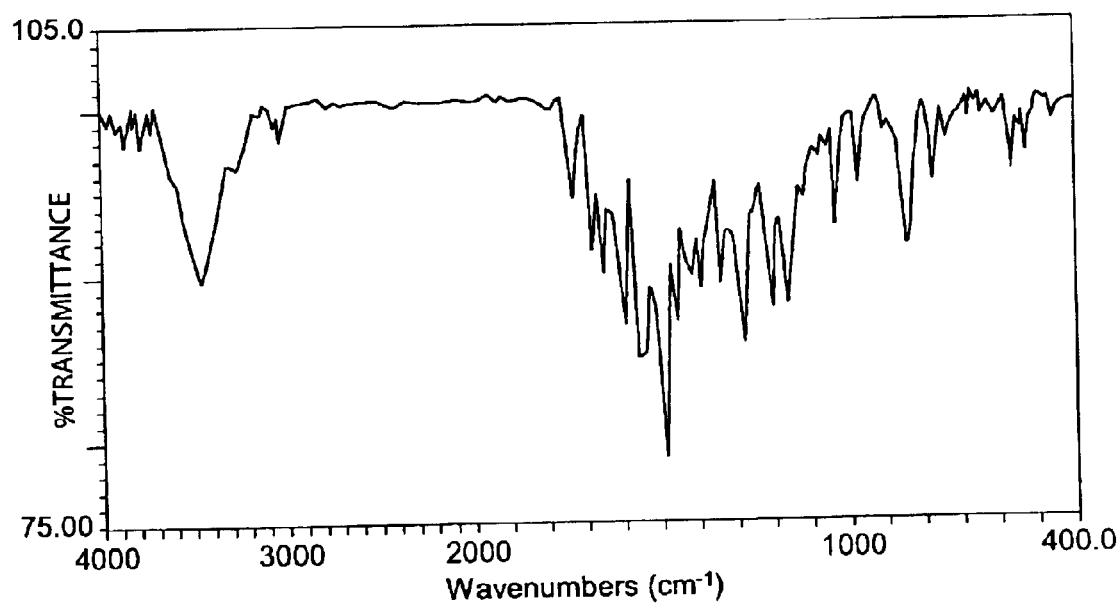
FIG. 59 is a graph showing an example of an infrared spectrum of an azo compound.

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-9 | P52 | 1.11 (76.5) | 76.76 (76.84) | 4.42 (4.58) | 8.45 (8.67) | FIG. 45 |
| Mfg. Ex. VII-10 | P77 | 0.72 (56.5) | 73.32 (73.46) | 4.14 (4.27) | 11.09 (10.98) | FIG. 46 |
| Mfg. Ex. VII-11 | P24 | 0.69 (54.3) | 70.60 (70.88) | 3.40 (3.69) | 10.02 (9.92) | FIG. 47 |
| Mfg. Ex. VII-12 | P53 | 0.99 (70.0) | 77.78 (77.69) | 4.86 (4.92) | 8.99 (8.91) | FIG. 48 |
| Mfg. Ex. VII-13 | P27 | 0.68 (55.9) | 72.46 (72.59) | 3.11 (3.23) | 10.30 (10.37) | FIG. 49 |
| Mfg. Ex. VII-14 | P57 | 0.78 (57.1) | 76.21 (76.30) | 3.88 (3.97) | 9.15 (9.20) | FIG. 50 |
| Mfg. Ex. VII-15 | P81 | 0.61 (51.2) | 72.48 (72.60) | 3.42 (3.55) | 11.56 (11.76) | FIG. 51 |
| Mfg. Ex. VII-16 | P28 | 0.59 (48.4) | 70.29 (70.37) | 3.33 (3.32) | 10.13 (10.26) | FIG. 52 |
| Mfg. Ex. VII-17 | P58 | 0.79 (57.3) | 77.56 (77.44) | 4.66 (4.63) | 9.11 (9.18) | FIG. 53 |
| Mfg. Ex. VII-18 | P59 | 0.90 (65.0) | 74.20 (74.30) | 3.98 (4.05) | 9.06 (9.12) | FIG. 54 |
| Mfg. Ex. VII-19 | P38 | 0.96 (70.7) | 75.51 (75.55) | 3.00 (3.12) | 12.34 (12.38) | FIG. 55 |
| Mfg. Ex. VII-20 | P66 | 1.25 (83.0) | 78.67 (78.71) | 3.68 (3.80) | 11.24 (11.27) | FIG. 56 |
| Mfg. Ex. VII-21 | P86 | 0.98 (73.5) | 75.51 (75.72) | 3.30 (3.40) | 13.40 (13.67) | FIG. 57 |
| Mfg. Ex. VII-22 | P39 | 0.96 (74.0) | 71.90 (72.10) | 3.10 (3.26) | 11.23 (11.32) | FIG. 58 |
| Mfg. Ex. VII-23 | P67 | 1.09 | 78.40 | 4.39 | 9.92 | FIG. 59 |

TABLE 67-2

Figure 60:
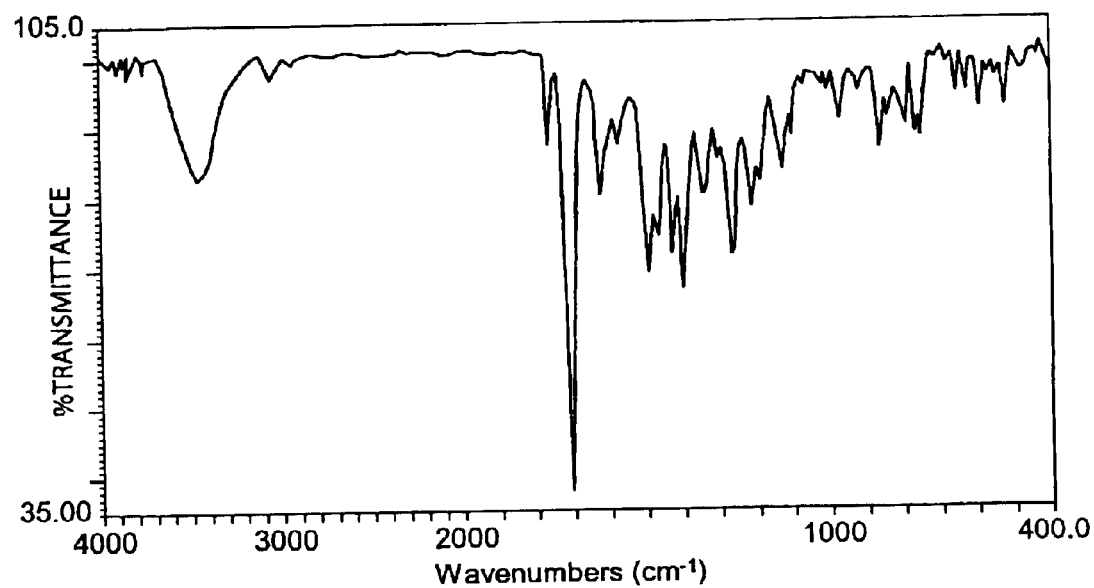
FIG. 60 is a graph showing an example of an infrared spectrum of an azo compound.
Figure 61:
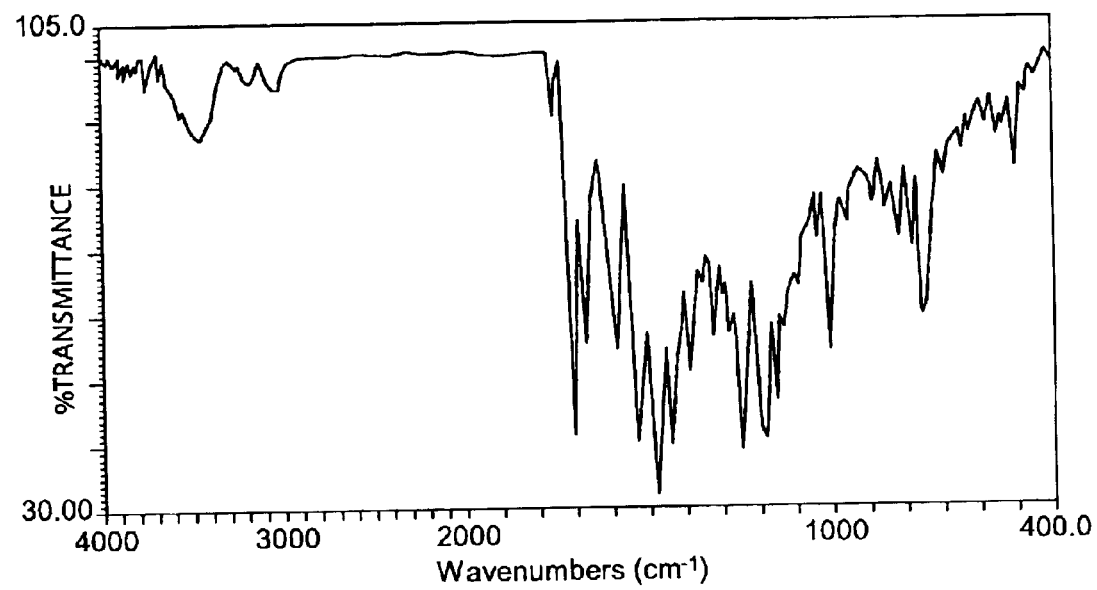
FIG. 61 is a graph showing an example of an infrared spectrum of an azo compound.
Figure 62:
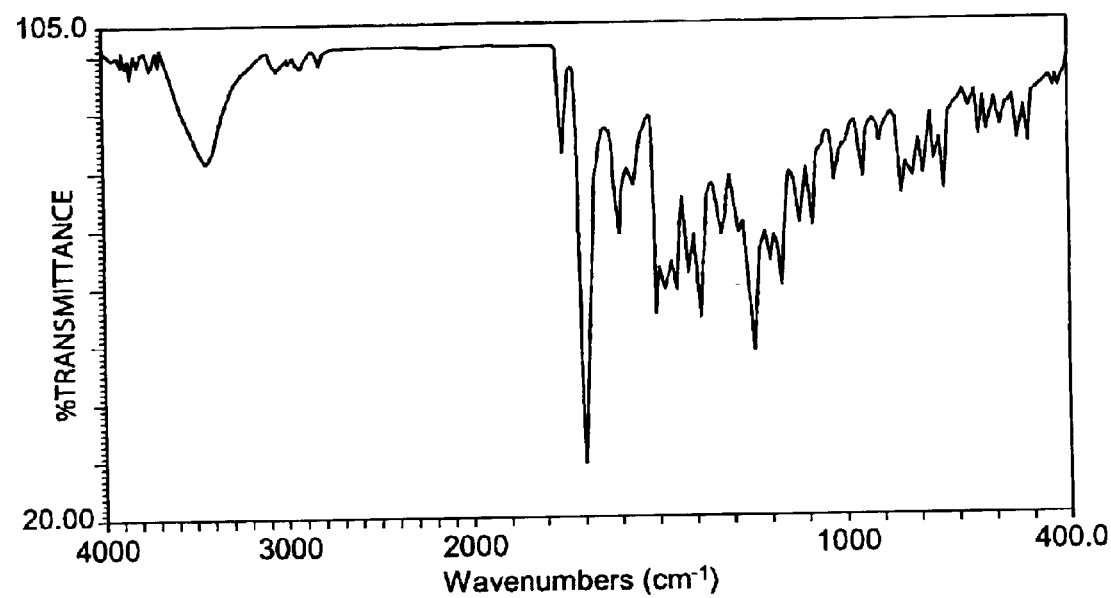
FIG. 62 is a graph showing an example of an infrared spectrum of an azo compound.
Figure 63:
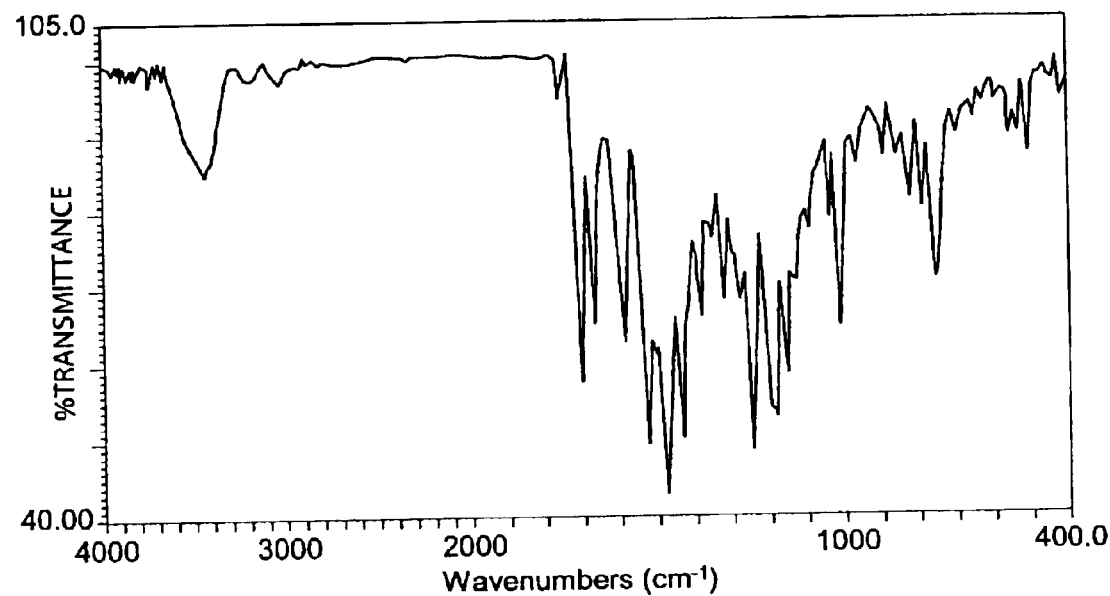
FIG. 63 is a graph showing an example of an infrared spectrum of an azo compound.
Figure 64:
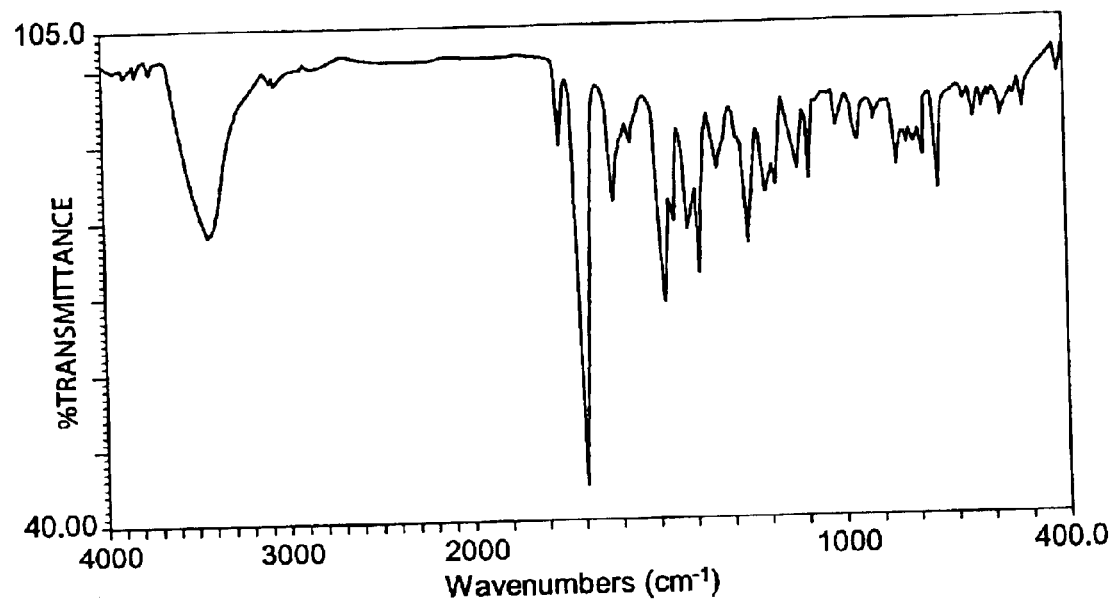
FIG. 64 is a graph showing an example of an infrared spectrum of an azo compound.
Figure 65:
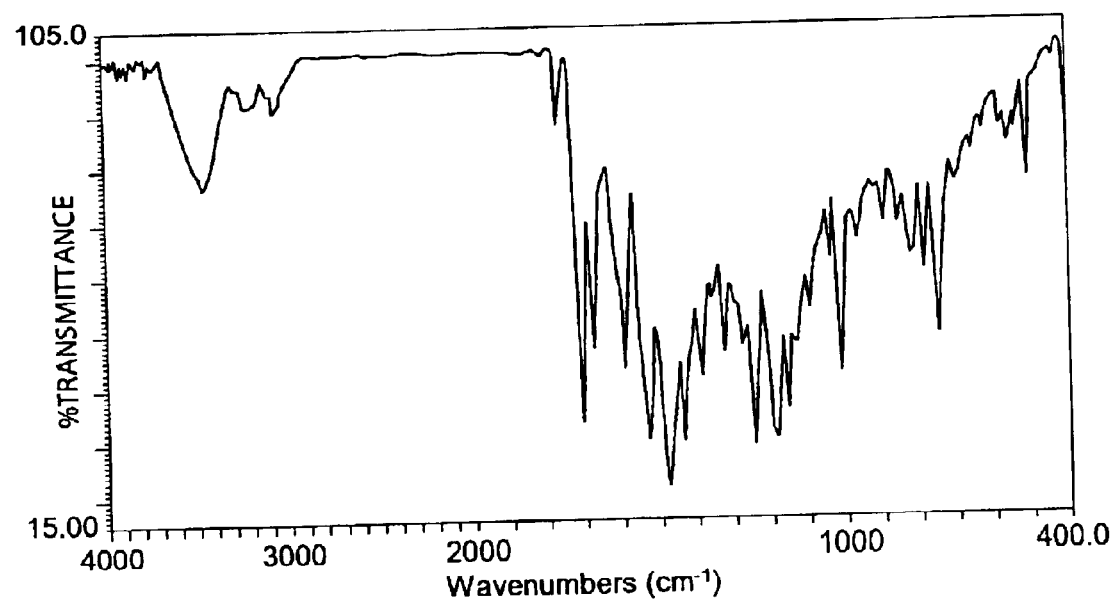
FIG. 65 is a graph showing an example of an infrared spectrum of an azo compound.
Figure 66:
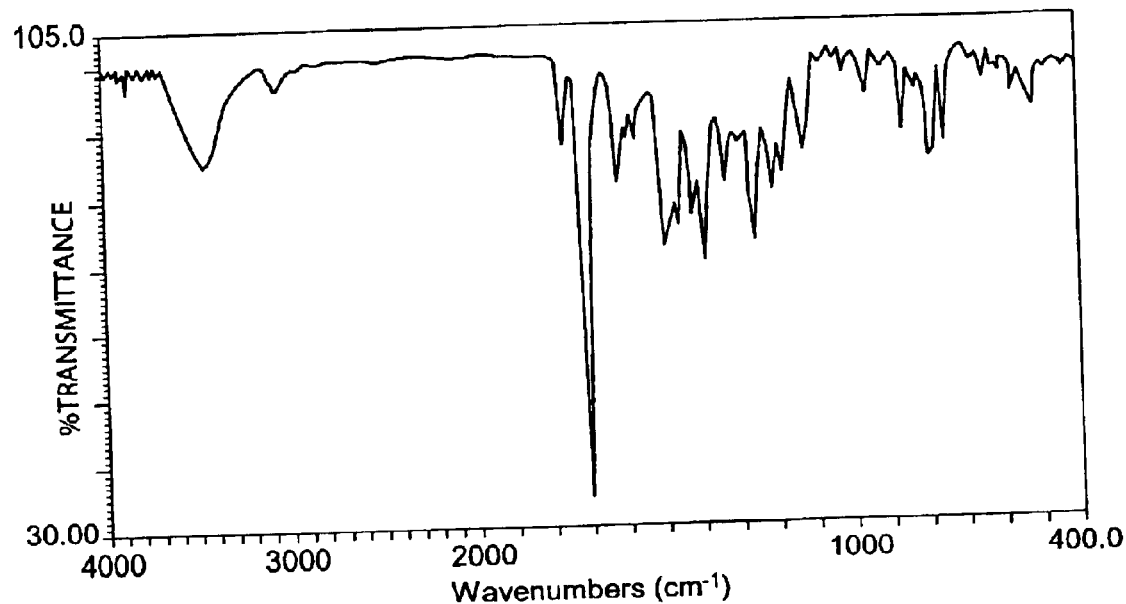
FIG. 66 is a graph showing an example of an infrared spectrum of an azo compound.
Figure 67:
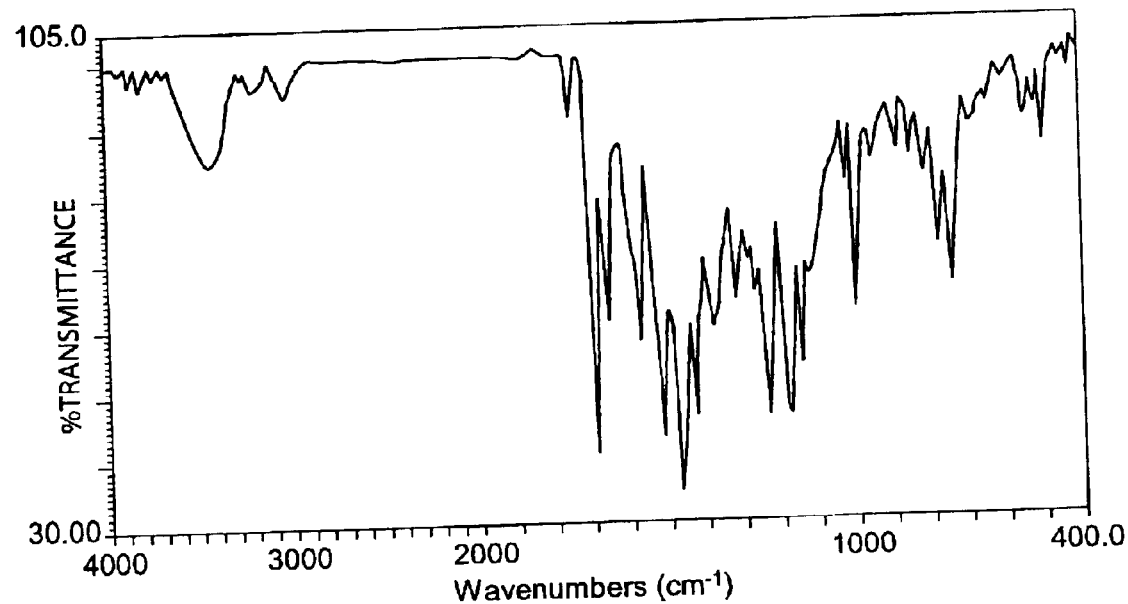
FIG. 67 is a graph showing an example of an infrared spectrum of an azo compound.
Figure 68:
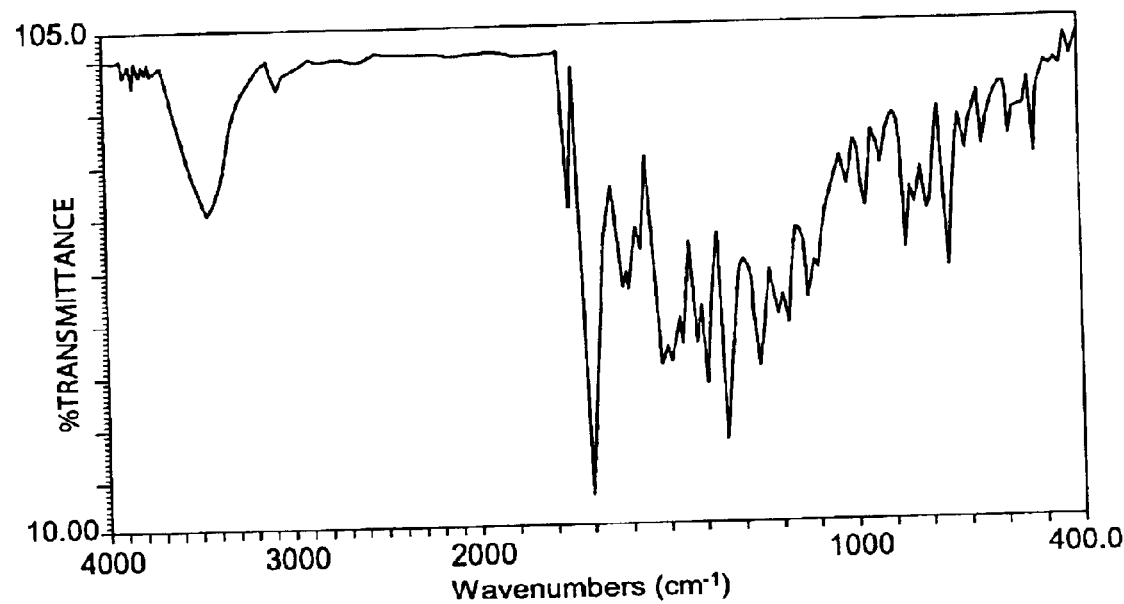
FIG. 68 is a graph showing an example of an infrared spectrum of an azo compound.
Figure 69:
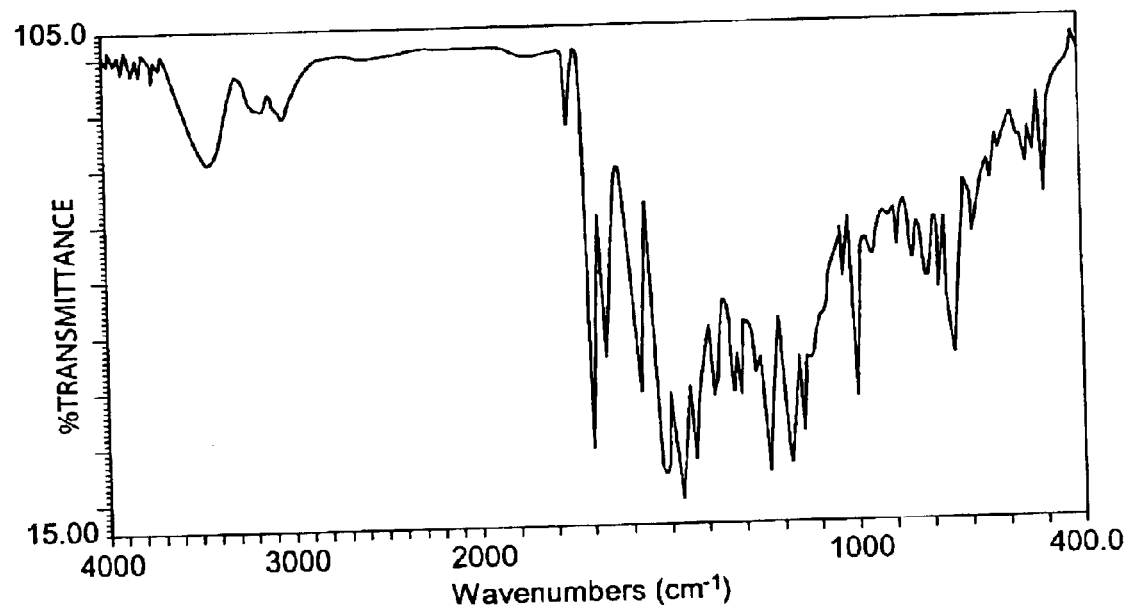
FIG. 69 is a graph showing an example of an infrared spectrum of an azo compound.

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-24 | P102 | 0.75 (57.9) | 73.24 (73.43) | 3.87 (3.95) | 9.64 (9.69) | FIG. 60 |
| Mfg. Ex. VII-25 | P103 | 0.78 (61.5) | 70.73 (70.88) | 3.57 (3.69) | 9.88 (9.92) | FIG. 61 |
| Mfg. Ex. VII-26 | P21 | 0.64 (47.3) | 70.68 (70.82) | 3.68 (3.81) | 9.29 (9.35) | FIG. 62 |
| Mfg. Ex. VII-27 | P104 | 0.72 (55.4) | 69.43 (69.56) | 3.55 (3.62) | 9.64 (9.74) | FIG. 63 |
| Mfg. Ex. VII-28 | P134 | 0.96 (70.7) | 67.49 (67.48) | 2.98 (3.11) | 9.11 (9.26) | FIG. 64 |
| Mfg. Ex. VII-29 | P135 | 0.79 (60.8) | 67.84 (67.83) | 3.07 (3.25) | 9.86 (9.68) | FIG. 65 |
| Mfg. Ex. VII-30 | P22 | 0.77 (54.8) | 75.20 (75.47) | 3.40 (3.65) | 8.79 (8.95) | FIG. 66 |
| Mfg. Ex. VII-31 | P105 | 0.80 (60.3) | 71.88 (72.07) | 3.50 (3.54) | 9.48 (9.51) | FIG. 67 |
| Mfg. Ex. VII-32 | P112 | 0.93 (66.5) | 65.84 (65.95) | 2.96 (3.04) | 11.96 (12.06) | FIG. 68 |
| Mfg. Ex. VII-33 | P113 | 0.75 (57.2) | 66.99 (67.01) | 3.16 (3.21) | 10.92 (11.16) | FIG. 69 |
| Mfg. Ex. VII-34 | P114 | 0.87 (58.8) | 76.17 (76.35) | 3.73 (3.86) | 8.42 (8.48) | FIG. 70 |
| Mfg. Ex. VII-35 | P115 | 0.70 (51.1) | 72.44 (72.64) | 3.52 (3.66) | 9.37 (9.24) | FIG. 71 |

TABLE 67-3

Figure 96:
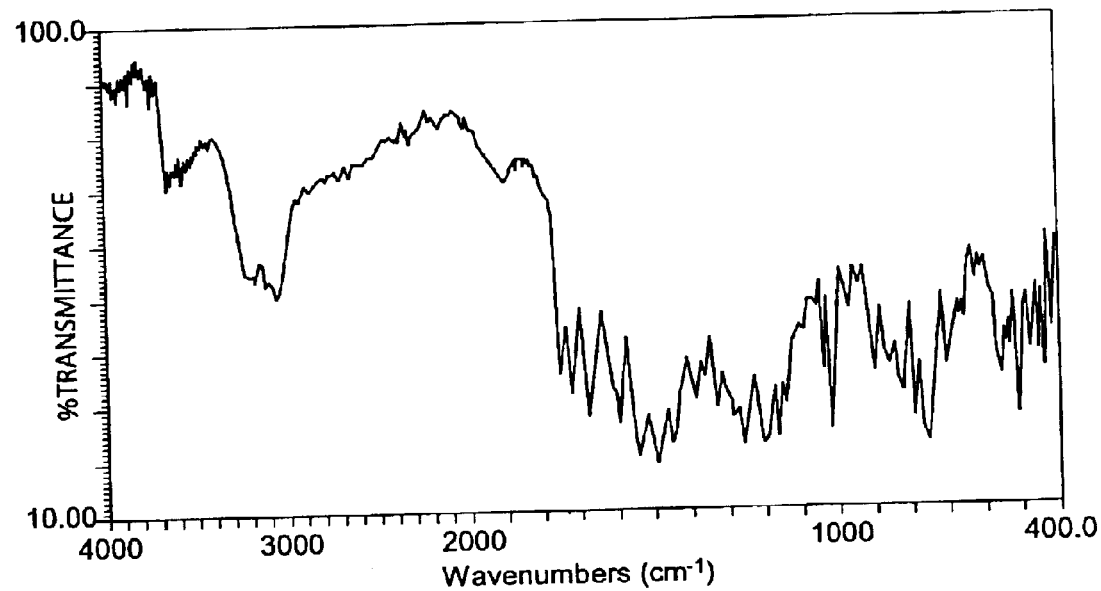
FIG. 96 is a graph showing an example of an infrared spectrum of an azo compound.
Figure 97:
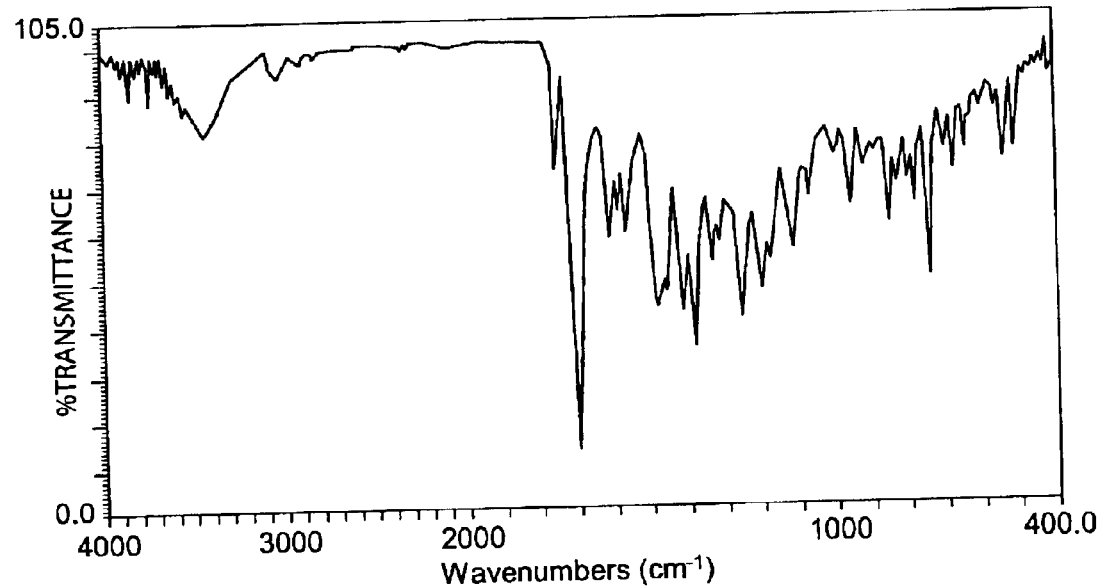
FIG. 97 is a graph showing an example of an infrared spectrum of an azo compound.
Figure 98:
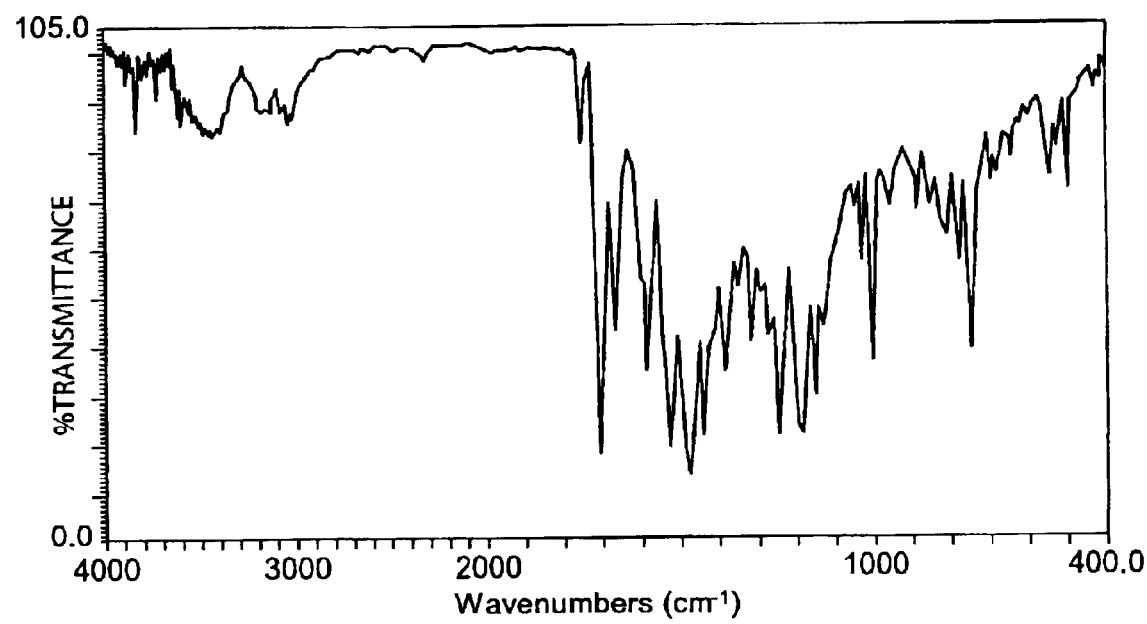
FIG. 98 is a graph showing an example of an infrared spectrum of an azo compound.
Figure 99:
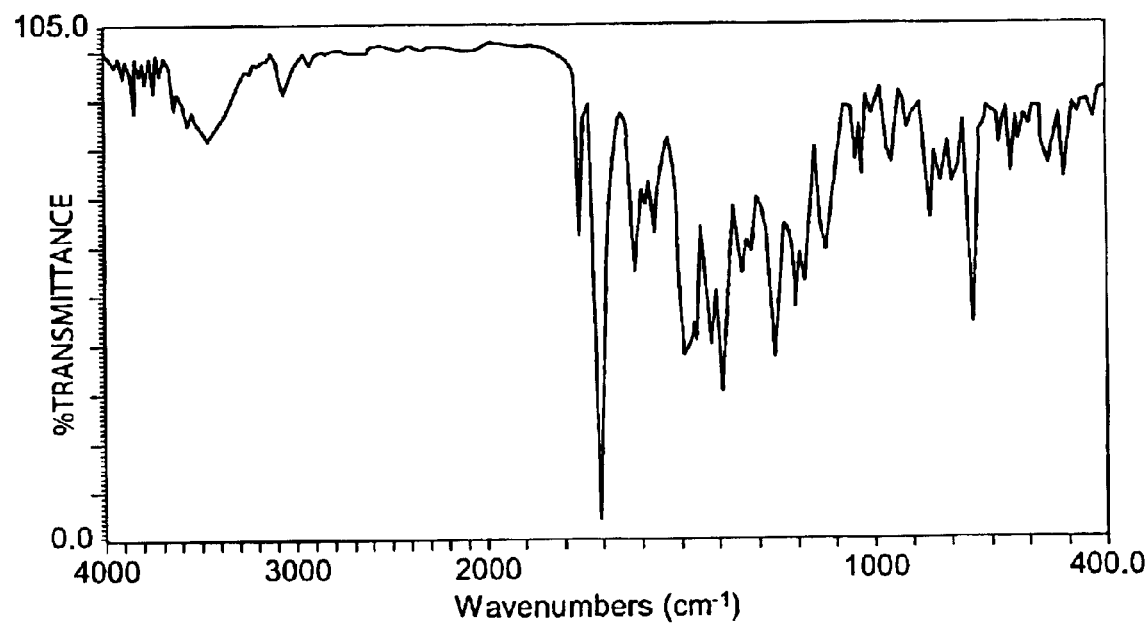
FIG. 99 is a graph showing an example of an infrared spectrum of an azo compound.
Figure 100:
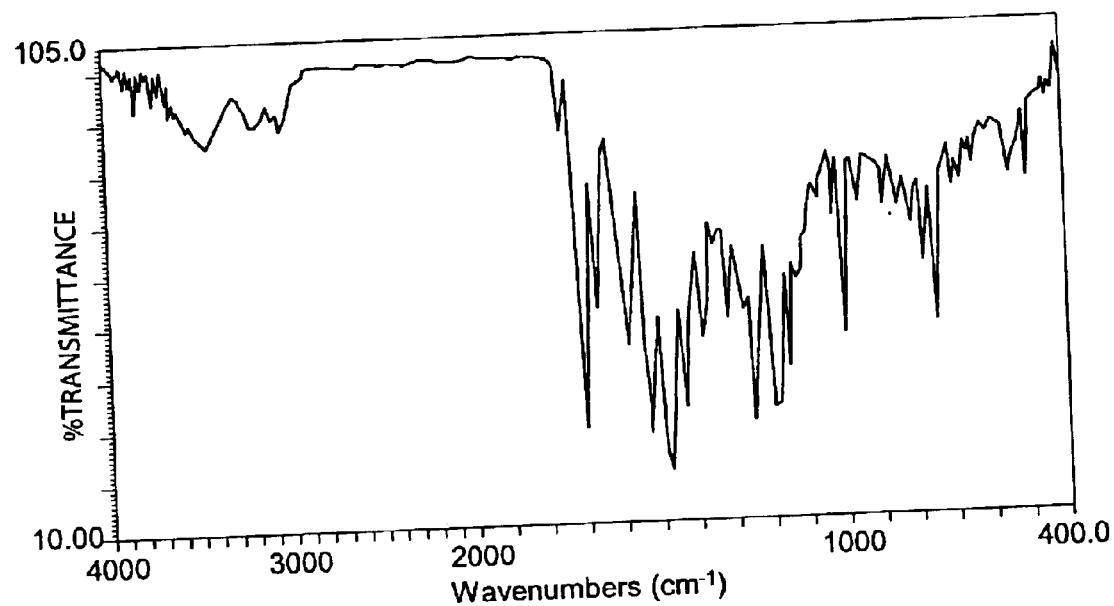
FIG. 100 is a graph showing an example of an infrared spectrum of an azo compound.
Figure 101:
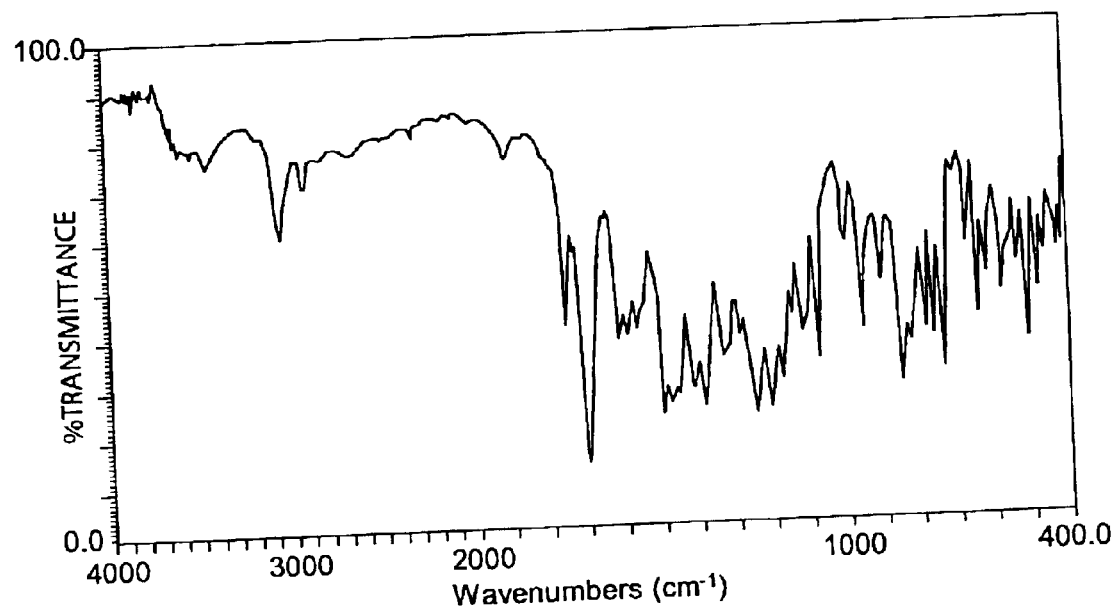
FIG. 101 is a graph showing an example of an infrared spectrum of an azo compound.
Figure 102:
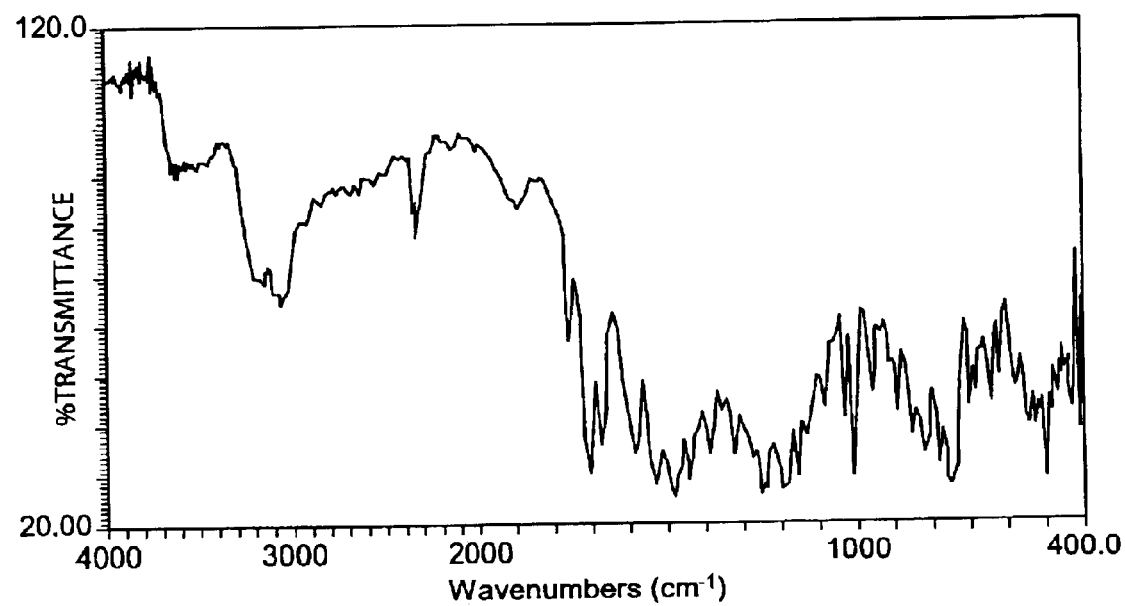
FIG. 102 is a graph showing an example of an infrared spectrum of an azo compound.
Figure 103:
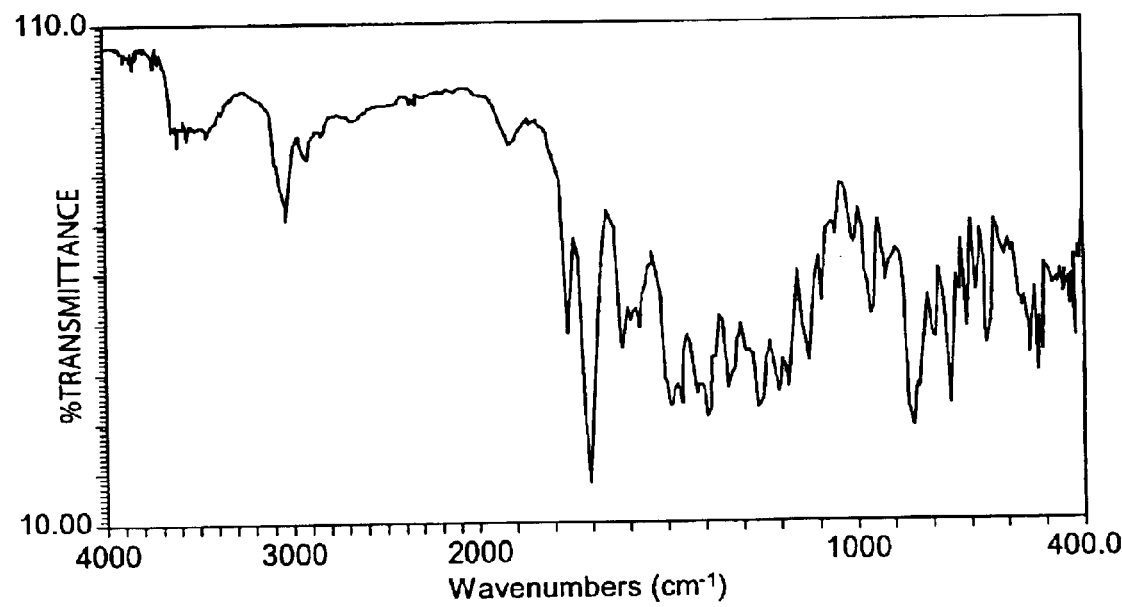
FIG. 103 is a graph showing an example of an infrared spectrum of an azo compound.
Figure 104:
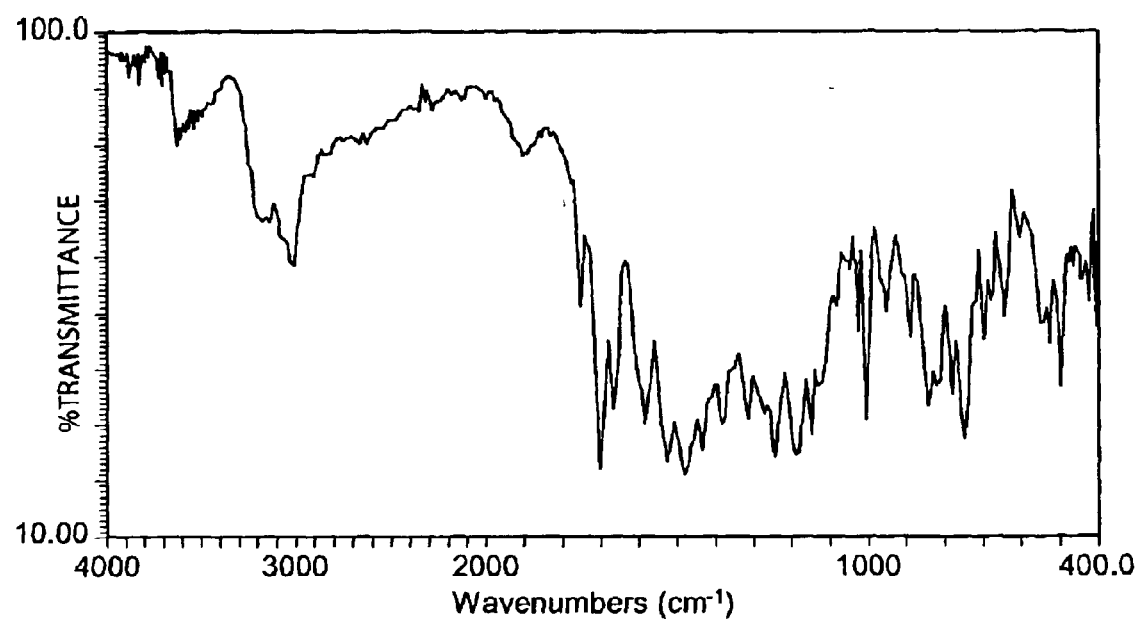
FIG. 104 is a graph showing an example of an infrared spectrum of an azo compound.
Figure 105:
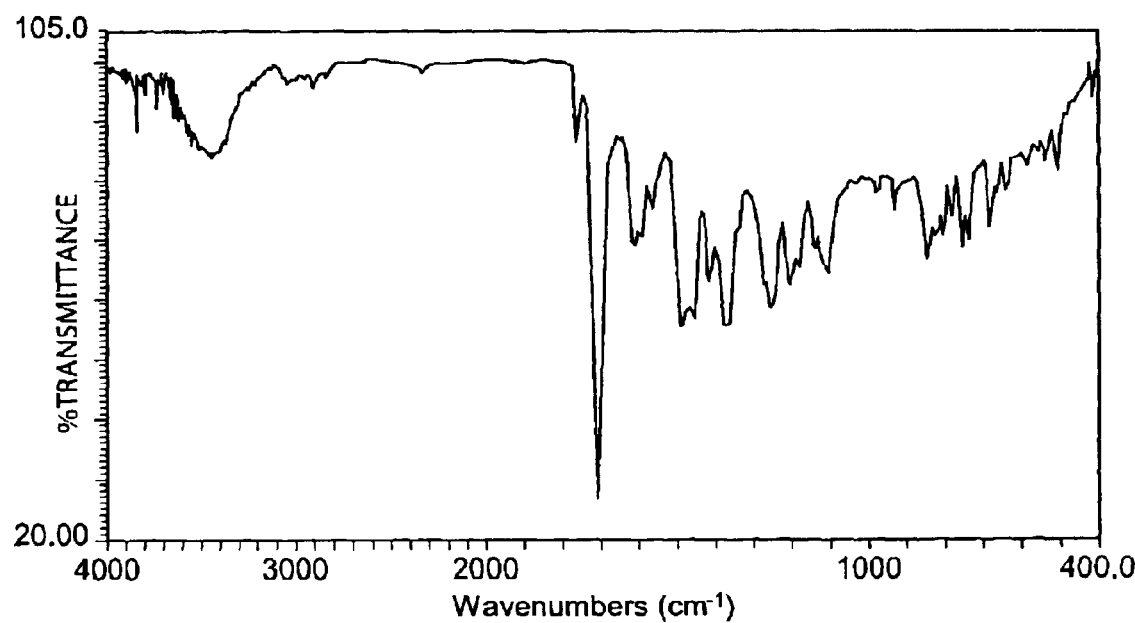
FIG. 105 is a graph showing an example of an infrared spectrum of an azo compound.
Figure 106:
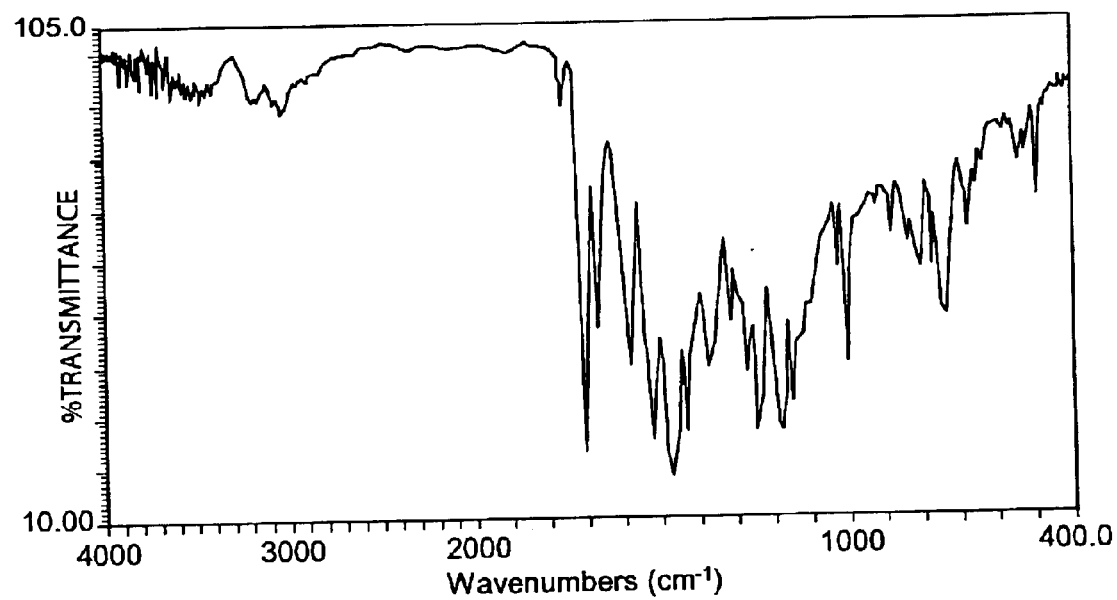
FIG. 106 is a graph showing an example of an infrared spectrum of an azo compound.

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-36 | P35 | 0.61 (49.8) | 70.41 (70.63) | 3.05 (3.21) | 11.90 (12.01) | FIG. 96 |
| Mfg. Ex. VII-37 | P106 | 0.82 (60.2) | 67.46 (67.48) | 3.07 (3.11) | 9.16 (9.26) | FIG. 97 |
| Mfg. Ex. VII-38 | P107 | 0.78 (59.6) | 67.70 (67.83) | 3.11 (3.25) | 9.78 (9.68) | FIG. 98 |
| Mfg. Ex. VII-39 | P108 | 0.80 (58.6) | 67.51 (67.48) | 2.95 (3.11) | 9.37 (9.26) | FIG. 99 |
| Mfg. Ex. VII-40 | P109 | 0.86 (66.2) | 67.94 (67.83) | 3.13 (3.25) | 9.62 (9.68) | FIG. 100 |
| Mfg. Ex. VII-41 | P110 | 0.86 (65.2) | 70.05 (70.02) | 2.98 (3.23) | 9.80 (9.61) | FIG. 101 |
| Mfg. Ex. VII-42 | P111 | 0.81 (63.4) | 68.87 (69.14) | 3.11 (3.32) | 10.15 (9.87) | FIG. 102 |
| Mfg. Ex. VII-43 | P116 | 1.12 (68.3) | 78.30 (78.01) | 3.82 (4.06) | 7.43 (7.69) | FIG. 103 |
| Mfg. Ex. VII-44 | P117 | 0.97 (67.0) | 73.59 (73.78) | 3.64 (3.78) | 8.65 (8.75) | FIG. 104 |
| Mfg. Ex. VII-45 | P120 | 0.86 (66.4) | 73.18 (73.43) | 3.87 (3.95) | 9.74 (9.69) | FIG. 105 |
| Mfg. Ex. VII-46 | P121 | 0.84 (66.2) | 70.65 (70.88) | 3.56 (3.69) | 9.91 (9.92) | FIG. 106 |

TABLE 67-4

Figure 107:
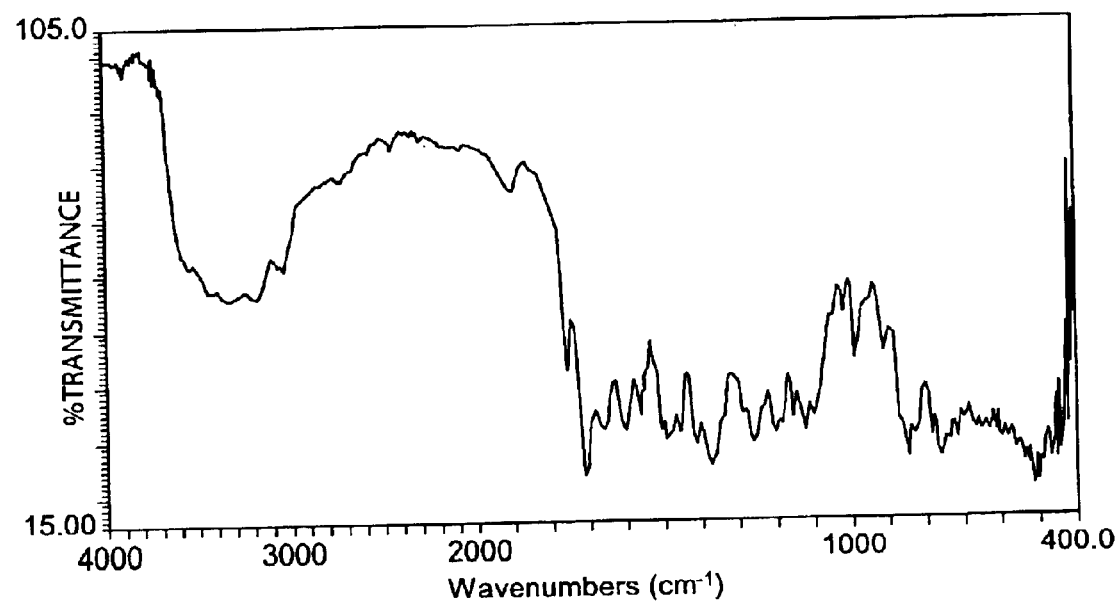
FIG. 107 is a graph showing an example of an infrared spectrum of an azo compound.
Figure 108:
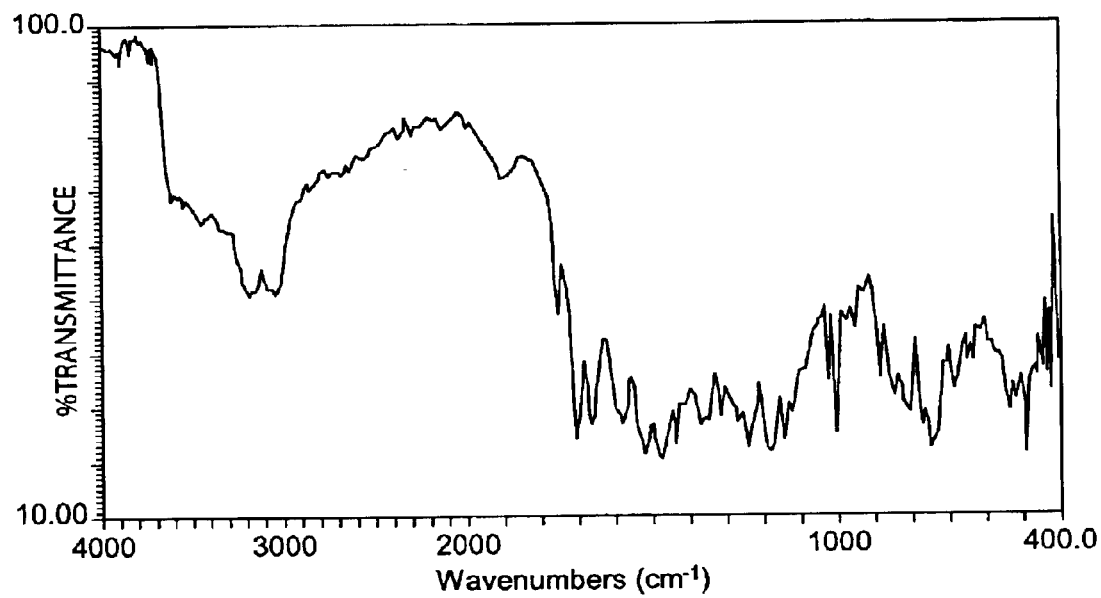
FIG. 108 is a graph showing an example of an infrared spectrum of an azo compound.
Figure 109:
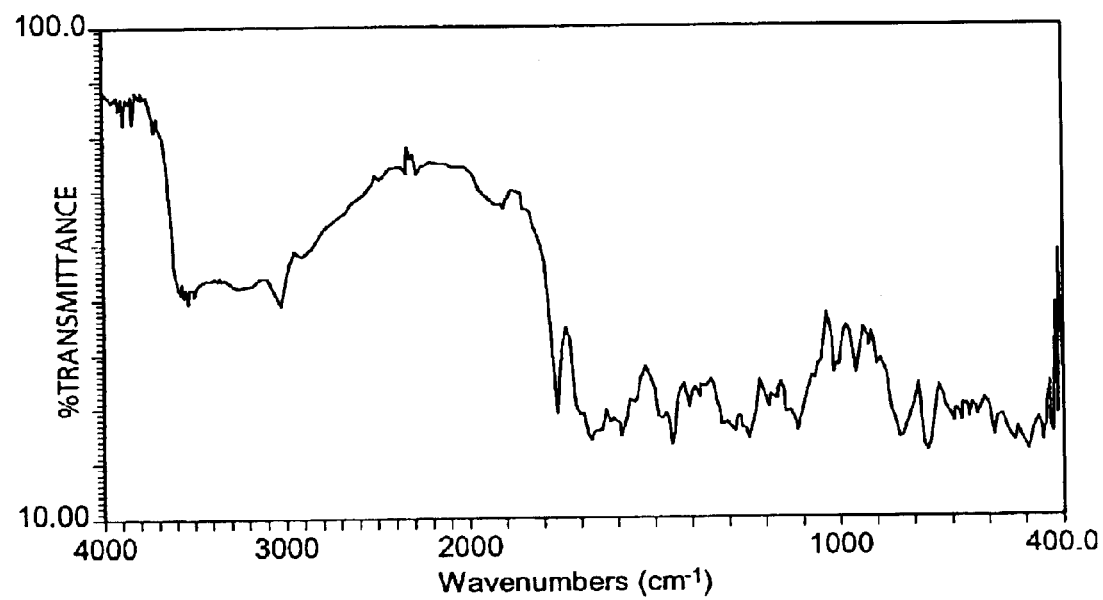
FIG. 109 is a graph showing an example of an infrared spectrum of an azo compound.
Figure 110:
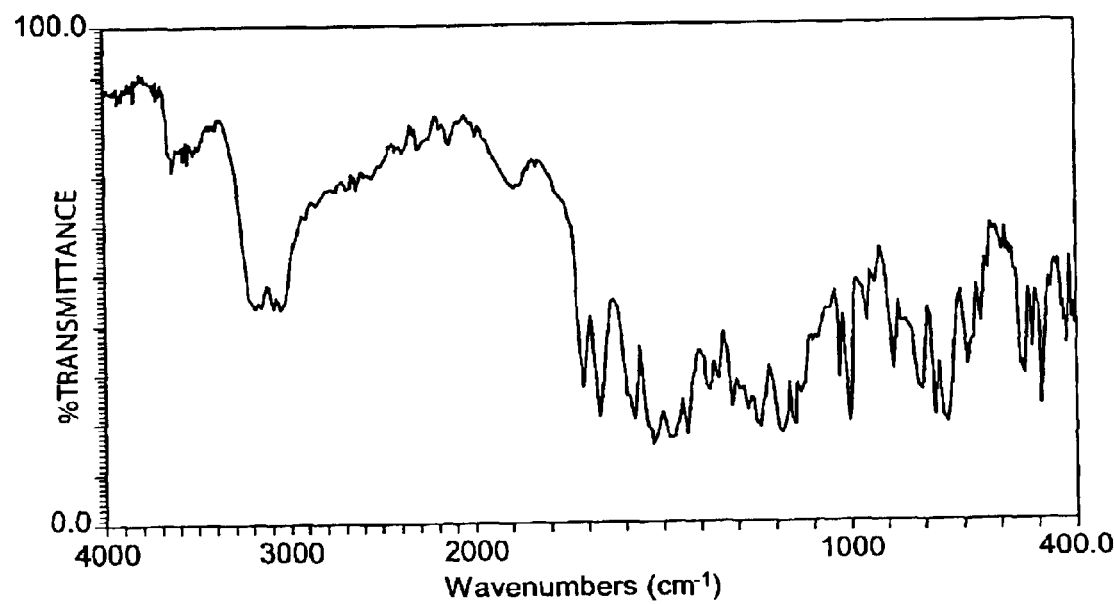
FIG. 110 is a graph showing an example of an infrared spectrum of an azo compound.
Figure 111:
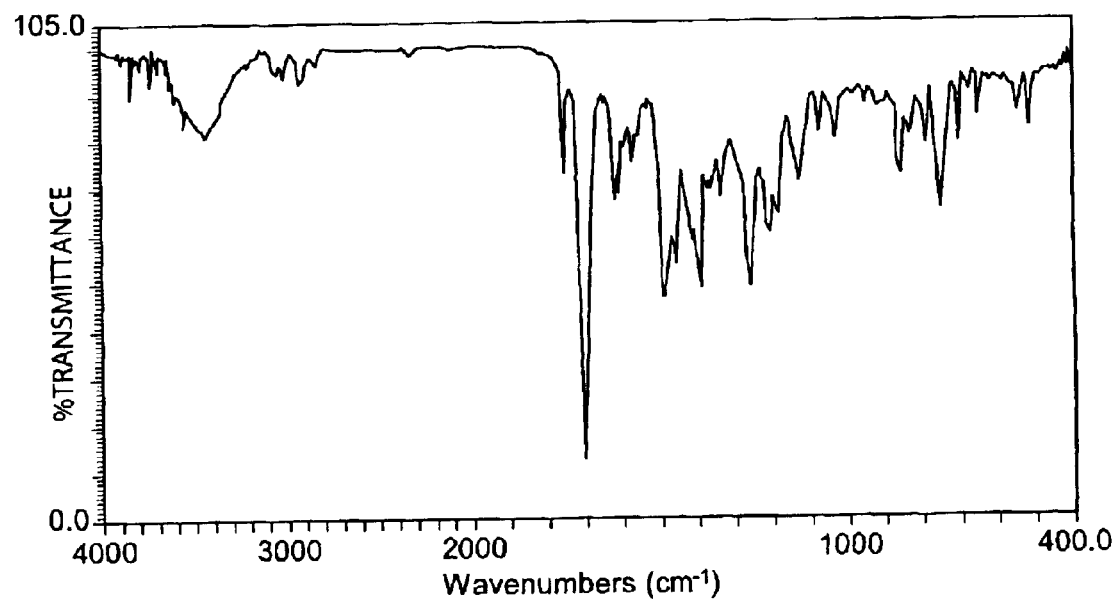
FIG. 111 is a graph showing an example of an infrared spectrum of an azo compound.
Figure 112:
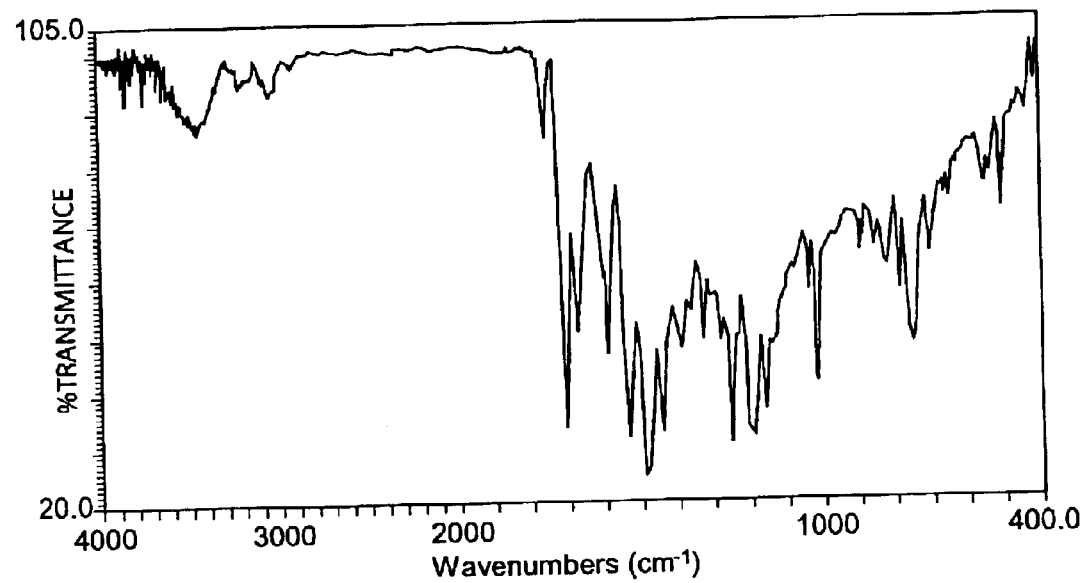
FIG. 112 is a graph showing an example of an infrared spectrum of an azo compound.
Figure 113:
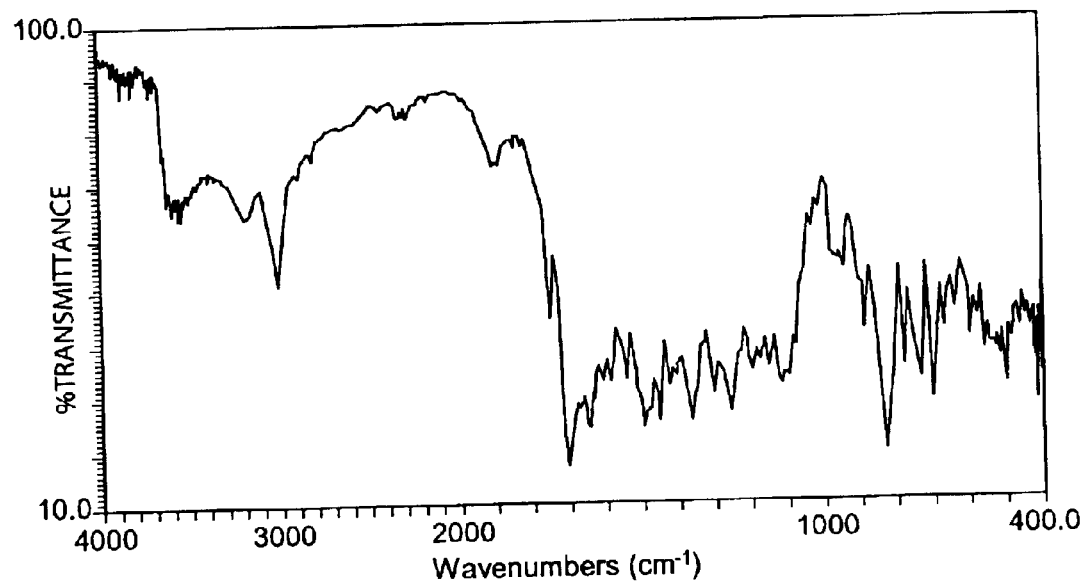
FIG. 113 is a graph showing an example of an infrared spectrum of an azo compound.
Figure 114:
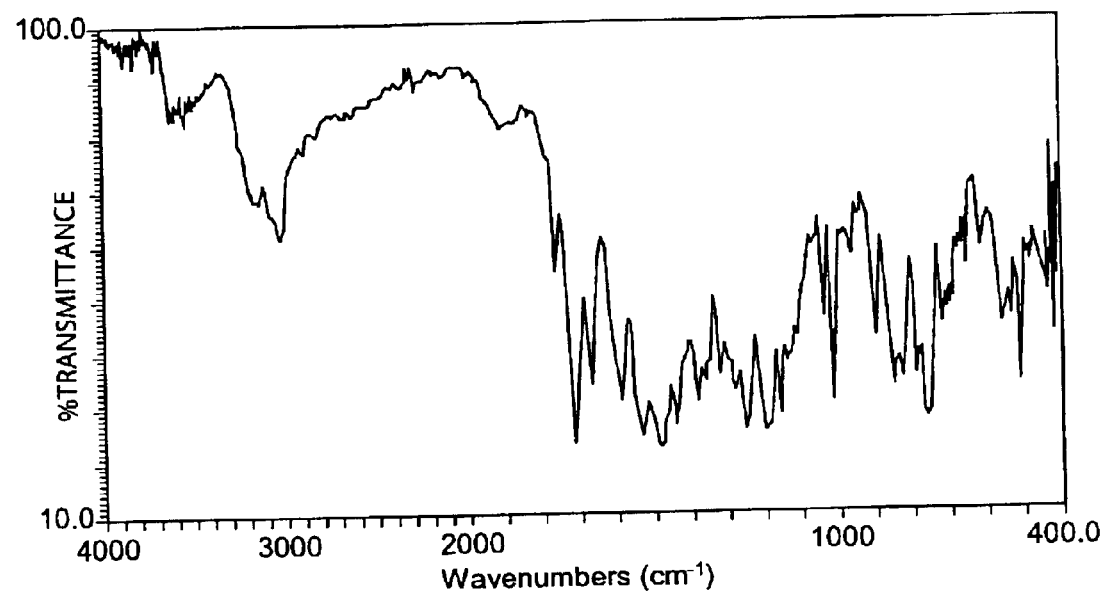
FIG. 114 is a graph showing an example of an infrared spectrum of an azo compound.
Figure 115:
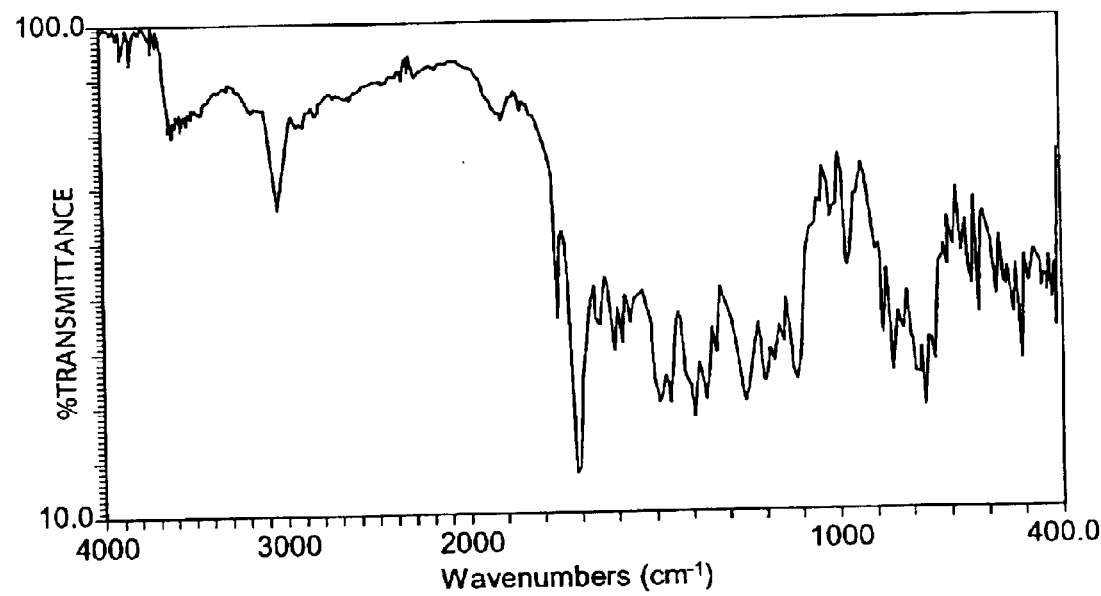
FIG. 115 is a graph showing an example of an infrared spectrum of an azo compound.
Figure 116:
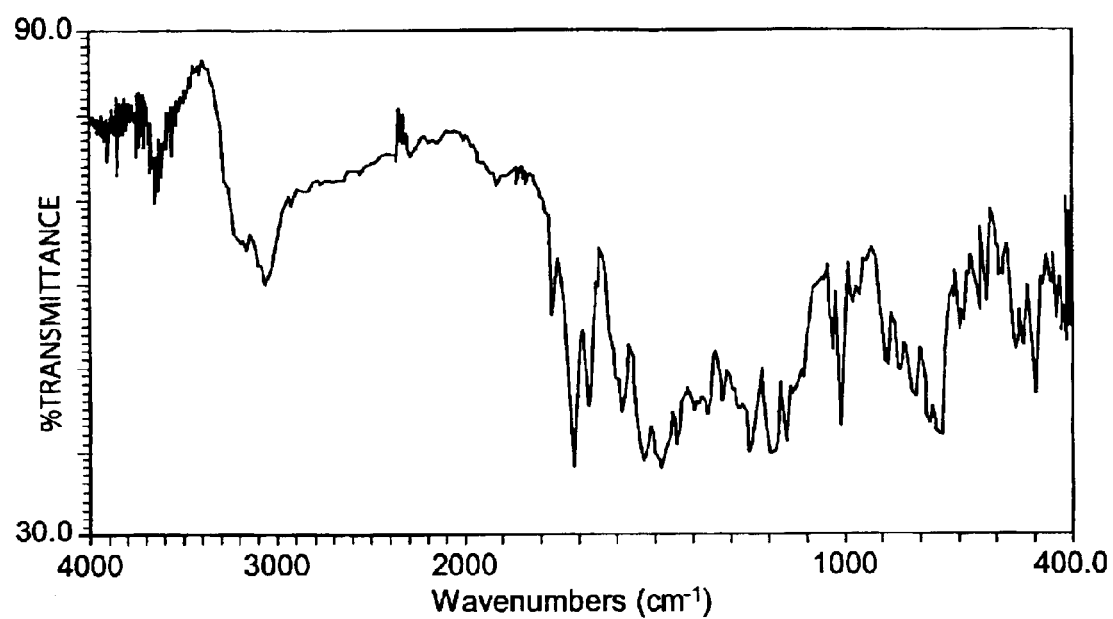
FIG. 116 is a graph showing an example of an infrared spectrum of an azo compound.

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-47 | P122 | 0.63 (46.7) | 68.03 (68.30) | 3.44 (3.15) | 12.21 (12.49) | FIG. 107 |
| Mfg.Ex. VII-48 | P123 | 0.63 (48.3) | 68.06 (68.25) | 3.14 (3.27) | 11.13 (11.37) | FIG. 108 |
| Mfg. Ex. VII-49 | P132 | 0.30 (23.0) | 70.97 (71.16) | 2.94 (2.81) | 12.89 (13.02) | FIG. 109 |
| Mfg. Ex. VII-50 | P133 | 0.35 (27.4) | 69.49 (69.71) | 3.07 (3.10) | 11.48 (11.61) | FIG. 110 |
| Mfg. Ex. VII-51 | P136 | 0.89 (66.3) | 73.87 (73.81) | 4.22 (4.28) | 9.46 (9.39) | FIG. 111 |
| Mfg. Ex. VII-52 | P137 | 0.79 (64.1) | 70.88 (71.12) | 3.57 (3.86) | 10.02 (9.76) | FIG. 112 |
| Mfg. Ex. VII-53 | P138 | 0.89 (55.9) | 77.55 (77.81) | 3.55 (3.78) | 7.60 (7.89) | FIG. 113 |
| Mfg. Ex. VII-54 | P139 | 0.89 (62.5) | 73.42 (73.61) | 3.44 (3.62) | 8.80 (8.88) | FIG. 114 |
| Mfg. Ex. VII-55 | P140 | 0.64 (47.0) | 74.86 (75.16) | 3.12 (3.32) | 9.07 (9.23) | FIG. 115 |
| Mfg. Ex. VII-56 | P141 | 0.84 (64.4) | 71.65 (71.85) | 3.09 (3.36) | 9.65 (9.76) | FIG. 116 |

TABLE 67-5

Figure 117:
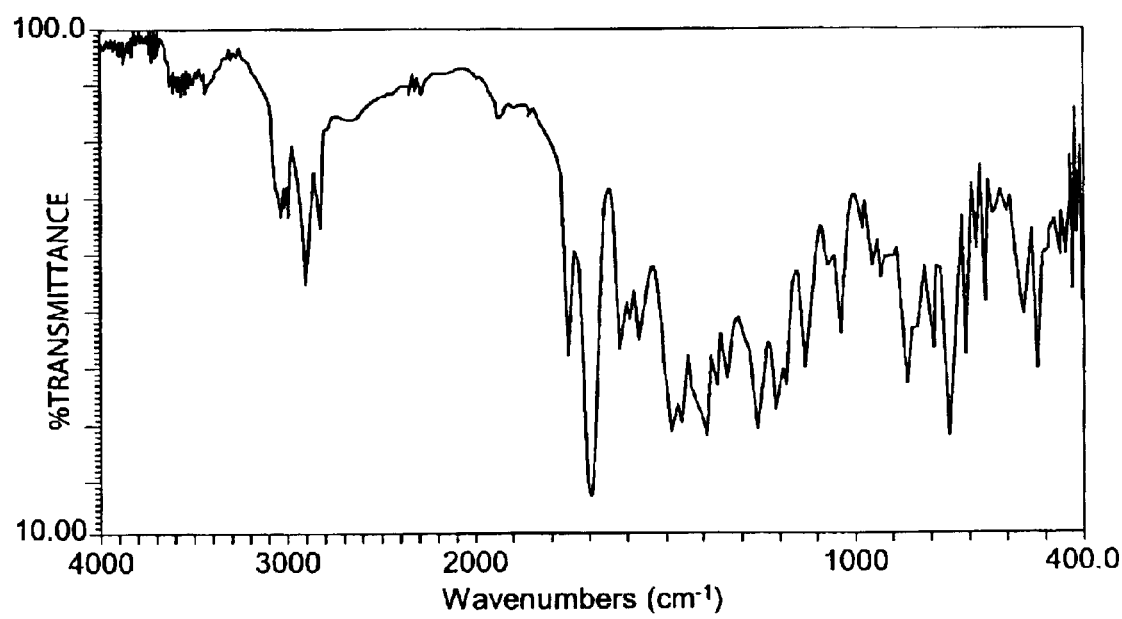
FIG. 117 is a graph showing an example of an infrared spectrum of an azo compound.

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-57 | P142 | 0.96 (69.4) | 74.27 (74.17) | 4.46 (4.59) | 9.14 (9.10) | FIG. 117 |

TABLE 67-5-continued

Figure 118:
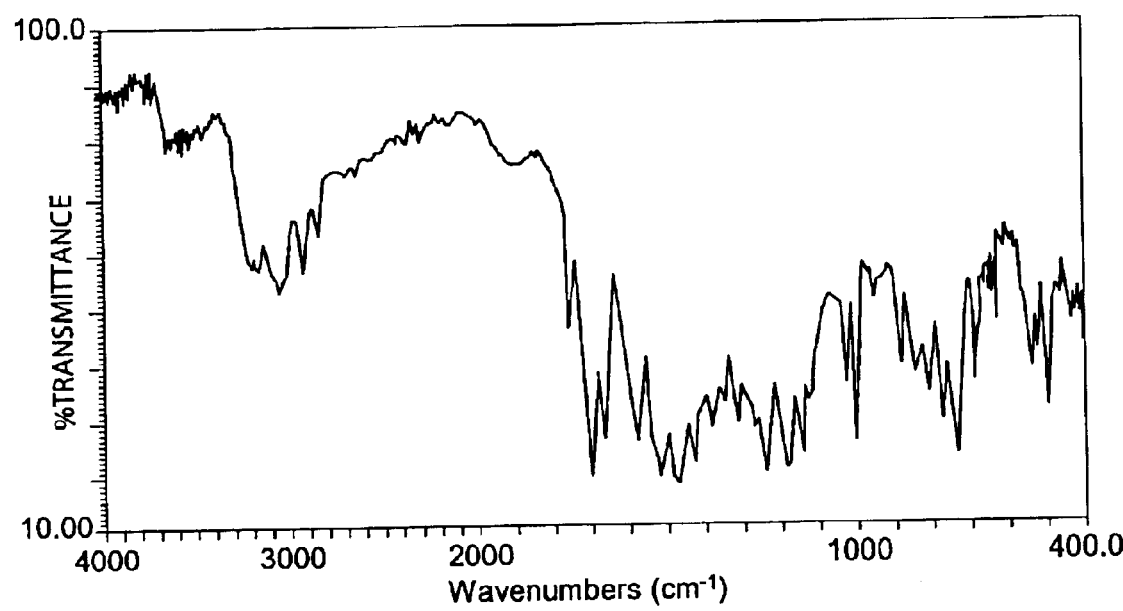
FIG. 118 is a graph showing an example of an infrared spectrum of an azo compound.
Figure 119:
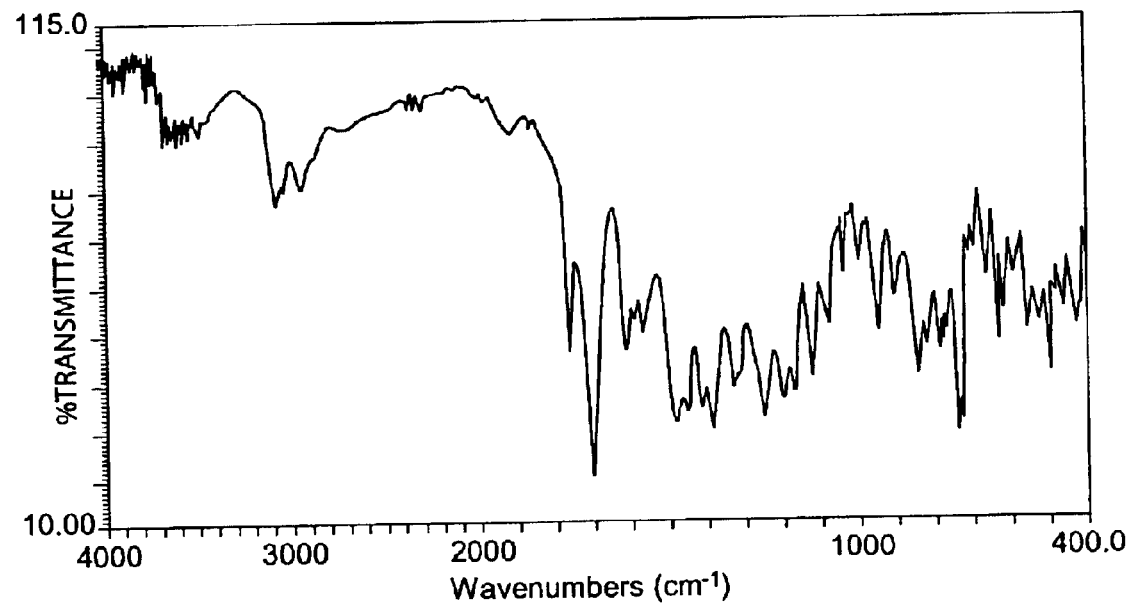
FIG. 119 is a graph showing an example of an infrared spectrum of an azo compound.
Figure 120:
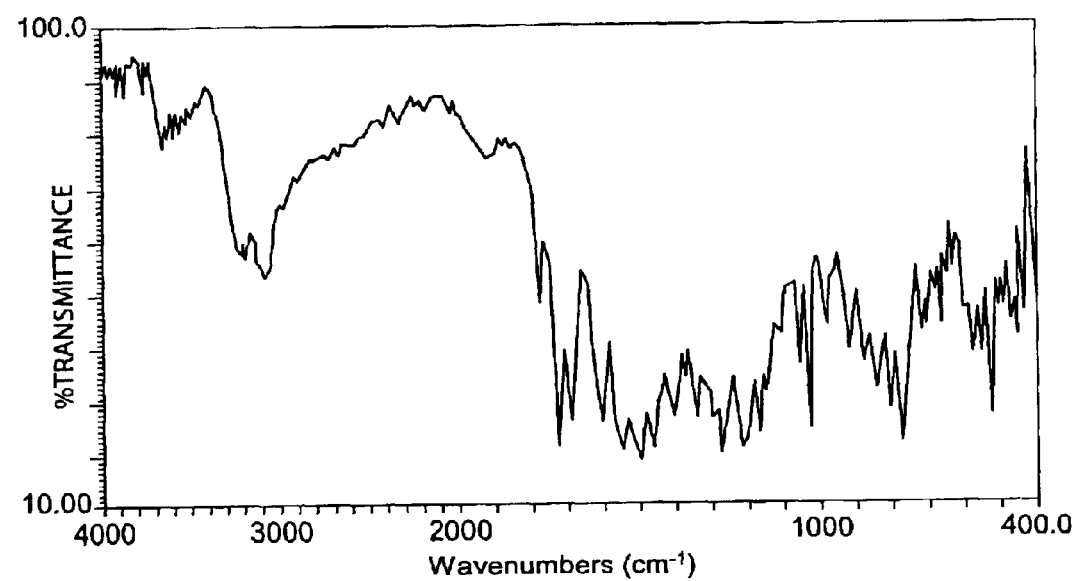
Figure 121:
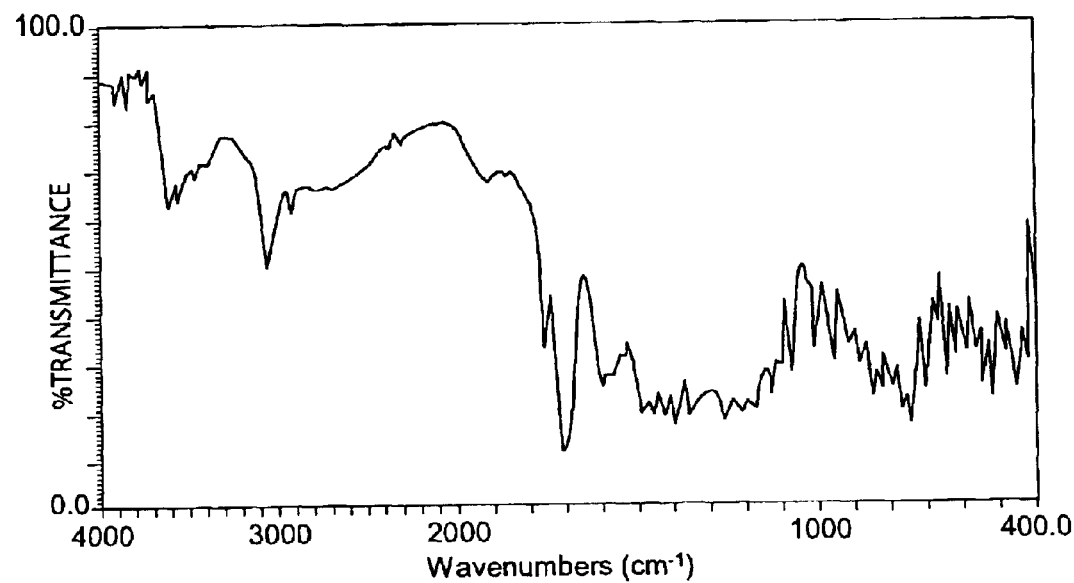
Figure 122:
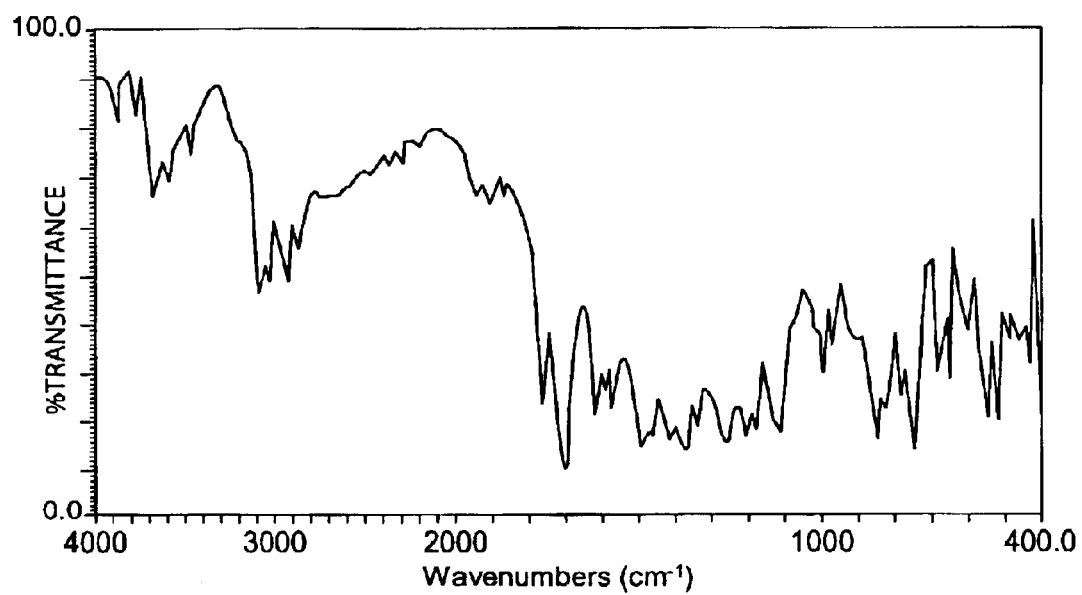
Figure 123:
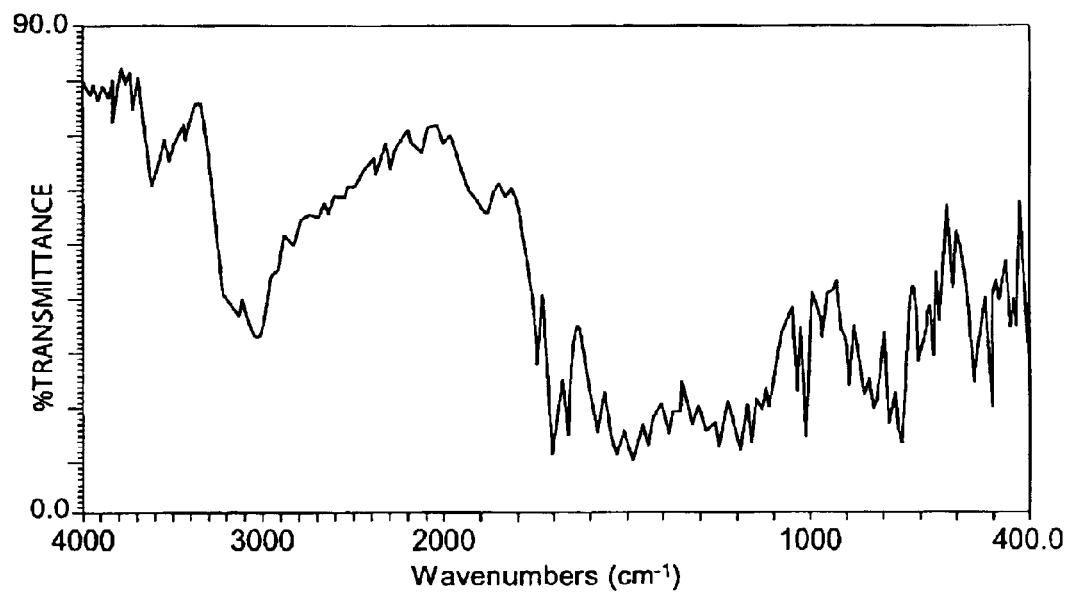
Figure 125:
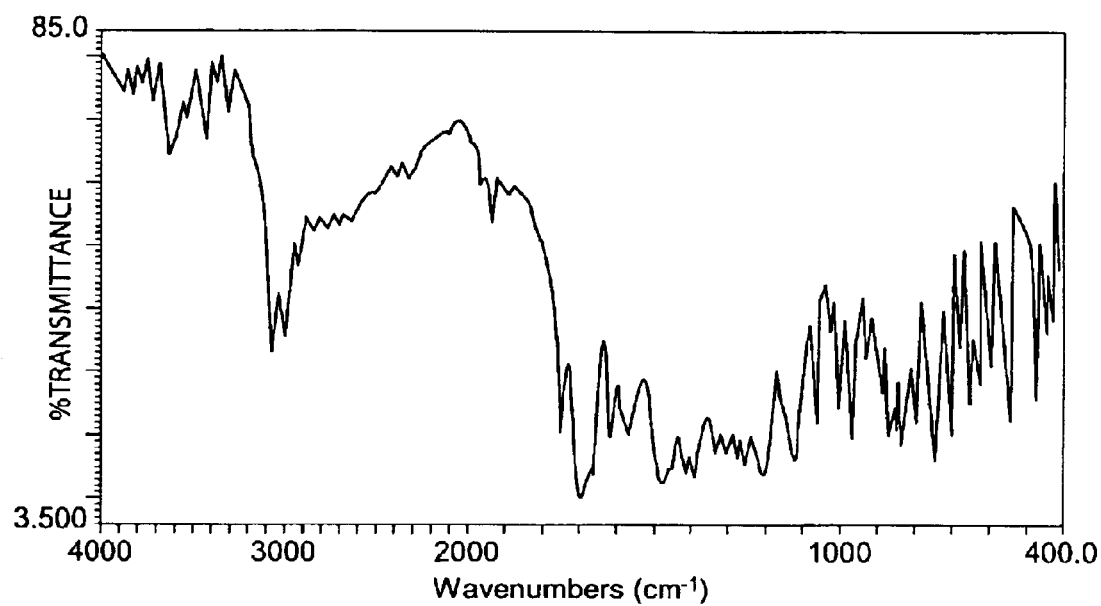
Figure 126:
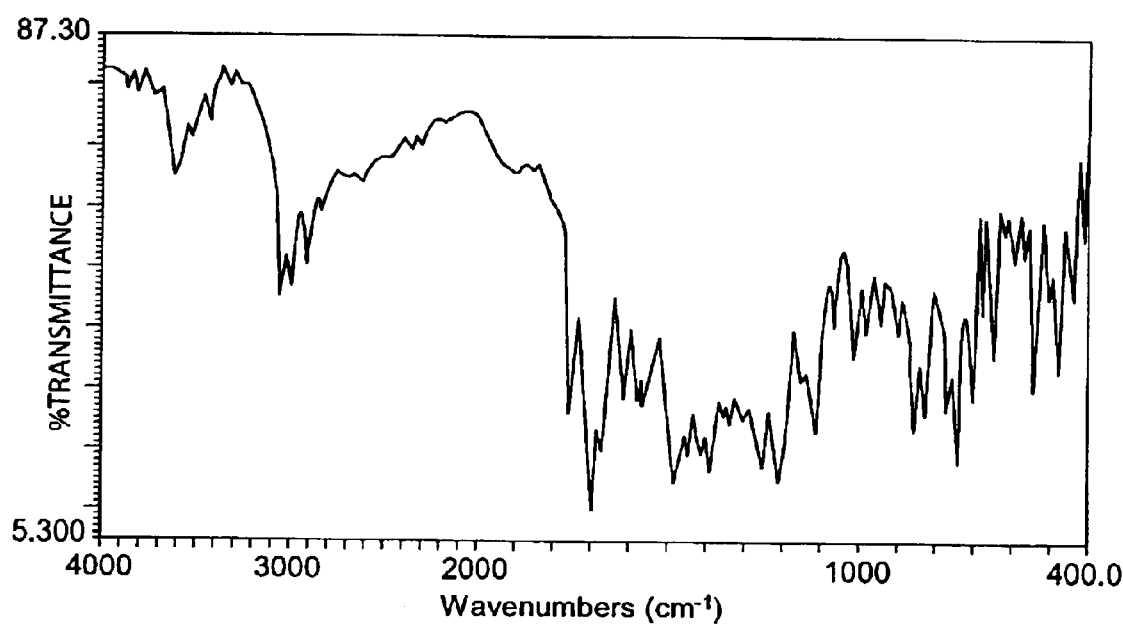
Figure 127:
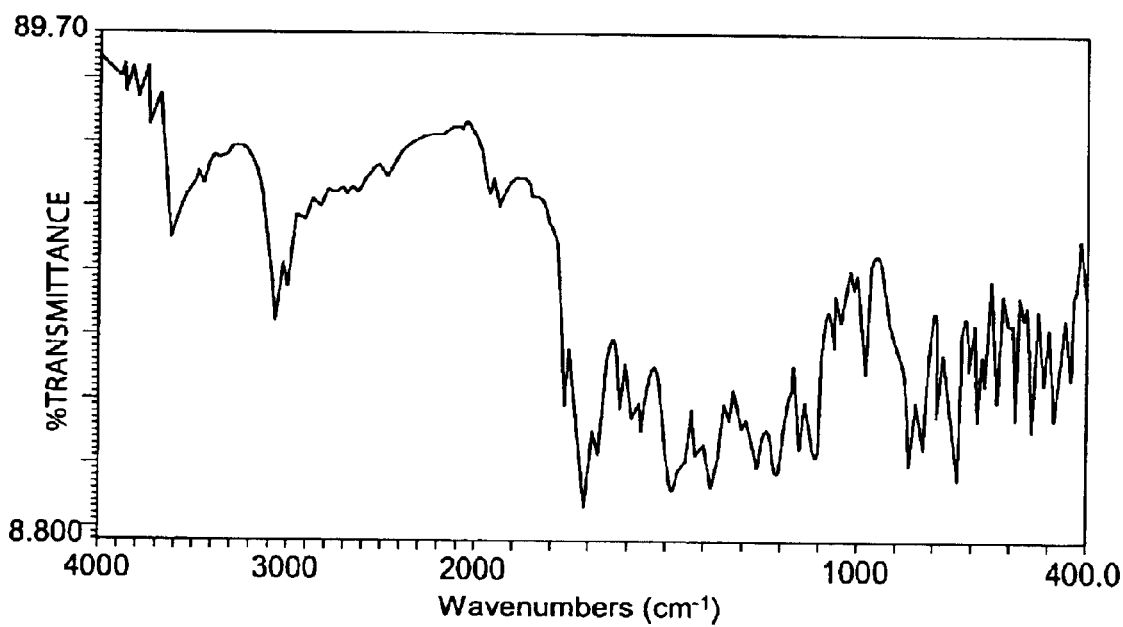
Figure 128:
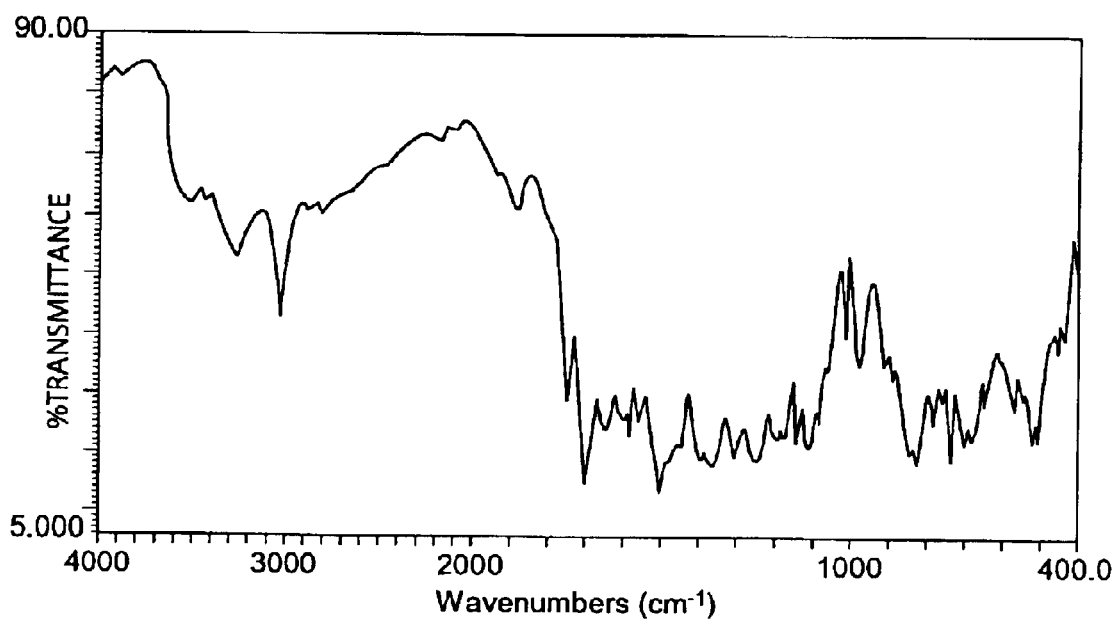

| Mfg. Ex. No. | Azo Compound No. | Yield amount (g) (Yield ratio (%)) | Elemental analysis (%) Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-58 | P143 | 0.82 (62.1) | 71.11 (71.35) | 3.80 (4.03) | 9.85 (9.60) | FIG. 118 |
| Mfg. Ex. VII-59 | P144 | 0.76 (58.3) | 73.25 (73.43) | 3.72 (3.95) | 9.65 (9.69) | FIG. 119 |
| Mfg. Ex. VII-60 | P145 | 0.75 (58.8) | 70.67 (70.88) | 3.45 (3.69) | 10.12 (9.92) | FIG. 120 |
| Mfg. Ex. VII-61 | P146 | 0.85 (69.0) | 72.82 (73.08) | 3.06 (3.31) | 11.71 (11.93) | FIG. 121 |
| Mfg. Ex. VII-62 | P153 | 0.82 (61.0) | 73.88 (74.15) | 3.71 (3.85) | 9.36 (9.43) | FIG. 122 |
| Mfg. Ex. VII-63 | P154 | 0.74 (56.4) | 71.43 (71.68) | 3.47 (3.59) | 9.45 (9.64) | FIG. 123 |
| Mfg. Ex. VII-64 | P88 | 0.86 (66.1) | 71.87 (72.05) | 3.21 (3.49) | 9.54 (9.70) | FIG. 125 |
| Mfg. Ex. VII-65 | P89 | 0.92 (68.5) | 72.19 (72.48) | 3.63 (3.83) | 9.09 (9.39) | FIG. 126 |
| Mfg. Ex. VII-66 | P91 | 0.90 (71.5) | 71.32 (71.60) | 3.00 (3.12) | 9.79 (10.02) | FIG. 127 |
| Mfg. Ex. VII-67 | P124 | 0.78 (50.0) | 71.94 (72.13) | 3.28 (3.46) | 10.39 (10.68) | FIG. 128 |

TABLE 67-6

Figure 129:
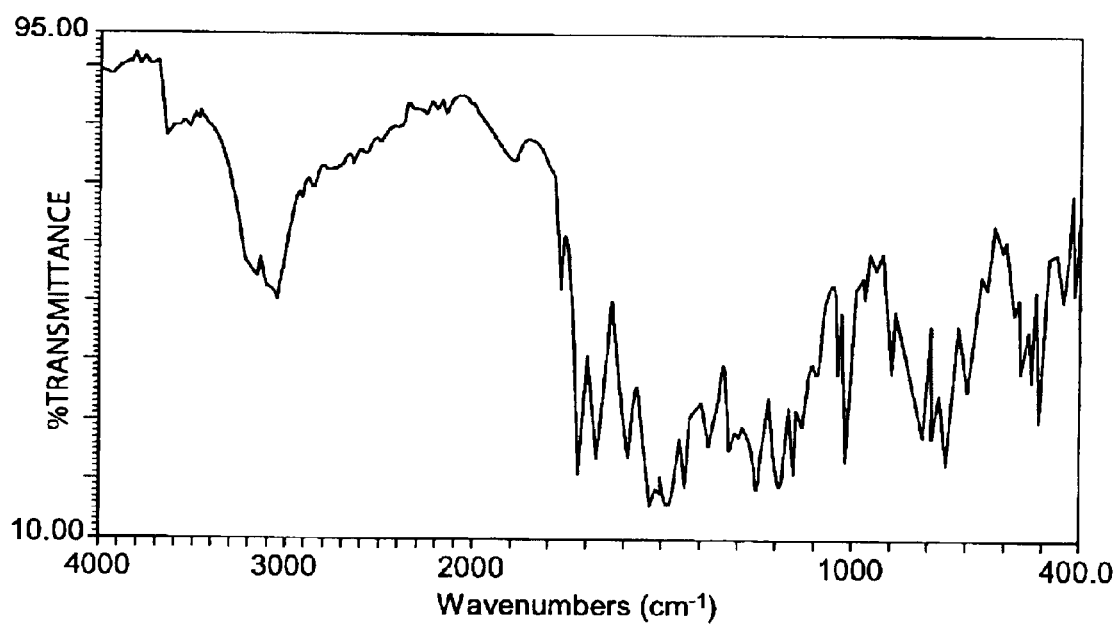
Figure 130:
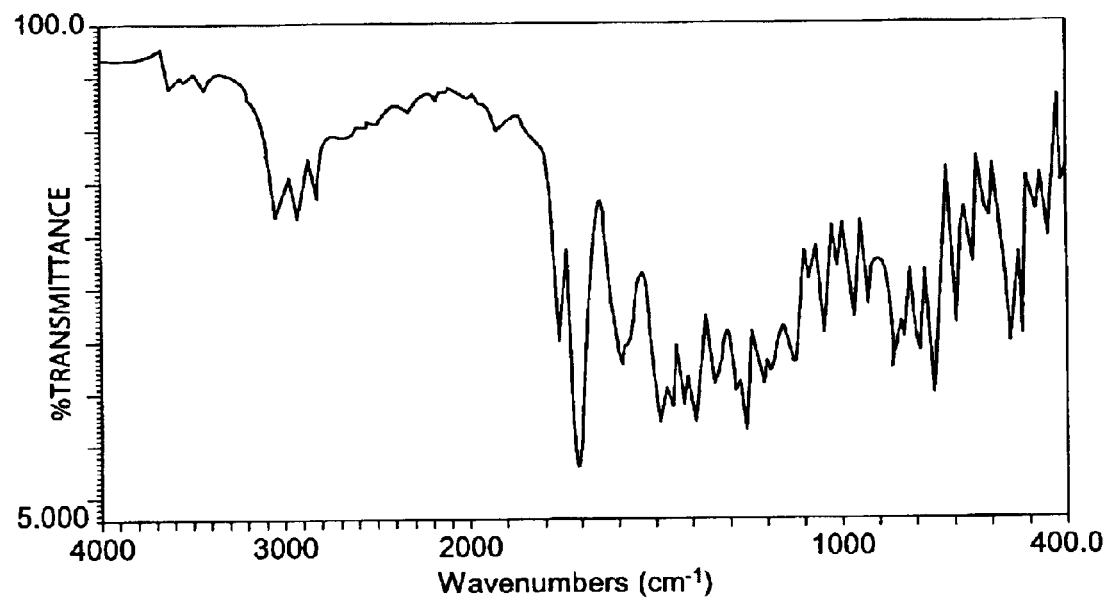
Figure 131:
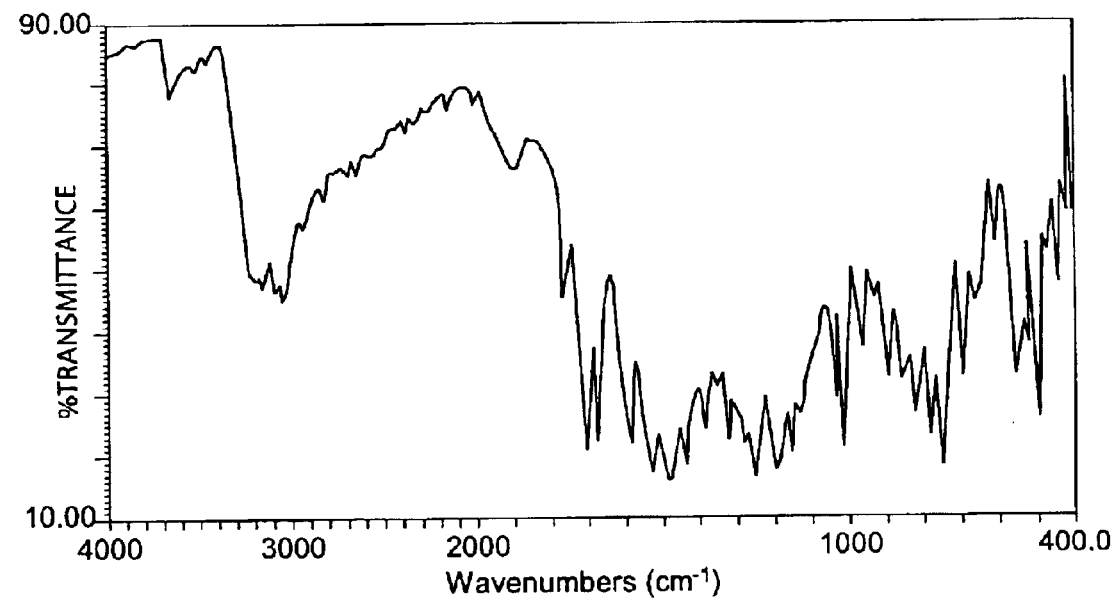

| Mfg. Ex. No. | Azo Compound No. | Yield amount (g) (Yield ratio (%)) | Elemental analysis (%) Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-68 | P125 | 0.71 (50.6) | 70.04 (70.40) | 3.31 (3.44) | 10.29 (10.45) | FIG. 129 |
| Mfg. Ex. VII-69 | P147 | 0.78 (58.1) | 70.54 (70.82) | 3.61 (3.81) | 9.09 (9.35) | FIG. 130 |
| Mfg. Ex. VII-70 | P148 | 0.64 (49.3) | 69.48 (69.56) | 3.37 (3.62) | 9.90 (9.74) | FIG. 131 |
| Mfg. Ex. VII-71 | P149 | 0.51 (37.8) | 70.50 (70.82) | 3.54 (3.81) | 9.08 (9.35) | FIG. 132 |
| Mfg. Ex. VII-72 | P150 | 0.65 (50.2) | 69.28 (69.56) | 3.39 (3.62) | 9.78 (9.74) | FIG. 133 |
| Mfg. Ex. VII-73 | P155 | 0.66 (49.2) | 73.91 (74.15) | 3.62 (3.85) | 9.15 (9.43) | FIG. 134 |
| Mfg. Ex. VII-74 | P156 | 0.64 (49.0) | 71.50 (71.68) | 3.44 (3.59) | 9.87 (9.64) | FIG. 135 |
| Mfg. Ex. VII-75 | P157 | 0.75 (55.8) | 76.52 (76.84) | 4.04 (4.30) | 9.17 (9.43) | FIG. 136 |
| Mfg. Ex. VII-76 | P158 | 0.70 (52.6) | 71.80 (71.90) | 3.53 (3.76) | 9.22 (9.49) | FIG. 137 |
| Mfg. Ex. VII-77 | P159 | 0.66 (45.2) | 65.03 (65.30) | 2.54 (2.90) | 8.30 (8.62) | FIG. 138 |
| Mfg. Ex. VII-78 | P160 | 0.61 (45.3) | 66.29 (66.63) | 2.95 (3.13) | 9.08 (9.32) | FIG. 139 |

TABLE 67-7

| Mfg. Ex. No. | Azo Compound No. | Yield amount (g) (Yield ratio (%)) | Elemental analysis (%) Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-79 | P161 | 0.76 (51.8) | 65.18 (65.30) | 2.75 (2.90) | 8.41 (8.62) | FIG. 140 |

TABLE 67-7-continued

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-80 | P162 | 0.68 (50.3) | 66.76 (66.63) | 3.10 (3.13) | 9.22 (9.32) | FIG. 141 |
| Mfg. Ex. VII-81 | P163 | 0.70 (48.0) | 64.96 (65.30) | 2.56 (2.90) | 8.30 (8.62) | FIG. 142 |
| Mfg. Ex. VII-82 | P164 | 0.65 (48.3) | 66.28 (66.63) | 2.83 (3.13) | 8.95 (9.32) | FIG. 143 |
| Mfg. Ex. VII-83 | P169 | 0.57 (43.5) | 73.23 (73.43) | 3.73 (3.95) | 9.46 (9.69) | FIG. 144 |
| Mfg. Ex. VII-84 | P170 | 0.62 (49.1) | 70.50 (70.88) | 3.38 (3.69) | 9.71 (9.92) | FIG. 145 |
| Mfg. Ex. VII-85 | P173 | 0.57 (45.9) | 73.38 (73.55) | 3.32 (3.39) | 13.22 (13.45) | FIG. 146 |
| Mfg. Ex. VII-86 | P174 | 0.66 (52.8) | 70.51 (70.88) | 3.25 (3.40) | 11.55 (11.81) | FIG. 147 |
| Mfg. Ex. VII-87 | P180 | 0.86 (69.3) | 72.24 (72.63) | 3.42 (3.66) | 9.91 (10.16) | FIG. 148 |
| Mfg. Ex. VII-88 | P181 | 0.80 (63.4) | 72.48 (72.85) | 3.69 (3.84) | 10.26 (10.00) | FIG. 149 |
| Mfg. Ex. VII-89 | P182 | 0.96 (69.3) | 72.50 (72.88) | 3.99 (4.15) | 8.88 (9.11) | FIG. 150 |

TABLE 67-8

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-90 | P183 | 0.83 (64.7) | 72.77 (73.06) | 3.81 (4.01) | 10.12 (9.83) | FIG. 151 |
| Mfg. Ex. VII-91 | P184 | 0.79 (64.8) | 72.27 (72.41) | 3.20 (3.47) | 10.17 (10.34) | FIG. 152 |
| Mfg. Ex. VII-92 | P185 | 1.07 (76.5) | 74.34 (74.67) | 2.67 (3.03) | 11.84 (12.01) | FIG. 153 |
| Mfg. Ex. VII-93 | P186 | 0.80 (62.0) | 73.65 (74.03) | 3.08 (3.40) | 11.01 (11.40) | FIG. 154 |
| Mfg. Ex. VII-94 | P187 | 0.91 (70.5) | 71.88 (72.55) | 3.03 (3.28) | 12.78 (13.02) | FIG. 155 |
| Mfg. Ex. VII-95 | P188 | 0.75 (60.7) | 71.84 (72.90) | 3.31 (3.55) | 11.75 (11.90) | FIG. 156 |

Further, the present invention is hereinafter explained concretely with reference to applied embodiments. However, the embodiments of the present invention are not limited thereto.

(Applied Embodiment 1)

Azo compounds 7.5 volumes of the example VII-10 (azo compound No.P19) of the present invention and 0.5% by weight tetra hydro furan liquid solution 500 volumes of polyester resin (VYLON®200: TOYOBO Co., Ltd.) were crushed and mixed in a ball mill, obtained dispersion liquid was doctor-bladed on an aluminium evaporation polyester film, then dried in a natural condition, thus an charge generating layer having the thickness of 1 μm was formed.

Then, charge transporting substance 1 volume, polycarbonate resin (Panlite® K1300: TEJIN KASEI Co., Ltd.) 1 volume, and tetra hydro furan 8 volumes charge transporting layer coating liquid indicated by the following structural formula (D-1) were prepared, coated by the doctor blade on the aforementioned charge generating layer, then dried at the temperature of 80° C. for 2 minutes and further at the temperature of 120° C. for 5 minutes, thus a charge transporting layer having the thickness of 20 μm was formed.

Structural Formula (D-1)

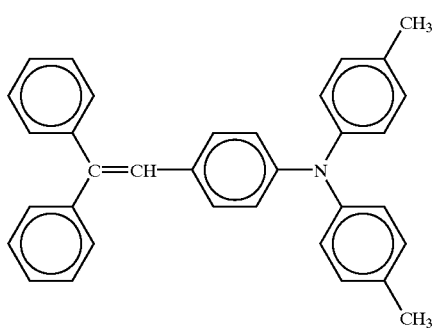

For thus obtained electrophotographic photoconductor, under the condition of 25° C./55%RH, −6 KV corona discharge was performed for 20 seconds and this photoconductor was charged using the electrostatic copying paper tester EPA-8100(KAWAGUCHI ELECTRIC Co., Ltd.) in a dark place. Then the photoconductor was left as it was for 20 seconds, and surface electrokinetic potential $V_0$ (V) at that time was measured. Succeedingly, light was given as irradiation by a tungsten lamp in order for a photoconductor surface's illumination unit to become 5.3 luxes, and time (second) till its surface electrokinetic potential became a half of $V_0$ was obtained, thus exposing volume $E_{1/2}$ (lux·second) was calculated. The results therefor were $V_0$=−938 volts, $E_{1/2}$=2.0 luxes·second.

In this way, obviously in the detailed and concrete explanation, azo compound manufacturing raw material (coupler compound) of the present invention can be manufactured easily compared with a conventional coupler compound. By utilizing an azo compound using this manufacturing raw material (coupler compound) as a charge generating substance, a high sensitive electrophotographic photoconductor can be provided. Further, a novel coupler of the present invention affects excellent advantageous points as manufacturing pigments of an azo compound as an organic photo conductor.

Then, concrete explanation is made using embodiments for azo compounds, azo compound manufacturing raw material, and their methods for producing indicated by the general formula <<101>> of the present invention. However, the embodiments of the present invention are not limited thereto.

Example VII-1

Manufacturing 2-(t-butoxy)7,8-naphthalic acid dimethyl ester [$R_1$=$R_2$=$R_3$=$R_4$=H, $R_5$=$CH_3$, $R_6$=t-$C_4H_9$ Compound of a General Formula <<120>>]

P-t-butoxy styrene 35.25 g (0.2 mol) and acetylene carboxylic acid dimethyl ester 56.84 g (0.4 mol) were dissolved in 200 ml of nitrobenzene, then reacted and cooled at the temperature of 140° C. for 5 hours. Further, nitrobenzene was removed under reduced pressure, and a treatment of silica gel column chromatography (n-hexane:acetic acid ethyl=9:1 as developing solvent) was performed to the residual, then 40.78 g of the objective crude material was obtained.

Further, 36.63 g (yield 57.9%) objective naphthalene compounds were obtained by recrystallizing through diisopropyl ether. Melt points were 82.0° C. to 83.0° C. This naphthalene compound's infrared absorption spectrum is indicated in FIG. 1.

TABLE 58

|  | Elemental analysis value (%) | |
| --- | --- | --- |
|  | C | H |
| Actual measurement value | 68.32 | 6.46 |
| Calculation value | 68.34 | 6.37 |

Example VII-2

Manufacturing 2-hydroxy-7,8-naphthalic acid dimethyl ester [$R_1$=$R_2$=$R_3$=$R_4$=H, $R_5$=$CH_3$ Compound of a General Formula <<149>>]

2-(t-butoxy)7,8-naphthalic acid dimethyl ester 31.63 g (0.1 mol) obtained in the example VII-1 was dissolved in 120 ml chloride methylene, mixed at a room temperature, then trifluoro acetic acid 57.01 g (0.5 mol) was dropped for 10 minutes. Further, mixing reaction was continued for 3 hours under the same condition (room temperature). After reaction, reacted material was poured on an ice, water was added, and then phase splitting was performed. A chloride methylene phase was further washed twice using water and dehydrated through sulfuric anhydride magnesium. Sulfuric magnesium was removed by filtering, then the objective naphthalene compound, 24.31 g (yield 93.4%), was obtained by recrystallizing the residual material from which chloride methylene was removed through toluene. Melt points were 139.0–139.8° C. This naphthalene compound's infrared absorption spectrum is indicated in FIG. 2.

TABLE 59

|  | Elemental analysis value (%) | |
| --- | --- | --- |
|  | C | H |
| Actual measurement value | 64.60 | 4.56 |
| Calculation value | 64.61 | 4.65 |

Example VII-3

Manufacturing N-n-hexyl-2-hydroxy-7,8-naphthalic acid imido [$R_1$=$R_2$=$R_3$=$R_4$=H, X=$C_6H_{13}$-n <coupler No. C1> Compound of a General Formula <<122>>]

2-hydroxy-7,8-naphthalic acid dimethyl ester 10.41 g (0.04 mol) and n-hexyl amine 12.14 g (0.12 mol) obtained in the example VII-2 were mixed and reacted in ethylene glycol 100 ml for 2 hours under a nitrogen gas air stream at the temperature of 120° C. for 4 hours. After reaction ended and cooled, after reacted material was poured on an ice, hydrochlorix acid was made, extracted crystal was filtered and washed using 500 ml ion exchange water, then dried under reduced pressure at the temperature of 60° C., thus crude objects 9.73 g were obtained.

Obtained crude material was processed by silica gel column chromatography (toluene: acetic acid ethyl=4:1 as developing solvent) and recrystallized by toluene, thus 7.12 g (yield 59.9%) yellow coupler compound <coupler No. C1> was obtained. Melt points were 165.5–166.5° C. The infrared absorption spectrum of this coupler compound <coupler No. C1> is shown in FIG. 3.

TABLE 60

|  | Elemental analysis value (%) | | |
| --- | --- | --- | --- |
|  | C | H | N |
| Actual measurement value | 72.84 | 6.51 | 4.68 |
| Calculation value | 72.71 | 6.44 | 4.71 |

Example VII-4

N-benzyl-2-hydroxy-7,8-naphthalic acid imido [$R_1=R_2=R_3=R_4=H, X=$

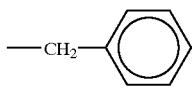

of the General Formula <<122>>]

Manufacturing <Coupler No. C5> Compounds 2-hydroxy-7,8-naphthalic acid dimethyl ester 10.41 g (0.04 mol) and benzyl amine 8.57 g (0.08 mol) obtained in the example VII-2 were mixed and reacted for 6 hours using ethylene glycol 100 ml under a nitrogen gas air stream at the temperature of 140° C. After reaction and cooling, reacted material was poured on a ice, hydrochlorid acid was made, then extracted crystal was filtered, it was washed by 500 ml of ion exchange water, by drying at the temperature of 60° C. under reduced pressure, thus objective crude material 10.21 g was obtained. Obtained crude material was recrystallized by n-butanol, and 9.57 g (yield 78.9%) orange color coupler compound <coupler No. C5> was obtained. Melt points were 255.2° C. to 259.0° C. This coupler compound <coupler No. C5> infrared absorption spectrum is shown in FIG. 4.

TABLE 61

|  | Elemental analysis value (%) | | |
| --- | --- | --- | --- |
|  | C | H | N |
| Actual measurement value | 75.30 | 4.29 | 4.60 |
| Calculation value | 75.24 | 4.32 | 4.62 |

Example VII-5

N-(2-phenyl ethyl)-2-hydroxy-7,8-naphthalic acid imido [$R_1=R_2=R_3=R_4=H, X=$

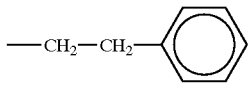

of a General Formula <<122>>]

Manufacturing <Coupler No. C14> Compounds

Except that benzyl amine 8.57 g (0.08 mol) was used in phenethyl amine 9.69 g (0.08 mol), crude object material 10.48 g was obtained in the same reaction as the example VII-4. Obtained crude material was recrystallized by n-butanol, and 9.95 g (yield 78.4%) yellow color coupler compound <coupler No. C14> was obtained. Melt points were 233.5° C. to 236.5° C. This coupler compound's <coupler No. C14> infrared absorption spectrum is shown in FIG. 5.

TABLE 62

|  | Elemental analysis value (%) | | |
| --- | --- | --- | --- |
|  | C | H | N |
| Actual measurement value | 75.78 | 4.71 | 4.36 |
| Calculation value | 75.70 | 4.77 | 4.41 |

Example VII-6

N-phenyl-2-hydroxy-7,8-naphthalic acid imido [$R_1=R_2=R_3=R_4=H, X=$

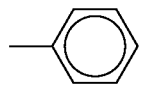

of a General Formula <<122>>]

Manufacturing <Coupler No. C28> Compound

Except that Benzyl amine 8.57 g (0.08 mol) was used in aniline 7.45 g (0.08 mol), the objective crude material 12.04 g was obtained in the same reaction as the example VII-4. Obtained crude material was recrystallized by n-butanol/toluene (1/1 vol), and 8.15 g (yield 69.7%) orange color coupler compound <coupler No. C28> was obtained. Melt points were 245.5° C. to 248.9° C. This coupler compound's <coupler No. C28> infrared absorption spectrum is shown in FIG. 6.

TABLE 63

|  | Elemental analysis value (%) | | |
| --- | --- | --- | --- |
|  | C | H | N |
| Actual measurement value | 74.79 | 3.88 | 4.83 |
| Calculation value | 74.73 | 3.83 | 4.84 |

Example VII-7

12-hydroxy-benzo[6,7]isoindole[2,1-a]perimysin-14-on or 9-hydroxy-benzo[4,5]isoindole[2,1-a]perimysin-14-on [$R_1=R_2=R_3=R_4=H, Y=$

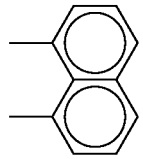

of a General Formula <<124>>]

Manufacturing <Coupler No. E23> Compound 2-hydroxy-7,8-naphthalic acid dimethyl ester 10.41 g (0.04 mol) and 1,8-diamino naphthalene 12.66 g (0.08 mol) obtained in the example VII-2 were mixed and reacted in ethylene glycol 100 ml under a nitrogen gas air stream at the temperature of 160° C. for 8 hours. After reaction and cooling, reacted material was poured on a ice, hydrochlorid acid was made, then extracted crystal was filtered, it was washed by 500 ml ion exchange water, by drying at the temperature of 60° C. under reduced pressure, thus objective crude material 9.96 g was obtained. Obtained crude material was recrystallized by nitrobenzene, and 8.80 g (yield 65.4%) orange color coupler compound <coupler No. E23> was obtained. The decomposition point was 398° C. This coupler compound's <coupler No.E23> infrared absorption spectrum is shown in FIG. 7.

TABLE 64

| | Elemental analysis value (%) | | |
|---|---|---|---|
| | C | H | N |
| Actual measurement value | 78.50 | 3.57 | 8.32 |
| Calculation value | 78.56 | 3.60 | 8.33 |

Example VII-8 to Example VII-13

Except that benzyl amine was used instead of various amine compounds expressed by the general formula <<28>> in the example VII-4, the same reaction was performed, and the following compound was obtained. Melt points, element analysis values, and a chart for the infrared absorption spectrum for are shown in Table 65.

TABLE 65

| Ex. | Coupler (Cp) No. | Melting Point (° C.) <Dissolving point (° C.)> | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Ex. VII-8 | C9 | 238.3~243.1 | 75.82 (75.70) | 4.71 (4.77) | 4.32 (4.41) | FIG. 31 |
| Ex. VII-9 | C10 | 212.9~219.0 | 72.13 (72.06) | 4.40 (4.54) | 4.11 (4.20) | FIG. 32 |
| Ex. VII-10 | C11 | 239.3~244.0 | 67.66 (67.57) | 3.38 (3.58) | 4.11 (4.15) | FIG. 33 |
| Ex. VII-11 | C13 | 258.8~263.2 | 78.23 (78.18) | 4.25 (4.28) | 3.93 (3.96) | FIG. 34 |
| Ex. VII-12 | C59 | 254.0~256.2 | 65.56 (65.52) | 3.39 (3.47) | 7.96 (8.04) | FIG. 35 |
| Ex. VII-13 | C60 | 263.1~267.2 | 79.21 (79.14) | 4.50 (4.52) | 3.59 (3.69) | FIG. 36 |

Example VII-14 to Example VII-35

Except that benzyl amine was used instead of various amine compounds expressed by the general formula <<28>> in the example VII-4, the same reaction was performed, and the following compounds were obtained. Melt points, element analysis values, and a chart for the infrared absorption spectrum are shown in Table 65.

TABLE 66-1

| Ex. | Coupler (Cp) No. | Melting Point (° C.) <Dissolving point (° C.)> | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Ex. VII-14 | C12 | 225.0~229.1 | 72.27 (72.06) | 4.46 (4.54) | 4.12 (4.20) | FIG. 72 |
| Ex. VII-15 | C24 | 206.9~212.0 | 76.20 (76.12) | 5.33 (5.17) | 4.21 (4.23) | FIG. 73 |
| Ex. VII-16 | C37 | 285.9~288.6 | 77.51 (77.87) | 3.89 (3.86) | 4.11 (4.13) | FIG. 74 |
| Ex. VII-17 | C40 | 353.3~356.0 | 81.38 (81.35) | 3.51 (3.66) | 3.47 (3.39) | FIG. 75 |
| Ex. VII-18 | C49 | 236.9~241.9 | 72.17 (72.06) | 4.57 (4.54) | 4.09 (4.20) | FIG. 76 |
| Ex. VII-19 | C50 | 255.9~257.9 | 75.48 (75.70) | 4.67 (4.77) | 4.29 (4.41) | FIG. 77 |
| Ex. | C54 | 253.7~258.2 | 67.49 | 3.49 | 4.24 | FIG. 78 |

TABLE 66-1-continued

| | | | Elemental analysis (%) | | | |
|---|---|---|---|---|---|---|
| Ex. | Coupler (Cp) No. | Melting Point (° C.) <Dissolving point (° C.)> | Actual measurement value C (Calculation value C) | Actual measurement value H (Calculation value H) | Actual measurement value N (Calculation value N) | Infrared absorption spectrum Fig. |
| Ex. VII-20 | | | (67.56) | (3.58) | (4.15) | |
| Ex. VII-21 | C55 | 235.9~239.4 | 67.37 (67.56) | 3.48 (3.58) | 4.24 (4.15) | FIG. 79 |
| Ex. VII-22 | C56 | 262.9~266.6 | 70.90 (71.02) | 3.59 (3.76) | 4.36 (4.36) | FIG. 80 |
| Ex. VII-23 | C61 | 304.4~310.9 | 81.63 (81.49) | 3.95 (4.01) | 3.12 (3.28) | FIG. 81 |
| Ex. VII-24 | C83 | 263.8~265.8 | 75.53 (75.70) | 4.67 (4.77) | 4.48 (4.41) | FIG. 82 |
| Ex. VII-25 | C92 | 254.5~258.4 | 68.85 (68.67) | 3.66 (3.64) | 8.41 (8.42) | FIG. 83 |

TABLE 66-2

| | | | Elemental analysis (%) | | | |
|---|---|---|---|---|---|---|
| Ex. | Coupler (Cp) No. | Melting Point (° C.) <Dissolving point (° C.)> | Actual measurement value C (Calculation value C) | Actual measurement value H (Calculation value H) | Actual measurement value N (Calculation value N) | Infrared absorption spectrum Fig. |
| Ex. VII-26 | C95 | 323.0~325.0 | 73.44 (73.52) | 3.88 (3.95) | 6.79 (6.86) | FIG. 84 |
| Ex. VII-27 | C101 | 235.2~242.5 | 65.72 (65.89) | 3.09 (2.91) | 7.98 (8.09) | FIG. 85 |
| Ex. VII-28 | C104 | 275.8~278.3 | 76.40 (76.58) | 4.49 (4.59) | 4.29 (4.25) | FIG. 86 |
| Ex. VII-29 | C105 | 229.5~232.8 | 76.47 (76.58) | 4.49 (4.59) | 4.21 (4.25) | FIG. 87 |
| Ex. VII-30 | C106 | 230.6~234.6 | 76.95 (76.95) | 4.95 (4.99) | 4.09 (4.08) | FIG. 88 |
| Ex. VII-31 | C107 | 243.7~246.4 | 64.63 (64.70) | 3.22 (3.26) | 3.71 (3.77) | FIG. 89 |
| Ex. VII-32 | C109 | 263.1~265.7 | 64.84 (64.70) | 3.21 (3.26) | 3.81 (3.77) | FIG. 90 |
| Ex. VII-33 | C110 | 165.2~167.8 | 76.65 (76.50) | 5.69 (5.54) | 4.00 (4.06) | FIG. 91 |
| Ex. VII-34 | C113 | 198.3~203.5 | 75.62 (75.70) | 4.65 (4.77) | 4.38 (4.41) | FIG. 92 |
| Ex. VII-35 | C108 | 228.2~239.5 | 64.79 (64.70) | 3.09 (3.26) | 3.63 (3.77) | FIG. 124 |

Example VII-36
Manufacturing <coupler No.E12> Compound

Except that 1,8-diamino naphthalene 12.66 g (0.08 mol) was used in o-phenylene diamine 8.65 g (0.08 mol), reaction was performed in the same way as the example VII-7, thus objective crude material 6.70 g was obtained. Obtained crude material was recrystallized by n-butanol, thus 4.07 g (33.5%) objective <coupler No. E12> was obtained. Melt points were 338.1° C. to 340.9° C. The infrared absorption spectrum of a coupler compound <coupler No. E12> is shown in FIG. 70.

Example VII-37
Manufacturing <Coupler No. E30> Compound

Except that 1,8-diamino naphthalene 12.66 g (0.08 mol) was used in o-amino benzyl amine 9.77 g (0.08 mol), reaction was made in the same way as the example VII-7, thus objective crude material 12.06 g was obtained. Obtained crude material was recrystallized by cyclo hexanoate/dimethyl formamide, thus 9.19 g (76.5%) Of objective material <coupler No. E30> was obtained. Melt points were 347.0° C. to 361.1° C. The infrared absorption spectrum for a coupler compound <coupler No. E30> is shown in FIG. 71.

Example VII-38
Manufacturing <Coupler No. E31> Compound

Except that 1,8-diamino naphthalene 12.66 g (0.08 mol) was used in o-amino benzamide 10.89 g (0.08 mol), reaction was performed in the same way as the example VII-7, thus objective crude material 9.15 g was obtained. Obtained crude material was recrystallized by cyclo hexanoate/dimethyl formamide, thus objective material <No. E31>7.09 g (56.4%) was obtained. Melt points were 369.6° C. to 372.9° C. The infrared absorption spectrum for a coupler compound <coupler No. E31> for is shown in FIG. 72.

Manufacturing Example 1
Manufacturing Azo Compound (Azo Compound No. P1)

N-n-hexyl-2-hydroxy-7,8-naphthalic acid imido (coupler No. C1 compound) 0.89 g (3 mmol) was dissolved in DMF 80 ml, and 4-nitrobenzene diazonium tetra fluoro borate 0.71 g (3 mmol) was added thereto at a room temperature. Then, 10% by weight acetic acid sodium liquid solution 4.92 g was dropped for 10 minutes, reacted material, in which mixing reaction was performed for 6 hours at a room temperature, was poured on ice, then water was added thereto. After mixing was performed for more or less 1 hour, extracted crystal was filtered, then it was dried at the temperature of 50° C., thus objective material composition 1.03 g was obtained. Obtained composition material was processed by a silicagel column chromatography (toluene: acetic acid ethyl=4:1 as developing solvent) and recrystallized by toluene/ethanol, thus orange color azo compound (azo compound No. P1) was obtained. Obtained volume (yield), infrared absorption spectrum, and element analysis results are shown together in Table 67.

Manufacturing Example 2

Manufacturing Azo Compounds (Azo Compounds No. P17)

Except that 9-fluorenone-2,7-bis diazonium tetra fluoro borate 0.61 g (1.5 mmol) synthesized by 2,7-diamino-9-fluorenone in advance was used instead of 4-nitrobenzene diazonium tetra fluoro borate 0.71 g (3 mmol) in the example VII-1, objective material was manufactured in the same way as the example VII-1. Obtained volume (yield), an infrared absorption spectrum, and element analysis results are shown together in Table 67.

Manufacturing Example 3

Manufacturing Azo Compounds (Azo Compounds No. P19)

N-benzyl-2-hydroxy-7,8-naphthalic acid imido (coupler No. C5 compound) 0.91 g (3 mmol) manufactured in the example VII-4 was dissolved in DMF 100 ml, then at a room temperature, 9-fluorenone-2,7-bis diazonium tetra fluoro borate 0.61 g (1.5 mmol) synthesized by 2,7-diamino-9-fluorenone in advance was added thereto. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P19) was obtained by drying at the temperature of 70° C. under a reduced pressure condition. The volume (yield), an infrared absorption spectrum, and element analysis results are indicated in Table 67.

Manufacturing Example 4

Manufacturing Azo Compounds (Azo Compounds No. P49)

Except that 1,4-dis tirril benzene-4',4"-diil-4',4"-bis diazonium tetra fluoro borate 0.77 g (1.5 mmol) synthesized by 4',4"-diamino-1,4-distirril benzene-4',4"-diil in advance was used instead of 9-fluorenone-2,7-bis diazonium tetra fluoro borate 0.61 g (1.5 mmol) in the example VII-10, objective material was manufactured in the same way as the Example 10. The volume (yield), an infrared absorption spectrum, and element analysis results are indicated in Table 67.

Manufacturing Example 5

Manufacturing Azo Compounds (Azo Compounds No. P74)

Except that triphenyl amine-4,4',4"-tris diazonium tetra fluoro borate 0.59 g (1.0 mmol) synthesized by -4,4',4"-triaminotriphenyl amine in advance was used instead of 9-fluorenone-2,7-bis diazonium tetra fluoro borate 0.61 g (1.5 mmol) in the example VII-10, objective material was manufactured in the same way as the example VII-10. The volume (yield), an infrared absorption spectrum, and element analysis results are indicated in Table 39.

Manufacturing Example 6

Manufacturing Azo Compounds (Azo Compounds No. P20

N-benzyl-2-hydroxy-7,8-naphthalic acid imido (coupler No. C5 compound) 0.46 g (1.5 mmol) was dissolved in DMF 60 ml, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at a room temperature. Then, liquid solution composed of 2-hydroxy-3-(2-chloro phenyl carbamoyl)naphthalene (coupler No. 17 compound) 0.45 g (1.5 mmol) and DMF 40 ml were added thereto. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P20) was obtained by drying at the temperature of 70° C. under a reduced pressure condition. The volume (yield), an infrared absorption spectrum, and element analysis results are indicated in Table 67.

Manufacturing Example 7

Manufacturing Azo Compound (Azo compound No. P50)

Except that 2-hydroxy-3-(2,4-dimethyl phenyl carbamoyl)naphthalene (coupler No. 43 compound) 0.44 g (1.5 mmol) was used instead of 9-fluorenone-2,7-bis diazonium tetra fluoro borate 0.61 g (1.5 mmol) in the example VII-13, 1,4-dis tirril benzene-4',4"-diil-4',4"-bis diazonium tetra fluoro borate 0.77 g (1.5 mmol), and 2-hydroxy-3-(2-chloro phenyl carbamoyl)naphthalene (coupler No.17 compound) 0.45 g (1.5 mmol) synthesized by 4',4"-diamino-1,4-dis tirril benzene 4',4"-diil in advance, objective material was manufactured in the same way as the example VII-13. The volume (yield), an infrared absorption spectrum, and element analysis results are indicated in Table 67.

Manufacturing Example 8

Manufacturing Azo Compounds (Azo Compounds No. P23)

N-(2-phenyl, ethyl)-2-hydroxy-7,8-naphthalic acid imido (coupler No. C14 compound) 0.95 g (3 mmol) manufactured in the example VII-5 was dissolved in DMF 100m, then 9-fluorenone-2,7-bis diazonium tetra fluoro borate 0.61 g (1.5 mmol) synthesized by 2,7-diamino-9-fluorenone in advance was added thereto at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P23) was obtained by drying at the temperature of 70° C. under a reduced pressure condition. The volume (yield), an infrared absorption spectrum, and element analysis results are indicated in Table 67.

Manufacturing Example 9

Manufacturing Azo Compounds (Azo Compounds No. P52)

Except that 1,4-dis tirril benzene-4',4"-diil-4,4"-bis diazonium tetra fluoro borate 0.77 g (1.5 mmol) synthesized by 4',4"-diamino-1,4-dis tirril benzene-4',4"-diil in advance was used instead of 9-fluorenone-2,7-bis diazonium tetra fluoro borate 0.61 g (1.5 mmol) in the example 8, objective material was manufactured in the same way as the Manufacturing Example 8. The volume (yield), an infrared absorption spectrum, and element analysis results are indicated in Table 67.

Manufacturing Example 10
Manufacturing Azo Compounds (Azo Compound No. P77)

Except that triphenyl amine-4,4',4"-tris diazonium tetra fluoro borate 0.59 g (1.0 mmol) synthesized by 4,4',4"-triaminotriphenyl amine in advance was used instead of 9-fluorenone-2,7-bis diazonium tetra fluoro borate 0.61 g (1.5 mmol) in the example 8, objective material was manufactured in the same way as the Manufacturing Example 8. The volume (yield), an infrared absorption spectrum, and element analysis results are indicated in Table 67.

Manufacturing Example 11
Manufacturing Azo Compounds (Azo Compounds No. P24)

N-(2-phenyl ethyl)-2-hydroxy-7,8-naphthalic acid imido (coupler No. C14 compound) 0.48 g (1.5 mmol) manufactured in the example VII-5 was dissolved in DMF 60 ml, 9-fluorenone-2,7-bis diazonium tetra fluoro borate 0.61 g (1.5 mmol) synthesized by 2,7-diamino-9-fluorenone in advance was added at a room temperature, then mixing was performed for 30 minutes. Then, liquid solution composed of 2-hydroxy-3-(2-chloro phenyl carbamoyl)naphthalene (coupler No. 17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P24) was obtained by drying at the temperature of 70° C. under a reduced pressure condition. The volume (yield), an infrared absorption spectrum, and element analysis results are indicated in Table 67.

Manufacturing Example 12
Manufacturing Azo Compounds (Azo Compounds No. P53)

In the Manufacturing Example 11, instead of 9-fluorenone-2,7-bis diazonium tetra fluoro borate 0.61 g (1.5 mmol), 2-hydroxy-3-(2,4-dimethyl phenyl carbamoyl) naphthalene (coupler No.43 compound) 0.44 g (1.5 mmol) was used instead of 1,4-dis tirril benzene-4',4"-diil-4',4"-bis diazonium tetra fluoro borate 0.77 g (1.5 mmol) and 2-hydroxy-3-(2-chloro phenyl carbamoyl)naphthalene (coupler No.17 compound) 0.45 g (1.5 mmol) synthesized by 4',4"-diamino-1,4-dis tirril benzene-4',4"-diil in advance, objective material was manufactured in the same way as the Manufacturing Example 11. The volume (yield), an infrared absorption spectrum, and element analysis results are indicated in Table 67.

Manufacturing Example 13
Manufacturing Azo Compounds (Azo Compounds No. P27)

N-phenyl-2-hydroxy-7,8-naphthalic acid imido (coupler No. C28 compound) 0.87 g (3 mmol) manufactured in the example VII-6 was dissolved in DMF 100 ml, and 9-fluorenone-2,7-bis diazonium tetra fluoro borate 0.61 g (1.5 mmol) synthesized by 2,7-diamino-9-fluorenone in advance was added at a room temperature. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P27) was obtained by drying at the temperature of 70° C. under a reduced pressure condition. The volume (yield), an infrared absorption spectrum, and element analysis results are indicated in Table 67.

Manufacturing Example 14
Manufacturing Azo Compounds (Azo Compounds No. P57)

Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance in the Manufacturing Example 13 was used instead of 9-fluorenone-2,7-bis diazonium tetra fluoro borate 0.61 g (1.5 mmol) in the Manufacturing Example 13, objective material was manufactured in the same way as the Manufacturing Example 13. The volume (yield), an infrared absorption spectrum, and element analysis results are indicated in Table 67.

Manufacturing Example 15
Manufacturing Azo Compounds (Azo Compounds No. P81)

Except that triphenyl amine 4,4',4"-tris diazonium tetra fluoro borate 0.59 g (1.0 mmol) synthesized by 4,4',4"-triamino triphenyl amine in advance was used instead of 9-fluorenone-2,7-bis diazonium tetra fluoro borate 0.61 g (1.5 mmol) in the Manufacturing Example 13, objective material was manufactured in the same way as the Manufacturing Example 13. The volume (yield), an infrared absorption spectrum, and element analysis results are indicated in Table 67.

Manufacturing Example 16
Manufacturing Azo Compounds (Azo Compounds No. P28)

N-phenyl-2-hydroxy-7,8-naphthalic acid imido (coupler No. C28 compound) 0.43 g (1.5 mmol) was dissolved in DMF 60 ml at a room temperature, 9-fluorenone-2,7-bis diazonium tetra fluoro borate 0.61 g (1.5 mmol) synthesized by 2,7-diamino-9-fluorenone in advance was added, then mixing was performed thereto for 30 minutes at a room temperature. Then, liquid solution composed of 2-hydroxy-3-(2-chloro phenyl carbamoyl)naphthalene (coupler No. 17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P28) was obtained by drying at the temperature of 70° C. under a reduced pressure condition. The volume (yield), an infrared absorption spectrum, and element analysis results are indicated in Table 67.

Manufacturing Example 17
Manufacturing Azo Compounds (Azo Compounds No. P58)

In the Manufacturing Example 16, instead of 9-fluorenone-2,7-bis diazonium tetra fluoro borate 0.61 g (1.5 mmol), 2-hydroxy-3-(2,4-dimethyl phenyl carbamoyl) naphthalene (coupler No.43 compound) 0.44 g (1.5 mmol) was used instead of 1,4-dis tirril benzene-4',4"-diil-4',4"-bis diazonium tetra fluoro borate 0.77 g (1.5 mmol) and 2-hydroxy-3-(2-chloro phenyl carbamoyl)naphthalene (coupler No.17 compound) 0.45 g (1.5 mmol) synthesized by 4',4"-diamino-1,4-dis tirril benzene-4',4"-diil in advance, objective material was manufactured in the same way as the Manufacturing Example 16. The volume (yield), an infrared absorption spectrum, and element analysis results are indicated in Table 67.

Manufacturing Example 18
Manufacturing Azo Compounds (Azo Compounds No. P59)

Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance in the Manufacturing Example 16 was used instead of 9-fluorenone-2,7-bis diazonium tetra fluoro borate 0.61 g (1.5 mmol) in the Manufacturing Example 13, objective material was manufactured in the same way as the Manufacturing Example 16. The volume (yield), an infrared absorption spectrum, and element analysis results are indicated in Table 67.

Manufacturing Example 19
Manufacturing Azo Compounds (Azo Compounds No. P38)
    12-hydroxy-benzo[6,7]isoindole[2,1-a]perimysin-14-on, or 9-hydroxy-benzo[4,5]isoindole[2,1-a]perimysin-14-on [coupler No. E23 compound] 1.01 g (3 mmol) manufactured in the example VII-7 was dissolved in DMSO 100 ml at the temperature of 80° C., after cooling at a room temperature, 9-fluorenone-2,7-bis diazonium tetra fluoro borate 0.61 g (1.5 mmol) synthesized by 2,7-diamino-9-fluorenone in advance was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P38) was obtained by drying at the temperature of 70° C. under a reduced pressure condition. The volume (yield), an infrared absorption spectrum, and element analysis results are indicated in Table 67.

Manufacturing Example 20
Manufacturing Azo Compounds (Azo Compounds No. P66)
    Except that 1,4-dis tirril benzene-4',4"-diil-4',4"-bis diazonium tetra fluoro borate 0.77 g (1.5 mmol) synthesized by 4',4"-diamino-1,4-dis tirril benzene-4',4"-diil in advance in the Manufacturing Example 19 was used instead of 9-fluorenone-2,7-bis diazonium tetra fluoro borate 0.61 g (1.5 mmol) in the Manufacturing Example 13, objective material was manufactured in the same way as the Manufacturing Example 19. The volume (yield), an infrared absorption spectrum, and element analysis results are indicated in Table 67.

Manufacturing Example 21
Manufacturing Azo Compounds (Azo Compounds No. P86)
    Except that triphenyl amine-4,4',4"-tris diazonium tetra fluoro borate 0.59 g (1.0 mmol) synthesized by 4,4',4"-triamino triphenyl amine in advance was used instead of 9-fluorenone-2,7-bis diazonium tetra fluoro borate 0.61 g (1.5 mmol) in the Manufacturing Example 19, objective material was manufactured in the same way as the Manufacturing Example 19. The volume (yield), an infrared absorption spectrum, and element analysis results are indicated in Table 67.

Manufacturing Example 22
Manufacturing Azo Compounds (Azo Compounds No. P39)
    12-hydroxy-benzo[6,7]isoindole[2,1-a]perimysin-14-on, or 9-hydroxy-benzo[4,5]isoindole[2,1-a]perimysin-14-on [coupler No. E23 compound] 0.50 g (1.5 mmol) manufactured in the example VII-7 was dissolved in DMSO 60 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at a room temperature. Then, liquid solution composed of 2-hydroxy-3-(2-chlorophenyl carbamoyl)naphthalene (coupler No. 17 compound) 0.45 g (1.5 mmol) and DMF 40 ml was added. Then, 10% by weight acetic acid sodium solution 4.92 g was dropped for 10 minutes, it was mixed and reacted for 6 hours at a room temperature. Produced precipitation was filtered, washed three times using DMF 120 ml at a room temperature, and then washed twice using water 120 ml. Thus, an azo compound (No. P39) was obtained by drying at the temperature of 70° C. under a reduced pressure condition. The volume (yield), an infrared absorption spectrum, and element analysis results are indicated in Table 67.

Manufacturing Example 23
Manufacturing Azo Compounds (Azo Compounds No. P67)
    Instead of 9-fluorenone-2,7-bis diazonium tetra fluoro borate 0.61 g (1.5 mmol) in the example VII-29, except that 2-hydroxy-3-(2,4-dimethyl phenyl carbamoyl)naphthalene (coupler No. 43 compound) 0.44 g (1.5 mmol) was used instead of 1,4-dis tirril benzene-4',4"-diil 4',4"-bis diazonium tetra fluoro borate 0.77 g (1.5 mmol) and 2-hydroxy-3-(2-chloro phenyl carbamoyl)naphthalene (coupler No. 17 compound) 0.45 g (1.5 mmol) synthesized by 4',4"-diamino-1,4-dis tirril benzene-4',4"-diil in advance, objective material was manufactured in the same way as the example VII-29. The volume (yield), an infrared absorption spectrum, and element analysis results are indicated in Table 30.

Manufacturing Example 24
Manufacturing Azo Compounds (Azo Compounds No. 102)
    Except that n-(4-dimethyl benzyl)-2-hydroxy-7,8-naphthalic acid imido (coupler No. C9 compound) 0.95 g (3 mmol) manufactured in the example VII-8 was used instead of N-benzyl-2-hydroxy-7,8-naphthalic acid imido 0.91 g (3 mmol) in the Manufacturing Example 3, objective material was manufactured in the same way as the Manufacturing Example 3. The volume (yield), an infrared absorption spectrum, and element analysis results are indicated in Table 30.

Manufacturing Example 25
Manufacturing Azo Compounds (Azo Compounds No. 103)
    Except that N-(4-dimethyl benzyl)-2-hydroxy-7,8-naphthalic acid imido (coupler No. C9 compound) 0.48 g (1.5 mmol) manufactured in the example VII-8 was used instead of N-benzyl-2-hydroxy-7,8-naphthalic acid imido 0.46 g (1.5 mmol) in the Manufacturing Example 6, objective material was manufactured in the same way as the Manufacturing Example 6. The volume (yield), an infrared absorption spectrum, and element analysis results are indicated in Table 67.

Manufacturing Example 26
Manufacturing Azo Compounds (Azo Compounds No.P21)
    Except that N-(4-methoxy benzyl)-2-hydroxy-7,8-naphthalic acid imido (coupler No. C10 compound) 1.00 g (3 mmol) manufactured in the example VII-9 was used instead of n-benzyl-2-hydroxy-7,8-naphthalic acid imido 0.91 g (3 mmol) in the Manufacturing Example 3, objective material was manufactured in the same way as the Manufacturing Example 3. Obtained volume (yield), an infrared absorption spectrum, and element analysis results are shown together in Table 67.

Manufacturing Example 27
Manufacturing Azo Compounds (Azo Compounds No.P104)
    Except that N-(4-methoxy benzyl)-2-hydroxy-7,8-naphthalic acid imido (coupler No. C10 compound) 0.50 g (1.5 mmol) manufactured in the example VII-9 was used

Manufacturing Example 28
Manufacturing Azo Compounds (Azo Compounds No. P134)

Except that N-(4-chloro dibenzyl)-2-hydroxy-7,8-naphthalic acid imido (coupler No. C11 compound) 1.01 g (3 mmol) manufactured in the example VII-10 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), an infrared absorption spectrum, and element analysis results are shown together in Table 67.

Manufacturing Example 29
Manufacturing Azo Compounds (Azo Compounds No. P135)

Except that N-(4-chloro dibenzyl)-2-hydroxy-7,8-naphthalic acid imido (coupler No. C11 compound) 0.51 g (1.5 mmol) manufactured in the example VII-10 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), an infrared absorption spectrum, and element analysis results are shown together in Table 67.

Manufacturing Example 30
Manufacturing Azo Compounds (Azo Compounds No.P22)

Except that N-(1-naphthyl dimethyl)-2-hydroxy-7,8-naphthalic acid imido (coupler No. C13 compound) 1.06 g (3 mmol) manufactured in the example VII-11 was used instead of N-benzyl-2-hydroxy-7,8-naphthalic acid imido 0.91 g (3 mmol) in the example 3, objective material was manufactured in the same way as the Manufacturing Example 3. Obtained volume (yield), an infrared absorption spectrum, and element analysis results are shown together in Table 67.

Manufacturing Example 31
Manufacturing Azo Compounds (Azo Compounds No.P105)

Except that N-(1-naphthyl dimethyl)-2-hydroxy-7,8-naphthalic acid imido (coupler No. C13 compound) 0.53 g (1.5 mmol) manufactured in the example VII-11 was used instead of N-benzyl-2-hydroxy-7,8-naphthalic acid imido 0.46 g (1.5 mmol) in the example 6, objective material was manufactured in the same way as the Manufacturing Example 6. Obtained volume (yield), an infrared absorption spectrum, and element analysis results are shown together in Table 67.

Manufacturing Example 32
Manufacturing Azo Compounds (Azo Compounds No. P11)

Except that N-(4-nitrobenzyl)-2-hydroxy-7,8-naphthalic acid imido (coupler No. C59 compound) 1.05 g (3 mmol) manufactured in the example VII-12 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), an infrared absorption spectrum, and element analysis results are shown together in Table 67.

Manufacturing Example 33
Manufacturing Azo Compounds (Azo Compounds No. P113)

Except that N-(4-nitrobenzyl)-2-hydroxy-7,8-naphthalic acid imido (coupler No. C59 compound) 0.52 g (1.5 mmol) manufactured in the example VII-12 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), an infrared absorption spectrum, and element analysis results are shown together in Table 67.

Manufacturing Example 34
Manufacturing Azo Compounds (Azo Compounds No. P11)

Except that N-(4-biphenyl dimethyl)-2-hydroxy-7,8-naphthalic acid imido (coupler No. C60 compound) 1.14 g (3 mmol) manufactured in the example VII-12 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), an infrared absorption spectrum, and element analysis results are shown together in Table 67.

Manufacturing Example 35
Manufacturing Azo Compounds (Azo Compounds No. P115)

Except that N-(4-biphenyl dimethyl)-2-hydroxy-7,8-naphthalic acid imido (coupler No. C60 compound) 0.57 g (1.5 mmol) manufactured in the example VII-13 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), an infrared absorption spectrum, and element analysis results are shown together in Table 67.

Manufacturing Example 36
Manufacturing Azo Compounds (Azo Compounds No. P35)

Except that coupler compound (coupler No. E12) 0.43 g (1.5 mmol) manufactured in the example VII-35 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), an infrared absorption spectrum, and element analysis results are shown together in Table 67.

Manufacturing Example 37
Manufacturing Azo Compounds (Azo Compounds No. P106)

Except that coupler compounds (coupler No. C54) 1.01 g (3 mmol) manufactured in the example VII-20 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 38
Manufacturing Azo Compounds (Azo Compounds No. P107)

Except that coupler compounds (coupler No. C54) 0.51 g (1.5 mmol) manufactured in the example VII-20 was used instead of N-benzyl-2-hydroxy-7,8-naphthalic acid imido 0.46 g (1.5 mmol) in the Manufacturing Example 6, objec-

Manufacturing Example 39
Manufacturing Azo Compounds (Azo Compounds No. P108)

Except that coupler compounds (coupler No. C55) 1.01 g (3 mmol) manufactured in the example VII-21 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 40
Manufacturing Azo Compounds (Azo Compounds No. P109)

Except that coupler compounds (coupler No. C55) 0.51 g (1.5 mmol) manufactured in the example VII-21 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 41
Manufacturing Azo Compounds (Azo Compounds No. P110)

Except that coupler compounds (coupler No. C56) 0.96 g (3 mmol) manufactured in the example VII-22 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 42
Manufacturing Azo Compounds (Azo Compounds No. P111)

Except that coupler compounds (coupler No. C56) 0.48 g (1.5 mmol) manufactured in the example VII-22 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 43
Manufacturing Azo Compounds (Azo Compounds No. P116)

Except that coupler compounds (coupler No. C61) 1.28 g (3 mmol) manufactured in the example VII-23 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 44
Manufacturing Azo Compounds (Azo Compounds No. P117)

Except that coupler compounds (coupler No. C61) 0.64 g (1.5 mmol) manufactured in the example VII-23 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 45
Manufacturing Azo Compounds (Azo Compounds No. P120)

Except that coupler compounds (coupler No. C83) 0.95 g (3 mmol) manufactured in the example VII-24 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 46
Manufacturing Azo Compounds (Azo Compounds No. P121)

Except that coupler compounds (coupler No. C83) 0.48 g (1.5 mmol) manufactured in the example VII-24 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 47
Manufacturing Azo Compounds (Azo Compounds No. P122)

Except that coupler compounds (coupler No. C92) 1.00 g (3 mmol) manufactured in the example VII-25 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 48
Manufacturing Azo Compounds (Azo Compounds No. P123)

Except that coupler compounds (coupler No. C92) 0.50 g (1.5 mmol) manufactured in the example VII-25 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 49
Manufacturing Azo Compounds (Azo Compounds No. P132)

Except that coupler compounds (coupler No. E31) 0.94 g (3 mmol) manufactured in the example VII-37 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 50

Manufacturing Azo Compounds (Azo Compounds No. P133)

Except that coupler compounds (coupler No. E31) 0.47 g (1.5 mmol) manufactured in the example VII-37 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 51

Manufacturing Azo Compounds (Azo Compounds No. P136)

Except that coupler compounds (coupler No. C24) 0.99 g (3 mmol) manufactured in the example VII-15 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 52

Manufacturing Azo Compounds (Azo Compounds No. P137)

Except that coupler compounds (coupler No. C24) 0.50 g (1.5 mmol) manufactured in the example VII-15 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 53

Manufacturing Azo Compounds (Azo Compounds No. P138)

Except that coupler compounds (coupler No. C40) 1.24 g (3 mmol) manufactured in the example VII-22 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 54

Manufacturing Azo Compounds (Azo Compounds No. P139)

Except that coupler compounds (coupler No. C40) 0.62 g (1.5 mmol) manufactured in the example VII-17 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 55

Manufacturing Azo Compounds (Azo Compounds No. P140)

Except that coupler compounds (coupler No. C37) 1.02 g (3 mmol) manufactured in the example VII-16 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 56

Manufacturing Azo Compounds (Azo Compounds No. P141)

Except that coupler compounds (coupler No. C37) 0.62 g (1.5 mmol) manufactured in the example VII-16 was used instead of N-benzyl-2-hydroxy-7,8-naphthalic acid imido 0.51 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 57

Manufacturing Azo Compounds (Azo Compounds No. P142)

Except that coupler compounds (coupler No. C110) 1.04 g (3 mmol) manufactured in the example VII-33 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 58

Manufacturing Azo Compounds (Azo Compounds No. P143)

Except that coupler compounds (coupler No. C11) 0.52 g (1.5 mmol) manufactured in the example VII-33 was used instead of N-benzyl-2-hydroxy-7,8-naphthalic acid imido 0.51 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 59

Manufacturing Azo Compounds (Azo Compounds No. P144)

Except that coupler compounds (coupler No. C50) 0.95 g (3 mmol) manufactured in the example VII-19 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 60

Manufacturing Azo Compounds (Azo Compounds No. P145)

Except that coupler compounds (coupler No. C50) 0.48 g (1.5 mmol) manufactured in the example VII-19 was used instead of N-benzyl-2-hydroxy-7,8-naphthalic acid imido 0.51 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 61

Manufacturing Azo Compounds (Azo Compounds No. P14)

Except that 2(5)-hydroxy-7H-benzimidazo [2,1-a] benzisoquinoline-7 (coupler No. 195 compound) 0.43 g (1.5 mmol) was used instead of 2-hydroxy-3-(2-chloro phenyl carbamoyl)naphthalene (compound of coupler No.17) 0.45 g (1.5 mmol) in the Manufacturing Example 6, objective material was manufactured in the same way as the Manufacturing Example 6. Obtained volume (yield), an infrared absorption spectrum, and element analysis results are shown together in Table 67.

Manufacturing Example 62

Manufacturing Azo Compounds (Azo Compounds No. P153)

Except that coupler compounds (coupler No. C104) 0.99 g (3 mmol) manufactured in the example VII-28 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 63

Manufacturing Azo Compounds (Azo Compounds No. P154)

Except that coupler compounds (coupler No. C104) 0.49 g (1.5 mmol) manufactured in the example VII-28 was used instead of N-benzyl-2-hydroxy-7,8-naphthalic acid imido 0.51 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 64

Manufacturing Azo Compounds (Azo Compounds No. P88)

N-benzyl-2-hydroxy-7,8-naphthalic acid imido (coupler No. C5 compound) 0.91 g (3 mmol) in the example VII-4 was dissolved in DMF 100 ml, then 9,10-phenanthrene quinone 2,7-bis diazonium tetra fluoro borate 0.70 g (1.5 mmol) synthesized by 2,7-diamino-9,10-phenanthrene quinone at a room temperature in advance was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P88) were obtained. Obtained volume (yield), infrared absorption spectrum, and element analysis results are shown together in Table 67.

Manufacturing Example 65

Manufacturing Azo Compounds (Azo Compounds No. P89)

Except that coupler compounds (coupler No. C14) 0.95 g (3 mmol) manufactured in the example VII-5 was used instead of N-benzyl-2-hydroxy-7,8-naphthalic acid imido 0.91 g (3 mmol) in the Manufacturing Example 64, objective material was manufactured in the same way as the Manufacturing Example 64. Obtained volume (yield), infrared absorption spectrum, and element analysis results are shown together in Table 67.

Manufacturing Example 66

Manufacturing Azo Compounds (Azo Compounds No. P91)

Except that coupler compounds (coupler No. C28) 0.87 g (3 mmol) manufactured in the example VII-6 was used instead of N-benzyl-2-hydroxy-7,8-naphthalic acid imido 0.91 g (3 mmol) in the Manufacturing Example 64, objective material was manufactured in the same way as the Manufacturing Example 64. Obtained volume (yield), infrared absorption spectrum, and element analysis results are shown together in Table 67.

Manufacturing Example 67

Manufacturing Azo Compounds (Azo Compounds No. P124)

Except that coupler compounds (coupler No. C95) 1.23 g (3 mmol) manufactured in the example VII-26 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 68

Manufacturing Azo Compounds (Azo Compounds No. P125)

Except that coupler compounds (coupler No. C95) 0.61 g (1.5 mmol) manufactured in the example VII-26 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 69

Manufacturing Azo Compounds (Azo Compounds No. P147)

Except that coupler compounds (coupler No. C12) 1.00 g (3 mmol) manufactured in the example VII-14 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 70

Manufacturing Azo Compounds (Azo Compounds No. P148)

Except that coupler compounds (coupler No. C12) 0.50 g (1.5 mmol) manufactured in the example VII-14 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 71

Manufacturing Azo Compounds (Azo Compounds No. P149)

Except that coupler compounds (coupler No. C49) 1.00 g (3 mmol) manufactured in the example VII-18 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 72
Manufacturing Azo Compounds (Azo Compounds No. P150)

Except that coupler compounds (coupler No. C49) 0.50 g (1.5 mmol) manufactured in the example VII-18 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 73
Manufacturing Azo Compounds (Azo Compounds No. P155)

Except that coupler compounds (coupler No. C105) 0.99 g (3 mmol) manufactured in the example VII-29 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 74
Manufacturing Azo Compounds (Azo Compounds No. P156)

Except that coupler compounds (coupler No. C105) 0.49 g (1.5 mmol) manufactured in the example VII-29 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 75
Manufacturing Azo Compounds (Azo Compounds No. P157)

Except that coupler compounds (coupler No. C106) 1.03 g (3 mmol) manufactured in the example VII-30 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 76
Manufacturing Azo Compounds (Azo Compounds No. P158)

Except that coupler compounds (coupler No. C106) 0.52 g (1.5 mmol) manufactured in the example VII-30 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 77
Manufacturing Azo Compounds (Azo Compounds No. P159)

Except that coupler compounds (coupler No. C107) 1.11 g (3 mmol) manufactured in the example VII-31 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 78
Manufacturing Azo Compounds (Azo Compounds No. P160)

Except that coupler compounds (coupler No. C107) 0.56 g (1.5 mmol) manufactured in the example VII-31 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 79
Manufacturing Azo Compounds (Azo Compounds No. P161)

Except that coupler compounds (coupler No. C108) 1.11 g (3 mmol) manufactured in the example VII-35 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 80
Manufacturing Azo Compounds (Azo Compounds No. P162)

Except that coupler compounds (coupler No. C108) 0.56 g (1.5 mmol) manufactured in the example VII-35 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 81
Manufacturing Azo Compounds (Azo Compounds No. P163)

Except that coupler compounds (coupler No. C109) 1.11 g (3 mmol) manufactured in the example VII-32 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 82
Manufacturing Azo Compounds (Azo Compounds No. P164)

Except that coupler compounds (coupler No. C109) 0.56 g (1.5 mmol) manufactured in the example VII-32 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 83
Manufacturing Azo Compounds (Azo Compounds No. P169)

Except that coupler compounds (coupler No. C113) 0.95 g (3 mmol) manufactured in the example VII-34 was used instead of N-benzyl-2-hydroxy-7,8-naphthalic acid imido 0.91 g (3 mmol) in the Manufacturing Example 3, objective material was manufactured in the same way as the Manufacturing Example 3. Obtained volume (yield), infrared absorption spectrum, and element analysis results are shown together in Table 67.

Manufacturing Example 84
Manufacturing Azo Compounds (Azo Compounds No. P170)

Except that coupler compounds (coupler No. C113) 0.48 g (1.5 mmol) manufactured in the example VII-34 was used instead of N-benzyl-2-hydroxy-7,8-naphthalic acid imido 0.46 g (1.5 mmol) in the Manufacturing Example 6, objective material was manufactured in the same way as the Manufacturing Example 6. Obtained volume (yield), infrared absorption spectrum, and element analysis results are shown together in Table 67.

Manufacturing Example 85
Manufacturing Azo Compounds (Azo Compounds No. P173)

Coupler compound (coupler No. E30) 0.90 g (3 mmol) manufactured in the example VII-37 was dissolved in DMF 100 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone at a room temperature in advance was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P173 were obtained. Obtained volume (yield), infrared absorption spectrum, and element analysis results are shown together in Table 67.

Manufacturing Example 86
Manufacturing Azo Compounds (Azo Compounds No. P174)

Coupler compound (coupler No. E30) 0.45 g (1.5 mmol) manufactured in the example VII-37 was dissolved in DMF 60 ml at the temperature of 80° C., after cooling it till it reached a room temperature, 9-fluorenone-2,7-bis diazonium tetra fluoro borate 0.61 g (1.5 mmol) synthesized by 2,7-diamino-9-fluorenone in advance at a room temperature was added, then mixing was performed for 30 minutes at the room temperature. Then, liquid solution composed of 2-hydroxy-3-(2-chloro phenyl carbamoyl)naphthalene (coupler No.17 compound) 0.45 g (1.5 mmol) and DMF 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P174) were obtained. Obtained volume (yield), infrared absorption spectrum, and element analysis results are shown together in Table 67.

Manufacturing Example 87
Manufacturing Azo Compounds (Azo Compounds No. P180)

N-benzyl-2-hydroxy-7,8-naphthalic acid imido(coupler No. C5 compound) 0.46 g (1.5 mmol) manufactured in the example VII-4 was dissolved in DMF 60 ml, then 9,10-phenanthrene quinone-2,7-bis diazonium tetra fluoro borate 0.70 g (1.5 mmol) synthesized by 2,7-diamino-9,10-phenanthrene quinone in advance at a room temperature was added, further mixing was performed for 30 minutes at the room temperature. Then, liquid solution composed of 2-hydroxy-3-phenyl carbamoyl naphthalene (No.1 compound) 0.39 g (1.5 mmol) and DMF 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P180) were obtained. Obtained volume (yield), infrared absorption spectrum, and element analysis results are shown together in Table 67.

Manufacturing Example 88
Manufacturing Azo Compounds (Azo Compounds No. P181)

Except that coupler compounds (coupler No. C14) 0.48 g (1.5 mmol) manufactured in the example VII-5 was used instead of N-benzyl-2-hydroxy-7,8-naphthalic acid imido 0.46 g (1.5 mmol) in the Manufacturing Example 87, objective material was manufactured in the same way as the Manufacturing Example 87. Obtained volume (yield), infrared absorption spectrum, and element analysis results are shown together in Table 67.

Manufacturing Example 89
Manufacturing Azo Compounds (Azo Compounds No. P182)

Except that coupler compounds (coupler No. C24) 0.99 g (3 mmol) manufactured in the example VII-15 was used instead of N-benzyl-2-hydroxy-7,8-naphthalic acid imido 0.91 g (3 mmol) in the Manufacturing Example 64, objective material was manufactured in the same way as the Manufacturing Example 64. Obtained volume (yield), infrared absorption spectrum, and element analysis results are shown together in Table 67.

Manufacturing Example 90
Manufacturing Azo Compounds (Azo Compounds No. P183)

Except that coupler compounds (coupler No. C24) 0.50 g (1.5 mmol) manufactured in the example VII-15 was used instead of N-benzyl-2-hydroxy-7,8-naphthalic acid imido 0.46 g (1.5 mmol) in the Manufacturing Example 87, objective material was manufactured in the same way as the Manufacturing Example 87. Obtained volume (yield), infrared absorption spectrum, and element analysis results are shown together in Table 67.

Manufacturing Example 91
Manufacturing Azo Compounds (Azo Compounds No. P184)

Except that coupler compounds (coupler No. C28) 0.43 g (1.5 mmol) manufactured in the example VII-6 was used instead of N-benzyl-2-hydroxy-7,8-naphthalic acid imido 0.46 g (1.5 mmol) in the Manufacturing Example 87, objective material was manufactured in the same way as the Manufacturing Example 87. Obtained volume (yield), infrared absorption spectrum, and element analysis results are shown together in Table 67.

Manufacturing Example 92
Manufacturing Azo Compounds (Azo Compounds No. P185)

12-hydroxy-benzo[6,7]isoindole[2,1-a]perimysin-14-on, or 9-hydroxy-benzo[4,5]isoindole[2,1-a]perimysin-14-on [coupler No.E23 compound] 1.01 g (3 mmol) manufactured in the example VII-7 was dissolved in DMSO 100 ml at the temperature of 80° C., after cooling it till it reached a room temperature, then 9,10-phenanthrene quinone-2,7-bis diazonium tetra fluoro borate 0.70 g (1.5 mmol) synthesized by 2,7-diamino-9,10-phenanthrene quinone in advance at a room temperature was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P185) were obtained. Obtained volume (yield), infrared absorption spectrum, and element analysis results are shown together in Table 67.

Manufacturing Example 93
Manufacturing Azo Compounds (Azo Compounds No. P186)

12-hydroxy-benzo[6,7]isoindole[2,1-a]perimysin-14-on, or 9-hydroxy-benzo[4,5]isoindole[2,1-a]perimysin-14-on (coupler No.E23 compound) 0.50 g (1.5 mmol) manufactured in the example VII-7 was dissolved in DMSO 60 ml at the temperature of 80° C., after cooling it till it reached a room temperature, 9,10-phenanthrene quinone-2,7-bis diazonium tetra fluoro borate 0.70 g (1.5 mmol) synthesized by 2,7-diamino-9,10-phenanthrene quinone in advance at a room temperature was added, then mixing was performed for 30 minutes at the room temperature. Then, liquid solution composed of 2-hydroxy-3-phenyl carbamoyl naphthalene (coupler No.1 compound) 0.39 g (1.5 mmol) and DMSO 40 ml was added. Then, 10% by weight acetic acid sodium aqueous solution 4.92 g was dropped for 10 minutes, and mixing reaction was performed at a room temperature for 6 hours. Created precipitations were filtered, rinsed three times using DMF 120 ml at a room temperature, and further rinsed twice by water 120 ml. Then, it was dried under reduced pressure at the temperature of 70° C., and azo compounds (compound No. P186) were obtained. Obtained volume (yield), infrared absorption spectrum, and element analysis results are shown together in Table 67.

Manufacturing Example 34
Manufacturing Azo Compounds (Azo Compounds No. P187)

Except that coupler compound (coupler No. E30) 0.90 g (3 mmol) manufactured in the example VII-37 was used instead of 12-hydroxy benzo[6,7]isoindole[2,1-a]perimysin-14-on, or 9-hydroxy-benzo[4,5]isoindole[2,1-a]perimysin-14-on (coupler No. E23 compound) 1.01 g (3 mmol) in the Manufacturing Example 92, objective material was manufactured in the same way as the Manufacturing Example 92. Obtained volume (yield), an infrared absorption spectrum, and element analysis results are shown together in Table 67.

Manufacturing Example 95
Manufacturing Azo Compounds (Azo Compounds No. P188)

Except that coupler compounds (coupler No. E30) 0.45 g (1.5 mmol) manufactured in the example VII-37 were used instead of benzo[6,7]isoindole[2,1-a]perimidine-14-on, or 9-hydroxybenzo 4, 5]isoindole 2,1-a]perimidine-14-on (coupler No. E23 compound) 0.50 g (1.5 mmol) in Manufacturing Example 93, objective material was manufactured in the same way as the Manufacturing Example 93. Obtained volume (yield), infrared absorption spectrum, and element analysis results are shown together in Table 67-1 through 67-8.

TABLE 67-1

| Mfg. Ex. No. | Azo Compound No. | Yield amount (g) (Yield ratio (%)) | Elemental analysis (%) Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-1 | P1 | 0.86 (64.2) | 64.45 (64.57) | 5.01 (4.97) | 12.53 (12.55) | FIG. 37 |
| Mfg. Ex. VII-2 | P17 | 0.87 (70.1) | 70.99 (71.17) | 5.07 (5.12) | 10.15 (10.16) | FIG. 38 |
| Mfg. Ex. VII-3 | P19 | 0.64 (50.8) | 72.91 (73.02) | 3.51 (3.60) | 9.94 (10.02) | FIG. 39 |
| Mfg. Ex. VII-4 | P49 | 1.21 (86.0) | 76.43 (76.58) | 4.16 (4.28) | 8.84 (8.93) | FIG. 40 |
| Mfg. Ex. VII-5 | P74 | 0.68 (55.2) | 72.88 (73.04) | 3.87 (3.92) | 11.27 (11.36) | FIG. 41 |
| Mfg. Ex. VII-6 | P20 | 0.68 (54.4) | 70.55 (70.63) | 3.35 (3.51) | 9.93 (10.08) | FIG. 42 |
| Mfg. Ex. VII-7 | P50 | 0.98 (70.0) | 77.75 (77.57) | 4.71 (4.77) | 8.93 (9.05) | FIG. 43 |
| Mfg. Ex. VII-8 | P23 | 0.74 (56.9) | 73.32 (73.43) | 3.77 (3.95) | 9.55 (9.69) | FIG. 44 |
| Mfg. Ex. VII-9 | P52 | 1.11 (76.5) | 76.76 (76.84) | 4.42 (4.58) | 8.45 (8.67) | FIG. 45 |
| Mfg. Ex. VII-10 | P77 | 0.72 (56.5) | 73.32 (73.46) | 4.14 (4.27) | 11.09 (10.98) | FIG. 46 |
| Mfg. Ex. VII-11 | P24 | 0.69 (54.3) | 70.60 (70.88) | 3.40 (3.69) | 10.02 (9.92) | FIG. 47 |
| Mfg. Ex. VII-12 | P53 | 0.99 (70.0) | 77.78 (77.69) | 4.86 (4.92) | 8.99 (8.91) | FIG. 48 |

TABLE 67-1-continued

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-13 | P27 | 0.68 (55.9) | 72.46 (72.59) | 3.11 (3.23) | 10.30 (10.37) | FIG. 49 |
| Mfg. Ex. VII-14 | P57 | 0.78 (57.1) | 76.21 (76.30) | 3.88 (3.97) | 9.15 (9.20) | FIG. 50 |
| Mfg. Ex. VII-15 | P81 | 0.61 (51.2) | 72.48 (72.60) | 3.42 (3.55) | 11.56 (11.76) | FIG. 51 |
| Mfg. Ex. VII-16 | P28 | 0.59 (48.4) | 70.29 (70.37) | 3.33 (3.32) | 10.13 (10.26) | FIG. 52 |
| Mfg. Ex. VII-17 | P58 | 0.79 (57.3) | 77.56 (77.44) | 4.66 (4.63) | 9.11 (9.18) | FIG. 53 |
| Mfg. Ex. VII-18 | P59 | 0.90 (65.0) | 74.20 (74.30) | 3.98 (4.05) | 9.06 (9.12) | FIG. 54 |
| Mfg. Ex. VII-19 | P38 | 0.96 (70.7) | 75.51 (75.55) | 3.00 (3.12) | 12.34 (12.38) | FIG. 55 |
| Mfg. Ex. VII-20 | P66 | 1.25 (83.0) | 78.67 (78.71) | 3.68 (3.80) | 11.24 (11.27) | FIG. 56 |
| Mfg. Ex. VII-21 | P86 | 0.98 (73.5) | 75.51 (75.72) | 3.30 (3.40) | 13.40 (13.67) | FIG. 57 |
| Mfg. Ex. VII-22 | P39 | 0.96 (74.0) | 71.90 (72.10) | 3.10 (3.26) | 11.23 (11.32) | FIG. 58 |
| Mfg. Ex. VII-23 | P67 | 1.09 | 78.40 | 4.39 | 9.92 | FIG. 59 |

TABLE 67-2

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-24 | P102 | 0.75 (57.9) | 73.24 (73.43) | 3.87 (3.95) | 9.64 (9.69) | FIG. 60 |
| Mfg. Ex. VII-25 | P103 | 0.78 (61.5) | 70.73 (70.88) | 3.57 (3.69) | 9.88 (9.92) | FIG. 61 |
| Mfg. Ex. VII-26 | P21 | 0.64 (47.3) | 70.68 (70.82) | 3.68 (3.81) | 9.29 (9.35) | FIG. 62 |
| Mfg. Ex. VII-27 | P104 | 0.72 (55.4) | 69.43 (69.56) | 3.55 (3.62) | 9.64 (9.74) | FIG. 63 |
| Mfg. Ex. VII-28 | P134 | 0.96 (70.7) | 67.49 (67.48) | 2.98 (3.11) | 9.11 (9.26) | FIG. 64 |
| Mfg. Ex. VII-29 | P135 | 0.79 (60.8) | 67.84 (67.83) | 3.07 (3.25) | 9.86 (9.68) | FIG. 65 |
| Mfg. Ex. VII-30 | P22 | 0.77 (54.8) | 75.20 (75.47) | 3.40 (3.65) | 8.79 (8.95) | FIG. 66 |
| Mfg. Ex. VII-31 | P105 | 0.80 (60.3) | 71.88 (72.07) | 3.50 (3.54) | 9.48 (9.51) | FIG. 67 |
| Mfg. Ex. VII-32 | P112 | 0.93 (66.5) | 65.84 (65.95) | 2.96 (3.04) | 11.96 (12.06) | FIG. 68 |
| Mfg. Ex. VII-33 | P113 | 0.75 (57.2) | 66.99 (67.01) | 3.16 (3.21) | 10.92 (11.16) | FIG. 69 |
| Mfg. Ex. VII-34 | P114 | 0.87 (58.8) | 76.17 (76.35) | 3.73 (3.86) | 8.42 (8.48) | FIG. 70 |
| Mfg. Ex. VII-35 | P115 | 0.70 (51.1) | 72.44 (72.64) | 3.52 (3.66) | 9.37 (9.24) | FIG. 71 |

TABLE 67-3

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-36 | P35 | 0.61 (49.8) | 70.41 (70.63) | 3.05 (3.21) | 11.90 (12.01) | FIG. 96 |
| Mfg. Ex. VII-37 | P106 | 0.82 (60.2) | 67.46 (67.48) | 3.07 (3.11) | 9.16 (9.26) | FIG. 97 |
| Mfg. Ex. VII-38 | P107 | 0.78 (59.6) | 67.70 (67.83) | 3.11 (3.25) | 9.78 (9.68) | FIG. 98 |
| Mfg. Ex. VII-39 | P108 | 0.80 (58.6) | 67.51 (67.48) | 2.95 (3.11) | 9.37 (9.26) | FIG. 99 |
| Mfg. Ex. VII-40 | P109 | 0.86 (66.2) | 67.94 (67.83) | 3.13 (3.25) | 9.62 (9.68) | FIG. 100 |
| Mfg. Ex. VII-41 | P110 | 0.86 (65.2) | 70.05 (70.02) | 2.98 (3.23) | 9.80 (9.61) | FIG. 101 |
| Mfg. Ex. VII-42 | P111 | 0.81 (63.4) | 68.87 (69.14) | 3.11 (3.32) | 10.15 (9.87) | FIG. 102 |
| Mfg. Ex. VII-43 | P116 | 1.12 (68.3) | 78.30 (78.01) | 3.82 (4.06) | 7.43 (7.69) | FIG. 103 |
| Mfg. Ex. VII-44 | P117 | 0.97 (67.0) | 73.59 (73.78) | 3.64 (3.78) | 8.65 (8.75) | FIG. 104 |
| Mfg. Ex. VII-45 | P120 | 0.86 (66.4) | 73.18 (73.43) | 3.87 (3.95) | 9.74 (9.69) | FIG. 105 |
| Mfg. Ex. VII-46 | P121 | 0.84 (66.2) | 70.65 (70.88) | 3.56 (3.69) | 9.91 (9.92) | FIG. 106 |

TABLE 67-4

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-47 | P122 | 0.63 (46.7) | 68.03 (68.30) | 3.44 (3.15) | 12.21 (12.49) | FIG. 107 |
| Mfg. Ex. VII-48 | P123 | 0.63 (48.3) | 68.06 (68.25) | 3.14 (3.27) | 11.13 (11.37) | FIG. 108 |
| Mfg. Ex. VII-49 | P132 | 0.30 (23.0) | 70.97 (71.16) | 2.94 (2.81) | 12.89 (13.02) | FIG. 109 |
| Mfg. Ex. VII-50 | P133 | 0.35 (27.4) | 69.49 (69.71) | 3.07 (3.10) | 11.48 (11.61) | FIG. 110 |
| Mfg. Ex. VII-51 | P136 | 0.89 (66.3) | 73.87 (73.81) | 4.22 (4.28) | 9.46 (9.39) | FIG. 111 |
| Mfg. Ex. VII-52 | P137 | 0.79 (64.1) | 70.88 (71.12) | 3.57 (3.86) | 10.02 (9.76) | FIG. 112 |
| Mfg. Ex. VII-53 | P138 | 0.89 (55.9) | 77.55 (77.81) | 3.55 (3.78) | 7.60 (7.89) | FIG. 113 |
| Mfg. Ex. VII-54 | P139 | 0.89 (62.5) | 73.42 (73.61) | 3.44 (3.62) | 8.80 (8.88) | FIG. 114 |
| Mfg. Ex. VII-55 | P140 | 0.64 (47.0) | 74.86 (75.16) | 3.12 (3.32) | 9.07 (9.23) | FIG. 115 |
| Mfg. Ex. VII-56 | P141 | 0.84 (64.4) | 71.65 (71.85) | 3.09 (3.36) | 9.65 (9.76) | FIG. 116 |

TABLE 67-5

| Mfg. Ex. No. | Azo Compound No. | Yield amount (g) (Yield ratio (%)) | Actual measurement value C (Calculation value C) | Actual measurement value H (Calculation value H) | Actual measurement value N (Calculation value N) | Infrared absorption spectrum Fig. |
|---|---|---|---|---|---|---|
| Mfg. Ex. VII-57 | P142 | 0.96 (69.4) | 74.27 (74.17) | 4.46 (4.59) | 9.14 (9.10) | FIG. 117 |

TABLE 67-5-continued

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-58 | P143 | 0.82 (62.1) | 71.11 (71.35) | 3.80 (4.03) | 9.85 (9.60) | FIG. 118 |
| Mfg. Ex. VII-59 | P144 | 0.76 (58.3) | 73.25 (73.43) | 3.72 (3.95) | 9.65 (9.69) | FIG. 119 |
| Mfg. Ex. VII-60 | P145 | 0.75 (58.8) | 70.67 (70.88) | 3.45 (3.69) | 10.12 (9.92) | FIG. 120 |
| Mfg. Ex. VII-61 | P146 | 0.85 (69.0) | 72.82 (73.08) | 3.06 (3.31) | 11.71 (11.93) | FIG. 121 |
| Mfg. Ex. VII-62 | P153 | 0.82 (61.0) | 73.88 (74.15) | 3.71 (3.85) | 9.36 (9.43) | FIG. 122 |
| Mfg. Ex. VII-63 | P154 | 0.74 (56.4) | 71.43 (71.68) | 3.47 (3.59) | 9.45 (9.64) | FIG. 123 |
| Mfg. Ex. VII-64 | P88 | 0.86 (66.1) | 71.87 (72.05) | 3.21 (3.49) | 9.54 (9.70) | FIG. 125 |
| Mfg. Ex. VII-65 | P89 | 0.92 (68.5) | 72.19 (72.48) | 3.63 (3.83) | 9.09 (9.39) | FIG. 126 |
| Mfg. Ex. VII-66 | P91 | 0.90 (71.5) | 71.32 (71.60) | 3.00 (3.12) | 9.79 (10.02) | FIG. 127 |
| Mfg. Ex. VII-67 | P124 | 0.78 (50.0) | 71.94 (72.13) | 3.28 (3.46) | 10.39 (10.68) | FIG. 128 |

TABLE 67-6

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-68 | P125 | 0.71 (50.6) | 70.04 (70.40) | 3.31 (3.44) | 10.29 (10.45) | FIG. 129 |
| Mfg. Ex. VII-69 | P147 | 0.78 (58.1) | 70.54 (70.82) | 3.61 (3.81) | 9.09 (9.35) | FIG. 130 |
| Mfg. Ex. VII-70 | P148 | 0.64 (49.3) | 69.48 (69.56) | 3.37 (3.62) | 9.90 (9.74) | FIG. 131 |
| Mfg. Ex. VII-71 | P149 | 0.51 (37.8) | 70.50 (70.82) | 3.54 (3.81) | 9.08 (9.35) | FIG. 132 |
| Mfg. Ex. VII-72 | P150 | 0.65 (50.2) | 69.28 (69.56) | 3.39 (3.62) | 9.78 (9.74) | FIG. 133 |
| Mfg. Ex. VII-73 | P155 | 0.66 (49.2) | 73.91 (74.15) | 3.62 (3.85) | 9.15 (9.43) | FIG. 134 |
| Mfg. Ex. VII-74 | P156 | 0.64 (49.0) | 71.50 (71.68) | 3.44 (3.59) | 9.87 (9.64) | FIG. 135 |
| Mfg. Ex. VII-75 | P157 | 0.75 (55.8) | 76.52 (76.84) | 4.04 (4.30) | 9.17 (9.43) | FIG. 136 |
| Mfg. Ex. VII-76 | P158 | 0.70 (52.6) | 71.80 (71.90) | 3.53 (3.76) | 9.22 (9.49) | FIG. 137 |
| Mfg. Ex. VII-77 | P159 | 0.66 (45.2) | 65.03 (65.30) | 2.54 (2.90) | 8.30 (8.62) | FIG. 138 |
| Mfg. Ex. VII-78 | P160 | 0.61 (45.3) | 66.29 (66.63) | 2.95 (3.13) | 9.08 (9.32) | FIG. 139 |

TABLE 67-7

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-79 | P161 | 0.76 (51.8) | 65.18 (65.30) | 2.75 (2.90) | 8.41 (8.62) | FIG. 140 |

TABLE 67-7-continued

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-80 | P162 | 0.68 (50.3) | 66.76 (66.63) | 3.10 (3.13) | 9.22 (9.32) | FIG. 141 |
| Mfg. Ex. VII-81 | P163 | 0.70 (48.0) | 64.96 (65.30) | 2.56 (2.90) | 8.30 (8.62) | FIG. 142 |
| Mfg. Ex. VII-82 | P164 | 0.65 (48.3) | 66.28 (66.63) | 2.83 (3.13) | 8.95 (9.32) | FIG. 143 |
| Mfg. Ex. VII-83 | P169 | 0.57 (43.5) | 73.23 (73.43) | 3.73 (3.95) | 9.46 (9.69) | FIG. 144 |
| Mfg. Ex. VII-84 | P170 | 0.62 (49.1) | 70.50 (70.88) | 3.38 (3.69) | 9.71 (9.92) | FIG. 145 |
| Mfg. Ex. VII-85 | P173 | 0.57 (45.9) | 73.38 (73.55) | 3.32 (3.39) | 13.22 (13.45) | FIG. 146 |
| Mfg. Ex. VII-86 | P174 | 0.66 (52.8) | 70.51 (70.88) | 3.25 (3.40) | 11.55 (11.81) | FIG. 147 |
| Mfg. Ex. VII-87 | P180 | 0.86 (69.3) | 72.24 (72.63) | 3.42 (3.66) | 9.91 (10.16) | FIG. 148 |
| Mfg. Ex. VII-88 | P181 | 0.80 (63.4) | 72.48 (72.85) | 3.69 (3.84) | 10.26 (10.00) | FIG. 149 |
| Mfg. Ex. VII-89 | P182 | 0.96 (69.3) | 72.50 (72.88) | 3.99 (4.15) | 8.88 (9.11) | FIG. 150 |

TABLE 67-8

| Mfg. Ex. No. | Azo Compound No. | Yield amount (g) (Yield ratio (%)) | Elemental analysis (%) | | | Infrared absorption spectrum Fig. |
|---|---|---|---|---|---|---|
| | | | Actual measurement value C (Calculation value C) | Actual measurement value H (Calculation value H) | Actual measurement value N (Calculation value N) | |
| Mfg. Ex. VII-90 | P183 | 0.83 (64.7) | 72.77 (73.06) | 3.81 (4.01) | 10.12 (9.83) | FIG. 151 |
| Mfg. Ex. VII-91 | P184 | 0.79 (64.8) | 72.27 (72.41) | 3.20 (3.47) | 10.17 (10.34) | FIG. 152 |
| Mfg. Ex. VII-92 | P185 | 1.07 (76.5) | 74.34 (74.67) | 2.67 (3.03) | 11.84 (12.01) | FIG. 153 |
| Mfg. Ex. VII-93 | P186 | 0.80 (62.0) | 73.65 (74.03) | 3.08 (3.40) | 11.01 (11.40) | FIG. 154 |
| Mfg. Ex. VII-94 | P187 | 0.91 (70.5) | 71.88 (72.55) | 3.03 (3.28) | 12.78 (13.02) | FIG. 155 |
| Mfg. Ex. VII-95 | P188 | 0.75 (60.7) | 71.84 (72.90) | 3.31 (3.55) | 11.75 (11.90) | Fig. 156 |

Further, the present invention is hereinafter explained concretely with reference to applied embodiments. However, the embodiments of the present invention are not limited thereto.

(Applied Embodiment 1)

Azo compounds 7.5 volumes of the example VII-10 (azo compound No.P19) of the present invention and 0.5% by weight tetra hydro furan liquid solution 500 volumes of polyester resin (VYLON® 200: TOYOBO Co., Ltd.) were crushed and mixed in a ball mill, obtained dispersion liquid was doctor-bladed on an aluminium evaporation polyester film, then dried in a natural condition, thus an charge generating layer having the thickness of 1 μm was formed.

Then, charge transporting substance 1 volume, polycarbonate resin (Panlite® K1300: TEJIN KASEI Co., Ltd.) 1 volume, and tetra hydro furan 8 volumes charge transporting layer coating liquid indicated by the following structural formula (D-1) were prepared, coated by the doctor blade on the aforementioned charge generating layer, then dried at the temperature of 80° C. for 2 minutes and further at the temperature of 120° C. for 5 minutes, thus a charge transporting layer having the thickness of 20 μm was formed.

Structual Formula (D-1)

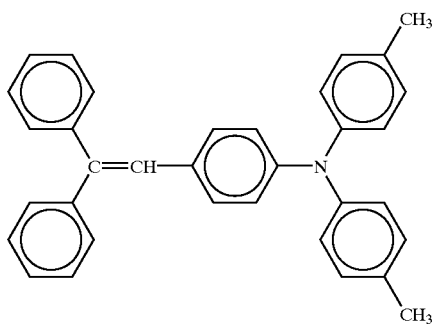

For thus obtained electrophotographic photoconductor, under the condition of 25° C./55%RH, −6 KV corona discharge was performed for 20 seconds and this photoconductor was charged using the electrostatic copying paper tester EPA-8100(KAWAGUCHI ELECTRIC Co., Ltd.) in a dark place. Then the photoconductor was left as it was for 20 seconds, and surface electrokinetic potential $V_0$ (V) at that time was measured. Succeedingly, light was given as irradiation by a tungsten lamp in order for a photoconductor surface's illumination unit to become 5.3 luxes, and time (second) till its surface electrokinetic potential became a half of $V_0$ was obtained, thus exposing volume $E_{1/2}$ (lux·second) was calculated. The results therefor were $V_0$=−938 volts, $E_{1/2}$=2.0 luxes·second.

In this way, obviously in the detailed and concrete explanation, azo compound manufacturing raw material (coupler compound) of the present invention can be manufactured easily compared with a conventional coupler compound. By utilizing an azo compound using this manufacturing raw material (coupler compound) as a charge generating substance, a high sensitive electrophotographic photoconductor can be provided. Further, a novel coupler of the present invention affects excellent advantageous points as manufacturing pigments of an azo compound as an organic photo conductor.

What is claimed is:

1. An electrophotographic photoconductor comprising:

a conductive support; and a photoconductive layer disposed on the photoconductive support;

wherein the photoconductive layer contains an azo compound expressed by a general formula <<1>>:

Ar—(N=N—Cp)$_n$   general formula <<1>> wherein in the general formula <<1>>, Ar expresses one of a substituted or non-substituted aromatic hydrocarbon group and heterocyclic ring aromatic series group which can be combined by way of a bonding group; Cp expresses a coupler residual group; n expresses an integer of one of 1, 2, 3, and 4; at least one of the Cp is a coupler residual group selected from one of the following general formulae <<2>>, <<3>>, and <<4>>:

general formula <<2>>
   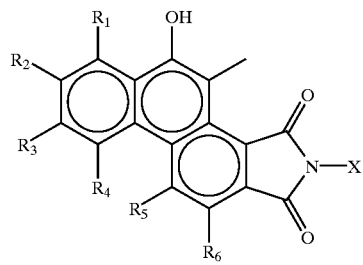

general formula <<3>>
   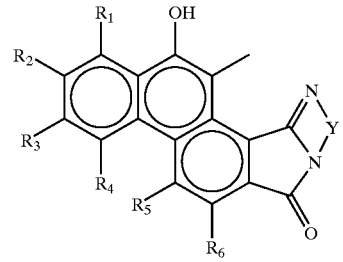

general formula <<4>>
   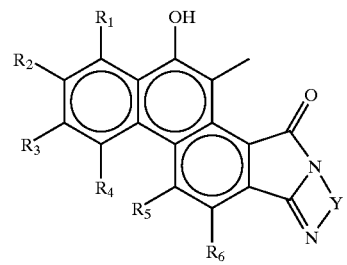

wherein in the general formulae <<2>>, <<3>>, and <<4>>, $R_1$, $R_2$, $R_3$, $R_4$, $R_5$ and $R_6$ each expresses one of a hydrogen atom, an alkyl group, an alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; and Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group, in which Z represents one of a substituted or non-substituted alkylene group, a substituted or non-substituted aromatic series divalent organic residual group, and a substituted or non-substituted heterocyclic ring aromatic series divalent organic residual group.

2. An electrophotographic photoconductor according to claim 1, wherein the coupler residual group expressed by the general formula <<2>> in the azo compound is a coupler residual group expressed by a general formula <<5>>:

general formula <<5>>
   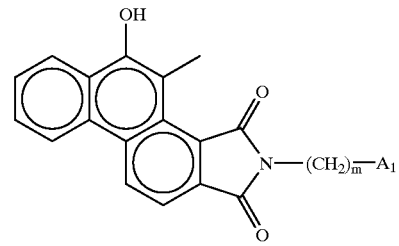

wherein in the general formula <<5>>, $A_1$ expresses one of a substituted or non-substituted aromatic series hydrocarbon group, and a substituted or non-substituted heterocyclic ring group; and m is an integer of 1 to 6.

3. An electrophotographic photoconductor according to claim 1, wherein in the azo compound, at least one of the Cp is a coupler residual group expressed by the general formula <<6>>, when n is one of 2, 3, and 4:

general formula <<6>>

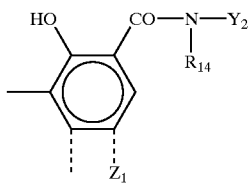

wherein in the general formula <<6>>, $Z_1$ represents one of a hydrocarbon ring or a substituted hydrocarbon ring, and a heterocyclic ring group or a substituted heterocyclic ring group; $R_{14}$ is one of hydrogen, an alkyl group or a substituted alkyl group, and a phenyl group or a substituted phenyl group; $Y_2$ represents one of a hydrocarbon ring group or a substituted hydrocarbon ring, and a heterocyclic ring group or a substituted heterocyclic ring group.

4. An electrophotographic photoconductor according to claim 1, wherein in the azo compound, at least one of the Cp is a coupler residual group selected from one of a general formula <<7>> and a general formula <<8>>, when n is one of 2, 3, and 4:

general formula <<7>>

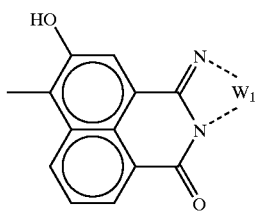

general formula <<8>>

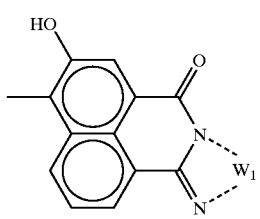

wherein in the general formulae <<7>> and <<8>>, $W_1$ represents an aromatic hydrocarbon divalent group or a heterocyclic ring divalent group having a nitrogen atom in a ring, wherein said rings may be substituted or non-substituted.

5. An electrophotographic photoconductor according to claim 1, wherein the azo compound is a disazo compound expressed by a general formula <<9>>:

general formula <<9>>

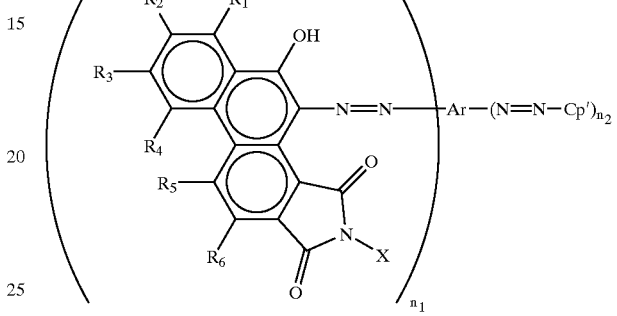

wherein in the general formula <<9>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2 and $n_2$ expresses an integer of 0 or 1.

6. An electrophotographic photoconductor according to claim 5, wherein the disazo compound is a disazo compound expressed by a general formula <<10>>:

general formula <<10>>

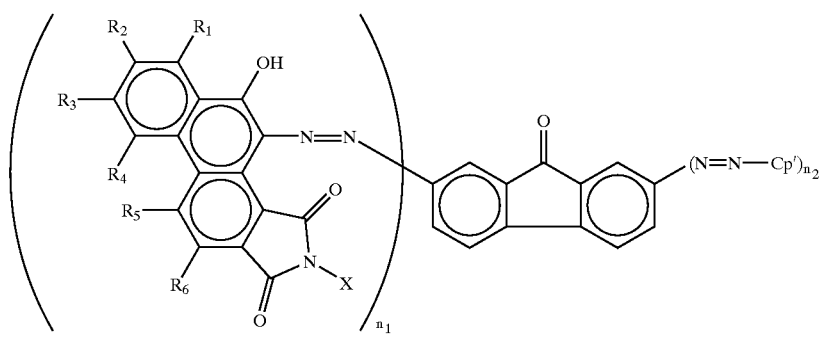

wherein in the general formula <<10>>, Cp' represents a coupler residual group; $R_1$, $R_2$, $R_3$, $R_4$, $R_5$ and $R_6$ each represents one of a hydrogen atom, alkyl group, alkoxy group, a halogen atom, an amino group, a hydroxy group, a nitro group, and a cyano group; X represents one of a hydrogen atom, a substituted or non-substituted alkyl group, a substituted or non-substituted aromatic series hydrocarbon group, a substituted or non-substituted heterocyclic ring group, and a substituted or non-substituted amino group; $n_1$ expresses an integer of 1 or 2; $n_2$ expresses an integer of 0 or 1. 7. An electrophotographic photoconductor according to claim 1, wherein the azo compound is a disazo compound expressed by one of general formulae <<11>> and <<12>>:

general formula <<11>>

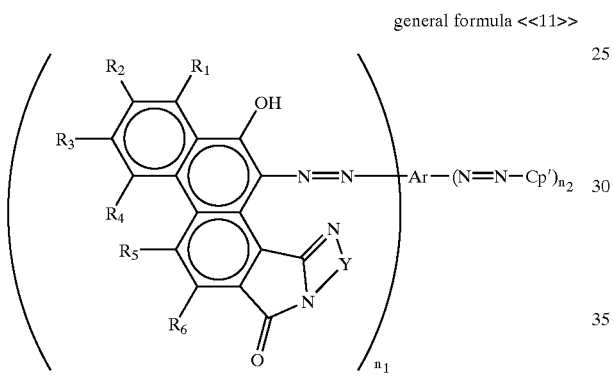

-continued general formula <<12>> wherein in the general formulae <<11>> and <<12>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and carbonyl group containing divalent organic residual group expressed by —CO—Z—, in which Z represents one of a substituted or non-substituted alkylene group, a substituted or non-substituted aromatic series divalent organic residual group, and a substituted or non-substituted heterocyclic ring aromatic series divalent organic residual group; and $n_1$ expresses an integer of 1 or 2; and $n_2$ expresses an integer of 0 or 1.

8. An electrophotographic photoconductor according to claim 7, wherein the disazo compound is a disazo compound expressed by one of a general formulae <<13>> and <<14>>:

general formula <<13>>

-continued

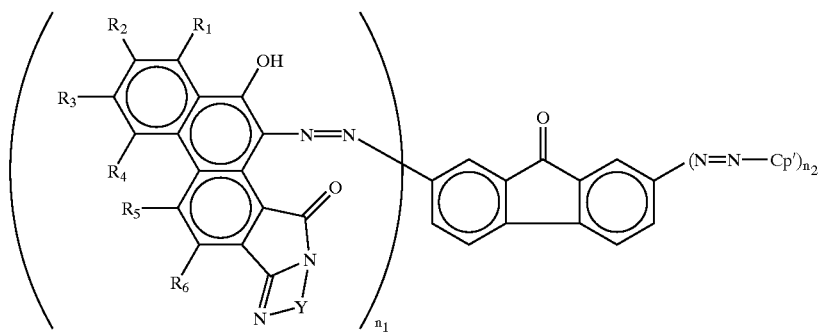

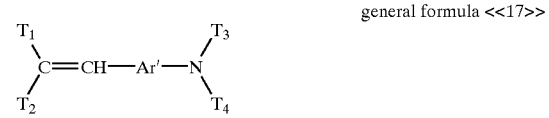

general formula <<14>> wherein in the general formulae <<13>> and <<14>>, Ar represents one of a substituted or non-substituted aromatic series hydrocarbon group, and an aromatic series heterocyclic ring group which may be combined by way of a bonding group; Cp' represents a coupler residual group; $R_1$, $R_2$, $R_3$, $R_4$, $R_5$ and $R_6$ each represents one of a hydrogen atom, an alkyl group, an alkoxy group, a halogen atom, an amino group, a hydroxy group, a nitro group, and a cyano group; Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, in which Z represents one of a substituted or non-substituted alkylene group, a substituted or non-substituted aromatic series divalent organic residual group, and a substituted or non-substituted heterocyclic ring aromatic series divalent organic residual group; and $n_1$ expresses an integer of 1 or 2; and $n_2$ expresses an integer of 0 or 1.

9. An electrophotographic photoconductor according to claim 1, wherein the azo compound of the general formula <<1>> is an azo compound which is obtained by reacting a diazonium salts compound expressed by a general formula <<15>> to a coupler compound expressed by a general formula <<16>>:

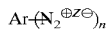   general formula <<15>>

H—Cp   general formula <<16>> wherein in the general formulae <<15>> and <<16>>, Ar represents one of a substituted or non-substituted aromatic series hydrocarbon group, and an aromatic series heterocyclic ring group which may be combined by way of a bonding group; Cp represents a coupler residual group; Z— represents an anion function; and n expresses an integer of 1, 2, 3 and 4.

10. An electrophotographic photoconductor according to claim 1, wherein the photoconductive layer is a single layer formed on a conductive support by one of directly and intervening an intermediate layer.

11. An electrophotographic photoconductor according to claim 10, wherein the photoconductive layer further contains a charge transporting substance.

12. An electrophotographic photoconductor according to claim 11, wherein the charge transporting substance is a stilbene compound expressed by a general formula <<17>>:

wherein in the general formula <<17>>, $T_1$ and $T_2$ each independently represents one of a substituted or non-substituted alkyl group, and a substituted or non-substituted aryl group; $T_3$ and $T_4$ each independently represents one of a hydrogen atom, a substituted or non-substituted alkyl group, a substituted or non-substituted aryl group, and a heterocyclic ring group; $T_1$ and $T_2$ may form a ring with each other; Ar' expresses one of a substituted or non-substituted aryl group, and a heterocyclic ring group.

13. An electrophotographic photoconductor according to claim 11, wherein the charge transporting substance is a polymer.

14. An electrophotographic photoconductor according to claim 13, wherein the polymer is at least one polymer selected from the group consisting of polycarbonate, polyurethane, polyester, and polyether.

15. An electrophotographic photoconductor according to claim 13, wherein the polymer has a structure of triaryl amine.

16. An electrophotographic photoconductor according to claim 13, wherein the charge transporting substance is a polycarbonate having a triaryl amine structure.

17. An electrophotographic photoconductor according to claim 16, wherein the polycarbonate having the triaryl amine structure is a charge transporting substance expressed by a general formula (1D):

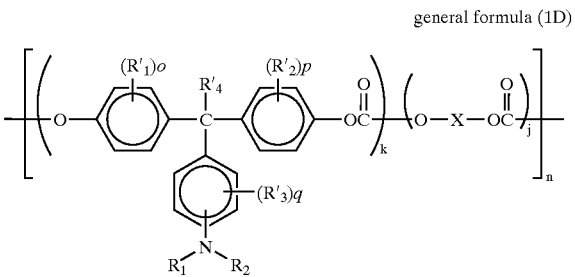

general formula (1D)

wherein in the formula (1D), $R'_1$, $R'_2$, and $R'_3$ each independently expresses a substituted or non-substituted alkyl group or a halogen atom;

$R'_4$ represents a hydrogen atom or a substituted or non-substituted alkyl group; $R_1$ and $R_2$ each represents a substituted or non-substituted aryl group; o, p, and q may each independently represents an integer of 0 to 4;

k and j each satisfies $0.1 \leq k \leq 1$ and $0 \leq j \leq 0.9$; n represents a repeating unit of 5 to 5000; and X is one member selected from the group consisting of an aliphatic divalent group, a divalent cycloaliphatic group, and a general formula (A):

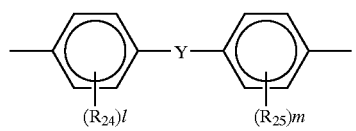

general formula (A)

wherein in the formula (A), $R_{24}$ and $R_{25}$ each independently represents one of a substituted or non-substituted alkyl group, an aryl group, and a halogen atom; l and m each represents an integer of 0 to 4;

Y represents one of a single bond, a linear chain having a carbon atom number of 1 to 12, a branched alkylene or a cycloalkylene group, —O—, —S—, —SO—, —SO$_2$—, —CO—, —CO—O—Z—O—CO—, in which Z represents an aliphatic divalent group, and a group expressed by a general formula (B):

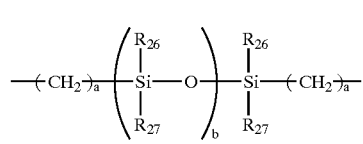

general formula (B)

wherein in the formula (B), a represents an integer of 1 to 20, b represents an integer of 1 to 2000, and each of $R_{26}$ and $R_{27}$ represents substituted or non-substituted alkyl group or aryl group, and $R_{24}$, $R_{25}$, $R_{26}$, and $R_{27}$ may be the same or may be different.

18. An electrophotographic photoconductor according to claim 16, wherein the polycarbonate having the triaryl amine structure is a charge transporting substance expressed by a general formula (2D):

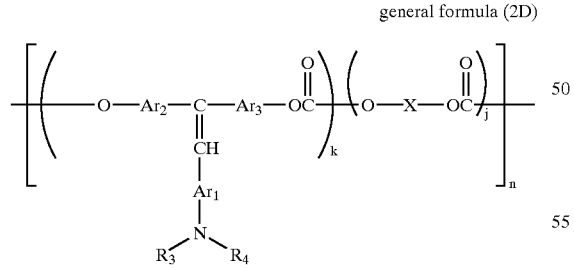

general formula (2D)

wherein in the formula (2D), $R_3$ and $R_4$ represent a substituted or non-substituted aryl group;

$Ar_1$, $Ar_2$, and $Ar_3$ each represents the same or different arylene group;

k and j each satisfies $0.1 \leq k \leq 1$ and $0 \leq j \leq 0.9$;

n represents a repeating unit of 5 to 5000; and

X is one of an aliphatic divalent group, a divalent cycloaliphatic group, and a general formula (A):

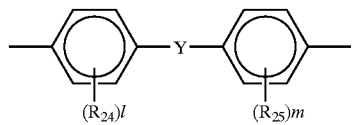

general formula (A)

wherein in the formula (A), $R_{24}$ and $R_{25}$ each independently represents a substituted or non-substituted alkyl group, an aryl group or a halogen atom; each of l and m represents an integer of 0 to 4;

Y represents one of a single bond, a linear chain having a carbon atom number 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

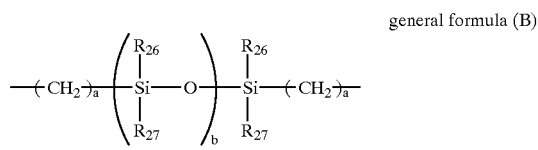

general formula (B)

wherein in the formula (B), a represents an integer of 1 to 20; b represents an integer of 1 to 2000; $R_{26}$ and $R_{27}$ each represents substituted or non-substituted alkyl group or aryl group, and $R_{24}$, $R_{25}$, $R_{26}$, and $R_{27}$ may be the same or may be different.

19. An electrophotographic photoconductor according to claim 16, wherein the polycarbonate having the triaryl amine structure is a charge transporting substance expressed by a general formula (3D):

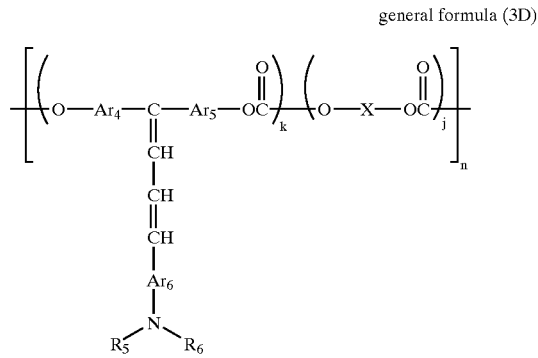

general formula (3D)

wherein in the formula (3D), $R_5$ and $R_6$ each represents a substituted or non-substituted aryl group;

$Ar_4$, $Ar_5$, and $Ar_6$ each represents a same or different arylene group;

k and j each satisfies $0.1 \leq k \leq 1$ and $0 \leq j \leq 0.9$;

n represents a repeating unit of 5 to 5000; and

X is one of an aliphatic divalent group, a divalent cycloaliphatic group, and a general formula (A):

general formula (A)

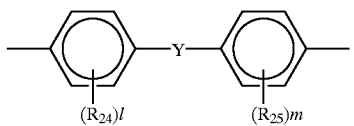

wherein in the formula (A), $R_{24}$ and $R_{25}$ each independently represents a substituted or non-substituted alkyl group, an aryl group or a halogen atom; each of l and m represents an integer of 0 to 4;

Y represents one of a single bond, a linear chain having a carbon atom number 1 to 12, a branched alkylene or a cycloalkylene group, —O—, —S—, —SO—, —SO$_2$—, —CO—, —CO—O—Z—O—CO—, in where Z represents an aliphatic divalent group), and a divalent group expressed by a general formula (B):

general formula (B)

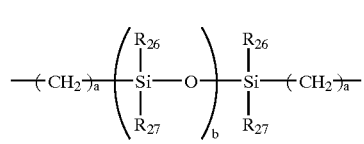

wherein in the formula (B), a represents an integer of 1 to 20; b represents an integer of 1 to 2000; and $R_{26}$ and $R_{27}$ each represents a substituted or non-substituted alkyl group or aryl group, and $R_{24}$, $R_{25}$, $R_{26}$, and $R_{27}$ may be the same or may be different.

20. An electrophotographic photoconductor according to claim 16, wherein the polycarbonate having the triaryl amine structure is a charge transporting substance expressed by a general formula (4D):

general formula (4D)

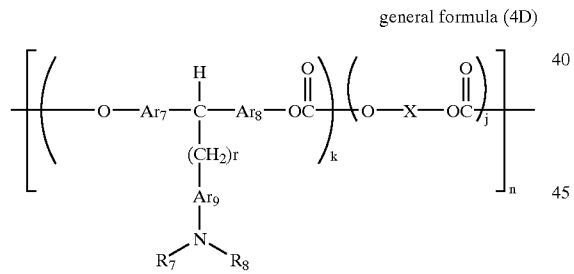

wherein in the formula (4D), each of $R_7$ and $R_8$ represents a substituted or non-substituted aryl group;

each of $Ar_7$, $Ar_8$, and $Ar_9$ represents the same or a different arylene group;

each of k and j satisfies 0.1—k≦1 and 0≦j≦0.9;

n represents a repeating unit of 5 to 5000;

r represents an integer of 1 to 5; and

X is one of an aliphatic divalent group, a divalent cycloaliphatic group, and a substance expressed by the general formula (A):

general formula (A)

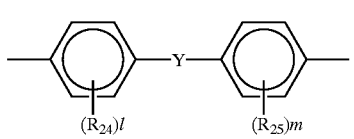

wherein in the formula (A), $R_{24}$ and $R_{25}$ each independently represents a substituted or non-substituted alkyl group, an aryl group or a halogen atom; each of l and m represents an integer of 0 to 4; Y represents one of a single bond, a linear chain having a carbon atom number of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

general formula (B)

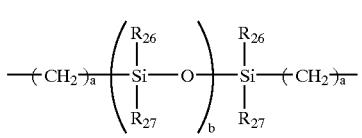

wherein in the formula (B), a represents an integer of 1 to 20; b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

21. An electrophotographic photoconductor according to claim 16, wherein the polycarbonate having the triaryl amine structure is a charge transporting substance expressed by a general formula (5D):

general formula (5D)

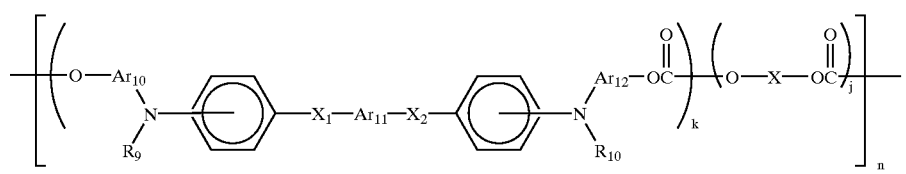

wherein in the formula (5D), each of $R_9$ and $R_{10}$ represents one of a substituted and non-substituted aryl group;

each of $Ar_{10}$, $Ar_{11}$, and $Ar_{12}$ represents the same or a different arylene group; each of $X_1$ and $X_2$ represents one of a substituted or non-substituted ethylene group, and a substituted or non-substituted vinylene group;

each of k and j satisfies $0.1 \leq k \leq 1$ and $0 \leq j \leq 0.9$;

n represents a repeating unit numbers of 5 to 5000; and

X is one of an aliphatic divalent group, a divalent cycloaliphatic group, and a general formula (A):

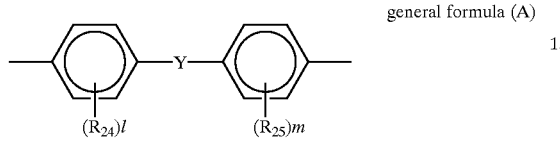

general formula (A)

wherein in the formula (A), $R_{24}$ and $R_{25}$ each independently represents one of a substituted or non-substituted alkyl group, an aryl group and a halogen atom; each of l and m represents an integer of 0 to 4; Y represents one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

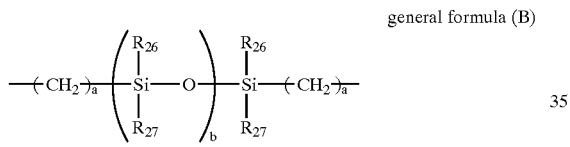

general formula (B)

wherein in the formula (B), a represents an integer of 1 to 20; b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

22. An electrophotographic photoconductor according to claim 16, wherein the polycarbonate having the triaryl amine structure is a charge transporting substance expressed by a general formula (6D):

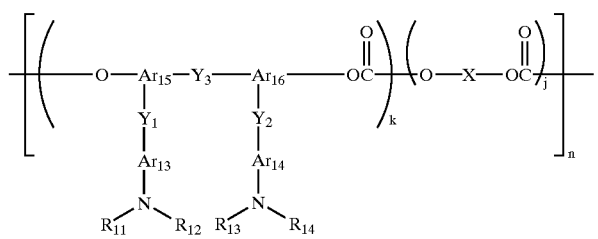

general formula (6D)

wherein in the formula (6D), each of $R_{11}$, $R_{12}$, $R_{13}$ and $R_{14}$ represents one of a substituted and a non-substituted aryl group;

each of $Ar_{13}$, $Ar_{14}$, $Ar_{15}$ and $Ar_{16}$ represents the same or a different arylene group;

each of $Y_1$, $Y_2$, and $Y_3$ represents one of a single bond, a substituted or non-substituted alkylene group, a substituted or non-substituted cyclo alkylene group, a substituted or non-substituted alkyl ether group, oxygen atom, sulfur atom, and a vinylene group, which may be the same or maybe different;

k and j each satisfies $0.1 \leq k \leq 1$ and $0 \leq j \leq 0.9$;

n represents a repeating unit number of 5 to 5000; and

X is one of an aliphatic divalent group, a divalent cycloaliphatic group, and a general formula (A):

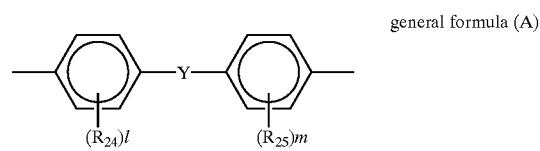

general formula (A)

wherein in the formula (A), $R_{24}$ and $R_{25}$ independently represents a substituted or non-substituted alkyl group, an aryl group or a halogen atom; each of l and m represents an integer of 0 to 4;

Y represents a one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

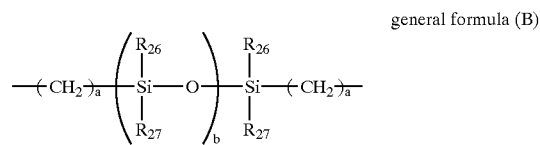

general formula (B)

wherein in the formula (B), a represents an integer of 1 to 20; b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

23. An electrophotographic photoconductor according to claim 16, wherein the polycarbonate having the triaryl amine structure is a charge transporting substance expressed by a general formula (7D):

general formula (7D)

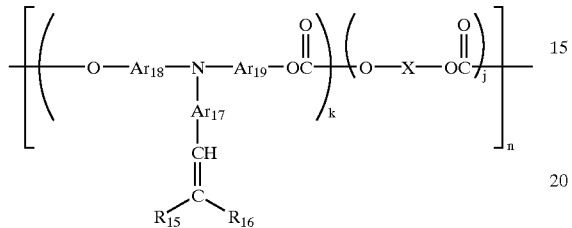

wherein in the formula (7D), each of $R_{15}$ and $R_{16}$ represents a hydrogen atom, a substituted or non-substituted aryl group;

each of $R_{15}$ and $R_{16}$ may form a ring;

$Ar_{17}$, $Ar_{18}$ and $Ar_{19}$ may each represents the same or a different arylene group;

k and j each satisfies $0.1 \text{—} k \leq 1$ and $0 \leq j \leq 0.9$;

n represents a repeating unit of 5 to 5000; and

X is one of an aliphatic divalent group, a divalent cycloaliphatic group, and a general formula (A):

general formula (A)

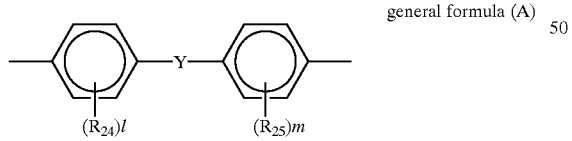

wherein in the formula (A), each of $R_{24}$ and $R_{25}$ independently represents a substituted or non-substituted alkyl group, an aryl group, or a halogen atom; each of l and m represents an integer of 0 to 4;

Y represents a one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

general formula (B)

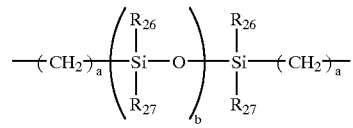

wherein in the formula (B), a represents an integer of 1 to 20, b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

24. An electrophotographic photoconductor according to claim 16, wherein the polycarbonate having the triaryl amine structure is a charge transporting substance expressed by a general formula (8D):

general formula (8D)

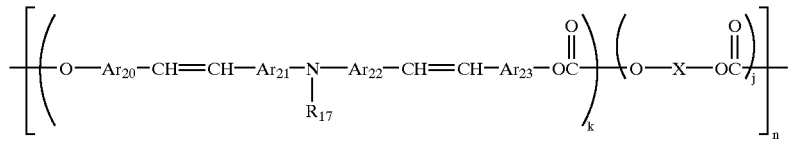

wherein in the formula (8D), $R_{17}$ represents a substituted or non-substituted aryl group; each of $Ar_{20}$, $Ar_{21}$, $Ar_{22}$ and $Ar_{23}$ represents the same or a different arylene group;

each of k and j satisfies $0.1 \leq k \leq 1$ and $0 \leq j \leq 0.9$;

n represents a repeating unit of 5 to 5000; and

X is one of an aliphatic divalent group, a divalent cycloaliphatic group, and a general formula (A):

general formula (A)

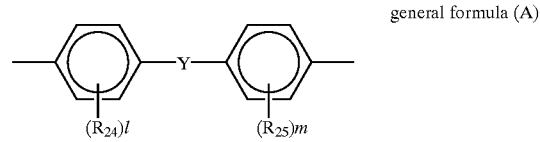

wherein in the formula (A), each of $R_{24}$ and $R_{25}$ independently represents one of a substituted or non-substituted alkyl group, and an aryl group or a halogen atom; each of l and m represents an integer of 0 to 4;

Y represents one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

general formula (B)

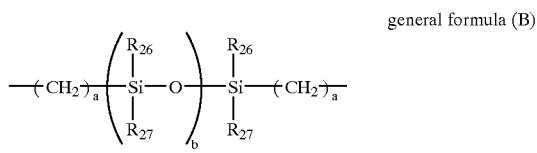

wherein in the formula (B), a represents an integer of 1 to 20; b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

25. An electrophotographic photoconductor according to claim 16, wherein the polycarbonate having the triaryl amine structure is a charge transporting substance expressed by a general formula (9D):

general formula (9D)

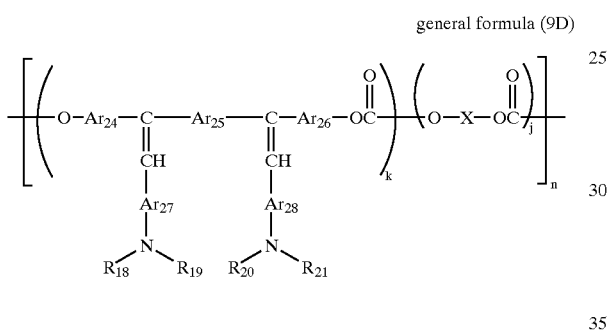

wherein in the formula (9D), each of $R_{18}$, $R_{19}$, $R_{20}$ and $R_{21}$ represents a substituted or non-substituted aryl group;

each of $Ar_{24}$, $Ar_{25}$, $Ar_{26}$, $Ar_{27}$, and $Ar_{28}$ represents the same or a different arylene group;

each of k and j satisfies $0.1 \leq k \leq 1$ and $0 \leq j \leq 0.9$;

n represents a repeating unit of 5 to 5000; and

X is one of an aliphatic divalent group, a divalent cycloaliphatic group, and a general formula (A):

general formula (A)

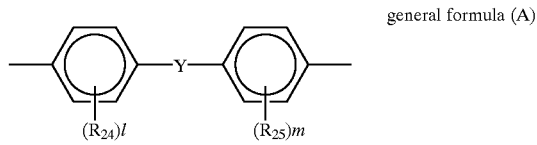

wherein in the formula (A), each of $R_{24}$ and $R_{25}$ independently represents one of a substituted or non-substituted alkyl group, and an aryl group or a halogen atom; each of l and m represents an integer of 0 to 4;

Y represents a one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

general formula (B)

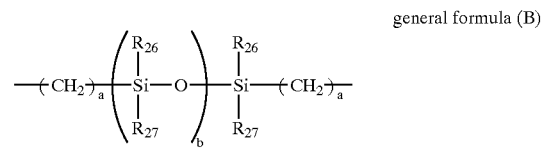

wherein in the formula (B), a represents an integer of 1 to 20; b represents an integer of 1 to 2000; and each of $R_{26}$ and $R_{27}$ represents substituted or non-substituted alkyl group or aryl group, and $R_{24}$, $R_{25}$, $R_{26}$, and $R_{27}$ may be the same or may be different.

26. An electrophotographic photoconductor according to claim 16, wherein the polycarbonate having the triaryl amine structure is a charge transporting substance expressed by a general formula (10D):

general formula (10D)

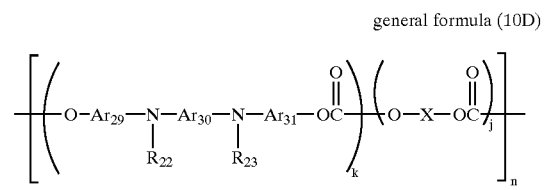

wherein in the formula (10D), each of $R_{22}$, and $R_{23}$ represents a substituted or non-substituted aryl group;

each of $Ar_{29}$, $Ar_{30}$, and $Ar_{31}$ represents the same or a different arylene group; each of k and j satisfies $0.1 \leq k \leq 1$ and $0 \leq j \leq 0.9$; n represents a repeating unit of 5 to 5000; and X is one of an aliphatic divalent group, a divalent cycloaliphatic group, and a general formula (A):

general formula (A)

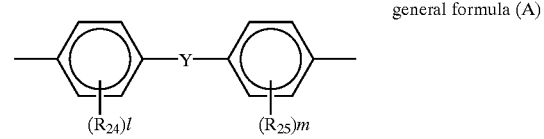

wherein in the formula (A), each of $R_{24}$ and $R_{25}$ independently represents a substituted or non-substituted alkyl group, an aryl group or a halogen atom; each of l and m represents an integer of 0 to 4;

Y represents a one of a single bond, a linear chain having carbon atom numbers of 1 to 12, a branched alkylene or a cycloalkylene group, —O—, —S—, —SO—, —SO$_2$—, —CO—, —CO—O—Z—O—CO—, in which Z represents an aliphatic divalent group, and a divalent group expressed by a general formula (B):

general formula (B)

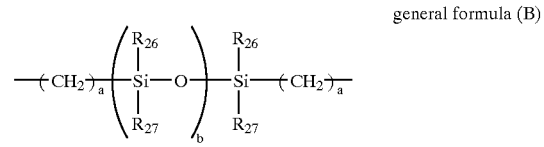

wherein in the formula (B), a represents an integer of 1 to 20; b represents an integer of 1 to 2000; and each of $R_{26}$ and $R_{27}$ represents substituted or non-substituted alkyl group or aryl group, and R$_{24}$, R$_{25}$, R$_{26}$, and R$_{27}$ may be the same or may be different.

27. An electrophotographic photoconductor according to claim 16, wherein a polycarbonate having a triaryl amine is a charge transporting substance expressed by a general formula (11D):

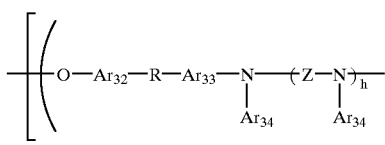

general formula (11D)

wherein in the formula (11D), each of Ar$_{32}$, Ar$_{33}$, Ar$_{35}$ and Ar$_{36}$ represents substituted or non-substituted arylene group;

Ar$_{34}$ represents a substituted or non-substituted aryl group;

Z represents arylene group or —Ar$_{37}$—Za—Ar$_{37}$—, in which Ar$_{37}$ represents substituted or non-substituted arylene group;

Za represents O, S, or an alkylene group;

each of R and R' represents a linear chain or branched alkylene group or —O—;

h represents 0 or 1;

each of k and j satisfies $0.1 \leq k \leq 1$ and $0 \leq j \leq 0.9$; n represents a repeating unit of 5 to 5000; and X is one of a substituted or non-substituted aliphatic divalent group, a substituted or non-substituted divalent cycloaliphatic group, a substituted or non-substituted aromatic series divalent group, a divalent group formed by bonding them, and a divalent group expressed by one of general formulae (A'), (F), and (G):

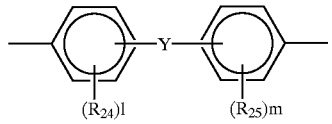

general formula (A')

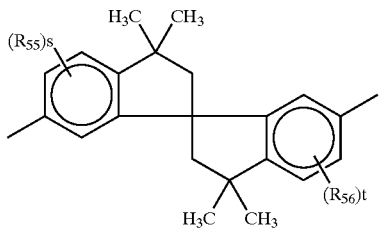

general formula (F)

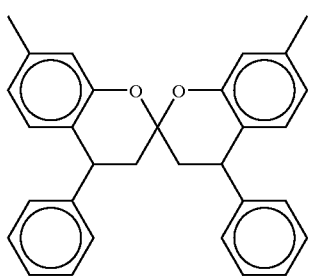

general formula (G)

wherein in the formulae (A'), (F) and (G), each of R$_{24}$, R$_{25}$, R$_{55}$ and R$_{56}$ each independently represents a substituted or non-substituted alkyl group, a substituted or non-substituted aryl group or a halogen atom;

l and m may each independently represents an integer of 0 to 4;

each of s and t independently represents an integer of 0 to 3;

when R$_{24}$, R$_{25}$, R$_{55}$ and R$_{56}$ respectively has a plurality of elements, they may be the same or may be different; and Y represents one of a single bond, a linear chain having a carbon atom number of 1 to 12, a branched alkylene or a cycloalkylene group, a divalent group formed of at least one alkylene group having a carbon atom number of 1 to 10 and at least one oxygen atom and sulfur atom, —O—, —S—, —SO—, SO$_2$—, —CO—, —COO—, —CO—O—Z$_1$—O—CO—, —CO—Z$_2$—CO—, in which each of Z$_1$ and Z$_2$ is a substituted or non-substituted aliphatic divalent group, or substituted or non-substituted arylene group, and one of general formulae (B), and general formulae (H) to (N):

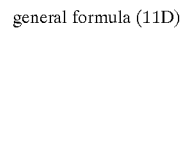

general formula (B)

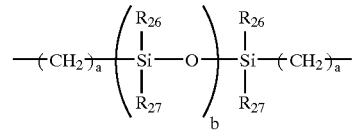

general formula (H)

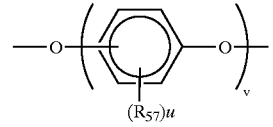

general formula (I)

general formula (J)

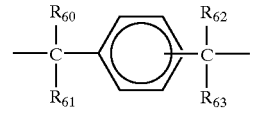

general formula (K)

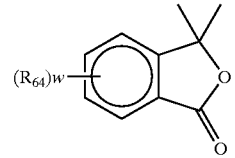

general formula (L)

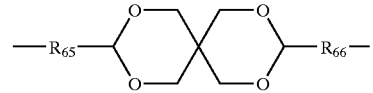

-continued

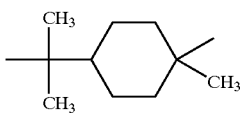
general formula (M)

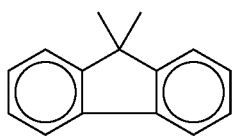
general formula (N)

wherein in the formulae (B), (H) to (N), each of $R_{26}$ and $R_{27}$ independently represents one of a substituted or non-substituted alkyl group, and a substituted or non-substituted aryl group;

each of $R_{57}$, $R_{58}$ and $R_{64}$ represents a halogen atom, a substituted or non-substituted alkyl group, a substituted or non-substituted alkoxy group, a substituted or non-substituted aryl group;

each of $R_{59}$, $R_{60}$, $R_{61}$, $R_{62}$ and $R_{63}$ independently represents one of a hydrogen atom or halogen atom, a substituted or non-substituted alkyl group, a substituted or non-substituted alkoxy group, and a substituted or non-substituted aryl group;

$R_{58}$ and $R_{59}$ may be combined and form a carbon ring having a carbon numbers of 5 to 12;

each of $R_{65}$ and $R_{66}$ represents a single bond or an alkylene group having a carbon number of 1 to 4; a represents an integer of 1 to 20;

b represents an integer of 1 to 2000;

each of u and w is an integer of 0 to 4; and v represents 1 or 2; and when each of the $R_{26}$, $R_{27}$, $R_{57}$ and $R_{64}$ has a plurality of elements, they may be the same or may be different.

28. An electrophotographic photoconductor according to claim 11, wherein the photoconductive layer further contains an acceptor compound.

29. An electrophotographic photoconductor according to claim 28, wherein the acceptor compound is a 2,3-diphenyl indene compound expressed by a general formula <<18>>:

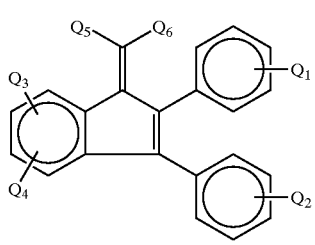
general formula <<18>> wherein in the formula <<18>>, each of $Q_1$, $Q_2$, $Q_3$ and $Q_4$ is a one of a hydrogen atom, a halogen atom, a substituted or non-substituted alkyl group, a cyano group, and a nitro group; and each of $Q_5$ and $Q_6$ is one of a hydrogen atom, substituted or non-substituted aryl group, a cyano group, an alkoxy carbonyl group, and an aryl oxy carbonyl group.

30. An electrophotographic photoconductor according to claim 28, wherein the photoconductive layer further contains a phenol compound.

31. An electrophotographic photoconductor according to claim 30, wherein the phenol compound is a phenol compound expressed by a general formula <<19>>:

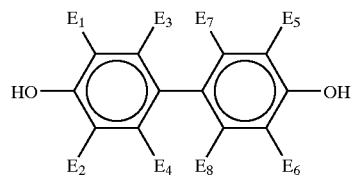
general formula <<19>> wherein in general formula <<19>>, each of $E_1$ to $E_8$ is one of a hydrogen atom, a substituted or non-substituted alkyl group, a substituted or non-substituted alkoxy carbonyl group, substituted or non-substituted aryl group, and a substituted or non-substituted alkoxy group.

32. An electrophotographic photoconductor comprising:

a conductive support;

a photoconductive layer which contains a charge generating substance and a charge transporting substance on the conductive support;

wherein the charge generating substance is an azo compound expressed by a following general formula <<1>>:

$$\text{Ar}\text{-}(\text{N}=\text{N}-\text{Cp})_n \qquad \text{general formula <<1>>}$$

wherein in the general formula <<1>>, Ar is a substituted or non-substituted aromatic series hydrocarbon group or an aromatic series heterocyclic ring group, which can be bonded by way of a bonding group; Cp is a coupler residual group; n represents an integer of any one of 1, 2, 3, and 4; and at least one of the Cp is a coupler residual group selected from one of a general formula <<2>>, general formula <<3>>, and general formula <<4>>:

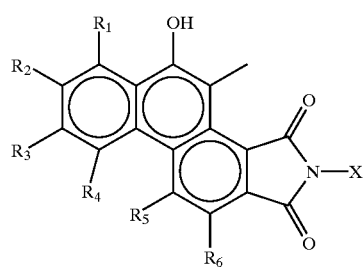
general formula <<2>>

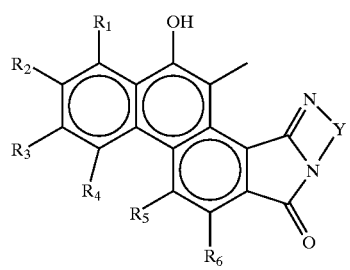
general formula <<3>> general formula <<4>>

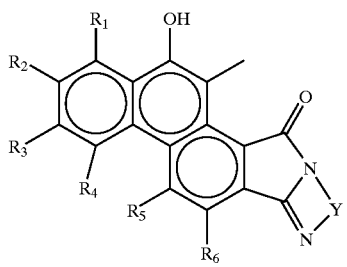

wherein in the general formula <<2>>, the general formula <<3>>, and the general formula <<4>>, each of $R_1$, $R_2$, $R_3$, $R_4$, $R_5$, and $R_6$ is one of a hydrogen atom, an alkyl group, an alkoxy group, a halogen atom, an amino group, a hydroxy group, a nitro group, and a cyano group;

X represents one of a hydrogen atom, a substituted or non-substituted alkyl group, a substituted or non-substituted aromatic series hydrocarbon group, a substituted or non-substituted heterocyclic ring group, and a substituted or non-substituted amino group; and Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, in which Z represents one of a substituted or non-substituted alkylene group, a substituted or non-substituted aromatic series divalent organic residual group, and a substituted or non-substituted heterocyclic ring aromatic series divalent organic residual group.

33. An azo compound comprising an azo compound expressed by a general formula <<1'>>, wherein at least one of the Cp is a coupler residual group selected from following general formulae <<2'>>, <<3'>> and <<4'>>:

Ar—(N═N—Cp)$_n$    general formula <<1'>> wherein in the formula <<1'>>, Ar expresses one of a substituted or non-substituted aromatic hydrocarbon group, and an heterocyclic ring aromatic series group, which can be combined by way of a bonding group; and Cp expresses a coupler residual group; n expresses an integer of any of 1, 2, 3, and 4, general formula <<2'>>

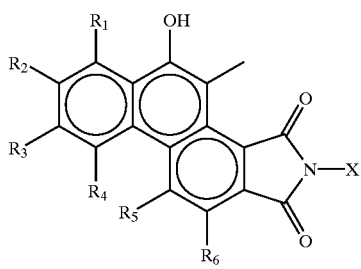

general formula <<3'>>

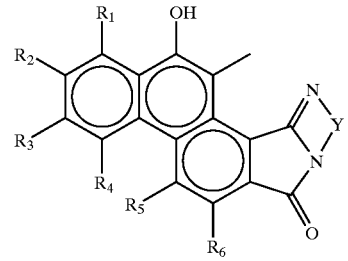

general formula <<4'>>

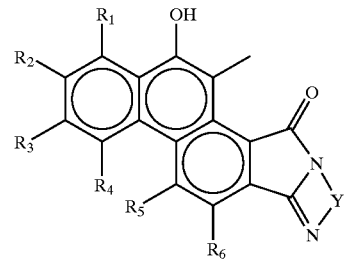

wherein in the formulae <<2'>>, <<3'>> and <<4'>>, each of $R_1$, $R_2$, $R_3$, $R_4$, $R_5$ and $R_6$ is one of a hydrogen atom, an alkyl group, an alkoxy group, and a halogen atom;

X represents one of a hydrogen atom, a substituted or non-substituted alkyl group, a substituted or non-substituted aromatic series hydrocarbon group, and a substituted or non-substituted heterocyclic ring group; and Y represents one of a substituted or non-substituted alkylene group, a substituted or non-substituted aromatic series divalent organic residual group, a substituted or non-substituted heterocyclic ring aromatic series divalent organic residual group, and a —CO—Z— carbonyl group containing divalent organic residual group, in which Z represents one of a substituted or non-substituted alkylene group, a substituted or non-substituted aromatic series divalent organic residual group, and a substituted or non-substituted heterocyclic ring aromatic series divalent organic residual group.

34. An azo compound according to claim 33, wherein in the general formula <<1'>>, at least one of the Cp is a coupler residual group expressed by a general formula <<5'>>:

general formula <<5'>>

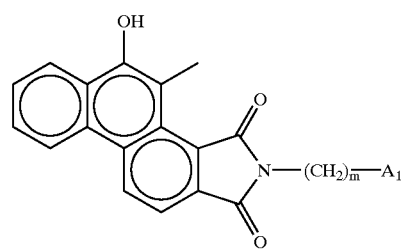

wherein in the general formula <<5'>>, $A_1$ represents one of a substituted or non-substituted aromatic series hydrocarbon group, and a substituted or non-substituted heterocyclic ring group; where m is an integer of 1 to 6.

35. An azo compound according to claim 33, wherein in the general formula <<1'>>, at least one of the Cp is a coupler residual group expressed by a general formula <<6'>> when n is one of 2, 3 and 4:

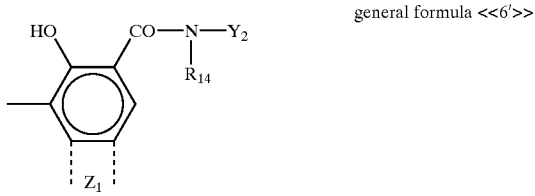

general formula <<6'>> wherein in general formula <<6'>>, $Z_1$ represents one of a hydrocarbon ring or a substituted hydrocarbon ring, and a heterocyclic ring group or a substituted heterocyclic ring group; $R_{14}$ is one of hydrogen, an alkyl group or a substituted alkyl group, and a phenyl group or a substituted phenyl group; and $Y_2$ represents one of a hydrocarbon ring group or a substituted hydrocarbon ring, and a heterocyclic ring group or a substituted heterocyclic ring group.

36. An electrophotographic photoconductor according to claim 33, wherein in the general formula <<1'>>, at least one of the Cp is a coupler residual group selected by one of a general formulae <<7>> and <<8>>, when n is one of 2, 3, and 4:

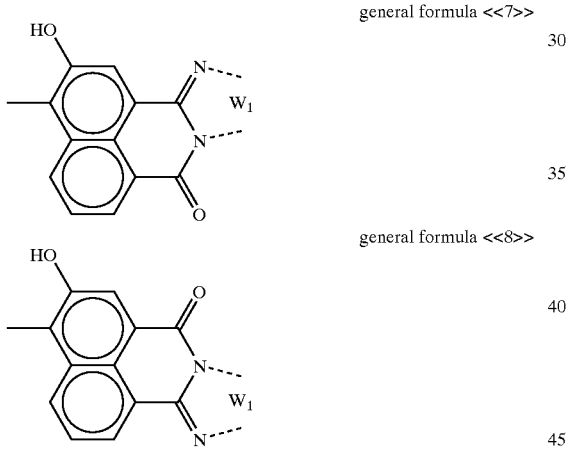

general formula <<7>> general formula <<8>> wherein in the general formula <<7>> and <<8>>, W1 represents an aromatic series hydrogen divalent group or a heterocyclic ring divalent group including a nitrogen atom in a ring, wherein these rings may be substituted or non-substituted.

37. An apparatus for forming an image comprising:
an electrophotographic photoconductor;
means for charging an electrophotographic photoconductor;
means for exposing the electrophotographic photoconductor charged by the means for charging and forming a latent electrostatic image;
means for developing the latent electrostatic image, visualizing the latent electrostatic image, and forming a developed image; and
means for transferring the developed image formed by the means for developing onto a transferring substance, wherein the electrophotographic photoconductor comprises a photoconductive layer which contains an azo compound expressed by a general formula <<1>> on a photoconductive layer:

general formula <<1>> wherein in the general formula <<1>>, Ar expresses one of a substituted or non-substituted aromatic hydrocarbon group, and an heterocyclic ring aromatic series group which can be combined by way of a bonding group; Cp expresses a coupler residual group; n expresses an integer of any one of 1, 2, 3, and 4, wherein at least one of the Cp is a coupler residual group selected from general formulae <<2>>, <<3>>, and <<4>>:

general formula <<2>>

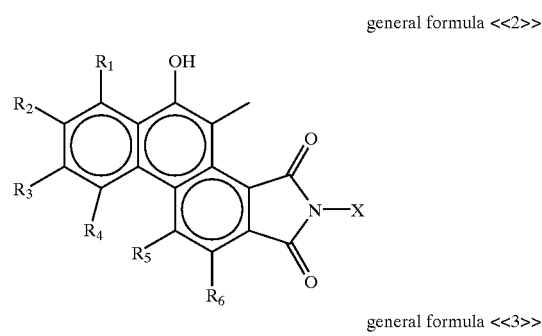

general formula <<3>>

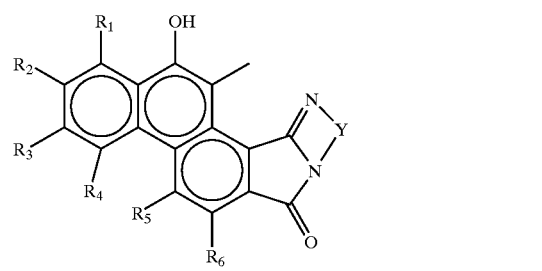

general formula <<4>>

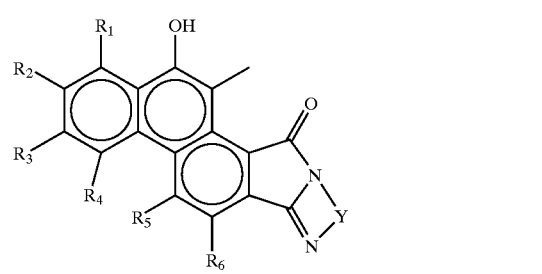

wherein in the general formulae <<2>>, <<3>>, and <<4>>, each of $R_1$, $R_2$, $R_3$, $R_4$, $R_5$ and $R_6$ is one of a hydrogen atom, an alkyl group, an alkoxy group, a halogen atom, an amino group, a hydroxy group, a nitro group, and a cyano group;
X represents a hydrogen atom, a substituted or non-substituted alkyl group, a substituted or non-substituted aromatic series hydrocarbon group, a substituted or non-substituted heterocyclic ring group, and a substituted or non-substituted amino group; and
Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, in which Z represents one of a substituted or non-substituted alkylene group, a substituted or non-substituted aromatic series divalent organic residual group, and a substituted or non-substituted heterocyclic ring aromatic series divalent organic residual group.

38. A process cartridge freely attachable and detachable to an apparatus for forming an image, comprising an electrophotographic photoconductor and at least one means selected from: means for charging; means for image exposing; means for developing; means for transferring; and means for cleaning, wherein the electrophotographic photoconductor comprises a photoconductive layer which contains an azo compound expressed by a general formula <<1>> formed on a conductive support:

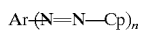      general formula <<1>> wherein in the general formula <<1>>, Ar expresses one of a substituted or non-substituted aromatic hydrocarbon group, and an heterocyclic ring aromatic series group which can be combined by way of a bonding group; and Cp expresses a coupler residual group; n expresses an integer of any one of 1, 2, 3, and 4, wherein at least one of the Cp is a coupler residual group selected from general formulae <<2>>, <<3>>, and <<4>>:

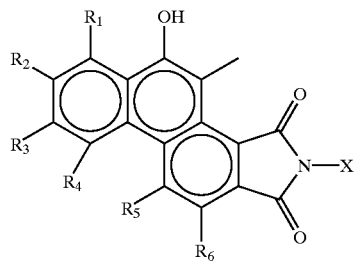      general formula <<2>>

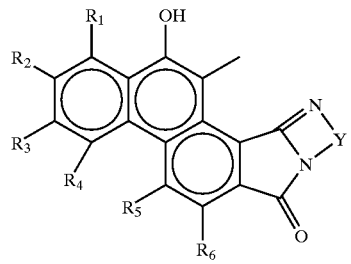      general formula <<3>>

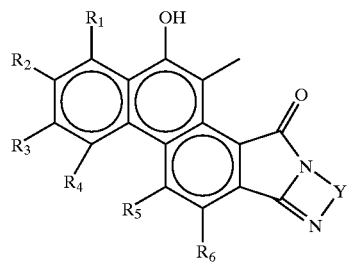      general formula <<4>> wherein in the general formulae <<2>>, <<3>>, and <<4>>, each of $R_1$, $R_2$, $R_3$, $R_4$, $R_5$ and $R_6$ is one of a hydrogen atom, an alkyl group, an alkoxy group, a halogen atom, an amino group, a hydroxy group, a nitro group, and a cyano group;

X represents one of a hydrogen atom, a substituted or non-substituted alkyl group, a substituted or non-substituted aromatic series hydrocarbon group, a substituted or non-substituted heterocyclic ring group, and a substituted or non-substituted amino group; and Y represents one of a substituted or non-substituted alkylene group, a substituted or non-substituted aromatic series divalent organic residual group, a substituted or non-substituted heterocyclic ring aromatic series divalent organic residual group, and a carbonyl group containing divalent organic residual group expressed by —CO—Z—, in which Z represents one of a substituted or non-substituted alkylene group, a substituted or non-substituted aromatic series divalent organic residual group, and a substituted or non-substituted heterocyclic ring aromatic series divalent organic residual group.

* * * * *